United States Patent
Smith et al.

(10) Patent No.: US 12,290,538 B2
(45) Date of Patent: May 6, 2025

(54) METHODS AND PRODUCTS FOR TREATMENT OF GASTROINTESTINAL DISORDERS

(71) Applicants: Finch Therapeutics Holdings LLC, Somerville, MA (US); Millennium Pharmaceuticals, Inc., Cambridge, MA (US)

(72) Inventors: Mark Smith, Somerville, MA (US); Anh-Thu Elaine Vo, Somerville, MA (US); Rotem Sadovsky, Somerville, MA (US); John Henske, Somerville, MA (US); Ylaine Gerardin, Somerville, MA (US); Sonia Timberlake, Somerville, MA (US); Cosmas Giallourakis, Cambridge, MA (US); Ewan Taylor, San Diego, CA (US)

(73) Assignees: Finch Therapeutics Holdings LLC, Boston, MA (US); Millennium Pharmaceuticals, Inc., Cambridge, MA (US)

( * ) Notice: Subject to any disclaimer, the term of this patent is extended or adjusted under 35 U.S.C. 154(b) by 417 days.

(21) Appl. No.: 17/628,339

(22) PCT Filed: Jul. 17, 2020

(86) PCT No.: PCT/US2020/042541
§ 371 (c)(1),
(2) Date: Jan. 19, 2022

(87) PCT Pub. No.: WO2021/016081
PCT Pub. Date: Jan. 28, 2021

(65) Prior Publication Data
US 2022/0257673 A1    Aug. 18, 2022

Related U.S. Application Data

(60) Provisional application No. 63/001,888, filed on Mar. 30, 2020, provisional application No. 62/876,350, filed on Jul. 19, 2019.

(51) Int. Cl.
*A61K 35/741* (2015.01)
*A61P 1/04* (2006.01)

(52) U.S. Cl.
CPC .............. *A61K 35/741* (2013.01); *A61P 1/04* (2018.01)

(58) Field of Classification Search
CPC ................................. A61K 35/471; A61P 1/04
See application file for complete search history.

(56) References Cited

U.S. PATENT DOCUMENTS

| | | |
|---|---|---|
| 3,192,116 A | 6/1965 | Möse et al. |
| 3,320,130 A | 5/1967 | Henry |
| 3,713,836 A | 1/1973 | Carlsson |
| 4,098,728 A | 7/1978 | Rosenblatt |
| 4,196,564 A | 4/1980 | Bodenmann et al. |
| 4,196,565 A | 4/1980 | Bodenmann et al. |
| 4,247,006 A | 1/1981 | Bodenmann et al. |
| 4,250,997 A | 2/1981 | Bodenmann et al. |
| 4,268,265 A | 5/1981 | Von Wattenwyl |
| 4,309,782 A | 1/1982 | Paulin |
| 4,332,790 A | 6/1982 | Sozzi et al. |
| 4,335,107 A | 6/1982 | Snoeyenbos et al. |
| 4,394,377 A | 7/1983 | Spires |
| 4,452,779 A | 6/1984 | Cockerill |
| 4,536,409 A | 8/1985 | Farrell et al. |
| 4,537,776 A | 8/1985 | Cooper |
| 4,657,762 A | 4/1987 | Mikkola et al. |
| 4,710,379 A | 12/1987 | Kawai et al. |
| 4,892,731 A | 1/1990 | Arai et al. |
| 4,975,286 A | 12/1990 | Hechter |
| 5,213,807 A | 5/1993 | Chemburkar et al. |
| 5,266,315 A | 11/1993 | Taguchi et al. |
| 5,317,849 A | 6/1994 | Sauter |
| 5,443,826 A | 8/1995 | Borody |
| 5,599,795 A | 2/1997 | McCann et al. |
| 5,728,380 A | 3/1998 | Allen et al. |
| 5,800,821 A | 9/1998 | Acheson et al. |
| 5,837,238 A | 11/1998 | Casas et al. |
| 5,858,356 A | 1/1999 | Wolf et al. |
| 5,902,578 A | 5/1999 | Halpin-Dohnalek et al. |
| 5,902,743 A | 5/1999 | Luchansky et al. |
| 6,087,386 A | 7/2000 | Chen et al. |
| 6,162,464 A | 12/2000 | Jacob et al. |
| 6,245,740 B1 | 6/2001 | Goldenberg et al. |

(Continued)

FOREIGN PATENT DOCUMENTS

| | | |
|---|---|---|
| AU | 2001276160 B2 | 3/2007 |
| CA | 1333564 | 12/1994 |

(Continued)

OTHER PUBLICATIONS

Farraye et al. ACG Clinical Guideline: Preventive Care in Inflammatory Bowel Disease, 2017, American Journal of Gastroenterology, 112-241 (Year: 2017).*

(Continued)

*Primary Examiner* — Oluwatosin A Ogunbiyi
(74) *Attorney, Agent, or Firm* — Arnold & Porter Kaye Scholer LLP

(57) ABSTRACT

Described herein are compositions and methods for the delivery of microbial therapeutics useful for the treatment of disorders related to intestinal dysbiosis.

15 Claims, 19 Drawing Sheets
Specification includes a Sequence Listing.

(56) References Cited

U.S. PATENT DOCUMENTS

| | | |
|---|---|---|
| 6,284,274 B1 | 9/2001 | Merrill et al. |
| 6,428,783 B1 | 8/2002 | Khachatrian et al. |
| 6,479,051 B1 | 11/2002 | Bruce et al. |
| 6,514,531 B1 | 2/2003 | Alaux et al. |
| 6,572,892 B1 | 6/2003 | Ioulalen et al. |
| 6,645,530 B1 | 11/2003 | Borody |
| 6,649,397 B1 | 11/2003 | Nakamura |
| 6,756,032 B1 | 6/2004 | Tepper et al. |
| 6,926,907 B2 | 8/2005 | Plachetka |
| 6,979,674 B1 | 12/2005 | Goldenberg et al. |
| 6,984,513 B2 | 1/2006 | Brown et al. |
| 7,018,629 B2 | 3/2006 | Jacob et al. |
| 7,374,753 B1 | 5/2008 | Farmer et al. |
| 7,541,091 B2 | 6/2009 | Sisson et al. |
| 7,712,634 B2 | 5/2010 | MacMichael et al. |
| 7,749,509 B2 | 7/2010 | Cobb et al. |
| 7,763,276 B1 | 7/2010 | Shodai et al. |
| 7,799,328 B2 | 9/2010 | Hublot et al. |
| 7,799,341 B2 | 9/2010 | Porzio et al. |
| 7,815,956 B2 | 10/2010 | Lee et al. |
| 7,845,475 B2 | 12/2010 | Shiraishi et al. |
| 7,888,062 B1 | 2/2011 | Garner et al. |
| 7,998,510 B2 | 8/2011 | Caswell |
| 8,074,835 B2 | 12/2011 | MacMichael et al. |
| 8,168,171 B2 | 5/2012 | Mogna et al. |
| 8,398,912 B2 | 3/2013 | Goossens et al. |
| 8,440,224 B2 | 5/2013 | Clarke et al. |
| 8,460,648 B2 | 6/2013 | Borody |
| 8,535,713 B2 | 9/2013 | Coulter |
| 8,557,294 B2 | 10/2013 | Scott et al. |
| 8,586,029 B2 | 11/2013 | Kasper et al. |
| 8,637,297 B2 | 1/2014 | Vieites Fernandez et al. |
| 8,646,591 B2 | 2/2014 | De Ruijter et al. |
| 8,658,153 B2 | 2/2014 | Daube et al. |
| 8,739,812 B2 | 6/2014 | Brandon-Jones et al. |
| 8,771,673 B2 | 7/2014 | Cobb et al. |
| 8,810,259 B2 | 8/2014 | Herrmann et al. |
| 8,852,631 B2 | 10/2014 | Cade et al. |
| 8,911,777 B2 | 12/2014 | Coulter |
| 8,911,788 B2 | 12/2014 | Ioualalen et al. |
| 9,040,036 B2 | 5/2015 | Borody |
| 9,050,358 B2 | 6/2015 | Borody |
| 9,308,226 B2 | 4/2016 | Borody |
| 9,320,763 B2 | 4/2016 | Borody |
| 9,408,872 B2 | 8/2016 | Borody |
| 9,468,658 B2 | 10/2016 | Borody |
| 9,572,841 B2 | 2/2017 | Borody |
| 9,572,842 B2 | 2/2017 | Borody |
| 9,610,308 B2 | 4/2017 | Borody |
| 9,623,056 B2 | 4/2017 | Borody |
| 9,682,108 B2 | 6/2017 | Borody |
| 9,719,144 B2 | 8/2017 | Krajmalnik-Brown et al. |
| 9,737,574 B2 | 8/2017 | Borody |
| 9,789,140 B2 | 10/2017 | Borody |
| 9,867,858 B2 | 1/2018 | Borody |
| 9,901,603 B2 | 2/2018 | Borody |
| 9,901,604 B2 | 2/2018 | Borody |
| 9,962,413 B2 | 5/2018 | Borody |
| 9,962,414 B2 | 5/2018 | Borody |
| 9,968,638 B2 | 5/2018 | Sadowsky et al. |
| 10,022,406 B2 | 7/2018 | Borody |
| 10,028,980 B2 | 7/2018 | Sadowsky et al. |
| 10,064,899 B1 | 9/2018 | Borody |
| 10,092,601 B2 | 10/2018 | Borody |
| 10,195,235 B2 | 2/2019 | Borody |
| 10,251,914 B2 | 4/2019 | Sadowsky et al. |
| 10,278,997 B2 | 5/2019 | Borody |
| 10,286,011 B2 | 5/2019 | Sadowsky et al. |
| 10,286,012 B2 | 5/2019 | Sadowsky et al. |
| 10,328,107 B2 | 6/2019 | Borody |
| 10,369,175 B2 | 8/2019 | Borody |
| 10,463,702 B2 | 11/2019 | Borody |
| 2001/0014322 A1 | 8/2001 | Chen et al. |
| 2002/0013270 A1 | 1/2002 | Bolte |
| 2002/0022019 A1 | 2/2002 | Laulund |
| 2002/0039599 A1 | 4/2002 | Lin et al. |
| 2003/0092163 A1 | 5/2003 | Collins et al. |
| 2003/0092724 A1 | 5/2003 | Kao et al. |
| 2003/0147858 A1 | 8/2003 | Renaud et al. |
| 2004/0062757 A1 | 4/2004 | Finegold |
| 2004/0167062 A1 | 8/2004 | Bolte |
| 2004/0170617 A1 | 9/2004 | Finegold |
| 2004/0223956 A1 | 11/2004 | Naidu et al. |
| 2006/0001896 A1 | 1/2006 | Sakamoto |
| 2006/0076536 A1 | 4/2006 | Barshied |
| 2006/0099197 A1 | 5/2006 | Farmer |
| 2006/0115465 A1 | 6/2006 | Macfarlane et al. |
| 2006/0177424 A1 | 8/2006 | Cobb et al. |
| 2006/0275223 A1 | 12/2006 | Burr |
| 2007/0059296 A1 | 3/2007 | Chen |
| 2007/0292523 A1 | 12/2007 | Moodley et al. |
| 2008/0020018 A1 | 1/2008 | Moodley et al. |
| 2008/0113031 A1 | 5/2008 | Moodley et al. |
| 2008/0254009 A1 | 10/2008 | Finegold |
| 2008/0299197 A1 | 12/2008 | Toneguzzo et al. |
| 2010/0112003 A1 | 5/2010 | Collins et al. |
| 2010/0178349 A1 | 7/2010 | Kolter et al. |
| 2010/0178413 A1 | 7/2010 | Gorris |
| 2010/0184785 A1 | 7/2010 | Kolter et al. |
| 2010/0203120 A1 | 8/2010 | Coulter |
| 2010/0222311 A1 | 9/2010 | Thommes et al. |
| 2010/0226866 A1 | 9/2010 | Yamashiro et al. |
| 2010/0233278 A1 | 9/2010 | Ookawa et al. |
| 2010/0239667 A1 | 9/2010 | Hemmingsen et al. |
| 2010/0247489 A1 | 9/2010 | Saur-Brosch |
| 2010/0247665 A1 | 9/2010 | Takahashi |
| 2010/0255087 A1 | 10/2010 | Coulter |
| 2010/0255231 A1 | 10/2010 | Chau et al. |
| 2010/0255307 A1 | 10/2010 | Gonze et al. |
| 2010/0278930 A1 | 11/2010 | Okumura et al. |
| 2010/0285164 A1 | 11/2010 | Schaible et al. |
| 2010/0289164 A1 | 11/2010 | Porzio et al. |
| 2010/0297031 A1 | 11/2010 | Úbeda Pérez et al. |
| 2010/0297221 A1 | 11/2010 | Coulter |
| 2011/0008554 A1 | 1/2011 | Chen et al. |
| 2011/0045222 A1 | 2/2011 | Peters |
| 2011/0052645 A1 | 3/2011 | Coulter |
| 2011/0081320 A1 | 4/2011 | Westall et al. |
| 2011/0091431 A1 | 4/2011 | Olmstead |
| 2011/0200570 A1 | 8/2011 | Mosbaugh et al. |
| 2011/0218216 A1 | 9/2011 | Vivek et al. |
| 2012/0020941 A1 | 1/2012 | Wacklin et al. |
| 2012/0039853 A1 | 2/2012 | Corveleyn et al. |
| 2012/0064133 A1 | 3/2012 | Chauhan et al. |
| 2012/0087895 A1 | 4/2012 | Mazmanian et al. |
| 2012/0129773 A1 | 5/2012 | Geier et al. |
| 2012/0141531 A1 | 6/2012 | Coulter et al. |
| 2012/0141585 A1 | 6/2012 | Coulter et al. |
| 2012/0183612 A1 | 7/2012 | Brögmann et al. |
| 2012/0252775 A1 | 10/2012 | Finegold |
| 2013/0022622 A1 | 1/2013 | Ben-Ari et al. |
| 2013/0045274 A1 | 2/2013 | Hlavka |
| 2013/0184290 A1 | 7/2013 | Padval et al. |
| 2013/0195804 A1 | 8/2013 | Borody |
| 2013/0243873 A1 | 9/2013 | Aversa et al. |
| 2013/0259899 A1 | 10/2013 | Allen-Vercoe et al. |
| 2013/0287842 A1 | 10/2013 | Cade et al. |
| 2013/0295188 A1 | 11/2013 | Cade et al. |
| 2013/0307962 A1 | 11/2013 | Humphries et al. |
| 2013/0316394 A1 | 11/2013 | Stimpson |
| 2013/0330411 A1 | 12/2013 | Coulter |
| 2014/0017313 A1 | 1/2014 | Coulter et al. |
| 2014/0065132 A1 | 3/2014 | Hsiao et al. |
| 2014/0086877 A1 | 3/2014 | Hlavka |
| 2014/0088202 A1 | 3/2014 | Cade et al. |
| 2014/0147417 A1 | 5/2014 | Sadowsky et al. |
| 2014/0147425 A1 | 5/2014 | Henn et al. |
| 2014/0227357 A1 | 8/2014 | Vertommen et al. |
| 2014/0234260 A1 | 8/2014 | Borody |
| 2014/0234418 A1 | 8/2014 | Coulter et al. |
| 2014/0255351 A1 | 9/2014 | Berstad et al. |
| 2014/0302132 A1 | 10/2014 | Brown |
| 2014/0328803 A1 | 11/2014 | Mckenzie et al. |
| 2014/0341921 A1 | 11/2014 | Honda et al. |

(56) References Cited

U.S. PATENT DOCUMENTS

| | | |
|---|---|---|
| 2014/0342438 A1 | 11/2014 | Allen-Vercoe et al. |
| 2014/0363397 A1 | 12/2014 | Allen-Vercoe et al. |
| 2014/0363398 A1 | 12/2014 | Jones et al. |
| 2015/0044173 A1 | 2/2015 | Jones et al. |
| 2015/0050246 A1 | 2/2015 | Jones et al. |
| 2015/0093360 A1 | 4/2015 | McKenzie et al. |
| 2015/0143557 A1 | 5/2015 | Honda et al. |
| 2015/0152484 A1 | 6/2015 | Krajmalnik-Brown et al. |
| 2015/0190435 A1 | 7/2015 | Henn et al. |
| 2015/0224152 A1 | 8/2015 | Littman et al. |
| 2015/0238544 A1 | 8/2015 | Jones et al. |
| 2015/0238545 A1 | 8/2015 | Borody |
| 2015/0238546 A1 | 8/2015 | Borody |
| 2015/0293072 A1 | 10/2015 | Geigenmuller et al. |
| 2015/0297642 A1 | 10/2015 | Borody |
| 2015/0306144 A1 | 10/2015 | Borody |
| 2015/0306155 A1 | 10/2015 | Borody |
| 2015/0306156 A1 | 10/2015 | Borody |
| 2015/0374761 A1 | 12/2015 | Sadowsky et al. |
| 2016/0040215 A1* | 2/2016 | Henn .................. C12Q 1/689 435/6.12 |
| 2016/0089363 A1 | 3/2016 | Borody |
| 2016/0091480 A1 | 3/2016 | Geigenmuller et al. |
| 2016/0143962 A1 | 5/2016 | Berry et al. |
| 2016/0151429 A1 | 6/2016 | Borody |
| 2016/0151431 A1 | 6/2016 | Borody |
| 2016/0151432 A1 | 6/2016 | Borody |
| 2016/0151433 A1 | 6/2016 | Borody |
| 2016/0158294 A1 | 6/2016 | Von Maltzahn et al. |
| 2016/0243175 A1 | 8/2016 | Bushman et al. |
| 2016/0279178 A1 | 9/2016 | Borody |
| 2016/0279179 A1 | 9/2016 | Borody |
| 2016/0339065 A1 | 11/2016 | Adams et al. |
| 2017/0165302 A1 | 6/2017 | Henn et al. |
| 2017/0216378 A1 | 8/2017 | Honda et al. |
| 2017/0246220 A1 | 8/2017 | Sato et al. |
| 2017/0319627 A1 | 11/2017 | Sadowsky et al. |
| 2017/0348360 A1 | 12/2017 | Borody |
| 2018/0110810 A1 | 4/2018 | Sadowsky et al. |
| 2018/0153943 A1 | 6/2018 | Borody |
| 2018/0169153 A1 | 6/2018 | Berry et al. |
| 2018/0200310 A1 | 7/2018 | McKenzie et al. |
| 2018/0256652 A1 | 9/2018 | Borody |
| 2018/0353554 A1 | 12/2018 | Henn et al. |
| 2019/0015460 A1 | 1/2019 | Borody |
| 2019/0015461 A1 | 1/2019 | Borody |
| 2019/0015462 A1 | 1/2019 | Borody |
| 2019/0046589 A1 | 2/2019 | Borody |
| 2019/0070225 A1 | 3/2019 | Strandwitz et al. |
| 2019/0134106 A1 | 5/2019 | Borody |
| 2019/0134144 A1 | 5/2019 | Adams et al. |
| 2019/0144923 A1 | 5/2019 | Krajmalnik-Brown et al. |
| 2019/0175665 A1 | 6/2019 | Borody |
| 2019/0216860 A1 | 7/2019 | Borody |
| 2019/0247445 A1 | 8/2019 | Hamilton et al. |
| 2019/0290704 A1 | 9/2019 | Borody |
| 2019/0328825 A1 | 10/2019 | Adams et al. |
| 2019/0343897 A1 | 11/2019 | Borody |
| 2019/0358274 A1 | 11/2019 | Adams et al. |

FOREIGN PATENT DOCUMENTS

| | | |
|---|---|---|
| CA | 2 391 422 A1 | 1/2004 |
| CN | 1561387 A | 1/2005 |
| CN | 101496819 A | 8/2009 |
| CN | 201441672 U | 4/2010 |
| DE | 2 134 179 A1 | 1/1973 |
| EP | 0 303 246 A2 | 2/1989 |
| EP | 0 303 426 A2 | 2/1989 |
| EP | 0456 418 B1 | 11/1991 |
| EP | 0 433 299 B1 | 5/1998 |
| EP | 1 514 572 A2 | 3/2005 |
| EP | 1 514 572 A3 | 11/2006 |
| EP | 1 800 688 A1 | 6/2007 |
| EP | 1 514 572 B1 | 12/2008 |
| EP | 2 823 822 B1 | 10/2016 |
| EP | 3424515 A2 | 1/2019 |
| EP | 3 610 881 A1 | 2/2020 |
| FR | 1275 M | 5/1962 |
| FR | 2427 M | 3/1964 |
| FR | 2828 M | 10/1964 |
| FR | 5528 M | 11/1967 |
| FR | 2 244 464 A1 | 4/1975 |
| GB | 1 271 674 A | 4/1972 |
| JP | 64-067192 | 3/1989 |
| JP | H05-306221 A | 11/1993 |
| JP | H07-242539 A | 9/1995 |
| JP | H07-242557 A | 9/1995 |
| JP | 3 144 556 B2 | 3/2001 |
| JP | 2004-501095 | 1/2004 |
| JP | 2005-118544 A | 5/2005 |
| JP | 2008-106066 | 5/2008 |
| JP | 2010-513359 | 4/2010 |
| JP | 2010-520234 A | 6/2010 |
| JP | 2014-507481 A | 3/2014 |
| JP | 2015-520176 A | 7/2015 |
| JP | 2016-519664 A | 7/2016 |
| JP | 2016-155880 A | 9/2016 |
| JP | 2016-509003 A5 | 3/2017 |
| JP | 2017-514872 A | 6/2017 |
| KR | 10-0913405 B1 | 8/2009 |
| WO | WO 90/01335 A1 | 2/1990 |
| WO | WO 95/33046 A1 | 12/1995 |
| WO | WO 96/11014 A1 | 4/1996 |
| WO | WO 98/13068 A1 | 4/1998 |
| WO | WO 00/07571 A2 | 2/2000 |
| WO | WO 00/015760 A1 | 3/2000 |
| WO | WO 00/42168 A2 | 7/2000 |
| WO | WO 02/07741 A1 | 1/2002 |
| WO | WO 03/033681 A2 | 4/2003 |
| WO | WO 2005/017095 A2 | 2/2005 |
| WO | WO 2006/127355 A2 | 11/2006 |
| WO | WO 2007/122374 A2 | 11/2007 |
| WO | WO 2008/077614 A2 | 7/2008 |
| WO | WO 2008/105715 A2 | 9/2008 |
| WO | WO 2008/117266 A2 | 10/2008 |
| WO | WO 2008/117267 A2 | 10/2008 |
| WO | WO 2008/135090 A1 | 11/2008 |
| WO | WO 2008/077614 A3 | 1/2009 |
| WO | WO 2009/024429 A2 | 2/2009 |
| WO | WO 2009/026306 A2 | 2/2009 |
| WO | WO 2009/055362 A1 | 4/2009 |
| WO | WO 2010/036876 A2 | 4/2010 |
| WO | WO 2010/040020 A1 | 4/2010 |
| WO | WO 2011/033310 A1 | 3/2011 |
| WO | WO 2011/110347 A2 | 9/2011 |
| WO | WO 2011/151941 A1 | 12/2011 |
| WO | WO 2011/152566 A2 | 12/2011 |
| WO | WO 2012/013861 A2 | 2/2012 |
| WO | WO 2012/016287 A2 | 2/2012 |
| WO | WO 2012/016287 A3 | 2/2012 |
| WO | WO 2012/045150 A1 | 4/2012 |
| WO | WO 2012/122478 A1 | 9/2012 |
| WO | WO 2012/142605 A1 | 10/2012 |
| WO | WO 2013/037067 A1 | 3/2013 |
| WO | WO 2013/037068 A1 | 3/2013 |
| WO | WO 2013/053836 A1 | 4/2013 |
| WO | WO 2013/090825 A1 | 6/2013 |
| WO | WO 2013/176774 A1 | 11/2013 |
| WO | WO 2014/036182 A2 | 3/2014 |
| WO | WO 2014/070014 A1 | 5/2014 |
| WO | WO 2014/078911 A1 | 5/2014 |
| WO | WO 2014/152338 A1 | 9/2014 |
| WO | WO 2014/152484 A1 | 9/2014 |
| WO | WO 2015/006355 A2 | 1/2015 |
| WO | WO 2015/051323 A1 | 4/2015 |
| WO | WO 2015/077794 A1 | 5/2015 |
| WO | WO 2015/095241 A2 | 6/2015 |
| WO | WO 2015/124637 A1 | 8/2015 |
| WO | WO 2016/133450 A1 | 8/2016 |
| WO | WO 2016/183577 A1 | 11/2016 |
| WO | WO 2016/191356 A1 | 12/2016 |
| WO | WO 2017/075098 A1 | 5/2017 |

(56) References Cited

FOREIGN PATENT DOCUMENTS

| | | |
|---|---|---|
| WO | WO 2017/091783 A2 | 6/2017 |
| WO | WO 2017/134240 | 8/2017 |
| WO | WO 2017/152137 A2 | 9/2017 |
| WO | WO 2017/210428 A1 | 12/2017 |
| WO | WO 2018/006088 A1 | 1/2018 |
| WO | WO 2018/026913 A1 | 2/2018 |
| WO | WO 2018/057914 | 3/2018 |
| WO | WO 2018/075886 | 4/2018 |
| WO | WO 2018/187272 | 10/2018 |
| WO | WO 2018/187272 A1 | 10/2018 |
| WO | WO 2018/187467 A1 | 10/2018 |
| WO | WO 2019/032572 | 2/2019 |
| WO | WO 2019/032572 A1 | 2/2019 |
| WO | WO 2019/032573 | 2/2019 |
| WO | WO 2019/032573 A1 | 2/2019 |
| WO | WO 2019/032575 A1 | 2/2019 |
| WO | WO 2019/041141 A1 | 3/2019 |
| WO | WO 2019/051380 A1 | 3/2019 |
| WO | WO 2019/075344 A1 | 4/2019 |
| WO | WO 2019/165285 A1 | 8/2019 |

OTHER PUBLICATIONS

Panes et al.Improving quality of care in inflammatory bowel disease: What changes can be made today< 2014, Journal of Crohn's and Colitis, 8: 919-926 (Year: 2014).*
Center for Disease Control (Inflammatory Bowel Disease (IBD), What Is It? 2018 https://www.cdc.gov/ibd/features/inflammatory-bowel-disease/index.html Last accessed Mar. 13, 2023 (Year: 2018).*
Mayo Foundation for Medical Education and Research. Inflammatory Bowel Disease (IBD) Copyright 1998-2024. https://www.mayoclinic.org/diseases-conditions/inflammatory-bowel-disease/symptoms-causes/syc-20353315 Last accessed Mar. 19, 2024 (Year: 1998).*
Encyclopedia.com. Disease Prevention. 2019. https://www.encyclopedia.com/education/encyclopedias-almanacs-transcripts-and-maps/disease-prevention Last accessed Mar. 19, 2024 (Year: 2019).*
Martin-Dejardin, et al., "A way to follow the viability of encapsulated Bifidobacterium bifidum subjected to a freeze-drying process in order to target the colon: Interest of flow cytometry," European Journal of Pharmaceutical Sciences, 49:166-74 (2013).
Maslowski, et al., "Diet, gut microbiota and immune responses," Nat Immunol., 12(1):5-9 (2011).
McDonald, et al., "An Epidemic, Toxin Gene-Variant Strain of Clostridium difficile," N Engl J Med., 353(23):2433-41 (2005).
McDonald, et al., "Clostridium difficile Infection in Patients Discharged from US Short-stay Hospitals, 1996-2003" Emerg. Infect. Dis, 12(3):409-415 (2006).
McFarland, et al., "Breaking the Cycle: Treatment Strategies for 163 Cases of Recurrent Clostridium difficile Disease," Am. J. Gastroenterol., 97(7):1769-1775 (2002).
McFarland, et al., "Implications of the changing face of Clostridium difficile disease for health care practitioners," Am J Infect Control., 35(4):237-253 (2007).
McFarland, et al., "Meta-Analysis of Probiotics for the Prevention of Antibiotic Associated Diarrhea and the Treatment of Clostridium difficile Disease," Am J Gastroenterol., 101(4):812-22 (2006).
McFarland, et al., "Nosocomial Acquisition of Clostridium Difficile Infection," N Engl J Med., 320(4):204-210 (1989).
McFarland, et al., "Recurrent Clostridium Difficile Disease: Epidemiology and Clinical Characteristics," Infect Control Hosp Epidemiol., 20(1):43-50 (1999).
McFarland, et al., "Renewed interest in a difficult disease: Clostridium difficile infections—epidemiology and current treatment strategies," Curr Opin Gastroenterol., 25(1):24-35 (2008).
Meadows, "Gut Bacteria May Override Genetic Protections against Diabetes," PLOS Biology, 9(12):e1001215 (2011).
Miller, et al., "Health care-associated Clostridium difficile infection in Canada: patient age and infecting strain type are highly predictive of severe outcome and mortality," Clin Infect Dis., 50(2):194-201 (2010).
Miller, et al., "Long-term follow-up of patients with fulminant Clostridium difficile colitis," J. Gastrointest. Surg., 13(5):956-959 (2009).
Miller, et al., "Morbidity, mortality, and healthcare burden of nosocomial Clostridium difficile-associated diarrhea in Canadian hospitals," Infect Control Hosp Epidemiol., 23(3):137-40 (2002).
Miller, "The fascination with probiotics for Clostridium difficile infection: lack of evidence for prophylactic or therapeutic efficacy," Anaerobe, 15(6):281-284 (2009).
Minami, et al., "Effects of lipopolysaccharides and chelator onmercury content in the cerebrum of thimerosal administered mice," Environmental Toxicology and Pharmacology, 24:316-320 (2007).
Minami, et al., "Roles of nitric oxide prostaglandins in the increased permeability of the blood-brain barrier caused by lipopolysaccharide," Environmental Toxicology and Pharmacology, 5:35-41 (1998).
Moayyedi, et al., "Fecal Microbiota Transplantation Induces Remission in Patients With Active Ulcerative Colitis in a Randomized Controlled Trial," Gastroenterology, 149(1):102-9 (2015).
Molecular Studies in Autism, 2004 Funding Cycle, Cure Autism Now, Cure Autism Now Foundation, pp. 1-7 (2005) www.cureautismnow.org.
Molloy & Manning-Courtney, "Prevalence of chronic gastrointestinal symptoms in children with autism and autistic spectrum disorders,"Autism 7(2):165-171 (2003).
Momose, et al., "16S rRNA gene sequence-based analysis of clostridia related to conversion of germfree mice to the normal state," Journal of Applied Microbiology, 107:2088-2097 (2009).
Morris, et al., "Clostridium difficile Colitis: An Increasingly Aggressive Iatrogenic Disease?" Arch Surg., 137(10):1096-1100 (2002).
Mucosal immunity: homeostasis (WS-064): Chairpersons: Toshiaki Ohteki, Makoto Iwata, International Immunology, 22:Suppl 1 Pt. 3, 1-9 (2010).
Mullard, "Microbiology: The Inside Story," Nature, 453:578-580 (2008).
Mulloy, et al., "Gluten-free and casein-free diets in the treatment of autism spectrum disorders: A systematic review," Research in Autism Spectrum Disorders, 4:328-339 (2010).
Murai, et al., "Interleukin 10 acts on regulatory T cells to maintain expression of the transcription factor Foxp3 and suppressive function in mice with colitis," Nat Immunol., pp. 1-20 (2009).
Mutaflor, "Brief Summary of Therapeutic Principles," Ardeypharm GmbH 0796 D-58313 Herdecke Germany, 6 pgs (2006).
Mutaflor, "For Functional and Inflammatory Bowel Diseases for Extraintestinal Manifestations for Activation of the Body's In-Built Defences," Ardeypharm GmbH 0796, D-58313 Herdecke Germany, 8 pgs (2006).
Mutaflor, "Safety of Therapy," Ardeypharm GmbH 0796, D-58313 Herdecke Germany, 4 pgs (1988).
Muto, et al., "A Large Outbreak of Clostridium difficile-Associated Disease with an Unexpected Proportion of Deaths and Colectomies at a Teaching Hospital Following Increased Fluoroquinolone Use," Infect Control Hosp Epidemiol., 26(3):273-80 (2005).
Niehus & Lord, "Early Medical History of Children with Autism Spectrum Disorders," Journal of Developmental Behavioral Pediatrics, 27(2):S120-S127 (2006).
Niu, et al., "Prevalence and Impact of Bacteriophages on the Presence of *Escherichia coli* 0157:H7 in Feedlot Cattle and Their Environment," Applied and Environmental Microbiology, 75(5): 1271-8 (2009).
O'Hara, et al., "The gut flora as a forgotten organ," EMBO Rep., 7(7):688-693 (2006).
O'Brien, et al., "The emerging infectious challenge of clostridium difficile-associated disease in Massachusetts hospitals: clinical and economic consequences," Infect Control Hosp Epidemiol., 28(11):1219-27 (2007).
Ochoa-Reparaz, et al., "Gut, Bugs, and Brain: Role of Commensal Bacteria in the Control of Central Nervous System Disease", Annals Neurology, 69:240-247 (2011).
O'Connor, et al., "Clostridium difficile Infection Caused by the Epidemic BI/NAP1/027 Strain," Gastroenterology, 136(6):1913-1924 (2009).

(56) References Cited

OTHER PUBLICATIONS

O'Garra, et al., "IL-10—producing and naturally occuring CD4+ Tregs: limiting collateral damage," The Journal of Clinical Investigation, 114:1372-1378 (2004).
O'Hara, et al., "Functional modulation of human intestinal epithelial cell responses by Bifidobacterium infantis and Lactobacillus salivarius," Immunology 118:202-215 (2006).
Okada, et al., "Effects of Fecal Microorganisms and Their Chloroform-Resistant Variants Derived from Mice, Rats, and Humans on Immunological and Physiological Characteristics of the Intestines of Ex-germfree Mice," Infection and Immunity, 62(12):5442-5446 (1994).
Olson, et al., "The Gut Microbiota Mediates the Anti-Seizure Effects of the Ketogenic Diet," Cell, 173:1728-1741 (2018) https://linkinghub.elsevier.com/retrieve/pii/S0092867418305208.
Ott, et al., "Efficacy of Sterile Fecal Filtrate Transfer for Treating Patients With Clostridium difficile Infection," Gastroenterology, 152(4):799-811 (2017).
Paramsothy, et al., "Multidonor intensive faecal microbiota transplantation for active ulcerative colitis: a randomised placebo-controlled trial," The Lancet, published online, 11 pages (2017).
Paramsothy, et al., "Gastroenterologist perceptions of faecal microbiota transplantation," World J Gastroenterol, 21(38): 10907-10914 (2015).
Parracho, et al., "Differences between the gut microflora of children with autistic spectrum disorders and that of healthy children," Journal of Medicine Microbiology, 54:987-991 (2005).
Patterson, et al., "Special organism isolation: attempting to bridge the gap," Infect Control Hosp Epidemiol., 15(5):335-338 (1994).
Pearce, et al., "Modification of the colonic microflora using probiotics: The way forward?," Gut, 41(Suppl 3):A63 (1997).
Pearce, et al., "The use of probiotic therapy as a novel approach to the management of irritable bowel syndrome: a preliminary study," J Gastroenterol & Hepatol, 12(Suppl):A129 (1997).
Pépin, et al., "Clostridium difficile-associated diarrhea in a region of Quebec from 1991 to 2003: a changing pattern of disease severity," CMAJ, 171(5):466-472 (2004).
Pépin, et al., "Emergence of Fluoroquinolones as the Predominant Risk Factor for Clostridium difficile-Associated Diarrhea: A Cohort Study During an Epidemic in Quebec," Clin Infect Dis., 41(9):1254-1260 (2005).
Pépin, et al., "Management and Outcomes of a First Recurrence of Clostridium difficile-Associated Disease in Quebec, Canada," Clin. Infect. Dis., 42:758-764 (2006).
Persky, et al., "Treatment of recurrent Clostridium difficile-associated diarrhea by administration of donated stool directly through a colonoscope," Am J Gastroenterol., 95(11):3283-3285 (2000).
Petrof, et al., "Stool substitute transplant therapy for the eradication of Clostridium difficile infection: 'RePOOPulating' the gut," Microbiome, 1:3 (2013).
Petrof, "Harnessing the healthy gut microbiota to cure patients with recurrent C. difficile infection," U.S. National Institutes of Health, Clinical Study No. NCT01372943, pp. 1-2, last updated Nov. 6, 2013, Web, May 22, 2014 http://clinicaltrials.gov/ct2/show/NCT01372943.
Pillai, et al., "Probiotics for treatment of Clostridium difficile-associated colitis in adults (Review)," Cochrane Database Syst Rev., (1):CD004611 (2008).
Poster 064-03 presented at the 14th International Congress of Immunology, Aug. 22-27, 2010, in Kyoto (Atarashi et al., Regulation of colonic regulatory T cells by Clostridium species).
Prakash, et al., "Colon-targeted delivery of live bacterial cell biotherapeutics including microencapsulated live bacterial cells," Biologics: Targets & Therapy, 2(3):355-378 (2008).
Prevention of Sudden Infant Death Syndrome, Healthtouch.com, Thomson Micromedex, pp. 1-4, n.d., Web, Nov. 23, 2005.
Qin, et al., "A human gut microbial gene catalogue established by metagenomic sequencing," Nature 464:59-67 (2010).

Qiu, et al., "Faecalibacterium prausnitzii upregulates regulatory T cells and anti-inflammatory cytokines in treating TNBS-induced colitis," Journal of Crohn's and Colitis, 7:e558-e568 (2013).
Rabeneck, et al., "Bleeding and perforation after outpatient colonoscopy and their risk factors in usual clinical practice," Gastroenterology, 135(6):1899-1906 (2008).
Rager, et al., "Evaluation of rumen transfaunation after surgical correction of left-sided displacement of the abomasum in cows," J. Am. Vet. Med. Assoc., 225(6):915-920 (2004).
Ramesh, et al., "Prevention of Clostridium difficile-induced ileocecitis with Bacteriophage," Anaerobe, 5:69-78 (1999).
Rao, et al., "Evaluation of gastrointestinal transit in clinical practice: position paper of the American and European Neurogastroenterology and Motility Societies," Neurogastroenterol. Motil., 23(1):8-23 (2011).
Rautava, "Potential uses of probiotics in the neonate," Seminars in Fetal & Neonatal Medicine, 12:45-53 (2007).
Rea, et al., "Gut solutions to a gut problem: bacteriocins, probiotics and bacteriophage for control of Clostridium difficile infection," Journal of Medical Microbiology, 62:1369-1378 (2013).
Redelings, et al., "Increase in Clostridium difficile-related mortality rates, United States, 1999-2004," Emerg Infect Dis., 13(9):1417-1419 (2007).
Rex, et al., "American College of Gastroenterology guidelines for colorectal cancer screening 2008," Am. J. Gastroenterol., 104(3):739-750 (2009).
Ricciardi, et al., "Increasing prevalence and severity of Clostridium difficile colitis in hospitalized patients in the United States," Arch Surg., 142(7):624-631 (2007).
Roberts, Generation and Development Microbial Drug Products, CSO Vedanta Biosciences, 1st Microbiome Drug Development Summit, pp. 1-17 (2016).
Robertson, et al., "Intestinal Permeability and Glucagon-like peptide-2 in Children with Autism: A Controlled Pilot Study", Journal of Autism Development Disorder, 38:10661071 (2008).
Robinson, et al., "Characterization of the Cecal Bacteria of Normal Pigs", Applied and Environmental Microbiology, 41(4):950-955 (1981).
Rodemann, et al., "Incidence of Clostridium difficile infection in inflammatory bowel disease," Clin Gastroenterol Hepatol., 5(3):339-344 (2007).
Rohlke, et al., "Fecal flora reconstitution for recurrent Clostridium difficile infection: results and methodology," J Clin Gastroenterol., 44(8):567-570 (2010).
Roid, et al., Leiter International Performance Scale—Revised, Stoelting (1997).
Rolfe, et al., "Bacterial interference between Clostridium difficile and normal fecal flora," J Infect Dis., 143(3):470-475 (1981).
Rossen, et al., "Findings From a Randomized Controlled Trial of Fecal Transplantation for Patients with Ulcerative Colitis," Gastroenterology, 149(1):110-8 (2015).
Round, et al., "Inducible Foxp3+ regulatory T-cell development by a commensal bacterium of the intestinal microbiota," PNAS, 107(27):12204-12209 (2010).
Round, et al., "The Toll-like receptor pathway establishes commensal gut colonization," Science, 332(6032):974-977 (2011).
Round, et al., "The gut microbiota shapes intestinal immune responses during health and disease," Nat. Rev. Immunol., 9(5):313-323 (2009).
Rupnik, et al., "Clostridium difficile infection: new developments in epidemiology and pathogenesis," Nat. Rev. Microbiol., 7(7):526-536 (2009).
Russell, et al., "Fecal bacteriotherapy for relapsing Clostridium difficile infection in a child: a proposed treatment protocol," Pediatrics, 126(1):e239-42 (2010).
Salazar, et al., "Exopolysaccharides Produced by Intestinal Bifidobacterium Strains Act as Fermentable Substrates for Intestinal Bacteria", Applied and Environmental Microbiology, 74(15):4737-4745 (2008).
Sambol, et al., "Colonization for the prevention of Clostridium difficile disease in hamsters," J. Infect. Dis., 186(12):1781-1789 (2002).

(56) References Cited

OTHER PUBLICATIONS

Sanchez, et al., "The Role of Natural Regulatory T cells in Infection," Immunol Res., 49(0):124-134 (2011).
Sandler, et al., "Possible Gut-Brain Interaction Contributing to Delayed Onset Autism Symptomatology," Fourth Int. Symp. Brain-Gut Interactions, Blackwell Science Ltd., 10(4):33 (1998).
Sandler, et al., "Short-Term Benefit From Oral Vancomycin Treatment of Regressive-Onset Autism," Journal of Child Neurology, 15(7):429-435 (2000).
Sartor, "Therapeutic correction of bacterial dysbiosis discovered by molecular techniques," PNAS, 105(43):16413-16414 (2008).
Schauer & Falkow, "Attaching and Effacing Locus of a Citrobacter freundii BiotypeThat Cuases Transmissible Murine Colonic Hyperplasia," Infection and Immunity, 61(6):2486-2492 (1993).
Schiller, "Review article," the therapy of constipation, Ailment Pharmacol. Ther. 15:749-763 (2001).
Schloss, et al., "Introducing mothur: Open-Source, Platform-Independent, Community-Supported Software for Describing and Comparing Microbial Communities," Applied and Environmental Microbiology, 75(23):7537-7541 (2009).
Schneider, et al., "Oral Human Immunoglobulin for Children with Autism and Gastrointestinal Dysfunction: A Prospective, Open-Label Study," Journal of Autism Development Disorder, 36:1053-1064 (2006).
Schopler, et al., "Childhood autism rating scale-second edition (CARS2)," Western Psychological Services, 4-5, 93 (2010).
Schwan, et al., "Relapsing Clostridium Difficile Enterocolitis Cured by Rectal Infusion of Homologous Faeces," The Lancet, 322(8354):845 (1983).
Schwan, et al., "Relapsing Clostridium difficile Enterocolitis Cured by Rectal Infusion of Normal Faeces," Scand. J. Infect. Dis., 16(2):211-215 (1984).
Seeff, et al., "How many endoscopies are performed for colorectal cancer screening? Results from CDC's survey of endoscopic capacity," Gastroenterology, 127:1670-1677 (2004).
Sekirov, et al., "Gut microbiota in health and disease," Physiol. Rev., 90(3):859-904 (2010).
Sell, et al., "Bacteriophage and Bacteriocin Typing Scheme for Clostridium difficile,"Journal of Clinical Microbiology, 17(6):1148-1152 (1983).
Setlow, "I Will Survive: Protecting and Repairing Spore DNA," Journal of Bacteriology, 174(9):2737-2741 (1992).
Setlow, "The bacterial spore: nature's survival package," Culture, 26(2):1-4 (2005).
Sghir, et al., "Quantification of Bacterial Groups within Human Fecal Flora by Oligonucleotide Prode Hybridization," Applied and Environmental Microbiology, 66(5):2263-2266 (2000).
Shi, et al., "Fecal Microbiota Transplantation for Ulcerative Colitis: A Systematic Review and Meta-Analysis," PLOS One, 1-18 (2016).
Shim, et al., "Primary symptomless colonisation by Clostridium difficile and decreased risk of subsequent diarrhea," The Lancet, 351(9103):633-666 (1998).
Silverman, et al., "Success of self-administered home fecal transplantation for chronic Clostridium difficile infection," Clin. Gastroenterol. Hepatol., 8(5):471-473 (2010).
Simor, et al., "Clostridium difficile in long-term-care facilities for the elderly," Infect Control Hosp Epidemiol., 23(11):696-703 (2002).
Singh, et al., "Do NSAIDs, antibiotics, infections, or stress trigger flares in IBD?" Am J Gastroenterol., 104(5):1298-1313 (2009).
Sleator, "The human superorganism—of microbes and men," Med. Hypotheses, 74(2):214-215 (2010).
Smits, et al., "Therapeutic potential of fecal microbiota transplantation," Gastroenterology, 145:946-953 (2013).
Sokol, et al., Faecalibacterium prausnitzii is an anti-inflammatory commensal bacterium identified by gut microbiota analysis of Crohn disease patients, Proceedings of the National Academy of Sciences, 105(43):16731-16736 (2008).
Sokol, et al., "Low Counts of Faecalibacterium prausnitzii in Colitis Microbiota," Inflamm. Bowel Dis., pp. 1-7 (2009).
Song, et al, "Real-Time PCR Quant tation of Clostridia in Feces of Autistic Children" Applied and Environmental Microbiology, 70(11):6459-6465 (2004).
Sparrow, et al., "Vineland Adaptive Behavior Scales," 2nd Edition American Guidance Service, 3 (2005).
Stocks, "Mechanism and Use of the Commercially Available Viability Stain, BacLight," Cytometry Part A, 61(A):189-195 (2004).
Blaser, et al., "What are the consequences of the disappearing human microbiota?" Nat. Rev. Microbiol., 7(12):887-894 (2009).
Blaser, "Who are we? Indigenous microbes and the ecology of human diseases," EMBO Rep, 7(10):956-960 (2006).
Bolte, "Autism and Clostridium tetani," Medical Hypotheses, 51(2):133-144 (1998).
Bolte, "Therapies for Gastrointestinal and Neurological Disorders," U.S. Appl. No. 60/214,813, filed Jun. 28, 2000.
Borody, et al., "The GI Microbiome and its Role in Chronic Fatigue Syndrome: a Summary of Bacteriotherapy," ACNEM Journal, 31(3):3-8 (2012).
Borody, et al., "Anti-MAP Rescues Anti-TNF Failures for Over 4 Years," Gastroenterol, 136(5)Suppl 1:A-681 (2009).
Borody, et al., "Anti-MAP Therapy for Pediatric Crohn's Disease," Am J Gastroenterol, 108(Suppl 1):S516 (2013).
Borody, et al., "Anti-MAP Therapy in the Treatment of Active Crohn's Disease," J Gastroenterol & Hepatol, 20(Suppl):A2 (2005).
Borody, et al., "Anti-mycobacterial therapy in Crohn's disease heals mucosa with longitudinal scars," Digestive & Liver Disease, 39(5):438-444 (2007).
Borody, et al., "Bacteriotherapy in Chronic Fatigue Syndrome (CFS): A retrospective review," Am J Gastro, 107(S1):A1481 (2012).
Borody, et al., "Bacteriotherapy Using Fecal Flora: toying with human motions" J. Clin. Gastroenterol., 38(6):475-483 (2004).
Borody, et al., "Bowel-flora alteration: a potential cure for inflammatory bowel disease and irritable bowel syndrome?" Med. J. Aust., 150:604 (1989).
Borody, et al., "Changes in Crohn's Disease Activity Index and C-Reactive Protein Levels During Anti-MAP Therapy," Am J Gastro, 104(S3):A1293 (2009).
Borody, et al., "Could fecal microbiota transplantation cure all Clostridium difficile infections?," Future Microbiol, 9:1-3 (2014).
Borody, et al., "Entamoeba histolytica: another cause of Crohn's Disease," Am J Gastro, 104(S3):A990 (2009).
Borody, et al., "Faecal bacteriotherapy (FB) for chronic C. difficile (Cd) syndromes," J Gastroenterol Hepatol, 18(Suppl.):B8 (Abstract) (2003).
Borody, et al., "Fecal bacteriotherapy in the treatment of recurrent C. difficile infection," UpToDate, pp. 1-6 (2006).
Borody, et al., "Fecal Microbiota Transplantation (FMT) in Multiple Sclerosis (MS)," Am J Gastro, 106(S2):A942 (2011).
Borody, et al., "Fecal microbiota transplantation and emerging applications," Nat. Rev. Gastroenterol. Hepatol., 9(2):88-96 (2011).
Borody, et al., "Fecal microbiota transplantation for Clostridium difficile infection: A surgeon's perspective" Seminars in Colon and Rectal Surgery, 25:163-166 (2014).
Borody, et al., "Fecal microbiota transplantation in gastrointestinal diseases—What practicing physicians should know," Polish Archives of Internal Medicine, 125(11):852-858 (2015).
Borody, et al., "Fecal microbiota transplantation in the treatment of recurrent Clostridium difficile infection," UpToDate, pp. 1-4, (2015).
Borody, et al., "Fecal Microbiota Transplantation in Ulcerative Colitis: Review of 24 Years Experience," Am J Gastro, 107(Supp 1):A1644 (2012).
Borody, et al., "Fecal microbiota transplantation: a new standard treatment option for Clostridium difficile infection," Expert Rev Anti Infect Ther., 11(5):447-449 (2013).
Borody, et al., "Fecal microbiota transplantation: current status and future directions," Expert Review of Gastroenterology & Hepatology, 5(6):653-655 (2011).
Borody, et al., "Fecal Microbiota Transplantation: Expanding Horizons for Clostridium difficile Infections and Beyond," Antibiotics, 4:254-266 (2015).

(56) References Cited

OTHER PUBLICATIONS

Borody, et al., "Fecal Microbiota Transplantation: Indications, Methods, Evidence, and Future Directions," Curr Gastroenterol Rep, 15:337-344 (2013).
Borody, et al., "Fecal Microbiota Transplantation: Techniques, Applications, and Issues," Gastroenterol Clin North Am, 41:781-803 (2012).
Borody, et al., "Irritable Bowel Syndrome and Dientamoeba Fragilis," ASM Sydney National Conference, pp. 4-5 (2002).
Borody, et al., "Is Crohn's Disease Ready for Fecal Microbiota Transplantation?," J Clin Gastroenterol, 48(7):582-583 (2014).
Borody, et al., "Myoclonus-dystonia affected by GI Microbiota?" Am J Gastro, 106(S2):A940 (2011).
Borody, et al., "Novel appearance of healing mucosa following anti-*Mycobacterium avium* paratuberculosis therapy for Crohn's disease," J Gastroenterol Hepatol, 19(Suppl):A210 (2004).
Borody, et al., Reversal of Idiopathic Thrombocytopenia Purpura [ITP] with Fecal Microbiota Transplantation [FMT], Am J Gastro, 106(S2):A941 (2011).
Borody, et al., "Reversal of Inflammatory Bowel Disease (IBD) with Recurrent Faecal Microbiota Transplants (FMT)," Am J Gastro, 106(S2):A979 (2011).
Borody, et al., "Severe recurrent Crohn's Disease of ileocolonic anastomosis and antimicrobial (anti-mycobacterial therapy)," Gut, 55:1211 (2006).
Borody, et al., "Therapeutic faecal microbiota transplantation: current status and future developments," Curr Opin Gastroenterol, 30:97-105 (2014).
Borody, et al., "Treatment of chronic constipation and colitis using human probiotic infusions," Proceedings of Prebiotics and Probiotics and the New Foods Conference, 2-4:228 Abstract (2001).
Borody, et al., "Treatment of First-time Clostridium difficile Infection with Fecal Microbiota Transplantation," Poster Presentation, 2015 ACG Annual Scientific Meeting, Honolulu, Hawaii, USA (2015).
Borody, et al., "Treatment of Severe Constipation Improves Parkinson's Disease (PD) Symptoms," Am J Gastro, 104(S3):A999 (2009).
Borody, et al., "Treatment of Severe Crohn's Disease (CD)—Using Rifabutin-Macrolide-Clofazimine Combination: Results at 30-37 Months," Gastroenterology, 118(4):A1334 Abstract (2000).
Borody, et al., Treatment of Severe Crohn's Disease Using Rifabutin-Macrolide-Clofazimine Combination—Results at 38-43 Months, J Gastroenterol & Hepatol, 15(Suppl.):J102 (2000).
Borody, et al., "Treatment of Severe Crohn's disease using antimycobacterial triple therapy—approaching a cure?" Digest Liver Dis, 34(1):29-38 (2002).
Borody, et al., "Treatment of ulcerative colitis using fecal bacteriotherapy," J. Clin. Gastroenterol., 37(1):42-47 (2003).
Borody, "Bacteriotherapy for Chronic Fatigue Syndrome—A Long Term Follow-Up Study," Proceedings of ACMA Complementary Medicine Sydney, p. 1 (1995).
Borody, "Flora Power"—Fecal Bacteria Cure Chronic C. difficile Diarrhoea, Am J Gastroenterol, 95(11):3028-3029 (2000).
Borody, "Is the Infected Patient too 'Difficile' to Treat?," The Australian Society for Microbiology 2009 Perth, SY03 & SY03.1, p. 27 & 56, (2009).
Borody, "Letter to the Editor—Response to Drs. Famularo et al.," AJG, 96(7):2262-2264 (2001).
Borriello, "Clostridial Disease of the Gut," Clinical Infectious Diseases, The University of Chicago, 20(Suppl 2):S242-S250 (1995).
Brandt, et al., "Long-Term Follow-Up Study of Fecal Microbiota Transplantation (FMT) for Ulcerative Colitis (UC)," Am. J. Gastroenterol., 107(Suppl I):S657 (2012).
Brandt, et al., "Endoscopic Fecal Microbiota Transplantation: "First-Line" Treatment for Severe Clostridium difficile Infection?" J. Clin. Gastroenterol., 45(8):655-657 (2011).
Brandt, et al., "Fecal microbiota transplantation for recurrent Clostridium difficile infection," J Clin Gastroenterol., 45(Suppl):S159-S167 (2011).
Browne, et al., "Culturing of 'unculturable' human microbiota reveals novel taxa and extensive sporulation," Nature, 533(7604):543-546 (2016).
Bueche, et al., "Quantification of Endospore-Forming Firmicutes by Quantitative PCR with the Functional Gene spo0A," Applied and Environmental Microbiology, 79(17):5302-5312 (2013).
Tonnesen, et al., Clostridium difficile-associated diarrhea treated with homologous feces, Journal of the Norwegian Medical Association, Mar. 10, 1998, 118(7); 1027-30, 4 pages.
International Preliminary Report on Patentability completed Mar. 12, 2015, in International Application No. PCT/AU2013/001362, 29 pgs.
International Preliminary Report on Patentability issued Sep. 10, 2013, in International Application No. PCT/US2012/028484, 10 pgs.
International Search Report and the Written Opinion mailed Aug. 22, 2016, in International Application No. PCT/US2016/033747.
International Search Report and Written Opinion (WO) dated Feb. 2, 2018 in International Application No. PCT/US2017/055618.
International Search Report and Written Opinion (WO) dated Feb. 2, 2018 in International Application No. PCT/US2017/056131.
International Search Report and Written Opinion (WO) dated Feb. 21, 2018 in International Application No. PCT/US2017/056129.
International Search Report and Written Opinion (WO) dated Feb. 26, 2018 in International Application PCT/US2017/061104.
International Search Report and Written Opinion (WO) dated Jan. 17, 2018, in International Application No. PCT/US2017/045092.
International Search Report and Written Opinion (WO) dated Jan. 31, 2018 in International Application PCT/US2017/056126.
International Search Report and Written Opinion dated Aug. 17, 2018, in International Application No. PCT/US2018/034673.
International Search Report and Written Opinion dated Aug. 2, 2018, in International Application No. PCT/US2018/026074.
International Search Report and Written Opinion dated Jul. 30, 2018, in International Application No. PCT/US2018/026080.
International Search Report and Written Opinion mailed Aug. 8, 2016, in International Application No. PCT/US2016/032695, 10 pgs.
International Search Report and Written Opinion mailed Feb. 5, 2014, in International Application No. PCT/AU2013/001362, 17 pgs.
International Search Report and Written Opinion mailed Jan. 5, 2017, in International Application No. PCT/US2016/058938.
International Search Report and Written Opinion mailed Jul. 31, 2014, in International Application No. PCT/US2014/027391, 16 pgs.
International Search Report and Written Opinion mailed Oct. 28, 2011, in International No. PCT/AU2011/000987, 18 pgs.
International Search Report mailed Aug. 10, 2012, in International Application No. PCT/US2012/028484, 7 pgs.
International Search Report mailed Jul. 29, 2014, in International Application No. PCT/AU2014/000478, 7 pgs.
International Search Report mailed Jul. 5, 2013, in International Application No. PCT/US2013/032668, 4 pgs.
International Search Report mailed Sep. 22, 2017, in International Application No. PCT/US2017/040591, 12 pgs.
Irrgang, et al., "The historical Development of Mutaflor therapy," Ardeypharm GmbH, pp. 1-38 (1988) http://www.ardeypharm.de/pdfs/en/mutaflor_historical_e.pdf?.
Irritable Bowel Syndrome (IBS), Health A to Z, InteliHealth, pp. 1-4, n.d., Web, Oct. 23, 2005 http://www.intelihealth.com.
Issa, et al., "Clostridium difficile and Inflammatory Bowel Disease," Inflamm Bowel Dis., 14(10):1432-1442 (2008).
Issa, et al., "Impact of Clostridium difficile on inflammatory bowel disease," Clin. Gastroenterol. Hepatol., 5(3):345-351 (2007).
Itoh, et al., "Characterization of clostridia isolated from faeces of limited flora mice and their effect on caecal size when associated with germ-free mice," Laboratory Animals, 19:111-118 (1985).
Itoh, et al., "Intestinal bacteria antagonistic to Clostridium difficile in mice," Laboratory Animals, 21:20-25 (1987).
Ivanov, et al., "Induction of intestinal Th17 cells by segmented filamentous bacteria," Cell, 139(3):485-498 (2009).

(56) References Cited

OTHER PUBLICATIONS

Ivanov, et al., "Specific Microbiota Direct the Differentiation of IL-17-Producing T-Helper Cells in the Mucosa of the Small Intestine," Cell Host & Microbe, 4:337-349 (2008).
Jacob, et al., "Single Delivery of High-Diversity Fecal Microbiota Preparation by Colonoscopy Is Safe and Effective in Increasing Microbial Diversity in Active Ulcerative Colitis," Inflamm Bowel Dis., 0(0):1-9 (2017).
James, et al., "Metabolic biomarkers of increased oxidative stress and impaired methylation capacity in children with autism," American Journal of Clinical Nutrition, 80:1611-1617 (2008).
Janeway, et al., "Adaptive Immunity to Infection," Immunobiology, 6th Edition, Chapter 10, p. 414 (2005).
Janeway, Jr., et al., "Autoimmune responses are directed against self antigens," Immunobiology: The Immune System in Health and Disease, 5th Edition, pp. 1-4 (2001).
Jarvis, et al., "National point prevalence of Clostridium difficile in US health care facility inpatients, 2008," Am. J. Infect. Control, 37:263-270 (2009).
Jia, et al., "Gut microbiota: a potential new territory for drug targeting," Nature Reviews-Drug Discovery, 7:123-129 (2008).
Johnson, et al., "Interruption of Recurrent Clostridium difficile-Associated Diarrhea Episodes by Serial Therapy with Vancomycin and Rifaximin," Clin. Infect. Dis., 44(6):846-848 (2007).
Johnson, et al., "Rifaximin Redux: Treatment of recurrent Clostridium difficile infections with Rifaximin immediately post-vancomycin treatment," Anaerobe, 15(6):290-291 (2009).
Kageyama, et al., "Emendation of genus *Collinsella* and proposal of *Collinsella stercoris* sp. nov. and *Collinsella intestinalis* sp. nov.," International Journal of Systematic and Evolutionary Microbiology, 50:1767-1774 (2000).
Kageyama, et al., "Phylogenetic and phenotypic evidence for the transfer of Eubacterium aerofaciens to the genus *Collinsella* as *Collinsella aerofaciens* gen. nov., comb. nov.," International Journal of Systematic Bacteriology, 49:557-565 (1999).
Kakihana, et al., "Fecal microbiota transplantation for patients with steriod-resistant acute graft-versus-host disease of the gut," Blood, 128(16):2083-2088 (2016).
Kamboj, et al., "Relapse versus reinfection: surveillance of Clostridium difficile infection," Clin Infect Dis., 53(10):1003-1006 (2011).
Kang, et al., "Microbiota Transfer Therapy alters gut ecosystem and improves gastrointestinal and autism symptoms: and open-label study," Microbiome, 5:10, 16 pages (2017).
Kang, et al., "Reduced Incidence of Prevotella and Other Fermenters in Intestinal Microflora of Autistic Children," PLOS One, 8(7):e68322, 14 pages (2013).
Kaper, et al., "Pathogenic *Escherichia Coli*," Nature Reviews—Microbiology, 2:123-140 (2004).
Karas, et al., "A review of mortality due to Clostridium difficile infection," J Infect., 61(1):1-8 (2010).
Kassam, et al., "Fecal transplant via retention enema for refractory or recurrent Clostridium difficile infection," Arch Intern Med., 172(2):191-193 (2012).
Kelly, et al., "Commensal gut bacteria: mechanisms of immune modulation," Trends in Immunology, 26(6):326-333 (2005).
Kelly, et al., "Clostridium difficile—more difficult than ever," N. Engl. J. Med., 359(18):1932-1940 (2008).
Kelly, et al., "Clostridium difficile colitis," N. Engl. J. Med., 330(4):257-62 (1994).
Kelly, et al., "Fecal Microbiota Transplant for Treatment of Clostridium difficile Infection in Immunocompromised Patients," Am J Gastroenterol, 109:1065-1071 (2014).
Kelly, et al., "Fecal microbiota transplantation for relapsing Clostridium difficile infection in 26 patients: methodology and results," J. Clin. Gastroenterol., 46(2):145-149 (2012).
Keynan, et al., "The Role of Regulatory T Cells in Chronic and Acute Viral Infections," Clinical Infectious Diseases, 46:1046-1052 (2008).
Khanna, et al., "A Novel Microbiome Therapeutic Increases Gut Microbial Diversity and Prevents Recurrent Clostridium difficile Infection," The Journal of Infectious Diseases, 214:173-81 (2016).
Khanna, et al., "The epidemiology of community-acquired Clostridium difficile infection: a population-based study," Am J Gastroenterol., 107(1):89-95 (2012).
Khanna, et al., "The growing incidence and severity of Clostridium difficile infection in inpatient and outpatient settings," Expert Rev Gastroenterol Hepatol., 4(4):409-16 (2010).
Kharidia, et al., "The Activity of a Small Lytic Peptide PTP-7 on *Staphylococcus aureus* Biofilms," J. Microbiol., 49(4):663-668 (2011).
Khoruts, et al., "Changes in the composition of the human fecal microbiome after bacteriotherapy for recurrent Clostridium difficile-associated diarrhea," J. Clin. Gastroenterol., 44(5):354-360 (2010).
Khoruts, et al., "Therapeutic transplantation of the distal gut microbiota," Mucosal Immunol., 4(1):4-7 (2011).
Zoppi, et al., "Oral Bacteriotherapy in Clinical Practice," Eur J. Pediatr, 139(1):22-24 (1982).
"ARGF—'Autologous Rehabilitation of Gastrointestinal Flora,'" Medipex Report for Medilink NW, pp. 1-42, n.d., Web, Feb. 10, 2012 http://www.bacteriotherapy.org/docs/medipex-report.pdf.
"Autoimmune Disease List," American Autoimmune Related Diseases Association, pp. 1-4 (2017) https://www.aarda.org/diseaselist/.
"Certain infectious and parasitic diseases (A00-B99)," International Statistical Classification of Diseases and Related Health Problems, 10th Revision (ICD-10)—WHO Version, Chapter 1, pp. 1 (2016) www.apps.who.int/classifications/icd10/browse/2016/en#/1.
"Frequently Asked Questions about Clostridium difficile for Healthcare Providers," Healthcare-associated Infections (HAIs), Centers for Disease Control and Prevention, pp. 1-6, Nov. 25, 2010, updated Mar. 6, 2012, Web, May 19, 2014 http://www.cdc.gov/HAI/organisms/cdiff/Cdiff_faqs_HCP.html.
"Functional Anatomy of Prokaryotic and Eukaryotic Cells," printed Mar. 16, 2017 from http://classes.midlandstech.edu/carterp/courses/bio225/chap04/lecture2.htm.
"Monilia," Def. 1, Stedman's Medical Dictionary, n.d., Web, Nov. 22, 2005.
"Probiotic," Def. 1, MSN Encarta—Dictionary, Encarta, n.d., Web, Dec. 1, 2005.
"Spore-Forming Gram-Positive Bacilli: Bacillus and *Clostridium* Species," Jawetz, Melnick, & Adelberg's Medical Microbiology, 26th Edition, Chapter 11, pp. 1-15 (2012).
"Autism Treatment Evaluation Checklist (ATEC)," Autism Research Institute. https://www.autism.com/ind_atec.
"Studies confirm validity of ATEC Report," Autism Research Institute. https://www.autism.com/ind_atec_report.
Aas, et al., "Recurrent Clostridium difficile Colitis: Case Series Involving 18 Patients Treated with Donor Stool Administered via a Nasogastric Tube," Clinical Infectious Diseases, 36(5):580-585 (2003).
Abrams, "Open-Label, Uncontrolled Trial of Bowel Sterilization and Repopulation with Normal Bowel Flora for Treatment of Inflammatory Bowel Disease," Current Therapeutic Research, 58(12):1001-1012 (1997).
Acha, et al., "Changes of viability and composition of the *Escherichia coli* flora in faecal samples during long time storage," Journal of Microbiological Methods, Elsevier, 63(3):229-238 (2005).
Adams, et al., "Effect of a Vitamin/Mineral Supplement on Children with Autism," BMC Pediatrics, 11:111 (2011).
Adams, et al., "Gastrointestinal flora and gastrointestinal status in children with autism-comparisons to typical children and correlation with autism severity," BMC Gastroenterology, 11:22 (2011).
Adams, et al., "Mercury in first-cut baby hair of children with autism versus typically-developing children," Toxicological & Environmental Chemistry, 90(4): 739-753 (2008).
Adams, et al., "The Severity of Autism is Associated with Toxic Metal Body Burden and Red Blood Cell Glutathione Levels," J. Toxicol, 2009:532640 (2009).
Agrawal, et al., "'Global warming' to *Mycobacterium avium* subspecies paratuberculosis," Future Microbiol, 9(7):829-832 (2014).

(56) References Cited

OTHER PUBLICATIONS

Agrawal, et al., "A Long-Term Follow-Up Study of the Efficacy and Safety of Fecal Microbiota Transplant (FMT) for Recurrent/Severe/Complicated C. difficile Infection (CDI) in the Elderly," Gastroenterol, 146(5)(Suppl 1):S42-43 (2014).
Aitken, et al., "Demonstration of Intracellular *Mycobacterium* Species in Crohn's Disease Using Novel Technologies," Poster Presentation—2015 ACG Annual Scientific Meeting, Honolulu, Hawaii, USA (2015).
Akao, et al., "A Purgative Action of Barbaloin Is Induced by *Eubacterium* sp. Strain BAR, a Human Intestinal Anaerobe, Capable of Transforming Barbaloin to Aloe-Emodin Anthrone," Biol. Pharm., 19(1):136-138 (1996).
Al-Eidan, et al., "Clostridium difficile-associated diarrhoea in hospitalised patients," J. Clin. Pharm. Ther., 25(2):101-109 (2000).
Al-Nassir, et al., "Comparison of Clinical and Microbiological Response to Treatment of Clostridium difficile-Associated Disease with Metronidazole and Vancomycin," Clin Infect Dis., 47(1):56-62 (2008).
Aman, et al., "Outcome Measures for Clinical Drug Trials in Autism," CNS Spectr., 9(1):36-47 (2004).
Aman, et al., "Psychometric Characteristics of the Aberrant Behavior Checklist," Am. J. Ment. Defic., 89(5):492-502 (1985).
Ananthakrishnan, et al., "Excess hospitalisation burden associated with Clostridium difficile in patients with inflammatory bowel disease," Gut, 57(2):205-210 (2007).
Anderson, et al., "Systematic review: faecal microbiota transplantation in the management of inflammatory bowel disease," Aliment. Pharmacol. Ther., 36:503-16 (2012).
Andoh, et al., "Terminal restriction fragment polymorphisum analyses of fecal microbiota in five siblings including two with ulcerative colitis," Journal of Clinical Gastroenterology, 2:343-345 (2009).
Andrews, et al., Chronic Constipation (CC) may be reversed by "Bacteriotherapy," Gastroenterol, 106:A459 (1994).
Andrews, et al., "Chronic constipation reversed by restoration of bowel flora. A case and a hypothesis," European Journal of Gastroenterology & Hepatology, 4:245-247 (1992).
Anorexia nervosa, Encyclopedia Index A, healthAtoZ, Medical Network, Inc., pp. 1-7, n.d., Web, Nov. 23, 2005 http://www.healthatoz.com/healthatoz/Atoz/ency/anorexia_nervosa.jsp.
Aroniadis, et al., "Intestinal Microbiota and the Efficacy of Fecal Microbiota Transplantation in Gastrointestinal Disease," Gastroenterology and Hepatology, 10(4): 230-7 (2014).
Aroniadis, et al., "Long-Term Follow-up Study of Fecal Microbiota Transplantation (FMT) for Severe or Complicated Clostridium difficile Infection (CDI)," Gastroenterol, 144(Suppl 1):S185 (2013).
Arumugam, et al., "Enterotypes of the human gut microbiome," Nature, 473:174-180 (2011).
Atarashi, et al., "Induction of Colonic Regulatory T Cells by Indigenous Clostridium Species," Science, 331(6015):337-341, published online Dec. 23, 2010.
Atarashi, et al., "Treg induction by a rationally selected mixture of Clostridia strains from the human microbiota," Nature, 500(7461):232-236 (2013).
Atarashi, et al., "WS/PP-064-03 Regulation of colonic regulatory T cells by *Clostridium* species," International Immunology, 22(Suppl 1, Part 3), pp. 1-3 (2010).
Atarashi, et al., WS-064 Mucosal immunity: homeostasis, 14th ICIC Abstract book, 14th International Congress of Immunology, pp. iii131-iii133 (2010).
Autism, Health Encyclopedia—Diseases and Conditions, The Health Scout Network, pp. 1-5, n.d., Web, Nov. 22, 2005 www.healthscout.com.
Autism, Treatment, Prognosis, Healthcommunities.com, Inc., pp. 1-4, n.d., Web. Jan. 28, 2009 http://www.neurologychannel.com/common/PrintPage.php.
Autism: Mayo Clinic.com, Mayo Foundation for Medical Education and Research, pp. 1-7, May 31, 2008, Web. Jan. 28, 2009 http://www.mayoclinic.com/print/autism/DS00348/METHOD=print&DSECTION=all.

Backhed, et al., "Host-bacterial mutualism in the human intestine," Science, 307(5717):1915-1920 (2005).
Backhed, et al., "Mechanisms underlying the resistance to diet-induced obesity in germ-free mice," PNAS USA, 104(3):979-984 (2007).
Backhed, et al., "The gut microbiota as an environmental factor that regulates fat storage," PNAS USA, 101(44):15718-15723 (2004).
Bakken, et al., "Fecal bacteriotherapy for recurrent Clostridium difficile infection," Anaerobe, 15(6):285-289 (2009).
Bakken, et al., "Treating Clostridium difficile Infection with Fecal Microbiota Transplantation," Clinical Gastroenterology and Hepatology, 9(12):1044-1049 (2011).
Bartlett, et al., "Clinical recognition and diagnosis of Clostridium difficile infection," Clin Infect Dis., 46(Suppl 1):S12-S18 (2008).
Bartlett, "Clostridium difficile-associated Enteric Disease," Curr Infect Dis Rep., 4(6):477-483 (2002).
Belkaid, et al., "Natural regulatory T cells in infectious disease," Nature Immunology, 6(4):353-360 (2005).
Bengmark, et al., "Bioecological control of inflammatory bowel disease," Clinical Nutrition, 26(2):169-181 (2007).
Bennet, et al., "Treatment of ulcerative colitis by implantation of normal colonic flora," Lancet, 333(8630):164 (1989).
Benson, et al., "Changing epidemiology of Clostridium difficile-associated disease in children," Infect Control Hosp Epidemiol., 28(11):1233-1235 (2007).
Berg, "The indigenous gastrointestinal microflora," Trends Microbiol., 4(11):430-435 (1996).
Bergey's Manual of Systematic Bacteriology, Second Edition, vol. Three, The Firmicutes, pp. 1-16 (2009).
Sullivan, et al., "Effect of supplement with lactic-acid producing bacteria on fatigue and physical activity in patients with chronic fatigue syndrome," Nutritional Journal, 8(4):1-6 (2009).
Sun, et al., "Tag-Encoded FLX Amplicon Pyrosequencing for the Elucidation of Microbial and Functional Gene Diversity in Any Environment", Methods and Applications, Methods in Molecular Biology, 733:129-141 (2011).
Sunil, et al., "Design and evaluation of lornoxicam bilayered tablets for biphasic release," Brazilian Journal of Pharmaceutical Sciences, 48(4):609-19 (2012).
Surawicz, et al., "Treatment of refractory and recurrent Clostridium difficile infection," Nat. Rev. Gastroenterol. Hepatol., 8(6):330-339 (2011).
Surawicz, "Reining in Recurrent Clostridium difficile Infection—Who's at Risk?,"Gastroenterology, 136:1152-1154 (2009).
Sutherland, et al., "Lyophilized Clostridium perfringens 3 alpha- and Clostridium bifermentans 7 alpha-hydroxysteroid dehydrogenases: two new stable enzyme preparations for routine bile acid analysis," Biochim Biophys Acta, 962(1):116-121 (1988).
Takaishi, et al., "Imbalance in intestinal microflora constitution could be involved in the pathogenesis of inflammatory bowel disease," J. Med. Microbiol., 298:463-472 (2008).
Takeda, et al., "Serum Haloperidol Levels of Schizophrenics Receiving Treatment for Tuberculosis," Clinical Neuropharmacology, 9(4):386-397 (1986).
Tannock, et al., "A new macrocyclic antibiotic, fidaxomicin (OPT-80), causes less alteration to the bowel microbiota of Clostridium difficile-infected patients than does vancomycin," Microbiology, 156(11):3354-3359 (2010).
Tanoue, et al., "Immune response to gut microbiota-commensals and pathogens," Gut Microbes, 1(4):224-233 (2010).
Tap, et al., "Towards the human intestinal microbiota phylogenetic core," Environmental Microbiology, 11(10):2574-2584 (2009).
Taras, et al., "Reclassification of Eubacterium formicigenerans Holdeman and Moore 1974 as *Dorea formicigenerans* gen. nov., comb. nov., and description of *Dorea longicatena* sp. nov., isolated from human faeces," International Journal of Systematic and Evolutionary Microbiology, 52:423-428 (2002).
Teasley, et al., "Prospective randomised trial of metronidazole versus vancomycin for Clostridium-difficile-associated diarrhoea and colitis," The Lancet, 2(8358):1043-1046 (1983).
Tian, et al., "Freeze-dried, Capsulized Fecal Microbiota Transplantation for Relapsing Clostridium difficile Infection," Journal of Clinical Gastroenterology, 49(6):537-538 (2015).

(56) References Cited

OTHER PUBLICATIONS

Tilg, et al., "Gut microbiome, obesity, and metabolic dysfunction," J. Clin. Invest., 121(6):2126-2132 (2011).

Tremaroli, et al., "Function interactions between the gut microbiota and host metabolism," Nature, 489:242-249 (2012).

Trent, et al., "Diversity of endotoxin and its impact on pathogenesis," Journal Endotoxin Research, 12(4):205-223 (2006).

Turnbaugh, et al., "A core gut microbiorne in obese and lean twins," Nature, 457(7228):480-484 (2009).

Tvede, et al., "Bacteriotherapy for chronic relapsing Clostridium difficile diarrhea in six patients," The Lancet, 1:1156-1160 (1989).

Udall, et al., "Development of Gastrointestinal Mucosal Barrier. I. The Effect of Age on Intestinal Permeability to Macromolecules," Journal of Pediatric Research, 15:241-244 (1981).

Van Andel, et al., "Interleukin-12 Has a Role in Mediating Resistance of Murine Strains to Tyzzer's Disease," Infect. Immun., 66(10):4942-4946 (1998).

Van Der Waaij, et al., "Direct Flow Cytometry of Anaerobic Bacteria in Human Feces,"Cytometry, 16:270-279 (1994).

Van Immerseel, et al., "Butyric acid-producing anaerobic bacteria as a novel probiotic treatment approach for inflammatory bowel disease," Journal of Medical Microbiology, 59:141-143 (2010).

Van Nood, et al., "Struggling with Recurrent Clostridium difficile Infections: Is Donor Faeces the Solution?," Euro Surveill., 14(34):1-6 (2009).

Van Nood, "Duodenal infusion of donor feces for recurrent Clostridium difficile," New England Journal of Medicine, 368(5):407-415 (2013).

Van Passel, et al., "The Genome of Akkermansia muciniphila, a Dedicated Intestinal Mucin Degrader, and Its Use in Exploring Intestinal Metagenomesvan," Plos One 6(3):e16876 (2011).

Vaughn, et al., "Novel treatment options for ulcerative colitis," Future Science, 1-20 (2013).

Veldhuyzen Van Zanten, et al., "Drug Treatment of Functional Dyspepsia: A Systematic Analysis of Trial Methodology with Recommendations for Design of Future Trials," Am. J. Gastroenterol., 91(4):660-673 (1996).

Veldhuyzen Van Zanten, et al., "Validation of a 7-point Global Overall Symptom scale to measure the severity of dyspepsia symptoms in clinical trials," Ailment Pharmacol. Ther., 23(4):521-529 (2006).

Venugopal, et al., "Fidaxomicin: A Novel Macrocyclic Antibiotic Approved for Treatment of Clostridium difficile Infection," Clin Infect Dis, 54(4):568-74 (2012).

Vidhyalakshmi, et al., "Encapsulation "The Future of Probiotics"—A Review," Advances in Biological Research, 3(3-4):96-103 (2009).

Vrieze, et al., "The environment within: how gut microbiota may influence metabolism and body composition," Diabetologia, 53(4):606-613 (2010).

Vulevic, et al., "Modulation of the fecal microflora profile and immune function by a novel trans-galactooligosaccharide mixture (B-GOS) in healthy elderly volunteers," Am J Clin Nutr, 88:1438-46 (2008).

Wachsmann, et al., "Characterization of an Orotic Acid Fermenting Bacterium, *Zymobacterium oroticum*, nov. gen., nov. spec.," Journal of Bacteriology, 68(4):400-404 (1954).

Walter, et al., "Host-microbial symbiosis in the vertebrate gastrointestinal tract and the Lactobacillus reuteri paradigm," PNAS USA, 108(Suppl 1):4645-4652 (2011).

Wang, et al., "Low Relative Abundances of the Mucolytic Bacterium Akkermansia muciniphila and *Bifidobacterium* spp. in Feces of Children with Autism," Applied and Environmental Microbiology, 77(18):6718-6721 (2011).

Warnock & Peck, "A roadmap for biomarker qualification," Nature Biotechnology, 28(5):444-445 (2010).

Warny, et al., "Toxin production by an emerging strain of Clostridium difficile associated with outbreaks of severe disease in North America and Europe," Lancet, 366(9491):1079-84 (2005).

Warren, et al., "*Clostridium aldenense* sp. nov. and *Clostridium citroniae* sp. nov. Isolated from Human Clinical Infections," Journal of Clinical Microbiology, 44(7):2416-2422 (2006).

Wasfy, et al., "Comparison of Preservation Media for Storage of Stool Samples," Journal of Clinical Microbiology, 33(8):2176-2178 (1995).

Weingarden, et al., "Dynamic changes in short- and long-term bacterial composition following fecal microbiota transplantation for recurrent Clostridium difficile infection," Microbiome, 3(10), 8 pages (2015).

Weissman, et al., "Stool Transplants: Ready for Prime Time?" Current Gastroenterology Reports, 14:313-316 (2012).

Wells, et al., "Clostridia: Sporeforming Anaerobic Bacilli," Medical Microbiology—NCBI Bookshelf, 4th Edition, Chapter 18, pp. 1-20 (1996) https://www.nobi.nim.nih.gov/books/NBK8219/?report=printable.

Wenisch, et al., "Comparison of Vancomycin, Teicoplanin, Metronidazole, and Fusidic Acid for the Treatment of Clostridium difficile-Associated Diarrhea," Clin Infect Dis., 22(5):813-818 (1996).

Wettstein, et al., "Fecal Bacteriotherapy—An effective Treatment for Relapsing Symptomatic Clostridium difficile Infection," Abstract, 15th United European Gastroenterology Week (UEGW) Poster presentations, United European Gastroenterology Federation, France, A303 (2007).

Wettstein, et al., "Skewered diverticulum: another cause of abdominal pain," Internal Med J, 31(8):495-496 (2001).

Wikoff, et al., "Metabolomics analysis reveals large effects of gut microflora on mammalian blood metabolites," PNAS, 106(10):3698-3703 (2009).

Williams, et al., "Impaired Carbohydrate Digestion and Transport and Mucosal Dysbiosis in the Intestines of Children with Autism and Gastrointestinal Disturbances," PLoS One, 6(9):e24585 (Sep. 2011).

Willing, et al., "Shifting the balance: antibiotic effects on host-microbiota mutualism," Nature Reviews-Microbiology, 9:233-243 (2011).

Wilson, et al., "Human Colonic Biota Studied by Ribosomal DNA Sequence Analysis," Appl. Environ. Microbiol., 2(7):2273-2278 (1996).

Wolcott, et al., "Evaluation of the bacterial diversity among and within individual venous leg ulcers using bacterial tag-encoded FLX and Titanium amplicon pyrosequencing and metagenomic approaches," BMC Microbiology, 9:226 (2009).

Wu, et al., "Focused Evolution of HIV-1 Neutralizing Antibodies Revealed by Structures and Deep Sequencing," Science, 333:1593-1602 (2011).

Yoon, et al., "Treatment of Refractory/Recurrent C. difficile-associated Disease by Donated Stool Transplanted Via Colonoscopy: A Case Series of 12 patients," J Clin Gastroenterol., 44(8):562-566 (2010).

You, et al., "Successful treatment of fulminant Clostridium difficile infection with fecal bacteriotherapy," Ann. Intern. Med., 148(8):632-633 (2008).

Youngster, et al., "Oral, Capsulized, Frozen Microbiota Transplantation for Relapsing Clostridium difficile Infection," American Medical Association, 312 (174) 1772-1778 (2014).

Yue, et al., "Similarity Measure Based on Species Proportions," Commun. Stat. Theor. Methods, 34(11):2123-2131 (2005).

Zar, et al., "A Comparison of Vancomycin and Metronidazole for the Treatment of Clostridium difficile-Associated Diarrhea, Stratified by Disease Severity," Clin Infect Dis., 45(3):302-307 (2007).

Zhang, et al., "Influence of Microbiota on Intestinal Immune System in Ulcerative Colitis and Its Intervention," Frontiers in Immunology, 8(Article 1674): 1-11 (2017).

Extended European Search Report dated Mar. 24, 2023, in European Patent Application No. 20844975.1.

Uchiyama et al., "Intestinal microbiome as a novel therapeutic target for local and systematic inflammation," *Pharmacology & Therapeutics*, vol. 199, pp. 164-172 (Jul. 2019).

International Search Report & Written Opinion, PCT Application No. PCT/US20/42541, dated Oct. 26, 2020, 11 pages.

(56) References Cited

OTHER PUBLICATIONS

Kim, et al., "Effect of Rifampin on the Plasma Concentration and the Clinical Effect of Haloperidol Concomitantly Administered to Schizophrenic Patients," Journal of Clinical Psychopharmacology, 16(3):247-252 (1996).
Kim, et al., "In Vitro Culture Conditions for Maintaining a Complex Population of Human Gastrointestinal Tract Microbiota," Journal of Biomedicine and Biotechnology, 2011(Article ID 838040):1-10 (2011) http://www.hindawi.com/journals/bmri/2011/838040/.
Kitajka, et al., "Effects of dietary omega-3 polyunsaturated fatty acids on brain gene expression," PNAS, 101(30):10931-10936 (2004).
Klaenhammer, "Bacteriocins of lactic acid bacteria," Biochimie, 70:337-49 (1988).
Kleiman, et al., "Comparison of two coprological methods for the veterinary diagnosis of fasciolosis," Arquivo Brasileiro de Medicina Veterinária e Zootécnica, 55(2):181-185 (2005).
Kobashi, et al., "Metabolism of Sennosides by Human Intestinal Bacteria," Journal of Medicinal Plant Research, 40(3):225-236 (1980).
Koch, "What size should a bacterium be? A question of scale," Annu. Rev. Microbiol., 50:317-48 (1996).
Kostic, et al., "Genomic analysis identifies association of Fusobacterium with colorectal carcinoma," Genome Research 22:292-298 (2011).
Krogius-Kurikka, et al., "Sequence analysis of percent G+C fraction libraries of human faecal bacterial DNA reveals a high number of Antinobacteria," BMC Microbiology, 9(68):1-13 (2009).
Kuijper, et al. "Update of Clostridium difficile Infection due to PCR Ribotype 027 in Europe, 2008," Euro. Surveill., 13(31):Article 5 (2008).
Kuksal, et al., "Formulation and In Vitro, In Vivo Evaluation of Extended-release Matrix Tablet of Zidovudine: Influence of Combination of Hydrophilic and Hydrophobic Matrix Formers," AAPS Pharm., 7(1):E1-E9 (2006).
Kunde, et al., "Safety, Tolerability, and Clinical Response After Fecal Transplantation in Children and Young Adults With Ulcerative Colitis," JPNG, 56(6):597-601 (2013).
Kushak, et al., "Intestinal disaccharidase activity in patients with autism," Autism, 15(3):285-294 (2011).
Kyne, et al., "Association between antibody response to toxin A and protection against recurrent Clostridium difficile diarrhea," Lancet, 357(9251):189-93 (2001).
Kyne, et al., "Asymptomatic carriage of Clostridium difficile and serum levels of IgG antibody against toxin A," N Engl J Med., 342(6):390-397 (2000).
Kyne, et al., "Factors associated with prolonged symptoms and severe disease due to Clostridium difficile," Age and Ageing, 28(2):107-13 (1999).
Kysela, et al., "Serial analysis of V6 ribosomal sequence tags (SARST-V6): a method for efficient, high-throughput analysis of microbial community composition," Environmental Microbiology, 7(3):356-364 (2005).
Kyselova, et al., "Alterations in the Serum Glycome Due to Metastatic Prostate Cancer," Journal of Proteome Research, 6:1822-1832 (2007).
Labbé, et al., "Clostridium difficile infections in a Canadian tertiary care hospital before and during a regional epidemic associated with the BI/NAP1/027 strain," Antimicrob Agents Chemother., 52(9):3180-7 (2008).
Lamontagne, et al., "Impact of emergency colectomy on survival of patients with fulminant Clostridium difficile colitis during an epidemic caused by a hypervirulent strain," Ann. Surg., 245(2):267-272 (2007).
Larsen, et al., "Gut Microbiota in Human Adults with Type 2 Diabetes Differs from Non-Diabetic Adults," PLoS One, 5(2):e9085 (2010).
Lau, et al., "Bacteraemia caused by Anaerotruncus colihominisand emended description of the species," J Clin Pathol, 59:748-752 (2006).
Lawson, et al., "*Anaerotruncus colihominis* gen. nov., sp. nov., from human faeces," International Journal of Systematic and Evolutionary Microbiology, 54:413-417 (2004).
Lawson, et al., "Anaerotruncus," Bergey's Manual of Systematics of Archae and Bacteria, pp. 1-4 (2009).
Lederberg, "Infectious History", Science, 288(5464):287-293 (2000).
Lee & Mazmanian, "Has the Microbiota Played a critical Role in the Evolution of the Adaptive Immune System?," 330:1768-1773 (2010).
Lee, et al., "Discriminative prediction of mammalian enhancers from DNA sequence," Genome Research 21:2167-2180 (2011).
Lee, et al., "Prioritizing candidate disease genes by network-based boosting of genome-wide association data," Genome Research, 21(1):1109-1121 (2011).
Lee, et al., "The outcome and long-term follow-up of 94 patients with recurrent and refractory Clostridium difficile infection using single to multiple fecal microbiota transplantation vie retention enema," European Journal Clinical Microbiology Infect Dis., 33:1425-1428 (2014).
Leis, et al., "Fecal microbiota transplantation: A 'How-To' guide for nurses," Collegian, 22:445-451 (2015).
Leslie, et al., "Trehalose and Sucrose Protect Both Membranes and Proteins in Intact Bacteria during Drying," Applied and Environmental Microbiology, 61:3592-3597 (1995).
Lewis, et al., "Stool form scale as a useful guide to intestinal transit time," Scand. J. Gastroenterol., 32(9):920-924 (1997).
Ley, et al., "Ecological and evolutionary forces shaping microbial diversity in the human intestine," Cell, 124:837-848 (2006).
Ley, et al., "Evolution of mammals and their gut microbes," Science, 320(5883):1647-1651 (2008).
Ley, et al., "Microbial ecology: human gut microbes associated with obesity," Nature, 444(7122):1022-3 (2006).
Ley, et al., "Worlds within worlds: evolution of the vertebrate gut microbiota," Nat. Rev. Microbiol., 6(10):776-788 (2008).
Lin, et al., "Twelve Week Storage Trial of Microbial Viability in Lyophilized and Frozen Fecal Microbiota Preparations," Poster Presentation—Digestive Disease Week 2015, Washington, D.C. USA.
Longstreth, "Irritable bowel syndrome: A multibillion-dollar problem," Gastroenterology, 109(6):2029-2031 (1995).
Lonsdale, et al., "Treatment of autism spectrum children with thiamine tetrahydrofurfuryl disulfide: A pilot study," Neuroendocrinology Letters, 23:303-308 (2002).
Loo, et al., "A predominantly clonal multiinstitutional outbreak of Clostridium difficile-associated diarrhea with high morbidity and mortality," N Engl J Med, 353(23):2442-9 (2005).
Loo, et al., "Host and pathogen factors for Clostridium difficile infection and colonization," N Engl J Med, 365(18):1693-703 (2011).
Louie, et al., "Fidaxomicin versus vancomycin for Clostridium difficile infection," N. Engl. J. Med., 364(5):422-431 (2011).
Louie, et al., "Home-based fecal flora infusion to arrest multiply-recurrent C. difficile infection," ICAAC/IDSA Conference, Abstract #K-4201 (2008).
Louis, et al., "Diversity, metabolism and microbial ecology of butyrate-producing bacteria from the human large intestine," FEMS Microbiology Letters, 294:1-8 (2009).
Lu, "Taboo transplant: How new poo defeats superbugs," Science News, 1:90-91 (2011).
Ludwig, et al., "Taxonomic outline of the phylum Firmicutes," Bergey's Manual of Systematic Bacteriology, 3:15-17 (2009).
Lund-Tonnesen, et al., "Clostridium difficile-associated diarrhea treated with homologous faeces," Tidsskr Nor Lageforen, 118:1027-1030 (1998).
Macconnachie, et al., "Faecal transplant for recurrent Clostridium difficile-associated diarrhoea: a UK case series," QJM, 102(11):781-784 (2009).
MacDonald, et al., "Formation of Ursodeoxycholic Acid from Chenodeoxycholic Acid by a 7β-Hydroxysteroid Dehydrogenase-Elaborating Eubacterium aerofaciens Strain Cocultured with 7α-Hydroxysteroid Dehydrogenase-Elaborating Organisms," Applied and Environmental Microbiology, 44(5):1187-1195 (1982).

(56) References Cited

OTHER PUBLICATIONS

MacFabe, et al., "Short-chain fatty acid fermentation products of the gut microbiome: implications in autism spectrum disorders," Microbial Ecology in Health & Disease, 23:19260 (2012).
MacPherson, et al., "Induction of Protective IgA by Intestinal Dendritic Cells Carrying Commensal Bacteria," Science, 303:1662-1665 (2004).
Madsen, "The use of probiotics in gastrointestinal disease," Can J Gastroenterol, 15(12):817-22 (2001).
Magistris, et al., "Alterations of the Intestinal Barrier in Patients with Autism Spectrum Disorders and in Their First-degree Relatives,"Gastroenterology 51(4):418-424 (2010).
Maizels, et al., "Regulatory T cells in Infection," Advances in Immunology, Chapter 3, 112:73-136 (2011).
Manichanh, et al., "Reshaping the gut microbiome with bacterial transplantation and antibiotic intake," Genome Research 20:1411-1419 (2010).
Marchesi, et al., "The normal intestinal microbiota," Curr. Opin. Infect. Dis., 20(5):508-513 (2007).
Martin, "Development and Delivery of a Treatment for Clostridium difficile," Bacteriotherapy, pp. 1-2, n.d., Web, Feb. 10, 2012 wotherapy.org.
Zhang, et al., "Altered gut microbiome composition in children with refractory epilepsy after ketogenic diet," Epilepsy Research (2018) https://doi.org/10.1016/j.eplepsyres.2018.06.15.
Zhang, et al., "Human gut microbiota in obesity and after gastric bypass," PNAS, 106(7):2365-2370 (2009).
Zhao, et al., "Gut Microbiota Composition Modifies Fecal Metabolic Profiles in Mice," Journal of Proteome, 12:2987-2999 (2013).
Zheng, et al., "The Footprints of Gut Microbial—Mammalian Co-Metabolism," Journal of Proteome, 10:5512-5522 (2011).
Zhou, et al., "Total fecal microbiota transplantation alleviates high-fat diet-induced steatohepatitis in mice via beneficial regulation of gut microbiota," Scientific Reports (Nature), 7(1529):1-11 (2017).
Zhu, et al., "Altered giutathione homeostasis in animals prenatally exposed to lipopolysaccharide," Neurochemistry International, 50(4):671-680 (2007).
Zilberberg, et al., "Clostridium difficile Infections among Hospitalized Children, United States, 1997-2006," Emerg. Infect. Dis, 16(4):604-609 (2010).
Zilberberg, et al., "Clostridium difficile-related Hospitalizations among US Adults, 2006," Emerg. Infect. Dis, 15(1):122-124 (2009).
Zilberberg, et al., "Increase in Adult Clostridium difficile-related Hospitalizations and Case-Fatality Rate, United States, 2000-2005," Emerg. Infect. Dis, 14(6):929-931 (2008).
Zilberberg, et al., "Increase in Clostridium difficile-related Hospitalizations Among Infants in the United States, 2000-2005," Pediatr Infect Dis J., 27(12):1111-1113 (2008).
Zoppi, et al., "Oral Bacteriotherapy in Clinical Practice," Eur J. Pediatr, 139(1):18-21 (1982).
Zoppi, et al., "The Intestinal Ecosystem in Chronic Functional Constipation," ACTA Paediatr, Scandinavian University Press, p. 836-841 (1998).
Buie, et al., "Evaluation, Diagnosis, and Treatment of Gastrointestinal Disorders in Individuals With ASDs: A Consensus Report," Pediatrics, 125:S1-S18 (2010).
Cammarota, et al., "Randomised clinical trial: faecal microbiota transplantation by colonoscopy vs. vancomycin for the treatment of recurrent Clostridium difficile infection," Alimentary Pharmacology & Therapeutics, 41(9):835-843 (2015).
Cammarota, et al., "Review article: biofile formation by Helicobacter pylori as a target for eradication of resistant infection," Aliment Pharmacol Ther, 36:222-30 (2012).
Campbell, et al., "The many faces of Crohn's Disease: Latest concepts in etiology," OJIM, 2(2):107-115 (2012).
Cangelosi, et al., "Dead or Alive: Molecular Assessment of Microbial Viability," Appl. Environ. Microbiol., 80(19):5884-5891 (2014).
Cano, et al., "Revival and identification of bacterial spores in 25-40 million year old Dominican Amber Science," Science, 268(5213):1060-1064 (1995).
Cato, et al., "*Clostridium oroticum* comb. nov. amended description," International Journal of Systematic Bacteriology, 17(1):9-13 (1968).
Celik, et al., "Factors influencing the stability of freeze-dried stress-resilient and stress-sensitive strains of bifidobacteria," J. Dairy Sci., 96(6):3506-16 (2013).
Center for Disease Control, "Severe Clostridium difficile-associated disease in populations previously at low risk- four states, 2005." Morbidity and Mortality Weekly Report, 54(47):1201-1205 (2005).
Chamberlain, et al., "MAP-associated Crohn's Disease, MAP, Koch's postulates, causality and Crohn's Disease," Digestive and Liver Disease, 39:790-794 (2007).
Chamberlain, et al., "Primary treatment of Crohn's disease: combined antibiotics taking center stage," Expert Rev. Clin. Immunol., 7(6):751-760 (2011).
Chang, et al., "Decreased diversity of the fecal Microbiome in recurrent Clostridium difficile-associated diarrhea," J. Infect. Dis., 197(3):435-438 (2008).
Chao, et al., "Estimating the Number via Sample Coverage," Journal of the American Statistical Association, 87(417):210-217 (1992).
Chen, et al., "A mouse model of Clostridium difficile-associated disease," Gastroenterology, 135(6):1984-1992 (2008).
Cherif, et al., "Thuricin 7: a novel bacteriocin produced by Bacillus thuringiensis BMG1.7, a new strain isolated from soil," Letters in Applied Microbiology, 32:243-7 (2001).
Chibani-Chennoufi, et al., "In Vitro and In Vivo Bacteriolytic Activities of *Escherichia coli* Phages: Implications for Phage Therapy," Antimicrobial Agents and Chemotherapy, 48(7):2558-2569 (2004).
Choi, et al., "Fecal Microbiota Transplantation: Current Applications, Effectiveness, and Future Perspectives," Clin. Endosc., 49:257-265 (2016).
Chopra, et al., "Recent epidemiology of Clostridium difficile infection during hematopoietic stem cell transplantation," Clin Transplant., 25(1):E82-E87 (2011).
Chu, et al., "Profiling Living Bacteria Informs Preparation of Fecal Microbiota Transplantations," PLOS One, 1-16 (2017).
Citron, et al., "In Vitro Activities of CB-183,315, Vancomycin, and Metronidazole against 556 Strains of Clostridium difficile, 445 Other Intestinal Anaerobes, and 56 *Enterobacteriaceae* Species," Antimicrob Agents Chemother., 56(3):1613-1615 (2012).
Claesson, et al., "Comparison of two next-generation sequencing technologies for resolving highly complex microbiota composition using tandem variable 16S rRNA gene regions," Nucleic Acids Research, 38(22):1-13 (2010).
Clancy, et al., "Anti-MAP Therapy Induces and Maintains Remission in Severe Crohn's Disease," Ann NY Acad Sci, p. 1 (2005).
Claus, et al., "Colonization-induced host-gut microbial metabolic interaction," MBio, 2(2):e00271-00210 (2011).
Claus, et al., "Systemic multicompartmental effects of the gut microbiome on mouse metabolic phenotypes," Mol. Syst. Biol., 4(1):219 (2008).
Cohen, et al., "The PDD Behavior Inventory: A Rating Scale for Assessing Response to Intervention in Children with Pervasive Development Disorder," J. Autism Dev. Disord., 33(1):31-45 (2003).
Cohen, et al., "Clinical practice guidelines for Clostridium difficile infection in adults: 2010 update by the society for healthcare epidemiology of America (SHEA) and the infectious diseases society of America (IDSA)," Infect Control Hosp Epidemiol., 31(5):431-55 (2010).
Cole, et al., "Psychological Risk Factors for HIV Pathogenesis: Mediation by the Autonomic Nervous System," Society of Biological Psychiatry, 54:1444-1456 (2003).
Cole, et al., "The Ribosomal Database Project (RDP-II): previewing a new autoaligner that allows regular updates and the new prokaryotic taxonomy," Nucleic Acids Research 31(1):442-443 (2003).
Cole, J.R., et al., "The Ribosomal Database Project: improved alignments and new tools for rRNA analysis," Nucleic Acids Research, 37:D141-D145 (2008).
Collins & Bercik, "The Relationship Between Intestinal Microbiota and the Central Nervous System in Normal Gastrointestinal Function and Disease," Gastroenterology, 136:2003-2014 (2009).

(56) References Cited

OTHER PUBLICATIONS

Collins, et al., "The Phylogeny of the Genus Clostridium: Proposal of Five New Genera and Eleven New Species Combinations," International Journal of Systematic Bacteriology, pp. 812-826 (1994).
Constantino, et al., "Validation of a Brief Quantitative Measure of Autistic Traits: Comparison of the Social Responsiveness Scale with the Autism Diagnostic Interview-Revised," J. Autism Dev. Disord., 33(4):427-433 (2003).
Crohn's Disease, Prevention, Health Guide A-Z, WebMDHealth, pp. 1-2, n.d., Web, Oct. 23, 2005 http:/mywebmd.com/hw/inflammatory.sub.--bowel/uf6012.asp.
Crowther, "Transport and Storage of Faeces for Bacteriological Examination," Journal of Applied Bacteriology, 34(2):477-483 (1971).
Dale, et al., "Molecular interactions between bacterial symbionts and their hosts," Cell, 126(3):453-465 (2006).
Dan, et al., "Comparison of preservation media and freezing conditions for storage of specimens of faeces," J. Med Microbiology, 28:151-154 (1989).
De Giulio, et al., "Use of Algiinate and Cryo-Protective Sugars to Improve the Viability of Lactic Acid Bacteria After Freezing and Freeze-Drying," World Journal of Microbiology & Biotechnology, 21:739-746 (2005).
Defang, et al., "In vitro and in vivo evaluation of two extended release preparations of combination metformin and glipizide," Drug Develop. & Indust. Pharm., 31:677-685 (2005).
Definition of Kit, Merriam-Webster, pp. 1-10., Web., 2019, https://www.merriam-webster.com/dictionary/kit.
Dendukuri, et al., "Probiotic therapy for the prevention and treatment of Clostridium difficile-associated diarrhea: a systematic review," CMAJ, 173(2):167-170 (2005).
Derrien, et al., "*Akkermansia muciniphila* gen. nov., sp. Nov., a human intestinal mucin-degrading bacterium," International Journal of Systematic and Evolutionary Microbiology, 54:1469-1476 (2004).
Derwent Abstract Accession No. 98-230427/20, WO 98/13068 A, (Kuperman VB) Apr. 2, 1998.
Dethlefsen, et al., "An ecological and evolutionary perspective on human-microbe mutualism and disease," Nature, 449(7164):811-818 (2007).
D'Eufemia, et al., "Abnormal intestinal permeability in children with autism," Acta Paediatr, 85:1076-1079 (1996).
Dewhirst, et al., "Phylogeny of the Defind Murine Microbiota: Altered Schaedler Flora," Applied and Environmental Microbiology, 65(8):3287-3292 (1999).
Dorn, et al., "Invasion of Human Oral Epithelial Cells by Prevotella intermedia," 66(12):6054-6057 (1998).
Duncan, et al., "Acetate Utilization and Butyryl Coenzyme A (CoA): Acetate-CoA Transferase in Butyrate-Producing Bacteria from the Human Large Intestine," Applied and Environmental Microbiology, 68(10):5186-5190 (2002).
Dupont, "The search for effective treatment of Clostridium difficile infection," N Engl J Med., 364(5):473-475 (2011).
Eckburg, et al., "Diversity of the human intestinal microbial flora," Science, 308(5728):1635-1638 (2005).
Edgar, "Search and clustering orders of magnitude faster than Blast," Bioinformatics 26(19):2460-2461 (2010).
Eller, et al., "Anaerobic Roll Tube Media for Nonselective Enumeration and Isolation and Bacteria in Human Feces," Applied Microbiology 1971, vol. 22, p. 522-529.
Extended European Search Report dated Apr. 3, 2014, in European Patent Application No. 11813951.8.
Extended European Search Report dated Mar. 16, 2018, in European Patent Application No. 17203052.0.
Extended European Search Report dated Nov. 30, 2016, in European Patent Application No. 16193790.9.
Faust, et al., "Treatment of recurrent pseudomembranous colitis (RPMC) with stool transplantation (ST): Report of six (6) cases," Can J Gastroenterol., 16:A43 (2002).
Fenton, et al., "Pseudomembranous colitis associated with antibiotic therapy—an emerging entity," Can Med Assoc J., 111(10):1110-1111 (1974).
Filippo, et al., "Impact of diet in shaping gut microbiota revealed by a comparative study in children from Europe and rural Africa," PNAS, 107(33):14691-14696 (2010).
Finegold, et al., "Gastrointestinal Microflora Studies in Late-Onset Autism," Clinical Infectious Diseases 35:S6 (2002).
Finegold, et al., "Pyrosequencing study of fecal microflora of autistic and control children," Anaerobe 16:444-453 (2010).
Floch, et al., "Probiotics and Dietary Fiber, The Clinical Coming of Age of Intestinal Microecology," J. Clin. Gastroenterology, 27(2):99-100 (1998).
Floch, "Fecal Bacteriotherapy, Fecal Transplant, and the Microbiome," J. Clin. Gastroenterol., 44(8):529-530 (2010).
Fogarty, et al., Comparison of Bacteroides-Provetella 16S rRNA Genetic Markers for Fecal Samples from Different Animal Species, Applied and Environmental Microbiology, 71(10):5999-6007 (Oct. 2005).
Frank, et al., "Molecular-phylogenetic characterization of microbial community imbalances in human inflammatory bowel diseases," PNAS, 104(34):13780-13785 (2007).
Frantzen, et al., "Empirical evaluation of preservation methods for faecal DNA," Molecular Ecology, 7(10):1423-1428 (1998).
Freeman, et al., "The changing epidemiology of Clostridium difficile infections," Clin Microbiol. Rev., 23(3):529-549 (2010).
Frese, et al., "The evolution of host specialization in the vertebrate gut symbiont Lactobacillus reuteri," PloS Genet., 7(2):e1001314 (2011).
Gaboriau-Routhiau, et al., "The Key Role of Segmented Filamentous Bacteria in the Coordinated Maturation of Gut Helper T Cell Responses," Immunity, 31(4):677-689 (2009).
Garborg, et al., "Results of faecal donor instillation therapy for recurrent Clostridium difficile-associated diarrhoea," Scand J Infect Dis., 42(11-12):857-61 (2010).
Garcia-Pena, et al., "Anaerobic digestion and co-digestion processes of vegetable and fruit residues: Process and microbial ecology," Bioresource Technology 102:9447-9455 (2011).
Garey, et al., "Meta-analysis to assess risk factors for recurrent Clostridium difficile infection," J. Hosp. Infect., 70(4):298-304 (2008).
Geier, et al., "A Comparison of the Autism Treatment Evaluation Checklist (ATEC) and the Childhood Autism Rating Scale (CARS) for the Quantitative Evaluation of Autism," Journal of Mental Health Research in Intellectual Disabilities, 6:255-67 (2013).
Gerding, "Management of Clostridium difficile infection: thinking inside and outside the box," Clin Infect Dis., 51(11):1306-13 (2010).
Geuking, et al., "Intestinal Bacterial Colonization Induces Mutualistic Regulatory T Cell Responses," Immunity, 34:794-806 (2011).
Gill, et al., "Metagenomic Analysis of the Human Distal Gut Microbiome", Science, 312(5778):1355-1359 (2006).
Gitlin, et al., "*Mycobacterium avium* ss paratuberculosis-associated Diseases: Piecing the Crohn's Puzzle Together," J Clin Gastroenterol, 46(8):649-655 (2012).
Goehler, et al., "Campylobacter jejuni infection increases anxiety-like behavior in the holeboard: possible anatomical substrates for viscerosensory modulation of exploratory behavior," Brain Behavior Immunology, 22(3):354-366 (2008).
Gondalia, et al., "Faecal microbiota of individuals with autism spectrum disorder," Electronic Journal of Applied Psychology, 6(2):24-29 (2010).
Gough, et al., "Systematic review of intestinal microbiota transplantation (fecal bacteriotherapy) for recurrent Clostridium difficile infection," Clin. Infect. Dis., 53(10):994-1002 (2011).
Gregersen, et al., "Duodenal administered seal oil for patients with subjective food hypersensitivity: an explorative open pilot study," International Journal of General Medicine, 2010(3):383-92.
Grehan, et al., "Durable alteration of the colonic microbiota by the administration of donor fecal flora," Journal of Clinical Gastroenterology, 44(8):551-561 (2010).
Guarner, et al., "Gut flora in health and disease," Lancet, 361(9356):512-519 (2003).
Gustafsson, et al., "Faecal Short-Chain Fatty Acids in Patients with Antibiotic-Associated Diarrhoea, before and after Faecal Enema Treatment," Scand J Gastroenterol, 33:721-727 (1998).

(56) References Cited

OTHER PUBLICATIONS

Gustafsson, et al., "The Effect of Faecal Enema on Five Microflora-Associated Characteristics in Patients with Antibiotic-Associated Diarrhoea," Scandinavian Journal of Gastroenterology, 34:580-586 (1999).
Hamilton, et al., "Change in microbial community composition of in patients with recalcitrant Clostridium difficile colitis treated with fecal bacteriotherapy," International Human Microbiome Congress, Poster and Presentation, Vancouver, ON, Canada, Mar. 9-11, 2011.
Hamilton, et al., "High-throughput DNA sequence analysis reveals stable engraftment of gut microbiota following transplantation of gut microbiota following transplantation of previously frozen fecal bacteria," Gut Microbes, 4(2):1-11 (2013).
Hamilton, et al., "Standardized Frozen Preparation for Transplantation of Fecal Microbiota for Recurrent Clostridium difficile Infection," Article and Supplementary Material, Am. J. Gastroenterol., 107(5):761-767 (2012).
Hammock, et al., "2003 Progress Report: Environmental Factors in the Etiology of Autism Analytic Biomarkers (xenobiotic) core," EPA Extramural Report, (2003).
Hanley & McNeil,"The Meaning and Use of the Area under a Receiver Operating Characteristic Curve," Radiology 143:29-36 (1982).
Hayashi, et al., "Phylogenetic Analysis of the Human Gut Microbiota Using 16S rDNA Clone Libraries and Strictly Anaerobic Culture-Based Methods," Microbiol. Immunol., 46(8):535-548 (2002).
Hayashi, et al., "*Prevotella copri* sp. nov. and *Prevotella stercorea* sp. nov., isolated from human faeces," International Journal of Systematic and Evolutionary Microbiology, 57:941-946 (2007).
Hecker, et al., "Fecal Microbiota Transplantation by Freeze-Dried Oral Capsules for Recurrent Clostridium difficile Infection," Open Forum Infect Dis, 3(2): 1-2 (2016).
Hellemans, et al., "Fecal transplantation for recurrent Clostridium difficile colitis, an underused treatment modality," Acta Gastroenterol Belg., 72(2):269-70 (2009).
Henriksson, et al., "Probiotics under the regulatory microscope," Expert Opin. Drug Saf., 4(6):1-9 (2005).
Hensel, et al., "Vagal Ascent and Distribution of 125 I-Tetanus Toxin after Injection into the Anterior Wall of the Stomach," Naunyn-Schmiedeberg's Arch. Pharmacol, 276:395-402 (1973).
Holst, et al., "Biochemistry and cell biology of bacterial endotoxins," FEMS Immunology and Medical Microbiology, 16:83-104 (1996).
Honda, et al., "Regulation of T Cell Responses by Intestinal Commensal Bacteria," Journal of Intestinal Microbiology, vol. 25, 2nd Edition:104 (2011).
Hongliang, et al., "Freeze-dried, Capsulized Fecal Microbiota Transplantation for Relapsing Clostridium difficile Infection," Journal of Clinical Gastroenterology, 43(6):537-538 (2015).
Hooper, et al., "How host-microbial interactions shape the nutrient environment of the mammalian intestine," Annu. Rev. Nutr., 22:283-307 (2002).
Hope, et al., "Sporadic colorectal cancer-role of the commensal microbiota," FEMS Microbiol. Lett., 244:1-7 (2005).
Horvath, et al., "Gastrointestinal abnormalities in children with autistic disorder," Journal of Pediatrics 135(5):559-563 (1999).
Hota, et al., "Determining Mortality Rates Attributable to Clostridium difficile Infection," Emerg. Infect. Dis., 18(2):305-307 (2012).
Hota, et al., "Oral Vancomycin Followed by Fecal Transplant Versus Tapering Oral Vancomycin," U.S. National Institutes of Health, Clinical Study No. NCT01226992, Oct. 20, 2010, last updated Jan. 14, 2013, Web, May 20, 2014, pp. 1-4 http://clinicaltrials.gov/ct2/show/NCT01226992.
Hsu, et al., "IL-10 Potentiates Differentiation of Human Induced Regulatory T Cells via STAT3 and Foxol," The Journal of Immunology, 3665-3674 (2015).
Hu, et al., "Prospective derivation and validation of a clinical prediction rule for recurrent Clostridium difficile infection," Gastroenterology, 136:1206-1214 (2009).

Huang, et al., "Once-daily propranolol extended-release tablet dosage form: formulation design and in vitro/in vivo investigation," European J. of Pharm. & Biopharm., 58:607-614 (2004).
Huttenhower, et al., "Structure, function and diversity of the healthy human microbiome," The Human Microbiome Project Consortium, Nature, 486:207-214 (2012).
Huws, et al., "As yet uncultured bacteria phylogenetically classified as Prevotella, Lachnospiraceae incertae sedis and unclassified Bacteroidales, Clostridiales and Ruminococcaceae may play a predominant role in ruminal biohydrogenationemion", Environmental Microbiology, 13(6):1500-1512 (2011).
Inflammatory Bowel Disease Facts, Disease Prevention and Treatment Strategies, Crohn's Disease and Inflammatory Bowel Disease (IBD), HealingWithNutrition.com, pp. 1-4, n.d., Web, Oct. 23, 2005 http://www.HealingWithNutrition.com/disease/inflambowels/chrohns.html.
International Preliminary Examination Report completed Nov. 19, 2002, in International Application No. PCT/AU2001/000907, 19 pgs.
International Preliminary Report on Patentability completed Dec. 12, 2012, in International No. PCT/AU2011/000987, 35 pgs.
Anand et al., "Epidemiology, clinical manifestations, and outcome of Clostridium difficile-associated diarrhea," *The american Journal of Gastroenterology*, 89(4):519-23 (Apr. 1994).
Arkkila et al., "Fecal Bacteriotherapy for Recurrent *Clostridium difficile Infection*," *Gastroenterology*, 138(5):S5 (May 2010).
Andrews et al., "Putting back bugs': Bacterial Treatment Relieves Chronic Constipation and Symptoms of Irritable Bowel Syndrome," *Medical Journal of Australia*, 159(9):633-634 (Nov. 1993).
Andrews et al., "Bacteriotherapy for Chronic Constipation—A Long Term Follow-Up," *Gastroenterology*, 108:A563 Abstract (Apr. 1995).
Baron et al., "Variation Between Observers in Describing Mucosal Appearances in Proctocolitis," *British Medical Journal*, 1:89-92 (Jan. 1964).
Borody et al., "Anti-*Mycobacterium avium* SS *Paratuberculosis* (MAP) Therapy and Fistula Closure in Patients with Severe Crohn's Disease," *The American Journal of Gastroenterology*, 101:S440, Anstract 1124 (Sep. 2006).
Borody et al., "Clostridium *difficile* Complicating Inflammatory Bowel Disease: Pre- and Post-Treatment Findings," *Gastroenterology*, 134(4, Suppl 1):A-361 (Apr. 2008).
Bowden et al., "Pseudomembraneous enterocolitis: mechanism of restoring floral homeostasis," *The American Surgeon.*, 47(4):178-183 (Apr. 1981).
Brandt et al., "Safety of Fecal Microbiota Transplantation (FMT) in Immunocompromised (Ic) Patients with Inflammatory Bowel Disease (IBD)," *The American Journal of Gastroenterology*, 108(Suppl_1):S556 (Oct. 2013).
Bryant et al., "Bacteroides Ruminicola N. SP. and the New Genus and Species Succinimonas Amylolytica," *Journal of Bacteriol.*, 76:15-23 (1958).
Chassaing et al., "Dextran Sulfate Sodium (DSS)—Induced Colitis in Mice," *Curr Protoc Immunol.*, 104:Unit-15.25 (Feb. 2015).
Cutolo et al., "Fecal feedings as a therapy in *Staphylococcus enterocolitis*," *New York State Journal of Medicine*, 59:3831-3833 (Oct. 1959).
Dieterle et al., "Renal Biomarker qualification submission: a dialog between the FDA-EMEA and Predictive Safety Testing Consortium," *Nature Biotechnology*, 28(5):455462 (May 2010).
Drossman et al., "Health Status and Health Care Use in Persons with Inflammatory Bowel Disease. A National Sample," *Digestive Diseases Sciences*, 36(12):1746-1755 (Dec. 1991).
Eiseman et al., "Fecal enema as an adjunct in the treatment of pseudomembranous enterocolitis," *Surgery*, 44(5):854-859 (Nov. 1958).
European Office Action dated Sep. 18, 2015, in European Patent Application No. 11 728 077.6, 4 pages.
Flotterod et al., "Refractory Clostridium difficile infection. Untraditional treatment of antibiotic-induced colitis" *Tidsskr Nor Laegeforen*, 111(11):1364-1365 (Apr. 1991) (English Abstract).

(56) References Cited

OTHER PUBLICATIONS

Geboes et al., "A reproducible grading scale for histological assessment of inflammatory in ulcerative colitis," *Gut*, 47(3):404-409 (Sep. 2000).
Hanauer et al., "Budesonide Enema for the Treatment of Active, Distal Ulcerative Colitis and Proctitis: A Dose-Ranging Study," *Gastroenterology*, 115(3):525-532 (Sep. 1998).
Hanauer et al., "Mesalamine Capsules for Treatment of Active Ulcerative Colitis: Results of a Controlled Trial," *The American Journal of Gastroenterology*, 88(8):1188-1197 (Aug. 1993).
Higgins et al., "Is Endoscopy Necessary for the Measurement of Disease Activity in Ulcerative Colitis?," *American Journal of Gastroenterology*, 100:355-361 (2005).
Immunology in the 21st Century: Defeating Infection, Autoimmunity, Allergy, and Cancer, ICI 2010 Wrap-up Report, 14 International Congress of Immunology, 217 pages (Aug. 2010) (English translation).
Irvine et al., "Quality of Life: A Valid Reliable Measure of Therapeutic Efficacy in the Treatment of Inflammatory Bowel Disease," *Gastroenterology*, 106(2):287-296 (Feb. 1994).
Kawada et al., "Insights from advances in research of chemically induced experimental models of human inflammatory bowel disease," *World Journal of Gastroenterology*, 13(42):5581-5593 (Nov. 2007).
Lee, "Multi-Centre Trial of Fresh vs. Frozen-and-Thawed HBT (Fecal Transplant) for Recurrent CDI," U.S. National Institutes of Health, Clinical Study No. NCT01398969, pp. 1-4, last updated Feb. 27, 2014, Web, May 20, 2014, http://clinicaltrials.gov/ct2/show/NCT01398969.
Lémann et al., "Comparison of budesonide and 5-aminosalicylic acid enemas in active distal ulcerative colitis," *Aliment Pharmacol Ther.*, 9(5):557-562 (Oct. 1995).
Levine et al., "A Randomized, Double Blind, Dose-Response Comparison of Balsalazide (6.75g), Balsalazide (2.25g), and Mesalamine (2.4g) in the Treatment of Active, Mild-to-Moderate Ulcerative Colitis," *The American Journal of Gastroenterology*, 97(6):1398-1407 (Jun. 2002).
Li et al., "In Vitro Evaluation of Dissolution Behavior for a Colon-Specific Drug Delivery System (CODES™) in Multi-pH Media Using United States Pharmacopeia Apparatus II and III," *AAPS PharmSciTech*, 3(4):1-9 (Dec. 2002).
Lichtiger et al., "Preliminary report: cyclosporin in treatment of severe active ulcerative colitis," *The Lancet*, 336(8706):16-19 (Jul. 1990).
Low et al., "Animal models of ulcerative colitis and their application in drug research," *Drug Design, Development and Therapy*, 7:1341-1357 (2013).
Morgan et al., "Dysfunction of the intestinal microbiome in inflammatory bowel disease and treatment," *Genome Biology*, 13:R79, pp. 1-18 (2012).
Nieuwdrop et al., ["Treatment of recurrent Clostridium difficile-associated diarrhoea with a suspension of donor faeces"], *Nederlands Tijdschrift Voor Geneeskunde*, 152(35):1927-1932 (Aug. 2008) English abstract).
Papa et al., "Non-Invasive Mapping of the Gastrointestinal Microbiota Identifies Children with Inflammatory Bowel Disease," *PLOS One*, 7(6):e39242, pp. 1-12 (Jun. 2012).
Paterson et al., "Putting back the bugs: bacterial treatment relieves chronic diarrhoea," *The Medical Journal of Australia*, 160(4):232-233 (Feb. 1994).
Porter, "Coating of Pharmaceutical dosage forms," In D.B. Troy (Ed.), Remington: The Science and Practice of Pharmacy, Chapter 46, pp. 929-938 (2005).
Powell-Tuck et al., "Correlations Between Defined Sigmoidoscopic Appearances and Other Measures of Disease Activity in Uncerative Colitis," *Digestive Diseases and Sciences*, 27(6):533-537 (Jun. 1982).
Rachmilewitz, "Coated mesalazine (5-aminosalicylic acid) versus sulphasalazine in the treatment of active ulcerative colitis: a randomised trial," *British Medical Journal*, 298:82-86 (Jan. 1989).
Riley et al., "Microscopic activity in ulcerative colitis: what does it mean?," *Gut*, 32:174-178 (1991).
Rubin et al., "Increased Degree of Histological Inflammation Predicts Colectomy and Hospitalization in Patients with Ulcerative Colitis," *Gastroenterology*, 132(Suppl. 1):A-19 (Abstract 103) (2007).
Rutgeerts et al., "Infliximab for Induction and Maintenance Therapy for Ulcerative Colitis," *The New England Journal of Medicine*, 353(23):2462-2476 (Dec. 2005).
Schroeder et al., "Coated Oral 5-Aminosalicylic Acid Therapy for Mildly to Moderately Active Ulcerative Colitis, A Randomized Study," *The New England Journal of Medicine*, 317(26):1625-1629 (Dec. 1987).
Seo et al., "Index of Disease Activity in Patients with Ulcerative Colitis," *The American Journal of Gastroenterology*, 87(8):971-976 (Aug. 1992).
Seo et al., "Evaluation of Disease Activity in Patients with Moderately Active Ulcerative Colitis: Comparisons Between a New Activity Index and Truelove and Witts' Classification," *The American Journal of Gastroenterology*, 90(10):1759-1763 (Oct. 1995).
Shannon et al., "The Mathematical Theory of Communication", The University of Illinois Press, Urbana 117pp. (1949).
Singaporean Search Report and Written Opinion dated Apr. 4, 2024, in Singaporean Application No. 11202113642S, 9 pages.
Sutherland et al., "5-Aminosalicylic Acid Enema in the Treatment of Distal Ulcerative Colitis, Proctosigmoiditis," *Gastroenterology*, 92(6):1894-1898 (Jun. 1987).
Travis et al., "Review article: defining remission in ulcerative colitis," *Alimentary Pharmacology and Therapeutics*, 34(2):113-124 (May 2011).
Truelove et al., "Cortisone in Ulcerative Colitis: Final Report on a Therapeutic Trial," *British Medical Journal*, 2:1041-1048 (Oct. 1955).
Walmsley et al., "A simple clinical activity index," *Gut*, 43:29-32 (Feb. 1998).
Ware et al., "The MOS 36-Item Short-Form Health Survey (SF-36). I. Conceptual Framework and Item Selection," *Medical Care*, 30(6):473-483 (Jun. 1992).
Neff et al., "Diverse intestinal bacterial contain putative zwitterionic capsular polysaccarides with anti-inflammatory properties," *Cell Host Microbe*, 20(4):535-547 (Oct. 2016).

\* cited by examiner

```
SEQUENCE LISTING

<160> NUMBER OF SEQ ID NOS: 37

<210> SEQ ID NO 1
<211> LENGTH: 1509
<212> TYPE: DNA
<213> ORGANISM: Artificial Sequence
<220> FEATURE:
<223> OTHER INFORMATION: Synthetic Polynucleotide

<400> SEQUENCE: 1
tataaagagt ttgatcctgg ctcaggacga acgctggcgg cgcgcctaac acatgcaagt      60
cgaacgagcg agagagagct tgctttctcg agcgagtggc gaacgggtga gtaacgcgtg     120
aggaacctgc ctcaaagagg gggacaacag ttggaaacga ctgctaatac cgcataagcc     180
cacggctcgg catcgagcag agggaaaagg agcaatccgc tttgagatgg cctcgcgtcc     240
gattagctag ttggtgaggt aacggcccac caaggcaacg atcggtagcc ggactgagag     300
gttgaacggc cacattggga ctgagacacg gcccagactc ctacgggagg cagcagtggg     360
gaatattgca caatggggga aaccctgatg cagcgacgcc gcgtggagga agaaggtctt     420
cggattgtaa actcctgttg ttggggaaga taatgacggt acccaacaag gaagtgacgg     480
ctaactacgt gccagcagcc gcggtaaaac gtaggtcaca agcgttgtcc ggaattactg     540
ggtgtaaagg gagcgcaggc gggaagacaa gttggaagtg aaatctatgg gctcaaccca     600
taaactgctt tcaaaactgt ttttcttgag tagtgcagag gtaggcggaa ttcccggtgt     660
agcggtggaa tgcgtagata tcgggaggaa caccagtggc gaaggcggcc tactgggcac     720
caactgacgc tgaggctcga aagtgtgggt agcaaacagg attagatacc ctggtagtcc     780
acaccgtaaa cgatgattac taggtgttgg aggattgacc ccttcagtgc cgcagttaac     840
acaataagta atccacctgg ggagtacgac cgcaaggttg aaactcaaag gaattgacgg     900
```

```
gggcccgcac aagcagtgga gtatgtggtt taattcgacg caacgcgaag aaccttacca    960
agtcttgaca tcccttgaca gacatagaaa tatgtaatct cttcggagca aggagacagg   1020
tggtgcatgg ttgtcgtcag ctcgtgtcgt gagatgttgg gttaagtccc gcaacgagcg   1080
caacccttat ggtcagttac tacgcaagag gactctggcc agactgccgt tgacaaaacg   1140
gaggaaggtg gggatgacgt caaatcatca tgccctttat gacttgggct acacacgtac   1200
tacaatggcg ttaaacaaag agaagcaaga ccgcgaggtg gagcaaaact cagaaacaac   1260
gtcccagttc ggactgcagg ctgcaactcg cctgcacgaa gtcggaattg ctagtaatcg   1320
tggatcagca tgccacggtg aatacgttcc cgggccttgt acacaccgcc cgtcacacca   1380
tgagagccgg ggggacccga agtcggtagt ctaaccgcaa ggaggacgcc gccgaaggta   1440
aaactggtga ttggggtgaa gtcgtaacaa ggtagccgta ggagaacctg cggctggatc   1500
acctcctttt                                                          1509
```

<210> SEQ ID NO 2
<211> LENGTH: 1381
<212> TYPE: DNA
<213> ORGANISM: Artificial Sequence
<220> FEATURE:
<223> OTHER INFORMATION: Synthetic Polynucleotide

<400> SEQUENCE: 2

```
ggggtatagc ccatggaaac gtggattaac accccatagt acttttatcc tgcatgggat     60
gtgagttaaa tgttcaaggt atcggatggg catgcgtcct attagttagt ggcggggta    120
acagcccacc aagacgatga taggtagggg ttctgagagg aaggtccccc acattggaac    180
tgagacacgg tccaaactcc tacgggaggc agcagtgagg aatattggtc aatggacgta    240
agtctgaacc agccaagtcg cgtgagggaa gactgcccta tgggttgtaa acctctttta    300
taagggaaga ataagttcta cgtgtagaat gatgcctgta ccttatgaat aagcatcggc    360
taactccgtg ccagcagccg cggtaatacg gaggatgcga gcgttatccg gatttattgg    420
gtttaaaggg tgcgtaggcg gtttattaag ttagtggtta aatatttgag ctaaactcaa    480
ttgtgccatt aatactggta aactggagta cagacgaggt aggcggaata agttaagtag    540
cggtgaaatg catagatata acttagaact ccgatagcga aggcagctta ccagactgta    600
actgacgctg atgcacgaga gcgtgggtag cgaacaggat tagatacct ggtagtccac    660
gccgtaaacg atgctcactg gttctgtgcg atatattgta cgggattaag cgaaagtatt    720
aagtgagcca cctggggagt acgtcggcaa cgatgaaact caaaggaatt gacggggggcc    780
cgcacaagcg gaggaacatg tggtttaatt cgatgatacg cgaggaacct tacctgggtt    840
taaatgggaa atgccgtatt tggaaacaga tattctcttc ggagcgtttt tcaaggtgct    900
gcatggttgt cgtcagctcg tgccgtgagg tgtcgggtta agtcccataa cgagcgcaac    960
ccttaccgtt agttgctagc atgtaatgat gagcactcta acgggactgc accgtaagg    1020
tgagaggaag gcggggatga cgtcaaatca gcacggccct acacccagg ctacacacg    1080
tgttacaatg gccggtacag agggccgcta ccaggtgact ggatgccaat ctcaaaagcc   1140
ggtcgtagtt cggattggag tctgtaaccc gactccatga agttggattc gctagtaatc   1200
gcgcatcagc catggcgcgg tgaatacgtt cccgggcctt gtacacaccg cccgtcaagc   1260
catggaagcc gggggtgcct gaagtccgta accgcgagga tcggcctagg caaaactgg    1320
taactggggc taagtcgtaa caaggtagcc gtaccggaag gtgcggctgg aacacctcct   1380
```

<210> SEQ ID NO 3
<211> LENGTH: 1299
<212> TYPE: DNA
<213> ORGANISM: Artificial Sequence
<220> FEATURE:
<223> OTHER INFORMATION: Synthetic Polynucleotide

<400> SEQUENCE: 3

```
tggtacagga tggacccgcg tctgattagc tggttggtga ggtaacggct caccaaggcg      60
acgatcagta gccggcttga gagagtgaac ggccacattg ggactgagac acggcccaaa     120
ctcctacggg aggcagcagt ggggaatatt gcacaatggg ggaaaccctg atgcagcgac     180
gccgcgtgag tgaagaagta tctcggtatg taaagctcta tcagcaggga agaaaatgac     240
ggtacctgac taagaagccc cggctaacta cgtgccagca gccgcggtaa tacgtagggg     300
gcaagcgtta tccggaatta ctgggtgtaa aggtgcgta ggtggtatgg caagtcagaa      360
gtgaaaaccc agggcttaac tctggactg cttttgaaac tgtcagacta gagtgcagga     420
gaggtaagcg gaattcctag tgtagcggtg aaatgcgtag atattaggag gaacatcagt     480
ggcgaaggcg gcttactgga ctgaaactga cactgaggca cgaaagcgtg gggagcaaac     540
aggattagat accctggtag tccacgccgt aaacgatgaa tactaggtgt cggggccgta     600
gaggcttcgg tgccgcagcc aacgcagtaa gtattccacc tggggagtac gttcgcaaga     660
atgaaactca aaggaattga cggggacccg cacaagcggt ggagcatgtg gtttaattcg     720
aagcaacgcg aagaacctta cctggtcttg acatccttct gaccggtcct taaccggact     780
tttccttcgg gacaggagtg acaggtggtg catggttgtc gtcagctcgt gtcgtgagat     840
gttgggttaa gtcccgcaac gagcgcaacc cctatcttta gtagccagca tataaggtgg     900
gcactctaga gagactgcca gggataacct ggaggaaggt ggggacgacg tcaaatcatc     960
atgccccta tgaccagggc tacacacgtg ctacaatggc gtaaacagag ggaagcagcc    1020
tcgtgagagt gagcaaatcc caaaaataac gtctcagttc ggattgtagt ctgcaactcg    1080
actacatgaa gctggaatcg ctagtaatcg cgaatcagaa tgtcgcggtg aatacgttcc    1140
cgggtcttgt acacaccgcc cgtcacacca tgggagtcag taacgcccga agtcagtgac    1200
ccaaccgtaa ggagggagct gccgaaggcg ggaccgataa ctggggtgaa gtcgtaacaa    1260
ggtagccgta tcggaaggtg cggctggatc acctccttt                            1299
```

<210> SEQ ID NO 4
<211> LENGTH: 800
<212> TYPE: DNA
<213> ORGANISM: Artificial Sequence
<220> FEATURE:
<223> OTHER INFORMATION: Synthetic Polynucleotide

<400> SEQUENCE: 4

```
tgtgtatcgc cgacaacgag ttatcatcgt ttactgcgtg gactaccagg gtatctaatc      60
ctgtttgctc cccacgcttt cgtgcctcaa cgtcagatat agtttggtaa gctgccttcg     120
caatcggtgt tctgtatgat ctctaagcat ttcaccgcta caccatacat tccgcctacc     180
gcaactactc tctagtctaa cagtattaga ggcagttccg gagttaagcc cgggatttc      240
acctctaact tatcaaaccg cctacgcacc ctttaaaccc aataaatccg gataacgctt     300
gaatcctccg tattaccgcg gctgctggca cggagttagc cgatccttat tcgtacgata     360
cttcagtca cctacacgta ggtgagttta ccctcgtaca aaagcagttt acaactcata     420
```

```
gagccgtctt cctgcacgcg gcatggctgg ttcagacttg cgtccattga ccaatattcc    480
tcactgctgc ctcccgtagg agtctgatcc gtgtctcagt accagtgtgg ggggttaacc    540
tctcagtccc cctatgtatc gttgccttgg tgagccgtta cctcaccaac tagctaatac    600
aacgcatgtc catctataac caccggagtt ttcaacccgg agagatgcct ctccgaatat    660
tatggggaat tagtaccaat ttctcagtgt tatgcccctg ttataggtag gttacatacg    720
cgttacgcac ccgtgcgccg gtcgccggca attgaagcaa gcttcaatcc cgatgcccct    780
cgacttgcat gtgttaggcc                                                800

<210> SEQ ID NO 5
<211> LENGTH: 1527
<212> TYPE: DNA
<213> ORGANISM: Artificial Sequence
<220> FEATURE:
<223> OTHER INFORMATION: Synthetic Polynucleotide

<400> SEQUENCE: 5
cgaagagttt gatcctggct caggatgaac gctagcgaca ggcttaacac atgcaagtcg     60
aggggcagca tgatttgtag caatacagat tgatggcgac cggcgcacgg gtgagtaacg    120
cgtatgcaac ttacctatca gaggggggata gcccggcgaa agtcggatta atacccccata    180 aaacaggggt cccgcatggg aatatttgtt aaagattcat cgctgataga taggcatgcg    240
ttccattagg cagttggcgg ggtaacggcc caccaaaccg acgatggata ggggttctga    300
gaggaaggtc ccccacattg gtactgagac acggaccaaa ctcctacggg aggcagcagt    360
gaggaatatt ggtcaatggc cgagaggctg aaccagccaa gtcgcgtgaa ggaagaagga    420
tctatggttt gtaaacttct tttatagggg aataaagtgg aggacgtgtc ctttttttgta    480 tgtaccctat gaataagcat cggctaactc cgtgccagca gccgcggtaa tacgaggat     540 gcgagcgtta tccggattta ttgggtttaa agggtgcgta ggtggtgatt taagtcagcg    600
gtgaaagttt gtggctcaac cataaaattg ccgttgaaac tgggttactt gagtgtgttt    660
gaggtaggcg gaatgcgtgg tgtagcggtg aaatgcatag atatcacgca gaactccgat    720
tgcgaaggca gcttactaaa ccataactga cactgaagca cgaaagcgtg gggatcaaac    780
aggattagat accctggtag tccacgcagt aaacgatgat tactaggagt ttgcgataca    840
atgtaagctc tacagcgaaa gcgttaagta atccacctgg ggagtacgcc ggcaacggtg    900
aaactcaaag gaattgacgg gggcccgcac aagcggagga acatgtggtt taattcgatg    960
atacgcgagg aaccttaccc gggtttgaac gtagtctgac cggagtggaa acactctttc   1020
tagcaatagc agattacgag gtgctgcatg gttgtcgtca gctcgtgccg tgaggtgtcg   1080
gcttaagtgc cataacgagc gcaacccctta tcactagtta ctaacaggtg aagctgagga   1140
ctctggtgag actgccagcg taagctgtga ggaaggtggg gatgacgtca atcagcacg    1200 gcccttacat ccggggcgac acacgtgtta caatggcatg gacaaagggc agctacctgg   1260
cgacaggatg ctaatctcca aaccatgtct cagttcggat cggagtctgc aactcgactc   1320
cgtgaagctg gattcgctag taatcgcgca tcagccatgg cgcggtgaat acgttcccgg   1380
gccttgtaca caccgcccgt caagccatgg agccggggg tacctgaagt ccgtaaccgc    1440
aaggatcggc ctagggtaaa actggtgact ggggctaagt cgtaacaagg tagccgtacc   1500
ggaaggtgcg gctggaacac ctccttt                                      1527

<210> SEQ ID NO 6
```

<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 6

```
aacgagagtt tgatcctggc tcaggatgaa cgctggcggc gtgcttaaca catgcaagtc      60
gagcgaagca ctttggaaag attcttcgga tgatttcctt tgtgactgag cggcggacgg     120
gtgagtaacg cgtgggtaac ctgcctcata caggggata  acagttagaa atgactgcta     180
ataccgcata agaccacggt accgcatggt acagtggtaa aaactccggt ggtatgagat     240
ggacccgcgt ctgattaggt agttggtggg gtaacggcct accaagccga cgatcagtag     300
ccgacctgag agggtgaccg gccacattgg gactgagaca cggcccagac tcctacggga     360
ggcagcagtg gggaatattg cacaatggag gaaactctga tgcagcgacg ccgcgtgaag     420
gatgaagtat ttcggtatgt aaacttctat cagcagggaa gaaaatgacg gtacctgact     480
aagaagcccc ggctaactac gtgccagcag ccgcggtaat acgtagggg  caagcgttat     540
ccggatttac tgggtgtaaa gggagcgtag acggcacggc aagccagatg tgaaagcccg     600
gggctcaacc ccgggactgc atttggaact gctgagctag agtgtcggag aggcaagtgg     660
aattcctagt gtagcggtga aatgcgtaga tattaggagg aacaccagtg gcgaaggcgg     720
cttgctggac gatgactgac gttgaggctc gaaagcgtgg ggagcaaaca ggattagata     780
ccctggtagt ccacgccgta aacgatgact gctaggtgtc gggtggcaaa gccattcggt     840
gccgcagcta acgcaataag cagtccacct ggggagtacg ttcgcaagaa tgaaactcaa     900
aggaattgac ggggacccgc acaagcggtg gagcatgtgg tttaattcga agcaacgcga     960
agaaccttac ctgatcttga catcccgatg accgcttcgt aatggaagtt tttcttcgga    1020
acatcggtga caggtggtgc atggttgtcg tcagctcgtg tcgtgagatg ttgggttaag    1080
tcccgcaacg agcgcaaccc ctatcttcag tagccagcag gttaagctgg cactctgga    1140
gagactgcca gggataacct ggaggaaggt ggggatgacg tcaaatcatc atgcccctta    1200
tgaccagggc tacacacgtg ctacaatggc gtaaacaaag agaagcgaac tcgcgagagt    1260
aagcaaatct caaaaataac gtctcagttc ggattgtagt ctgcaactcg actacatgaa    1320
gctggaatcg ctagtaatcg cagatcagaa tgctgcggtg aatacgttcc cgggtcttgt    1380
acacaccgcc cgtcacacca tgggagtcag taacgcccga agtcagtgac ccaaccgtaa    1440
ggagggagct gccgaaggtg ggaccgataa ctggggtgaa gtcgtaacaa ggtagccgta    1500
tcggaaggtg cggctggatc acctccttt                                      1529
```

<210> SEQ ID NO 7
<211> LENGTH: 1509
<212> TYPE: DNA
<213> ORGANISM: Artificial Sequence
<220> FEATURE:
<223> OTHER INFORMATION: Synthetic Polynucleotide

<400> SEQUENCE: 7

```
tataaagagt ttgatcctgg ctcaggacga acgctggcgg cgcgcctaac acatgcaagt     60
cgaacgagag agaaggagct tgcttcttcg atcgagtggc gaacgggtga gtaacgcgtg    120
aggaacctgc ctcaaagagg gggacaacag ttggaaacga ctgctaatac cgcataagcc    180
cacgggtcgg catcgaccag agggaaaagg agcaatccgc tttgagatgg cctcgcgtcc    240
gattagctag ttggtgaggt aatggcccac caaggcgacg atcggtagcc ggactgagag    300
```

```
gttgaacggc cacattggga ctgagacacg gcccagactc ctacgggagg cagcagtggg    360
gaatattgca caatggggga aaccctgatg cagcgacgcc gcgtggagga agaaggtctt    420
cggattgtaa actcctgttg ttgaggaaga taatgacggt actcaacaag gaagtgacgg    480
ctaactacgt gccagcagcc gcggtaaaac gtaggtcaca agcgttgtcc ggaattactg    540
ggtgtaaagg gagcgcaggc gggaagacaa gttggaagtg aaatccatgg gctcaaccca    600
tgaactgctt tcaaaactgt ttttcttgag tagtgcagag gtaggcgaaa ttcccggtgt    660
agcggtggaa tgcgtagata tcgggaggaa caccagtggc gaaggcggcc tactgggcac    720
caactgacgc tgaggctcga aagtgtgggt agcaaacagg attagatacc ctggtagtcc    780
acaccgtaaa cgatgattac taggtgttgg aggattgacc ccttcagtgc cgcagttaac    840
acaataagta atccacctgg ggagtacgac cgcaaggttg aaactcaaag gaattgacgg    900
gggcccgcac aagcagtgga gtatgtggtt taattcgacg caacgcgaag aaccttacca    960
agtcttgaca tcctgcgacg gacatagaaa tatgtctttc cttcgggacg cagagacagg   1020
tggtgcatgg ttgtcgtcag ctcgtgtcgt gagatgttgg gttaagtccc gcaacgagcg   1080 caaccccttat ggtcagttac tacgcaagag gactctggcc agactgccgt tgacaaaacg   1140
gaggaaggtg gggatgacgt caaatcatca tgccctttat gacttgggct acacacgtac   1200
tacaatggcg ttaaacaaag agaagcaaga ccgcgaggtg gagcaaaact cagaaacaac   1260
gtcccagttc ggactgcagg ctgcaactcg cctgcacgaa gtcggaattg ctagtaatcg   1320
tggatcagca tgccacggtg aatacgttcc cgggccttgt acacaccgcc cgtcacacca   1380
tgagagccgg ggggacccga agtcggtagt ctaaccgcaa ggaggacgcc gccgaaggta   1440
aaactggtga ttggggtgaa gtcgtaacaa ggtagccgta ggagaacctg cggctggatc   1500
acctcctttt                                                           1509
```

<210> SEQ ID NO 8
<211> LENGTH: 1529
<212> TYPE: DNA
<213> ORGANISM: Artificial Sequence
<220> FEATURE:
<223> OTHER INFORMATION: Synthetic Polynucleotide

<400> SEQUENCE: 8

```
atgagagttt gatcctggct caggatgaac gctggcggcg tgcttaacac atgcaagtcg     60
aacgaagcac tttatttgat ttccttcggg actgattatt ttgtgactga gtggcggacg    120
ggtgagtaac gcgtgggtaa cctgccttgt acaggggat aacagttgga aacggctgct    180
aataccgcat aagcgcacag catcgcatga tgcagtgtga aaaactccgg tggtataaga    240
tggacccgcg ttggattagc tagttggtga ggtaacggcc caccaaggcg acgatccata    300
gccgacctga gagggtgacc ggccacattg gactgagac acggcccaaa ctcctacggg    360
aggcagcagt ggggaatatt gcacaatggg cgaaagcctg atgcagcgac gccgcgtgag    420
cgaagaagta tttcggtatg taaagctcta tcagcaggga agataatgac ggtacctgac    480
taagaagcac cggctaaata cgtgccagca gccgcggtaa tacgtatggt gcaagcgtta    540
tccggattta ctgggtgtaa agggagcgca ggcggtgcgg caagtctgat gtgaaagccc    600
ggggctcaac cccggtactg cattggaaac tgtcgtacta gagtgtcgga ggggtaagcg    660
gaattcctag tgtagcggtg aaatgcgtag atattaggag gaacaccagt ggcgaaggcg    720
gcttactgga cgataactga cgctgaggct cgaaagcgtg gggagcaaac aggattagat    780
```

```
acctggtag tccacgccgt aaacgatgaa tactaggtgt tgggaagcat tgcttctcgg      840
tgccgtcgca aacgcagtaa gtattccacc tggggagtac gttcgcaaga atgaaactca      900
aaggaattga cggggacccg cacaagcggt ggagcatgtg gtttaattcg aagcaacgcg      960 aagaaccta ccaagtcttg acatccttct gaccggtact taaccgtacc ttctcttcgg     1020
agcaggagtg acaggtggtg catggttgtc gtcagctcgt gtcgtgagat gttgggttaa    1080
gtcccgcaac gagcgcaacc cttatcttta gtagccagcg gtttggccgg cactctaga     1140 gagactgcca gggataacct ggaggaaggc ggggatgacg tcaaatcatc atgcccctta    1200
tgacttgggc tacacacgtg ctacaatggc gtaaacaaag ggaagcaaag ctgtgaagcc    1260
gagcaaatct caaaaataac gtctcagttc ggactgtagt ctgcaacccg actacacgaa    1320
gctggaatcg ctagtaatcg cagatcagaa tgctgcggtg aatacgttcc cgggtcttgt    1380
acacaccgcc cgtcacacca tgggagttgg gaatgcccga agccagtgac ctaaccgaaa    1440
ggaaggagct gtcgaaggca ggctcgataa ctggggtgaa gtcgtaacaa ggtagccgta    1500
tcggaaggtg cggctggatc acctcctt                                       1529
```

<210> SEQ ID NO 9
<211> LENGTH: 1118
<212> TYPE: DNA
<213> ORGANISM: Artificial Sequence
<220> FEATURE:
<223> OTHER INFORMATION: Synthetic Polynucleotide

<400> SEQUENCE: 9

```
aacggccaca ttgggactga gacacggccc agactcctac gggaggcagc agtggggaat     60
attgcacaat gggggaaacc ctgatgcagc gacgccgcgt gaaggaagaa gtatctcggt    120
atgtaaactt ctatcagcag ggaagatagt gacggtacct gactaagaag ccccggctaa    180
ctacgtgcca gcagccgcgg taatacgtag ggggcaagcg ttatccggat ttactgggtg    240
taaagggagc gtagacggac tggcaagtct gatgtgaaag gcggggggctc aacccctgga    300 ctgcattgga aactgttagt cttgagtgcc ggagaggtaa gcggaattcc tagtgtagcg    360
gtgaaatgcg tagatattag gaggaacacc agtggcgaag gcggcttact ggacggtaac    420
tgacgttgag gctcgaaagc gtggggagca acaggatta gataccctgg tagtccacgc    480
cgtaaacgat gaatactagg tgttggggag caaagctctt cggtgccgcc gcaaacgcat    540
taagtattcc acctggggag tacgttcgca agaatgaaac tcaaaggaat tgacggggac    600
ccgcacaagc ggtggagcat gtggtttaat tcgaagcaac gcgaagaacc ttaccaagtc    660
ttgacatccc tctgaccgtt ccttaaccgg aactttcctt cgggacaggg gagacaggtg    720
gtgcatggtt gtcgtcagct cgtgtcgtga tgttgggt taagtcccgc aacgagcgca    780 accctatcc ccagtagcca gcagtccggc tgggcactct gaggagactg ccagggataa    840
cctggaggaa ggcggggatg acgtcaaatc atcatgcccc ttatgatttg gctacacac    900 gtgctacaat ggcgtaaaca agggaagca agcctgcgaa ggtaagcaaa tcccaaaaat    960
aacgtcccag ttcggactgc agtctgcaac tcgactgcac gaagctggaa tcgctagtaa   1020
tcgcggatca gaatgccgcg gtgaatacgt tcccgggtct tgtacacacc gcccgtcaca   1080
ccatgggagt cagtaacgcc cgaagtcagt gacctaac                           1118
```

<210> SEQ ID NO 10
<211> LENGTH: 1531
<212> TYPE: DNA
<213> ORGANISM: Artificial Sequence

```
<220> FEATURE:
<223> OTHER INFORMATION: Synthetic Polynucleotide

<400> SEQUENCE: 10
aaaggaggtg atccagccgc accttccgat acggctacct tgttacgact tcacccagt       60 tacctgcccc gccttcggca gctccctcct gttaaggttg ggtcactgac ttcgggcgtt     120
gctgactccc atggtgtgac gggcggtgtg tacaagaccc gggaacgtat tcaccgcggc     180
attctgatcc gcgattacta gcgattccag cttcgtgtag tcgggttgca gactacagtc     240
cgaactggga cgttattttt gggatttgct tgccttcgca gggtcgcctc cctttgttta     300
cgccattgta gcacgtgtgt agcccaaatc ataaggggca tgatgatttg acgtcatccc     360
caccttcctc caggttatcc ctggcagtct ccctagagtg cccaccacga cgtgctggct     420
actaaggata agggttgcgc tcgttgcggg acttaaccca acatctcacg acacgagctg     480
acgacaacca tgcaccacct gtctctcttg ccccgaaggg aaggcgccgt tacacgccgg     540
tcaagaggat gtcaagactt ggtaaggttc ttcgcgttgc ttcgaattaa accacatgct     600
ccaccgcttg tgcgggtccc cgtcaattcc tttgagtttc attcttgcga acgtactccc     660
caggtggaat gcttattgcg ttagcggcgg caccgaaggg ctttgccccc cgacacctag     720
cattcatcgt ttacggcgtg gactaccagg gtatctaatc ctgtttgctc cccacgcttt     780
cgagcctcaa cgtcagttac agtccagtaa gccgccttcg ccactggtgt tcctcctaat     840
atctacgcat ttcaccgcta cactaggaat tccacttacc tctcctgcac tccagcagca     900
cagtttccaa agcagtcccg ggttgggcc ccgggctttc actccagact gcgtcgccg      960 tctacgctcc ctttacaccc agtaaatccg gataacgctt gccccctacg tattaccgcg    1020
gctgctggca cgtagttagc cggggcttct tagtcaggta ccgtcatttt cttccctgct    1080
gatagagctt tacataccga gatacttctt cactcacgcg gcgtcgctgc atcaggcttg    1140
cgcccattgt gcaatattcc ccactgctgc ctcccgtagg agtttgggcc gtgtctcagt    1200
cccaatgtgg ccggtcaccc tctcaggtcg gctactgatc gtcgctttgg tgggccgtta    1260
ccccgccaac tggctaatca gacgcggatc catctcacac cacctgggtt tttcacaccg    1320
taccatgcgg tactgtgcgc ttatgcggta ttagcagcca tttctaactg ttatccccca    1380
gtgtgaggca ggttatccac gcgttactca cccgtccgcc actcagtcaa ccaggaatcc    1440
atccgaaaac ttcatcctaa tcgcttcgtt cgacttgcat gtgttaggca cgccgccagc    1500
gttcatcctg agccaggatc aaactctcaa a                                   1531

<210> SEQ ID NO 11
<211> LENGTH: 1523
<212> TYPE: DNA
<213> ORGANISM: Artificial Sequence
<220> FEATURE:
<223> OTHER INFORMATION: Synthetic Polynucleotide

<400> SEQUENCE: 11
atgaagagtt tgatcctggc tcaggatgaa cgctagctac aggcttaaca catgcaagtc      60
gaggggcagc atgaacttag cttgctaagt ttgatggcga ccggcgcacg ggtgagtaac     120
acgtatccaa cctgccgatg actcggggat agcctttcga agaaagatt aatacccgat      180 ggcatagttc ttccgcatgg tggaactatt aaagaatttc ggtcatcgat ggggatgcgt     240
tccattaggt tgttggcggg gtaacggccc accaagcctt cgatggatag ggttctgag      300 aggaaggtcc cccacattgg aactgagaca cggtccaaac tcctacggga ggcagcagtg     360
```

| | |
|---|---:|
| aggaatattg gtcaatggac gagagtctga accagccaag tagcgtgaag gatgactgcc | 420 |
| ctatgggttg taaacttctt ttatacggga ataaagtgag gcacgtgtgc cttttttgtat | 480 |
| gtaccgtatg aataaggatc ggctaactcc gtgccagcag ccgcggtaat acggaggatc | 540 |
| cgagcgttat ccggatttat tgggtttaaa gggagcgtag gcggacgctt aagtcagttg | 600 |
| tgaaagtttg cggctcaacc gtaaaattgc agttgatact gggtgtcttg agtacagtag | 660 |
| aggcaggcgg aattcgtggt gtagcggtga aatgcttaga tatcacgaag aactccgatt | 720 |
| gcgaaggcag cttgctggac tgtaactgac gctgatgctc gaaagtgtgg gtatcaaaca | 780 |
| ggattagata ccctggtagt ccacacagta acgatgaat actcgctgtt tgcgatatac | 840 |
| agtaagcggc caagcgaaag cgttaagtat tccacctggg gagtacgccg gcaacggtga | 900 |
| aactcaaagg aattgacggg ggcccgcaca agcggaggaa catgtggttt aattcgatga | 960 |
| tacgcgagga accttacccg ggcttgaatt gcaactgaat gatgtggaga catgtcagcc | 1020 |
| gcaaggcagt tgtgaaggtg ctgcatggtt gtcgtcagct cgtgccgtga ggtgtcggct | 1080 |
| taagtgccat aacgagcgca acccttatcg atagttacca tcaggttatg ctggggactc | 1140 |
| tgtcgagact gccgtcgtaa gatgtgagga aggtggggat gacgtcaaat cagcacggcc | 1200 |
| cttacgtccg gggctacaca cgtgttacaa tgggggggtac agaaggcagc tacacggcga | 1260 |
| cgtgatgcta atcccgaaag cctctctcag ttcggattgg agtctgcaac ccgactccat | 1320 |
| gaagctggat tcgctagtaa tcgcgcatca gccacgcgc ggtgaatacg ttcccgggcc | 1380 |
| ttgtacacac cgcccgtcaa gccatgaaag ccgggggtac ctgaagtgcg taaccgcaag | 1440 |
| gagcgcccta gggtaaaaact ggtgattggg gctaagtcgt aacaaggtag ccgtaccgga | 1500 |
| aggtgcggct ggaacaccctc ctt | 1523 |

<210> SEQ ID NO 12
<211> LENGTH: 1319
<212> TYPE: DNA
<213> ORGANISM: Artificial Sequence
<220> FEATURE:
<223> OTHER INFORMATION: Synthetic Polynucleotide

<400> SEQUENCE: 12

| | |
|---|---:|
| tgattaaagg tattccggta gacgatgggg atgcgttcca ttagatagta ggcggggtaa | 60 |
| cggcccacct agtcttcgat ggatagggt tctgagagga aggtccccca cattggaact | 120 |
| gagacacggt ccaaactcct acgggaggca gcagtgagga atattggtca atgggcgcag | 180 |
| gcctgaacca gccaagtagc gtgaaggatg actgccctat gggttgtaaa cttctttttat | 240 |
| aaaggaataa agtcgggtat gtataccccgt ttgcatgtac tttatgaata aggatcggct | 300 |
| aactccgtgc cagcagccgc ggtaatacgg aggatccgag cgttatccgg atttattggg | 360 |
| tttaagggga gcgtagatgg atgtttaagt cagttgtgaa agtttgcggc tcaaccgtaa | 420 |
| aattgcagtt gatactggat atcttgagtg cagttgaggc aggcgaatt cgtggtgtag | 480 |
| cggtgaaatg cttagatatc acgaagaact ccgattgcga aggcagcctg ctaagctgca | 540 |
| actgacattg aggctcgaaa gtgtgggtat caaacaggat tagatacct ggtagtccac | 600 |
| acggtaaacg atgaatactc gctgtttgcg atatacggca agcggccaag cgaaagcgtt | 660 |
| aagtattcca cctggggagt acgccggcaa cggtgaaact caaaggaatt gacggggcc | 720 |
| cgcacaagcg gaggaacatg tggtttaatt cgatgatacg cgaggaacct tacccgggct | 780 |
| taaattgcag atgaattacg gtgaaagccg taagccgcaa ggcatctgtg aaggtgctgc | 840 |
| atggttgtcg tcagctcgtg ccgtgaggtg tcggcttaag tgccataacg agcgcaaccc | 900 |

```
ttgttgtcag ttactaacag gtttcgctga ggactctgac aagactgcca tcgtaagatg    960
tgaggaaggt ggggatgacg tcaaatcagc acggcccta cgtccggggc tacacacgtg   1020
ttacaatggg gggtacagag ggccgctacc acgcgagtgg atgccaatcc ccaaaacctc   1080
tctcagttcg gactggagtc tgcaacccga ctccacgaag ctggattcgc tagtaatcgc   1140
gcatcagcca cggcgcggtg aatacgttcc cgggccttgt acacaccgcc cgtcaagcca   1200
tgggagccgg gggtacctga agtgcgtaac cgcgaggagc gccctagggt aaaactggtg   1260 actgggcta agtcgtaaca aggtagccgt accggaaggt gcggctggaa cacctcctt    1319
```

<210> SEQ ID NO 13
<211> LENGTH: 1523
<212> TYPE: DNA
<213> ORGANISM: Artificial Sequence
<220> FEATURE:
<223> OTHER INFORMATION: Synthetic Polynucleotide

<400> SEQUENCE: 13

```
atgaagagtt tgatcctggc tcaggatgaa cgctagctac aggcttaaca catgcaagtc     60
gaggggcagc atcatcaaag cttgctttga tggatggcga ccggcgcacg ggtgagtaac    120
acgtatccaa cctgccgaca cactgggat agcctttcga agaaagatt ataccggat    180 ggcatagttt tcccgcatgg gataattatt aaagaatttc ggttgtcgat ggggatgcgt    240
tccattaggc agttggcggg gtaacggccc accaaaccaa cgatggatag ggttctgag    300 aggaaggtcc cccacattgg aactgagaca cggtccaaac tcctacggga ggcagcagtg    360
aggaatattg gtcaatggac gagagtctga accagccaag tagcgtgaag gatgactgcc    420 ctatggttg taaacttctt ttatacggga ataaagtgag ccacgtgtgg cttttttgtat    480 gtaccgtatg aataaggatc ggctaactcc gtgccagcag ccgcggtaat acggaggatc    540
cgagcgttat ccggatttat tgggtttaaa gggagcgtag gcgggttgtt aagtcagttg    600
tgaaagtttg cggctcaacc gtaaaattgc agttgatact ggcgaccttg agtgcaacag    660
aggtaggcgg aattcgtggt gtagcggtga atgcttaga tatcacgaag aactccgatt    720
gcgaaggcag cttactggat tgtaactgac gctgatgctc gaaagtgtgg gtatcaaaca    780
ggattagata ccctggtagt ccacacagta acgatgaat actcgctgtt ggcgatatac    840
ggtcagcggc caagcgaaag cattaagtat tccacctggg gagtacgccg gcaacggtga    900
aactcaaagg aattgacggg ggcccgcaca agcggaggaa catgtggttt aattcgatga    960
tacgcgagga accttacccg gcttaaatt gcaactgacg gaaccggaaa cggttctttc   1020
ttcggacagt tgtgaaggtg ctgcatggtt gtcgtcagct cgtgccgtga ggtgtcggct   1080
taagtgccat aacgagcgca acccttacgg gtagttacca tcaggttatg ctgggactc    1140 tacccggact gccgtcgtaa gatgtgagga aggtgggat gacgtcaaat cagcacggcc   1200
cttacgtccg gggctacaca cgtgttacaa tgggggggac agaaggcagc tacacggcga   1260
cgtggtgcta atcccaaaag cctctctcag ttcggattgg agtctgcaac ccgactccat   1320
gaagctggat tcgctagtaa tcgcgcatca gccacggcgc ggtgaatacg ttcccgggcc   1380
ttgtacacac cgcccgtcaa gccatgaaag ccggggtac ctgaagtacg taaccgcgag   1440
gagcgtccta gggtaaaact ggtgattggg ctaagtcgt aacaaggtag ccgtaccgga   1500
aggtgcggct ggaacacctc ctt                                          1523
```

<210> SEQ ID NO 14

```
<211> LENGTH: 1519
<212> TYPE: DNA
<213> ORGANISM: Artificial Sequence
<220> FEATURE:
<223> OTHER INFORMATION: Synthetic Polynucleotide

<400> SEQUENCE: 14
atgaagagtt tgatcctggc tcaggatgaa cgctagctac aggcttaaca catgcaagtc      60 gagggggcagc atgacctagc aataggttga tggcgaccgg cgcacgggtg agtaacacgt     120
atccaaccta ccggttattc cgggatagcc tttcgaaaga aagattaata ccggatagta     180
taacgagaag gcatcttttt gttattaaag aatttcgata accgatgggg atgcgttcca     240
ttagtttgtt ggcggggtaa cggcccacca agacatcgat ggataggggt tctgagagga     300
aggtccccca cattggaact gagacacggt ccaaactcct acgggaggca gcagtgagga     360
atattggtca atggacgaga gtctgaacca gccaagtagc gtgaaggatg actgccctat     420
gggttgtaaa cttctttat  atgggaataa agtgagccac gtgtggcttt tgtatgtac      480 catacgaata aggatcggct aactccgtgc cagcagccgc ggtaatacgg aggatccgag     540
cgttatccgg atttattggg tttaaaggga gcgtaggcgg actattaagt cagctgtgaa     600
agtttgcggc tcaaccgtaa aattgcagtt gatactggtc gtcttgagtg cagtagaggt     660
aggcggaatt cgtggtgtag cggtgaaatg cttagatatc acgaagaact ccgattgcga     720
aggcagctta ctggactgta actgacgctg atgctcgaaa gtgtgggtat caaacaggat     780
tagataccct ggtagtccac acagtaaacg atgaatactc gctgtttgcg atatacagca     840
agcggccaag cgaaagcatt aagtattcca cctggggagt acgccggcaa cggtgaaact     900
caaaggaatt gacggggggcc cgcacaagcg gaggaacatg tggtttaatt cgatgatacg     960
cgaggaacct acccgggct aaattgcat ctgaataatt tggaaacaga ttagccgcaa     1020
ggcagatgtg aaggtgctgc atggttgtcg tcagctcgtg ccgtgaggtg tcggcttaag    1080
tgccataacg agcgcaaccc ttatctttag ttactaacag gtcatgctga ggactctaga    1140
gagactgccg tcgtaagatg tgaggaaggt ggggatgacg tcaaatcagc acggccctta    1200 cgtccgggc tacacacgtg ttacaatggg ggtacagaa ggcagctaca cagcgatgtg     1260
atgctaatcc caaaagcctc tctcagttcg gattggagtc tgcaacccga ctccatgaag    1320
ctggattcgc tagtaatcgc gcatcagcca cggcgcggtg aatacgttcc cgggccttgt    1380
acacaccgcc cgtcaagcca tgaaagccgg gggtacctga agtccgtaac cgtaaggagc    1440
ggcctagggt aaaactggta attggggcta agtcgtaaca aggtagccgt accggaaggt    1500
gcggctggaa cacctcctt                                                 1519

<210> SEQ ID NO 15
<211> LENGTH: 1521
<212> TYPE: DNA
<213> ORGANISM: Artificial Sequence
<220> FEATURE:
<223> OTHER INFORMATION: Synthetic Polynucleotide

<400> SEQUENCE: 15
atggagagtt tgatcctggc tcaggatgaa cgctagcggc aggcctaaca catgcaagtc      60 gagggggcatc acgaggtagc aatactttgg tggcgaccgg cgcacgggtg cgtaacgcgt    120
atgtaaccta cctataacag gggcataaca ctgagaaatt ggtactaatt ccccataata    180
ttcggagagg catctctccg ggttgaaaac tccggtggtt atagatggac atgcgttgta    240
ttagctagtt ggtgaggtaa cggctcacca aggcaacgat acatagggggg actgagaggt    300
```

```
taaccccca cactggtact gagacacgga ccagactcct acgggaggca gcagtgagga    360
atattggtca atggacgcaa gtctgaacca gccatgccgc gtgcaggaag acggctctat    420
gagttgtaaa ctgcttttgt acgagggtaa actcacctac gtgtaggtga ctgaaagtat    480
cgtacgaata aggatcggct aactccgtgc cagcagccgc ggtaatacgg aggattcaag    540
cgttatccgg atttattggg tttaaagggt gcgtaggcgg tttgataagt tagaggtgaa    600 atcccgggc ttaactccgg aactgcctct aatactgtta gactagagag tagttgcggt    660
aggcggaatg tatggtgtag cggtgaaatg cttagagatc atacagaaca ccgattgcga    720
aggcagctta ccaaactata tctgacgttg aggcacgaaa gcgtggggag caaacaggat    780 tagatacct ggtagtccac gcagtaaacg atgataactc gttgtcggcg atacacagtc    840
ggtgactaag cgaaagcgat aagttatcca cctggggagt acgttcgcaa gaatgaaact    900
caaaggaatt gacggggcc cgcacaagcg gaggaacatg tggtttaatt cgatgatacg    960
cgaggaacct acccgggct tgaaagttac tgacgattct ggaaacagga tttccctttg    1020
gggcaggaaa ctaggtgctg catggttgtc gtcagctcgt gccgtgaggt gtcgggttaa    1080
gtcccataac gagcgcaacc cctaccgtta gttgccatca ggtcaagctg gcactctgg    1140 cgggactgcc ggtgtaagcc gagaggaagg tggggatgac gtcaaatcag cacggccctt    1200
acgtccgggg ctacacacgt gttacaatgg taggtacaga gggtcgctac tccgtgagga    1260
gatgccaatc tcgaaagcct atctcagttc ggattggagg ctgaaacccg cctccatgaa    1320
gttggattcg ctagtaatcg cgcatcagcc atggcgcggt gaatacgttc ccgggccttg    1380
tacacaccgc ccgtcaagcc atggaagctg ggggtgcctg aagttcgtga ccgcaaggag    1440
cgacctaggg caaaaccggt aactggggct aagtcgtaac aaggtagccg taccggaagg    1500
tgcggctgga cacctccttt                                                1521
```

<210> SEQ ID NO 16
<211> LENGTH: 1523
<212> TYPE: DNA
<213> ORGANISM: Artificial Sequence
<220> FEATURE:
<223> OTHER INFORMATION: Synthetic Polynucleotide

<400> SEQUENCE: 16

```
atgaagagtt tgatcctggc tcaggatgaa cgctagctac aggcttaaca catgcaagtc     60
gaggggcagc atgaacttag cttgctaagt ttgatggcga ccggcgcacg ggtgagtaac    120
acgtatccaa cctgccgatg actcggggat agcctttcga aagaaagatt aatacccgat    180
ggcatagttc ttccgcatgg tagaactatt aaagaatttc ggtcatcgat ggggatgcgt    240
tccattaggt tgttggcggg gtaacggccc accaagcctt cgatggatag ggttctgag    300 aggaaggtcc cccacattgg aactgagaca cggtccaaac tcctacggga ggcagcagtg    360
aggaatattg gtcaatggac gagagtctga accagccaag tagcgtgaag gatgactgcc    420
ctatgggttg taaacttctt ttatacggga ataaagtgag gcacgtgtgc cttttttgtat    480 gtaccgtatg aataaggatc ggctaactcc gtgccagcag ccgcggtaat acggaggatc    540
cgagcgttat ccggatttat tgggtttaaa gggagcgtag gcggacgctt aagtcagttg    600
tgaaagtttg cggctcaacc gtaaaattgc agttgatact gggtgtcttg agtacagtag    660
aggcaggcgg aattcgtggt gtagcggtga aatgcttaga tatcacgaag aactccgatt    720
gcgaaggcag cttgctggac tgtaactgac gctgatgctc gaaagtgtgg gtatcaaaca    780
```

```
ggattagata ccctggtagt ccacacagta aacgatgaat actcgctgtt tgcgatatac    840
agtaagcggc caagcgaaag cgttaagtat tccacctggg gagtacgccg gcaacggtga    900
aactcaaagg aattgacggg ggcccgcaca agcggaggaa catgtggttt aattcgatga    960
tacgcgagga accttacccg ggcttgaatt gcaactgaat gatgtggaga catgtcagcc   1020
gcaaggcagt tgtgaaggtg ctgcatggtt gtcgtcagct cgtgccgtga ggtgtcggct   1080
taagtgccat aacgagcgca acccttatcg atagttacca tcaggttatg ctggggactc   1140
tgtcgagact gccgtcgtaa gatgtgagga aggtggggat gacgtcaaat cagcacggcc   1200
cttacgtccg gggctacaca cgtgttacaa tggggggtac agaaggcagc tacacggcga   1260
cgtgatgcta atccctaaag cctctctcag ttcggattgg agtctgcaac ccgactccat   1320
gaagctggat tcgctagtaa tcgcgcatca gccacggcgc ggtgaatacg ttcccgggcc   1380
ttgtacacac cgcccgtcaa gccatgaaag ccggggggtac ctgaagtgcg taaccgcaag   1440
gagcgcccta gggtaaaact ggtgattggg gctaagtcgt aacaaggtag ccgtaccgga   1500
aggtgcggct ggaacacctc ctt                                           1523

<210> SEQ ID NO 17
<211> LENGTH: 1527
<212> TYPE: DNA
<213> ORGANISM: Artificial Sequence
<220> FEATURE:
<223> OTHER INFORMATION: Synthetic Polynucleotide

<400> SEQUENCE: 17
acgagagttt gatcctggct caggatgaac gctggcggcg tgcttaacac atgcaagtcg     60
aacgaagcac ctggatttga ttcttcggat gaagatcctt gtgactgagt ggcggacggg    120
tgagtaacgc gtgggtaacc tgcctcatac agggggataa cagttagaaa tgactgctaa    180
taccgcataa gaccacaggg tcgcatgacc tggtgggaaa actccggtg gtatgagatg    240 gacccgcgtc tgattaggta gttggtgggg taacggccta ccaagccgac gatcagtagc    300
cgacctgaga gggtgaccgg ccacattggg actgagacac ggcccaaact cctacgggag    360
gcagcagtgg ggaatattgc acaatggggg aaaccctgat gcagcgacgc cgcgtgagcg    420
aagaagtatt tcggtatgta aagctctatc agcagggaag aaaatgacgg tacctgacta    480
agaagcaccg gctaaatacg tgccagcagc cgcggtaata cgtatggtgc aagcgttatc    540
cggatttact gggtgtaaag ggagcgtaga cggctgtgta agtctgaagt gaaagcccgg    600
ggctcaaccc cgggactgct ttggaaacta tgcagctaga gtgtcggaga ggtaagtgga    660
attcccagtg tagcggtgaa atgcgtagat attgggagga acaccagtgg cgaaggcggc    720
ttactggacg atgactgacg ttgaggctcg aaagcgtggg gagcaaacag gattagatac    780
cctggtagtc cacgccgtaa acgatgacta ctaggtgtcg gggagcaaag ctcttcggtg    840
ccgcagcaaa cgcaataagt agtccacctg gggagtacgt tcgcaagaat gaaactcaaa    900
ggaattgacg gggacccgca caagcggtgg agcatgtggt ttaattcgaa gcaacgcgaa    960
gaaccttacc tgctcttgac atccggtga ccggcatgta atgatgcctt tcttcggaa   1020 caccggtgac aggtggtgca tggttgtcgt cagctcgtgt cgtgagatgt tgggttaagt   1080
cccgcaacga gcgcaaccct tatcttcagt agccagcatt taggtgggc actctggaga   1140 gactgccagg gataacctgg aggaaggtgg ggatgacgtc aaatcatcat gccccttatg   1200
agcagggcta cacacgtgct acaatggcgt aaacaaaggg aagcaaacct gtgagggtaa   1260
gcaaatctca aaaataacgt ctcagttcgg attgtagtct gcaactcgac tacatgaagc   1320
```

```
tggaatcgct agtaatcgcg aatcagcatg tcgcggtgaa tacgttcccg ggtcttgtac    1380
acaccgcccg tcacaccatg ggagttggta acgcccgaag tcagtgactc aaccgtaagg    1440
agagagctgc cgaaggtggg accgataact ggggtgaagt cgtaacaagg tagccgtatc    1500
ggaaggtgcg gctggatcac ctccttt                                        1527
```

<210> SEQ ID NO 18
<211> LENGTH: 1521
<212> TYPE: DNA
<213> ORGANISM: Artificial Sequence
<220> FEATURE:
<223> OTHER INFORMATION: Synthetic Polynucleotide

<400> SEQUENCE: 18

```
atggagagtt tgatcctggc tcaggatgaa cgctagcggc aggcctaaca catgcaagtc      60
gaggggcagc acggtgtagc aatacactgg tgcgaccgg cgcacgggtg cgtaacgcgt     120
atgcaaccta cccataacag ggggataaca ctgagaaatt ggtactaata ccccataaca    180
tcaggaccgg catcggttct ggttgaaaac tccggtggtt atggatgggc atgcgttgta    240
ttagctggtt ggtgaggtaa cggctcacca aggcaacgat acataggggg actgagaggt    300 taaccccca cattggtact gagacacgga ccaaactcct acgggaggca gcagtgagga    360
atattggtca atggacgcaa gtctgaacca gccatgccgc gtgcaggaag acggctctat    420
gagttgtaaa ctgcttttgt acgagagtaa acgctcttac gtgtaagagc ctgaaagtat    480
cgtacgaata aggatcggct aactccgtgc cagcagccgc ggtaatacgg aggatccaag    540
cgttatccgg atttattggg tttaaagggt gcgtaggcgg tttgataagt tagaggtgaa    600
ataccggtgc ttaacaccgg aactgcctct aatactgttg aactagagag tagttgcggt    660
aggcggaatg tatggtgtag cggtgaaatg cttagagatc atacagaaca ccgattgcga    720
aggcagctta ccaaactata tctgacgttg aggcacgaaa gcgtggggag caaacaggat    780
tagataccct ggtagtccac gcagtaaacg atgataactc gctgtcggcg atacacggtc    840
ggcggctaag cgaaagcgat aagttatcca cctggggagt acgttcgcaa gaatgaaact    900
caaaggaatt gacggggggcc cgcacaagcg gaggaacatg tggtttaatt cgatgatacg    960
cgaggaacct tacccgggct tgaaagttac tgacgattct ggaaacagga tttcccttcg   1020
gggcaggaaa ctaggtgctg catggttgtc gtcagctcgt gccgtgaggt gtcgggttaa   1080
gtcccataac gagcgcaacc cctaccgtta gttgccatca ggtcaagctg ggcactctgg   1140
cgggactgcc ggtgtaagcc gagaggaagt ggggatgac gtcaaatcag cacggccctt    1200
acgtccgggg ctacacacgt gttacaatgg taggtacaga gggcagctac ccagtgatgg   1260
gatgcgaatc tcgaaagcct atctcagttc ggatcgagg ctgaaacccg cctccgtgaa    1320
gttggattcg ctagtaatcg cgcatcagcc atggcgcggt gaatacgttc ccgggccttg   1380
tacacaccgc ccgtcaagcc atggaagctg ggggtgcctg aagttcgtga ccgcaaggag   1440
cgacctaggg caaaaccggt gactggggct aagtcgtaac aaggtagccg taccggaagg   1500
tgcggctgga acacctcctt t                                              1521
```

<210> SEQ ID NO 19
<211> LENGTH: 1530
<212> TYPE: DNA
<213> ORGANISM: Artificial Sequence
<220> FEATURE:
<223> OTHER INFORMATION: Synthetic Polynucleotide

<400> SEQUENCE: 19

```
atgagagttt gatcctggct caggatgaac gctggcggcg tgcttaacac atgcaagtcg    60
aacgaagcac tctatttgat tttcttcgga atgaagatt ttgtgactga gtggcggacg   120
ggtgagtaac gcgtgggtaa cctgcctcat acagggggat aacagttgga aacgactgct   180
aataccgcat aagcgcacag gatcacatga tccggtgtga aaaactccgg tggtatgaga   240
tggacccgcg tctgattagc cagttggcag ggtaacggcc taccaaagcg acgatcagta   300
gccgacctga gagggtgacc ggccacattg ggactgagac acggcccaaa ctcctacggg   360
aggcagcagt ggggaatatt gcacaatggg gaaaccctg atgcagcgac gccgcgtgag   420
cgaagaagta tttcggtatg taaagctcta tcagcaggga agaagaatga cggtacctga   480
ctaagaagca ccggctaaat acgtgccagc agccgcggta atacgtatgg tgcaagcgtt   540
atccggattt actgggtgta aagggagcgc aggcggtgcg gcaagtctga tgtgaaagcc   600
cggggctcaa ccccggtact gcattggaaa ctgtcgtact agagtgtcgg aggggtaagt   660
ggaattccta gtgtagcggt gaaatgcgta gatattagga ggaacaccag tggcgaaggc   720
ggcttactgg acgataactg acgctgaggc tcgaaagcgt ggggagcaaa caggattaga   780
taccctggta gtccacgccg taaacgatga atactaggtg tcggggagca ttgctcttcg   840
gtgccgcagc aaacgcaata agtattccac ctggggagta cgttcgcaag aatgaaactc   900
aaaggaattg acgggacccc gcacaagcgg tggagcatgt ggtttaattc gaagcaacgc   960
gaagaacctt accaagtctt gacatcccga tgacagggta tgtaatgtac tttctcttcg  1020
gagcatcggt gacaggtggt gcatggttgt cgtcagctcg tgtcgtgaga tgttgggtta  1080
agtcccgcaa cgagcgcaac ccctgtcctt agtagccagc ggttcggccg ggcactctag  1140
ggagactgcc agggataacc tggaggaagg cggggatgac gtcaaatcat catgcccctt  1200
atgacttggg ctacacacgt gctacaatgg cgtaaacaaa gggaagcgga gccgtgaggc  1260
cgagcaaatc tcaaaaataa cgtctcagtt cggactgtag tctgcaaccc gactacacga  1320
agctggaatc gctagtaatc gcagatcaga atgctgcggt gaatacgttc ccgggtcttg  1380
tacacaccgc ccgtcacacc atgggagttg gaaatgcccg aagtcagtga cccaaccgca  1440
aggagggagc tgccgaaggc aggttcgata actggggtga agtcgtaaca aggtagccgt  1500
atcggaaggt gcggctggat cacctccttt                                    1530
```

<210> SEQ ID NO 20
<211> LENGTH: 1509
<212> TYPE: DNA
<213> ORGANISM: Artificial Sequence
<220> FEATURE:
<223> OTHER INFORMATION: Synthetic Polynucleotide

<400> SEQUENCE: 20

```
atggagagtt tgattctggc tcagaacgaa cgctggcggc gtggataaga catgcaagtc    60
gaacgagaga attgctagct tgctaataat tctctagtgg cgcacgggtg agtaacacgt   120
gagtaacctg cccccgagag cgggatagcc ctgggaaact gggattaata ccgcatagta   180
tcgaaagatt aaagcagcaa tgcgcttggg atgggctcg cggcctatta gttagttggt   240
gaggtaacgg ctcaccaagg cgatgacggg tagccggtct gagaggatgt ccggccacac   300
tggaactgag acacggtcca gacacctacg ggtggcagca gtcgagaatc attcacaatg   360
gggaaaccc tgatggtgcg acgccgcgtg ggggaatgaa ggtcttcgga ttgtaaaccc   420
ctgtcatgtg ggagcaaatt aaaaagatag taccacaaga ggaagagacg gctaactctg   480
```

```
tgccagcagc cgcggtaata cagaggtctc aagcgttgtt cggaatcact gggcgtaaag      540
cgtgcgtagg ctgtttcgta agtcgtgtgt gaaaggcgcg ggctcaaccc gcggacggca      600
catgatactg cgagactaga gtaatggagg gggaaccgga attctcggtg tagcagtgaa      660
atgcgtagat atcgagagga acactcgtgg cgaaggcggt tcctggaca ttaactgacg       720 ctgaggcacg aaggccaggg gagcgaaagg gattagatac ccctgtagtc ctggcagtaa      780
acggtgcacg cttggtgtgc ggggaatcga ccccctgcgt gccggagcta acgcgttaag      840
cgtgccgcct ggggagtacg gtcgcaagat taaaactcaa agaaattgac ggggacccgc      900
acaagcggtg gagtatgtgg cttaattcga tgcaacgcga agaaccttac ctgggcttga      960
catgtaatga acaacatgtg aaagcatgcg actcttcgga ggcgttacac aggtgctgca     1020
tggccgtcgt cagctcgtgt cgtgagatgt tgggttaagt ccagcaacga gcgcaacccc     1080
tgttgccagt taccagcacg tgaaggtggg gactctggcg agactgccca gatcaactgg     1140
gaggaaggtg gggacgacgt caggtcagta tggcccttat gcccagggct gcacacgtac     1200
tacaatgccc agtacagagg gggccgaagc cgcgaggcgg aggaaatcct aaaaactggg     1260
cccagttcgg actgtaggct gcaacccgcc tacacgaagc cggaatcgct agtaatggcg     1320
catcagctac ggcgccgtga atacgttccc gggtcttgta cacaccgccc gtcacatcat     1380
ggaagccggt cgcacccgaa gtatctgaag ccaaccgcaa ggaggcaggg tcctaaggtg     1440
agactggtaa ctgggatgaa gtcgtaacaa ggtagccgta ggggaacctg cggctggatc     1500
acctcctttt                                                            1509

<210> SEQ ID NO 21
<211> LENGTH: 1557
<212> TYPE: DNA
<213> ORGANISM: Artificial Sequence
<220> FEATURE:
<223> OTHER INFORMATION: Synthetic Polynucleotide

<400> SEQUENCE: 21
attggagagt ttgatcctgg ctcaggacga acgctggcgg cgtgcctaac acatgcaagt       60
cgaacggaga attttatttc ggtagaattc ttagtggcga acgggtgagt aacgcgtagg      120
caacctgccc tttagacggg gacaacattc gaaaggagt gctaataccg gatgtgatca       180
tcgtgccgca tggcaggatg aagaaagatg gcctctacaa gtaagctatc gctaaaggat      240
gggcctgcgt ctgattagct agttggtagt gtaacggact accaaggcga tgatcagtag      300
ccggtctgag aggatgaacg gccacattgg gactgagaca cggcccaaac tcctacggga      360
ggcagcagtg gggaatcttc cgcaatggac gaaagtctga cggagcaacg ccgcgtgagt      420
gatgaaggat ttcggtctgt aaagctctgt tgtttatgac gaacgtgcag tgtgtgaaca      480
atgcattgca atgacggtag taaacgagga agccacggct aactacgtgc cagcagccgc      540
ggtaatacgt aggtggcgag cgttgtccgg aattattggg cgtaaagagc atgtaggcgg      600
cttaataagt cgagcgtgaa aatgcggggc tcaacccgt atggcgctgg aaactgttag       660
gcttgagtgc aggagaggaa agggaattc ccagtgtagc ggtgaaatgc gtagatattg       720
ggaggaacac cagtggcgaa ggcgcctttc tggactgtgt ctgacgctga gatgcgaaag      780
ccagggtagc gaacgggatt agataccccg gtagtcctgg ccgtaaacga tgggtactag      840
gtgtaggagg tatcgacccc ttctgtgccg gagttaacgc aataagtacc cgcctgggg      900 agtacggccg caaggttgaa actcaaagga attgacgggg cccgcacaa gcggtggagt       960
```

| | | |
|---|---|---|
| atgtggttta attcgacgca acgcgaagaa ccttaccaag gcttgacatt gattgaacgc | 1020 | |
| tctagagata gagatttccc ttcggggaca agaaaacagg tggtgcatgg ctgtcgtcag | 1080 | |
| ctcgtgtcgt gagatgttgg gttaagtccc gcaacgagcg caaccccat cctatgttac | 1140 | |
| cagcaagtaa agttggggac tcatgggaga ctgccaggga caacctggag gaaggcgggg | 1200 | |
| atgacgtcaa gtcatcatgc cccttatgtc ttgggctaca cacgtactac aatggtcgga | 1260 | |
| aacagaggga agcgaagccg cgaggcagag caaaccccag aaaccccgatc tcagttcgga | 1320 | |
| tcgcaggctg caacccgcct gcgtgaagtc ggaatcgcta gtaatcgcag gtcagcatac | 1380 | |
| tgcggtgaat acgttcccgg gccttgtaca caccgcccgt cacaccacga agttggtaa | 1440 | |
| cacccgaagc cggtgaggta acctataagg agccagccgt ctaaggtggg gccgatgatt | 1500 | |
| ggggtgaagt cgtaacaagg tagccgtatc ggaaggtgcg gctggatcac ctccttt | 1557 | |

```
<210> SEQ ID NO 22
<211> LENGTH: 809
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (631)..(631)
<223> OTHER INFORMATION: n is a, c, g, or t

<400> SEQUENCE: 22
```

| | | |
|---|---|---|
| ctgaggggt caatccccca acacctagta atcatcgttt acggcatgga ctaccagggt | 60 | |
| atctaatcct gtttgctacc catgctttcg agcctcagcg tcagttggtg cccagtagac | 120 | |
| cgccttcgcc actggtgttc ctcccgatat ctacgcattc caccgctaca ccgggaattc | 180 | |
| catctacctc tgcactactc aagaaaaaca gttttgaaag caattcatgg gttgagccca | 240 | |
| tggttttcac ttccaacttg tcttcccgcc tgcgctccct ttacacccag taattccgga | 300 | |
| caacgcttgc accctacgtt ttaccgcggc tgctggcacg tagttagccg gtgctttctt | 360 | |
| gttaggtacc gtcattatcg tccctaacga caggagttta caatccgaaa accttcttcc | 420 | |
| tccacgcggc gtcgctgcat cagggtttcc cccattgtgc aatatccccc actgctgcct | 480 | |
| cccgtaggag tctgggccgt gtctcagtcc caatgtggcc gttcaacctc tcagtccggc | 540 | |
| taccaatcgt cgccttggtg ggccgttacc tcaccaacta gctaattgga cgcgagtcca | 600 | |
| tcctaaagcg aataaatcct tttccctcag naccatgcgg taccgtgggc ttatgcggta | 660 | |
| ttagcagtcg tttccaactg ttgtcccccca ctctagggca ggttactcac gcgttactca | 720 | |
| cccgttcgcc actaagctta aaaagcaagc tctctaagct ccgttcgact tgcatgtgtt | 780 | |
| aggcgcgccg ccagcgttcg tcctgagcc | 809 | |

```
<210> SEQ ID NO 23
<211> LENGTH: 902
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (796)..(796)
<223> OTHER INFORMATION: n is a, c, g, or t
<220> FEATURE:
<221> NAME/KEY: misc_feature
<222> LOCATION: (825)..(825)
<223> OTHER INFORMATION: n is a, c, g, or t
<220> FEATURE:
<221> NAME/KEY: misc_feature
```

<222> LOCATION: (838)..(838)
<223> OTHER INFORMATION: n is a, c, g, or t
<220> FEATURE:
<221> NAME/KEY: misc_feature
<222> LOCATION: (841)..(841)
<223> OTHER INFORMATION: n is a, c, g, or t
<220> FEATURE:
<221> NAME/KEY: misc_feature
<222> LOCATION: (881)..(881)
<223> OTHER INFORMATION: n is a, c, g, or t

<400> SEQUENCE: 23

```
tgctttctcg agcgagtggc gaacgggtga gtaacgcgtg aggaacctgc ctcaaagagg      60
gggacaacag ttggaaacga ctgctaatac cgcataagcc cacgacccgg catcgggtag     120
agggaaaagg agcaatccgc tttgagatgg cctcgcgtcc gattagctag ttggtgaggt     180
aacggcccac caaggcgacg atcggtagcc ggactgagag gttgaacggc cacattggga     240
ctgagacacg gcccagactc ctacgggagg cagcagtggg gaatattgca caatggggga     300
aaccctgatg cagcgacgcc gcgtggagga agaaggtctt cggattgtaa actcctgttg     360
ttgaggaaga taatgacggt actcaacaag gaagtgacgg ctaactacgt gccagcagcc     420
gcggtaaaac gtaggtcaca agcgttgtcc ggaattactg ggtgtaaagg gagcgcaggc     480
gggaaggcaa gttggaagtg aaatccatgg gctcaaccca tgaactgctt tcaaaactgt     540
ttttcttgag tagtgcagag gtaggcgaa ttcccggtgt agcggtggaa tgcgtagata     600
tcgggaggaa caccagtggc gaaggcggcc tactgggcac caactgacgc tgaggctcga     660
aagtgtgggt agcaaacagg attagatacc ctggtagtcc acactgtaaa cgatgattac     720
taggtgttgg aggattgacc ccttcagtgc cgcagttaac acaataagta atccacctgg     780
ggagtacgac cgcaanggtt gaaactcaaa ggaattgacg ggggnccgca caagcagngg     840
ngtatgtggt ttaattcgac gcaacgcgaa gaaccttacc nagtcttgac atcctgcgac     900
gg                                                                    902
```

<210> SEQ ID NO 24
<211> LENGTH: 1000
<212> TYPE: DNA
<213> ORGANISM: Artificial Sequence
<220> FEATURE:
<223> OTHER INFORMATION: Synthetic Polynucleotide

<400> SEQUENCE: 24

```
ataccttgat ggcgaccggc gcacgggtga gtaacgcgta tgcaacctgc ctgataccgg      60
ggtatagccc atgaaacgt ggattaacac cccatagtac ttttatcctg catgggatgt     120
gagttaaatg ttcaaggtat cggatgggca tgcgtcctat tagttagttg gcggggtaac     180
agccaccaa gacgatgata ggtaggggtt ctgagaggaa ggtcccccac attggaactg     240
agacacggtc caaacttcta cgggaggcag cagtgaggaa tattggtcaa tggacgtaag     300
tctgaaccag ccaagtcgcg tgagggaaga ctgccctatg ggttgtaaac ctcttttata     360
agggaagaat aagttctacg tgtagaatga tgcctgtacc ttatgaataa gcatcggcta     420
actccgtgcc agcagccgcg gtaatacgga ggatgcgagc gttatccgga tttattgggt     480
ttaagggtg cgtaggcggt ttattaagtt agtggttaaa tatttgagct aaactcaatt     540
gtgccattaa tactggtaaa ctggagtaca gacgaggtag gcggaataag ttaagtagcg     600
gtgaaatgca tagatataac ttagaactcc gatagcgaag gcagcttacc agactgtaac     660
tgacgctgat gcacgagagc gtgggtagcg aacaggatta gataccctgg tagtccacgc     720
```

```
cgtaaacgat gctcactggt tctgtgcgat atattgtacg ggattaagcg aaagtattaa    780
gtgagccacc tggggagtac gtcggcaacg atgaaactca aaggaattga cggggcccgc    840
acaagcggag gaacatgtgg tttaattcga tgatacgcga ggaaccttac ctgggtttaa    900
atgggaatgt cgtatttggg aacagatatt ctcttcgagc gttttttcaag gtgctgcatg  960 gttgtcgtca gctcgtgcgg tgaggggtcg gtagtccata                          1000
```

<210> SEQ ID NO 25
<211> LENGTH: 982
<212> TYPE: DNA
<213> ORGANISM: Artificial Sequence
<220> FEATURE:
<223> OTHER INFORMATION: Synthetic Polynucleotide

<400> SEQUENCE: 25

```
ttttcttcgg aactgaagat ttggtgattg agtggcggac gggtgagtaa cgcgtgggta    60
acctgccctg tacaggggga taacagtcag aaatgactgc taataccgca taagaccaca   120
gcaccgcatg gtgcagggt aaaaactccg gtggtacagg atggacccgc gtctgattag    180
ctggttggtg aggtaacggc tcaccaaggc gacgatcagt agccggcttg agagagtgaa   240
cggccacatt gggactgaga cacggcccaa actcctacgg gaggcagcag tggggaatat   300
tgcacaatgg gggaaaccct gatgcagcga cgccgcgtga gtgaagaagt atctcggtat   360
gtaaagctct atcagcaggg aagaaaatga cggtacctga ctaagaagcc ccggctaact   420
acgtgccagc agccgcggta atacgtaggg ggcaagcgtt atccggaatt actgggtgta   480
aagggtgcgt aggtggtatg gcaagtcaga agtgaaaacc cagggcttaa ctctgggact   540
gcttttgaaa ctgtcagact ggagtgcagg agaggtaagc ggaattccta gtgtagcggt   600
gaaatgcgta gatattagga ggaacatcag tggcgaaggc ggcttactgg actgaaactg   660
acactgaggc acgaaagcgt ggggagcaaa caggattaga taccctggta gtccacgccg   720
taacgatgaa actaggtgt cggggccgta gaggcttcgg tgccgcagcc aacgcagtaa    780
gtattccacc tggggagtac gttcgcaaga atgaaactca aaggaattga cggggacccg   840
cacaagcggt ggagcatgtg gtttattcga agcaacgcga gaaccttac ctggtcttga    900 catccttctg accggtcctt aaccggactt ccttcgggga cagagtgaca aggtggtgca    960
tgtgtcgtca gctcgtgtct ga                                            982
```

<210> SEQ ID NO 26
<211> LENGTH: 387
<212> TYPE: DNA
<213> ORGANISM: Artificial Sequence
<220> FEATURE:
<223> OTHER INFORMATION: Synthetic Polynucleotide

<400> SEQUENCE: 26

```
agcaatactt tgggtggcga ccggcgcacg ggtgcgtaac gcgtatgtaa cctacctata    60 acagggcat aacactgaga aattggtact aattccccat aatattcgga gaggcatctc    120
tccgggttga aaactccggt ggttatagat ggacatgcgt tgtattagct agttggtgag   180
gtaacggctc accaaggcaa cgatacatag ggggactgag aggttaaccc cccacactgg   240
tactgagaca cggaccagac tcctacggga ggcagcagtg aggaatattg gtcaatggac   300
gcaagtctga accagccagg ccgcgtgcag gaagacggct ctatgagttg taaactgctt   360
ttgtacgagg gtaaactcac ctacgtg                                       387
```

<210> SEQ ID NO 27
<211> LENGTH: 843
<212> TYPE: DNA
<213> ORGANISM: Artificial Sequence
<220> FEATURE:
<223> OTHER INFORMATION: Synthetic Polynucleotide

<400> SEQUENCE: 27

```
attgtatcgc aaactcctag taatcatcgt ttactgcgtg gactaccagg gtatctaatc      60
ctgtttgatc cccacgcttt cgtgcttcag tgtcagttat ggtttagtaa gctgccttcg     120
caatcggagt tctgcgtgat atctatgcat ttcaccgcta caccacgcat tccgcctacc     180
tcaaacacac tcaagtaacc cagtttcaac ggcaatttta tggttgagcc acaaactttc     240
accgctgact taaatcacca cctacgcacc ctttaaaccc aataaatccg gataacgctc     300
gcatcctccg tattaccgcg gctgctggca cggagttagc cgatgcttat tcatagggta     360
catacaaaaa aggacacgtc ctccacttta ttcccctata aaagaagttt acaaaccata     420
gatccttctt ccttcacgcg acttggctgg ttcagcctct cggccattga ccaatattcc     480
tcactgctgc ctcccgtagg agtttggtcc gtgtctcagt accaatgtgg gggaccttcc     540
tctcagaacc cctatccatc gtcggtttgg tgggccgtta ccccgccaac tgcctaatgg     600
aacgcatgcc tatctatcag cgatgaatct ttaacaaata ttcccatgcg ggaccctgt      660
tttatggggt attaatccga ctttcgccgg gctatccccc tctgataggt aagttgcata     720
cgcgttactc acccgtgcgc cggtcgccat caatctgtat tgctacaaat catgctgccc     780
ctcgacttgc atgtgttaag cctgtcgcta gcgttcatcc tgagccagat tcaaactcta     840
taa                                                                  843
```

<210> SEQ ID NO 28
<211> LENGTH: 939
<212> TYPE: DNA
<213> ORGANISM: Artificial Sequence
<220> FEATURE:
<223> OTHER INFORMATION: Synthetic Polynucleotide

<400> SEQUENCE: 28

```
gaagcttcgg cagatttggc cggtttctag tggcggacgg gtgagtaacg cgtgggtaac      60
ctgcccttata caggggata caaccagaa atggttgcta ataccgcata agcgcacagg      120
accgcatggt ccagtgtgaa aaactccggt ggtataagat ggacccgcgt tggattagct     180
agttggcagg gtaacggcct accaaggcga cgatccatag ccggcctgag agggtgaacg     240
gccacattgg gactgagaca cggcccagac tcctacggga ggcagcagtg gggaatattg     300
cacaatgggg gaaaccctga tgcagcgacg ccgcgtgaag gaagaagtat ctcggtatgt     360
aaacttctat cagcagggaa gatagtgacg gtacctgact aagaagcccc ggctaactac     420
gtgccagcag ccgcggtaat acgtaggggg caagcgttat ccggatttac tgggtgtaaa     480
gggagcgtag acggactggc aagtctgatg tgaaaggcgg gggctcaacc cctgactgc      540
attggaaact gttagtcttg agtgccggag aggtaagcgg aattcctagt gtagcggtga     600
aatgcgtaga tattaggagg aacaccagtg gcgaaggcgg cttactggac ggtaactgac     660
gttgaggctc gaaagcgtgg ggagcaaaca ggattagata ccctgggtag tccacgccgt     720
aaacgatgaa tactaggtgt tgggggagca agctcttcg gtgccgccgc aaacgcatta     780
agtattccac ctggggagta cgttcgcaag aatgaaactc aaaggatttg acggggaccc     840
gcacaagcgt ggagcatgtg tttattcgaa gcaaccggaa gaacttacca ggcttgacat     900
```

```
cctctgacgt tcgtaacgga actttcttcg gacaggaaa                              939
```

<210> SEQ ID NO 29
<211> LENGTH: 956
<212> TYPE: DNA
<213> ORGANISM: Artificial Sequence
<220> FEATURE:
<223> OTHER INFORMATION: Synthetic Polynucleotide

<400> SEQUENCE: 29

```
tgctaaggcc gatggcgacc ggcgcacggg tgagtaacac gtatccaacc tgccgtctac        60
tcttggacag cctt ctgaaa ggaagattaa tacaagatgg catcatgagt ccgcatgttc      120
acatgattaa aggtattccg gtagacgatg gggatgcgtt ccattagata gtaggcgggg      180
taacggccca cctagtcttc gatggatagg ggttctgaga ggaaggtccc ccacattgga      240
actgagacac ggtccaaact cctacgggag gcagcagtga ggaatattgg tcaatgggcg      300
caggcctgaa ccagccaagt agcgtgaagg atgactgccc tatgggttgt aaacttcttt      360
tataaaggaa taaagtcggg tatgtatacc cgtttgcatg tactttatga ataaggatcg      420
gctaactccg tgccagcagc cgcggtaata cggaggatcc gagcgttatc cggatttatt      480
gggtttaaag ggagcgtaga tggatgttta agtcagttgt gaaagtttgc ggctcaaccg      540
taaaattgca gttgatactg gatatcttga gtgcagttga ggcaggcgga attcgtggtg      600
tagcggtgaa atgcttagat atcacgaaga actccgattg cgaaggcagc tgctaagct       660
gcaactgaca ttgaggctcg aaagtgtggg tatcaaacag gattagatac cctggtagtc      720
cacacgg taa acgatgaata ctcgctgttt gcgatatacg gcaagcggcc aagcgaaagc      780
gttaagtatt ccacctgggg agtacgccgg caacggtgaa ctcaaaggaa ttgacggggc      840
ccgcacaagc ggagaacatg tggtttaatt cgatgatacg cgaggacctt acccggctta      900
aattgcagat gaattacgtg aagccgtaag ccgcaagcat ctgtgaagtg ctgcat          956
```

<210> SEQ ID NO 30
<211> LENGTH: 980
<212> TYPE: DNA
<213> ORGANISM: Artificial Sequence
<220> FEATURE:
<223> OTHER INFORMATION: Synthetic Polynucleotide

<400> SEQUENCE: 30

```
taggttgatg gcgaccggcg cacgggtgag taacacgtat ccaacctacc ggttattccg        60
ggatagcctt tcgaaagaaa gattaatacc ggatagtata acgagaaggc atcttttgt       120
tattaaagaa tttcgataac cgatgggat gcgttccatt agtttgttgg cggggtaacg       180
gcccaccaag acatcgatgg ataggggttc tgagaggaag gtcccccaca ttggaactga      240
gacacggtcc aaactcctac gggaggcagc agtgaggaat attggtcaat ggacgagagt      300
ctgaaccagc caagtagcgt gaaggatgac tgccctatgg gttgtaaact tcttttatat      360
gggaataaag tgagccacgt gtggcttttt gtatgtacca tacgaataag gatcggctaa      420
ctccgtgcca gcagccgcgg taatacggag gatccgagcg ttatccggat ttattgggtt      480
taagggagc gtaggcggac tattaagtca gctgtgaaag tttgcggctc aaccgtaaaa      540
ttgcagttga tactggtcgt cttgagtgca gtagaggtag gcggaattcg tggtgtagcg      600
gtgaaatgct tagatatcac gaagaactcc gattgcgaag gcagcttact ggactgtaac      660
tgacgctgat gctcgaaagt gtgggtatca aacaggatta gataccctgg tagtccacac      720
agtaaacgat gaatactcgc tgtttgcgat atacagcaag cggccaagcg aaagcattaa      780
```

```
gtattccacc tggggagtac gccggcaacg gtgaaactca aaggaattga cgggggcccg    840
cacaagcgag aacatgtggt ttaattcgat gatacgcgag aaccttaccg ggcttaaatt    900
gcatctgaat aatttggaaa cagattagcc gcaagcagat gtgaaggtgc tgcatggtgt    960
cgtcagctcg tgcgtgaggt                                                980
```

<210> SEQ ID NO 31
<211> LENGTH: 867
<212> TYPE: DNA
<213> ORGANISM: Artificial Sequence
<220> FEATURE:
<223> OTHER INFORMATION: Synthetic Polynucleotide

<400> SEQUENCE: 31

```
tgcttcaatt gccggcgacc ggcgcacggg tgcgtaacgc gtatgtaacc tacctataac     60
aggggcataa cactgagaaa ttggtactaa ttccccataa tattcggaga ggcatctctc    120
cgggttgaaa actccggtgg ttatagatgg acatgcgttg tattagctag ttggtgaggt    180
aacggctcac caaggcaacg atacataggg ggactgagag gttaaccccc cacactggta    240
ctgagacacg gaccagactc ctacgggagg cagcagtgag gaatattggt caatggacgc    300
aagtctgaac cagccatgcc gcgtgcagga agacggctct atgagttgta aactgctttt    360
gtacgagggt aaactcacct acgtgtaggt gactgaaagt atcgtacgaa taaggatcgg    420
ctaactccgt gccagcagcc gcggtaatac ggaggattca agcgttatcc ggatttattg    480
ggtttaaagg gtgcgtaggc ggtttgataa gttagaggtg aaatcccggg gcttaactcc    540
ggaactgcct ctaatactgt tagactagag agtagttgcg gtaggcggaa tgtatggtgt    600
agcggtgaaa tgcttagaga tcatacagaa caccgattgc gaaggcagct taccaaacta    660
tatctgacgt tgaggcacga aagcgtgggg agcaaaacag gattagatac cctggtagtc    720
cacgcagtaa acgatgataa ctcgttgtcg gcgatacaca gtcggtgact aagcgaaagc    780
gataagttat ccacctgggg agtacgttcg caagaatgaa cttaaaggaa ttgacggggc    840
ccgcacaagc ggagaactgt ggttatt                                        867
```

<210> SEQ ID NO 32
<211> LENGTH: 261
<212> TYPE: DNA
<213> ORGANISM: Artificial Sequence
<220> FEATURE:
<223> OTHER INFORMATION: Synthetic Polynucleotide

<400> SEQUENCE: 32

```
ttgctaagtt tgatggcgac cggcgcacgg gtgagtaaca cgtatccaac ctgccgatga     60
ctcggggata gcctttcgaa agaaagatta atacccgatg gcatatttct tccgcatggt    120
agaattatta aagaatttcg gtcatcgatg gggatgcgtt ccattaggtt gttggcgggg    180
taacggccca ccaagccttc gatggatagg ggttctgaga ggaaggtccc ccacattgga    240
actgagccag gatcccacca t                                              261
```

<210> SEQ ID NO 33
<211> LENGTH: 832
<212> TYPE: DNA
<213> ORGANISM: Artificial Sequence
<220> FEATURE:
<223> OTHER INFORMATION: Synthetic Polynucleotide

<400> SEQUENCE: 33

| | | |
|---|---|---|
| gtgtatcgcc gacaacgagt tatcatcgtt tactgcgtgg actaccaggg tatctaatcc | 60 | |
| tgtttgctcc ccacgctttc gtgcctcaac gtcagatata gtttggtaag ctgccttcgc | 120 | |
| aatcggtgtt ctgtatgatc tctaagcatt tcaccgctac accatacatt ccgcctaccg | 180 | |
| caactactct ctagtctaac agtattagag gcagttccgg agttaagccc cgggatttca | 240 | |
| cctctaactt atcaaaccgc ctacgcaccc tttaaaccca ataaatccgg ataacgcttg | 300 | |
| aatcctccgt attaccgcgg ctgctggcac ggagttagcc gatccttatt cgtacgatac | 360 | |
| tttcagtcac ctacacgtag gtgagtttac cctcgtacaa aagcagttta caactcatag | 420 | |
| agccgtcttc ctgcacgcgg catggctggt tcagacttgc gtccattgac caatattcct | 480 | |
| cactgctgcc tcccgtagga gtctggtccg tgtctcagta ccagtgtggg gggttaacct | 540 | |
| ctcagtcccc ctatgtatcg ttgccttggt gagccgttac ctcaccaact agctaataca | 600 | |
| acgcatgtcc atctataacc accggagttt tcaacccgga gagatgcctc tccgaatatt | 660 | |
| atggggaatt agtaccaatt tctcagtgtt atgcccctgt tataggtagg ttacatacgc | 720 | |
| gttacgcacc cgtgcgccgg tcgccaccaa agtattgcta cctcgtgatg cccctcgact | 780 | |
| tgcatgtgtt aggcctgccg ctagcgttca tcctgagcca gattcaaact ct | 832 | |

<210> SEQ ID NO 34
<211> LENGTH: 1527
<212> TYPE: DNA
<213> ORGANISM: Artificial Sequence
<220> FEATURE:
<223> OTHER INFORMATION: Synthetic Polynucleotide

<400> SEQUENCE: 34

| | | |
|---|---|---|
| tcagagagtt tgatcctggc tcaggatgaa cgctggcggc gtgcttaaca catgcaagtc | 60 | |
| gaacgggaaa cctttattg aagcttcggc agatttagat tgtttctagt ggcggacggg | 120 | |
| tgagtaacgc gtgggtaacc tgccttatac aggggggataa cagtcagaaa tgactgctaa | 180 | |
| taccgcataa gcgcacagag ctgcatggct cggtgtgaaa aactccggtg gtataagatg | 240 | |
| gacccgcgtt ggattagcta gttggtgagg taacggccca ccaaggcgac gatccatagc | 300 | |
| cggcctgaga gggtgaacgg ccacattggg actgagacac ggcccagact cctacgggag | 360 | |
| gcagcagtgg ggaatattgc acaatggggg aaaccctgat gcagcgacgc cgcgtgaagg | 420 | |
| aagaagtatc tcggtatgta aacttctatc agcagggaag aaaatgacgg tacctgacta | 480 | |
| agaagccccg gctaactacg tgccagcagc cgcggtaata cgtaggggggc aagcgttatc | 540 | |
| cggatttact gggtgtaaag ggagcgtaga cggatggaca agtctgatgt gaaaggctgg | 600 | |
| ggctcaaccc cgggactgca ttggaaactg cccgtcttga gtgccggaga ggtaagcgga | 660 | |
| attcctagtg tagcggtgaa atgcgtagat attaggagga acaccagtgg cgaaggcggc | 720 | |
| ttactggacg gtaactgacg ttgaggctcg aaagcgtggg gagcaaacag gattagatac | 780 | |
| cctggtagtc cacgcggtaa acgatgaatg ctaggtgtcg gggagcaaag ctcttcggtg | 840 | |
| ccgccgcaaa cgcattaagc attccacctg gggagtacgt tcgcaagaat gaaactcaaa | 900 | |
| ggaattgacg gggacccgca caagcggtgg agcatgtggt ttaattcgaa gcaacgcgaa | 960 | |
| gaaccttacc aagtcttgac atccttctga ccggaactta accgttcctt cccttcgggg | 1020 | |
| cagaagtgac aggtggtgca tggttgtcgt cagctcgtgt cgtgagatgt tgggttaagt | 1080 | |
| cccgcaacga gcgcaacccc tatcctcagt agccagcata aaggtgggc actctgggga | 1140 | |
| gactgccagg gataacctgg aggaaggcgg ggatgacgtc aaatcatcat gccccttatg | 1200 | |
| atttgggcta cacacgtgct acaatggcgt aaacaaaggg aagcgaacct gcgagggtgg | 1260 | |

| | |
|---|---|
| gcaaatccca aaaataacgt cccagttcgg actgtagtct gcaacccgac tacacgaagc | 1320 |
| tggaatcgct agtaatcgcg gatcagaatg ccgcggtgaa tacgttcccg ggtcttgtac | 1380 |
| acaccgcccg tcacaccatg ggagtcagta acgcccgaag tcagtgacct aaccgcaagg | 1440 |
| aaggagctgc cgaaggcggg accgatgact ggggtgaagt cgtaacaagg tagccgtatc | 1500 |
| ggaaggtgcg gctggatcac ctccttt | 1527 |

<210> SEQ ID NO 35
<211> LENGTH: 1055
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (868)..(868)
<223> OTHER INFORMATION: n is a, c, g, or t
<220> FEATURE:
<221> NAME/KEY: misc_feature
<222> LOCATION: (917)..(917)
<223> OTHER INFORMATION: n is a, c, g, or t
<220> FEATURE:
<221> NAME/KEY: misc_feature
<222> LOCATION: (925)..(925)
<223> OTHER INFORMATION: n is a, c, g, or t
<220> FEATURE:
<221> NAME/KEY: misc_feature
<222> LOCATION: (984)..(986)
<223> OTHER INFORMATION: n is a, c, g, or t
<220> FEATURE:
<221> NAME/KEY: misc_feature
<222> LOCATION: (1002)..(1002)
<223> OTHER INFORMATION: n is a, c, g, or t
<220> FEATURE:
<221> NAME/KEY: misc_feature
<222> LOCATION: (1015)..(1015)
<223> OTHER INFORMATION: n is a, c, g, or t
<220> FEATURE:
<221> NAME/KEY: misc_feature
<222> LOCATION: (1020)..(1020)
<223> OTHER INFORMATION: n is a, c, g, or t
<220> FEATURE:
<221> NAME/KEY: misc_feature
<222> LOCATION: (1049)..(1049)
<223> OTHER INFORMATION: n is a, c, g, or t

<400> SEQUENCE: 35

| | |
|---|---|
| gaggggcatg ccatgatgga gtagtaatat ctatggtggc agaccggcgc acgggtgcgt | 60 |
| aacgcgtatg caacctacct ttaacagggg gataacactg agaaattggt actaataccc | 120 |
| cataatatca tagaaggcat cttttatggt tgaaaattcc gatggttaga gatgggcatg | 180 |
| cgttgtatta gctagttggt ggggtaacgg ctcaccaagg cgacgataca tagggggact | 240 |
| gagaggttaa ccccccacac tggtactgag acacggacca gactcctacg ggaggcagca | 300 |
| gtgaggaata ttggtcaatg gacgcaagtc tgaaccagcc atgccgcgtg caggatgacg | 360 |
| gctctatgag ttgtaaactg cttttgtacg agggtaaacg cagatacgtg tatctgtctg | 420 |
| aaagtatcgt acgaataagg atcggctaac tccgtgccag cagccgcggt aatacggagg | 480 |
| attcaagcgt tatccggatt tattgggttt aaagggtgcg taggcggttt gataagttag | 540 |
| aggtgaaatt tcggggctca accctgaacg tgcctctaat actgttgagc tagagagtag | 600 |
| ttgcggtagg cggaatgtat ggtgtagcgg tgaaatgctt agagatcata cagaacaccg | 660 |
| attgcgaagg cagcttacca aactatatct gacgttgagg cacgaaagcg tggggagcaa | 720 |
| acaggattag ataccctggt agtccacgca gtaaacgatg ataactcgtt gtcggcgata | 780 |

| | |
|---|---|
| cacagtcggt gactaagcga aagcgataag ttatccacct ggggagtacg ttcgcaagaa | 840 |
| tgaaactcaa aggaattgac gggggccncg cacaagcgga ggaacatgtg ggtttaattc | 900 |
| gatgatacgc gaggaancct taccncgggc ttgaaagtta gcgacgattc ttgaaagagg | 960 |
| atttcccttc ggggcgcgaa actnnngctg catggttgtc gncagctcgt gccgngaggn | 1020 |
| gtcgggttaa gtcccataac gagcgcacnc cctac | 1055 |

```
<210> SEQ ID NO 36
<211> LENGTH: 988
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (5)..(5)
<223> OTHER INFORMATION: n is a, c, g, or t

<400> SEQUENCE: 36
```

| | |
|---|---|
| acacntgcag tcgaggggca gcataatgga tagcaatatc tatggtggcg accggcgcac | 60 |
| gggtgcgtaa cgcgtatgca acctaccttt aacaggggga taacactgag aaattggtac | 120 |
| taatacccca taatatcata gaaggcatct tttatggttg aaaattccga tggttagaga | 180 |
| tgggcatgcg ttgtattagc tagttggtgg ggtaacggct caccaaggcg acgatacata | 240 |
| gggggactga gaggttaacc ccccacactg gtactgagac acggaccaga ctcctacggg | 300 |
| aggcagcagt gaggaatatt ggtcaatgga cgcaagtctg aaccagccat gccgcgtgca | 360 |
| ggatgacggc tctatgagtt gtaaactgct tttgtacgag ggtaaacgca gatacgtgta | 420 |
| tctgtctgaa agtatcgtac gaataaggat cggctaactc cgtgccagca gccgcggtaa | 480 |
| tacgaggat tcaagcgtta tccggattta ttgggtttaa agggtgcgta ggcggtttga | 540 |
| taagttagag gtgaaatttc ggggctcaac cctgaacgtg cctctaatac tgttgagcta | 600 |
| gagagtagtt gcgtaggcg gaatgtatgg tgtagcggtg aaatgcttag agatcataca | 660 |
| gaacaccgat tgcgaaggca gcttaccaaa ctatatctga cgttgaggca cgaaagcgtg | 720 |
| gggagcaaac aggattagat accctggtag tccacgcagt aaacgatgat aactcgttgt | 780 |
| cggcgataca cagtcggtga ctaagcgaaa gcgataagtt atccacctgg ggagtacgtt | 840 |
| cgcaagaatg aaactcaaag gaattgacgg ggcccgcac aagcggagga acatgtggtt | 900 |
| taattcgatg atacgcgagg aaccttaccc gggcttgaaa gttagcgacg attcttgaaa | 960 |
| gaggatttcc ctttcggggc gcgaaact | 988 |

```
<210> SEQ ID NO 37
<211> LENGTH: 1029
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (989)..(991)
<223> OTHER INFORMATION: n is a, c, g, or t

<400> SEQUENCE: 37
```

| | |
|---|---|
| acacntggaa gtcgaggggc agcataatgg atagcaatat ctatggtggc gaccggcgca | 60 |
| cgggtgcgta acgcgtatgc aacctacctt taacaggggg ataacactga gaaattggta | 120 |

```
ctaatacccc ataatatcat agaaggcatc ttttatggtt gaaaattccg atggttagag     180
atgggcatgc gttgtattag ctagttggtg gggtaacggc tcaccaaggc gacgatacat     240 aggggactg  agaggttaac cccccacact ggtactgaga cacggaccag actcctacgg     300
gaggcagcag tgaggaatat tggtcaatgg acgcaagtct gaaccagcca tgccgcgtgc     360
aggatgacgg ctctatgagt tgtaaactgc ttttgtacga gggtaaacgc agatacgtgt     420
atctgtctga aagtatcgta cgaataagga tcggctaact ccgtgccagc agccgcggta     480
atacggagga ttcaagcgtt atccggattt attgggttta aagggtgcgt aggcggtttg     540
ataagttaga ggtgaaattt cggggctcaa ccctgaacgt gcctctaata ctgttgagct     600
agagagtagt tgcggtaggc ggaatgtatg gtgtagcggt gaaatgctta gagatcatac     660
agaacaccga ttgcgaaggc agcttaccaa actatatctg acgttgaggc acgaaagcgt     720
ggggagcaaa caggattaga taccctggta gtccacgcag taaacgatga taactcgttg     780
tcggcgatac acagtcggtg actaagcgaa agcgataagt tatccacctg gggagtacgt     840 tgcaagaat  gaaactcaaa ggaattgacg ggggcccgca caagcggagg aacatgtggt     900
ttaattcgat gatacgcgag gaaccttacc cgggcttgaa agttagcgac gattcttgaa     960
agaggatttc ccttcgggc  gcgaaactnn ngctgcatgg tgtcgtcagc tcgtgccgtg    1020
aggtgtcgg                                                            1029
```

METHODS AND PRODUCTS FOR TREATMENT OF GASTROINTESTINAL DISORDERS

PRIORITY

This application is a U.S. National Stage Application under 37 U.S.C. § 371 of International Application No. PCT/US2020/042541, filed Jul. 17, 2020, which claims the benefit of, and priority to, U.S. Provisional Application No. 62/876,350, filed Jul. 19, 2019, and U.S. Provisional Application No. 63/001,888, filed Mar. 30, 2020, the contents of each of which are hereby incorporated by reference in their entirety.

FIELD OF THE INVENTION

The present invention relates to, in part, compositions and methods for the delivery of bacterial isolates and/or cocktails of bacterial isolates useful for the treatment of disorders related to intestinal dysbiosis.

DESCRIPTION OF THE TEXT FILE SUBMITTED ELECTRONICALLY

This application contains a sequence listing. It has been submitted electronically via EFS-Web as an ASCII text file entitled "FIN-019_ST25". The sequence listing is 65,867 bytes in size, and was prepared on Jan. 18, 2022. The sequence listing is hereby incorporated by reference in its entirety.

BACKGROUND

The human GI tract harbors a diverse microbial community of over one thousand distinct bacterial species and an estimated excess of $1 \times 10^{14}$ microorganisms. This microbial community, also referred to as the microbiota (and the genetic component being the microbiome), has proven to be critical for human health. For example, a healthy microbiome provides the human host with multiple benefits, including resistance to pathogen infection, nutrient biosynthesis and absorption, and immune stimulation. A dysbiosis or disruption of the microbiome results in increased susceptibility to pathogens, altered metabolic profiles, and systemic inflammation or autoimmunity. Indeed, dysbiosis of the microbiome (i.e., intestinal dysbiosis) can predispose the human host to a variety of pathological conditions including gastrointestinal disorders such as inflammatory bowel disease (IBD) and irritable bowel syndrome (IBS) as well as infections by pathogens including *Clostridium difficile* (*C. diff*, e.g. *Clostridium difficile* infection (CDI)).

IBD affects over 1.6 million Americans with as many as 70,000 new cases being diagnosed in the United States each year. IBD is characterized by chronic inflammation in the GI tract. The two most common forms of IBD include ulcerative colitis (UC) and Crohn's Disease (CD). UC occurs in the colon while CD may be present in the entire GI tract. The clinical symptoms are diarrhea, abdominal pain, occasional rectal bleeding, weight loss, tiredness and sometimes fever. For most patients, IBD is a chronic condition with symptoms lasting for months to years. Currently, there are no medical cures for IBD. Instead, current therapies are directed to controlling the GI symptoms by reducing inflammation. In severe cases, surgical procedures including colectomy, proctocolectomy, and ileostomy may be used.

Researchers have attempted to restore a healthy microbiome in such patients to alleviate or eliminate these diseases. For instance, one approach involves transplantation of a fecal microbiota derived from stool of a healthy human donor, to repopulate the gut (so-called Fecal Microbiota Transplant (FMT)). However, this treatment is not ideal and particularly unpalatable. Accordingly, a more recent approach is to develop a rationally selected, defined mix of bacteria, which could be taken by patients and replace fecal transplants. This "bugs as drugs" concept looks to convert the therapeutic benefits of FMT to a more standardized and drugable system. Unfortunately, but not surprisingly, this approach has been met with early stumbles. For example, a recent clinical trial with SER-109, a mix of bacterial spores designed to treat patients with CDI, failed to meet its main goal in a Phase 2 trial. This drug failed to reduce the relative risk of CDI recurrence, compared to a placebo, up to eight weeks after treatment.

Accordingly, there remains a need for effective therapeutics that can restore a healthy intestinal microbiota thereby providing effective treatments for a variety of disorders related to intestinal dysbiosis, e.g., gastrointestinal disorders.

SUMMARY

In various aspects, the present invention provides compositions and methods that are useful treating or preventing inflammatory bowel disease (IBD) in a subject in need thereof. For instance, the present invention, in part, relates to a plurality of bacterial isolates, wherein at least two of the plurality of bacterial isolates are isolated from a stool of different human donors.

An aspect of the present invention is a method of treating or preventing inflammatory bowel disease (IBD) in a subject in need thereof, the method comprising administering to the subject a plurality of bacterial isolates, wherein the plurality of bacterial isolates comprises *Bacteroides stercoris*, and at least two of *Bacteroides cellulosilyticus, Bacteroides uniformis, Subdoligranulum variabile, Anaerostipes hadrus, Odoribacter splanchnicus, Roseburia faecis, Faecalibacterium prausnitzii, Akkermansia muciniphila, Alistipes shahii*, and *Eubacterium rectale*, wherein at least two of the plurality of bacterial isolates are isolated from a stool of different human donors.

An aspect of the present invention is a pharmaceutical composition comprising a plurality of bacterial isolates, wherein the plurality of bacterial isolates comprise *Bacteroides* stercoris, and at least two of *Bacteroides cellulosilyticus, Bacteroides uniformis, Subdoligranulum variabile, Anaerostipes hadrus, Odoribacter splanchnicus, Roseburia faecis, Faecalibacterium prausnitzii, Akkermansia muciniphila, Alistipes shahii*, and *Eubacterium rectale*, wherein at least two of the plurality of bacterial isolates are isolated from a stool of different human donors.

In embodiments, the plurality of bacterial isolates comprises at least two, or at least three, or at least four, or at least five, or at least six, or at least seven, or at least eight, or at least nine, or each of *Bacteroides cellulosilyticus, Bacteroides uniformis, Odoribacter splanchnicus, Roseburia faecis, Anaerostipes hadrus, Faecalibacterium prausnitzii, Subdoligranulum variabile, Akkermansia muciniphila, Alistipes shahii*, and *Eubacterium rectale*.

In embodiments, the plurality of bacterial isolates comprises at least three of *Bacteroides cellulosilyticus, Bacteroides uniformis, Subdoligranulum variabile, Anaerostipes hadrus, Odoribacter splanchnicus, Roseburia faecis, Fae-*

*calibacterium prausnitzii, Akkermansia muciniphila, Alistipes shahii*, and *Eubacterium rectale*. In embodiments, the plurality of bacterial isolates comprises at least four of *Bacteroides cellulosilyticus, Bacteroides uniformis, Subdoligranulum variabile, Anaerostipes hadrus, Odoribacter splanchnicus, Roseburia faecis, Faecalibacterium prausnitzii, Akkermansia muciniphila, Alistipes shahii*, and *Eubacterium rectale*. In embodiments, the plurality of bacterial isolates comprises at least five of *Bacteroides cellulosilyticus, Bacteroides uniformis, Subdoligranulum variabile, Anaerostipes hadrus, Odoribacter splanchnicus, Roseburia faecis, Faecalibacterium prausnitzii, Akkermansia muciniphila, Alistipes shahii*, and *Eubacterium rectale*. In embodiments, the plurality of bacterial isolates comprises at least five of *Bacteroides cellulosilyticus, Bacteroides uniformis, Subdoligranulum variabile, Anaerostipes hadrus, Odoribacter splanchnicus, Roseburia faecis, Faecalibacterium prausnitzii, Akkermansia muciniphila, Alistipes shahii*, and *Eubacterium rectale*. In embodiments, the plurality of bacterial isolates comprises at least six of *Bacteroides cellulosilyticus, Bacteroides uniformis, Subdoligranulum variabile, Anaerostipes hadrus, Odoribacter splanchnicus, Roseburia faecis, Faecalibacterium prausnitzii, Akkermansia muciniphila, Alistipes shahii*, and *Eubacterium rectale*. In embodiments, the plurality of bacterial isolates comprises at least seven of *Bacteroides cellulosilyticus, Bacteroides uniformis, Subdoligranulum variabile, Anaerostipes hadrus, Odoribacter splanchnicus, Roseburia faecis, Faecalibacterium prausnitzii, Akkermansia muciniphila, Alistipes shahii*, and *Eubacterium rectale*. In embodiments, the plurality of bacterial isolates comprises at least eight of *Bacteroides cellulosilyticus, Bacteroides uniformis, Subdoligranulum variabile, Anaerostipes hadrus, Odoribacter splanchnicus, Roseburia faecis, Faecalibacterium prausnitzii, Akkermansia muciniphila, Alistipes shahii*, and *Eubacterium rectale*.

In embodiments, the composition comprises a 16S rRNA sequence that is at least about 95%, or at least about 97%, or at least about 98%, or at least about 99% sequence identity with nucleotide sequences selected from SEQ ID NOs: 1, 2, 3, 7, 8, 11, 14, 18, 19, 20, 22 and 23. In embodiments, the pharmaceutical composition comprises at least two bacterial isolates comprising *Faecalibacterium prausnitzii*, wherein the at least two bacterial isolates comprise different 16S rRNA sequences. In embodiments, the pharmaceutical composition comprises 16S rRNA sequences that are at least about 95%, or at least about 97%, or at least about 98%, or at least about 99% identity sequence identity with nucleotide sequences of SEQ ID NOs: 1 and 7.

In embodiments, the *Bacteroides stercoris* comprises a 16S ribosomal ribonucleic acid (rRNA) sequence that has at least about 95%, or at least about 97%, or at least about 98%, or at least about 99% sequence identity with the nucleotide sequence of SEQ ID NO: 13. In embodiments, the plurality of bacterial isolates comprises at least three of *Bacteroides cellulosilyticus, Bacteroides uniformis, Odoribacter splanchnicus, Roseburia faecis, Anaerostipes hadrus, Faecalibacterium prausnitzii, Subdoligranulum variabile, Akkermansia muciniphila, Alistipes shahii*, and *Eubacterium rectale*. In embodiments, the plurality of bacterial isolates comprises at least three, or at least four, or at least five, or at least six, or at least seven, or at least eight, or at least nine, or each of *Bacteroides cellulosilyticus, Bacteroides uniformis, Odoribacter splanchnicus, Roseburia faecis, Anaerostipes hadrus, Faecalibacterium prausnitzii, Subdoligranulum variabile, Akkermansia muciniphila, Alistipes shahii*, and *Eubacterium rectale*.

In embodiments, the plurality of bacterial isolates comprises a 16S rRNA sequence that has at least about 95%, or at least about 97%, or at least about 98%, or at least about 99% sequence identity with nucleotide sequences selected from SEQ ID NOs: 1, 2, 3, 7, 8, 11, 14, 18, 19, 20, 22 and 23.

In embodiments, the plurality of bacterial isolates comprises at least two bacterial isolates comprising *Faecalibacterium prausnitzii*, wherein the at least two bacterial isolates comprise different 16S rRNA sequences. In embodiments, the at least two bacterial isolates comprising *Faecalibacterium prausnitzii* comprise 16S rRNA sequences that are at least about 95%, or at least about 97%, or at least about 98%, or at least about 99% identity sequence identity with nucleotide sequences of SEQ ID NOs: 1 and/or 7. In embodiments, the at least two bacterial isolates comprising *Faecalibacterim prausnitzii* are isolated from a stool of different human donors.

Described herein are compositions and methods for protecting the GI microbiome of a subject. In various embodiments, provided herein is a pharmaceutical composition comprising an isolated or purified bacterial isolate and/or a cocktail of isolated or purified bacterial isolates (e.g. from a human, e.g. from stool of a healthy human).

Disclosed herein is a pharmaceutical composition comprising a cocktail of bacterial isolates, wherein at least one of the bacterial isolates comprises a 16S rRNA sequence that is at least 95% identical to a 16S rRNA sequence of a bacterial isolate provided in Table 1. In embodiments, at least two of the bacterial isolates comprise a 16S rRNA sequence that is at least 95% identical to a 16S rRNA sequence of a bacterial isolate provided in Table 1. In embodiments, at least three of the bacterial isolates comprise a 16S rRNA sequence that is at least 95% identical to a 16S rRNA sequence of a bacterial isolate provided in Table 1. In embodiments, at least four of the bacterial isolates comprise a 16S rRNA sequence that is at least 95% identical to a 16S rRNA sequence of a bacterial isolate provided in Table 1. In embodiments, at least five of the bacterial isolates comprise a 16S rRNA sequence that is at least 95% identical to a 16S rRNA sequence of a bacterial isolate provided in Table 1. In embodiments, at least six of the bacterial isolates comprise a 16S rRNA sequence that is at least 95% identical to a 16S rRNA sequence of a bacterial isolate provided in Table 1. In embodiments, at least seven of the bacterial isolates comprise a 16S rRNA sequence that is at least 95% identical to a 16S rRNA sequence of a bacterial isolate provided in Table 1. In embodiments, at least eight of the bacterial isolates comprise a 16S rRNA sequence that is at least 95% identical to a 16S rRNA sequence of a bacterial isolate provided in Table 1. In embodiments, at least nine of the bacterial isolates comprise a 16S rRNA sequence that is at least 95% identical to a 16S rRNA sequence of a bacterial isolate provided in Table 1. In embodiments, at least ten of the bacterial isolates comprise a 16S rRNA sequence that is at least 95% identical to a 16S rRNA sequence of a bacterial isolate provided in Table 1.

Disclosed herein is a pharmaceutical composition comprising a plurality of bacterial isolates, wherein the plurality of bacterial isolates comprises at least two bacterial isolates selected from the group consisting of *Eubacterium rectale, Odoribacter splanchnicus* and *Subdoligranulum variabile*. In embodiments, the *Subdoligranulum variabile* comprises a 16S rRNA sequence that is at least 95% identical to at least one of SEQ ID NO: 22 or SEQ ID NO: 23. In embodiments, the Odoribacter comprises a 16S rRNA sequence that is at least 95% identical to SEQ ID NO: 2. In embodiments, the

*Eubacterium rectale* comprises a 16S rRNA sequence that is at least 95% identical to SEQ ID NO: 8. In embodiments, the at least two bacterial isolates do not include *Eubacterium rectale*. In embodiments, the at least two bacterial isolates do not include *Odoribacter splanchnicus*. In embodiments, the at least two bacterial isolates do not include *Subdoligranulum variabile*.

In embodiments, the at least two bacterial isolates comprise *Odoribacter splanchnicus* and *Eubacterium rectale*. In embodiments, the plurality of bacterial isolates comprises *Odoribacter splanchnicus* and *Eubacterium rectale*, and further comprises at least one of *Bacteroides cellulosilyticus, Faecalibacterium prausnitzii, Alistipes shahii*, and *Blautia obeum*. In embodiments, the plurality of bacterial isolates comprises *Odoribacter splanchnicus* and *Eubacterium rectale*, and further comprises each of *Bacteroides cellulosilyticus, Faecalibacterium prausnitzii, Alistipes shahii*, and *Blautia obeum*. In embodiments, the *Bacteroides cellulosilyticus* comprises a 16S rRNA sequence that is at least 95% identical to SEQ ID NO: 14. In embodiments, the *Faecalibacterium prausnitzii* comprises a 16S rRNA sequence that is at least 95% identical to at least one of SEQ ID NO: 1 or SEQ ID NO: 7. In embodiments, the *Alistipes shahii* comprises a 16S rRNA sequence that is at least 95% identical to SEQ ID NO: 18. In embodiments, the *Blautia obeum* comprises a 16S rRNA sequence that is at least 95% identical to SEQ ID NO: 9.

In embodiments, the plurality of bacterial isolates comprises *Odoribacter splanchnicus* and *Eubacterium rectale*, and further comprises at least one of *Bacteroides cellulosilyticus, Bacteroides stercoris, Faecalibacterium prausnitzii, Alistipes shahii, Anaerostipes hadrus, Roseburia faecis*, and *Blautia obeum*. In embodiments, the plurality of bacterial isolates does not comprise at least one of *Blautia obeum* and *Anaerostipes hadrus*. In embodiments, the plurality of bacterial isolates comprises *Odoribacter splanchnicus* and *Eubacterium rectale*, and further comprises each of *Bacteroides cellulosilyticus, Bacteroides stercoris, Faecalibacterium prausnitzii, Alistipes shahii, Anaerostipes hadrus*, and *Roseburia faecis* In embodiments, the *Bacteroides cellulosilyticus* comprises a 16S rRNA sequence that is at least 95% identical to SEQ ID NO: 14. In embodiments, the *Bacteroides stercoris* comprises a 16S rRNA sequence that is at least 95% identical to SEQ ID NO: 13. In embodiments, the *Faecalibacterium prausnitzii* comprises a 16S rRNA sequence that is at least 95% identical to at least one of SEQ ID NO: 1 or SEQ ID NO: 7. In embodiments, the *Alistipes shahii* comprises a 16S rRNA sequence that is at least 95% identical to SEQ ID NO: 18. In embodiments, the *Anaerostipes hadrus* comprises a 16S rRNA sequence that is at least 95% identical to SEQ ID NO: 3. In embodiments, the *Roseburia faecis* comprises a 16S rRNA sequence that is at least 95% identical to SEQ ID NO: 19.

In embodiments, the plurality of bacterial isolates comprises *Odoribacter splanchnicus* and *Eubacterium rectale*, and further comprises each of *Bacteroides cellulosilyticus, Bacteroides stercoris, Faecalibacterium prausnitzii, Alistipes shahii, Blautia obeum*, and *Roseburia faecis*. In embodiments, the *Bacteroides cellulosilyticus* comprises a 16S rRNA sequence that is at least 95% identical to SEQ ID NO: 14. In embodiments, the *Bacteroides stercoris* comprises a 16S rRNA sequence that is at least 95% identical to SEQ ID NO: 13. In embodiments, the *Faecalibacterium prausnitzii* comprises a 16S rRNA sequence that is at least 95% identical to at least one of SEQ ID NO: 1 or SEQ ID NO: 7. In embodiments, the *Alistipes shahii* comprises a 16S rRNA sequence that is at least 95% identical to SEQ ID NO: 18. In embodiments, the *Blautia obeum* comprises a 16S rRNA sequence that is at least 95% identical to SEQ ID NO: 9. In embodiments, the *Roseburia faecis* comprises a 16S rRNA sequence that is at least 95% identical to SEQ ID NO: 19.

In embodiments, the plurality of bacterial isolates comprises *Odoribacter splanchnicus* and *Eubacterium rectale*, and further comprises at least one of *Bacteroides cellulosilyticus, Bacteroides stercoris, Alistipes shahii*, and *Roseburia faecis*. In embodiments, the plurality of bacterial isolates comprises *Odoribacter splanchnicus* and *Eubacterium rectale*, and further comprises each of *Bacteroides cellulosilyticus, Bacteroides stercoris, Alistipes shahii*, and *Roseburia faecis*. In embodiments, the *Bacteroides cellulosilyticus* comprises a 16S rRNA sequence that is at least 95% identical to SEQ ID NO: 14. In embodiments, the *Bacteroides stercoris* comprises a 16S rRNA sequence that is at least 95% identical to SEQ ID NO: 13. In embodiments, the *Roseburia faecis* comprises a 16S rRNA sequence that is at least 95% identical to SEQ ID NO: 19. In embodiments, the *Alistipes shahii* comprises a 16S rRNA sequence that is at least 95% identical to SEQ ID NO: 18.

In embodiments, the plurality of bacterial isolates comprises *Odoribacter splanchnicus* and *Eubacterium rectale*, and further comprises at least one of *Faecalibacterium prausnitzii, Bacteroides stercoris, Roseburia faecis*, and *Anaerostipes hadrus*. In embodiments, the plurality of bacterial isolates comprises *Odoribacter splanchnicus* and *Eubacterium rectale*, and further comprises each of *Faecalibacterium prausnitzii, Bacteroides stercoris, Roseburia faecis*, and *Anaerostipes hadrus*. In embodiments, the *Faecalibacterium prausnitzii* comprises a 16S rRNA sequence that is at least 95% identical to at least one of SEQ ID NO: 1 or SEQ ID NO: 7. In embodiments, the *Bacteroides stercoris* comprises a 16S rRNA sequence that is at least 95% identical to SEQ ID NO: 13. In embodiments, the *Roseburia faecis* comprises a 16S rRNA sequence that is at least 95% identical to SEQ ID NO: 19. In embodiments, the *Anaerostipes hadrus* comprises a 16S rRNA sequence that is at least 95% identical to SEQ ID NO: 3.

In embodiments, the plurality of bacterial isolates comprises *Odoribacter splanchnicus* and *Eubacterium rectale*, and further comprises at least one of *Bacteroides cellulosilyticus, Bacteroides stercoris, Blautia obeum*, and *Alistipes shahii*. In embodiments, the plurality of bacterial isolates comprises *Odoribacter splanchnicus* and *Eubacterium rectale*, and further comprises each of *Bacteroides cellulosilyticus, Bacteroides stercoris, Blautia obeum*, and *Alistipes shahii*. In embodiments, the *Bacteroides cellulosilyticus* comprises a 16S rRNA sequence that is at least 95% identical to SEQ ID NO: 14. In embodiments, the *Bacteroides stercoris* comprises a 16S rRNA sequence that is at least 95% identical to SEQ ID NO: 13. In embodiments, the *Blautia obeum* comprises a 16S rRNA sequence that is at least 95% identical to SEQ ID NO: 9. In embodiments, the *Alistipes shahii* comprises a 16S rRNA sequence that is at least 95% identical to SEQ ID NO: 18.

In embodiments, the plurality of bacterial isolates comprises *Odoribacter splanchnicus* and *Eubacterium rectale*, and further comprises at least one of *Faecalibacterium prausnitzii, Bacteroides stercoris, Alistipes shahii*, and *Roseburia* faecis. In embodiments, the plurality of bacterial isolates comprises *Odoribacter splanchnicus* and *Eubacterium rectale*, and further comprises each of *Faecalibacterium prausnitzii, Bacteroides stercoris, Alistipes shahii*, and *Roseburia* faecis. In embodiments, the *Faecalibacterium prausnitzii* comprises a 16S rRNA sequence that is at least 95% identical to at least one of SEQ ID NO: 1 or SEQ ID NO: 7. In embodiments, the *Bacteroides stercoris* comprises a 16S rRNA sequence that is at least 95% identical to SEQ ID NO: 13. In embodiments, the *Alistipes shahii* comprises a 16S rRNA sequence that is at least 95% identical to SEQ ID NO: 18. In embodiments, the *Roseburia* faecis comprises a 16S rRNA sequence that is at least 95% identical to SEQ ID NO: 19.

In embodiments, the plurality of bacterial isolates comprises *Odoribacter splanchnicus* and *Eubacterium rectale*, and further comprises at least one of *Faecalibacterium prausnitzii, Bacteroides stercoris, Blautia obeum*, and *Roseburia faecis*. In embodiments, the plurality of bacterial isolates comprises *Odoribacter splanchnicus* and *Eubacterium rectale*, and further comprises each of *Faecalibacterium prausnitzii, Bacteroides stercoris, Blautia obeum*, and *Roseburia faecis*. In embodiments, the *Faecalibacterium prausnitzii* comprises a 16S rRNA sequence that is at least 95% identical to at least one of SEQ ID NO: 1 or SEQ ID NO: 7. In embodiments, the *Bacteroides stercoris* comprises a 16S rRNA sequence that is at least 95% identical to SEQ ID NO: 13. In embodiments, the *Blautia obeum* comprises a 16S rRNA sequence that is at least 95% identical to SEQ ID NO: 9. In embodiments, the *Roseburia* faecis comprises a 16S rRNA sequence that is at least 95% identical to SEQ ID NO: 19.

In embodiments, the plurality of bacterial isolates comprises at least one of *Bacteroides stercoris* and *Clostridium aldenense*. In embodiments, the plurality of bacterial isolates produces an aryl hydrocarbon for binding to an aryl hydrocarbon receptor. In embodiments, the aryl hydrocarbon receptor is expressed by a cell of a subject administered the composition. In embodiments, the cell is an intestinal cell or an immune cell. In embodiments, the aryl hydrocarbon is selected from the group consisting of indole, indole-3-acetic acid (IAA), indole-3-aldehyde (IAId), indole-3-lactic acid, indole-3-carbinol (I3C), indole-3-acetonitrile (I3ACN), 3,3'-diindolylmethane (DIM), 2-(indol-3-ylmethyl)-3,3'-diindolylmethane (Ltr-1), indolo[3,2-b]carbazole (ICZ), 2-(1'H-indole-3' carbonyl)-thiazole-4-carboxylic acid methyl ester (ITE), 3-methyl-indole (skatole), tryptamine, kynurenine, kynurenate, indigo, indirubin, indoxyl-3-sulfate (I3S), xanthurenic acid, cinnabarinic acid, and any combination thereof. In embodiments, the aryl hydrocarbon is IAA. In embodiments, the IAA is secreted at a concentration of at least 1 µM. In embodiments, the IAA is secreted at a concentration of at least 10 µM. In embodiments, the IAA is secreted at a concentration of at least 20 µM. In embodiments, the IAA is secreted at a concentration of at least 40 µM. In embodiments, the IAA is secreted at a concentration of at least 50 µM. In embodiments, the IAA is secreted at a concentration of at least 75 µM. In embodiments, the IAA is secreted at a concentration of at least 100 µM.

In embodiments, the at least two bacterial isolates comprise *Eubacterium rectale* and *Subdoligranulum variabile*. In embodiments, the plurality of bacterial isolates comprises *Eubacterium rectale* and *Subdoligranulum variabile*, and further comprises at least one of *Faecalibacterium prausnitzii, Coprococcus comes, Anaerostipes hadrus*, and *Roseburia faecis*. In embodiments, the plurality of bacterial isolates comprises *Eubacterium rectale* and *Subdoligranulum variabile*, and further comprises each of *Faecalibacterium prausnitzii, Coprococcus comes, Anaerostipes hadrus*, and *Roseburia faecis*. In embodiments, the *Faecalibacterium prausnitzii* comprises a 16S rRNA sequence that is at least 95% identical to at least one of SEQ ID NO: 1 or SEQ ID NO: 7. In embodiments, the *Anaerostipes hadrus* comprises a 16S rRNA sequence that is at least 95% identical to SEQ ID NO: 3. In embodiments, the *Roseburia faecis* comprises a 16S rRNA sequence that is at least 95% identical to SEQ ID NO: 19. In embodiments, the *Coprococcus comes* comprises a 16S rRNA sequence that is at least 95% identical to SEQ ID NO: 17.

In embodiments, the plurality of bacterial strains does not include at least one of *Faecalibacterium prausnitzii, Roseburia faecis, Bacteroides cellulosilyticus, Alistipes shahii*, or *Blautia obeum*.

An aspect of the present invention is a pharmaceutical composition comprising a plurality of bacterial isolates, wherein the plurality of bacterial isolates comprise *Bacteroides stercoris*, and at least two of *Bacteroides cellulosilyticus, Bacteroides uniformis, Subdoligranulum variabile, Anaerostipes hadrus, Odoribacter splanchnicus, Roseburia faecis, Faecalibacterium prausnitzii, Akkermansia muciniphila, Alistipes shahii*, and *Eubacterium rectale*, wherein at least two of the plurality of bacterial isolates are isolated from a stool of different human donors.

Disclosed herein is a pharmaceutical composition comprising a plurality of bacterial isolates, wherein the plurality of bacterial isolates comprises *Roseburia faecis* and *Bacteroides cellulosilyticus*, and at least one of *Faecalibacterium prausnitzii* and *Alistipes shahii*. In embodiments, the plurality of bacterial isolates further comprises at least one of *Eubacterium rectale, Anaerostipes hadrus*, and *Blautia obeum*. In embodiments, the plurality of bacterial isolates does not comprise at least one of *Anaerostipes hadrus* and *Blautia obeum*. In embodiments, the plurality of bacterial isolates comprises each of *Roseburia faecis, Bacteroides cellulosilyticus, Faecalibacterium prausnitzii, Alistipes shahii, Eubacterium rectale*, and *Anaerostipes hadrus*. In embodiments, the *Roseburia faecis* comprises a 16S rRNA sequence that is at least 95% identical to SEQ ID NO: 19. In embodiments, the *Bacteroides cellulosilyticus* comprises a 16S rRNA sequence that is at least 95% identical to SEQ ID NO: 14. In embodiments, the *Faecalibacterium prausnitzii* comprises a 16S rRNA sequence that is at least 95% identical to at least one of SEQ ID NO: 1 or SEQ ID NO: 7. In embodiments, the *Alistipes shahii* comprises a 16S rRNA sequence that is at least 95% identical to SEQ ID NO: 18. In embodiments, the *Eubacterium rectale* comprises a 16S rRNA sequence that is at least 95% identical to SEQ ID NO: 8. In embodiments, the *Anaerostipes hadrus* comprises a 16S rRNA sequence that is at least 95% identical to SEQ ID NO: 3.

In embodiments, the plurality of bacterial isolates comprises each of *Roseburia faecis, Bacteroides cellulosilyticus, Faecalibacterium prausnitzii, Alistipes shahii, Eubacterium rectale*, and *Blautia obeum*. In embodiments, the *Roseburia faecis* comprises a 16S rRNA sequence that is at least 95% identical to SEQ ID NO: 19. In embodiments, the *Bacteroides cellulosilyticus* comprises a 16S rRNA sequence that is at least 95% identical to SEQ ID NO: 14. In embodiments, the *Faecalibacterium prausnitzii* comprises a 16S rRNA sequence that is at least 95% identical to at least one of SEQ ID NO: 1 or SEQ ID NO: 7. In embodiments, the *Alistipes shahii* comprises a 16S rRNA sequence that is at least 95% identical to SEQ ID NO: 18. In embodiments, the *Eubacterium rectale* comprises a 16S rRNA sequence that is at least 95% identical to SEQ ID NO: 8. In embodiments, the *Blautia obeum* comprises a 16S rRNA sequence that is at least 95% identical to SEQ ID NO: 9.

In embodiments, one or more of the plurality of bacterial isolates in the above pharmaceutical compositions secretes a short-chain fatty acid (SCFA) in an intestine of a subject administered the composition. In embodiments, the SCFA is selected from the group consisting of acetic acid, butyric acid, caproic acid, formic acid, heptanoic acid, isobutyric acid, isocaproic acid, isovaleric acid, propionic acid, valeric acid, and a combination thereof. In embodiments, the SCFA is butyric acid. In embodiments, a level of the butyric acid produced by the one or more bacterial isolates over a period of 24 hours is at least 5 mM. In embodiments, a level of the butyric acid produced by the one or more bacterial isolates over a period of 24 hours is at least 10 mM. In embodiments, a level of the butyric acid produced by the one or more bacterial isolates over a period of 24 hours is at least 15 mM. In embodiments, a level of the butyric acid produced by the one or more bacterial isolates over a period of 24 hours is at least 20 mM. In embodiments, a level of the butyric acid produced by the one or more bacterial isolates over a period of 24 hours is at least 25 mM. In embodiments, a level of the butyric acid produced by the one or more bacterial isolates over a period of 24 hours is at least 30 mM. In embodiments, a level of the butyric acid produced by the one or more bacterial isolates over a period of 24 hours is at least 35 mM. In embodiments, a level of the butyric acid produced by the one or more bacterial isolates over a period of 24 hours is at least 40 mM. In embodiments, the one or more bacterial isolates producing at least one SCFA comprises a 16S rRNA sequence that is at least 95% identical to a 16S rRNA sequence of a bacterial isolate provided in Table 2.

Disclosed herein is a pharmaceutical composition comprising a plurality of bacterial isolates, wherein the plurality of bacterial isolates comprises a bacterial isolate comprising *Parabacteroides merdae* and at least one of *Alistipes finegoldii* and *Alistipes onderdonkii*. In embodiments, the plurality of bacterial isolates comprises both *Alistipes finegoldii* and *Alistipes onderdonkii*. In embodiments, the plurality of bacterial isolates does not include one of *Alistipes finegoldii* and *Alistipes onderdonkii*. In embodiments, the plurality of bacterial isolates further comprises at least one of *Akkermansia muciniphila*, *Dorea longicatena*, *Blautia obeum*, *Blautia* sp., *Bacteroides uniformis* or *Bacteroides vulgatus*. In embodiments, the plurality of bacterial isolates comprises *Parabacteroides merdae* and each of *Akkermansia muciniphila*, *Alistipes finegoldii*, *Dorea longicatena*, *Alistipes onderdonkii*, *Blautia* sp., *Bacteroides uniformis* and *Bacteroides vulgatus*. In embodiments, the *Parabacteroides merdae* comprises a 16S rRNA sequence that is at least 95% identical to SEQ ID NO: 5. In embodiments, the *Akkermansia muciniphila* comprises a 16S rRNA sequence that is at least 95% identical to SEQ ID NO: 20. In embodiments, the *Alistipes finegoldii* comprises a 16S rRNA sequence that is at least 95% identical to SEQ ID NO: 15. In embodiments, the *Dorea longicatena* comprises a 16S rRNA sequence that is at least 95% identical to SEQ ID NO: 6. In embodiments, the *Alistipes onderdonkii* comprises a 16S rRNA sequence that is at least 95% identical to SEQ ID NO: 4. In embodiments, the *Blautia* sp. comprises a 16S rRNA sequence that is at least 95% identical to SEQ ID NO: 34. In embodiments, the *Bacteroides uniformis* comprises a 16S rRNA sequence that is at least 95% identical to at least one of SEQ ID NO: 11 and SEQ ID NO: 16. In embodiments, the *Bacteroides vulgatus* comprises a 16S rRNA sequence that is at least 95% identical to SEQ ID NO: 12.

In embodiments, the plurality of bacterial isolates comprises *Parabacteroides merdae* and each of *Akkermansia muciniphila*, *Alistipes finegoldii*, *Dorea longicatena*, *Blautia obeum*, *Blautia* sp., *Bacteroides uniformis* and *Bacteroides vulgatus*. In embodiments, the *Parabacteroides merdae* comprises a 16S rRNA sequence that is at least 95% identical to SEQ ID NO: 5. In embodiments, the *Akkermansia muciniphila* comprises a 16S rRNA sequence that is at least 95% identical to SEQ ID NO: 20. In embodiments, the *Alistipes finegoldii* comprises a 16S rRNA sequence that is at least 95% identical to SEQ ID NO: 15. In embodiments, the *Dorea longicatena* comprises a 16S rRNA sequence that is at least 95% identical to SEQ ID NO: 6. In embodiments, the *Blautia obeum* comprises a 16S rRNA sequence that is at least 95% identical to SEQ ID NO: 9. In embodiments, the *Blautia* sp. comprises a 16S rRNA sequence that is at least 95% identical to SEQ ID NO: 34. In embodiments, the *Bacteroides uniformis* comprises a 16S rRNA sequence that is at least 95% identical to at least one of SEQ ID NO: 11 and SEQ ID NO: 16. In embodiments, the *Bacteroides vulgatus* comprises a 16S rRNA sequence that is at least 95% identical to SEQ ID NO: 12.

Disclosed herein is a pharmaceutical composition comprising a plurality of bacterial isolates, wherein the plurality of bacteria isolates comprises *Alistipes finegoldii* and at least one of *Bacteroides uniformis* and *Dorea longicatena*. In embodiments, the plurality of bacterial isolates does not comprise one of *Bacteroides uniformis* or *Dorea longicatena*. In embodiments, the plurality of bacterial isolates further comprises at least one of *Akkermansia muciniphila*, *Bacteroides vulgatus*, and *Blautia* sp. In embodiments, the plurality of bacterial isolates comprises each of *Alistipes finegoldii*, *Bacteroides uniformis*, *Dorea longicatena*, *Akkermansia muciniphila*, *Bacteroides vulgatus*, and *Blautia* sp. In embodiments, the *Alistipes finegoldii* comprises a 16S rRNA sequence that is at least 95% identical to SEQ ID NO: 15. In embodiments, the *Bacteroides uniformis* comprises a 16S rRNA sequence that is at least 95% identical to SEQ ID NO: 11. In embodiments, the *Dorea longicatena* comprises a 16S rRNA sequence that is at least 95% identical to SEQ ID NO: 6. In embodiments, the *Akkermansia muciniphila* comprises a 16S rRNA sequence that is at least 95% identical to SEQ ID NO: 20. In embodiments, the *Bacteroides vulgatus* comprises a 16S rRNA sequence that is at least 95% identical to SEQ ID NO: 12. In embodiments, the *Blautia* sp. comprises a 16S rRNA sequence that is at least 95% identical to SEQ ID NO: 34.

In embodiments, the plurality of bacterial isolates of any of the above pharmaceutical compositions comprises at least one bacterial isolate provided in Table 3. In embodiments, the at least one bacterial isolate modulates cytokine production or release by a eukaryotic cell. In embodiments, the at least one bacterial isolate decreases production or release of a pro-inflammatory cytokine by the eukaryotic cell. In embodiments, the pro-inflammatory cytokine is selected from the group consisting of: IFNγ, IL-12p70, IL-1 (e.g., IL-1α, IL-1β), IL-6, IL-8, IL-12, IL-17, IL-18, IL-23, MCP1, MIP1α, MIP1β, TNFα, TNF-γ, and a combination thereof. In embodiments, the at least one bacterial isolate increases production or release of an anti-inflammatory cytokine by the eukaryotic cell. In embodiments, the anti-inflammatory cytokine is selected from the group consisting of IL-10, IL-13, IL-4, IL-5, TGF-β, and a combination thereof. In embodiments, the anti-inflammatory cytokine is IL-10. In embodiments, the at least one bacterial isolate induces the eukaryotic cell to produce or release at least 500 pg/ml of IL-10. In embodiments, the at least one bacterial isolate induces the eukaryotic cell to produce or release at least 1000 pg/ml of IL-10. In embodiments, the at least one bacterial isolate induces the eukaryotic cell to produce or release at least 1500 pg/ml of IL-10. In embodiments, the at least one bacterial isolate induces the eukaryotic cell to produce or release at least 2000 pg/ml of IL-10. In embodiments, the at least one bacterial isolate induces the eukaryotic cell to produce or release at least 2500 pg/ml of IL-10. In embodiments, the at least one bacterial isolate induces the eukaryotic cell to produce or release at least 3000 pg/ml of IL-10. In embodiments, the eukaryotic cell is a cultured cell. In embodiments, the eukaryotic cell is a cultured peripheral blood mononuclear cell (PBMC). In embodiments, the eukaryotic cell is a cell of a subject administered the composition. In embodiments, the cell of the subject is selected from the group consisting of: an epithelial cell, an intestinal lamina propria cell, an endothelial cell, a fibroblast, a stromal cell, a macrophage, a B lymphocyte, a T lymphocyte, a mast cell, and a peripheral blood mononuclear cell (PBMC). In embodiments, the cell of the subject is an epithelial cell and the epithelial cell is an intestinal epithelial cell.

In embodiments, the pharmaceutical composition is formulated as a capsule for oral administration. In embodiments, the capsule comprises a delayed-release coating. In embodiments, the capsule comprises a hydrophobic coating. In embodiments, the pharmaceutical composition is formulated for delivery of the microbial cocktail to the intestine. In embodiments, the pharmaceutical composition is formulated for delivery of the microbial cocktail to the small intestine. In embodiments, the composition is formulated for delivery of the microbial cocktail to the large intestine. In embodiments, the microbial cocktail is lyophilized. In embodiments, the pharmaceutical composition further comprises at least one of a pharmaceutically acceptable antioxidant, cryoprotectant, lyoprotectant, binder, disintegrant, excipient, filler, preservative, acid suppressant, antacid, H2 antagonist, and/or proton pump inhibitor.

In embodiments, the pharmaceutical composition is for administration to a subject having a disorder related to an intestinal dysbiosis. In embodiments, the disorder is selected from the group consisting of inflammatory bowel disease (IBD), irritable bowel syndrome (IBS), *C. difficile* infection (CDI), *C. difficile*-associated disease (CDAD), an antibiotic-induced adverse effect, and a combination thereof.

Disclosed herein is a method of treating or preventing inflammatory bowel disease in a subject in need thereof, comprising administering to the subject a bacterial isolate comprising *Bacteroides cellulosilyticus*. In embodiments, the *Bacteroides cellulosilyticus* comprises a 16S rRNA sequence that is at least 95% identical to SEQ ID NO: 26. In embodiments, the method further comprises administering to the subject a bacterial isolate comprising *Odoribacter splanchnicus* and/or a bacterial isolate comprising *Subdoligranulum* sp.

Disclosed herein is a method of manufacturing a pharmaceutical composition containing a cocktail of bacterial isolates, the method comprising selecting a first bacterial isolate based on a level of a short-chain fatty acid (SCFA) produced by the first bacterial isolate; selecting a second bacterial isolate based on a relative abundance of a corresponding bacterial strain in a healthy human subject versus a subject having inflammatory bowel disease, wherein the second bacterial isolate comprises a 16S rRNA sequence at least 97% identical to a 16S rRNA sequence of the corresponding bacterial strain; and combining the first and second bacterial isolates to produce the cocktail of bacterial isolates. In embodiments, the first bacterial isolate comprises a 16S rRNA sequence at least 95% identical to a 16S rRNA sequence of a bacterial isolate provided in Table 2. In embodiments, the second bacterial isolate comprises a 16S rRNA sequence at least 95% identical to a 16S rRNA sequence of a bacterial isolate provided in Table 4. In embodiments, the method further comprises selecting a third bacterial isolate based on a modulation of a cytokine's level induced by the bacterial isolate. In embodiments, the third bacterial isolate comprises a 16S rRNA sequence at least 95% identical to a 16S rRNA sequence of a bacterial isolate provided in Table 3. In embodiments, the method further comprises selecting a fourth bacterial isolate based on a level of an aryl hydrocarbon produced by the third bacterial isolate. In embodiments, the fourth bacterial isolate comprises a 16S rRNA sequence at least 95% identical to a 16S rRNA sequence of a bacterial isolate provided in Table 6.

Disclosed herein is a pharmaceutical composition, comprising: a first human-derived bacterial isolate which induces at least one of an IL-10:IL-12 ratio of at least 50 or an IL-10:TNF-alpha ratio of at least 1 when incubated with a population of eukaryotic cells in a first functional assay; and a second human-derived bacterial isolate which produces a short chain fatty acid (SCFA) at a concentration of at least 10 mM as measured by a second functional assay; wherein the first and second bacterial isolates are capable of engrafting into the intestine of a subject following administration of the pharmaceutical composition to the subject.

In an aspect, the IL-10:IL-12 ratio is at least 100. In an aspect, the IL-10:IL-12 ratio is at least 500. In an aspect, the IL-10:IL-12 ratio is at least 1000. In an aspect, the IL-10:IL-12 ratio is at least 2000. In an aspect, the IL-10:TNF-alpha ratio is at least 2. In an aspect, the IL-10:TNF-alpha ratio is at least 5. In an aspect, the IL-10:TNF-alpha ratio is at least 10. In an aspect, the IL-10:TNF-alpha ratio is at least 20. In an aspect, the population of eukaryotic cells comprises a population of PBMCs. In an aspect, the first human-derived bacterial isolate is incubated with the population of eukaryotic cells for about 24 hours. In an aspect, the SCFA is butyrate. In an aspect, the SCFA is produced at a concentration of at least 20 mM. In an aspect, the SCFA is produced at a concentration of at least 25 mM. In an aspect, the SCFA is produced at a concentration of at least 30 mM. In an aspect, the SCFA is produced at a concentration of at least 35 mM. In an aspect, the SCFA is butyrate.

In an aspect, the second functional assay comprises incubating the second bacterial isolate with a substrate. In an aspect, the substrate comprises at least one of an oligosaccharide, sunfiber, or barley malt. In an aspect, the oligosaccharide comprises at least one of a fructooligosaccharide (FOS) and an xylooligosaccharide (XOS). In an aspect, the substrate comprises both of a fructooligosaccharide (FOS) and an xylooligosaccharide (XOS). In an aspect, the second bacterial isolate comprises a 16S rRNA sequence at least 95% identical to a 16S rRNA sequence of a bacterial isolate provided in Table 2. In an aspect, the second bacterial isolate comprises *Anaerostipes* sp. In an aspect, the *Anaerostipes* sp. is *Anaerostipes hadrus*. In an aspect, the second bacterial isolate comprises a 16S rRNA sequence at least 95% identical to the sequence corresponding to SEQ ID NO: 3. In an aspect, the second bacterial isolate comprises *Roseburia* sp. In an aspect, the *Roseburia* sp. is *Roseburia faecis*. In an aspect, the second bacterial isolate comprises a 16S rRNA sequence at least 95% identical to the sequence corresponding to SEQ ID NO: 19. In an aspect, the second bacterial isolate comprises *Eubacterium* sp. In an aspect, the *Eubacterium* sp. is *Eubacterium rectale*. In an aspect, the second bacterial isolate comprises a 16S rRNA sequence at least 95% identical to the sequence corresponding to SEQ ID NO: 8. In an aspect, the second bacterial isolate comprises *Coprococcus* sp. In an aspect, the *Coprococcus* sp. is *Coprococcus comes*. In an aspect, the second bacterial isolate comprises a 16S rRNA sequence at least 95% identical to the sequence corresponding to SEQ ID NO: 17. In an aspect, the first bacterial isolate comprises a 16S sequence at least 95% identical to a 16S rRNA sequence of a bacterial isolate provided in Table 3.

A pharmaceutical composition, comprising: a first human-derived bacterial isolate which produces a short chain fatty acid (SCFA) at a concentration of at least 10 mM as measured by a first functional assay; and a second human-derived bacterial isolate which, as measured by a second functional assay, produces at least one of: (i) indole at a level at least 5× greater than a level of indole produced by a control bacterial strain; (ii) tryptamine at a level at least 1.4× greater than a level of tryptamine produced by a control bacterial strain; (iii) kynurenate at a level at least 1.4× greater than a level of kynurenate produced by a control bacterial strain; (iv) kynurenine at a level at least 2.5× greater than a level of kynurenine produced by a control bacterial strain; and (v) indole-3-acetic acid at a level at least 2× greater than a level of indole-3-acetic acid produced by a control bacterial strain; wherein the control bacterial strain is selected from at least one of *Peptostreptococcus russellii* and *Peptostreptococcus anaerobius*; wherein the first and second bacterial isolates are capable of engrafting into the intestine of a subject following administration of the pharmaceutical composition to the subject.

In an aspect, the second functional assay comprises separately incubating the second bacterial isolate and the control strain with tryptophan. In an aspect, the second bacterial isolate produces indole at a level at least 50× greater than the level of indole produced by the control bacterial strain. In an aspect, the second bacterial isolate produces indole at a level at least 100× greater than the level of indole produced by the control bacterial strain. In an aspect, the second bacterial isolate produces indole at a level at least 150× greater than the level of indole produced by the control bacterial strain. In an aspect, the second bacterial isolate comprises *Clostridium aldenense*. In an aspect, the second bacterial isolate comprises a 16S rRNA sequence at least 95% identical to SEQ ID NO: 10.

In an aspect, the second bacterial isolate produces tryptamine at a level at least 1.5× greater than the level of tryptamine produced by the control bacterial strain. In an aspect, the second bacterial isolate comprises *Odoribacter splanchnicus*. In an aspect, the second bacterial isolate comprises a 16S rRNA sequence at least 95% identical to SEQ ID NO: 2.

In an aspect, the second bacterial isolate produces kynurenate at a level at least 1.5× greater than the level of kynurenate produced by the control bacterial strain. In an aspect, the second bacterial isolate comprises *Odoribacter splanchnicus*. In an aspect, the second bacterial isolate comprises a 16S rRNA sequence at least 95% identical to SEQ ID NO: 2. In an aspect, the second bacterial isolate produces kynurenine at a level at least 3× greater than the level of tryptamine produced by the control bacterial strain. In an aspect, the second bacterial isolate comprises *Odoribacter splanchnicus* or *Bacteroides stercoris*. In an aspect, the second bacterial isolate comprises a 16S rRNA sequence at least 95% identical to SEQ ID NO: 2 or SEQ ID NO: 13. In an aspect, the control bacterial strain comprises *Peptostreptococcus anaerobius*.

In an aspect, the second bacterial isolate produces indole-3-acetic acid at a level at least 3× greater than the level of indole-3-acetic acid produced by the control bacterial strain. In an aspect, the second bacterial isolate produces indole-3-acetic acid at a level at least 8× greater than the level of indole-3-acetic acid produced by the control bacterial strain.

In an aspect, the second bacterial isolate comprises *Odoribacter splanchnicus* or *Clostridium aldenense*. In an aspect, the second bacterial isolate comprises a 16S rRNA sequence at least 95% identical to SEQ ID NO: 2 or SEQ ID NO: 10.

In an aspect, the SCFA is butyrate. In an aspect, the SCFA is produced at a concentration of at least 20 mM. In an aspect, the SCFA is produced at a concentration of at least 25 mM. In an aspect, the SCFA is produced at a concentration of at least 30 mM. In an aspect, the SCFA is produced at a concentration of at least 35 mM. In an aspect, the second functional assay comprises incubating the second bacterial isolate with a substrate. In an aspect, the substrate comprises at least one of an oligosaccharide, sunfiber, or barley malt. In an aspect, the oligosaccharide comprises at least one of a fructooligosaccharide (FOS) and an xylooligosaccharide (XOS). In an aspect, the substrate comprises both of a fructooligosaccharide (FOS) and an xylooligosaccharide (XOS). In an aspect, the second bacterial isolate comprises a 16S rRNA sequence at least 95% identical to a 16S rRNA sequence of a bacterial isolate provided in Table 2.

Disclosed herein is a method of treating inflammatory bowel disease comprising administering the pharmaceutical composition comprising the first and second human-derived bacterial isolates to a subject in need thereof. In an aspect, the dosage of at least one of the first and second bacterial isolates is less than $10^{10}$ cells/ml.

In an aspect, there is provided a pharmaceutical composition comprising a plurality of bacterial isolates, wherein the plurality of bacterial isolates comprises *Bacteroides cellulosilyticus* and at least one of *Odoribacter splanchnicus, Roseburia faecis, Faecalibacterium prausnitzii, Akkermansia muciniphila, Alistipes shahii, Subdoligranulum variabile*, and *Eubacterium rectale*, wherein at least two of the plurality of bacterial isolates are isolated from stool samples of different donors.

In embodiments, the plurality of bacterial isolates comprises *Odoribacter splanchnicus*. In embodiments, the plurality of bacterial isolates comprises *Faecalibacterium prausnitzii*. In embodiments, the plurality of bacterial isolates comprises two different bacterial isolates that are each members of the species *Faecalibacterium prausnitzii*. In embodiments, the plurality of bacterial isolates comprises *Subdoligranulum variabile*. In embodiments, the plurality of bacterial isolates comprises *Roseburia faecis, Akkermansia muciniphila, Alistipes shahii*, and *Eubacterium rectale*. In embodiments, the plurality of bacterial isolates comprises *Roseburia faecis, Akkermansia muciniphila, Alistipes shahii*, and *Eubacterium rectale*.

In an aspect, there is provided a pharmaceutical composition comprising a plurality of bacterial isolates, wherein the plurality of bacterial isolates comprises two different bacterial isolates that are each members of the species *Faecalibacterium prausnitzii*.

In embodiments, the two different bacterial isolates are isolated from stool samples of different human donors. In embodiments, the plurality of bacterial isolates further comprises at least one of *Bacteroides cellulosilyticus, Odoribacter splanchnicus, Roseburia faecis, Akkermansia muciniphila, Alistipes shahii*, and *Eubacterium rectale*. In embodiments, the plurality of bacterial isolates further comprises each of *Bacteroides cellulosilyticus, Odoribacter splanchnicus, Roseburia faecis, Akkermansia muciniphila, Alistipes shahii*, and *Eubacterium rectale*.

In an aspect, there is provided a method of treating or preventing irritable bowel syndrome in a subject in need thereof, comprising administering to the subject a plurality of bacterial isolates, wherein one of the bacterial isolates comprises *Bacteroides cellulosilyticus*, and wherein at least two of the plurality of bacterial isolates are administered to the subject in different pharmaceutical compositions.

In embodiments, the plurality of bacterial isolates further comprises at least one of *Faecalibacterium prausnitzii, Odoribacter splanchnicus, Roseburia faecis, Akkermansia muciniphila, Alistipes shahii, Subdoligranulum variabile* and *Eubacterium rectale*. In embodiments, the plurality of bacterial isolates further comprises each of *Faecalibacterium prausnitzii, Odoribacter splanchnicus, Roseburia faecis, Akkermansia muciniphila, Alistipes shahii, Subdoligranulum variabile* and *Eubacterium rectale*. In embodiments, the plurality of bacterial isolates further comprises each of *Odoribacter splanchnicus, Roseburia faecis, Akkermansia muciniphila, Alistipes shahii, Eubacterium rectale*, and two different bacterial isolates that are each members of the species *Faecalibacterium prausnitzii*.

In an aspect, there is provided a method of manufacture, the method comprising culturing *Bacteroides cellulosilyticus* as a pure culture; and lyophilizing bacteria from the pure culture of *B. cellulosilyticus* to produce a *B. cellulosilyticus* lyophilate.

In embodiments, the method further comprises combining the *B. cellulosilyticus* lyophilate with a second lyophilate, wherein the second lyophilate is produced by lyophilizing bacteria from a pure culture of at least one of *Faecalibacterium prausnitzii, Odoribacter splanchnicus, Roseburia faecis, Akkermansia muciniphila, Alistipes shahii, Subdoligranulum variabile* and *Eubacterium rectale*.

In an aspect, there is provided a pharmaceutical composition comprising a plurality of bacterial isolates, wherein an amount of cells of a first bacterial isolate of the plurality of bacterial isolates is at least 10% greater than an amount of cells of a second bacterial isolate of the plurality of bacterial isolates, wherein the plurality of bacterial isolates are selected from the group consisting of: *Bacteroides cellulosilyticus, Faecalibacterium prausnitzii, Subdogranulum variabile, Eubacterium rectale, Odoribacter splanchnicus, Alistipes shahii,* and *Akkermansia muciniphila*.

In embodiments, the amount of cells of the first bacterial isolate is at least 10% greater than the amount of cells of the second bacterial isolate. In embodiments, the first bacterial isolate comprises one of *Eubacterium rectale* and *Faecalibacterium prausnitzii*. In embodiments, the second bacterial isolate comprises one of *Alistipes shahii,* and *Akkermansia muciniphila*. In embodiments, the first and second bacterial isolates comprises *Faecalibacterium prausnitzii*. In embodiments, the first bacterial isolate comprises a 16S rRNA sequence that is at least 95% identical to SEQ ID NO: 7. In embodiments, the second bacterial isolate comprises a 16S rRNA sequence that is at least 95% identical to SEQ ID NO: 1.

In an aspect, there is provided a pharmaceutical composition comprising a plurality of bacterial isolates, wherein an amount of cells of a first bacterial isolate of the plurality of bacterial isolates is at least 10% greater than an amount of cells of a second bacterial isolate of the plurality of bacterial isolates, wherein each of the first and second bacterial isolates comprises *Faecalibacterium prausnitzii*.

In embodiments, the amount of cells of the first bacterial isolate is at least 10% greater than the amount of cells of the second bacterial isolate. In embodiments, the first bacterial isolate comprises a 16S rRNA sequence that is at least 95% identical to SEQ ID NO: 7. In embodiments, the second bacterial isolate comprises a 16S rRNA sequence that is at least 95% identical to SEQ ID NO: 1.

In an aspect, there is provided a pharmaceutical composition comprising a bacterial isolate, wherein the bacterial isolate comprises a 16S rRNA sequence that is at least 97% identical to a 16S rRNA sequence of a bacterial strain that is either (i) enriched in a group of healthy subjects over a group of patients with ulcerative colitis (UC) and/or (ii) correlated with clinical remission of one or more UC symptoms in a group of patients following treatment of each patient of the group of patients with a fecal microbiota transplant, wherein a cross-sectional combined p-value of the bacterial strain is less than $1\times10^{-10}$.

In embodiments, the bacterial isolate comprises a 16S rRNA sequence that is at least 99% identical to a 16S rRNA sequence of the bacterial strain. In embodiments, the bacterial isolate comprises at least one of *Odoribacter splanchnicus, Eubacterium rectale, Bacteroides cellulosilyticus* and *Alistipes shahii*. In embodiments, the cross-sectional combined p-value of the bacterial strain is less than $1\times10^{-14}$. In embodiments, the bacterial isolate comprises at least one of *Odoribacter splanchnicus* and *Alistipes shahii*. In embodiments, the cross-sectional combined p-value of the bacterial strain is less than $1\times10^{-20}$. In embodiments, the bacterial isolate comprises *Alistipes shahii*. In embodiments, the *Alistipes shahii* comprises a 16S rRNA sequence that is at least 97% identical to SEQ ID NO: 18.

In embodiments, the plurality of bacterial isolates comprises lyophilized bacteria. In embodiments, the plurality of bacterial isolates does not include *Escherichia coli*. In embodiments, the pharmaceutical composition of any of the embodiments disclosed herein is not a stoll sample or a minimally processed version thereof.

In embodiments, there is provided a pharmaceutical composition comprising (a) a bacterial isolate and (b) a pharmaceutically acceptable antioxidant, cryoprotectant, lyoprotectant, binder, disintegrant, excipient, filler, preservative, acid suppressant, antacid, H2 antagonist, and/or proton pump inhibitor; the bacterial isolate comprising one, or two, or three, or four, or five, or six, or seven, or eight, or nine, or ten (in the case of Tables 42 or 43) of the bacterial isolates of any one of Tables 36-43. In embodiments, there is provided a pharmaceutical composition comprising (a) a bacterial isolate and (b) a pharmaceutically acceptable antioxidant, cryoprotectant, lyoprotectant, binder, disintegrant, excipient, filler, preservative, acid suppressant, antacid, H2 antagonist, and/or proton pump inhibitor; the bacterial isolate comprising nine of the bacterial isolates of any one of Tables 36-43. In embodiments, there is provided a pharmaceutical composition comprising (a) a bacterial isolate and (b) a pharmaceutically acceptable antioxidant, cryoprotectant, lyoprotectant, binder, disintegrant, excipient, filler, preservative, acid suppressant, antacid, H2 antagonist, and/or proton pump inhibitor; the bacterial isolate consisting of nine of the bacterial isolates of any one of Tables 36-43.

In aspects, there is provided a method of treating inflammatory bowel disease comprising administering the pharmaceutical composition described herein to a subject in need thereof.

In aspects, there is provided a method of treating inflammatory bowel disease comprising administering a bacterial isolate comprising one, or two, or three, or four, or five, or six, or seven, or eight, or nine, or ten (in the case of Tables 42 or 43) of the bacterial isolates of any one of Tables 36-43. In embodiments, the bacterial isolate(s) are co-formulated and/or co-administered. In embodiments, there is provided a method of treating inflammatory bowel disease comprising administering a pharmaceutical composition comprising (a) a bacterial isolate and (b) a pharmaceutically acceptable antioxidant, cryoprotectant, lyoprotectant, binder, disintegrant, excipient, filler, preservative, acid suppressant, antacid, H2 antagonist, and/or proton pump inhibitor; the bacterial isolate comprising one, or two, or three, or four, or five, or six, or seven, or eight, or nine, or ten (in the case of Tables 42 or 43) of the bacterial isolates of any one of Tables 36-43. In embodiments, there is provided a method of treating inflammatory bowel disease comprising administering a pharmaceutical composition comprising (a) a bacterial isolate and (b) a pharmaceutically acceptable antioxidant, cryoprotectant, lyoprotectant, binder, disintegrant, excipient, filler, preservative, acid suppressant, antacid, H2 antagonist, and/or proton pump inhibitor; the bacterial isolate comprising nine of the bacterial isolates of any one of Tables 36-43. In embodiments, there is provided a method of treating inflammatory bowel disease comprising administering a pharmaceutical composition comprising (a) a bacterial isolate and (b) a pharmaceutically acceptable antioxidant, cryoprotectant, lyoprotectant, binder, disintegrant, excipient, filler, preservative, acid suppressant, antacid, H2 antagonist, and/or proton pump inhibitor; the bacterial isolate consisting of nine of the bacterial isolates of any one of Tables 36-43.

Any aspect or embodiment described herein can be combined with any other aspect or embodiment as disclosed herein.

DETAILED DESCRIPTION

Figure 1A:
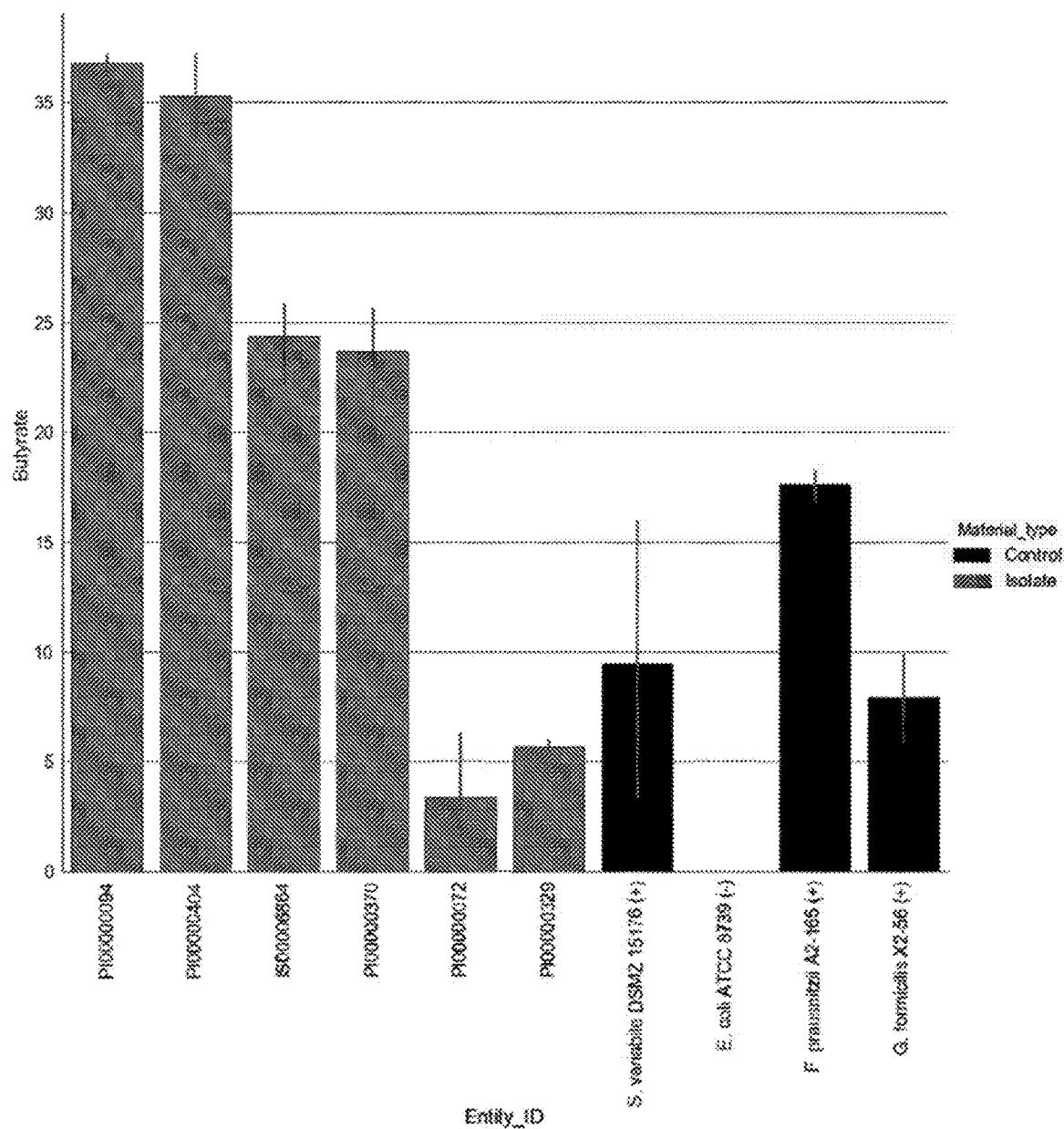
FIG. 1A is a graph showing the results of a short-chain fatty acid (SCFA) quantification assay measuring butyrate concentration (in mM) secreted by various bacterial isolates after a twenty-four incubation in substrate buffer.

Described herein are bacterial isolates and cocktails of bacterial isolates that can be utilized for the effective prevention and/or treatment of various disorders related to an intestinal dysbiosis.

Unless defined otherwise herein, terms are to be understood according to conventional usage by those of ordinary skill in the relevant art.

As used in the description of the disclosure and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The terms "about" and "approximately" as used herein when referring to a measurable value such as a percentage, density, volume and the like, is meant to encompass variations of 20%, 19%, 18%, 17%, 16%, 15%, 14%, 13%, 12%, 1% 10%, 9%, 8%, 7%, 6%, 5%, 4%, 3%, 2%, 1%, 0.5%, or even 0.1% of the specified amount.

As used herein, the term "substantially", when used to modify a quality, generally allows certain degree of variation without that quality being lost. For example, in certain aspects such degree of variation can be less than 0.1%, about 0.1%, about 0.2%, about 0.3%, about 0.4%, about 0.5%, about 0.6%, about 0.7%, about 0.8%, about 0.9%, about 1%, between 1-2%, between 2-3%, between 3-4%, between 4-5%, or greater than 5%.

As used herein, the term "treating" refers to (i) completely or partially inhibiting a disease, disorder or condition, for example, arresting its development; (ii) completely or partially relieving a disease, disorder or condition, for example, causing regression of the disease, disorder and/or condition; or (iii) completely or partially preventing a disease, disorder or condition from occurring in a patient that may be predisposed to the disease, disorder and/or condition, but has not yet been diagnosed as having it. Similarly, "treatment" refers to both therapeutic treatment and prophylactic or preventative measures.

As used herein, "therapeutically effective amount" or "pharmaceutically active dose" refers to an amount of a composition which is effective in treating the named disease, disorder or condition.

As used herein, "microbiota," and "flora" refer to a community of microbes that live in or on a subject's body, both sustainably and transiently, including eukaryotes, archaea, bacteria, and viruses (including bacterial viruses (i.e., phage)). A non-selected fecal microbiota refers to a community or mixture of fecal microbes derived from a donor's fecal sample without selection and substantially resembling microbial constituents and population structure found in such fecal sample.

As used herein, a "sterile fecal filtrate" or a "non-cellular fecal filtrate" refers to a liquid component of a fecal material, where the liquid component is free or substantially free of cell-based living organisms (e.g., bacteria, fungi, or their spores), but retains bacteriophages and non-cellular biological materials. In embodiments, a non-cellular or sterile fecal filtrate is also free of viruses for eukaryotic host cells.

As used herein, "eukaryotic" refers to belonging to a cell that contains a nucleus and membrane-bound organelles.

As used herein, "bacteria," "bacterium," and "archaea" refer to single-celled prokaryotes that lack membrane bound nuclei and organelles.

As used herein, "colony forming units" (cfu) refers to an estimate of the number of viable microorganism cells in a given sample.

As used herein, "viable" means possessing the ability to multiply. In one embodiment, a bacterial spore is viable. In another embodiment, a vegetative bacterial cell is viable.

As used herein, "fecal bacteria" refers to bacteria that can be found in fecal matter.

As used herein, "isolated" or "purified" refers to a bacterium or other entity or substance that has been (1) separated from at least some of the components with which it was associated when initially produced (whether in nature or in an experimental setting), and/or (2) produced, prepared, purified, and/or manufactured by the hand of man. Isolated or purified bacteria can be separated from at least about 10%, about 20%, about 30%, about 40%, about 50%, about 60%, about 70%, about 80%, about 90%, or more of the other components with which they were initially associated.

As used herein, "cytotoxic" activity or bacterium includes the ability to kill a bacterial cell, such as a pathogenic bacterial cell. A "cytostatic" activity or bacterium includes the ability to inhibit, partially or fully, growth, metabolism, and/or proliferation of a bacterial cell, such as a pathogenic bacterial cell.

As used herein, the terms "pathogen" and "pathogenic" in reference to a bacterium or any other organism or entity includes any such organism or entity that is capable of causing or affecting a disease, disorder or condition of a host organism containing the organism or entity.

As used herein, "spore" or a population of "spores" includes bacteria (or other single-celled organisms) that are generally viable, more resistant to environmental influences such as heat and bacteriocidal agents than vegetative forms of the same bacteria, and typically capable of germination and out-growth. "Spore-formers" or bacteria "capable of forming spores" are those bacteria containing the genes and other necessary abilities to produce spores under suitable environmental conditions.

As used herein, a "combination" of two or more bacteria includes the physical co-existence of the two bacteria, either in the same material or product or in physically connected products, as well as the temporal co-administration or co-localization of the two bacteria.

As used herein, a "bacterial isolate" refers to a population of substantially genetically identical bacterial cells generated by proliferation via binary fission from a single predecessor bacterial cell (e.g., by culturing the bacteria). Typically, a bacterial isolate is originally isolated as a genetically pure cell or population of cells, for example, as a single colony on solid culture media or via serial dilutions in liquid culture, and thereafter archived (e.g. as a frozen stock) to provide a consistent and stable source for the isolate. Once isolated, in some embodiments, bacterial isolate can be grown as a pure population of cells; in other embodiments, multiple isolates of bacteria can be grown simultaneously in the same vessel as a mixed culture. The term "substantially genetically identical" refers to the very high (>99%) genetic identity shared by different cells in uncontaminated mixtures, owing to their proliferation from a common predecessor, but accounts for minor genetic dissimilarity within the population due to accumulations of relatively rare mutations. Generally, a bacterial isolate is synonymous with a cultured population of cells. Typically, a bacterial isolate consists of non-pathogenic bacteria.

As used herein, the term "microbial cocktail", sometimes called a "microbial consortium" or "synthetic bacterial mixture" or "bacterial mixture", refers to an engineered composition (e.g. pharmaceutical composition) comprising a defined consortium of multiple bacterial isolates. The term "defined consortium of multiple bacterial isolates" means that the microbial cocktail contains two or more bacterial isolates, and that the number and identity of each bacterial isolate in the cocktail is known, and thus the cocktail can be consistently produced (e.g. by combining isolated bacterial strains) as a pharmaceutical composition having stable properties across separate batches. Herein "identity" of a bacterial isolate can refer to any characteristic of the isolate that uniquely identifies the isolate as different from one or more other isolates or bacterial strains. Examples of identifying characteristics include DNA sequences such as 16S rRNA sequence, the sequence of one or more coding or non-coding regions and entire genome sequences, levels of gene expression, physiological or metabolic traits, or anatomical traits such as staining pattern or cell wall characteristics.

A microbial cocktail or consortium described herein (e.g. derived from bacterial strains of fecal origin) can be distinguished from a composition (e.g. pharmaceutical composition) comprising an "uncultured fecal microbiota", which refers to a mixture of multiple bacterial strains that have been at least partially extracted or purified from a stool sample without culturing the strains in culture medium. Steps taken to extract a microbiota or fecal bacteria from a stool sample can include, for example, homogenization and filtering of the stool sample to separate the fecal bacterial strains from non-cellular stool material such as fiber and rough particulate matter, as well as, for example, eukaryotic host cells and viruses. Preparation of a pharmaceutical composition comprising an uncultured fecal microbiota can in some embodiments involve removal of certain types (e.g. species) of bacteria from the microbiota and/or addition of one or more bacterial strains to the microbiota. In certain embodiments, a pharmaceutical composition can comprise one or more cultured bacterial strains (e.g. bacterial isolates) combined with an uncultured fecal microbiota.

Herein "uncultured fecal bacteria" or a "preparation of uncultured fecal bacteria" refer to a preparation comprising multiple non-pathogenic viable bacterial strains that have been harvested, extracted or purified from one or more stool samples, without culturing the strains (e.g. in culturing medium). Such a preparation of uncultured fecal bacteria can also be referred to as a collection of uncultured fecal bacteria or a population of uncultured fecal bacteria. In certain embodiments, an uncultured fecal microbiota comprises a preparation of uncultured fecal bacteria.

The present disclosure contemplates compositions (e.g. pharmaceutical compositions) that comprise both a bacterial isolate (e.g., single microbial isolate or microbial cocktail) and an uncultured fecal microbiota or preparation of uncultured fecal bacteria. For example, in certain embodiments, a composition can comprise a substantially complete fecal microbiota or a preparation of uncultured fecal bacteria extracted or purified from a stool sample of a healthy individual supplemented or "spiked" with one or more bacterial isolates.

Herein the terms "microbial mixture" and "microbial therapeutic" are meant to broadly encompass any composition or treatment that incorporates a bacterial isolate, microbial cocktail, preparation of uncultured fecal bacteria and/or uncultured fecal microbiota.

Herein "at least 95% identical", when used with reference to a 16S rRNA sequence, refers to a subject DNA sequence that shares identity to a reference DNA sequence of at least 95%, at least 95.5%, at least 96%, at least 96.5%, at least 97%, at least 97.5%, at least 98%, at least 98.5%, at least 99%, at least 99.5% or 100%.

As used herein, a "subject" refers to any animal subject including humans, laboratory animals (e.g., primates, rats, mice), livestock (e.g., cows, sheep, goats, pigs, turkeys, chickens), and household pets (e.g., dogs, cats, rodents, etc.). In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish. Preferred subjects are human subjects. The human subject may be a pediatric, adult or a geriatric subject. In some embodiments, the terms "patient" and "subject" are used interchangeably.

As used herein, "Shannon Diversity Index" refers to a diversity index that accounts for abundance and evenness of species present in a given community using the formula $$H = -\sum_{i=1}^{R} p_i \ln p_i$$

where H is Shannon Diversity Index, R is the total number of species in the community, and $p_i$ is the proportion of R made up of the ith species. Higher values indicate diverse and equally distributed communities, and a value of 0 indicates only one species is present in a given community. For further reference, see Shannon and Weaver, (1949) *The mathematical theory of communication*. The University of Illinois Press, Urbana. 117 pp.

As used herein, "antibiotic" refers to a substance that is used to treat and/or prevent bacterial infection by killing bacteria, inhibiting the growth of bacteria, or reducing the viability of bacteria.

As used herein, an "intermittent dosing schedule" refers to a dosing schedule where a pharmaceutical composition is administered for a period of time (initial treatment period) which is then followed by a second period of time where treatment with such pharmaceutical composition is withheld (a rest period). The rest period can optionally be followed by a third period wherein the treatment is again administered (either at the same or different dosage as in the initial treatment period), which can be followed by further rest and treatment periods as needed. Intermittent dosing regimens can be expressed as treatment period in days or weeks/rest period in days or weeks. For example, a 4/1 intermittent dosing schedule refers to an intermittent dosing schedule where the treatment period is four weeks/days and the rest period is one week/day, as the case may be.

As used herein, a "continuous dosing schedule" refers to a dosing schedule where a pharmaceutical composition is administered during a treatment period without a rest period.

Throughout the treatment period of a continuous dosing schedule, a pharmaceutical composition can be administered, for example, daily, or every other day, or every third day.

On a day when a pharmaceutical composition is administered, it can be administered in a single dose, or in multiple doses throughout the day.

As used herein, "dosing frequency" refers to the frequency of administering doses of a pharmaceutical composition in a given time. Dosing frequency can be indicated as the number of doses per a given time, for example, once per day, once a week, or once in two weeks.

As used herein, "dosing interval" refers to the amount of time that elapses between consecutive doses of a pharmaceutical composition being administered to a subject.

As used herein, "a disorder related to an intestinal dysbiosis" or "a disorder related to an GI dysbiosis" or "dysbiosis" refers to a disorder or disease caused by an atypical or unhealthy microbiome, e.g., which comprises certain undesirable bacterial strains and/or lacks certain desirable bacterial strains. Examples include but are not limited to inflammatory bowel disease (IBD), irritable bowel syndrome (IBS), *C. difficile* infection (CDI), *C. difficile*-associated disease (CDAD), and antibiotic-induced adverse effect. Examples of IBD include ulcerative colitis (UC), Crohn's disease (CD), and pouchitis.

In one aspect, the subject has been diagnosed with a disorder related to an intestinal dysbiosis. In another aspect, a subject being treated is at risk for or is predisposed to having a disorder related to an intestinal dysbiosis is to be prevented. In aspects, a subject being treated is a subject in which a disorder related to an intestinal dysbiosis is to be prevented.

Bacterial Isolates and Microbial Cocktails

Described herein are pharmaceutical compositions, formulations, methods of manufacture, and uses of bacterial isolates and microbial cocktails of bacterial isolates in the treatment of various disorders related to an intestinal dysbiosis, e.g., gastrointestinal disorders.

An aspect of the present invention is a pharmaceutical composition comprising a plurality of bacterial isolates, wherein the plurality of bacterial isolates comprise *Bacteroides stercoris*, and at least two of *Bacteroides cellulosilyticus, Bacteroides uniformis, Subdoligranulum variabile, Anaerostipes hadrus, Odoribacter splanchnicus, Roseburia faecis, Faecalibacterium prausnitzii, Akkermansia muciniphila, Alistipes shahii*, and *Eubacterium rectale*, wherein at least two of the plurality of bacterial isolates are isolated from a stool of different human donors.

In embodiments, the plurality of bacterial isolates comprises at least three of *Bacteroides cellulosilyticus, Bacteroides uniformis, Subdoligranulum variabile, Anaerostipes hadrus, Odoribacter splanchnicus, Roseburia faecis, Faecalibacterium prausnitzii, Akkermansia muciniphila, Alistipes shahii*, and *Eubacterium rectale*. In embodiments, the plurality of bacterial isolates comprises at least four of *Bacteroides cellulosilyticus, Bacteroides uniformis, Subdoligranulum variabile, Anaerostipes hadrus, Odoribacter splanchnicus, Roseburia faecis, Faecalibacterium prausnitzii, Akkermansia muciniphila, Alistipes shahii*, and *Eubacterium rectale*. In embodiments, the plurality of bacterial isolates comprises at least five of *Bacteroides cellulosilyticus, Bacteroides uniformis, Subdoligranulum variabile, Anaerostipes hadrus, Odoribacter splanchnicus, Roseburia faecis, Faecalibacterium prausnitzii, Akkermansia muciniphila, Alistipes shahii*, and *Eubacterium rectale*. In embodiments, the plurality of bacterial isolates comprises at least five of *Bacteroides cellulosilyticus, Bacteroides uniformis, Subdoligranulum variabile, Anaerostipes hadrus, Odoribacter splanchnicus, Roseburia faecis, Faecalibacterium prausnitzii, Akkermansia muciniphila, Alistipes shahii*, and *Eubacterium rectale*. In embodiments, the plurality of bacterial isolates comprises at least six of *Bacteroides cellulosilyticus, Bacteroides uniformis, Subdoligranulum variabile, Anaerostipes hadrus, Odoribacter splanchnicus, Roseburia faecis, Faecalibacterium prausnitzii, Akkermansia muciniphila, Alistipes shahii*, and *Eubacterium rectale*. In embodiments, the plurality of bacterial isolates comprises at least seven of *Bacteroides cellulosilyticus, Bacteroides uniformis, Subdoligranulum variabile, Anaerostipes hadrus, Odoribacter splanchnicus, Roseburia faecis, Faecalibacterium prausnitzii, Akkermansia muciniphila, Alistipes shahii*, and *Eubacterium rectale*. In embodiments, the plurality of bacterial isolates comprises at least eight of *Bacteroides cellulosilyticus, Bacteroides uniformis, Subdoligranulum variabile, Anaerostipes hadrus, Odoribacter splanchnicus, Roseburia faecis, Faecalibacterium prausnitzii, Akkermansia muciniphila, Alistipes shahii*, and *Eubacterium rectale*.

In embodiments, the composition comprises a 16S rRNA sequence that is at least about 95%, or at least about 97%, or at least about 98%, or at least about 99% sequence identity with nucleotide sequences selected from SEQ ID NOs: 1, 2, 3, 7, 8, 11, 14, 18, 19, 20, 22 and 23. In embodiments, the pharmaceutical composition comprises at least two bacterial isolates comprising *Faecalibacterium prausnitzii*, wherein the at least two bacterial isolates comprise different 16S rRNA sequences. In embodiments, the pharmaceutical composition comprises 16S rRNA sequences that are at least about 95%, or at least about 97%, or at least about 98%, or at least about 99% identity sequence identity with nucleotide sequences of SEQ ID NOs: 1 and 7.

In aspects, a pharmaceutical composition comprises one or more bacterial isolates that comprised a 16S rRNA sequence at least 95% identical (e.g., at least 95% identical, at least 95.5% identical, at least 96% identical, at least 96.5% identical, at least 97% identical, at least 97.5% identical, at least 98% identical, at least 98.5% identical, at least 99% identical, at least 99.5% identical, or 100% identical) to the 16S rRNA sequence of one of the bacterial isolates provided in Table 1. In embodiments, the composition comprises a single bacterial isolate. In embodiments, the composition is a microbial cocktail that comprises at least two bacterial isolates, at least three bacterial isolates, at least four bacterial isolates, at least five bacterial isolates, at least six bacterial isolates, at least seven bacterial isolates, at least eight bacterial isolates, at least nine bacterial isolates, at least ten bacterial isolates, or a greater number of bacterial isolates, e.g., fifteen, twenty, twenty-five, thirty, or more bacterial isolates. In embodiments, each of the, for example, three, four, five, six, seven, eight, nine, or ten bacterial isolates comprises a 16S rRNA sequence that is at least 95% identical to the 16S rRNA sequence of one of the bacterial isolates provided in Table 1.

In one aspect, a pharmaceutical composition administered herein comprises fecal bacteria. In one aspect, a pharmaceutical composition administered herein comprises one or more bacterial isolates extracted, isolated and/or cultured from a stool sample of a healthy human donor. In one aspect, a pharmaceutical composition administered herein comprises one or more, two or more, three or more, four or more, or five or more isolated, purified, or cultured microorganisms selected from the group consisting of *Akkermansia, Alistipes, Anaerostipes, Bacillus, Bacteroides, Blautia, Clostridium, Collinsella, Coprococcus, Dorea, Eubacterium, Faecalibacterium, Fusobacterium, Odoribacter, Parabacteroides, Phascolarctobacterium, Propionibacterium, Roseburia, Subdoligranulum, Lactobacillus, Ruminococcus, Escherichia, Gemmiger, Desulfomonas, Peptostreptococcus*, and a combination thereof.

In one aspect, a pharmaceutical composition administered herein comprises at least one, at least two, at least three, at least four, at least five, at least six, or at least seven, at least eight, at least nine, at least ten, at least eleven, or at least twelve fecal microorganisms (e.g., bacterial isolates) selected from the group consisting of a *Faecalibacterium prausnitzii, Odoribacter splanchnicus, Anaerostipes hadrus, Alistipes onderdonkii, Alistipes putredinis, Parabacteroides merdae, Dorea longicatena, Eubacterium rectale, Blautia obeum, Blautia sp., Clostridium aldenense, Bacteroides uniformis, Bacteroides vulgatus, Bacteroides stercoris, Bacteroides cellulosilyticus, Alistipes finegoldii, Coprococcus comes, Alistipes shahii, Roseburia faecis, Akkermansia muciniphila, Phascolarctobacterium faecium, Subdoligranulum variabile*, and a combination thereof. In embodiments, a bacterial isolate comprises *Odoribacter* sp. In an embodiment, *Odoribacter* sp. comprises *Odoribacter splanchnicus*. In embodiments, a bacterial isolate comprising *Odoribacter* sp. comprises *Odoribacter laneus*. In embodiments, a bacterial isolate comprising *Blautia* sp. comprises *Blautia obeum*. In embodiments, a bacterial isolate comprising *Blautia* sp. comprises *Blautia massiliensis*. In embodiments, a bacterial isolate comprising *Blautia* sp. comprises *Blautia coccoides*. In embodiments, a bacterial isolate comprising *Blautia* sp. comprises *Blautia producta*. In embodiments, a bacterial isolate comprising *Blautia* sp. comprises *Blautia schinkii*. In embodiments, a bacterial isolate comprising *Blautia* sp. comprises *Blautia hydrogenotrophica*. In embodiments, a bacterial isolate comprising *Blautia* sp. comprises *Blautia luti*. In embodiments, a bacterial isolate comprising *Blautia* sp. comprises *Blautia hansenii*. In embodiments, a bacterial isolate comprising *Blautia* sp. comprises *Blautia faecis*. In embodiments, a bacterial isolate comprising *Blautia* sp. comprises *Blautia stercoris*. In embodiments, a bacterial isolate comprising *Blautia* sp. comprises *Blautia wexlerae*.

In one aspect, a pharmaceutical composition administered herein comprises no viable *Bacteroides, Fusobacterium, Propionibacterium, Lactobacillus, Ruminococcus, Escherichia coli, Gemmiger, Desulfomonas, Peptostreptococcus, Bifidobacterium, Monilia*, or any combination thereof. In another aspect, a pharmaceutical composition administered herein comprises no viable *Bacteroides fragilis* sp. *vulgatus, Collinsella aerofaciens, Bacteroides fragilis* sp. *thetaiotaomicron, Peptostreptococcus productus* II, *Parabacteroides distasonis, Fusobacterium prausnitzii, Coprococcus eutactus, Collinsella aerofaciens* III, *Peptostreptococcus productus* I, *Ruminococcus bromii, Bifidobacterium adolescentis, Gemmiger formicilis, Bifidobacterium longum, Eubacterium siraeum, Ruminococcus torques, Eubacterium rectale, Eubacterium eligens, Bacteroides eggerthii, Clostridium leptum, Bacteroides fragilis* sp. A, *Eubacterium biforme, Bifidobacterium infantis, Eubacterium rectale* III-F, *Coprococcus comes, Pseudoflavonifractor capillosus, Ruminococcus albus, Dorea formicigenerans, Eubacterium hallii, Eubacterium ventriosum* I, *Fusobacterium russi, Ruminococcus obeum, Eubacterium rectale, Clostridium ramosum, Lactobacillus leichmannii, Ruminococcus callidus, Butyrivibrio crossotus, Acidaminococcus fermentans, Eubacterium ventriosum, Bacteroides fragilis* sp. *fragilis, Bacteroides* AR, *Coprococcus catus, Aerostipes hadrus, Eubacterium cylindroides, Eubacterium ruminantium, Eubacterium* CH-1, *Staphylococcus epidermidis, Peptostreptococcus* BL, *Eubacterium limosum, Tissirella praeacuta, Bacteroides* L, *Fusobacterium mortiferum* I, *Fusobacterium naviforme, Clostridium innocuum, Clostridium ramosum, Propionibacterium acnes, Ruminococcus flavefaciens, Ruminococcus* AT, *Peptococcus* AU-1, *Bacteroides fragilis* sp. *ovatus*, -sp. d, -sp. f; *Bacteroides* L-1, L-5; *Fusobacterium nucleatum, Fusobacterium mortiferum, Escherichia coli, Gemella morbillorum, Finegoldia magnus, Peptococcus* G, -AU-2; *Streptococcus intermedius, Ruminococcus lactaris, Ruminococcus* CO *Gemmiger* X, *Coprococcus* BH, -CC; *Eubacterium tenue, Eubacterium ramulus, Bacteroides clostridiiformis* sp. *clostridliformis, Bacteroides coagulans, Prevotella oralis, Prevotella ruminicola, Odoribacter* sp. (e.g. *Odoribacter splanchnicus* and/or *Odoribacter laneus*), *Desuifomonas pigra, Lactobacillus* G, *Succinivibrio* A, or a combination thereof.

In various embodiments, the bacterial isolates described herein comprise bacteria isolated or purified from a human. In various embodiments, all or a subset of bacterial isolates incorporated into a microbial cocktail described herein are isolated or purified from a human.

For instance, one or more bacterial isolates can be purified or isolated from a stool sample of one or more healthy human donors pre-screened for infectious agents. In other examples, a bacterial isolate can be isolated or purified from aspirates of the fluid in the GI tract or mucosal biopsies from a site in the GI tract.

In embodiments, a pharmaceutical composition or microbial cocktail comprises a plurality of bacterial isolates isolated or purified from stool samples of multiple human donors.

In embodiments, a pharmaceutical composition or microbial cocktail comprises a plurality of bacterial isolates isolated or purified from a stool sample or stool samples of only a single human donor.

In some embodiments, a bacterial isolate incorporated into a pharmaceutical composition described herein comprises live, vegetative cells. In some embodiments, the bacterial isolate comprises bacteria capable of forming spores. In some embodiments, the bacterial isolate comprises bacteria in the form of spores, e.g. viable spores. In some embodiments, the bacterial isolate comprises bacteria in the form of live, vegetative cells and spores. In some embodiments, a bacterial isolate is substantially free of live, vegetative cells. In some embodiments, an entire microbial cocktail is substantially free of live vegetative cells. In some embodiments, a bacterial isolate is substantially free of spores. In some embodiments, an entire microbial cocktail is substantially free of spores.

In aspects, a pharmaceutical composition comprises at least one bacterial isolate provided in Table 1, or a bacterial isolate comprising a 16S rRNA sequence that is at least 95% identical to the 16S rRNA sequence of one or more of the bacterial isolates provided in Table 1. In certain embodiments, a pharmaceutical composition comprises a microbial cocktail comprising at least two bacterial isolates provided in Table 1, or at least two bacterial isolates comprising a 16S rRNA sequence that is at least 95% identical to the 16S rRNA sequence of one or more of the bacterial isolates provided in Table 1. Each bacterial isolate in Table 1 is identified by Latin name, an Identification Number (ID number), and the Sequence Identifier (SEQ ID NO) for its 16S rRNA sequence.

TABLE 1

| Isolate Latin Name | ID Number | SEQ ID NO for 16S rRNA Sequence |
|---|---|---|
| Faecalibacterium prausnitzii | PI00000329 | 1 |
| Odoribacter splanchnicus | PI00000072 | 2 |
| Anaerostipes hadrus | PI00000094 | 3 |
| Alistipes onderdonkii | IS00004389 | 4 |
| Parabacteroides merdae | IS00006167 | 5 |
| Dorea longicatena | IS00006618 | 6 |
| Faecalibacterium prausnitzii | IS00006632 | 7 |
| Eubacterium rectale | IS00006864 | 8 |
| Blautia obeum | PI00000053 | 9 |
| Clostridium aldenense | PI00000097 | 10 |
| Bacteroides uniformis | PI00000137 | 11 |
| Bacteroides vulgatus | PI00000138 | 12 |
| Bacteroides stercoris | PI00000146 | 13 |
| Bacteroides cellulosilyticus | PI00000316 | 14 |
| Alistipes finegoldii | PI00000340 | 15 |
| Bacteroides uniformis | PI00000352 | 16 |
| Coprococcus comes | PI00000370 | 17 |
| Alistipes shahii | PI00000395 | 18 |
| Roseburia faecis | PI00000404 | 19 |

TABLE 1-continued

| Isolate Latin Name | ID Number | SEQ ID NO for 16S rRNA Sequence |
|---|---|---|
| Akkermansia mucimphila | IS00007180 | 20 |
| Phascolarctobacterium faecium | PI00000289 | 21 |
| Subdoligranulum variabile | IS00007359 | 22 |
| Subdoligranulum variabile | IS00007357 | 23 |
| Blautia sp. | IS00002788 | 34 |
| Alistipes putredinis | IS00008139 | 35 |
| Alistipes putredinis | IS00008142 | 36 |
| Alistipes putredinis | IS00008177 | 37 |

In embodiments, the pharmaceutical composition comprises a microbial cocktail comprising about 2 to about 50 bacterial isolates, about 3 to about 50 bacterial isolates, about 3 to about 45 bacterial isolates, about 3 to about 40 bacterial isolates, about 3 to about 35 bacterial isolates, about 3 to about 30 bacterial isolates, about 3 to about 20 bacterial isolates, about 3 to about 15 bacterial isolates, about 3 to about 10 bacterial isolates, and about 3 to about 9 bacterial isolates. In embodiments, the pharmaceutical composition comprises a microbial cocktail comprising about 30 bacterial isolates, or about 29 bacterial isolates, or about 28 bacterial isolates, or about 27 bacterial isolates, or about 26 bacterial isolates, or about 25 bacterial isolates, or about 24 bacterial isolates, or about 23 bacterial isolates, or about 22 bacterial isolates, or about 21 bacterial isolates, or about 19 bacterial isolates, or about 18 bacterial isolates, or about 17 bacterial isolates, or about 16 bacterial isolates, or about 15 bacterial isolates, or about 14 bacterial isolates, or about 13 bacterial isolates, or about 12 bacterial isolates, or about 11 bacterial isolates. In embodiments, the pharmaceutical composition comprises a microbial cocktail comprising 10 bacterial isolates. In embodiments, the pharmaceutical composition comprises a microbial cocktail comprising 9 bacterial isolates. In embodiments, the pharmaceutical composition comprises a microbial cocktail comprising 8 bacterial isolates. In embodiments, the pharmaceutical composition comprises a microbial cocktail comprising 7 bacterial isolates. In embodiments, the pharmaceutical composition comprises a microbial cocktail comprising 6 bacterial isolates. In embodiments, the pharmaceutical composition comprises a microbial cocktail comprising 5 bacterial isolates. In embodiments, the pharmaceutical composition comprises a microbial cocktail comprising 4 bacterial isolates. In embodiments, the pharmaceutical composition comprises a microbial cocktail comprising 3 bacterial isolates. In embodiments, the pharmaceutical composition comprises a microbial cocktail comprising 2 bacterial isolates.

In embodiments, the microbial cocktail comprises at least two bacterial isolates, at least three bacterial isolates, at least four bacterial isolates, at least five bacterial isolates, at least six bacterial isolates, at least seven bacterial isolates, at least eight bacterial isolates, at least nine bacterial isolates, at least ten bacterial isolates, or a greater number of bacterial isolates, e.g., fifteen, twenty, twenty-five, thirty, or more bacterial isolates. In embodiments, each of the three, four, five, six, seven, eight, nine, or ten bacterial isolates comprises a 16S rRNA sequence that is at least 95% identical to the 16S rRNA sequence of at least one of the bacterial isolates provided in Table 1.

In embodiments, the pharmaceutical composition comprises a microbial cocktail comprising about 6 to about 20 bacterial isolates provided in Table 1, or having a 16S rRNA sequence that is at least 95% identical to the 16S rRNA sequence of at least one of the bacterial isolates provided in Table 1, or e.g., about 6 to about 15 bacterial isolates, about 6 to about 10 bacterial isolates, about 6 to about 9 bacterial isolates. In embodiments, the pharmaceutical composition comprises a microbial cocktail comprising 30 bacterial isolates, or 29 bacterial isolates, or 28 bacterial isolates, or 27 bacterial isolates, or 26 bacterial isolates, or 25 bacterial isolates, or 24 bacterial isolates, or 23 bacterial isolates, or 22 bacterial isolates, or 21 bacterial isolates, or 20 bacterial isolates, or 19 bacterial isolates, or 18 bacterial isolates, or 17 bacterial isolates, or 16 bacterial isolates, or 15 bacterial isolates, or 14 bacterial isolates, or 13 bacterial isolates, or 12 bacterial isolates, or 11 bacterial isolates, or 10 bacterial isolates, or 9 bacterial isolates, or 8 bacterial isolates, or 7 bacterial isolates, or 6 bacterial isolates, or 5 bacterial isolates, or 4 bacterial isolates, or 3 bacterial isolates, or 2 bacterial isolates, or 1 bacterial isolate provided in Table 1, or having a 16S rRNA sequence that is at least 95% identical to a 16S rRNA sequence of one or more bacterial isolates provided in Table 1. In embodiments, the pharmaceutical composition comprises a microbial cocktail comprising 8 bacterial isolates provided in Table 1, or having a 16S rRNA sequence that is at least 95% identical to a 16S rRNA sequence of one or more isolates provided in Table 1. In embodiments, the pharmaceutical composition comprises a microbial cocktail comprising 7 bacterial isolates provided in Table 1, or having a 16S rRNA sequence that is at least 95% identical to a 16S rRNA sequence of one or more bacterial isolates provided in Table 1. In embodiments, the pharmaceutical composition comprises a microbial cocktail comprising 6 bacterial isolates provided in Table 1, or having a 16S rRNA sequence that is at least 95% identical to a 16S rRNA sequence of one or more bacterial isolates provided in Table 1. In embodiments, the pharmaceutical composition comprises one bacterial isolate provided in Table 1, or having a 16S rRNA sequence that is at least 95% identical to a 16S rRNA sequence of one or more bacterial isolates provided in Table 1.

In embodiments, a bacterial isolate incorporated into a pharmaceutical composition described herein is capable of improving the health of a subject administered the composition. In embodiments, the bacterial isolate impacts the health of a subject by inducing or influencing one or more biological mechanisms that act in the subject to impact the health of the subject. Exemplary mechanisms include the production of SCFA by the bacterial isolate in the gut of the subject or the modulation by the bacterial isolate of cytokine production and/or release by a cell of the subject (e.g., intestinal cell). Another exemplary mechanism is the production by the bacterial isolate of an aryl hydrocarbon capable of binding to and activating an aryl hydrocarbon receptor (AhR) of a cell of the subject. In another example, a bacterial isolate is more abundant in the gut or fecal microbiota of a healthy human subject relative to a patient with an intestinal dysbiosis, or a more abundant in a human subject in remission from an intestinal dysbiosis relative to a patient having the intestinal dysbiosis. The increased abundance of the bacterial isolate in the intestine of a healthy subject can be indicative of a positive impact of the bacterial isolate on the health of the subject, even though the precise mechanism of action by which the bacterial isolate produces its effect may not be understood (i.e., the bacterial isolate has an impact on the health of the subject that is mechanism agnostic).

In embodiments, a pharmaceutical composition comprises one or more bacterial isolates having the ability to produce one or more SCFAs, or to enhance SCFA production by one or more bacterial strains. As used herein, an 'SCFA' refers to fatty acids with an aliphatic tail of one to six carbon atoms. SCFAs can be produced by bacteria during bacterial metabolism, such as during fermentation of, for example, carbohydrates, proteins, peptides and glycoprotein precursors. Illustrative SCFAs include, but are not limited to, acetic acid, butyric acid, caproic acid, formic acid, heptanoic acid, isobutyric acid, isocaproic acid, isovaleric acid, propionic acid, and valeric acid. Without wishing to be bound by theory, SCFAs are thought to play an essential role in maintaining the health of colonic mucosa, and the presence of gut SCFA-producing bacteria are associated with sustained clinical remission of certain gut dysbioses, such as UC. Accordingly, in some embodiments, a bacterial isolate incorporated into a pharmaceutical composition described herein can produce one or more SCFAs. For example, a bacterial isolate can produce one or more SCFAs in an intestine of a subject after the composition (e.g., comprising a microbial cocktail) is administered to the subject (e.g., a subject having UC). In another example, a bacterial isolate can produce one or more SCFAs in an in vitro assay capable of detecting and/or measuring SCFA production by bacteria.

In embodiments, a bacterial isolate described herein produces an SCFA selected from the group consisting of: acetic acid, butyric acid, caproic acid, formic acid, heptanoic acid, isobutyric acid, isocaproic acid, isovaleric acid, propionic acid, valeric acid, and a combination thereof.

In embodiments, a pharmaceutical composition comprises one or more bacterial isolates that produce an SCFA (e.g., butyrate) at a concentration of at least 5 mM, at least 10 mM, at least 15 mM, at least 20 mM, at least 25 mM, at least 30 mM, at least 35 mM, at least 40 mM, at least 45 mM at least 50 mM, at least 60 mM, at least 70 mM, at least 80 mM, at least 90 mM, at least 100 mM, at least 110 mM, at least 120 mM, at least 130 mM, at least 140 mM, at least 150 mM, or greater than 150 mM during a period of 24 hours. In an embodiment, the SCFA is measured in a functional assay (i.e., an assay conducted ex vivo and designed to measure the concentration or amount of an SCFA produced by a bacterial isolate, microbial cocktail, a preparation of uncultured fecal bacteria, or an uncultured fecal microbiota during a period of time (e.g., 24 hours)). For example, a functional assay can comprise incubating one or more bacterial isolates with a substrate (e.g., for 24 hours); and measuring the level of SCFA (e.g., butyrate) produced by the one or more bacterial isolates after metabolism of the substrate. In embodiments, the substrate can comprise at least one of an oligosaccharide (e.g., a fructooligosaccharide (FOS) or an xylooligosaccharide (XOS)), sunfiber/partially hydrolyzed guar gum (PHGG), or barley malt.

In an embodiment, the SCFA is produced in the intestine of a subject administered a composition described herein.

In an embodiment, a pharmaceutical composition comprises *Odoribacter splanchnicus*, wherein the *Odoribacter splanchnicus* produces an SCFA (e.g., butyrate) at a concentration of at least 20 mM, at least 21 mM, at least 22 mM, at least 23 mM, at least 24 mM, at least 25 mM, at least 26 mM, at least 27 mM, at least 28 mM, at least 29 mM, at least 30 mM, at least 31 mM, at least 32 mM, at least 33 mM, at least 34 mM, at least 35 mM, at least 36 mM, at least 37 mM, at least 38 mM, at least 39 mM, at least 40 mM, at least 41 mM, at least 42 mM, at least 43 mM, at least 44 mM, at least 45 mM, at least 46 mM, at least 47 mM, at least 48 mM, at least 49 mM, at least 50 mM, or greater than 50 mM over a period of 24 hours. In an embodiment, the *Odoribacter*

*splanchnicus* comprises a 16S rRNA sequence having at least 95% sequence identity to SEQ ID NO: 2.

In an embodiment, a pharmaceutical composition comprises *Roseburia* sp. (e.g., *Roseburia faecis*), wherein the *Roseburia* sp. produces an SCFA (e.g., butyrate) at a concentration of at least 20 mM, at least 21 mM, at least 22 mM, at least 23 mM, at least 24 mM, at least 25 mM, at least 26 mM, at least 27 mM, at least 28 mM, at least 29 mM, at least 30 mM, at least 31 mM, at least 32 mM, at least 33 mM, at least 34 mM, at least 35 mM, at least 36 mM, at least 37 mM, at least 38 mM, at least 39 mM, at least 40 mM, at least 41 mM, at least 42 mM, at least 43 mM, at least 44 mM, at least 45 mM, at least 46 mM, at least 47 mM, at least 48 mM, at least 49 mM, at least 50 mM, or greater than 50 mM over a period of 24 hours. In an embodiment, the *Roseburia* sp. comprises a 16S rRNA sequence having at least 95% sequence identity to SEQ ID NO: 19.

In an embodiment, a pharmaceutical composition comprises Eubacteria sp. (e.g., *Eubacteria rectale*), wherein the *Eubacteria* sp. produces an SCFA (e.g., butyrate) at a concentration of at least 20 mM, at least 21 mM, at least 22 mM, at least 23 mM, at least 24 mM, at least 25 mM, at least 26 mM, at least 27 mM, at least 28 mM, at least 29 mM, at least 30 mM, at least 31 mM, at least 32 mM, at least 33 mM, at least 34 mM, at least 35 mM, at least 36 mM, at least 37 mM, at least 38 mM, at least 39 mM, at least 40 mM, at least 41 mM, at least 42 mM, at least 43 mM, at least 44 mM, at least 45 mM, at least 46 mM, at least 47 mM, at least 48 mM, at least 49 mM, at least 50 mM, or greater than 50 mM over a period of 24 hours. In an embodiment, the *Eubacteria* sp. comprises a 16S rRNA sequence having at least 95% sequence identity to SEQ ID NO: 8.

In an embodiment, a pharmaceutical composition comprises *Coprococcus* sp. (e.g., *Coprococcus comes*), wherein the *Coprococcus* sp. produces an SCFA (e.g., butyrate) at a concentration of at least 20 mM, at least 21 mM, at least 22 mM, at least 23 mM, at least 24 mM, at least 25 mM, at least 26 mM, at least 27 mM, at least 28 mM, at least 29 mM, at least 30 mM, at least 31 mM, at least 32 mM, at least 33 mM, at least 34 mM, at least 35 mM, at least 36 mM, at least 37 mM, at least 38 mM, at least 39 mM, at least 40 mM, at least 41 mM, at least 42 mM, at least 43 mM, at least 44 mM, at least 45 mM, at least 46 mM, at least 47 mM, at least 48 mM, at least 49 mM, at least 50 mM, or greater than 50 mM over a period of 24 hours. In an embodiment, the *Coprococcus* sp. comprises a 16S rRNA sequence having at least 95% sequence identity to SEQ ID NO: 17.

In an embodiment, a pharmaceutical composition comprises a microbial cocktail comprising two or more bacterial isolates comprising *Odoribacter splanchnicus*, *Roseburia* sp. (e.g., *Roseburia faecis*), *Eubacteria* sp. (e.g., *Eubacteria rectale*), or *Coprococcus* sp. (e.g., *Coprococcus comes*), wherein the microbial cocktail produces an SCFA (e.g., butyrate) at a concentration of at least 20 mM, at least 21 mM, at least 22 mM, at least 23 mM, at least 24 mM, at least 25 mM, at least 26 mM, at least 27 mM, at least 28 mM, at least 29 mM, at least 30 mM, at least 31 mM, at least 32 mM, at least 33 mM, at least 34 mM, at least 35 mM, at least 36 mM, at least 37 mM, at least 38 mM, at least 39 mM, at least 40 mM, at least 41 mM, at least 42 mM, at least 43 mM, at least 44 mM, at least 45 mM, at least 46 mM, at least 47 mM, at least 48 mM, at least 49 mM, at least 50 mM, at least 60 mM, at least 65 mM, at least 70 mM, at least 75 mM, at least 80 mM, at least 85 mM, at least 90 mM, at least 95 mM, at least 100 mM, at least 105 mM, at least 110 mM, at least 115 mM, at least 120 mM, at least 125 mM, at least 130 mM, at least 135 mM, at least 140 mM, at least 145 mM, at least 150 mM, or greater than 150 mM over a period of 24 hours. In an embodiment, the *Odoribacter splanchnicus* comprises a 16S rRNA sequence having at least 95% sequence identity to SEQ ID NO: 2. In an embodiment, the *Roseburia* sp. comprises a 16S rRNA sequence having at least 95% sequence identity to SEQ ID NO: 19. In an embodiment, the *Eubacteria* sp. comprises a 16S rRNA sequence having at least 95% sequence identity to SEQ ID NO: 8. In an embodiment, the *Coprococcus* sp. comprises a 16S rRNA sequence having at least 95% sequence identity to SEQ ID NO: 17.

Additionally, in some embodiments, one or more bacterial isolates administered in a composition described herein can produce levels of SCFAs comparable to that of a healthy individual in a subject previously having a functionally deficient microbial community (e.g., the microbial community of an IBD patient) who exhibited SCFA production levels lower than that of the healthy individual.

In certain embodiments, a bacterial isolate described herein can induce one or more bacterial strains to produce one or more SCFAs when the bacterial isolate and the bacterial strain(s) are present together in a common microbiota. For example, a bacterial isolate, upon administration to a subject in a composition described herein, can induce one or more bacterial strains endogenous to a gut microbiota of the subject (i.e., present in the gut of the subject prior to administration of the microbial cocktail) to produce one or more SCFAs. In another example, a bacterial isolate administered to a subject in a composition described herein can induce a second bacterial isolate administered to the subject (either in the same or a different composition) to produce one or more SCFAs. Without wishing to be bound by theory, induction of SCFA production by a second bacterial isolate can involve, for example, the production and release (e.g., by secretion) by the first bacterial isolate of one or more compounds that can be utilized by the second bacterial isolate to generate an SCFA. In one example, the compound produced and released by the first bacterial isolate to be used by the second bacterial strain to generate an SCFA is succinate, lactic acid or a lactic acid derivative. In one embodiment, the SCFA produced by the second bacterial isolate in response to exposure to the compound (e.g., lactic acid or lactic acid derivative) produced by the first bacterial isolate is butyric acid. Non-limiting examples of lactic acid derivatives include sodium isostearoyl lactate, sodium lactate, calcium lactate, aluminum lactate, ammonium lactate, potassium lactate, cetyl lactate, myristyl lactate, sodium stearoyl lactate, lactide, butyl lactate, and ethyl lactate.

In embodiments, a lactic acid-producing bacterial isolate (i.e., first bacterial isolate) included in a pharmaceutical composition described herein belongs to the *Bifidobacterium* genus. For example, the lactic acid-producing bacterial isolate can belong to *Bifidobacterium longum* or *Bifidobacterium adolescentis*. In embodiments, a second bacterial isolate (e.g., included with a first bacterial isolate in a microbial cocktail described herein or in a separate composition) is capable of using lactic acid produced by the *Bifidobacterium* to generate one or more SCFAs. In certain examples, the second bacterial isolate comprises a 16S rRNA sequence that is at least 95% identical to the 16S rRNA sequence of one of the bacterial isolates provided in Table 2.

In embodiments, a bacterial isolate incorporated into a pharmaceutical composition is capable of using lactic acid produced by the gut microbiota following administration of the cocktail to generate one or more SCFAs. In certain examples, the bacterial isolate comprises a 16S rRNA sequence that is at least 95% identical to the 16S rRNA sequence of one of the bacterial isolates provided in Table 2.

In embodiments, upon administration of a first and a second bacterial isolate to a subject (e.g., in the form of a microbial cocktail or in separate compositions), the first bacterial isolate produces and secretes lactic acid, and the second bacterial isolate utilizes the lactic acid to generate one or more SCFAs (e.g., butyrate). Thus, multiple bacterial isolates administered to a subject can interact synergistically within the gut of the subject to produce therapeutic effects (e.g., generation of one or more SCFAs) for treatment of an intestinal dysbiosis (e.g., IBD or ulcerative colitis) of the subject.

In embodiments, one or more bacterial isolates described herein can be administered with a probiotic that includes one or more bacterial strains that when administered to a subject produce and release a compound that can be used by the bacterial isolate to produce one or more SCFAs. For example, the probiotic can include one or more bacterial strains belonging to the genus *Bifidobacterium* (e.g., *Bifidobacterium adolescentis* or *Bifidobacterium longum*). In embodiments, the probiotic can be administered to a subject at the same time as a bacterial isolate, before administration of the bacterial isolate, or after administration of the bacterial isolate. In embodiments, a pharmaceutical composition comprises the probiotic and the bacterial isolate. In other embodiments, the probiotic and the bacterial isolate are in separate compositions. In some embodiments, the composition comprises a microbial cocktail of bacterial isolates.

In embodiments, one or more bacterial isolates described herein can be administered together with a prebiotic (e.g., comprising lactic acid and/or high fiber) that provides a nutrient that when utilized (e.g., metabolized) by the bacterial isolate facilitates a therapeutic effect in the subject (e.g., production of an SCFA). In embodiments, the prebiotic can be administered to a subject at the same time as a bacterial isolate, before administration of the bacterial isolate, or after administration of the bacterial isolate. In embodiments, a pharmaceutical composition comprises the prebiotic and the bacterial isolate. In other embodiments, the prebiotic and the bacterial isolate are in separate compositions. In some embodiments, the composition comprises a microbial cocktail of bacterial isolates. In some embodiments, the prebiotic is selected from the group consisting of an amino acid, lactic acid, ammonium nitrate, amylose, barley mulch, biotin, carbonate, cellulose, chitin, choline, fructooligosaccharides (FOSs), fructose, galactooligosaccharides (GOSs), glucose, glycerol, heteropolysaccharide, histidine, homopolysaccharide, hydroxyapatite, inulin, isomaltulose, lactose, lactulose, maltodextrins, maltose, mannooligosaccharides, nitrogen, oligodextrose, oligofructoses, oligofructose-enriched inulin, an oligosaccharide, pectin, phosphate salts, phosphorus, a polydextrose, a polyol, potash, potassium, sodium nitrate, starch, sucrose, sulfur, sun fiber, tagatose, thiamine, trans-galactooligosaccharides, trehalose, a vitamin, a water-soluble carbohydrate, a xylooligosaccharide (XOS), and a combination thereof.

In embodiments, a bacterial isolate having the ability to produce one or more SCFAs (e.g., bacterial isolates listed in Table 2) refers to a bacterial isolate actually demonstrated (e.g., by a laboratory assay) to produce one or more SCFAs. Any method can be used to detect an SCFA produced by a bacterial strain, including chromatography (e.g., liquid or gas) and/or mass spectrometry. In other embodiments, a bacterial isolate having the ability to produce one or more SCFAs refers to a bacterial isolate predicted to produce butyrate. A prediction that a bacterial isolate can produce an SCFA can be based, for example, on the isolate's taxonomy (e.g., genus and/or species) and/or a sequence of a gene or polypeptide of the bacterial isolate known to mediate SCFA production. For example, an example of a gene known to mediate butyrate production is butyrate kinase. In an embodiment, a bacterial isolate is predicted to produce butyrate based on the identification of a butyrate kinase gene in the genome of the bacterial isolate. In an embodiment, the butyrate kinase gene when translated into a protein is predicted to generate a functional (i.e., enzymatically active) butyrate kinase enzyme.

Examples of bacterial isolates having the ability to produce SCFA are provided in Table 2. Each bacterial isolate is identified by Latin name, an Identification Number (ID number), and the Sequence Identifier (SEQ ID NO) for its 16S rRNA sequence. In aspects, a pharmaceutical composition (e.g., a microbial cocktail) comprises at least one bacterial isolate provided in Table 2, or at least one bacterial isolate comprising a 16S rRNA sequence at least 95% identical to the 16S rRNA sequence of one or more of the bacterial isolates provided in Table 2. In embodiments, the pharmaceutical composition comprises at least two bacterial isolates, at least three bacterial isolates, at least four bacterial isolates, at least five bacterial isolates, at least six bacterial isolates, at least seven bacterial isolates, at least eight bacterial isolates, or at least nine bacterial isolates that each comprise a 16S rRNA sequence at least 95% identical to a 16S rRNA sequence of at least one of the bacterial isolates provided in Table 2.

TABLE 2

| Isolate Latin Name | ID Number | SEQ ID NO for 16S rRNA Sequence |
| --- | --- | --- |
| *Faecalibacterium prausnitzii* | PI00000329 | 1 |
| *Odoribacter splanchnicus* | PI00000072 | 2 |
| *Anaerostipes hadrus* | PI00000094 | 3 |
| *Faecalibacterium prausnitzii* | IS00006632 | 7 |
| *Eubacterium rectale* | IS00006864 | 8 |
| *Coprococcus comes* | PI00000370 | 17 |
| *Roseburia faecis* | PI00000404 | 19 |
| *Subdoligranulum variabile* | IS00007359 | 22 |
| *Subdoligranulum variabile* | IS00007357 | 23 |

In embodiments, a pharmaceutical composition (e.g., comprising a microbial cocktail) comprises one or more bacterial isolates having the ability to modulate production of a cytokine (e.g., IL-10, GM-CSF, IFN-gamma, TNF-alpha, IL-23, and IL-12) by a eukaryotic cell. Herein "eukaryotic cell" refers to both a cell (e.g. intestinal cell) positioned 'in situ' within a body of a subject administered a composition described herein, as well as a cell grown or growing "ex vivo" outside of an organism, for example, in culture medium.

In one example, one or more bacterial isolates in a pharmaceutical composition described herein, once administered to a subject, can modulate production of a cytokine in a cell of the subject (referred to herein as a "host cell"). In embodiments, one or more bacterial isolates modulate production and/or secretion of a cytokine from a host cell of the subject, wherein the cytokine tends to exert anti-inflammatory effects on a tissue of the subject (e.g., intestinal tissue). Examples of such anti-inflammatory cytokines that can be produced and/or secreted from a host cell in response to the presence of a bacterial isolate administered in a composition described herein include IL-10, IL-13, IL-4, IL-5, TGF-β, and a combination thereof. In other embodiments, one or more bacterial isolates administered in a composition described herein inhibit production and/or secretion of a cytokine from a host cell of a subject, wherein the cytokine tends to exert pro-inflammatory effects on a tissue of the subject (e.g., intestinal tissue). Examples of such pro-inflammatory cytokines include IFNγ, IL-12p70, IL-1 (e.g., IL-1α, IL-1β), IL-6, IL-8, IL-12, IL-17, IL-18, IL-23, MCP1, MIP1α, MIP1β, TNFα, TNF-γ, and a combination thereof. By providing a composition containing one or more bacterial isolates that can induce a host cell to produce or secrete an anti-inflammatory cytokine and/or inhibit production and/or secretion by the host cell of a pro-inflammatory cytokine, the compositions (e.g., microbial cocktails) described herein can treat, alleviate, inhibit, and/or prevent inflammation associated with an intestinal dysbiosis of a subject, for example, Inflammatory Bowel Disease. Herein a bacterial isolate capable of modulating cytokine production and/or secretion by a host cell is referred to as an "immunomodulatory" bacterial isolate.

In embodiments, a bacterial isolate can directly and/or indirectly modulate production and/or release of a cytokine from a cell of a subject administered a pharmaceutical composition. In one embodiment an immunomodulatory bacterial isolate can act directly on a host cell of a subject via, for example, microbe-associated molecular patterns (MAMPS) secreted by the bacterial isolate or displayed on the surface of the bacterial isolate. Such MAMPS play a major role in host immune responses to particular bacterial species. MAMPS are sensed by pattern recognition receptors (PRRs) expressed on most host cell types that are in contact with bacteria. Examples of MAMPS of a bacterial isolate described herein include unmethylated 2'-deoxyribo (cytidine-phosphate-guanine) (CpG) dinucleotides, bacterial peptidogylcans, bacterial lipopolysaccharides (LPS, which interacts with co-receptors MD-2, CD14, and LPB to facilitate high affinity binding to TLR-4 and subsequent host cell activation), bacterial lipoproteins (LPs), lipoteichoic acid, flagellin, membrane vesicles, and exopolysaccharides. Examples of PRRs expressed by host cells in the gut and resident intestinal immune cells that can mediate modulation of cytokine production via interaction with MAMPS include Toll-like receptors (TLRs), nucleotide-binding oligomerization domains (Nods), NOD like receptors and C-type lectins. The interaction of intestinal cell PRRs and microbial ligands trigger signaling pathways associated with the innate and adaptive immune systems that are required to maintain immune tolerance and intestinal health.

In another embodiment, an immunomodulatory bacterial isolate can act indirectly on a cell (e.g., immune cell) of a subject administered a pharmaceutical composition by, for example, secreting a metabolite that modulates the activity of the host cell of the subject, for example, by inducing the cell to express a cytokine.

Examples of host cells whose production and/or release of cytokines can be modulated by a bacterial isolate described herein include an intestinal cell, an epithelial cell, an intestinal mucosal cell, an intestinal epithelial cell, an intestinal lamina propria cell, an endothelial cell, fibroblast, a stromal cell, a macrophage, a B lymphocyte, a T lymphocyte, a mast cell, and a peripheral blood mononuclear cell (PBMC).

In another embodiment, a bacterial isolate described herein can modulate cytokine production and/or release (e.g., increase cytokine production) by a eukaryotic cell (e.g., PBMC) situated or growing in culture medium, when the bacterial isolate is co-cultured with the eukaryotic cell.

In certain embodiments, a bacterial isolate described herein can induce production and/or release of a cytokine (e.g., IL-10) by a eukaryotic cell at a level of at least 500 pg/ml, at least 1000 pg/ml, at least 1500 pg/ml, at least 2000 pg/ml, at least 2500 pg/ml, or at least 3000 pg/ml. In an embodiment, the cytokine is measured in a functional assay (i.e., an assay conducted ex vivo and designed to measure the concentration or amount of a cytokine produced by a eukaryotic cell (e.g., PBMC) in contact with a bacterial isolate, microbial cocktail, a preparation of uncultured fecal bacteria, or an uncultured fecal microbiota during a period of time (e.g., 24 hours)). In an embodiment, the cytokine is produced in the intestine of a subject administered a composition described herein.

In certain embodiments, a bacterial isolate described herein can induce an anti-inflammatory cytokine profile. In an embodiment, a bacterial isolate exhibits an anti-inflammatory cytokine profile when it produces a level of IL-10 that is increased relative to that of a control strain. In an embodiment, a bacterial isolate exhibits an anti-inflammatory cytokine profile when it produces a level of IL-12 that is decreased relative to that of a control strain. In an embodiment, a bacterial isolate exhibits an anti-inflammatory cytokine profile when it produces a level of GM-CSF that is decreased relative to that of a control strain. In an embodiment, a bacterial isolate exhibits an anti-inflammatory cytokine profile when it produces a level of IFN-gamma that is decreased relative to that of a control strain. In an embodiment, a bacterial isolate exhibits an anti-inflammatory cytokine profile when it produces a level of TNF-alpha that is decreased relative to that of a control strain. In an embodiment, a bacterial isolate exhibits an anti-inflammatory cytokine profile when it produces a level of IL-23 that is decreased relative to that of a control strain. In an embodiment, a bacterial isolate exhibits an anti-inflammatory cytokine profile when it produces a level of IL-12 that is decreased relative to that of a control strain. In an embodiment, a bacterial isolate exhibits an anti-inflammatory cytokine profile when it produces a ration of IL-10:IL-12 that is increased relative to that of a control strain. In an embodiment, a bacterial isolate exhibits an anti-inflammatory cytokine profile when it produces a ration of IL-10:TNF-alpha that is increased relative to that of a control strain.

In embodiments, a pharmaceutical composition comprises one or more bacterial isolates which, when in contact with a eukaryotic cell (e.g., population of PBMCs) during a period of time (e.g., 24 hours), induce production of IL-10 at a concentration of at least 1000 pg/ml, at least 1500 pg/ml, at least 2000 pg/ml, at least 2500 pg/ml, at least 3000 pg/ml, at least 3500 pg/ml, at least 4000 pg/ml, at least 5000 pg/ml, at least 6000 pg/ml, at least 7000 pg/ml, at least 8000 pg/ml, at least 9000 pg/ml, at least 10,000 pg/ml, or greater than 10,000 pg/ml. In an embodiment, the bacterial isolate is provided in Table 3, or comprises a 16S rRNA sequence at least 95% identical to a 16S rRNA sequence corresponding to a SEQ ID NO of a bacterial isolate provided in Table 3.

In embodiments, a pharmaceutical composition comprises one or more bacterial isolates which, when in contact with a eukaryotic cell (e.g., population of PBMCs) during a period of time (e.g., 24 hours), limit production of GM-CSF to a concentration of no more than 5 pg/ml, 10 pg/ml, 15 pg/ml, 20 pg/ml, 25 pg/ml, 30 pg/ml, 35 pg/ml, 40 pg/ml, 45 pg/ml, 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, 100 pg/ml, 105 pg/ml, 110 pg/ml, 115 pg/ml, 120 pg/ml, 125 pg/ml, 130 pg/ml, 135 pg/ml, 140 pg/ml, 145 pg/ml, 150 pg/ml, 155 pg/ml, 160 pg/ml, 165 pg/ml, 170 pg/ml, 175 pg/ml, 180 pg/ml, 185 pg/ml, 190 pg/ml, 195 pg/ml, or 200 pg/ml. In an embodiment, the bacterial isolate is provided in Table 3, or comprises a 16S rRNA sequence at least 95% identical to a 16S rRNA sequence corresponding to a SEQ ID NO of a bacterial isolate provided in Table 3.

In embodiments, a pharmaceutical composition comprises one or more bacterial isolates which, when in contact with a eukaryotic cell (e.g., population of PBMCs) during a period of time (e.g., 24 hours), limit production of IL-12 (e.g., IL-12p70) to a concentration of no more than 5 pg/ml, 10 pg/ml, 15 pg/ml, 20 pg/ml, 25 pg/ml, 30 pg/ml, 35 pg/ml, 40 pg/ml, 45 pg/ml, 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, 100 pg/ml, 105 pg/ml, 110 pg/ml, 115 pg/ml, 120 pg/ml, 125 pg/ml, 130 pg/ml, 135 pg/ml, 140 pg/ml, 145 pg/ml, 150 pg/ml, 155 pg/ml, 160 pg/ml, 165 pg/ml, 170 pg/ml, 175 pg/ml, 180 pg/ml, 185 pg/ml, 190 pg/ml, 195 pg/ml, or 200 pg/ml. In an embodiment, the bacterial isolate is provided in Table 3, or comprises a 16S rRNA sequence at least 95% identical to a 16S rRNA sequence corresponding to a SEQ ID NO of a bacterial isolate provided in Table 3.

In embodiments, a pharmaceutical composition comprises one or more bacterial isolates which, when in contact with a eukaryotic cell (e.g., population of PBMCs) during a period of time (e.g., 24 hours), limit production of IFN-gamma to a concentration of no more than 5 pg/ml, 10 pg/ml, 15 pg/ml, 20 pg/ml, 25 pg/ml, 30 pg/ml, 35 pg/ml, 40 pg/ml, 45 pg/ml, 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, 100 pg/ml, 105 pg/ml, 110 pg/ml, 115 pg/ml, 120 pg/ml, 125 pg/ml, 130 pg/ml, 135 pg/ml, 140 pg/ml, 145 pg/ml, 150 pg/ml, 155 pg/ml, 160 pg/ml, 165 pg/ml, 170 pg/ml, 175 pg/ml, 180 pg/ml, 185 pg/ml, 190 pg/ml, 195 pg/ml, or 200 pg/ml. In an embodiment, the bacterial isolate is provided in Table 3, or comprises a 16S rRNA sequence at least 95% identical to a 16S rRNA sequence corresponding to a SEQ ID NO of a bacterial isolate provided in Table 3.

In embodiments, a pharmaceutical composition comprises one or more bacterial isolates which, when in contact with a eukaryotic cell (e.g., population of PBMCs) during a period of time (e.g., 24 hours), limit production of TNF-alpha to a concentration of no more than 20 pg/ml, 30 pg/ml, 40 pg/ml, 50 pg/ml, 75 pg/ml, 100 pg/ml, 150 pg/ml, 200 pg/ml, 250 pg/ml, 300 pg/ml, 350 pg/ml, 400 pg/ml, 450 pg/ml, 500 pg/ml, 550 pg/ml, 600 pg/ml, 650 pg/ml, 700 pg/ml, 750 pg/ml, 800 pg/ml, 850 pg/ml, 900 pg/ml, 950 pg/ml, 1000 pg/ml, 1100 pg/ml, 1200 pg/ml, 1300 pg/ml, 1400 pg/ml, 1500 pg/ml, 1600 pg/ml, 1700 pg/ml, 1800 pg/ml, 1900 pg/ml, 2000 pg/ml, 2100 pg/ml, 2200 pg/ml, 2300 pg/ml, 2400 pg/ml, or 2500 pg/ml. In an embodiment, the bacterial isolate is provided in Table 3, or comprises a 16S rRNA sequence at least 95% identical to a 16S rRNA sequence corresponding to a SEQ ID NO of a bacterial isolate provided in Table 3.

In embodiments, a pharmaceutical composition comprises one or more bacterial isolates which, when in contact with a eukaryotic cell (e.g., population of PBMCs) during a period of time (e.g., 24 hours), limit production of IL-23 to a concentration of no more than 5 pg/ml, 10 pg/ml, 15 pg/ml, 20 pg/ml, 25 pg/ml, 30 pg/ml, 35 pg/ml, 40 pg/ml, 45 pg/ml, 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, 100 pg/ml, 105 pg/ml, 110 pg/ml, 115 pg/ml, 120 pg/ml, 125 pg/ml, 130 pg/ml, 135 pg/ml, 140 pg/ml, 145 pg/ml, 150 pg/ml, 155 pg/ml, 160 pg/ml, 165 pg/ml, 170 pg/ml, 175 pg/ml, 180 pg/ml, 185 pg/ml, 190 pg/ml, 195 pg/ml, 200 pg/ml, 250 pg/ml, or 300 pg/ml. In an embodiment, the bacterial isolate is provided in Table 3, or comprises a 16S rRNA sequence at least 95% identical to a 16S rRNA sequence corresponding to a SEQ ID NO of a bacterial isolate provided in Table 3.

In embodiments, a pharmaceutical composition comprises one or more bacterial isolates which, when in contact with a eukaryotic cell (e.g., population of PBMCs) during a period of time (e.g., 24 hours), induce a ratio of IL-10:IL-12 of at least 20, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 325, at least 350, at least 375, at least 400, at least 425, at least 450, at least 475, at least 500, at least 550, at least 600, at least 650, at least 700, at least 750, at least 800, at least 850, at least 900, at least 950, at least 1000, at least 1100, at least 1200, at least 1300, at least 1400, at least 1500, at least 1600, at least 1700, at least 1800, at least 1900, at least 2000, at least 2200, at least 2400, at least 2600, at least 2800, at least 3000, at least 3200, at least 3400, at least 3600, at least 3800, at least 4000, or greater than 4000. In an embodiment, the bacterial isolate is provided in Table 3, or comprises a 16S rRNA sequence at least 95% identical to a 16S rRNA sequence corresponding to a SEQ ID NO of a bacterial isolate provided in Table 3.

In embodiments, a pharmaceutical composition comprises one or more bacterial isolates which, when in contact with a eukaryotic cell (e.g., population of PBMCs) during a period of time (e.g., 24 hours), induce a ratio of IL-10:TNF-alpha of at least 0.5, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, at least 55, at least 60, at least 65, at least 70, at least 75, at least 80, at least 85, at least 90, at least 95, or at least 100. In an embodiment, the bacterial isolate is provided in Table 3, or comprises a 16S rRNA sequence at least 95% identical to a 16S rRNA sequence corresponding to a SEQ ID NO of a bacterial isolate provided in Table 3.

Examples of bacterial isolates having the ability to modulate cytokine production by a host cell are provided in Table 3. Each isolate is identified by Latin name, an Identification Number (ID number), and the Sequence Identifier (SEQ ID NO) for its 16S rRNA sequence. In aspects, a pharmaceutical composition (e.g., comprising a microbial cocktail) comprises at least one bacterial isolate provided in Table 3, or at least one bacterial isolate that comprises a 16S rRNA sequence at least 95% identical to the 16S rRNA sequence of one or more of the bacterial isolates provided in Table 3. In embodiments, the pharmaceutical composition comprises at least two bacterial isolates, at least three bacterial isolates, at least four bacterial isolates, at least five bacterial isolates, at least six bacterial isolates, at least seven bacterial isolates, at least eight bacterial isolates, at least nine bacterial isolates, at least ten bacterial isolates, at least eleven bacterial isolates, at least twelve bacterial isolates, at least thirteen bacterial isolates, or at least fourteen bacterial isolates that each comprise a 16S rRNA sequence at least 95% identical to a 16S rRNA sequence of at least one of the bacterial isolates provided in Table 3.

TABLE 3

| Isolate Latin Name | ID Number | SEQ ID NO for 16S rRNA Sequence |
|---|---|---|
| Faecalibacterium prausnitzii | PI00000329 | 1 |
| Odoribacter splanchnicus | PI00000072 | 2 |
| Anaerostipes hadrus | PI00000094 | 3 |
| Faecalibacterium prausnitzii | IS00006632 | 7 |
| Clostridium aldenense | PI00000097 | 10 |
| Bacteroides uniformis | PI00000137 | 11 |
| Bacteroides vulgatus | PI00000138 | 12 |
| Bacteroides stercoris | PI00000146 | 13 |
| Bacteroides uniformis | PI00000352 | 16 |
| Coprococcus comes | PI00000370 | 17 |
| Alistipes shahii | PI00000395 | 18 |
| Akkermansia muciniphila | IS00007180 | 20 |
| Subdoligranulum variabile | IS00007359 | 22 |
| Subdoligranulum variabile | IS00007357 | 23 |

In embodiments, a pharmaceutical composition comprises at least one bacterial isolate corresponding to a bacterial strain having a greater relative abundance in a healthy human subject relative to a patient with an intestinal dysbiosis (e.g., an IBD such as UC), or a greater relative abundance in a human subject in remission from an intestinal dysbiosis relative to a patient having the intestinal dysbiosis. Herein the term "greater relative abundance" refers to a higher number of viable cells of the bacterial strain (i.e., corresponding to the bacterial isolate) in a healthy human subject (compared to a patient with an intestinal dysbiosis) or in a human subject in remission from an intestinal dysbiosis (compared to a patient having the dysbiosis). In some embodiments, the term "higher number of viable cells" refers to the absolute number of viable cells of the bacterial strain in an intestinal microbiota or portion thereof (e.g., in a stool sample), while in other embodiments, the term refers to the proportional number of viable cells of the bacterial strain relative to the approximate entire number of viable cells in the intestinal microbiota or portion thereof (e.g., in a stool sample). In certain examples, a bacterial strain corresponding to a bacterial isolate included in a pharmaceutical composition can have a greater relative abundance across multiple tested human subjects (e.g., healthy individuals, or individuals in remission from an intestinal dysbiosis), for example, at least 5 human subjects, at least 10 human subjects, at least 20 human subjects, at least 30 human subjects, at least 40 human subjects, at least 50 human subjects, at least 75 human subjects, at least 100 human subjects, at least 200 human subjects, at least 300 human subjects, at least 400 human subjects, at least 500 human subjects, at least 750 human subjects, at least 1000 human subjects, or greater than 1000 human subjects. In addition or alternatively, a bacterial strain corresponding to a bacterial isolate can have a greater relative abundance in a proportion of tested human subjects (e.g., healthy individuals, or individuals in remission from an intestinal dysbiosis), for example, at least 50% of tested individuals, at least 55% of tested individuals, at least 60% of tested individuals, at least 65% of tested individuals, at least 70% of tested individuals, at least 75% of tested individuals, at least 80% of tested individuals, at least 80% of tested individuals, at least 85% of tested individuals, at least 90% of tested individuals, at least 95% of tested individuals, or 100% of tested individuals. Herein a bacterial strain "corresponding to a bacterial isolate" refers to a bacterial strain in a gut microbiota of a subject, wherein the bacterial strain has a 16S rRNA sequence that typically shares at least 97% identity (e.g., at least 97.5% identity, at least 98% identity, at least 98.5% identity, at least 99% identity, at least 99.5% identity, or greater than 99.5% identity) to a 16S rRNA sequence of the bacterial isolate. Likewise, a bacterial isolate "corresponding to a bacterial strain" refers to a bacterial isolate that typically shares at least 97% identity (e.g., at least 97.5% identity, at least 98% identity, at least 98.5% identity, at least 99% identity, at least 99.5% identity, or greater than 99.5% identity) to a 16S rRNA sequence of a bacterial strain in a gut microbiota of a subject.

In embodiments, a bacterial isolate can correspond to a bacterial strain having a greater relative abundance in a human subject in remission from an intestinal dysbiosis relative to a patient having the intestinal dysbiosis. The increased abundance of the bacterial strain in the subject in remission identifies the bacterial isolate corresponding to the bacterial strain as potentially advantageous for the treatment of a disorder related to an intestinal dysbiosis, such as UC. The remission of the intestinal dysbiosis in the human subject can be related to or caused by an intervention administered to the subject while the dysbiosis is active. For example, the remission can arise following treatment of the subject with a microbial therapeutic. Examples of a microbial therapeutic include compositions comprising a preparation of uncultured fecal bacteria, an uncultured fecal microbiota, a cultured fecal microbiota, and/or a bacterial isolate. In embodiments, the microbial therapeutic which induces remission from an intestinal dysbiosis is a substantially complete uncultured fecal microbiota. For example, a subject can be administered a fecal microbiota transplant (FMT) to induce remission of the intestinal dysbiosis. In certain embodiments, the intestinal dysbiosis of the subject is due to ulcerative colitis (UC).

In an embodiment, this mechanism agnostic approach to identifying a bacterial isolate reduces the dysbiosis associated with Ulcerative Colitis (UC). In an embodiment, 16S ribosomal DNA (rDNA) and shotgun metagenomic sequences can be incorporated from for example interventional (FMT), cross-sectional and time series datasets to develop predictive features associated with either a healthy status or clinical response to FMT. These features can be used to rank and select bacterial phylogenetic clades for (i) enrichment in healthy subjects over patients diagnosed with UC; and/or (ii) association/correlation with clinical remission or response of UC symptoms in UC patients following FMT treatment. Clades can be ranked based on a "cross-sectional combined p-value" which compares the presence and abundances of bacterial strains in fecal material between healthy subjects and patients with UC. The lower the p-value, the more likely the organisms in the clade are having an effect on the treatment, inhibition or prevention of UC based on: (i) depletion of the strain in UC patients and/or (ii) high abundance of the strain in healthy subjects. Isolated bacterial strains can then be selected from donor stool samples by 16S rDNA similarity to the ranked phylogenetic clades or by ranking their 16S rDNA directly according to the aforementioned criteria.

In an embodiment, a value of a cross-sectional combined p-value is less than 0.1, less than 0.01, less than $1 \times 10^{-3}$, less than $1 \times 10^{-4}$, less than $1 \times 10^{-5}$, less than $1 \times 10^{-6}$, less than $1 \times 10^{-7}$, less than $1 \times 10^{-8}$, less than $1 \times 10^{-9}$, less than $1 \times 10^{-10}$, less than $1 \times 10^{-11}$, less than $1 \times 10^{-12}$, less than $1 \times 10^{-13}$, less than $1 \times 10^{-14}$, less than $1 \times 10^{-15}$, less than $1\times10^{-16}$, less than $1\times10^{-17}$, less than $1\times10^{-18}$, less than $1\times10^{-19}$, less than $1\times10^{-20}$, less than $1\times10^{-21}$, less than $1\times10^{-22}$, less than $1\times10^{-23}$, or less than $1\times10^{-24}$.

Table 4 lists examples of bacterial isolates which can be included in a pharmaceutical composition (e.g., comprising a microbial cocktail) that have corresponding bacterial strains present and/or more highly abundant in a healthy subject relative to a patient with UC. Each isolate is identified by Latin name, an Identification Number (ID number), and the Sequence Identifier (SEQ ID NO) for its 16S rRNA sequence. In aspects, a pharmaceutical composition comprises at least one bacterial isolate provided in Table 4, or at least one bacterial isolate that comprises a 16S rRNA sequence at least 95% identical to the 16S rRNA sequence of one or more of the bacterial isolates provided in Table 4. In embodiments, the pharmaceutical composition comprises at least two bacterial isolates, at least three bacterial isolates, at least four bacterial isolates, at least five bacterial isolates, at least six bacterial isolates, at least seven bacterial isolates, at least eight bacterial isolates, at least nine bacterial isolates, at least ten bacterial isolates, at least eleven bacterial isolates, at least twelve bacterial isolates, at least thirteen bacterial isolates, at least fourteen bacterial isolates, at least fifteen bacterial isolates, at least sixteen bacterial isolates, at least seventeen bacterial isolates, at least eighteen bacterial isolates, at least nineteen bacterial isolates, at least twenty bacterial isolates, at least twenty one bacterial isolates, at least twenty two bacterial isolates, or at least twenty three bacterial isolates that each comprise a 16S rRNA sequence at least 95% identical to a 16S rRNA sequence of at least one of the bacterial isolates provided in Table 4.

TABLE 4

| Isolate Latin Name | ID Number | SEQ ID NO for 16S rRNA Sequence |
|---|---|---|
| Faecalibacterium prausnitzii | PI00000329 | 1 |
| Odoribacter splanchnicus | PI00000072 | 2 |
| Anaerostipes hadrus | PI00000094 | 3 |
| Alistipes onderdonkii | IS00004389 | 4 |
| Parabacteroides merdae | IS00006167 | 5 |
| Dorea longicatena | IS00006618 | 6 |
| Faecalibacterium prausnitzii | IS00006632 | 7 |
| Eubacterium rectale | IS00006864 | 8 |
| Blautia obeum | PI00000053 | 9 |
| Bacteroides uniformis | PI00000137 | 11 |
| Bacteroides vulgatus | PI00000138 | 12 |
| Bacteroides cellulosilyticus | PI00000316 | 14 |
| Alistipes finegoldii | PI00000340 | 15 |
| Bacteroides uniformis | PI00000352 | 16 |
| Alistipes shahii | PI00000395 | 18 |
| Akkermansia muciniphila | IS00007180 | 20 |
| Phascolarctobacterium faecium | PI00000289 | 21 |
| Subdoligranulum variabile | IS00007359 | 22 |
| Subdoligranulum variabile | IS00007357 | 23 |
| Blautia sp. | IS00002788 | 34 |
| Alistipes putredinis | IS00008139 | 35 |
| Alistipes putredinis | IS00008142 | 36 |
| Alistipes putredinis | IS00008177 | 37 |

In an embodiment, a bacterial isolate is identified as suitable for inclusion in a pharmaceutical composition described herein (e.g., comprising a microbial cocktail) based on its correspondence to a bacterial strain that is abundant in healthy versus UC patients in the data set reported in Morgan et al., Genome Biology 13 (2012), the entire contents of which are hereby incorporated by reference.

In an embodiment, a bacterial isolate is identified as suitable for inclusion in a pharmaceutical composition described herein (e.g., comprising a microbial cocktail) based on its correspondence to a bacterial strain that is abundant in healthy versus UC patients in the data set reported in Papa et al., PLOS ONE 7, no. 6 (Jun. 29, 2012), the entire contents of which are hereby incorporated by reference.

In embodiments, a microbial cocktail described herein can contain two or more bacterial isolates which are related bacterial isolates. Herein "related bacterial isolates" have 16S rRNA sequences which typically share at least 95% sequence identity. In certain embodiments, related bacterial isolates have 16S sequences which share at least 97% sequence identity, and thus the bacterial isolates are members of the same species. In embodiments, a microbial cocktail contains two or more related bacterial isolates. In other embodiments, a microbial cocktail does not contain two related bacterial isolates. In embodiments, a first version of a microbial cocktail contains a first bacterial isolate, and a second version of a microbial cocktail contains a second bacterial isolate that is a related bacterial isolate to the first bacterial isolate.

Examples of related bacterial isolates to those listed in Table 4 that can be included in a microbial cocktail described herein are shown in Table 5. Like the bacterial isolates in Table 4, those in Table 5 correspond to bacterial strains that have a greater abundance in a healthy human subject relative to a patient with UC. Table 5 lists the bacterial isolates' identification numbers, the ID number of the corresponding bacterial isolate in Table 4, the percent identity of the related bacterial strain's 16S sequences to the sequence of the corresponding bacterial isolate in Table 4, and the Sequence Identifier (SEQ ID NO) for its 16S rRNA sequence.

TABLE 5

| ID Number | Related to ID Number of Table 4 | % identity of 16S rRNA Sequence to Related ID Number of Table 4 | SEQ ID NO for 16S rRNA Sequence |
|---|---|---|---|
| PI00000070 | PI00000072 | 98.6 | 24 |
| PI00000092 | PI00000094 | 98.1 | 25 |
| PI00000339 | IS00004389 | 96.6 | 26 |
| PI00000327 | IS00006167 | 99.4 | 27 |
| PI00000056 | PI00000053 | 96.2 | 28 |
| PI00000152 | PI00000138 | 98.7 | 29 |
| PI00000043 | PI00000316 | 99.2 | 30 |
| IS00003009 | PI00000340 | 97.6 | 31 |
| PI00000052 | PI00000352 | 96.6 | 32 |
| PI00000330 | PI00000395 | 95.3 | 33 |

In embodiments, a pharmaceutical composition (e.g., comprising a microbial cocktail) comprises one or more bacterial isolates having the ability to release (e.g., by secretion) one or more aryl hydrocarbons and/or tryptophan derivatives. Microbial metabolites are produced by the gut microbiota via metabolism of tryptophan from host dietary sources. Such metabolites, which are typically compounds containing an aryl hydrocarbon, can signal through the aryl hydrocarbon receptor (AhR) of a eukaryotic cell (e.g., a cell of a subject administered a pharmaceutical composition (e.g., comprising a microbial cocktail) described herein). AhR is a cytosolic ligand-activated transcription factor that regulates immunity and inflammation, intestinal mucosal barrier health and maintenance of intestinal homeostasis.

Once bound by an appropriate cytosolic ligand, AhR translocates to the nucleus and binds to specific DNA sequence elements to regulate transcription. Without wishing to be bound by theory, activation of AhR is associated with a reduction of intestinal inflammation in subjects with inflammatory bowel disease, release of anti-inflammatory cytokines (e.g., IL-10), and induction of regulatory T cells. Pharmaceutical compositions containing one or more bacterial isolates that produce ligands capable of activating the AhR can thus be effective to treat, alleviate, inhibit or prevent dysbiosis of the gut caused by disorders such as IBD (e.g., ulcerative colitis).

Examples of aryl hydrocarbons (e.g., microbial produced aryl hydrocarbons) capable of activating the AhR are indole and indole derivatives, indole-3-acetic acid (IAA), indole-3-aldehyde (IAId), indole-3-lactic acid, indole-3-carbinol (I3C), indole-3-acetonitrile (I3ACN), 3,3'-diindolylmethane (DIM), 2-(indol-3-ylmethyl)-3,3'-diindolylmethane (Ltr-1), indolo[3,2-b]carbazole (ICZ), 2-(1'H-indole-3' carbonyl)-thiazole-4-carboxylic acid methyl ester (ITE), 3-methyl-indole (skatole), tryptamine, kynurenine, kynurenate, indigo, indirubin, indoxyl-3-sulfate (I3S), xanthurenic acid, cinnabarinic acid, 3-indolepropionic acid (indole-3-propionate), and a combination thereof.

In an embodiment, an amount, concentration or level of one or more aryl hydrocarbons is measured in a functional assay (i.e., an assay conducted ex vivo or in vivo and designed to measure the concentration or amount of an aryl hydrocarbon produced by a bacterial isolate, microbial cocktail, a preparation of uncultured fecal bacteria, or an uncultured fecal microbiota during a period of time (e.g., at least 24 hours)). In an embodiment, the aryl hydrocarbon is produced in the intestine of a subject administered a composition described herein. In an example, the functional assay can comprise incubation of one or more bacterial isolates with tryptophan (or tryptophan derivative) for any period of time sufficient to allow conversion of the tryptophan to an aryl hydrocarbon, for example at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, at least 24 hours, at least 25 hours, at least 26 hours, at least 27 hours, at least 28 hours, at least 29 hours, at least 30 hours, at least 31 hours, at least 32 hours, at least 33 hours, at least 34 hours, at least 35 hours, at least 36 hours, at least 37 hours, at least 38 hours, at least 39 hours, at least 40 hours, at least 41 hours, at least 42 hours, at least 43 hours, at least 44 hours, at least 45 hours, at least 46 hours, at least 47 hours, at least 48 hours, or greater than 48 hours.

In embodiments, a functional assay can measure an absolute amount or concentration of one or more aryl hydrocarbons capable of activating an AhR of a host cell. In other embodiments, the functional assay can measure a relative amount of one or more aryl hydrocarbons. In an example, an amount of production of an aryl hydrocarbon by a bacterial isolate can be relative to blank media not containing a bacterial isolate. Alternatively, the functional assay can measure the amount or concentration of an aryl hydrocarbon produced by a bacterial isolate relative to that produced by one or more control bacterial strains. In an embodiment, the control bacterial strain is known to produce an aryl hydrocarbon, for example the aryl hydrocarbon being measured in the assay. Exemplary control strains that can be used in a functional assay to measure one or more aryl hydrocarbons are bacterial strains that are a member of the genus *Peptostreptococcus* (e.g., *Peptostreptococcus anaerobius* or *Peptostreptococcus russellii*) In an embodiment, the functional assay comprises comparison of a level of an aryl hydrocarbon produced by a bacterial isolate of interest over a period of time (e.g., 48 hours) to a level of the same aryl hydrocarbon produced by one or more of the control strains *Peptostreptococcus anaerobius* or *Peptostreptococcus russellii* over the same period of time. In certain embodiments, a pharmaceutical composition comprises a bacterial isolate capable of producing an aryl hydrocarbon at a level of at least 1.1×, at least 1.2×, at least 1.3×, at least 1.4×, at least 1.5×, at least 1.6×, at least 1.7×, at least 1.8×, at least 1.9×, at least 2×, at least 2.1×, at least 2.2×, at least 2.3×, at least 2.4×, at least 2.5×, at least 2.6×, at least 2.7×, at least 2.8×, at least 2.9×, at least 3×, at least 4×, at least 5×, at least 6×, at least 7×, at least 8×, at least 9×, at least 10×, at least 11×, at least 12×, at least 13×, at least 14×, at least 15×, at least 16×, at least 17×, at least 18×, at least 19×, at least 20×, at least 21×, at least 22×, at least 23×, at least 24×, at least 25×, at least 26×, at least 27×, at least 28×, at least 29×, at least 30×, at least 35×, at least 40×, at least 45×, at least 50×, at least 60×, at least 70×, at least 80×, at least 90×, at least 100×, at least 110×, at least 120×, at least 130×, at least 140×, at least 150×, at least 160×, at least 170×, at least 180×, at least 190×, at least 200×, at least 210×, at least 220×, at least 230×, at least 240×, at least 250×, or greater than 250× relative to a control bacterial strain (e.g. a *Peptostreptococcus* strain such as *Peptostreptococcus anaerobius* or *Peptostreptococcus russellii*)), or compared to blank media alone.

In embodiments, a pharmaceutical composition comprises a bacterial isolate that produces kynurenate (i.e., kynurenic acid), as measured by a functional assay. For example, a bacterial isolate can produce kynurenate at a concentration of at least 0.01 µM kynurenate, at least 0.02 µM kynurenate, at least 0.03 µM kynurenate, at least 0.04 µM kynurenate, at least 0.05 µM kynurenate, at least 0.06 µM kynurenate, at least 0.07 µM kynurenate, at least 0.08 µM kynurenate, at least 0.09 µM kynurenate, at least 0.1 µM kynurenate, at least 0.2 µM kynurenate, at least 0.3 µM kynurenate, at least 0.4 µM kynurenate, at least 0.5 µM kynurenate, at least 0.6 µM kynurenate, at least 0.7 µM kynurenate, at least 0.8 µM kynurenate, at least 0.9 µM kynurenate, at least 1 µM kynurenate, at least 1.5 µM kynurenate, at least 2 µM kynurenate, at least 2.5 µM kynurenate, at least 3 µM kynurenate, at least 3.5 µM kynurenate, at least 4 µM kynurenate, at least 4.5 µM kynurenate, at least 5 µM kynurenate, or greater than 5 µM kynurenate. In embodiments, a bacterial isolate does not produce kynurenate. In embodiments, the bacterial isolate is provided in Table 6, or comprises a 16S rRNA sequence at least 95% identical to a 16S rRNA sequence corresponding to a SEQ ID NO of a bacterial isolate provided in Table 6. In an embodiment, the bacterial isolate comprises *Odoribacter splanchnicus* In an embodiment, the bacterial isolate comprises a 16S rRNA sequence at least 95% identical to the 16S rRNA sequence corresponding to SEQ ID NO: 2.

In other embodiments, a bacterial isolate can produce kynurenate at a higher level than blank media or a control bacterial strain (e.g., positive control bacterial strain capable of producing kynurenate, such as a strain that is a member of the *Peptostreptococcus* genus), as measured in a functional assay. For example, a bacterial isolate can produce kynurenate at a higher level than at least one of the control strains *Peptostreptococcus anaerobius* or *Peptostreptococ-* cus russellii over a duration of time. In embodiments, a pharmaceutical composition comprises a bacterial isolate that can produce kynurenate at a level that is at least 1.1×, at least 1.2×, at least 1.3×, at least 1.4×, at least 1.5×, at least 1.6×, at least 1.7×, at least 1.8×, at least 1.9×, at least 2×, at least 2.1×, at least 2.2×, at least 2.3×, at least 2.4×, at least 2.5×, at least 2.6×, at least 2.7×, at least 2.8×, at least 2.9×, at least 3×, at least 4×, at least 5×, at least 6×, at least 7×, at least 8×, at least 9×, at least 10×, at least 11×, at least 12×, at least 13×, at least 14×, at least 15×, at least 16×, at least 17×, at least 18×, at least 19×, at least 20×, at least 21×, at least 22×, at least 23×, at least 24×, at least 25×, at least 26×, at least 27×, at least 28×, at least 29×, at least 30×, at least 35×, at least 40×, at least 45×, at least 50×, at least 60×, at least 70×, at least 80×, at least 90×, at least 100×, at least 110×, at least 120×, at least 130×, at least 140×, at least 150×, at least 160×, at least 170×, at least 180×, at least 190×, at least 200×, at least 210×, at least 220×, at least 230×, at least 240×, at least 250×, or greater than 250× relative to at least one of the control strains *Peptostreptococcus anaerobius* or *Peptostreptococcus russellii*, or relative to blank media alone. In embodiments, the bacterial isolate is provided in Table 6, or comprises a 16S rRNA sequence at least 95% identical to a 16S rRNA sequence corresponding to a SEQ ID NO of a bacterial isolate provided in Table 6. In an embodiment, the bacterial isolate comprises *Odoribacter splanchnicus* In an embodiment, the bacterial isolate comprises a 16S rRNA sequence at least 95% identical to the 16S rRNA sequence corresponding to SEQ ID NO: 2.

In embodiments, a pharmaceutical composition comprises one or more bacterial isolates that produce indole-3-acetic acid (IAA) capable of activating an AhR in a cell of a subject administered the pharmaceutical composition. For example, a bacterial isolate can produce IAA at a concentration of at least 0.1 µM IAA, at least 0.2 µM IAA, at least 0.3 µM IAA, at least 0.4 µM IAA, at least 0.5 µM IAA, at least 0.6 µM IAA, at least 0.7 µM IAA, at least 0.8 µM IAA, at least 0.9 µM IAA, at least 1 µM IAA, at least 1.5 µM IAA, at least 2 µM IAA, at least 2.5 µM IAA, at least 3 µM IAA, at least 4 µM IAA, at least 5 µM IAA, at least 6 µM IAA, at least 7 µM IAA, at least 8 µM IAA, at least 9 µM IAA, at least 10 µM IAA, at least 20 µM IAA, at least 30 µM IAA, at least 40 µM IAA, at least 50 µM IAA, at least 60 µM IAA, at least 70 µM IAA, at least 80 µM IAA, at least 90 µM IAA, at least 100 µM IAA, at least 110 µM IAA, at least 120 µM IAA, at least 130 µM IAA, at least 140 µM IAA, at least 150 µM IAA, at least 160 µM IAA, at least 170 µM IAA, at least 180 µM IAA, at least 190 µM IAA, at least 200 µM IAA or greater than 200 µM IAA. In embodiments, a bacterial isolate does not produce IAA. In embodiments, the bacterial isolate is provided in Table 6, or comprises a 16S rRNA sequence at least 95% identical to a 16S rRNA sequence corresponding to a SEQ ID NO of a bacterial isolate provided in Table 6. In an embodiment, the bacterial isolate comprises *Odoribacter splanchnicus* In an embodiment, the bacterial isolate comprises a 16S rRNA sequence at least 95% identical to the 16S rRNA sequence corresponding to SEQ ID NO: 2. In an embodiment, the bacterial isolate comprises *Clostridium aldenense*. In an embodiment, the bacterial isolate comprises a 16S rRNA sequence at least 95% identical to the 16S rRNA sequence corresponding to SEQ ID NO: 10.

In other embodiments, a bacterial isolate can produce indole-3-acetic acid (IAA) at a higher level than blank media or a control bacterial strain (e.g., positive control bacterial strain capable of producing IAA, such as a strain that is a member of the *Peptostreptococcus* genus), as measured in a functional assay. For example, a bacterial isolate can produce IAA at a higher level than at least one of the control strains *Peptostreptococcus anaerobius* or *Peptostreptococcus russellii* over a duration of time. In embodiments, a pharmaceutical composition comprises a bacterial isolate that can produce IAA at a level that is at least 1.1×, at least 1.2×, at least 1.3×, at least 1.4×, at least 1.5×, at least 1.6×, at least 1.7×, at least 1.8×, at least 1.9×, at least 2×, at least 2.1×, at least 2.2×, at least 2.3×, at least 2.4×, at least 2.5×, at least 2.6×, at least 2.7×, at least 2.8×, at least 2.9×, at least 3×, at least 4×, at least 5×, at least 6×, at least 7×, at least 8×, at least 9×, at least 10×, at least 11×, at least 12×, at least 13×, at least 14×, at least 15×, at least 16×, at least 17×, at least 18×, at least 19×, at least 20×, at least 21×, at least 22×, at least 23×, at least 24×, at least 25×, at least 26×, at least 27×, at least 28×, at least 29×, at least 30×, at least 35×, at least 40×, at least 45×, at least 50×, at least 60×, at least 70×, at least 80×, at least 90×, at least 100×, at least 110×, at least 120×, at least 130×, at least 140×, at least 150×, at least 160×, at least 170×, at least 180×, at least 190×, at least 200×, at least 210×, at least 220×, at least 230×, at least 240×, at least 250×, or greater than 250× relative to at least one of the control strains *Peptostreptococcus anaerobius* or *Peptostreptococcus russellii*, or relative to blank media alone. In embodiments, the bacterial isolate is provided in Table 6, or comprises a 16S rRNA sequence at least 95% identical to a 16S rRNA sequence corresponding to a SEQ ID NO of a bacterial isolate provided in Table 6. In an embodiment, the bacterial isolate comprises *Odoribacter splanchnicus* In an embodiment, the bacterial isolate comprises a 16S rRNA sequence at least 95% identical to the 16S rRNA sequence corresponding to SEQ ID NO: 2. In an embodiment, the bacterial isolate comprises *Clostridium aldenense*. In an embodiment, the bacterial isolate comprises a 16S rRNA sequence at least 95% identical to the 16S rRNA sequence corresponding to SEQ ID NO: 10.

In embodiments, a pharmaceutical composition comprises one or more bacterial isolates that produce indole-3-lactic acid capable of activating an AhR of a subject administered the pharmaceutical composition. For example, a bacterial isolate can produce indole-3-lactic acid at a concentration of at least 0.1 µM indole-3-lactic acid, at least 0.2 µM indole-3-lactic acid, at least 0.3 µM indole-3-lactic acid, at least 0.4 µM indole-3-lactic acid, at least 0.5 µM indole-3-lactic acid, at least 0.6 µM indole-3-lactic acid, at least 0.7 µM indole-3-lactic acid, at least 0.8 µM indole-3-lactic acid, at least 0.9 µM indole-3-lactic acid, at least 1 µM indole-3-lactic acid, at least 1.5 µM indole-3-lactic acid, at least 2 µM indole-3-lactic acid, at least 2.5 µM indole-3-lactic acid, at least 3 µM indole-3-lactic acid, at least 3.5 µM indole-3-lactic acid, at least 4 µM indole-3-lactic acid, at least 4.5 µM indole-3-lactic acid, at least 5 µM indole-3-lactic acid, or greater than 5 µM indole-3-lactic acid. In embodiments, a bacterial isolate does not produce indole-3-lactic acid. In embodiments, the bacterial isolate is provided in Table 6, or comprises a 16S rRNA sequence at least 95% identical to a 16S rRNA sequence corresponding to a SEQ ID NO of a bacterial isolate provided in Table 6.

In other embodiments, a bacterial isolate can produce indole-3-lactic acid at a higher level than blank media or a control bacterial strain (e.g., positive control bacterial strain capable of producing indole-3-lactic acid, such as a strain that is a member of the *Peptostreptococcus* genus), as measured in a functional assay. For example, a bacterial isolate can produce indole-3-lactic acid at a higher level than at least one of the control strains *Peptostreptococcus*

*anaerobius* or *Peptostreptococcus russellii* over a duration of time. In embodiments, a pharmaceutical composition comprises a bacterial isolate that can produce indole-3-lactic acid at a level that is at least 1.1×, at least 1.2×, at least 1.3×, at least 1.4×, at least 1.5×, at least 1.6×, at least 1.7×, at least 1.8×, at least 1.9×, at least 2×, at least 2.1×, at least 2.2×, at least 2.3×, at least 2.4×, at least 2.5×, at least 2.6×, at least 2.7×, at least 2.8×, at least 2.9×, at least 3×, at least 4×, at least 5×, at least 6×, at least 7×, at least 8×, at least 9×, at least 10×, at least 11×, at least 12×, at least 13×, at least 14×, at least 15×, at least 16×, at least 17×, at least 18×, at least 19×, at least 20×, at least 21×, at least 22×, at least 23×, at least 24×, at least 25×, at least 26×, at least 27×, at least 28×, at least 29×, at least 30×, at least 35×, at least 40×, at least 45×, at least 50×, at least 60×, at least 70×, at least 80×, at least 90×, at least 100×, at least 110×, at least 120×, at least 130×, at least 140×, at least 150×, at least 160×, at least 170×, at least 180×, at least 190×, at least 200×, at least 210×, at least 220×, at least 230×, at least 240×, at least 250×, or greater than 250× relative to at least one of the control strains *Peptostreptococcus anaerobius* or *Peptostreptococcus russellii*, or relative to blank media alone. In embodiments, the bacterial isolate is provided in Table 6, or comprises a 16S rRNA sequence at least 95% identical to a 16S rRNA sequence corresponding to a SEQ ID NO of a bacterial isolate provided in Table 6.

In embodiments, a pharmaceutical composition comprises one or more bacterial isolates that produce indole capable of activating an AhR of a subject administered the pharmaceutical composition. For example, a bacterial isolate can produce indole at a concentration of at least 0.1 µM indole, at least 0.2 µM indole, at least 0.3 µM indole, at least 0.4 µM indole, at least 0.5 µM indole, at least 0.6 µM indole, at least 0.7 µM indole, at least 0.8 µM indole, at least 0.9 µM indole, at least 1 µM indole, at least 1.5 µM indole, at least 2 µM indole, at least 2.5 µM indole, at least 3 µM indole, at least 3.5 µM indole, at least 4 µM indole, at least 4.5 µM indole, at least 5 µM indole, or greater than 5 µM indole. In embodiments, a bacterial isolate does not produce indole. In embodiments, the bacterial isolate is provided in Table 6, or comprises a 16S rRNA sequence at least 95% identical to a 16S rRNA sequence corresponding to a SEQ ID NO of a bacterial isolate provided in Table 6. In an embodiment, the bacterial isolate comprises *Clostridium* sp. (e.g., *Clostridium aldenense*) In an embodiment, the bacterial isolate comprises a 16S rRNA sequence at least 95% identical to the 16S rRNA sequence corresponding to SEQ ID NO: 10.

In other embodiments, a bacterial isolate can produce indole at a higher level than blank media or a control bacterial strain (e.g., positive control bacterial strain capable of producing indole, such as a strain that is a member of the *Peptostreptococcus* genus), as measured in a functional assay. For example, a bacterial isolate can produce indole at a higher level than at least one of the control strains *Peptostreptococcus anaerobius* or *Peptostreptococcus russellii* over a duration of time. In embodiments, a pharmaceutical composition comprises a bacterial isolate that can produce indole at a level that is at least 1.1×, at least 1.2×, at least 1.3×, at least 1.4×, at least 1.5×, at least 1.6×, at least 1.7×, at least 1.8×, at least 1.9×, at least 2×, at least 2.1×, at least 2.2×, at least 2.3×, at least 2.4×, at least 2.5×, at least 2.6×, at least 2.7×, at least 2.8×, at least 2.9×, at least 3×, at least 4×, at least 5×, at least 6×, at least 7×, at least 8×, at least 9×, at least 10×, at least 11×, at least 12×, at least 13×, at least 14×, at least 15×, at least 16×, at least 17×, at least 18×, at least 19×, at least 20×, at least 21×, at least 22×, at least 23×, at least 24×, at least 25×, at least 26×, at least 27×, at least 28×, at least 29×, at least 30×, at least 35×, at least 40×, at least 45×, at least 50×, at least 60×, at least 70×, at least 80×, at least 90×, at least 100×, at least 110×, at least 120×, at least 130×, at least 140×, at least 150×, at least 160×, at least 170×, at least 180×, at least 190×, at least 200×, at least 210×, at least 220×, at least 230×, at least 240×, at least 250×, or greater than 250× relative to at least one of the control strains *Peptostreptococcus anaerobius* or *Peptostreptococcus russellii*, or relative to blank media alone. In embodiments, the bacterial isolate is provided in Table 6, or comprises a 16S rRNA sequence at least 95% identical to a 16S rRNA sequence corresponding to a SEQ ID NO of a bacterial isolate provided in Table 6. In an embodiment, the bacterial isolate comprises *Clostridium* sp. (e.g., *Clostridium aldenense*) In an embodiment, the bacterial isolate comprises a 16S rRNA sequence at least 95% identical to the 16S rRNA sequence corresponding to SEQ ID NO: 10.

In embodiments, a pharmaceutical composition comprises one or more bacterial isolates that produce kynurenine capable of activating an AhR of a subject administered the pharmaceutical composition. For example, a bacterial isolate can produce kynurenine at a concentration of at least 0.1 µM kynurenine, at least 0.2 µM kynurenine, at least 0.3 µM kynurenine, at least 0.4 µM kynurenine, at least 0.5 µM kynurenine, at least 0.6 µM kynurenine, at least 0.7 µM kynurenine, at least 0.8 µM kynurenine, at least 0.9 µM kynurenine, at least 1 µM kynurenine, at least 1.5 µM kynurenine, at least 2 µM kynurenine, at least 2.5 µM kynurenine, at least 3 µM kynurenine, at least 3.5 µM kynurenine, at least 4 µM kynurenine, at least 4.5 µM kynurenine, at least 5 µM kynurenine, or greater than 5 µM kynurenine. In embodiments, a bacterial isolate does not produce kynurenine. In embodiments, the bacterial isolate is provided in Table 6, or comprises a 16S rRNA sequence at least 95% identical to a 16S rRNA sequence corresponding to a SEQ ID NO of a bacterial isolate provided in Table 6.

In an embodiment, the bacterial isolate comprises *Odoribacter splanchnicus* In an embodiment, the bacterial isolate comprises a 16S rRNA sequence at least 95% identical to the 16S rRNA sequence corresponding to SEQ ID NO: 2. In an embodiment, the bacterial isolate comprises *Bacteroides stercoris*. In an embodiment, the bacterial isolate comprises a 16S rRNA sequence at least 95% identical to the 16S rRNA sequence corresponding to SEQ ID NO: 13.

In other embodiments, a bacterial isolate can produce kynurenine at a higher level than blank media or a control bacterial strain (e.g., positive control bacterial strain capable of producing kynurenine, such as a strain that is a member of the *Peptostreptococcus* genus), as measured in a functional assay. For example, a bacterial isolate can produce kynurenine at a higher level than at least one of the control strains *Peptostreptococcus anaerobius* or *Peptostreptococcus russellii* over a duration of time. In embodiments, a pharmaceutical composition comprises a bacterial isolate that can produce kynurenine at a level that is at least 1.1×, at least 1.2×, at least 1.3×, at least 1.4×, at least 1.5×, at least 1.6×, at least 1.7×, at least 1.8×, at least 1.9×, at least 2×, at least 2.1×, at least 2.2×, at least 2.3×, at least 2.4×, at least 2.5×, at least 2.6×, at least 2.7×, at least 2.8×, at least 2.9×, at least 3×, at least 4×, at least 5×, at least 6×, at least 7×, at least 8×, at least 9×, at least 10×, at least 11×, at least 12×, at least 13×, at least 14×, at least 15×, at least 16×, at least 17×, at least 18×, at least 19×, at least 20×, at least 21×, at least 22×, at least 23×, at least 24×, at least 25×, at least 26×, at least 27×, at least 28×, at least 29×, at least 30×, at least 35×, at least 40×, at least 45×, at least 50×, at least 60×, at least 70×, at least 80×, at least 90×, at least 100×, at least 110×, at least 120×, at least 130×, at least 140×, at least 150×, at least 160×, at least 170×, at least 180×, at least 190×, at least 200×, at least 210×, at least 220×, at least 230×, at least 240×, at least 250×, or greater than 250× relative to at least one of the control strains *Peptostreptococcus anaerobius* or *Peptostreptococcus russellii*, or relative to blank media alone. In an embodiment, the bacterial isolate comprises *Odoribacter splanchnicus*. In an embodiment, the bacterial isolate comprises a 16S rRNA sequence at least 95% identical to the 16S rRNA sequence corresponding to SEQ ID NO: 2. In an embodiment, the bacterial isolate comprises *Bacteroides stercoris*. In an embodiment, the bacterial isolate comprises a 16S rRNA sequence at least 95% identical to the 16S rRNA sequence corresponding to SEQ ID NO: 13.

In embodiments, a pharmaceutical composition comprises one or more bacterial isolates that produce tryptamine capable of activating an AhR of a subject administered the pharmaceutical composition. For example, a bacterial isolate can produce tryptamine at a concentration of at least 0.1 µM tryptamine, at least 0.2 µM tryptamine, at least 0.3 µM tryptamine, at least 0.4 µM tryptamine, at least 0.5 µM tryptamine, at least 0.6 µM tryptamine, at least 0.7 µM tryptamine, at least 0.8 µM tryptamine, at least 0.9 µM tryptamine, at least 1 µM tryptamine, at least 1.5 µM tryptamine, at least 2 µM tryptamine, at least 2.5 µM tryptamine, at least 3 µM tryptamine, at least 3.5 µM tryptamine, at least 4 µM tryptamine, at least 4.5 µM tryptamine, at least 5 µM tryptamine, or greater than 5 µM tryptamine. In embodiments, a bacterial isolate does not produce tryptamine. In embodiments, the bacterial isolate is provided in Table 6, or comprises a 16S rRNA sequence at least 95% identical to a sequence corresponding to a SEQ ID NO of a bacterial isolate provided in Table 6. In embodiments, the bacterial isolate is provided in Table 6, or comprises a 16S rRNA sequence at least 95% identical to a 16S rRNA sequence corresponding to a SEQ ID NO of a bacterial isolate provided in Table 6. In an embodiment, the bacterial isolate comprises *Odoribacter splanchnicus*. In an embodiment, the bacterial isolate comprises a 16S rRNA sequence at least 95% identical to the 16S rRNA sequence corresponding to SEQ ID NO: 2.

In other embodiments, a bacterial isolate can produce tryptamine at a higher level than blank media or a control bacterial strain (e.g., positive control bacterial strain capable of producing tryptamine, such as a strain that is a member of the *Peptostreptococcus* genus), as measured in a functional assay. For example, a bacterial isolate can produce tryptamine at a higher level than at least one of the control strains *Peptostreptococcus anaerobius* or *Peptostreptococcus russellii* over a duration of time. In embodiments, a pharmaceutical composition comprises a bacterial isolate that can produce tryptamine at a level that is at least 1.1×, at least 1.2×, at least 1.3×, at least 1.4×, at least 1.5×, at least 1.6×, at least 1.7×, at least 1.8×, at least 1.9×, at least 2×, at least 2.1×, at least 2.2×, at least 2.3×, at least 2.4×, at least 2.5×, at least 2.6×, at least 2.7×, at least 2.8×, at least 2.9×, at least 3×, at least 4×, at least 5×, at least 6×, at least 7×, at least 8×, at least 9×, at least 10×, at least 11×, at least 12×, at least 13×, at least 14×, at least 15×, at least 16×, at least 17×, at least 18×, at least 19×, at least 20×, at least 21×, at least 22×, at least 23×, at least 24×, at least 25×, at least 26×, at least 27×, at least 28×, at least 29×, at least 30×, at least 35×, at least 40×, at least 45×, at least 50×, at least 60×, at least 70×, at least 80×, at least 90×, at least 100×, at least 110×, at least 120×, at least 130×, at least 140×, at least 150×, at least 160×, at least 170×, at least 180×, at least 190×, at least 200×, at least 210×, at least 220×, at least 230×, at least 240×, at least 250×, or greater than 250× relative to at least one of the control strains *Peptostreptococcus anaerobius* or *Peptostreptococcus russellii*, or relative to blank media alone. In an embodiment, the bacterial isolate comprises *Odoribacter splanchnicus*. In embodiments, the bacterial isolate is provided in Table 6, or comprises a 16S rRNA sequence at least 95% identical to a 16S rRNA sequence corresponding to a SEQ ID NO of a bacterial isolate provided in Table 6. In an embodiment, the bacterial isolate comprises *Odoribacter splanchnicus*. In an embodiment, the bacterial isolate comprises a 16S rRNA sequence at least 95% identical to the 16S rRNA sequence corresponding to SEQ ID NO: 2.

In embodiments, an aryl hydrocarbon (i.e., AhR ligand) produced and/or released by a bacterial isolate described herein can bind to and/or activate an AhR expressed by a cell of a subject administered a pharmaceutical composition containing the bacterial isolate. Non-limiting examples of host cells that can express an AhR for binding to an aryl hydrocarbon released by a bacterial isolate include intestinal cells and immune cells. Examples of intestinal cells are an intestinal epithelial cell, an intestinal mucosal cell, or an intestinal lamina propria cell. Examples of immune cells include a B cell, a dendritic cell, a granulocyte, an innate lymphoid cell, a megakaryocyte, a monocyte, a macrophage, a myeloid-derived suppressor cell (MDSC), a natural killer cell (NK cell), a T cell, and a thymocyte.

In embodiments, a functional assay can be utilized to determine an ability of a bacterial isolate and/or an aryl hydrocarbon produced or secreted by a bacterial isolate to activate AhR. For example, activation of AhR can be determined or measured using an AhR-responsive reporter gene construct, e.g., comprising an AhR-responsive promoter fused to a reporter gene. The AhR-responsive reporter gene construct can then be transfected into cells (e.g., mammalian cell line such as Chinese hamster ovary cells or a human cell line), which can be exposed in the functional assay to a bacterial isolate or a supernatant extracted from the bacterial isolate cells after growth. The ability of an aryl hydrocarbon (e.g., secreted by the bacterial isolate during growth) to activate AhR in the transfected cell can then be measured as reporter gene activity or output. Non-limiting examples of reporter genes include coding sequences for β-galactosidase, Green Fluorescent Protein (GFP), Red Fluorescent Protein (RFP), and luciferase.

Examples of bacterial isolates having the ability to secrete an aryl hydrocarbon in an appreciable amount are provided in Table 6. Table 6 lists bacterial isolates which can be included in a pharmaceutical composition such as a microbial cocktail; each isolate is identified by Latin name, an Identification Number (ID number), and the Sequence Identifier (SEQ ID NO) for its 16S rRNA sequence. In aspects, a pharmaceutical composition (e.g., comprising a microbial cocktail) comprises at least one bacterial isolate provided in Table 6, or at least one bacterial isolate comprising a 16S rRNA sequence at least 95% identical to a 16S rRNA sequence of one or more of the bacterial isolates provided in Table 6. In embodiments, the pharmaceutical composition comprises at least two bacterial isolates, at least three bacterial isolates, at least four bacterial isolates, at least five bacterial isolates, at least six bacterial isolates, or at least seven bacterial isolates, that each comprise a 16S rRNA sequence at least 95% identical to a 16S rRNA sequence of at least one of the bacterial isolates provided in Table 6.

TABLE 6

| Isolate Latin Name | ID Number | SEQ ID NO. for 16S rRNA Sequence |
|---|---|---|
| Odoribacter splanchnicus | PI00000072 | 2 |
| Bacteroides stercoris | PI00000146 | 13 |
| Clostridium aldenense | PI00000097 | 10 |
| Dorea longicatena | IS00006618 | 6 |
| Parabacteroides merdae | IS00006167 | 5 |
| Bacteroides uniformis | PI00000352 | 16 |
| Bacteroides uniformis | PI00000137 | 11 |

In embodiments, a pharmaceutical composition comprises all or a subset of the bacterial isolates in at least one of Tables 1-4 and 6, or a bacterial isolate having a 16S rRNA sequence that is at least 95% identical to a 16S rRNA sequence of one or more of the bacterial isolates in Tables 1-4 and 6. In embodiments, all bacterial isolates in a pharmaceutical composition (e.g., comprising a microbial cocktail) are found in at least one of Tables 2-4 and 6, or share at least 95% identity in a 16S rRNA sequence to that of a bacterial isolate provided in at least one of Tables 2-4 and 6. In embodiments, all bacterial isolates in a pharmaceutical composition are listed together in one of Tables 2-4 and 6, or share at least 95% identity in a 16S rRNA sequence to that of a bacterial isolate provided in at least one of Tables 2-4 and 6. In an aspect, a pharmaceutical composition does not contain any bacterial isolates from at least one of Tables 2-4 and 6, or does not contain a bacterial isolate that shares 95% identity in a 16S rRNA sequence to that of a bacterial isolate provided in at least one of Tables 2-4 and 6.

In an aspect, a pharmaceutical composition can comprise one or more bacterial isolates (e.g., at least 1, at least 2, at least 3, at least 4, at least 5, at least 6, at least 7, at least 8, or at least 9 bacterial isolates) from Table 2, or comprising a 16S rRNA sequence that is at least 95% identical to a 16S rRNA sequence of one or more of the bacterial isolates provided in Table 2. A microbial cocktail described herein can therefore comprise multiple bacterial isolates capable of generating one or more SCFAs such as butyrate. By providing a microbial cocktail containing multiple bacterial isolates that produce an SCFA such as butyrate in a gut of a subject administered the cocktail, a pharmaceutical composition can induce a spike or elevation or 'burst' of butyrate in the gut of a subject (e.g., which is depleted of SCFAs). Table 7, Table 8 and Table 9 illustrate exemplary microbial cocktails containing bacterial isolates that are all found in Table 2; each isolate is identified by Latin name, an Identification Number (ID number), and the Sequence Identifier (SEQ ID NO) for its 16S rRNA sequence. In certain embodiments, a composition comprises a microbial cocktail comprising each of the bacterial isolates in one of Tables 7-9, or bacterial isolates comprising 16S rRNA sequences at least 95% identical to the 16S rRNA sequence of each of the bacterial isolates in one of Tables 7-9. In embodiments, the pharmaceutical composition comprises at least eight bacterial isolates that each comprise a 16S rRNA sequence at least 95% identical to a 16S rRNA sequence of at least one of the bacterial isolates provided in Table 7. In embodiments, the pharmaceutical composition comprises at least six bacterial isolates that each comprise a 16S rRNA sequence at least 95% identical to a 16S rRNA sequence of at least one of the bacterial isolates provided in one of Tables 8-9. In certain embodiments, a composition comprises a microbial cocktail consisting essentially of the bacterial isolates listed in one of Tables 7-9, or bacterial isolates comprising 16S rRNA sequences at least 95% identical to the 16S rRNA sequence of each of the bacterial isolates in one of Tables 7-9. In certain embodiments, a composition comprises a microbial cocktail consisting of the bacterial isolates listed in one of Tables 7-9, or bacterial isolates comprising 16S rRNA sequences at least 959 identical to the 16S rRNA sequence of each of the bacterial isolates in one of Tables 7-9.

TABLE 7

| Isolate Latin Name | ID Number | SEQ ID NO for 16S rRNA Sequence |
|---|---|---|
| Odoribacter splanchnicus | PI00000072 | 2 |
| Subdoligranulum variabile | IS00007359 | 22 |
| Subdoligranulum variabile | IS00007357 | 23 |
| Eubacterium rectale | IS00006864 | 8 |
| Roseburia faecis | PI00000404 | 19 |
| Faecalibacterium prausnitzii | PI00000329 | 1 |
| Faecalibacterium prausnitzii | IS00006632 | 7 |
| Anaerostipes hadrus | PI00000094 | 3 |

TABLE 8

| Isolate Latin Name | ID Number | SEQ ID NO for 16S rRNA Sequence |
|---|---|---|
| Faecalibacterium prausnitzii | PI00000329 | 1 |
| Coprococcus comes | PI00000370 | 17 |
| Anaerostipes hadrus | PI00000094 | 3 |
| Eubacterium rectale | IS00006864 | 8 |
| Roseburia faecis | PI00000404 | 19 |
| Subdoligranulum variabile | IS00007359 OR IS00007357 | 22 OR 23 |

TABLE 9

| Isolate Latin Name | ID Number | SEQ ID NO for 16S rRNA Sequence |
|---|---|---|
| Faecalibacterium prausnitzii | IS00006632 | 7 |
| Anaerostipes hadrus | PI00000094 | 3 |
| Eubacterium rectale | IS00006864 | 8 |
| Roseburia faecis | PI00000404 | 19 |
| Coprococcus comes | PI00000370 | 17 |
| Subdoligranulum variabile | IS00007359 OR IS00007357 | 22 OR 23 |

In embodiments, a pharmaceutical composition (e.g., comprising a microbial cocktail) can comprise one or more bacterial isolates (e.g., at least 1, at least 2, at least 3, at least 4, at least 5, at least 6, at least 7, at least 8, at least 9, at least 10, at least 11, at least 12, at least 13, at least 14, at least 15, or greater than 15 bacterial isolates) that are not in Table 2. In embodiments, a pharmaceutical composition lacks at least one of the bacterial isolates in Table 2, or lacks bacterial isolates comprising 16S rRNA sequences at least 95% identical to the 16S rRNA sequence of at least one of the bacterial isolates in Table 2. In embodiments, a pharmaceutical composition (e.g., comprising a microbial cocktail) does not contain any bacterial isolate from Table 2. A pharmaceutical composition described herein can therefore comprise or consist of one or more bacterial isolates which substantially do not produce an SCFA in the gut of a subject, and/or does not induce a spike of SCFA in the gut of the subject post-administration. Table 10, Table 11 and Table 12 illustrate exemplary microbial cocktails containing bacterial isolates that are not found in Table 2; each isolate is identified by Latin name, an Identification Number (ID number), and the Sequence Identifier (SEQ ID NO) for its 16S rRNA sequence. In certain embodiments, a composition comprises a microbial cocktail comprising each of the bacterial isolates in one of Tables 10-12, or bacterial isolates comprising 16S rRNA sequences at least 95% identical to the 16S rRNA sequence of each of the bacterial isolates in one of Tables 10-12. In embodiments, the pharmaceutical composition comprises at least eight bacterial isolates that each comprise a 16S rRNA sequence at least 95% identical to a 16S rRNA sequence of at least one of the bacterial isolates provided in one of Tables 10-11. In embodiments, the pharmaceutical composition comprises at least six bacterial isolates that each comprise a 16S rRNA sequence at least 95% identical to a 16S rRNA sequence of at least one of the bacterial isolates provided in Table 12. In certain embodiments, a composition comprises a microbial cocktail consisting essentially of the bacterial isolates listed in one of Tables 10-12, or bacterial isolates comprising 16S rRNA sequences at least 95% identical to the 16S rRNA sequence of each of the bacterial isolates in one of Tables 10-12. In certain embodiments, a composition comprises a microbial cocktail consisting of the bacterial isolates listed in one of Tables 10-12, or bacterial isolates comprising 16S rRNA sequences at least 95% identical to the 16S rRNA sequence of each of the bacterial isolates in one of Tables 10-12. In an embodiment, a microbial cocktail comprises bacterial isolates comprising 16S rRNA sequences at least 95% identical to the 16S rRNA sequence of each of the bacterial isolates in one of Tables 10-12, as well as an additional bacterial isolate. For example, the additional bacterial isolate can be a member of the genus *Blautia*.

TABLE 10

| Isolate Latin Name | ID Number | SEQ ID NO for 16S rRNA Sequence |
|---|---|---|
| Akkermansia muciniphila | IS00007180 | 20 |
| Parabacteroides merdae | IS00006167 | 5 |
| Bacteroides uniformis | PI00000137 | 11 |
|  | OR | OR |
|  | PI00000352 | 16 |
| Alistipes finegoldii | PI00000340 | 15 |
| Bacteroides vulgatus | PI00000138 | 12 |
| Dorea longicatena | IS00006618 | 6 |
| Blautia obeum | PI00000053 | 9 |
| Blautia sp. | IS00002788 | 34 |

TABLE 11

| Isolate Latin Name | ID Number | SEQ ID NO for 16S rRNA Sequence |
|---|---|---|
| Akkermansia muciniphila | IS00007180 | 20 |
| Parabacteroides merdae | IS00006167 | 5 |
| Bacteroides uniformis | PI00000137 | 11 |
|  | OR | OR |
|  | PI00000352 | 16 |
| Alistipes finegoldii | PI00000340 | 15 |
| Bacteroides vulgatus | PI00000138 | 12 |
| Dorea longicatena | IS00006618 | 6 |
| Alistipes onderdonkii | IS00004389 | 4 |
| Blautia sp. | IS00002788 | 34 |

TABLE 12

| Isolate Latin Name | ID Number | SEQ ID NO for 16S rRNA Sequence |
|---|---|---|
| Akkermansia muciniphila | IS00007180 | 20 |
| Bacteroides uniformis | PI00000137 | 11 |
|  | OR | OR |
|  | PI00000352 | 16 |
| Alistipes finegoldii | PI00000340 | 15 |
| Bacteroides vulgatus | PI00000138 | 12 |
| Dorea longicatena | IS00006618 | 6 |
| Blautia sp. | IS00002788 | 34 |

In embodiments, a pharmaceutical composition (e.g., comprising a microbial cocktail) can comprise one or more bacterial isolates (e.g., at least 1, at least 2, at least 3, at least 4, at least 5, at least 6, at least 7, at least 8, at least 9, at least 10, or 11 bacterial isolates) from Table 3, and/or one or more bacterial isolates (e.g., at least 1, at least 2, at least 3, at least 4, at least 5, at least 6, at least 7, at least 8, at least 9, at least 10, at least 11, at least 12, at least 13, at least 14, at least 15, or greater than 15 bacterial isolates) comprising a 16S rRNA sequence that is at least 95% identical to a 16S rRNA sequence of one or more bacterial isolates provided in Table 3. A microbial cocktail described herein can therefore comprise multiple bacterial isolates capable of modulating production and/or release of one or more cytokines from a eukaryotic cell (e.g., a cell of a subject administered a composition comprising the microbial cocktail).

In embodiments, a pharmaceutical composition (e.g., comprising a microbial cocktail) can comprise one or more bacterial isolates (e.g., at least 1, at least 2, at least 3, at least 4, at least 5, at least 6, at least 7, at least 8, at least 9, at least 10, at least 11, at least 12, at least 13, at least 14, at least 15, or greater than 15 bacterial isolates) that are not in Table 3. In embodiments, a pharmaceutical composition lacks at least one of the bacterial isolates in Table 3, or lacks bacterial isolates comprising 16S rRNA sequences at least 95% identical to the 16S rRNA sequence of at least one of the bacterial isolates in Table 2. In embodiments, a pharmaceutical composition (e.g., comprising a microbial cocktail) does not contain any bacterial isolate from Table 3. A pharmaceutical composition described herein can therefore comprise or consist of one or more bacterial isolates which do not substantially modulate production and/or release of one or more cytokines from a eukaryotic cell (e.g., a cell of a subject administered a composition comprising the microbial cocktail).

In embodiments, a pharmaceutical composition can comprise one or more bacterial isolates (e.g., at least 1, at least 2, at least 3, at least 4, at least 5, at least 6, at least 7, at least 8, at least 9, at least 10, at least 11, at least 12, at least 13, at least 14, at least 15, or greater than 15 bacterial isolates) from Table 4 comprising a 16S rRNA sequence that is at least 95% identical to a 16S rRNA sequence of one or more bacterial isolates provided in Table 4. A microbial cocktail described herein can therefore comprise multiple bacterial isolates corresponding to bacterial strains more highly abundant in a healthy subject relative to a patient with UC.

In embodiments, a pharmaceutical composition (e.g., comprising a microbial cocktail) can comprise one or more bacterial isolates (e.g., at least 1, at least 2, at least 3, at least 4, at least 5, at least 6, at least 7, at least 8, at least 9, at least 10, at least 11, at least 12, at least 13, at least 14, at least 15, or greater than 15 bacterial isolates) that are not in Table 4. In embodiments, a pharmaceutical composition lacks at least one of the bacterial isolates in Table 4, or lacks bacterial isolates comprising 16S rRNA sequences at least 95% identical to the 16S rRNA sequence of at least one of the bacterial isolates in Table 4. In embodiments, a pharmaceutical composition (e.g., comprising a microbial cocktail) does not contain any bacterial isolate from Table 4. A pharmaceutical composition described herein can therefore comprise or consist of one or more bacterial isolates which do not correspond to bacterial strains more highly abundant in a healthy subject relative to a patient with UC.

In embodiments, a pharmaceutical composition can comprise one or more bacterial isolates (e.g., one, two, and three bacterial isolates) from Table 6, and/or one or more bacterial isolates (e.g., at least 1, at least 2, at least 3, at least 4, at least 5, at least 6, at least 7, at least 8, at least 9, at least 10, at least 11, at least 12, at least 13, at least 14, at least 15, or greater than 15 bacterial isolates) comprising a 16S rRNA sequence that is at least 95% identical to a 16S rRNA sequence of one or more bacterial isolates provided in Table 6. A microbial cocktail described herein can therefore comprise multiple bacterial isolates that produce an aryl hydrocarbon capable of binding to and activating an AhR receptor.

In embodiments, a pharmaceutical composition (e.g., comprising a microbial cocktail) can comprise one or more bacterial isolates (e.g., at least 1, at least 2, at least 3, at least 4, at least 5, at least 6, at least 7, at least 8, at least 9, at least 10, at least 11, at least 12, at least 13, at least 14, at least 15, or greater than 15 bacterial isolates) that are not in Table 6. In embodiments, a pharmaceutical composition lacks at least one of the bacterial isolates in Table 6, or lacks bacterial isolates comprising 16S rRNA sequences at least 95% identical to the 16S rRNA sequence of at least one of the bacterial isolates in Table 6. In embodiments, a pharmaceutical composition (e.g., comprising a microbial cocktail) does not contain any bacterial isolate from Table 6. A pharmaceutical composition described herein can therefore comprise or consist of one or more bacterial isolates which do not substantially secrete an aryl hydrocarbon capable of binding to and activating an AhR receptor.

In embodiments, a microbial cocktail can comprise bacterial isolates comprising 16S rRNA sequences at least 95% identical to 16S rRNA sequences of bacterial isolates provided in more than one of Tables 2-4. Such a microbial cocktail can therefore advantageously influence the health of a subject administered the cocktail (e.g., in the form of a pharmaceutical composition) via multiple mechanisms. For example, a microbial cocktail can comprise one or more bacterial isolates that comprise a 16S rRNA sequence at least 95% identical to a 16S rRNA sequence of one or more bacterial isolates provided in Table 2, and one or more bacterial isolates that comprise a 16S rRNA sequence at least 95% identical to a 16S rRNA sequence of one or more bacterial isolates provided in Table 3. In such cases at least one bacterial isolate in the composition can produce one or more SCFAs to increase a level of SCFAs (e.g., butyrate) in the gut of the subject (i.e., 'Table 2 bacterial isolate') and at least one bacterial isolate administered to the subject can modulate production and/or release of a cytokine by a host cell of the subject (i.e., 'Table 3 bacterial isolate').

In another example, a microbial cocktail can comprise one or more bacterial isolates that comprise a 16S rRNA sequence at least 95% identical to a 16S rRNA sequence of one or more bacterial isolates provided in Table 2, and one or more bacterial isolates that comprise a 16S rRNA sequence at least 95% identical to a 16S rRNA sequence of one or more bacterial isolates provided in Table 4. In such cases, at least one bacterial isolate in the composition can produce one or more SCFAs to increase a level of SCFAs (e.g., butyrate) in the gut of the subject (i.e., 'Table 2 bacterial isolate') and at least one bacterial isolate in the composition corresponds to a bacterial strain more highly abundant in a healthy subject relative to a patient with UC ('Table 4 bacterial isolate').

In another example, a microbial cocktail can comprise one or more bacterial isolates that comprise a 16S rRNA sequence at least 95% identical to a 16S rRNA sequence of one or more bacterial isolates provided in Table 3, and one or more bacterial isolates that comprise a 16S rRNA sequence at least 95% identical to a 16S rRNA sequence of one or more bacterial isolates provided in Table 4. In such cases, at least one bacterial isolate in the composition can modulate production and/or release of a cytokine by a host cell of the subject (i.e., 'Table 3 bacterial isolate') and at least one bacterial isolate in the composition corresponds to a bacterial strain more highly abundant in a healthy subject relative to a patient with UC ('Table 4 bacterial isolate').

In another example, a microbial cocktail can comprise one or more bacterial isolates that comprise a 16S rRNA sequence at least 95% identical to a 16S rRNA sequence of one or more bacterial isolates provided in Table 2, one or more bacterial isolates that comprise a 16S rRNA sequence at least 95% identical to a 16S rRNA sequence of one or more bacterial isolates provided in Table 3, and one or more bacterial isolates that comprise a 16S rRNA sequence at least 95% identical to a 16S rRNA sequence of one or more bacterial isolates provided in Table 4. In such cases, at least one bacterial isolate in the composition can produce one or more SCFAs to increase a level of SCFAs in the gut of the subject (i.e., 'Table 2 bacterial isolate'), at least one bacterial isolate in the composition can modulate production and/or release of a cytokine by a host cell of the subject (i.e., 'Table 3 bacterial isolate'), and at least one bacterial isolate in the composition corresponds to a bacterial strain more highly abundant in a healthy subject relative to a patient with UC ('Table 4 bacterial isolate').

In embodiments, a microbial cocktail can comprise bacterial isolates comprising 16S rRNA sequences at least 95% identical to a 16S rRNA sequence of one or more bacterial isolates from Table 6 and one or more bacterial isolates of Tables 2-4. Such a microbial cocktail can therefore advantageously influence the health of a subject administered the cocktail (e.g., in the form of a pharmaceutical composition) via multiple mechanisms. For example, a microbial cocktail can comprise one or more bacterial isolates that comprise a 16S rRNA sequence at least 95% identical to a 16S rRNA sequence of one or more bacterial isolates provided in Table 2, and one or more bacterial isolates that comprise a 16S rRNA sequence at least 95% identical to a 16S rRNA sequence of one or more bacterial isolates provided in Table 6. In such cases, at least one bacterial isolate in the composition can produce one or more SCFAs to increase a level of SCFAs (e.g., butyrate) in the gut of the subject (i.e., 'Table 2 bacterial isolate'), and at least one bacterial isolate in the composition can produce a compound capable of binding to and activating AhR receptor (i.e., 'Table 6 bacterial isolate').

In another example, a microbial cocktail can comprise one or more bacterial isolates that comprise a 16S rRNA sequence at least 95% identical to a 16S rRNA sequence of one or more bacterial isolates provided in Table 4, and one or more bacterial isolates that comprise a 16S rRNA sequence at least 95% identical to a 16S rRNA sequence of one or more bacterial isolates provided in Table 6. In such cases, at least one bacterial isolate in the composition corresponds to a bacterial strain more highly abundant in a healthy subject relative to a patient with UC ('Table 4 bacterial isolate'), and at least one bacterial isolate in the composition can produce a ligand capable of binding to an AhR receptor (i.e., 'Table 6 bacterial isolate'). In another example, a microbial cocktail can comprise one or more bacterial isolates that comprise a 16S rRNA sequence at least 95% identical to a 16S rRNA sequence of one or more bacterial isolates provided in Table 3, and one or more bacterial isolates that comprise a 16S rRNA sequence at least 95% identical to a 16S rRNA sequence of one or more bacterial isolates provided in Table 6. In such cases, at least one bacterial isolate in the composition can modulate production and/or release of a cytokine by a host cell of the subject (i.e., 'Table 3 bacterial isolate'), and at least one bacterial isolate in the composition can produce a ligand capable of binding to an AhR receptor (i.e., 'Table 6 bacterial isolate').

In another example, a microbial cocktail can comprise one or more bacterial isolates that comprise a 16S rRNA sequence at least 95% identical to a 16S rRNA sequence of one or more bacterial isolates provided in Table 2, one or more bacterial isolates that comprise a 16S rRNA sequence at least 95% identical to a 16S rRNA sequence of one or more bacterial isolates provided in Table 3, and one or more bacterial isolates that comprise a 16S rRNA sequence at least 95% identical to a 16S rRNA sequence of one or more bacterial isolates provided in Table 6. In such cases, at least one bacterial isolate in the composition can produce one or more SCFAs to increase a level of SCFAs in the gut of the subject (i.e., 'Table 2 bacterial isolate'), at least one bacterial isolate in the composition can modulate production and/or release of a cytokine by a host cell of the subject (i.e., 'Table 3 bacterial isolate'), and at least one bacterial isolate in the composition can produce a ligand capable of binding to an AhR receptor (i.e., 'Table 6 bacterial isolate'). In another example, a microbial cocktail can comprise one or more bacterial isolates that comprise a 16S rRNA sequence at least 95% identical to a 16S rRNA sequence of one or more bacterial isolates provided in Table 2, one or more bacterial isolates that comprise a 16S rRNA sequence at least 95% identical to a 16S rRNA sequence of one or more bacterial isolates provided in Table 4, and one or more bacterial isolates that comprise a 16S rRNA sequence at least 95% identical to a 16S rRNA sequence of one or more bacterial isolates provided in Table 6. In such cases, at least one bacterial isolate in the composition can produce one or more SCFAs to increase a level of SCFAs in the gut of the subject (i.e., 'Table 2 bacterial isolate'), at least one bacterial isolate in the composition corresponds to a bacterial strain more highly abundant in a healthy subject relative to a patient with UC ('Table 4 bacterial isolate'), and at least one bacterial isolate in the composition can produce a ligand capable of binding to an AhR receptor (i.e., 'Table 6 bacterial isolate'). In another example, a microbial cocktail can comprise one or more bacterial isolates that comprise a 16S rRNA sequence at least 95% identical to a 16S rRNA sequence of one or more bacterial isolates provided in Table 3, one or more bacterial isolates that comprise a 16S rRNA sequence at least 95% identical to a 16S rRNA sequence of one or more bacterial isolates provided in Table 4, and one or more bacterial isolates that comprise a 16S rRNA sequence at least 95% identical to a 16S rRNA sequence of one or more bacterial isolates provided in Table 6. In such cases, at least one bacterial isolate in the composition can modulate production and/or release of a cytokine by a host cell of the subject (i.e., 'Table 3 bacterial isolate'), at least one bacterial isolate in the composition corresponds to a bacterial strain more highly abundant in a healthy subject relative to a patient with UC ('Table 4 bacterial isolate'), and at least one bacterial isolate in the composition can produce a ligand capable of binding to an AhR receptor (i.e., 'Table 6 bacterial isolate').

In another example, a microbial cocktail can comprise one or more bacterial isolates that comprise a 16S rRNA sequence at least 95% identical to a 16S rRNA sequence of one or more bacterial isolates provided in Table 2, one or more bacterial isolates that comprise a 16S rRNA sequence at least 95% identical to a 16S rRNA sequence of one or more bacterial isolates provided in Table 3, one or more bacterial isolates that comprise a 16S rRNA sequence at least 95% identical to a 16S rRNA sequence of one or more bacterial isolates provided in Table 4, and one or more bacterial isolates that comprise a 16S rRNA sequence at least 95% identical to a 16S rRNA sequence of one or more bacterial isolates provided in Table 6. In such cases, at least one bacterial isolate in the composition can produce one or more SCFAs to increase a level of SCFAs in the gut of the subject (i.e., 'Table 2 bacterial isolate'), at least one bacterial in the composition can modulate production and/or release of a cytokine by a host cell of the subject (i.e., 'Table 3 bacterial isolate'), at least one bacterial isolate in the composition corresponds to a bacterial strain more highly abundant in a healthy subject relative to a patient with UC ('Table 4 bacterial isolate'), and at least one bacterial isolate in the composition can produce a ligand capable of binding to an AhR receptor (i.e., 'Table 6 bacterial isolate').

Tables 13-35 illustrate different exemplary microbial cocktails containing bacterial isolates found in Tables 2-4 and/or 6, such that collectively the bacterial isolates in the microbial cocktail, once administered to a subject, can act to (i) increase a level of SCFAs in the gut of the subject; and (ii) modulate release of a cytokine by a host cell of the subject; and (iii) provide for bacterial isolates in the gut of the subject that correspond to bacterial strains more highly abundant in a healthy subject relative to a patient with UC; and/or (iv) release one or more hydrocarbons capable of binding to and activating an AhR receptor of a host cell of the subject. In each table, isolates are identified by Latin name, an Identification Number (ID number), the Sequence Identifier (SEQ ID NO) for its 16S rRNA sequence, and the above Table(s) (i.e., Table 2, 3, 4 and/or 6) in which the isolate appears.

In certain embodiments, a composition comprises a microbial cocktail comprising each of the bacterial isolates provided in one of Tables 13-35, or bacterial isolates having 16S rRNA sequences at least 95% identical to the 16S rRNA sequence of each of the bacterial isolates provided in one of Tables 13-35. In embodiments, the pharmaceutical composition comprises at least one, at least two, at least three, at least four, at least five, at least six, at least seven, or at least eight of the bacterial isolates provided in one of Tables 15-17, 17a, 17b, and 22-29, or at least one, at least two, at least three, at least four, at least five, at least six, at least seven, or at least eight bacterial isolates that each comprise a 16S rRNA sequence at least 95% identical to a 16S rRNA sequence of at least one of the bacterial isolates provided in one of Tables 15-17, 17a, 17b, and 22-29. In embodiments, the pharmaceutical composition comprises at least one, at least two, at least three, at least four, at least five, or at least six of the bacterial isolates provided in one of Tables 13, 14, 21 and 30-35, or at least one, at least two, at least three, at least four, at least five, or at least six bacterial isolates that each comprise a 16S rRNA sequence at least 95% identical to a 16S rRNA sequence of at least one of the bacterial isolates provided in one of Tables 13, 14, 21 and 30-35. In embodiments, the pharmaceutical composition comprises at least one, at least two, at least three, at least four, at least five, at least six, or at least seven of the bacterial isolates provided in one of Tables 18-20, or at least one, at least two, at least three, at least four, at least five, at least six, or at least seven bacterial isolates that each comprise a 16S rRNA sequence at least 95% identical to a 16S rRNA sequence of at least one of the bacterial isolates provided in one of Tables 18-20. In certain embodiments, a composition comprises a microbial cocktail consisting essentially of each of the bacterial isolates provided in one of Tables 13-35, or bacterial isolates having 16S rRNA sequences at least 95% identical to the 16S rRNA sequence of each of the bacterial isolates provided in one of Tables 13-35. In certain embodiments, a composition comprises a microbial cocktail consisting of each of the bacterial isolates provided in one of Tables 13-35, or bacterial isolates having 16S rRNA sequences at least 95% identical to the 16S rRNA sequence of each of the bacterial isolates provided in one of Tables 13-35.

TABLE 13

| Isolate Latin Name | ID Number | SEQ ID NO for 16S rRNA Sequence | Table* |
|---|---|---|---|
| Eubacterium rectale | IS00006864 | 8 | 2, 4 |
| Bacteroides cellulosilyticus | PI00000316 | 14 | 4 |
| Faecalibacterium prausnitzii | PI00000329 OR IS00006632 | 1 OR 7 | 2, 3, 4 |
| Alistipes shahii | PI00000395 | 18 | 3, 4 |
| Anaerostipes hadrus | PI00000094 | 3 | 2, 3, 4 |
| Roseburia faecis | PI00000404 | 19 | 2 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relative to a patient with UC.

TABLE 14

| Isolate Latin Name | ID Number | SEQ ID NO for 16S rRNA Sequence | Table* |
|---|---|---|---|
| Eubacterium rectale | IS00006864 | 8 | 2, 4 |
| Bacteroides cellulosilyticus | PI00000316 | 14 | 4 |
| Faecalibacterium prausnitzii | PI00000329 OR IS00006632 | 1 OR 7 | 2, 3, 4 |
| Alistipes shahii | PI00000395 | 18 | 3, 4 |
| Blautia obeum | PI00000053 | 9 | 4 |
| Roseburia faecis | PI00000404 | 19 | 2 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relative to a patient with UC.

TABLE 15

| Isolate Latin Name | ID Number | SEQ ID NO for 16S rRNA Sequence | Table(s)* |
|---|---|---|---|
| Odoribacter splanchnicus | PI00000072 | 2 | 2, 3, 4, 6 |
| Subdoligranulum variabile | IS00007359 OR IS00007357 | 22 OR 23 | 2, 4 |
| Eubacterium rectale | IS00006864 | 8 | 2, 4 |
| Alistipes shahii | PI00000395 | 18 | 3, 4 |
| Phascolarctobacterium faecium | PI00000289 | 21 | 4 |

TABLE 15-continued

| Isolate Latin Name | ID Number | SEQ ID NO for 16S rRNA Sequence | Table(s)* |
|---|---|---|---|
| Bacteroides cellulosilyticus | PI00000316 | 14 | 4 |
| Akkermansia muciniphila | IS00007180 | 20 | 4 |
| Anaerostipes hadrus | PI00000094 | 3 | 2, 3, 4 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relative to a patient with UC.
Table 6: Bacterial isolates that secrete a ligand for an AhR of a host cell.

TABLE 16

| Isolate Latin Name | ID Number | SEQ ID NO for 16S rRNA Sequence | Table(s)* |
|---|---|---|---|
| Odoribacter splanchnicus | PI00000072 | 2 | 2, 3, 4, 6 |
| Subdoligranulum variabile | IS00007359 OR IS00007357 | 22 OR 23 | 2, 4 |
| Eubacterium rectale | IS00006864 | 8 | 2, 4 |
| Alistipes onderdonkii | IS00004389 | 4 | 4 |
| Phascolarctobacterium faecium | PI00000289 | 21 | 4 |
| Bacteroides cellulosilyticus | PI00000316 | 14 | 4 |
| Akkermansia muciniphila | IS00007180 | 20 | 4 |
| Anaerostipes hadrus | PI00000094 | 3 | 2, 3, 4 |

*Table 2: Bacterial isolates capable of producing SCFAs in the gut of a subject.
Table 3: Bacterial isolates capable of modulating cytokine production by a host cell of a subject.
Table 4: Bacterial isolates that correspond to a bacterial strain more highly abundant in a healthy subject relative to a patient with UC.
Table 6: Bacterial isolates capable of producing a ligand for an AhR of a host cell.

TABLE 17

| Isolate Latin Name | ID Number | SEQ ID NO for 16S rRNA Sequence | Table(s)* |
|---|---|---|---|
| Odoribacter splanchnicus | PI00000072 | 2 | 2, 3, 4, 6 |
| Subdoligranulum variabile | IS00007359 OR IS00007357 | 22 OR 23 | 2, 4 |
| Eubacterium rectale | IS00006864 | 8 | 2, 4 |
| Alistipes finegoldii | PI00000340 | 15 | 4 |
| Phascolarctobacterium faecium | PI00000289 | 21 | 4 |
| Bacteroides cellulosilyticus | PI00000316 | 14 | 4 |
| Akkermansia muciniphila | IS00007180 | 20 | 4 |
| Anaerostipes hadrus | PI00000094 | 3 | 2, 3, 4 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relative to a patient with UC.
Table 6: Bacterial isolates that secrete a ligand for an AhR of a host cell.

TABLE 17a

| Isolate Latin Name | ID Number | SEQ ID NO for 16S rRNA Sequence | Table* |
|---|---|---|---|
| Odoribacter splanchnicus | PI00000072 | 2 | 2, 3, 4, 6 |
| Subdoligranulum variabile | IS00007359 OR IS00007357 | 22 OR 23 | 2, 4 |
| Eubacterium rectale | IS00006864 | 8 | 2, 4 |
| Alistipes shahii | PI00000395 | 18 | 3, 4 |
| Faecalibacterium prausnitzii | PI00000329 OR IS00006632 | 1 OR 7 | 2, 3, 4 |

TABLE 17a-continued

| Isolate Latin Name | ID Number | SEQ ID NO for 16S rRNA Sequence | Table* |
|---|---|---|---|
| Bacteroides cellulosilyticus | PI00000316 | 14 | 4 |
| Akkermansia muciniphila | IS00007180 | 20 | 4 |
| Roseburia faecis | PI00000404 | 19 | 2 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relative to a patient with UC.
Table 6: Bacterial isolates that secrete a ligand for an AhR of a host cell.

TABLE 17b

| Isolate Latin Name | ID Number | SEQ ID NO for 16S rRNA Sequence | Table* |
|---|---|---|---|
| Odoribacter splanchnicus | PI00000072 | 2 | 2, 3, 4, 6 |
| Faecalibacterium prausnitzii | IS00006632 | 7 | 2, 3, 4 |
| Eubacterium rectale | IS00006864 | 8 | 2, 4 |
| Alistipes shahii | PI00000395 | 18 | 3, 4 |
| Faecalibacterium prausnitzii | PI00000329 | 1 | 2, 3, 4 |
| Bacteroides cellulosilyticus | PI00000316 | 14 | 4 |
| Akkermansia muciniphila | IS00007180 | 20 | 4 |
| Roseburia faecis | PI00000404 | 19 | 2 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relative to a patient with UC.
Table 6: Bacterial isolates that secrete a ligand for an AhR of a host cell.

TABLE 18

| Isolate Latin Name | ID Number | SEQ ID NO for 16S rRNA Sequence | Table* |
|---|---|---|---|
| Odoribacter splanchnicus | PI00000072 | 2 | 2, 3, 4, 6 |
| Subdoligranulum variabile | IS00007359 OR IS00007357 | 22 OR 23 | 2, 4 |
| Eubacterium rectale | IS00006864 | 8 | 2, 4 |
| Alistipes shahii | PI00000395 | 18 | 3, 4 |
| Faecalibacterium prausnitzii | PI00000329 OR IS00006632 | 1 OR 7 | 2, 3, 4 |
| Bacteroides cellulosilyticus | PI00000316 | 14 | 4 |
| Anaerostipes hadrus | PI00000094 | 3 | 2, 3, 4 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relative to a patient with UC.
Table 6: Bacterial isolates that secrete a ligand for an AhR of a host cell.

TABLE 19

| Isolate Latin Name | ID Number | SEQ ID NO for 16S rRNA Sequence | Table* |
|---|---|---|---|
| Odoribacter splanchnicus | PI00000072 | 2 | 2, 3, 4, 6 |
| Subdoligranulum variabile | IS00007359 OR IS00007357 | 22 OR 23 | 2, 4 |
| Eubacterium rectale | IS00006864 | 8 | 2, 4 |
| Alistipes onderdonkii | IS00004389 | 4 | 4 |
| Faecalibacterium prausnitzii | PI00000329 OR IS00006632 | 1 OR 7 | 2, 3, 4 |
| Bacteroides cellulosilyticus | PI00000316 | 14 | 4 |
| Anaerostipes hadrus | PI00000094 | 3 | 2, 3, 4 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relative to a patient with UC.
Table 6: Bacterial isolates that secrete a ligand for an AhR of a host cell.

TABLE 20

| Isolate Latin Name | ID Number | SEQ ID NO for 16S rRNA Sequence | Table* |
|---|---|---|---|
| Odoribacter splanchnicus | PI00000072 | 2 | 2, 3, 4, 6 |
| Subdoligranulum variabile | IS00007359 OR IS00007357 | 22 OR 23 | 2, 4 |
| Eubacterium rectale | IS00006864 | 8 | 2, 4 |
| Alistipes finegoldii | PI00000340 | 15 | 4 |
| Faecalibacterium prausnitzii | PI00000329 OR IS00006632 | 1 OR 7 | 2, 3, 4 |
| Bacteroides cellulosilyticus | PI00000316 | 14 | 4 |
| Anaerostipes hadrus | PI00000094 | 3 | 2, 3, 4 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relative to a patient with UC.
Table 6: Bacterial isolates that secrete a ligand for an AhR of a host cell.

TABLE 21

| Isolate Latin Name | ID Number | SEQ ID NO for 16S rRNA Sequence | Table* |
|---|---|---|---|
| Odoribacter splanchnicus | PI00000072 | 2 | 2, 3, 4, 6 |
| Eubacterium rectale | IS00006864 | 8 | 2, 4 |
| Bacteroides cellulosilyticus | PI00000316 | 14 | 4 |
| Faecalibacterium prausnitzii | PI00000329 OR IS00006632 | 1 OR 7 | 2, 3, 4 |
| Alistipes shahii | PI00000395 | 18 | 3, 4 |
| Blautia obeum | PI00000053 | 9 | 4 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relative to a patient with UC.
Table 6: Bacterial isolates that secrete a ligand for an AhR of a host cell.

TABLE 22

| Isolate Latin Name | ID Number | SEQ ID NO for 16S rRNA Sequence | Table* |
|---|---|---|---|
| Odoribacter splanchnicus | PI00000072 | 2 | 2, 3, 4, 6 |
| Subdoligranulum variabile | IS00007359 OR IS00007357 | 22 OR 23 | 2, 4 |
| Eubacterium rectale | IS00006864 | 8 | 2, 4 |
| Alistipes shahii | PI00000395 | 18 | 3, 4 |
| Faecalibacterium prausnitzii | PI00000329 OR IS00006632 | PI00000329: 1 OR IS00006632: 7 | 2, 3, 4 |

TABLE 22-continued

| Isolate Latin Name | ID Number | SEQ ID NO for 16 S rRNA Sequence | Table* |
|---|---|---|---|
| *Bacteroides cellulosilyticus* | PI00000316 | 14 | 4 |
| *Bacteroides stercoris* | PI00000146 | 13 | 3, 6 |
| *Anaerostipes hadrus* | PI00000094 | 3 | 2, 3, 4 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relative to a patient with UC.
Table 6: Bacterial isolates that secrete a ligand for an AhR of a host cell.

TABLE 23

| Isolate Latin Name | ID Number | SEQ ID NO for 16 S rRNA Sequence | Table* |
|---|---|---|---|
| *Odoribacter splanchnicus* | PI00000072 | 2 | 2, 3, 4, 6 |
| *Subdoligranulum variabile* | IS00007359 OR IS00007357 | 22 OR 23 | 2, 4 |
| *Eubacterium rectale* | IS00006864 | 8 | 2, 4 |
| *Alistipes shahii* | PI00000395 | 18 | 3, 4 |
| *Faecalibacterium prausnitzii* | PI00000329 OR IS00006632 | PI00000329: 1 OR IS00006632: 7 | 2, 3, 4 |
| *Bacteroides cellulosilyticus* | PI00000316 | 14 | 4 |
| *Clostridium aldenense* | PI00000097 | 10 | 3, 6 |
| *Anaerostipes hadrus* | PI00000094 | 3 | 2, 3, 4 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relative to a patient with UC.
Table 6: Bacterial isolates that secrete a ligand for an AhR of a host cell.

TABLE 24

| Isolate Latin Name | ID Number | SEQ ID NO for 16 S rRNA Sequence | Table* |
|---|---|---|---|
| *Odoribacter splanchnicus* | PI00000072 | 2 | 2, 3, 4, 6 |
| *Subdoligranulum variabile* | IS00007359 OR IS00007357 | 22 OR 23 | 2, 4 |
| *Eubacterium rectale* | IS00006864 | 8 | 2, 4 |
| *Alistipes onderdonkii* | IS00004389 | 4 | 4 |
| *Faecalibacterium prausnitzii* | PI00000329 OR IS00006632 | PI00000329: 1 OR IS00006632: 7 | 2, 3, 4 |
| *Bacteroides cellulosilyticus* | PI00000316 | 14 | 4 |
| *Bacteroides stercoris* | PI00000146 | 13 | 3, 6 |
| *Anaerostipes hadrus* | PI00000094 | 3 | 2, 3, 4 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relative to a patient with UC.
Table 6: Bacterial isolates that secrete a ligand for an AhR of a host cell.

TABLE 25

| Isolate Latin Name | ID Number | SEQ ID NO for 16 S rRNA Sequence | Table* |
|---|---|---|---|
| *Odoribacter splanchnicus* | PI00000072 | 2 | 2, 3, 4, 6 |
| *Subdoligranulum variabile* | IS00007359 OR IS00007357 | 22 OR 23 | 2, 4 |
| *Eubacterium rectale* | IS00006864 | 8 | 2, 4 |
| *Alistipes onderdonkii* | IS00004389 | 4 | 4 |
| *Faecalibacterium prausnitzii* | PI00000329 OR IS00006632 | PI00000329: 1 OR IS00006632: 7 | 2, 3, 4 |
| *Bacteroides cellulosilyticus* | PI00000316 | 14 | 4 |
| *Clostridium aldenense* | PI00000097 | 10 | 3, 6 |
| *Anaerostipes hadrus* | PI00000094 | 3 | 2, 3, 4 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relative to a patient with UC.
Table 6: Bacterial isolates that secrete a ligand for an AhR of a host cell.

TABLE 26

| Isolate Latin Name | ID Number | SEQ ID NO for 16 S rRNA Sequence | Table* |
|---|---|---|---|
| *Odoribacter splanchnicus* | PI00000072 | 2 | 2, 3, 4, 6 |
| *Subdoligranulum variabile* | IS00007359 OR IS00007357 | 22 OR 23 | 2, 4 |
| *Eubacterium rectale* | IS00006864 | 8 | 2, 4 |
| *Alistipes finegoldii* | PI00000340 | 15 | 4 |
| *Faecalibacterium prausnitzii* | PI00000329 OR IS00006632 | PI00000329: 1 OR IS00006632: 7 | 2, 3, 4 |
| *Bacteroides cellulosilyticus* | PI00000316 | 14 | 4 |
| *Bacteroides stercoris* | PI00000146 | 13 | 3, 6 |
| *Anaerostipes hadrus* | PI00000094 | 3 | 2, 3, 4 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relative to a patient with UC.
Table 6: Bacterial isolates that secrete a ligand for an AhR of a host cell.

TABLE 27

| Isolate Latin Name | ID Number | SEQ ID NO for 16 S rRNA Sequence | Table* |
|---|---|---|---|
| *Odoribacter splanchnicus* | PI00000072 | 2 | 2, 3, 4, 6 |
| *Subdoligranulum variabile* | IS00007359 OR IS00007357 | 22 OR 23 | 2, 4 |
| *Eubacterium rectale* | IS00006864 | 8 | 2, 4 |
| *Alistipes finegoldii* | PI00000340 | 15 | 4 |
| *Faecalibacterium prausnitzii* | PI00000329 OR IS00006632 | PI00000329: 1 OR IS00006632: 7 | 2, 3, 4 |
| *Bacteroides cellulosilyticus* | PI00000316 | 14 | 4 |
| *Clostridium aldenense* | PI00000097 | 10 | 3, 6 |
| *Anaerostipes hadrus* | PI00000094 | 3 | 2, 3, 4 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relative to a patient with UC.
Table 6: Bacterial isolates that secrete a ligand for an AhR of a host cell.

TABLE 28

| Isolate Latin Name | ID Number | SEQ ID NO for 16 S rRNA Sequence | Table* |
|---|---|---|---|
| *Odoribacter splanchnicus* | PI00000072 | 2 | 2, 3, 4, 6 |
| *Eubacterium rectale* | IS00006864 | 8 | 2, 4 |
| *Bacteroides cellulosilyticus* | PI00000316 | 14 | 4 |

TABLE 28-continued

| Isolate Latin Name | ID Number | SEQ ID NO for 16 S rRNA Sequence | Table* |
|---|---|---|---|
| Bacteroides stercoris | PI00000146 | 13 | 3, 6 |
| Faecalibacterium prausnitzii | PI00000329 OR IS00006632 | PI00000329: 1 OR IS00006632: 7 | 2, 3, 4 |
| Alisapes shahii | PI00000395 | 18 | 3, 4 |
| Anaerosapes hadrus | PI00000094 | 3 | 2, 3, 4 |
| Roseburia faecis | PI00000404 | 19 | 2 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relative to a patient with UC.
Table 6: Bacterial isolates that secrete a ligand for an AhR of a host cell.

TABLE 29

| Isolate Latin Name | ID Number | SEQ ID NO for 16 S rRNA Sequence | Table* |
|---|---|---|---|
| Odoribacter splanchnicus | PI00000072 | 2 | 2, 3, 4, 6 |
| Eubacterium rectale | IS00006864 | 8 | 2, 4 |
| Bacteroides cellulosilyticus | PI00000316 | 14 | 4 |
| Bacteroides stercoris | PI00000146 | 13 | 3, 6 |
| Faecalibacterium prausnitzii | PI00000329 OR IS00006632 | PI00000329: 1 OR IS00006632: 7 | 2, 3, 4 |
| Alistipes shahii | PI00000395 | 18 | 3, 4 |
| Blautia obeum | PI00000053 | 9 | 4 |
| Roseburia faecis | PI00000404 | 19 | 2 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relative to a patient with UC.
Table 6: Bacterial isolates that secrete a ligand for an AhR of a host cell.

TABLE 30

| Isolate Latin Name | ID Number | SEQ ID NO for 16 S rRNA Sequence | Table* |
|---|---|---|---|
| Odoribacter splanchnicus | PI00000072 | 2 | 2, 3, 4, 6 |
| Eubacterium rectale | IS00006864 | 8 | 2, 4 |
| Bacteroides cellulosilyticus | PI00000316 | 14 | 4 |
| Bacteroides stercoris | PI00000146 | 13 | 3, 6 |
| Roseburia faecis | PI00000404 | 19 | 2 |
| Alistipes shahii | PI00000395 | 18 | 3, 4 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relative to a patient with UC.
Table 6: Bacterial isolates that secrete a ligand for an AhR of a host cell.

TABLE 31

| Isolate Latin Name | ID Number | SEQ ID NO for 16 S rRNA Sequence | Table* |
|---|---|---|---|
| Odoribacter splanchnicus | P100000072 | 2 | 2, 3, 4, 6 |
| Eubacterium rectale | IS00006864 | 8 | 2, 4 |
| Faecalibacterium prausnitzii | PI00000329 OR IS00006632 | PI00000329: 1 OR IS00006632: 7 | 2, 3, 4 |

TABLE 31-continued

| Isolate Latin Name | ID Number | SEQ ID NO for 16 S rRNA Sequence | Table* |
|---|---|---|---|
| Bacteroides stercoris | PI00000146 | 13 | 3, 6 |
| Roseburia faecis | PI00000404 | 19 | 2 |
| Anaerostipes hadrus | PI00000094 | 3 | 2, 3, 4 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relative to a patient with UC.
Table 6: Bacterial isolates that secrete a ligand for an AhR of a host cell.

TABLE 32

| Isolate Latin Name | ID Number | SEQ ID NO for 16 S rRNA Sequence | Table* |
|---|---|---|---|
| Odoribacter splanchnicus | PI00000072 | 2 | 2, 3, 4, 6 |
| Bacteroides stercoris | PI00000146 | 13 | 3, 6 |
| Faecalibacterium prausnitzii | PI00000329 OR IS00006632 | PI00000329: 1 OR IS00006632: 7 | 2, 3, 4 |
| Alistipes shahii | PI00000395 | 18 | 3, 4 |
| Roseburia faecis | PI00000404 | 19 | 2 |
| Anaerostipes hadrus | PI00000094 | 3 | 2, 3, 4 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relative to a patient with UC.
Table 6: Bacterial isolates that secrete a ligand for an AhR of a host cell.

TABLE 33

| Isolate Latin Name | ID Number | SEQ ID NO for 16 S rRNA Sequence | Table* |
|---|---|---|---|
| Odoribacter splanchnicus | PI00000072 | 2 | 2, 3, 4, 6 |
| Eubacterium rectale | IS00006864 | 8 | 2, 4 |
| Bacteroides cellulosilyticus | PI00000316 | 14 | 4 |
| Bacteroides stercoris | PI00000146 | 13 | 3, 6 |
| Blautia obeum | PI00000053 | 9 | 4 |
| Alistipes shahii | PI00000395 | 18 | 3, 4 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relative to a patient with UC.
Table 6: Bacterial isolates that secrete a ligand for an AhR of a host cell.

TABLE 34

| Isolate Latin Name | ID Number | SEQ ID NO for 16S rRNA Sequence | Table* |
|---|---|---|---|
| Odoribacter splanchnicus | PI00000072 | 2 | 2, 3, 4, 6 |
| Eubacterium rectale | IS00006864 | 8 | 2, 4 |
| Bacteroides stercoris | PI00000146 | 13 | 3, 6 |

TABLE 34-continued

| Isolate Latin Name | ID Number | SEQ ID NO for 16S rRNA Sequence | Table* |
|---|---|---|---|
| Faecalibacterium prausnitzii | PI00000329 OR IS00006632 | PI00000329: 1 OR IS00006632: 7 | 2, 3, 4 |
| Blautia obeum | PI00000053 | 9 | 4 |
| Roseburia faecis | PI00000404 | 19 | 2 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relativeto a patient with UC.
Table 6: Bacterial isolates that secrete a ligand for an AhR of a host cell.

TABLE 35

| Isolate Latin Name | ID Number | SEQ ID NO for 16S rRNA Sequence | Table* |
|---|---|---|---|
| Odoribacter splanchnicus | PI00000072 | 2 | 2, 3, 4, 6 |
| Eubacterium rectale | IS00006864 | 8 | 2, 4 |
| Bacteroides stercoris | PI00000146 | 13 | 3, 6 |
| Faeca/ibacterium prausnitzii | PI00000329 OR IS00006632 | PI00000329: 1 OR IS00006632: 7 | 2, 3, 4 |
| Alistipes shahii | PI00000395 | 18 | 3, 4 |
| Roseburia faecis | PI00000404 | 19 | 2 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relativeto a patient with UC.
Table 6: Bacterial isolates that secrete a ligand for an AhR of a host cell.

Tables 36-43 illustrate different exemplary microbial cocktails containing bacterial isolates found in Tables 2-4 and/or 6, such that collectively the bacterial isolates in the microbial cocktail, once administered to a subject, can act to (i) increase a level of SCFAs in the gut of the subject; (ii) modulate release of a cytokine by a host cell of the subject; (iii) provide for bacterial isolates in the gut of the subject that correspond to bacterial strains more highly abundant in a healthy subject relative to a patient with UC; and/or (iv) release one or more hydrocarbons capable of binding to and activating an AhR receptor of a host cell of the subject. In each table, isolates are identified by Latin name, an Identification Number (ID number), the Sequence Identifier (SEQ ID NO) for its 16S rRNA sequence, and the above Table(s) (i.e., Table 2, 3, 4 and/or 6) in which the isolate appears.

In certain embodiments, a composition comprises a microbial cocktail comprising each of the bacterial isolates provided in one of Tables 36-43, or bacterial isolates having 16S rRNA sequences at least 95% identical to the 16S rRNA sequence of each of the bacterial isolates provided in one of Tables 36-43. In embodiments, the pharmaceutical composition comprises one or more, two or more, three or more, four or more, five or more, six or more, seven or more, eight or more, or nine of the bacterial isolates provided in one of Tables 36-41, or one or more, two or more, three or more, four or more, five or more, six or more, seven or more, eight or more, or nine bacterial isolates that each comprise a 16S rRNA sequence at least 95% identical to a 16S rRNA sequence of at least one of the bacterial isolates provided in one of Tables 36-41. In embodiments, the pharmaceutical composition comprises one or more, two or more, three or more, four or more, five or more, six or more, seven or more, eight or more, or nine or more, or ten of the bacterial isolates provided in one of Tables 41-42, or one or more, two or more, three or more, four or more, five or more, six or more, seven or more, eight or more, or nine or more, or ten bacterial isolates that each comprise a 16S rRNA sequence at least 95% identical to a 16S rRNA sequence of at least one of the bacterial isolates provided in one of Tables 41-42.

In certain embodiments, a composition comprises a microbial cocktail consisting essentially of each of the bacterial isolates provided in one of Tables 36-43, or bacterial isolates having 16S rRNA sequences at least 95% identical to the 16S rRNA sequence of each of the bacterial isolates provided in one of Tables 36-43. In certain embodiments, a composition comprises a microbial cocktail consisting of each of the bacterial isolates provided in one of Tables 36-43, or bacterial isolates having 16S rRNA sequences at least 95% identical to the 16S rRNA sequence of each of the bacterial isolates provided in one of Tables 36-43.

TABLE 36

| Isolate Latin Name | ID Number | SEQ ID NO for 16S rRNA Sequence | Table* |
|---|---|---|---|
| Odoribacter splanchnicus | PI00000072 | 2 | 2, 3, 4, 6 |
| Subdoligranulum variabile | IS00007359 OR IS00007357 | 22 OR 23 | 2, 4 |
| Eubacterium rectale | IS00006864 | 8 | 2, 4 |
| Alistiapes finegoldii | PI00000340 | 15 | 4 |
| Faecalibacterium prausnitzii | PI00000329 OR IS00006632 | PI00000329: 1 OR IS00006632: 7 | 2, 3, 4 |
| Bacteroides cellulosilyticus | PI00000316 | 14 | 4 |
| Clostridium aldenense | PI00000097 | 10 | 3, 6 |
| Akkermansia muciniphila | IS00007180 | 20 | 4 |
| Anaerostipes hadrus | PI00000094 | 3 | 2, 3, 4 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relativeto a patient with UC.
Table 6: Bacterial isolates that secrete a ligand for an AhR of a host cell.

TABLE 37

| Isolate Latin Name | ID Number | SEQ ID NO for 16S rRNA Sequence | Table* |
|---|---|---|---|
| Odoribacter splanchnicus | PI00000072 | 2 | 2, 3, 4, 6 |
| Subdoligranulum variabile | IS00007359 OR IS00007357 | 22 OR 23 | 2, 4 |
| Eubacterium rectale | IS00006864 | 8 | 2, 4 |
| Alistipes finegoldii | PI00000340 | 15 | 4 |
| Faecalibacterium prausnitzii | PI00000329 OR IS00006632 | PI00000329: 1 OR IS00006632: 7 | 2, 3, 4 |
| Bacteroides cellulosilyticus | PI00000316 | 14 | 4 |
| Clostridium aldenense | PI00000097 | 10 | 3, 6 |
| Akkermansia muciniphila | IS00007180 | 20 | 4 |
| Alistipes shahii | PI00000395 | 18 | 3, 4 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relativeto a patient with UC.
Table 6: Bacterial isolates that secrete a ligand for an AhR of a host cell.

TABLE 38

| Isolate Latin Name | ID Number | SEQ ID NO for 16S rRNA Sequence | Table* |
|---|---|---|---|
| Bacteroides cellulosilyticus | PI00000316 | 14 | 4 |
| Odoribacter splanchnicus | PI00000072 | 2 | 2, 3, 4, 6 |
| Faecalibacterium prausnitzii | IS00006632 | 7 | 2, 3, 4 |
| Faecalibacterium prausnitzii | PI00000329 | 1 | 2, 3, 4 |
| Akkermansia muciniphila | IS00007180 | 20 | 4 |
| Bacteroides stercoris | PI00000146 | 13 | 6 |
| Alistipes shahii | PI00000395 | 18 | 3, 4 |
| Eubacterium rectale | IS00006864 | 8 | 2, 4 |
| Roseburia faecis | PI00000404 | 19 | 2 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relativeto a patient with UC.
Table 6: Bacterial isolates that secrete a ligand for an AhR of a host cell.

TABLE 39

| Isolate Latin Name | ID Number | SEQ ID NO for 16S rRNA Sequence | Table* |
|---|---|---|---|
| Bacteroides cellulosilyticus | PI00000316 | 14 | 4 |
| Odoribacter splanchnicus | PI00000072 | 2 | 2, 3, 4, 6 |
| Faecalibacterium prausnitzii | IS00006632 | 7 | 2, 3, 4 |
| Faecalibacterium prausnitzii | PI00000329 | 1 | 2, 3, 4 |
| Akkermansia muciniphila | IS00007180 | 20 | 4 |
| Clostridium aldenense | PI00000097 | 10 | 3, 6 |
| Alistipes shahii | PI00000395 | 18 | 3, 4 |
| Eubacterium rectale | IS00006864 | 8 | 2, 4 |
| Roseburia faecis | PI00000404 | 19 | 2 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relativeto a patient with UC.
Table 6: Bacterial isolates that secrete a ligand for an AhR of a host cell.

TABLE 40

| Isolate Latin Name | ID Number | SEQ ID NO for 16S rRNA Sequence | Table* |
|---|---|---|---|
| Bacteroides cellulosilyticus | PI00000316 | 14 | 4 |
| Odoribacter splanchnicus | PI00000072 | 2 | 2, 3, 4, 6 |
| Faecalibacterium prausnitzii | IS00006632 | 7 | 2, 3, 4 |
| Faecalibacterium prausnitzii | PI00000329 | 1 | 2, 3, 4 |
| Bacteroides uniformis | PI00000137 | 11 | 3, 4, 6 |
| Bacteroides stercoris | PI00000146 | 13 | 6 |
| Alistipes shahii | PI00000395 | 18 | 3, 4 |
| Eubacterium rectale | IS00006864 | 8 | 2, 4 |
| Roseburia faecis | PI00000404 | 19 | 2 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relativeto a patient with UC.
Table 6: Bacterial isolates that secrete a ligand for an AhR of a host cell.

TABLE 41

| Isolate Latin Name | ID Number | SEQ ID NO for 16S rRNA Sequence | Table* |
|---|---|---|---|
| Bacteroides cellulosilyticus | PI00000316 | 14 | 4 |
| Odoribacter splanchnicus | PI00000072 | 2 | 2, 3, 4, 6 |
| Faecalibacterium prausnitzii | IS00006632 | 7 | 2, 3, 4 |
| Faecalibacterium prausnitzii | PI00000329 | 1 | 2, 3, 4 |
| Akkermansia muciniphila | IS00007180 | 20 | 4 |
| Bacteroides stercoris | PI00000146 | 13 | 6 |
| Alistipes shahii | PI00000395 | 18 | 3, 4 |
| Eubacterium rectale | IS00006864 | 8 | 2, 4 |
| Subdoligranulum variabile | IS00007359 | 22 | 2, 4 |

TABLE 42

| Isolate Latin Name | ID Number | SEQ ID NO for 16S rRNA Sequence | Table* |
|---|---|---|---|
| Bacteroides cellulosilyticus | PI00000316 | 14 | 4 |
| Odoribacter splanchnicus | PI00000072 | 2 | 2, 3, 4, 6 |
| Faecalibacterium prausnitzii | IS00006632 | 7 | 2, 3, 4 |
| Faecalibacterium prausnitzii | PI00000329 | 1 | 2, 3, 4 |
| Akkermansia muciniphila | IS00007180 | 20 | 4 |
| Bacteroides stercoris | PI00000146 | 13 | 6 |
| Alistipes shahii | PI00000395 | 18 | 3, 4 |
| Eubacterium rectale | IS00006864 | 8 | 2, 4 |
| Roseburia faecis | PI00000404 | 19 | 2 |
| Subdoligranulum variabile | IS00007359 | 22 | 2, 4 |

TABLE 43

| Isolate Latin Name | ID Number | SEQ ID NO for 16S rRNA Sequence | Table* |
|---|---|---|---|
| Bacteroides cellulosilyticus | PI00000316 | 14 | 4 |
| Odoribacter splanchnicus | PI00000072 | 2 | 2, 3, 4, 6 |
| Faecalibacterium prausnitzii | IS00006632 | 7 | 2, 3, 4 |
| Faecalibacterium prausnitzii | PI00000329 | 1 | 2, 3, 4 |
| Akkermansia muciniphila | IS00007180 | 20 | 4 |
| Bacteroides stercoris | PI00000146 | 13 | 6 |
| Alistipes shahii | PI00000395 | 18 | 3, 4 |
| Eubacterium rectale | IS00006864 | 8 | 2, 4 |
| Roseburia faecis | PI00000404 | 19 | 2 |
| Bacteroides uniformis | PI00000137 | 11 | 3, 4, 6 |

In embodiments, a pharmaceutical composition described herein can comprise a bacterial mixture comprising multiple bacterial isolates that together provide for redundancy of one or more advantageous phenotypes in the bacterial mixture, which may include for example the ability to induce a particular mechanism or pathway in the intestine of the subject when the composition is administered to the subject. Such redundancy can increase the likelihood that a subject administered the composition will benefit from a particular advantageous trait or phenotype in common between the "redundant" isolates of bacteria (e.g. a propensity to increase a level of an SCFA in the gut of the subject). Without intending to be bound by theory, a reason for this is potential variation across subjects in the likelihood of a particular bacterial isolate to engraft in the intestine of each subject, which is typically necessary for the bacterial isolate to exert its beneficial effects. By formulating a composition comprising genetically distinct isolates that each exhibit the same phenotype of interest (e.g. the production of one or more SCFAs above a threshold level), the composition may exhibit enhanced efficacy across individuals (i.e., compared to a formulation without built-in redundancy), since the likelihood of at least one of the multiple redundant bacterial isolates engrafting is increased compared to the likelihood of engraftment of a single bacterial isolate without a redundant counterpart.

In an aspect, redundancy can be incorporated into the composition by including in the bacterial mixture multiple bacterial isolates that each possess at least one of the following phenotypes: (i) each of the multiple bacterial isolates produces a level of one or more SCFAs above a threshold level (e.g., by incorporating into the bacterial mixture or administering to the subject multiple bacterial isolates selected from Table 2); (ii) each of the multiple bacterial isolates induces release of a cytokine by a host cell of the subject (e.g., by incorporating into the bacterial mixture or administering to the subject multiple bacterial isolates selected from Table 3); (iii) each of the multiple bacterial isolates corresponds to a bacterial strain that is more highly abundant in a healthy subject relative to a patient with UC (e.g., by incorporating into the bacterial mixture or administering to the subject multiple bacterial isolates selected from Table 4); and/or (iv) each of the multiple bacterial isolates releases one or more aryl hydrocarbons capable of binding to and activating an AhR receptor of a host cell of the subject (e.g., by incorporating into the bacterial mixture or administering to the subject multiple bacterial isolates selected from Table 6).

In an aspect, a bacterial mixture comprising multiple bacterial isolates that provide for redundancy of phenotypes is shown in Table 38, which contains at least five bacterial isolates that produce significant levels of an SCFA (here butyrate; see Example 2) (i.e., *Odoribacter splanchnicus*, *Eubacterium rectale*, *Roseburia faecis*, and two isolates of *Faecalibacterium prausnitzii*), at least four bacterial isolates that induce release of pro-inflammatory cytokines by human cells (here PBMCs; see Example 3) (i.e., *Odoribacter sphlanchnicus*, *Alistipes shahii*, and two isolates of *Faecalibacterium prausnitzii*), at least two bacterial isolates that release aryl hydrocarbons capable of binding to and activating an AhR receptor of a host cell of the subject (see Example 5) (i.e., *Odoribacter sphlanchnicus* and *Bacteroides stercoris*), and at least seven bacterial isolates that correspond to bacterial strains more highly abundant in a healthy subject relative to a patient with UC (see Example 4) (i.e., *Bacteroides cellulosilyticus*, *Odoribacter splanchnicus*, *Akkermansia muciniphila*, *Alistipes shahii*, *Eubacterium rectale* and two isolates of *Faecalibacterium prausnitzii*).

In embodiments, a pharmaceutical composition can comprise multiple distinct bacterial isolates that are each a member of a particular genus, or multiple bacterial isolates that are each a member of a particular species. This can be advantageous, for example, by providing redundancy where multiple bacterial isolates of the same genus or species are capable of optimally inducing or influencing a particular mechanism of interest (e.g. by producing SCFA, inducing an anti-inflammatory profile, or producing aryl hydrocarbons). By including multiple taxonomically related bacterial isolates that each exhibit a similar optimal trait or phenotype (e.g. ability to produce high levels of an SCFA) in the same pharmaceutical composition, redundancy is built into the composition such that there is a higher likelihood that a subject administered the composition will benefit from the trait or phenotype. A reason for this is potential variation across subjects in the ability of a particular bacterial isolate to engraft in the intestines of the subjects, which is typically necessary for the bacterial isolate to exert its beneficial effects. For example, a pharmaceutical composition can comprise multiple (e.g. two, three, four, five, or more than five) bacterial isolates that are each a member of the genus *Faecalibacterium*, or multiple (e.g. two, three, four, five, or more than five) bacterial isolates that are each a member of the species *Faecalibacterium prausnitzii* (see e.g. Table 17b or Table 38). In another example, a pharmaceutical composition can comprise multiple (e.g. two, three, four, five, or more than five) bacterial isolates that are each a member of the genus *Bacteroides*, e.g. *B. cellulosilyticus* and *B. stercoris* (see e.g. Tables 26, 28 and 38).

In embodiments, a pharmaceutical composition can comprise only one bacterial isolate that is a member of a particular genus, or only one bacterial isolate that is a member of a particular species. This can be advantageous, for example, to minimize the total number of bacterial isolates in a pharmaceutical composition (e.g. to reduce costs and resources related to growing and formulating each bacterial isolate), while maintaining a diversity of taxa represented by the bacterial isolates, which can correspond to induction of multiple treatment-related mechanisms (e.g. SCFA production, anti-inflammatory cytokine induction, AhR activation) in a subject administered the composition. For example, a pharmaceutical composition can comprise only one bacterial isolate that is a member of the genus *Bacteroides*. In an embodiment, the single bacterial isolate from the genus *Bacteroides* is *B. cellulosilyticus* (see e.g. Tables 17a and 17b). In another example, a pharmaceutical composition can comprise only one bacterial isolate that is a member of the genus *Eubacterium*, or only one bacterial isolate that is a member of the species *Eubacterium rectale* (see e.g. Tables 17a and 17b and 38). In another example, a pharmaceutical composition can comprise only one bacterial isolate that is a member of the genus *Roseburia*, or only one bacterial isolate that is a member of *Roseburia faecis* (see e.g. Tables 17a and 17b and 38). In another example, a pharmaceutical composition can comprise only one bacterial isolate that is a member of the genus *Coprococcus*, or only one bacterial isolate that is a member of the species *Coprococcus comes*.

In another example, a pharmaceutical composition can comprise only one bacterial isolate that is a member of the genus *Alistipes*. In certain embodiments, a pharmaceutical composition comprises a bacterial isolate comprising *Alistipes shahii*, but does not comprise *Alistipes finegoldii* or *Alistipes putredinis* (see e.g. Tables 17a and 17b and 38). The inclusion of *A. shahii* over *A. finegoldii* and *A. putredinis* is consistent with the Examples below, which show that *A. shahii* has a lower cross sectional combined p-value than *A. finegoldii* and *A. putredinis* for (i) enrichment in healthy subjects over patients diagnosed with UC; and/or (ii) association/correlation with clinical remission or response of UC symptoms in UC patients following FMT treatment. In other embodiments, a pharmaceutical composition comprises a bacterial isolate comprising *Alistipes finegoldii*, but does not comprise *Alistipes shahii* or *Alistipes putredinis* (see e.g. Table 17). In certain embodiments, a pharmaceutical composition comprises a bacterial isolate comprising *Alistipes Alistipes putredinis*, but does not comprise *Alistipes shahii* or *Alistipes finegoldii*.

In embodiments, a pharmaceutical composition can exclude or omit a bacterial genus, species or strain that may not be beneficial, or may be detrimental, for treating a condition related to a gut dysbiosis (e.g., IBD including ulcerative colitis). For example, a pharmaceutical composition can exclude or omit a strain or bacterial isolate from the genus *Escherichia* (e.g., *Escherichia coli*). The below Examples show that *E. coli* produces little or no butyrate and is characterized by a cytokine profile that is pro-inflammatory (i.e. low ratios of IL-10/IL-12 and/or IL-10/TNF-alpha).

In other examples, a pharmaceutical composition can omit or exclude one or more of the following bacterial taxa: a member of the genus *Adlercreutzia, Adlercreutzia equolifaciens*, a member of the genus *Akkermansia, Akkermansia muciniphila*, a member of the genus *Alistipes, Alistipes finegoldii, Alistipes putredinis, Alistipes shahii*, a member of the genus *Bacteroides, Bacteroides capillosus, Bacteroides cellulosilyticus, Bacteroides eggerthii, Bacteroides ovatus, Bacteroides thetaiotaomicron, Bacteroides uniformis*, a member of the genus *Bacillus, Bacillus circulans, Bacillus simplex*, a member of the genus *Bifidobacterium, Bifidobacterium longum*, a member of the genus *Blautia, Blautia hydrogenotrophica*, a member of the genus *Brevibacillus, Brevibacillus parabrevis*, a member of the genus *Catabacter, Catabacter hongkongensis*, a member of the genus *Catenibacterium, Catenibacterium mitsuokai*, a member of the genus *Clostridium, Clostridium coccoides, Clostridium aldenense, Clostridium asparagiforme, Clostridium celerecrescens, Clostridium hathewayi, Clostridium hylemonae, Clostridium inocuum, Clostridium lavalense, Clostridium leptum, Clostridium scindens, Clostridium staminisolvens, Clostridium sulfatireducens, Clostridium symbiosum, Clostridium thermocellum*, a member of the genus *Collinsella, Collinsella aerofaciens*, a member of the genus *Coprococcus, Coprococcus catus, Coprococcus comes, Coprococcus eutactus*, a member of the genus *Dorea, Dorea formicigenerans, Dorea longicatena*, a member of the genus *Eubacterium, Eubacterium biforme, Eubacterium callanderi, Eubacterium dolichum, Eubacterium eligens, Eubacterium fissicatena, Eubacterium rectale, Eubacterium siraeum, Eubacterium ventriosum, Eubacterium xylanophilum*, a member of the genus *Faecalibacterium, Faecalibacterium prausnitzii*, a member of the genus *Holdemania, Holdemania filimormis*, a member of the genus *Subdoligranulum, Subdoligranulum variabile*, a member of the genus *Microbacterium, Microbacterium schleiferi, Micrococcus luteus*, a member of the genus *Odoribacter, Odoribacter splanchnicus*, a member of the genus *Oscillibacter, Oscillibacter valericigenes*, a member of the genus *Parabacteroides, Parabacteroides merdae, Parabacteroides gordonii*, a member of the genus *Parasutterella, Parasutterella excrementihominis*, a member of the genus *Phascolarctobacterium, Phascolarctobacterium faecium*, a member of the genus *Roseburia, Roseburia faecalis, Roseburia faecis, Roseburia hominis, Roseburia intestinalis*, a member of the genus *Ruminococcus, Ruminococcus albus, Ruminococcus bromii, Ruminococcus lactaris, Ruminococcus luti, Ruminococcus obeum, Ruminococcus torques*, a member of the genus *Staphylococcus, Staphylococcus epidermidis*, a member of the genus *Streptococcus, Streptococcus mitis, Streptococcus thermophilus*, a member of the genus *Synergistes*, a member of the genus *Turicibacter*, and *Turicibacter sanguinis*.

In embodiments, a bacterial isolate incorporated into a pharmaceutical composition can act through multiple mechanisms to advantageously impact the health of a subject. Such a bacterial isolate can therefore advantageously influence the health of a subject administered the cocktail (e.g., in the form of a pharmaceutical composition) via multiple mechanisms. For example, a pharmaceutical composition can comprise a bacterial isolate that when administered to a subject can produce one or more SCFAs to increase a level of SCFAs (e.g., butyrate) in the gut of the subject ('Table 2 bacterial isolate'), and can also modulate production and/or release of a cytokine by a host cell of the subject ('Table 3 bacterial isolate'). In another example, a pharmaceutical composition can comprise a bacterial isolate that when administered to a subject can produce one or more SCFAs to increase a level of SCFAs (e.g., butyrate) in the gut of the subject ('Table 2 bacterial isolate'), and also corresponds to a bacterial strain more highly abundant in a healthy subject relative to a patient with UC ('Table 4 bacterial isolate'). In another example, a pharmaceutical composition can comprise a bacterial isolate that when administered to a subject can modulate production and/or release of a cytokine by a host cell of the subject ('Table 3 bacterial isolate'), and also correspond to a bacterial strain more highly abundant in a healthy subject relative to a patient with UC ('Table 4 bacterial isolate'). In another example, a pharmaceutical composition can comprise a bacterial isolate that when administered to a subject can produce one or more SCFAs to increase a level of SCFAs (e.g., butyrate) in the gut of the subject ('Table 2 bacterial isolate'), can also modulate production and/or release of a cytokine by a host cell of the subject ('Table 3 bacterial isolate'), and also corresponds to a bacterial strain more highly abundant in a healthy subject relative to a patient with UC ('Table 4 bacterial isolate').

Table 44 illustrates exemplary bacterial isolates capable of positively affecting the health of a subject via multiple mechanisms (e.g., production of SCFAs, induction of cytokine release by host cells, or providing bacteria in the gut that correspond to bacterial strains more highly abundant in a healthy subject relative to a patient with UC). In Table 44, isolates are identified by Latin name, an Identification Number (ID number), the Sequence Identifier (SEQ ID NO) for its 16S rRNA sequence, and the above Tables 2-4 in which the bacterial isolate appears (with Table 2 representing bacterial isolates that secrete SCFAs in the gut of a subject, Table 3 representing bacterial isolates capable of modulating cytokine production by a host cell, Table 4 representing bacterial isolates corresponding to bacterial strains more highly abundant in a healthy subject than a patient with UC), and Table 6 representing bacterial isolates that secrete an aryl hydrocarbon for binding to an AhR of a cell of the subject). In certain embodiments, a pharmaceutical composition (e.g., a microbial cocktail) comprises one or more bacterial isolates provided in Table 44, and/or one or more bacterial isolates having a 16S rRNA sequence that is at least 95% identical to the 16S rRNA sequence of one or more of the bacterial isolates provided in Table 44.

TABLE 44

| Isolate Latin Name | ID Number | SEQ ID NO for 16S rRNA Sequence | Table* |
|---|---|---|---|
| *Faecalibacterium prausnitzii* | PI00000329 | 1 | 2, 3, 4 |
| *Odoribacter splanchnicus* | PI00000072 | 2 | 2, 3, 4, 6 |
| *Anaerostipes hadrus* | PI00000094 | 3 | 2, 3, 4 |
| *Parabacteroides merdae* | IS00006167 | 5 | 4, 6 |
| *Dorea longicatena* | IS00006618 | 6 | 4, 6 |
| *Faecalibacterium prausnitzii* | IS00006632 | 7 | 2, 3, 4 |
| *Eubacterium rectale* | IS00006864 | 8 | 2, 4 |
| *Bacteroides uniformis* | PI00000137 | 11 | 3, 4, 6 |
| *Bacteroides vulgatus* | PI00000138 | 12 | 3, 4 |
| *Bacteroides uniformis* | PI00000352 | 16 | 3, 4, 6 |
| *Coprococcus comes* | PI00000370 | 17 | 2, 3 |
| *Alistipes shahii* | PI00000395 | 18 | 3, 4 |

TABLE 44-continued

| Isolate Latin Name | ID Number | SEQ ID NO for 16S rRNA Sequence | Table* |
|---|---|---|---|
| Bacteroides stercoris | PI00000146 | 13 | 3, 6 |
| Clostridium aldenense | PI00000097 | 10 | 3, 6 |
| Subdoligranulum variabile | IS00007359 | 22 | 2, 4 |
| Subdoligranulum variabile | IS00007357 | 23 | 2, 4 |

*Table 2: Bacterial isolates that secrete SCFAs in the gut of a subject.
Table 3: Bacterial isolates capable of modulating cytokine production by a host cell of a subject.
Table 4: Bacterial isolates that correspond to a bacterial strain more highly abundant in a healthy subject relativeto a patient with UC.
Table 6: Bacterial isolates that secrete a ligand for an AhR of a host cell.

In embodiments, a bacterial isolate can comprise a 16S rRNA sequence that is at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the 16S rRNA sequence of at least one of the bacterial isolates provided in Table 1 to Table 44. In embodiments, a bacterial isolate comprises a 16S rRNA sequence that is at least 97% identical to the 16S rRNA sequence of at least one of the bacterial isolates provided in Table 1 to Table 44.

In embodiments, a pharmaceutical composition (e.g., comprising a microbial cocktail) described herein can comprise at least one bacterial isolate that has been previously identified. For example, in certain embodiments a known type strain (e.g., from the ATCC or DSM archived collections) can comprise a 16S rRNA sequence that is at least 95% identical (e.g., at least 97% identical) to a 16S rRNA sequence of a bacterial isolate provided in Table 1 to Table 44. Exemplary publicly available strains that can be included in a microbial cocktail described herein are provided in Table 45. In an embodiment, for a particular pharmaceutical composition, one or more bacterial isolates provided in Table 1 to Table 44 can be substituted with the corresponding representative strain (i.e., having the same taxonomic designation) from Table 45.

TABLE 45

| Isolate Latin Name | Representative Strain* |
|---|---|
| Faecalibacterium prausnitzii | ATCC 27768 |
| Odoribacter splanchnicus | ATCC 29572 |
| Odoribacter laneus | DSM 22474 |
| Anaerostipes hadrus | DSM 3319 |
| Alistipes onderdonkii | ATCC BAA-1178 |
| Parabacteroides merdae | ATCC 43184 |
| Dorea longicatena | DSM 13814 |
| Eubacterium rectale | ATCC 33656 |
| Blautia obeum | DSM 25238 |
| Clostridium aldenense | DSM 19262 |
| Bacteroides uniformis | ATCC 8492 |
| Bacteroides vulgatus | DSM 1447 |
| Bacteroides stercoris | ATCC 43183 |
| Bacteroides cellulosilyticus | DSM 14838 |
| Alistipes finegoldii | DSM 17242 |
| Coprococcus comes | ATCC 27758 |
| Alistipes shahii | ATCC BAA-1179 |

TABLE 45-continued

| Isolate Latin Name | Representative Strain* |
|---|---|
| Roseburia faecis | DSM 16840 |
| Akkermansia muciniphila | DSM 22959 |
| Phascolarctobacterium faecium | DSM 14760 |
| Subdoligranulum variabile | DSM 15176 |
| Alistipes putredinis | ATCC 29800 |

*DSM: Leibniz Institute DSMZ-German Collection of Microorganisms and Cell Cultures
ATCC: American Type Culture Collection In embodiments, a pharmaceutical composition or microbial cocktail comprises a plurality of bacterial isolates isolated or purified from stool samples of multiple different human donors. An advantage of sourcing bacterial isolates from stool samples of multiple human donors, rather than a single donor, is that stool samples of multiple donors offer a larger pool of bacterial strains that can be subjected to functional screens to identify bacterial isolates that optimally induce a particular mechanism of interest. For example, while the stool of one donor may carry one or more bacterial strains that produce a high (optimal) level of an SCFA (e.g., butyrate), the same donor's stool may carry bacterial isolates that only moderately induce an anti-inflammatory profile (e.g. moderate IL-10:IL-12 ratio) when subjected to a functional screen. Alternatively, a different donor's stool may carry one or more bacterial strains that induce an optimal anti-inflammatory profile (e.g. high IL-10: IL-12 ratio), but not carry bacterial strains that produce high levels of an SCFA.

Another advantage of using stool from multiple different donors as a basis of selection when identifying bacterial isolates to include within a pharmaceutical composition described herein is that microbiota from multiple donors yields a larger pool of bacterial strains within which to identify a bacterial isolate corresponding to a bacterial strain having (i) a greater relative abundance in a healthy human subject relative to a patient with an intestinal dysbiosis, or (ii) a greater relative abundance in a human subject in remission from an intestinal dysbiosis relative to a patient having the intestinal dysbiosis (i.e., bacterial isolates provided in Table 4).

In general, the match between a 16S rRNA sequence of a bacterial strain having (i) or (ii) above and the 16S rRNA sequence of a selected bacterial isolate should be as close as possible (e.g., at least 97%, at least 97.5%, at least 98%, at least 98.5%, at least 99%, at least 99.5%, or at least 100%). The likelihood of identifying the desired match increases with a greater pool of bacterial strains to select from, which is provided by sourcing stool from multiple donors.

Therefore, in general, the rational mechanism-based selection scheme set out herein to construct a microbial therapeutic favors increasing the pool of bacterial strains beyond those of a single donor to enable selection of optimal bacterial isolates for induction of each mechanism of interest in a subject administered the therapeutic. This multi-donor selection process is therefore advantageous over known approaches which attempt to recreate a synthetic version of a single donor's stool.

In other embodiments, a pharmaceutical composition or microbial cocktail comprises a plurality of bacterial isolates isolated or purified from a stool sample or stool samples of only a single human donor.

In various embodiments, a pharmaceutical composition (e.g., comprising a microbial cocktail) comprises one or more bacterial isolates capable of engrafting in a subject's GI tract following administration of the composition to the subject. Herein "engrafting" or "engraftment" refers to the stable presence over time of cells of a bacterial strain or bacterial isolate in the intestinal tract of a subject (e.g., after introducing the bacterial strain or isolate into the subject's intestinal tract by administering a composition described herein, for example, orally or rectally). Typically, engraftment of a bacterial isolate introduced into the intestine of a patient (e.g. by oral and/or rectal administration) is measured longitudinally, or over time, by comparing the abundance of the bacterial isolate in fecal samples of the subject before and after administration of the bacterial isolate to the subject. In an embodiment, the bacterial isolate introduced into the intestine of the subject was absent prior to the administration. In another embodiment, the bacterial isolate introduced into the intestine of the subject was present in the intestine prior to the administration, but is increased abundance following the administration. In certain embodiments, engraftment is determined by identifying an increase in abundance of a bacterial strain administered to an intestine of the subject after at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14, days, at least 1 week, at least 2 weeks, at least 3 weeks, at least 4 weeks, at least 5 weeks, at least 6 weeks, at least 7 weeks, at least 8 weeks, at least 1 month, at least 2 months, at least 3 months, at least 4 months, at least 5 months, at least 6 months, or greater than 6 months following administration of the bacterial strain to the subject.

In embodiments, engraftment of a bacterial isolate in an intestine of a subject occurs when the bacterial isolate is administered to the subject at or above a threshold dose. In embodiments, engraftment of a bacterial isolate in an intestine of a subject does not occur, or occurs with relative inefficiency (e.g., across patients), when the bacterial isolate is administered to the subject below the threshold dose. For example, engraftment of a bacterial isolate into the intestine of a subject can occur when the bacterial isolate is administered to the subject (e.g., orally or rectally in a pharmaceutical composition described herein) at a dose of at least $10^6$ cells, at least $10^7$ cells, at least $10^8$ cells, at least $10^9$ cells, at least $10^{10}$ cells, at least $10^{11}$ cells, or at least $10^{12}$ cells.

In embodiments, engraftment of a bacterial isolate in an intestine of a subject occurs when the bacterial isolate is administered to the subject at or below a threshold dose. In embodiments, engraftment of a bacterial isolate in an intestine of a subject does not occur, or occurs with relative inefficiency (e.g., across patients), when the bacterial isolate is administered to the subject above the threshold dose. For example, engraftment of a bacterial isolate into the intestine of a subject can occur when the bacterial isolate is administered to the subject (e.g., orally or rectally in a pharmaceutical composition described herein) at a dose of not more than $10^8$ cells, not more than $10^9$ cells, not more than $10^{10}$ cells, not more than $10^{11}$ cells, or not more than $10^{12}$ cells.

In embodiments, a dose of one or more bacterial isolates to a patient in need thereof can depend on the engraftment threshold of the bacterial isolate.

In embodiments, a bacterial isolate in a pharmaceutical composition administered to a subject engrafts in the duodenum of the subject. In embodiments, a bacterial isolate in a pharmaceutical composition administered to a subject engrafts in the jejunum of the subject. In embodiments, a bacterial isolate in a pharmaceutical composition administered to a subject engrafts in the ileum of the subject. In embodiments, a bacterial isolate in a pharmaceutical composition administered to a subject engrafts in the colon of the subject.

In various embodiments, the present pharmaceutical compositions (e.g., microbial cocktails) includes one or more bacterial isolates that interact, including synergistically, to have an inhibitory effect on the growth and/or survival of a pathogenic bacterium present in a gut of a subject administered the composition. For example, one or more bacterial isolates can have a cytotoxic or cytostatic effect on the pathogenic bacterium. In various embodiments, one or more bacterial isolates exert an inhibitory effect on a pathogenic bacterium present in or entering into the GI tract of a patient. In various embodiments, the one or more bacterial isolates augment growth of at least one type of bacteria not detectably present in a patient's GI tract prior to administration.

In various embodiments, a pharmaceutical composition (e.g., comprising a microbial cocktail) includes one or more isolated or purified bacterial strains that interact synergistically to have an inhibitory effect on the growth or survival of a pathogenic bacterium (e.g., via cytotoxic and/or cytostatic effects). Illustrative pathogenic bacteria that can be affected by administration of one or more bacterial isolates described herein include *C. difficile, Salmonella* sp., enteropathogenic *E. coli*, multi-drug resistant bacteria such as *Klebsiella*, and *E. coli*, Carbapenem-resistant Enterobacteriaceae (CRE), extended spectrum beta-lactam resistant Enterococci (ESBL), and vancomycin-resistant Enterococci (VRE). Further illustrative bacteria include *Yersinia, Vibrio, Treponema, Streptococcus, Staphylococcus, Shigella, Salmonella, Rickettsia, Orientia, Pseudomonas, Neisseria, Mycoplasma, Mycobacterium, Listeria, Leptospira, Legionella, Klebsiella, Helicobacter, Haemophilus, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus*, multi-drug resistant bacteria, extended spectrum beta-lactam resistant Enterococci (ESBL), Carbapenem-resistant Enterobacteriaceae (CRE), and vancomycin-resistant Enterococci (VRE). Illustrative pathogenic bacteria include *Aeromonas hydrophila, Campylobacter fetus, Plesiomonas shigelloides, Bacillus cereus, Campylobacter jejuni, Clostridium botulinum, Clostridium difficile, Clostridium perfringens*, enteroaggregative *Escherichia coli*, enterohemorrhagic *Escherichia coli*, enteroinvasive *Escherichia coli*, enterotoxigenic *Escherichia coli* (such as, but not limited to, LT and/or ST), *Escherichia coli* 0157:H7, *Helicobacter pylori, Klebsiellia pneumonia, Lysteria monocytogenes, Plesiomonas shigelloides, Salmonella* sp., *Salmonella typhi, Salmonella paratyphi, Shigella* sp., *Staphylococcus* sp., *Staphylococcus aureus*, vancomycin-resistant *enterococcus* sp., *Vibrio* sp., *Vibrio cholerae, Vibrio parahaemolyticus, Vibrio vulnficus*, and *Yersinia enterocolitica*.

In some embodiments, a bacterial isolate is a non-pathogenic bacterial strain. In embodiments, a non-pathogenic bacterial strain comprises a genome that lacks genes, or expression thereof, which cause virulence and/or toxicity. For instance, in some embodiments, a microbial cocktail comprising two or more bacterial isolates is substantially free of organisms or entities (e.g., substantially free of pathogenic bacteria) which are capable of causing a disease or disorder in a subject administered the microbial cocktail.

In embodiments, the microbial cocktail does not include bacterial cells other than the one or more bacterial isolates incorporated into the microbial cocktail during the manufacturing process. For example, the microbial cocktail can be free of particular species of bacteria, whether cultured or uncultured, including *Bacteroides, Bifidobacterium, Desulfomonas, Clostridium, Escherichia coli, Eubacterium, Fusobacterium, Lactobacillus, Monilia, Peptostreptococcus, Propionibacterium*, or *Ruminococcus*.

In embodiments, a bacterial isolate can be obtained from a laboratory stock or a bacterial cell bank of a bacterial strain originally obtained from a stool sample of a healthy human donor. For example, a fecal microbiota (e.g., purified from a stool sample using methods described herein) can be used as the source of a bacterial isolate incorporated into a pharmaceutical composition described herein. In certain embodiments, all or a portion of a fecal microbiota of a stool sample is cultured on a solid media substrate and one or more bacterial isolates are identified as single colonies. In other embodiments, all or a portion of a fecal microbiota can be inoculated into liquid culture to produce a mixed bacterial culture that is then serially diluted to produce a culture containing a single cell of a bacterial isolate. In embodiments, an identified bacterial isolate can then be cultured (e.g., in solid or liquid media) using known techniques and expanded. Methods for isolating, purifying, and/or culturing bacterial strains are described in Sadowsky et al., WO 2012/122478 and described in Borody et al., WO 2012/016287, each of which is incorporated herein by reference.

Uncultured Fecal Microbiota or Preparations of Uncultured Fecal Bacteria

In one aspect, a pharmaceutical composition administered herein comprises an uncultured fecal microbiota or a preparation of uncultured fecal bacteria. For example, an uncultured fecal microbiota can comprise a substantially complete fecal microbiota (e.g., purified from a healthy human donor).

In embodiments, the preparation of a fecal microbiota used herein, or the manufacture of a preparation of uncultured fecal bacteria, involves a treatment selected from the group consisting of ethanol treatment, detergent treatment, heat treatment, irradiation, and sonication. In another aspect, the preparation of a fecal microbiota or manufacture of a preparation of uncultured fecal bacteria used herein involves no treatment selected from the group consisting of ethanol treatment, detergent treatment, heat treatment, irradiation, and sonication. In one aspect, the preparation of a fecal microbiota or manufacture of a preparation of uncultured fecal bacteria used herein involves a separation step selected from the group consisting of density gradients, filtration (e.g., sieves, nylon mesh), and chromatography. In another aspect, the preparation of a fecal microbiota or manufacture of a preparation of uncultured fecal bacteria used herein involves no separation step selected from the group consisting of density gradients, filtration (e.g., sieves, nylon mesh), and chromatography. In another aspect, a fecal microbiota or preparation of uncultured fecal bacteria used herein comprises a donor's entire fecal microbiota. In another aspect, a pharmaceutical composition administered herein comprises a fecal microbiota or preparation of uncultured fecal bacteria substantially free of eukaryotic cells.

In another aspect, a pharmaceutical composition administered herein comprises an uncultured fecal microbiota, or a preparation of uncultured fecal bacteria, further supplemented, spiked, or enhanced with one or more bacterial isolates described herein. In one aspect, an uncultured fecal microbiota is spiked with a bacterial isolate provided in Table 1. In one aspect, an uncultured fecal microbiota, or a preparation of uncultured fecal bacteria, is supplemented with a non-pathogenic (or with attenuated pathogenicity) bacterium of *Clostridium, Collinsella, Dorea, Ruminococcus, Coprococcus, Prevotella, Veillonella, Bacteroides, Bacillus*, or a combination thereof. In another aspect, a pharmaceutical composition administered herein comprises an uncultured fecal microbiota or a preparation of uncultured fecal bacteria further supplemented, spiked, or enhanced with a species of *Veillonellaceae, Firmicutes, Gammaproteobacteria, Bacteroidetes*, or a combination thereof. In another aspect, a pharmaceutical composition administered herein comprises an uncultured fecal microbiota or a preparation of uncultured fecal bacteria further supplemented with fecal bacterial spores. In one aspect, fecal bacterial spores are *Clostridium* spores, *Bacillus* spores, or both.

In an aspect, a pharmaceutical composition comprises an uncultured fecal microbiota a preparation of uncultured fecal bacteria from a subject selected from the group consisting of a human, a bovine, a dairy calf, a ruminant, an ovine, a caprine, or a *cervine*. In another aspect, a pharmaceutical composition can be administered to a subject selected from the group consisting of a human, a bovine, a dairy calf, a ruminant, an ovine, a caprine, or a *cervine*. In an aspect, a pharmaceutical composition is substantially or nearly odorless.

In an aspect, a pharmaceutical composition provided or administered herein comprises an uncultured fecal microbiota a preparation of uncultured fecal bacteria comprising a Shannon Diversity Index of greater than or equal to 0.3, greater than or equal to 0.4, greater than or equal to 0.5, greater than or equal to 0.6, greater than or equal to 0.7, greater than or equal to 0.8, greater than or equal to 0.9, greater than or equal to 1.0, greater than or equal to 1.1, greater than or equal to 1.2, greater than or equal to 1.3, greater than or equal to 1.4, greater than or equal to 1.5, greater than or equal to 1.6, greater than or equal to 1.7, greater than or equal to 1.8, greater than or equal to 1.9, greater than or equal to 2.0, greater than or equal to 2.1, greater than or equal to 2.2, greater than or equal to 2.3, greater than or equal to 2.4, greater than or equal to 2.5, greater than or equal to 3.0, greater than or equal to 3.1, greater than or equal to 3.2, greater than or equal to 3.3, greater than or equal to 3.4, greater than or equal to 3.5, greater than or equal to 3.6, greater than or equal to 3.7, greater than or equal to 3.8, greater than or equal to 3.9, greater than or equal to 4.0, greater than or equal to 4.1, greater than or equal to 4.2, greater than or equal to 4.3, greater than or equal to 4.4, greater than or equal to 4.5, or greater than or equal to 5.0. In another aspect, a pharmaceutical composition comprises fecal microbiota comprising a Shannon Diversity Index of between 0.1 and 3.0, between 0.1 and 2.5, between 0.1 and 2.4, between 0.1 and 2.3, between 0.1 and 2.2, between 0.1 and 2.1, between 0.1 and 2.0, between 0.4 and 2.5, between 0.4 and 3.0, between 0.5 and 5.0, between 0.7 and 5.0, between 0.9 and 5.0, between 1.1 and 5.0, between 1.3 and 5.0, between 1.5 and 5.0, between 1.7 and 5.0, between 1.9 and 5.0, between 2.1 and 5.0, between 2.3 and 5.0, between 2.5 and 5.0, between 2.7 and 5.0, between 2.9 and 5.0, between 3.1 and 5.0, between 3.3 and 5.0, between 3.5 and 5.0, between 3.7 and 5.0, between 31.9 and 5.0, or between 4.1 and 5.0. In one aspect, a Shannon Diversity Index is calculated at the phylum level. In another aspect, a Shannon Diversity Index is calculated at the family level. In one aspect, a Shannon Diversity Index is calculated at the genus level. In another aspect, a Shannon Diversity Index is calculated at the species level. In a further aspect, a pharmaceutical composition comprises a preparation of flora in proportional content that resembles a normal healthy human fecal flora.

In a further aspect, a pharmaceutical composition comprises fecal bacteria from at least 1, 2, 3, 4, 5, 6, 7, 8, 9, or 10 different families. In another aspect, a pharmaceutical composition comprises fecal bacteria from at least 11, 12, 13, 14, 15, 16, 17, 18, 19, or 20 different families. In yet another aspect, a pharmaceutical composition comprises fecal bacteria from at least 21, 22, 23, 24, 25, 26, 27, 28, 29, or 30 different families. In a further aspect, a pharmaceutical composition comprises fecal bacteria from at least 31, 32, 33, 34, 35, 36, 37, 38, 39, or 40 different families. In another aspect, a pharmaceutical composition comprises fecal bacteria from at least 41, 42, 43, 44, 45, 46, 47, 48, 49, or 50 different families. In another aspect, a pharmaceutical composition comprises fecal bacteria from between 1 and 10, between 10 and 20, between 20 and 30, between 30 and 40, between 40 and 50 different families. In an aspect, a pharmaceutical composition provided or administered herein comprises an uncultured fecal microbiota a preparation of uncultured fecal bacteria a preparation of uncultured fecal bacteria comprising no greater than 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% weight non-living material/weight biological material. In another aspect, a pharmaceutical composition provided or administered herein comprises an uncultured fecal microbiota a preparation of uncultured fecal bacteria comprising no greater than 20%, 25%, 30%, 35%, 40%, 45%, 50%, 55%, 60%, 65%, 70%, 75%, 80%, 85%, 90%, or 95% weight non-living material/weight biological material. In another aspect, a pharmaceutical composition provided or administered herein comprises, consists of, or consists essentially of, particles of non-living material and/or particles of biological material of a fecal sample that passes through a sieve, a column, or a similar filtering device having a sieve, exclusion, or particle filter size of 2.0 mm, 1.0 mm, 0.5 mm, 0.33 mm, 0.25 mm, 0.212 mm, 0.180 mm, 0.150 mm, 0.125 mm, 0.106 mm, 0.090 mm, 0.075 mm, 0.063 mm, 0.053 mm, 0.045 mm, 0.038 mm, 0.032 mm, 0.025 mm, 0.020 mm, 0.01 mm, or 0.002 mm. "Non-living material" does not include an excipient, e.g., a pharmaceutically inactive substance, such as a cryoprotectant, added to a processed fecal material. "Biological material" refers to the living material in fecal material, and includes microbes including prokaryotic cells, such as bacteria and archaea (e.g., living prokaryotic cells and spores that can sporulate to become living prokaryotic cells), eukaryotic cells such as protozoa and fungi, and viruses. In one embodiment, "biological material" refers to the living material, e.g., the microbes, eukaryotic cells, and viruses, which are present in the colon of a normal healthy human. In an aspect, a pharmaceutical composition provided or administered herein comprises an extract of human stool, wherein the composition is substantially odorless. In an aspect, a pharmaceutical composition provided or administered herein comprises fecal material or a fecal floral preparation in a lyophilized, crude, semi-purified or purified formulation.

In an aspect, an uncultured fecal microbiota or a preparation of uncultured fecal bacteria in a pharmaceutical composition comprises highly refined or purified fecal flora, e.g., substantially free of non-floral fecal material. In an aspect, an uncultured fecal microbiota or a preparation of uncultured fecal bacteria can be further processed, e.g., to undergo microfiltration before, after, or before and after sieving. In another aspect, a highly purified fecal microbiota product is ultra-filtrated to remove large molecules but retain the therapeutic microflora, e.g., bacteria.

In another aspect, an uncultured fecal microbiota or a preparation of uncultured fecal bacteria in a pharmaceutical composition used herein comprises or consists essentially of a substantially isolated or a purified fecal flora or entire (or substantially entire) microbiota that is (or comprises) an isolate of fecal flora that is at least about 90%, 91%, 92%, 93%, 94%, 95%, 96%, 97%, 98%, 99%, 99.5%, 99.6%, 99.7%, 99.8% or 99.9% isolated or pure, or having no more than about 0.1%, 0.2%, 0.3%, 0.4%, 0.5%, 0.6%, 0.7%, 0.8%, 0.9% or 1.0% or more non-fecal floral material; or, a substantially isolated, purified, or substantially entire microbiota as described in Sadowsky et al., WO 2012/122478 A1, or as described in Borody et al., WO 2012/016287 A2.

In an aspect, an uncultured fecal microbiota or a preparation of uncultured fecal bacteria in a pharmaceutical composition comprises a donor's substantially entire or non-selected fecal microbiota. In another aspect, the fecal microbiota in a pharmaceutical composition comprises no antibiotic resistant population. In another aspect, a pharmaceutical composition comprises an uncultured fecal microbiota or a preparation of uncultured fecal bacteria and is largely free of extraneous matter (e.g., non-living matter including acellular matter such as residual fiber, DNA, RNA, viral coat material, non-viable material; and living matter such as eukaryotic cells from the fecal matter's donor).

In an aspect, an uncultured fecal microbiota or a preparation of uncultured fecal bacteria in a pharmaceutical composition used herein is derived from a disease-screened stool sample of a human donor. In an aspect, a stool sample does not include an antibiotic resistant population. For example, a fecal composition can comprise a preparation of viable flora which can in proportional content, resemble normal healthy human fecal flora which does not include antibiotic resistant populations. Suitable microorganisms in a flora can be selected from the following: *Bacteroides, Eubacterium, Fusobacterium, Propionibacterium, Lactobacillus, Ruminococcus, Escherichia coli, Gemmiger, Clostridium, Desulfomonas, Peptostreptococcus, Bifidobacterium, Collinsella, Coprococcus, Dorea*, and *Ruminococcus*.

In an aspect, a pharmaceutical composition used in a treatment disclosed herein comprises a sterile fecal filtrate or a non-cellular fecal filtrate. In one aspect, a sterile fecal filtrate originates from a donor stool. In another aspect, a sterile fecal filtrate originates from cultured microorganisms. In another aspect, a sterile fecal filtrate comprises a non-cellular non-particulate fecal component. In one aspect, a sterile fecal filtrate is made as described in WO2014/078911, published May 30, 2014. In another aspect, a sterile fecal filtrate is made as described in Ott et al., *Gastroenterology* 152:799-911(2017).

In one aspect, a fecal filtrate comprises secreted, excreted or otherwise liquid components or a microbiota, e.g., biologically active molecules (BAMs), which can be antibiotics or anti-inflammatories, are preserved, retained or reconstituted in a flora extract.

In one aspect, an exemplary pharmaceutical composition comprising a fecal filtrate comprises starting material from a donor from a defined donor pool, where this donor contributes a stool that is centrifuged, then filtered with very high-level filtration using e.g., either metal sieving or Millipore filters, or equivalent, to ultimately permit only cells of bacterial origin to remain, e.g., often less than about 5 micrometers diameter. After the initial centrifugation, the solid material can be separated from the liquid, and the solid is then filtered in progressively reducing size filters and tangential filters, e.g., using a Millipore filtration, and optionally, also comprising use of nano-membrane filtering. The filtering can also be done by sieves as described in WO 2012/122478, but in contrast using sieves that are smaller than 0.0120 mm, down to about 0.0110 mm, which ultimately result in having only bacterial cells present.

The supernatant separated during centrifugation can be filtered progressively in a filtering, e.g., a Millipore filtering or equivalent systems, to produce a liquid which is finely filtered through an about 0.22 micron filter. This removes all particulate matter including all living matter, including bacteria and viruses. The product then is sterile, but the aim is to remove the bacteria but to keep their secretions, especially antimicrobial bacteriocins, bacteria-derived cytokine-like products and all accompanying Biologically Active Molecules (BAMs), including: thuricin (which is secreted by bacilli in donor stools), bacteriocins (including colicin, troudulixine or putaindicine, or microcin or subtilosin A), lanbiotics (including nisin, subtilin, epidermin, mutacin, mersacidin, actagardine, cinnamycin), lacticins and other antimicrobial or anti-inflammatory compounds.

In one aspect, a pharmaceutical composition used herein comprises a reconstituted fecal flora consisting essentially of a combination of a purified fecal microbiota and a non-cellular fecal filtrate. In another aspect, a pharmaceutical composition used herein comprises a purified fecal microbiota supplemented with one or more non-cellular non-particulate fecal components. In one aspect, a pharmaceutical composition used here comprises one or more non-cellular non-particulate fecal components. In one aspect, one or more non-cellular non-particulate fecal components comprise synthetic molecules, biologically active molecules produced by a fecal microorganism, or both. In another aspect, one or more non-cellular non-particulate fecal components comprise biologically active proteins or peptides, micronutrients, fats, sugars, small carbohydrates, trace elements, mineral salts, ash, mucous, amino acids, nutrients, vitamins, minerals, or any combination thereof. In one aspect, one or more non-cellular non-particulate fecal components comprise one or more biologically active molecules selected from the group consisting of bacteriocin, lanbiotic, and lacticin. In another aspect, one or more non-cellular non-particulate fecal components comprise one or more bacteriocins selected from the group consisting of colicin, troudulixine, putaindicine, microcin, and subtilosin A. In one aspect, one or more non-cellular non-particulate fecal components comprise one or more lanbiotics selected from the group consisting of thuricin, nisin, subtilin, epidermin, mutacin, mersacidin, actagardine, and cinnamycin. In another aspect, one or more non-cellular non-particulate fecal components comprise an anti-spore compound, an antimicrobial compound, an anti-inflammatory compound, or any combination thereof. In a further aspect, one or more non-cellular non-particulate fecal components comprise an interleukin, a cytokine, a leukotriene, an eicosanoid, or any combination thereof.

In another aspect, a treatment method provided here comprises the use of both fecal bacterial cells, e.g., a partial or a complete representation of the human GI microbiota, and an isolated, processed, filtered, concentrated, reconstituted and/or artificial liquid component (e.g., fecal filtrate) of the flora (the microbiota) which comprises, among others ingredients, bacterial secretory products such as e.g., bacteriocins (proteinaceous toxins produced by bacteria, including colicin, troudulixine or putaindicine, or microcin or subtilosin A), lanbiotics (a class of peptide antibiotics that contain a characteristic polycyclic thioether amino acid lanthionine or methyllanthionine, and unsaturated amino acids dehydroalanine and 2-aminoisobutyric acid; which include thuricin (which is secreted by bacilli in donor stools), nisin, subtilin, epidermin, mutacin, mersacidin, actagardine, cinnamycin), a lacticin (a family of pore-forming peptidic toxins) and other antimicrobial or anti-inflammatory compounds and/or additional biologically active molecules (BAMs) produced by bacteria or other microorganisms of the microbiota, and/or which are found in the "liquid component" of a microbiota.

In one aspect, a fecal bacteria-based pharmaceutical composition is used concurrently with a fecal non-cellular filtrate-based pharmaceutical composition. In another aspect, a patient is treated with a first fecal non-cellular filtrate-based pharmaceutical composition before being given a second fecal bacteria-based pharmaceutical composition, or vice versa. In a further aspect, a treatment method comprises three steps: first, antibiotic pretreatment to non-selectively remove infectious pathogen(s); second, a fecal non-cellular filtrate-based treatment step to further suppress selected infectious pathogen(s); and third, giving the patient a fecal bacteria-based pharmaceutical composition to re-establish a functional intestinal microbiome.

In an aspect, a treatment method effects a cure, reduction of the symptoms, or a percentage reduction of symptoms of a disorder related to an intestinal dysbiosis. The change of flora can be as "near-complete" as possible and the flora is replaced by viable organisms which will crowd out any remaining, original flora. Typically, the change in enteric flora comprises introduction of an array of predetermined flora into the gastro-intestinal system, and thus in a preferred form the method of treatment comprises substantially or completely displacing pathogenic enteric flora in patients requiring such treatment.

In an aspect, uncultured fecal microbiota or a preparation of uncultured fecal bacteria for incorporation into a pharmaceutical composition comprises non-pathogenic spores of one or more, two or more, three or more, or four or more *Clostridium* species selected from the group consisting of *Clostridium absonum, Clostridium argentinense, Clostridium baratii, Clostridium botulinum, Clostridium cadaveris, Clostridium carnis, Clostridium celatum, Clostridium chauvoei, Clostridium clostridioforme, Clostridium cochlearium, Clostridium fallax, Clostridium felsineum, Clostridium ghonii, Clostridium glycolicum, Clostridium haemolyticum, Clostridium hastiforme, Clostridium histolyticum, Clostridium indolis, Clostridium irregulare, Clostridium limosum, Clostridium malenominatum, Clostridium novyi, Clostridium oroticum, Clostridium paraputrificum, Clostridium perfringens, Clostridium piliforme, Clostridium putrefaciens, Clostridium putrificum, Clostridium sardiniense, Clostridium sartagoforme, Clostridium scindens, Clostridium septicum, Clostridium sordelihi, Clostridium sphenoides, Clostridium spiroforme, Clostridium sporogenes, Clostridium subterminale, Clostridium symbiosum, Clostridium tertium, Clostridium tetani, Clostridium welchii,* and *Clostridium villosum.*

In an aspect, uncultured fecal microbiota or a preparation of uncultured fecal bacteria for incorporation into a pharmaceutical composition comprises purified, isolated, or cultured viable non-pathogenic *Clostridium* and a plurality of purified, isolated, or cultured viable non-pathogenic microorganisms from one or more genera selected from the group consisting of *Collinsella, Coprococcus, Dorea, Eubacterium,* and *Ruminococcus*. In another aspect, a pharmaceutical composition comprises a plurality of purified, isolated, or cultured viable non-pathogenic microorganisms from one or more genera selected from the group consisting of *Clostridium, Collinsella, Coprococcus, Dorea, Eubacterium,* and *Ruminococcus*.

In an aspect, uncultured fecal microbiota or a preparation of uncultured fecal bacteria for incorporation into a pharmaceutical composition comprises two or more genera selected from the group consisting of *Collinsella*, *Coprococcus*, *Dorea*, *Eubacterium*, and *Ruminococcus*. In another aspect, a pharmaceutical composition comprises two or more genera selected from the group consisting of *Coprococcus*, *Dorea*, *Eubacterium*, and *Ruminococcus*.

In a further aspect, a pharmaceutical composition comprises one or more, two or more, three or more, four or more, or five or more species selected from the group consisting of *Coprococcus catus*, *Coprococcus comes*, *Dorea longicatena*, *Eubacterium eligens*, *Eubacterium hadrum*, *Eubacterium hallii*, *Eubacterium rectale*, and *Ruminococcus torques*.

In one aspect, an uncultured fecal microbiota or a preparation of uncultured fecal bacteria for incorporation into a pharmaceutical composition described herein comprises at least about $10^5$, $10^6$, $10^7$, $10^8$, $10^9$, $10^{10}$, $10^{11}$, $10^{12}$, or $10^{13}$ cfu or total cell count. In another aspect, a pharmaceutical composition comprises at most about $10^5$, $10^6$, $10^7$, $10^8$, $10^9$, $10^{10}$, $10^{11}$, $10^{12}$, $10^{13}$ or $10^{14}$ cfu or total cell count.

In another aspect, an uncultured fecal microbiota or a preparation of uncultured fecal bacteria comprises at least about $10^5$, $10^6$, $10^7$, $10^8$, $10^9$, $10^{10}$, $10^{11}$, $10^{12}$, or $10^{13}$ cells or total cell count. In another aspect, a pharmaceutical composition comprises at most about $10^5$, $10^6$, $10^7$, $10^8$, $10^9$, $10^{10}$, $10^{11}$, $10^{12}$, $10^{13}$ or $10^{14}$ cells or total cell count.

Extraction and Purification of Bacteria from Stool

The pharmaceutical compositions described here can comprise microbes, e.g. bacteria, derived from a stool sample of a donor, e.g. a healthy human donor. In an aspect, a composition incorporates all or a portion of a fecal microbiota of a stool sample. For example, a composition can incorporate a substantially complete fecal microbiota of a stool sample of a healthy human donor. In an aspect, a composition incorporates a bacterial isolate of a fecal microbiota, wherein the bacterial isolate has been purified and/or cultured from all or a portion of the fecal microbiota. The extraction and/or purification of a fecal microbiota from a stool sample can thus be performed to prepare a composition comprising at least one of a fecal microbiota (e.g., a substantially complete fecal microbiota) or a bacterial isolate.

In one aspect, an exemplary fecal microbiota for use in preparing a composition described herein comprises starting material from a human donor. In another aspect, an exemplary fecal microbiota comprises material from one or more healthy human donors. In yet another aspect, an exemplary fecal microbiota comprises starting material from a pool of known, defined donors. In another aspect, a donor is an adult male. In a further aspect, a donor is an adult female. In yet another aspect, a donor is an adolescent male. In another aspect, a donor is an adolescent female. In another aspect, a donor is a female toddler. In another aspect, a donor is a male toddler. In another aspect, a donor is healthy. In one aspect, a human donor is a child below about 18, 15, 12, 10, 8, 6, 4, 3, 2, or 1-year-old. In another aspect, a human donor is an elderly individual. In a further aspect, a human donor is an individual above about 30, 35, 40, 45, 50, 55, 60, 65, 70, 75, 80, 85, 90, or 95 years old. In another aspect, a donor is between 1 and 5, between 2 and 10, between 3 and 18, between 21 and 50, between 21 and 40, between 21 and 30, between 50 and 90, between 60 and 90, between 70 and 90, between 60 and 80, or between 65 and 75 years old. In one aspect, a donor is a young old individual (65-74 years). In one aspect, a donor is a middle old individual (75-84 years). In one aspect, a donor is an old individual (>85 years). In yet another aspect, a donor is a carefully screened, healthy, neurotypical human.

In an aspect, a carefully screened donor undergoes a complete medical history and physical exam. Donors are excluded if they have a risk of infectious agents. Additional exclusion criteria comprise the following:
1. Known viral infection with Hepatitis B, C or HIV
2. Known exposure to HIV or viral hepatitis at any time
3. High risk behaviors including sex for drugs or money, men who have sex with men, more than one sexual partner in the preceding 12 months, any past use of intravenous drugs or intranasal cocaine, history of incarceration.
4. Tattoo or body piercing within 12 months.
5. Travel to areas of the world where risk of traveler's diarrhea is higher than the US.
6. Current communicable disease, e.g., upper respiratory viral infection.
7. History of irritable bowel syndrome. Specific symptoms can include frequent abdominal cramps, excessive gas, bloating, abdominal distension, fecal urgency, diarrhea, constipation.
8. History of inflammatory bowel disease such as Crohn's disease, ulcerative colitis, microscopic colitis.
9. Chronic diarrhea.
10. Chronic constipation or use of laxatives.
11. History of gastrointestinal malignancy or known colon polyposis.
12. History of any abdominal surgery, e.g., gastric bypass, intestinal resection, appendectomy, cholecystectomy, etc.
13. Use of Probiotics or any other over the counter aids used by the potential donor for purpose of regulating digestion. Yogurt and kefir products are allowed if taken merely as food rather than nutritional supplements.
14. Antibiotics for any indication within the preceding 6 months.
15. Any prescribed immunosuppressive or anti-neoplastic medications.
16. Metabolic Syndrome, established or emerging. Criteria used for definition here are stricter than any established criteria. These include history of increased blood pressure, history of diabetes or glucose intolerance.
17. Known systemic autoimmunity, e.g., connective tissue disease, multiple sclerosis.
18. Known atopic diseases including asthma or eczema.
19. Chronic pain syndromes including fibromyalgia, chronic fatigue syndrome.
20. Ongoing (even if intermittent) use of any prescribed medications, including inhalers or topical creams and ointments.
21. Neurologic, neurodevelopmental, and neurodegenerative disorders including autism, Parkinson's disease.
22. General. Body mass index >26 kg/m2, central obesity defined by waste:hip ratio >0.85 (male) and >0.80 (female).
23. Blood pressure >135 mmHg systolic and >85 mmHg diastolic.
24. Skin—presence of a rash, tattoos or body piercing placed within a year, or jaundice
25. Enlarged lymph nodes.
26. Wheezing on auscultation.
27. Hepatomegaly or stigmata of liver disease.
28. Swollen or tender joints. Muscle weakness.
29. Abnormal neurologic examination.

30. Positive stool *Clostridium difficile* toxin B tested by PCR.
31. Positive stool cultures for any of the routine pathogens including *Salmonella, Shigella, Yersinia, Campylobacter, E. coli* 0157:H7.
32. Abnormal ova and parasites examination.
33. Positive Giardia, *Cryptosporidium*, or *Helicobacter pylon* antigens.
34. Positive screening for any viral illnesses, including HIV 1 and 2, Viral Hepatitis A IgM, Hepatitis surface antigen and core Ab.
35. Abnormal RPR (screen for syphilis).
36. Any abnormal liver function tests including alkaline phosphatase, aspartate aminotransaminase, alanine aminotransferase.
37. Raised serum triglycerides >150 mg/Dl
38. HDL cholesterol <40 mg/dL (males) and <50 mg/dL (females)
39. High sensitivity CRP >2.4 mg/L
40. Raised fasting plasma glucose (>100 mg/dL)

In embodiments, the plurality of bacterial isolates comprises lyophilized bacteria. In embodiments, the plurality of bacterial isolates does not include *Escherichia coli*. In embodiments, the pharmaceutical composition of any of the embodiments disclosed herein is not a stoll sample or a minimally processed version thereof.

In one aspect, provided herein is a process for preparing fecal flora (e.g., an entire (or substantially entire) microbiota), first comprising a collection from one or more healthy (e.g., screened) donor(s). In one aspect, a fresh stool is transported via a stool collection device, which can provide or comprises a suitably oxygen free (or substantially oxygen free) appropriate container. In one aspect, the container can be made oxygen free by e.g., incorporating into the container a built in or clipped-on oxygen-scavenging mechanism, e.g., oxygen scavenging pellets as described e.g., in U.S. Pat. No. 7,541,091. In another aspect, the container itself is made of an oxygen scavenging material, e.g., oxygen scavenging iron, e.g., as described by O2BLOCK™, or equivalents, which uses a purified and modified layered clay as a performance-enhancing carrier of oxygen-scavenging iron; the active iron is dispersed directly in the polymer. In one aspect, oxygen-scavenging polymers are used to make the container itself or to coat the container, or as pellets to be added; e.g., as described in U.S. Pat. App. Pub. 20110045222, describing polymer blends having one or more unsaturated olefinic homopolymers or copolymers; one or more polyamide homopolymers or copolymers; one or more polyethylene terephthalate homopolymers or copolymers; that exhibit oxygen-scavenging activity. In one aspect, oxygen-scavenging polymers are used to make the container itself or to coat the container, or as pellets to be added; e.g., as described in U.S. Pat. App. Pub. 20110008554, describing compositions comprising a polyester, a copolyester ether and an oxidation catalyst, wherein the copolyester ether comprises a polyether segment comprising poly(tetramethylene-co-alkylene ether). In one aspect, oxygen-scavenging polymers are used to make the container itself or to coat the container, or as pellets to be added; e.g., as described in U.S. Pat. App. Pub. 201000255231, describing a dispersed iron/salt particle in a polymer matrix, and an oxygen scavenging film with oxygen scavenging particulates.

Alternatively, in addition to or in place of the oxygen-scavenging mechanism, the air in the container can be replaced (completely or substantially) with nitrogen and/or other inert non-reactive gas or gases. In one aspect, the container simulates (creates) partially, substantially or completely an anaerobic environment.

In one aspect, the stool (e.g., fecal sample) is held in an aesthetically acceptable container that will not leak nor smell yet maintain an anaerobic environment. In one aspect, the container is sterile before receiving the fecal flora.

In one aspect, a stool sample provided herein is maintained at room temperature during most or all of its transportation and/or storage at e.g., a "stool bank". For example, once delivered to a "processing stool bank" it is stored at ambient temperature, e.g., room temperature. In one aspect, stabilizing agents, such as glycerol, are added to the harvested and/or stored material.

In one aspect, the stool is tested for various pathogens, as noted above. In one aspect, once cleared of infective agents, a stool sample is homogenized and filtered to remove large particles of matter. In one aspect, the stool is subdivided into desired volumes, e.g., which can be between 5 cc and 3 or more liters. For example, in one aspect, a container comprises a 50 gram (g) stool, which can be held in an appropriate oxygen resistant plastic, e.g., a metallized polyethylene terephthalate polyester film, or a metallized MYLAR™.

In one aspect, the stool is subject to homogenization by for example, mixing, agitating, stirring or shaking. In certain aspects, a stool sample is diluted with a homogenization buffer prior to homogenization. A homogenization buffer can, for example, contain a cryoprotectant (e.g., trehalose), an antioxidant or reducing agent (e.g., cysteine), and a buffer (e.g., 0.25×PBS at pH 7.4).

In one aspect, to separate the non-bacterial components from the fecal microbiota, the stool can be homogenized and filtered from rough particulate matter. In one aspect, the microscopic fiber/nonliving matter is then separated from the bacteria. Several methods can be used, including e.g., recurrent filtration with filter sizes, e.g., progressively coming down to the size of a typical bacterium.

In one aspect, different filters are used to isolate bacterial sp., or a technique as used by Williams in WO 2011/033310A1, which uses a crude technique of filtration with a gauze.

In one aspect, a filtration procedure for filtering whole stool is suitably used to reach the highest concentration of almost 100% bacteria. In one aspect, the filtering procedure is a two-step procedure suitably using glass fibre depth filters for initial clarification. In one aspect, the stool is filtered under positive pressure. In one aspect, this would be using a combination or sandwich configuration with a 30 micron PVDF filter. In one aspect, this sandwich procedure will be filtering the product under positive pressure. Later, membrane concentration can, in one aspect, be used as another step to reduce the volume of the filtrate. In one aspect, this can be done prior to freeze drying or spray drying under nitrogen cover.

Alternative membranes that can be used for filtration include, but not limited to, nylon filters, cellulose nitrate filters, polyethersulfone (PES) filters, polytetrafluorethylene (PTFE) filters, TEFLON™ filters, mixed cellulose Ester filters, polycarbonate filters, polypropylene filters, Polyvinylchloride (PVC) filters or quartz filters. Various combinations of these can be used to achieve a high purity of bacteria with solids and liquid removed.

In one aspect, a subject in need thereof is administered a pharmaceutical composition comprising fecal microbiota or a preparation of uncultured fecal bacteria of multiple carefully screened, healthy donors. In an aspect, a subject is administered a pharmaceutical composition over a dosing period wherein a first dose comprises at least one pharmaceutical composition comprises fecal microbiota or a preparation of uncultured fecal bacteria of a single donor, and a second dose of a pharmaceutical composition comprises fecal microbiota or a preparation of uncultured fecal bacteria of a single donor different from the donor of the first dose. In another aspect, a first dose comprises a pharmaceutical composition comprising fecal microbiota or a preparation of uncultured fecal bacteria of a single donor and a second dose comprises fecal microbiota or a preparation of uncultured fecal bacteria of a donor pool. The first and second dose do not indicate the order of administration to a subject, but rather that fecal microbiota or preparations of uncultured fecal bacteria from separate donors can be used in a non-blended form.

In another aspect, the present disclosure provides for methods for treating a subject in need thereof with capsules containing a pharmaceutical composition comprising fecal microbiota from a single donor. In another aspect, a capsule comprises a pharmaceutical composition comprising fecal microbiota from multiple donors. In one aspect a subject is administered two or more pills comprising fecal microbiota from a single but different donor.

In one aspect, the present disclosure provides for methods for treating a subject in need thereof comprising administering a pharmaceutical composition orally or by infusions through a colonoscope, an enema or via a nasojejunal tube. In another aspect, each administration comprises a pharmaceutical composition comprising fecal microbiota of a single donor similar to or different from a prior administration in a treatment period. In another aspect, a treatment period includes administration of a first dose comprising a pharmaceutical composition comprising fecal microbiota of a single donor and administration of a second dose comprising a pharmaceutical composition comprising fecal microbiota of multiple donors.

Pharmaceutical compositions, Formulations, and Administration

Described herein are pharmaceutical compositions comprising one or more bacterial isolates (and/or additional therapeutic agents, e.g. a substantially complete fecal microbiota or preparation of uncultured fecal bacteria) in various formulations. Any pharmaceutical composition (and/or additional therapeutic agents) described herein can take the form of tablets, pills, pellets, capsules, capsules containing liquids, capsules containing multiparticulates, powders, solutions, emulsion, drops, suppositories, emulsions, aerosols, sprays, suspensions, delayed-release formulations, sustained-release formulations, controlled-release formulations, or any other form suitable for use.

The formulations comprising the pharmaceutical compositions can conveniently be presented in unit dosage forms. For example, the dosage forms can be prepared by methods which include the step of bringing the therapeutic agents into association with a carrier, which constitutes one or more accessory ingredients. For example, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by press tableting).

In another aspect, a pharmaceutical composition can be provided together with a pharmaceutically acceptable carrier. As used herein, a "pharmaceutically acceptable carrier" refers to a non-toxic solvent, dispersant, excipient, adjuvant, or other material which is mixed with a live bacterium in order to permit the formation of a pharmaceutical composition, e.g., a dosage form capable of administration to the patient. A pharmaceutically acceptable carrier can be liquid (e.g., saline), gel or solid form of diluents, adjuvant, excipients or an acid resistant encapsulated ingredient. Suitable diluents and excipients include pharmaceutical grades of physiological saline, dextrose, glycerol, mannitol, lactose, starch, magnesium stearate, sodium saccharin, cellulose, magnesium carbonate, and the like, and a combination thereof. In another aspect, a pharmaceutical composition can contain auxiliary substances such as wetting or emulsifying agents, stabilizing or pH buffering agents. In an aspect, a pharmaceutical composition contains about 1%-5%, 5%-10%, 10%-15%, 15-20%, 20%-25%, 25-30%, 30-35%, 40-45%, 50%-55%, 1%-95%, 2%-95%, 5%-95%, 10%-95%, 15%-95%, 20%-95%, 25%-95%, 30%-95%, 35%-95%, 40%-95%, 45%-95%, 50%-95%, 55%-95%, 60%-95%, 65%-95%, 70%-95%, 45%-95%, 80%-95%, or 85%-95% of active ingredient. In an aspect, a pharmaceutical composition contains about 2%-70%, 5%-60%, 10%-50%, 15%-40%, 20%-30%, 25%-60%, 30%-60%, or 35%-60% of active ingredient.

In an aspect, a pharmaceutical composition can be incorporated into tablets, drenches, boluses, capsules or premixes. Formulation of these active ingredients into such dosage forms can be accomplished by means of methods well known in the pharmaceutical formulation arts. See, e.g., U.S. Pat. No. 4,394,377. Filling gelatin capsules with any desired form of the active ingredients readily produces capsules. If desired, these materials can be diluted with an inert powdered diluent, such as sugar, starch, powdered milk, purified crystalline cellulose, or the like to increase the volume for convenience of filling capsules.

In an aspect, for preparing solid compositions such as tablets, an active ingredient is mixed with a pharmaceutical carrier, e.g., conventional tableting ingredients such as cornstarch, lactose, sucrose, sorbitol, talc, stearic acid, magnesium stearate, dicalcium phosphate or gums, or other pharmaceutical diluents, e.g. water, to form a solid preformulation composition containing a homogeneous mixture of a composition described herein. When referring to these preformulation compositions as homogeneous, it is meant that the active ingredient is dispersed evenly throughout the composition so that the composition can be readily subdivided into equally effective unit dosage forms such as tablets, pills and capsules. This solid preformulation composition is then subdivided into unit dosage forms of the type described above containing a desired amount of an active ingredient (e.g., at least about 105, $10^6$, $10^7$, $10^8$, $10^9$, $10^{10}$, $10^{11}$, $10^{12}$, or $10^{13}$ cfu). A pharmaceutical composition used herein can be flavored.

In one embodiment, a pharmaceutical composition comprising one or more bacterial isolates (and/or additional therapeutic agents) described herein is formulated as a composition adapted for a mode of administration described herein.

In various embodiments, the administration of the pharmaceutical compositions is any one of oral, intravenous, intraperitoneal, and parenteral. For example, routes of administration include, but are not limited to, oral, intraperitoneal, intravenous, intramuscular, or rectally. In various embodiments, the administration of the pharmaceutical compositions is oral, naso-gastric, antegrade gastrointestinal, retrograde gastrointestinal, endoscopic, or enemic.

In one embodiment, the pharmaceutical compositions described herein are formulated as a composition adapted for oral administration. Compositions for oral delivery can be in the form of tablets, lozenges, aqueous or oily suspensions, granules, powders, sprinkles, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration to provide a sustained action over an extended period of time. Selectively permeable membranes surrounding an osmotically active agent are also suitable for orally administered compositions. In these latter platforms, fluid from the environment surrounding the capsule is imbibed by a driving compound, which swells to displace the agent or agent composition through an aperture. These delivery platforms can provide an essentially zero order delivery profile as opposed to the spiked profiles of immediate release formulations. A time-delay material, such as glycerol monostearate or glycerol stearate, can also be useful. Oral compositions can include standard excipients such as mannitol, lactose, starch, magnesium stearate, sodium saccharin, cellulose, ethacrylic acid and derivative polymers thereof, and magnesium carbonate. In one embodiment, the excipients are of pharmaceutical grade. Suspensions, in addition to the active compounds, can contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

In various embodiments, the pharmaceutical compositions are formulated as solid dosage forms such as tablets, dispersible powders, granules, and capsules. In one embodiment, the pharmaceutical compositions are formulated as a capsule. In another embodiment, the pharmaceutical compositions are formulated as a tablet. In yet another embodiment, the pharmaceutical compositions are formulated as a soft-gel capsule. In a further embodiment, the pharmaceutical compositions are formulated as a gelatin capsule.

In an aspect, a pharmaceutical composition is in the form of: an enema composition which can be reconstituted with an appropriate diluent; enteric-coated capsules; enteric-coated microcapsules; acid-resistant tablet; acid-resistant capsules; acid-resistant microcapsules; powder for reconstitution with an appropriate diluent for naso-enteric infusion or colonoscopic infusion; powder for reconstitution with appropriate diluent, flavoring and gastric acid suppression agent for oral ingestion; powder for reconstitution with food or drink; or food or food supplement comprising enteric-coated and/or acid-resistant microcapsules of the composition, powder, jelly, or liquid.

In various embodiments, formulations can additionally comprise a pharmaceutically acceptable carrier or excipient. As one skilled in the art will recognize, the formulations can be in any suitable form appropriate for the desired use and route of administration.

In some dosage forms, the pharmaceutical compositions comprising one or more bacterial isolates described herein are mixed with at least one inert, pharmaceutically acceptable excipient or carrier such as sodium citrate, dicalcium phosphate, etc., and/or a) fillers or extenders such as starches, lactose, sucrose, glucose, mannitol, silicic acid, microcrystalline cellulose, and Bakers Special Sugar, etc., b) binders such as, for example, carboxymethylcellulose, alginates, gelatin, polyvinylpyrrolidone, sucrose, acacia, polyvinyl alcohol, polyvinylpyrrolidone, methylcellulose, hydroxypropyl cellulose (HPC), and hydroxymethyl cellulose etc., c) humectants such as glycerol, etc., d) disintegrating agents such as agar-agar, calcium carbonate, potato or tapioca starch, alginic acid, certain silicates, sodium carbonate, cross-linked polymers such as crospovidone (cross-linked polyvinylpyrrolidone), croscarmellose sodium (cross-linked sodium carboxymethylcellulose), sodium starch glycolate, etc., e) solution retarding agents such as paraffin, etc., f) absorption accelerators such as quaternary ammonium compounds, etc., g) wetting agents such as, for example, cetyl alcohol and glycerol monostearate, etc., h) absorbents such as kaolin and bentonite clay, etc., and i) lubricants such as talc, calcium stearate, magnesium stearate, solid polyethylene glycols, sodium lauryl sulfate, glyceryl behenate, etc., and mixtures of such excipients. One of skill in the art will recognize that particular excipients can have two or more functions in the oral dosage form. In the case of an oral dosage form, for example, a capsule or a tablet, the dosage form can also comprise buffering agents.

In embodiments, a pharmaceutical composition comprising one or more bacterial isolates is combined with one or more pharmaceutically acceptable cryoprotectants, lyoprotectants, binders, disintegrants, excipients, fillers, and/or preservatives, acid suppressants, antacids, H2 antagonists, and proton pump inhibitors, or combinations thereof.

In an aspect, a pharmaceutical composition is combined with other adjuvants such as antacids to dampen bacterial inactivation in the stomach. (e.g., Mylanta, Mucaine, Gastrogel).

In another aspect, acid secretion in the stomach could also be pharmacologically suppressed using H2-antagonists or proton pump inhibitors. An example H2-antagonist is ranitidine. An example proton pump inhibitor is omeprazole. In one aspect, an acid suppressant is administered prior to administering, or in co-administration with, a pharmaceutical composition.

In one aspect, a pharmaceutical composition administered herein further comprises an acid suppressant, an antacid, an H2 antagonist, a proton pump inhibitor or a combination thereof. In one aspect, a pharmaceutical composition administered herein substantially free of non-living matter. In another aspect, a pharmaceutical composition administered herein substantially free of acellular material selected from the group consisting of residual fiber, DNA, viral coat material, and non-viable material. In another aspect, a pharmaceutical composition administered does not comprise an acid suppressant, an antacid, an H2 antagonist, a proton pump inhibitor or a combination thereof. In yet another aspect, a pharmaceutical composition administered does not comprise an acid suppressant. In another aspect, a pharmaceutical composition administered does not comprise an antacid. In another aspect, a pharmaceutical composition administered does not comprise an H2 antagonist. In another aspect, a pharmaceutical composition administered does not comprise a proton pump inhibitor.

In another aspect, a pharmaceutical composition administered does not comprise metoclopramide.

In embodiments, the bacterial mixture is dry, e.g., when it includes lyophilized bacterial cells/spores or comprises dry binders, fillers, and dispersants. Alternately, the microbial cocktail comprising bacterial isolates is aqueous, e.g., when it comprises non-dry binders, fillers, and dispersants.

In embodiments, a bacterial mixture described herein can be subject to lyophilization.

As used herein, "lyophilization" or "freeze drying" refers to the process of drying a material by first freezing it and then encouraging the ice within it to sublimate in a vacuum environment.

Disclosed herein is a method of manufacturing a microbial cocktail, the method comprising culturing a first bacterial isolate as a pure culture; culturing a second bacterial isolate as a pure culture; lyophilizing the first bacterial isolate; lyophilizing the second bacterial isolate; and combining the first and second lyophilized bacterial isolates into the microbial cocktail. In another embodiment, disclosed herein is a method of manufacturing a microbial cocktail, the method comprising culturing a first bacterial isolate as a pure culture; culturing a second bacterial isolate as a pure culture; and combining the first bacterial isolate with the second bacterial isolate to form the microbial cocktail. Optionally, the microbial cocktail comprising the first and second bacterial isolates can be lyophilized. It will therefore be understood that a microbial cocktail can be lyophilized or non-lyophilized, and that a lyophilized microbial cocktail can be produced by lyophilizing bacterial isolates that form the cocktail before or after combining the bacterial isolates.

In one aspect, a bacterial mixture comprises a lyophilized formulation further comprising a reducing agent and/or antioxidant. In certain embodiments, the reducing agent comprises cysteine selected from the group consisting of D-cysteine and L-cysteine. In another aspect, cysteine is at a concentration of at least about 0.025%. In one aspect, cysteine is at a concentration of about 0.025%. In another aspect, cysteine is at a concentration of 0.025%. In another aspect, another reducing agent other than cysteine is used in lieu of, or in combination with cysteine. In an aspect, another reducing agent is selected from the group comprising ascorbic acid, sodium ascorbate, thioglycolic acid, sodium sulfite, sodium bisulfite, sodium metabisulfite, potassium metabisulfite, glutathione, methionine, thioglycerol, and alpha tocopherol.

In one aspect, cysteine is at a concentration of at least about 0.005%, at least about 0.010%, at least about 0.015%, at least about 0.02%, at least about 0.025%, at least about 0.03%, at least about 0.035%, at least about 0.04%, at least about 0.045%, at least about 0.05%, at least about 0.055%, at least about 0.06%, at least about 0.065%, at least about 0.07%, at least about 0.075%, at least about 0.08%, at least about 0.085%, at least about 0.09%, at least about 0.095%, at least about 0.1%, at least about 0.12%, at least about 0.14%, at least about 0.16%, at least about 0.18%, at least about 0.2%, at least about 0.25%, at least about 0.3%, at least about 0.4%, at least about 0.5%, at least about 0.6%, at least about 0.7%, at least about 0.8%, at least about 0.9%, at least about 1%, at least about 2%, at least about 4%, at least about 6%, at least about 8%, at least about 10%, at least about 12%, at least about 14%, at least about 16%, at least about 18%, at least about 20%, at least about 22%, at least about 24%, or at least about 26%.

In embodiments, a pharmaceutical composition comprising one or more bacterial isolates comprises a cryoprotectant or mixture of cryoprotectants. As used herein, a "cryoprotectant" refers to a substance that is added to a formulation in order to protect an active ingredient during freezing. For example, a cryoprotectant can comprise, consist essentially of, or consist of polyethylene glycol, skim milk, erythritol, arabitol, sorbitol, glucose, fructose, alanine, glycine, proline, sucrose, lactose, ribose, trehalose, dimethyl sulfoxide (DMSO) or equivalent, a glycerol, a polyethylene glycol (PEG) or equivalent, or an amino acid (e.g., alanine, glycine, proline). In embodiments of the present disclosure, a cryoprotectant can be selected from the group comprising 5% Sucrose; 10% Sucrose; 10% Skim milk; 10% Trehalose with 2.5% sucrose; 5% Trehalose with 2.5% sucrose; 5% Mannitol; 5% Mannitol with 0.1% Polysorbate 80; 10% Mannitol; 10% Mannitol with 0.1% Polysorbate 80; 5% Trehalose; 5% Trehalose with 0.1% Polysorbate 80; 10% Trehalose; and 10% Trehalose with 0.1% Polysorbate 80.

In embodiments, a pharmaceutical composition comprising one or more bacterial isolates comprises a lyoprotectant. As used herein, a "lyoprotectant" refers to a substance that is added to a formulation in order to protect an active ingredient during the stage of a lyophilization (also known as freeze-drying). In embodiments, the same substance or the same substance combination is used as both a cryoprotectant and a lyoprotectant. Exemplary lyoprotectants include sugars such as sucrose or trehalose; an amino acid such as monosodium glutamate or histidine; a methylamine such as betaine; a lyotropic salt such as magnesium sulfate; a polyol such as trihydric or higher sugar alcohols, e.g. glycerin, erythritol, glycerol, arabitol, xylitol, sorbitol, and mannitol; propylene glycol; polyethylene glycol; Pluronics; and a combination thereof. In embodiments, a lyoprotectant is a non-reducing sugar, such as trehalose or sucrose. In embodiments, a cryoprotectant or a lyoprotectant consists essentially of, or consists of, one or more substances mentioned in this paragraph and the paragraph above.

In embodiments, a cryoprotectant or a lyoprotectant comprise an intracellular agent, e.g., DMSO, Glycerol, or PEG, which penetrates inside the cell preventing the formation of ice crystals that could result in membrane rupture. In embodiments, a cryoprotectant or a lyoprotectant comprise an extracellular agent, e.g., sucrose, trehalose, or dextrose, which does not penetrate into the cell membrane but acts to improve the osmotic imbalance that occurs during freezing.

In one aspect, the present disclosure provides a pharmaceutical composition comprising a lyophilized fecal microbe preparation comprising a lyophilization formulation comprising at least about 12.5% trehalose.

In embodiments, a lyophilized formulation comprises trehalose. In embodiments, a lyophilized formulation comprises 2% to 30%, 3% to 25%, 4% to 20%, 5% to 15%, 6% to 10%, 2% to 30%, 2% to 25%, 2% to 20%, 2% to 15%, or 2% to 10% trehalose. In embodiments, a lyophilized formulation comprises at least 2%, 3%, 4%, 5%, 6%, 7%, 8%, 9%, 10%, or 15% trehalose. In embodiments, a lyophilized formulation comprises at most 2%, 3%, 4%, 5%, 6%, 7%, 8%, 9%, 10%, or 15% trehalose. In embodiments, a lyophilized formulation comprises about 5% trehalose. In embodiments, a lyophilized formulation comprises trehalose and sucrose. In embodiments, a lyophilized formulation comprises between about 8% and 12% trehalose with between about 1.5% and 3.5% sucrose and between about 0.5% and 1.5% NaCl.

In one aspect, a lyophilization formulation comprises at least about 5%, at least about 7.5%, at least about 10%, at least about 12.5%, at least about 13%, at least about 13.5%, at least about 14%, at least about 14.5%, at least about 15%, at least about 15.5%, at least about 16%, at least about 16.5%, at least about 17%, at least about 17.5%, at least about 18%, at least about 18.5%, at least about 19%, at least about 19.5%, at least about 20%, at least about 22.5%, at least about 25%, at least about 27.5%, at least about 30%, at least about 32.5%, at least about 35%, at least about 37.5%, at least about 40%, at least about 42.5%, at least about 45%, at least about 47.5%, at least about 50%, at least about 52.5%, at least about 55%, at least about 57.5%, or at least about 60% of trehalose.

In embodiments, a pharmaceutical composition provided here, after at least 12 weeks of storage at ambient temperature or lower, is effective for treating one or more disorders selected from the group consisting of recurrent or primary C.

*diff* infection, ulcerative colitis, Crohn's disease, and irritable bowel syndrome. In embodiments, a pharmaceutical composition remains effective after at least 4, 8, 10, 16, 20, 24, 30, 40, 50, 60, 70, 80 or 100 weeks of storage at ambient temperature or lower.

In embodiments, a pharmaceutical composition (e.g., comprising a microbial cocktail) described herein can be lyophilized or freeze dried and stored at ambient temperatures (e.g., room temperature), at a freezing temperature, or at between about 2° C. and 8° C. In embodiments, freeze-drying allows the majority of cells to remain viable, and produces a powdered form of the product that can be gently pulverized into a powder. The powder, or lyophilized or freeze-dried composition, then can be encapsulated into a carrier, e.g., a tablet, geltab, pill or capsule, e.g., an enteric-coated capsule, or placed into oil-filled capsules for ingestion. Alternatively, the freeze-dried or lyophilized product, or powder, can be reconstituted at ambient temperatures before delivery to an individual in e.g., a fluid, e.g., a sterile fluid, such as saline, a buffer or a media such as a fluid-glucose-cellobiose agar (RGCA) media.

For freeze-drying, in embodiments, bacterial isolates are held in a liquid that will prevent bursting of cells on thawing. This can include various stabilizers, e.g., glycerol and appropriate buffers, and/or ethylene glycol. In embodiments, the cryoprotecting process uses final concentrations of stabilizer(s) of between about 10% and 80%, 20% and 70%, 30% and 60%, or 40% and 50%, depending on the stabilizer(s) used; in embodiments, this helps stabilize proteins by preventing formation of ice crystals that would otherwise destroy protein structures.

In embodiments, stabilizers that help reduce destruction of living bacteria include skim milk, erythritol, arabitol, sorbitol, glucose, fructose and other polyols. Polymers such as dextran and polyethylene glycol can also be used to stabilize bacterial cells.

In embodiments, manufacturing a pharmaceutical composition can comprise steps of: (1) coating the exterior of a dissociated capsule (i.e., comprising separate capsule body and capsule cap) with the exterior enteric coating, (2) filling the capsule body with a pharmaceutical composition (e.g., comprising a microbial cocktail) comprising one or more bacterial isolates, and (3) closing the capsule cap over the capsule body, thereby encapsulating the composition comprising in the exterior, enteric-coated capsule.

Optionally, manufacturing a pharmaceutical composition can comprise steps of: (1) coating the exterior of a dissociated capsule (i.e., comprising separate capsule body and capsule cap) with the exterior enteric coating, (2) coating the interior of the dissociated capsule with an interior coating, (3) filling the capsule body with a pharmaceutical composition (e.g., comprising a microbial cocktail) comprising one or more bacterial isolates, and (4) closing the capsule cap over the capsule body, thereby encapsulating the composition in the dual-coated capsule.

Alternately, manufacturing a pharmaceutical composition can comprise step of: (1) coating the interior of the dissociated capsule (i.e., comprising separate capsule body and capsule cap) with an interior coating, (2) coating the exterior of a dissociated capsule with the exterior enteric coating, (3) filling the capsule body with a pharmaceutical composition (e.g., comprising a microbial cocktail) comprising bacterial isolates, and (4) closing the capsule cap over the capsule body, thereby encapsulating the composition in the dual-coated capsule.

In embodiments, one or more additional therapeutic agents can be combined with a pharmaceutical composition (e.g., comprising a microbial cocktail) and encapsulated by the capsule.

In embodiments, the bodies and caps of gelatin capsules (e.g., size #00) are separated. An exterior enteric coating suspension is prepared by dispersing one or more enteric coating polymers along with other components in a solution. The exterior enteric coating suspension is applied to the exterior of separated capsule bodies and caps, e.g., using a fluid bed Wurster column coater, Fluid Bed Coater, or an equivalent). The capsules are fluidized in the product bowl and the exterior enteric coating suspension is sprayed to produce the outer coating to a target of between about 2 mg/cm$^2$ and 6 mg/cm$^2$, e.g., 3 mg/cm$^2$. After completion of this step, the capsules are set to dry, e.g., between about 8 hours and 24 hours. After drying, exemplary capsules are weighed to calculate weight gain from the exterior enteric coating. Capsules can be inspected for irregularities.

In an embodiment, EUDRAGIT® S100 (poly(methacrylic acid, methylmethacrylate)), starch, triethyl citrate, and PlasACRYL™ T20 are dissolved in a solution of water, ethanol, and n-butanol, mixed, and then charged to a suitable spraying device. The solution is then spray coated on the outer surface of the capsule bodies and capsule caps to a target weight gain. The capsule bodies and capsule caps are allowed to dry for about 8 hours to about 24 hours, or longer, e.g., for a week, a month, or more, before further procession, e.g., filling with a microbial cocktail comprising bacterial isolates.

In embodiments, it may be desirable to provide an amount of the pharmaceutical composition (e.g., comprising a microbial cocktail) to a capsule's cap in addition to providing the composition in the capsule's body. In this embodiment, more of the composition will be included in a capsule and/or less air will be contained in a closed capsule.

In embodiments, the interior surface of a capsule is provided an internal coating.

Any of the above-described compositions (e.g., microbial cocktails), inner coatings, capsules, and outer coatings can be combined into a pharmaceutical composition described herein. A skilled artisan would know how to select an inner coating; capsule, and outer coating according to his/her present need, which could be based, for example, on the specific bacterial isolate(s) and/or the location in a subject (e.g., in the colon) where the bacterial isolate(s) should be delivered.

Additional relevant teachings are disclosed in WO 2007122374, which is hereby incorporated herein by reference in its entirety.

In embodiments, during the manufacture of a pharmaceutical composition, a pharmaceutically-acceptable cryoprotectant, lyoprotectant, binder, disintegrant, filler, preservative, acid suppressant, antacid, H2 antagonist, and proton pump inhibitor, or combination thereof can be mixed into the pharmaceutical composition (e.g., comprising a microbial cocktail) to promote desirable properties.

The pharmaceutical composition can additionally include a surface active agent. Surface active agents suitable for use include, but are not limited to, any pharmaceutically acceptable, non-toxic surfactant. Classes of surfactants suitable for use include, but are not limited to, polyethoxylated fatty acids, PEG-fatty acid diesters, PEG-fatty acid mono- and di-ester mixtures, polyethylene glycol glycerol fatty acid esters, alcohol-oil transesterification products, polyglycerized fatty acids, propylene glycol fatty acid esters, mixtures of propylene glycol esters-glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-olyoxypropylene block copolymers, sorbitan fatty acid esters, lower alcohol fatty acid esters, ionic surfactants, and mixtures thereof.

In some embodiments, compositions can comprise one or more surfactants including, but not limited to, sodium lauryl sulfate, polysorbate 20, polysorbate 40, polysorbate 60, polysorbate 80, and triethyl citrate.

The pharmaceutical composition can also contain pharmaceutically acceptable plasticizers to obtain the desired mechanical properties such as flexibility and hardness. Such plasticizers include, but are not limited to, triacetin, citric acid esters, triethyl citrate, phthalic acid esters, dibutyl sebacate, cetyl alcohol, polyethylene glycols, polysorbates or other plasticizers.

The pharmaceutical composition can also include one or more application solvents. Some of the more common solvents that can be used to apply, for example, a delayed-release coating composition include isopropyl alcohol, acetone, methylene chloride and the like.

The pharmaceutical composition can also include one or more alkaline materials. Alkaline material suitable for use in compositions include, but are not limited to, sodium, potassium, calcium, magnesium and aluminum salts of acids such as phosphoric acid, carbonic acid, citric acid and other aluminum/magnesium compounds. In addition, the alkaline material can be selected from antacid materials such as aluminum hydroxides, calcium hydroxides, magnesium hydroxides and magnesium oxide.

Besides inert diluents, the oral compositions can also include adjuvants such as sweetening, flavoring, and perfuming agents.

In various embodiments, the pharmaceutical compositions are formulated for systemic or local delivery. In an embodiment, administration is systemic. In another embodiment, it may be desirable to administer locally to the area in need of treatment.

Various methods can be used to formulate and/or deliver a pharmaceutical composition (e.g., comprising a microbial cocktail) described herein to a location of interest. For example, the pharmaceutical compositions can be formulated for delivery to the GI tract. The GI tract includes organs of the digestive system such as mouth, esophagus, stomach, duodenum, small intestine, large intestine and rectum and includes all subsections thereof (e.g. the small intestine may include the duodenum, jejunum and ileum; the large intestine may include the colon transversum, colon descendens, colon ascendens, colon sigmoidenum and cecum). For example, the compositions can be formulated for delivery to one or more of the stomach, small intestine, large intestine and rectum and includes all subsections thereof (e.g. duodenum, jejunum and ileum, colon transversum, colon descendens, colon ascendens, colon sigmoidenum and cecum). In some embodiments, the compositions described herein can be formulated to deliver to the upper or lower GI tract. In an embodiment, the compositions can be administered to a subject, by, for example, directly or indirectly contacting the mucosal tissues of the GI tract.

In various embodiments, the administration of the pharmaceutical compositions is into the GI tract via, for example, oral delivery, nasogastral tube, intestinal intubation (e.g. an enteral tube or feeding tube such as, for example, a jejunal tube or gastro-jejunal tube, etc.), direct infusion (e.g., duodenal infusion), endoscopy, colonoscopy, or enema.

In one aspect, a method comprises administering a pharmaceutical composition orally, by enema, or via rectal suppository. In one aspect, a pharmaceutical composition administered herein is formulated as an enteric coated (and/or acid-resistant) capsule or microcapsule, or formulated as part of or administered together with a food, a food additive, a dairy-based product, a soy-based product or a derivative thereof, a jelly, flavored liquid, ice block, ice cream, or a yogurt. In another aspect, a pharmaceutical composition administered herein is formulated as an acid-resistant enteric coated capsule. A pharmaceutical composition can be provided as a powder for sale in combination with a food or drink. A food or drink can be a dairy-based product or a soy-based product. In another aspect, a food or food supplement contains enteric-coated and/or acid-resistant microcapsules containing a pharmaceutical composition.

In an aspect, a pharmaceutical composition comprises a liquid culture. In another aspect, a pharmaceutical composition is homogenized, lyophilized, pulverized and powdered. It can then be infused, dissolved such as in saline, as an enema. Alternatively, the powder can be encapsulated as enteric-coated and/or acid-resistant delayed release capsules for oral administration. In an aspect, the powder can be double encapsulated with acid-resistant/delayed release capsules for oral administration. These capsules can take the form of enteric-coated and/or acid-resistant delayed release microcapsules. A powder can be provided in a palatable form for reconstitution for drinking or for reconstitution as a food additive. In a further aspect, a food is yogurt. In one aspect, a powder can be reconstituted to be infused via naso-duodenal infusion.

In another aspect, a pharmaceutical composition administered herein is in a liquid, frozen, freeze-dried, spray-dried, foam-dried, lyophilized, or powder form. In a further aspect, a pharmaceutical composition administered herein is formulated as a delayed or gradual enteric release form. In another aspect, a pharmaceutical composition administered herein comprises an excipient, a saline, a buffer, a buffering agent, or a fluid-glucose-cellobiose agar (RGCA) media. In another aspect, a pharmaceutical composition administered herein comprises a cryoprotectant. In one aspect, a cryoprotectant comprises polyethylene glycol, skim milk, erythritol, arabitol, sorbitol, glucose, fructose, alanine, glycine, proline, sucrose, lactose, ribose, trehalose, dimethyl sulfoxide (DMSO), glycerol, or a combination thereof.

In various embodiments, provided herein are modified-release formulations comprising one or more bacterial isolates (and/or additional therapeutic agents), wherein the formulation releases a substantial amount of the bacterial isolates (and/or additional therapeutic agents) into one or more regions of the GI tract. For example, the formulation can release at least about 60% of the bacterial isolates after the stomach and into one or more regions of the GI tract.

In various embodiments, the modified-release formulation can release at least 60% of the bacterial isolates (and/or additional therapeutic agents) after the stomach into one or more regions of the intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the bacterial isolates (and/or additional therapeutic agents) in the intestines.

In various embodiments, the modified-release formulation can release at least 60% of the bacterial isolates (and/or additional therapeutic agents) in the small intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the bacterial isolates (and/or additional therapeutic agents) in the small intestine (e.g., one or more of duodenum, jejunum, ileum, and ileocecal junction).

In various embodiments, the modified-release formulation can release at least 60% of the bacterial isolates (and/or additional therapeutic agents) in the large intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the bacterial isolates (and/or additional therapeutic agents) in the large intestine (e.g., one or more of cecum, ascending, transverse, descending or sigmoid portions of the colon, and rectum).

In some embodiments, the pharmaceutical composition is formulated for release in the stomach. In other embodiments, the pharmaceutical composition is formulated so as to not substantially release the bacterial isolates in the stomach.

In certain embodiments, the modified-release formulation releases the bacterial isolates (and/or additional therapeutic agents) at a specific pH. For example, in some embodiments, the modified-release formulation is substantially stable in an acidic environment and substantially unstable (e.g., dissolves rapidly or is physically unstable) in a near neutral to alkaline environment. In some embodiments, stability is indicative of not substantially releasing while instability is indicative of substantially releasing. For example, in some embodiments, the modified-release formulation is substantially stable at a pH of about 7.0 or less, or about 6.5 or less, or about 6.0 or less, or about 5.5 or less, or about 5.0 or less, or about 4.5 or less, or about 4.0 or less, or about 3.5 or less, or about 3.0 or less, or about 2.5 or less, or about 2.0 or less, or about 1.5 or less, or about 1.0 or less. In some embodiments, the present formulations are stable in lower pH areas and therefore do not substantially release in, for example, the stomach. In some embodiments, modified-release formulation is substantially stable at a pH of about 1 to about 4 or lower and substantially unstable at pH values that are greater. In these embodiments, the modified-release formulation does not substantially release in the stomach. In these embodiments, the modified-release formulation substantially releases in the small intestine (e.g. one or more of the duodenum, jejunum, and ileum) and/or large intestine (e.g. one or more of the cecum, ascending colon, transverse colon, descending colon, and sigmoid colon). In some embodiments, modified-release formulation is substantially stable at a pH of about 4 to about 5 or lower and consequentially is substantially unstable at pH values that are greater and therefore is not substantially released in the stomach and/or small intestine (e.g. one or more of the duodenum, jejunum, and ileum). In these embodiments, the modified-release formulation substantially releases in the large intestine (e.g. one or more of the cecum, ascending colon, transverse colon, descending colon, and sigmoid colon). In various embodiments, the pH values recited herein can be adjusted as known in the art to account for the state of the subject, e.g. whether in a fasting or postprandial state.

In some embodiments, the modified-release formulation is substantially stable in gastric fluid and substantially unstable in intestinal fluid and, accordingly, is substantially released in the small intestine (e.g. one or more of the duodenum, jejunum, and ileum) and/or large intestine (e.g. one or more of the cecum, ascending colon, transverse colon, descending colon, and sigmoid colon).

In some embodiments, the modified-release formulation is stable in gastric fluid or stable in acidic environments. These modified-release formulations release about 30% or less by weight of the pharmaceutical composition (e.g., comprising bacterial isolates of a microbial cocktail) in the modified-release formulation in gastric fluid with a pH of about 4 to about 5 or less, or simulated gastric fluid with a pH of about 4 to about 5 or less, in about 15, or about 30, or about 45, or about 60, or about 90 minutes. Modified-release formulations of can release from about 0% to about 30%, from about 0% to about 25%, from about 0% to about 20%, from about 0% to about 15%, from about 0% to about 10%, about 5% to about 30%, from about 5% to about 25%, from about 5% to about 20%, from about 5% to about 15%, from about 5% to about 10% by weight of the composition in the modified-release formulation in gastric fluid with a pH of 4-5, or less or simulated gastric fluid with a pH of 4-5 or less, in about 15, or about 30, or about 45, or about 60, or about 90 minutes. Modified-release formulations can release about 1%, about 2%, about 3%, about 4%, about 5%, about 6%, about 7%, about 8%, about 9%, or about 10% by weight of the total composition in the modified-release formulation in gastric fluid with a pH of 5 or less, or simulated gastric fluid with a pH of 5 or less, in about 15, or about 30, or about 45, or about 60, or about 90 minutes.

In some embodiments, the modified-release formulation is unstable in intestinal fluid. These modified-release formulations release about 70% or more by weight of the bacterial isolates and/or additional therapeutic agent in the modified-release formulation in intestinal fluid or simulated intestinal fluid in about 15, or about 30, or about 45, or about 60, or about 90 minutes. In some embodiments, the modified-release formulation is unstable in near neutral to alkaline environments. These modified-release formulations release about 70% or more by weight of the bacterial isolates and/or additional therapeutic agent in the modified-release formulation in intestinal fluid with a pH of about 4-5 or greater, or simulated intestinal fluid with a pH of about 4-5 or greater, in about 15, or about 30, or about 45, or about 60, or about 90 minutes. A modified-release formulation that is unstable in near neutral or alkaline environments can release 70% or more by weight of the pharmaceutical composition (e.g., comprising a microbial cocktail) in the modified-release formulation in a fluid having a pH greater than about 5 (e.g., a fluid having a pH of from about 5 to about 14, from about 6 to about 14, from about 7 to about 14, from about 8 to about 14, from about 9 to about 14, from about 10 to about 14, or from about 11 to about 14) in from about 5 minutes to about 90 minutes, or from about 10 minutes to about 90 minutes, or from about 15 minutes to about 90 minutes, or from about 20 minutes to about 90 minutes, or from about 25 minutes to about 90 minutes, or from about 30 minutes to about 90 minutes, or from about 5 minutes to about 60 minutes, or from about 10 minutes to about 60 minutes, or from about 15 minutes to about 60 minutes, or from about 20 minutes to about 60 minutes, or from about 25 minutes to about 90 minutes, or from about 30 minutes to about 60 minutes.

Examples of simulated gastric fluid and simulated intestinal fluid include, but are not limited to, those disclosed in the 2005 Pharmacopeia 23NF/28USP in Test Solutions at page 2858 and/or other simulated gastric fluids and simulated intestinal fluids known to those of skill in the art, for example, simulated gastric fluid and/or intestinal fluid prepared without enzymes.

In various embodiments, the modified-release formulation can be substantially stable in chyme. For example, there is, in some embodiments, a loss of less about 50% or about 40%, or about 30%, or about 20%, or about 10% of bacterial isolates activity in about 10, or 9, or 8, or 7, or 6, or 5, or 4, or 3, or 2, or 1 hour from administration.

In various embodiments, the modified-release formulations can be designed for immediate release (e.g. upon ingestion). In various embodiments, the modified-release formulations can have sustained-release profiles, i.e. slow release of the active ingredient(s) in the body (e.g., GI tract) over an extended period of time. In various embodiments, the modified-release formulations can have a delayed-release profile, i.e. not immediately release the active ingredient(s) upon ingestion; rather, postponement of the release of the active ingredient(s) until the composition is lower in the GI tract; for example, for release in the small intestine (e.g., one or more of duodenum, jejunum, ileum) or the large intestine (e.g., one or more of cecum, ascending, transverse, descending or sigmoid portions of the colon, and rectum). For example, a composition can be enteric coated to delay release of the active ingredient(s) until it reaches the small intestine or large intestine.

In various embodiments, the modified-release formulations can utilize one or more modified-release coatings such as delayed-release coatings to provide for effective, delayed yet substantial delivery of the bacterial isolates to the GI tract together with, optionally, additional therapeutic agents.

In one embodiment, the delayed-release coating includes an enteric agent that is substantially stable in acidic environments and substantially unstable in near neutral to alkaline environments. In an embodiment, the delayed-release coating contains an enteric agent that is substantially stable in gastric fluid. The enteric agent can be selected from, for example, solutions or dispersions of methacrylic acid copolymers, cellulose acetate phthalate, hydroxypropylmethyl cellulose phthalate, polyvinyl acetate phthalate, carboxymethylethylcellulose, and EUDRAGIT®-type polymer (poly (methacrylic acid, methylmethacrylate), hydroxypropyl methylcellulose acetate succinate, cellulose acetate trimellitate, shellac or other suitable enteric coating polymers. The EUDRAGIT®-type polymers include, for example, EUDRAGIT® FS 30D, L 30 D-55, L 100-55, L 100, L 12.5, L 12.5 P, RL 30 D, RL PO, RL 100, RL 12.5, RS 30 D, RS PO, RS 100, RS 12.5, NE 30 D, NE 40 D, NM 30 D, S 100, S 12.5, and S 12.5 P. Similar polymers include Kollicoat® MAE 30 DP and Kollicoat® MAE 100 P. In some embodiments, one or more of EUDRAGIT® FS 30D, L 30 D-55, L 100-55, L 100, L 12.5, L 12.5 P RL 30 D, RL PO, RL 100, RL 12.5, RS 30 D, RS PO, RS 100, RS 12.5, NE 30 D, NE 40 D, NM 30 D, S 100, S 12.5 S 12.5 P, Kollicoat® MAE 30 DP and Kollicoat® MAE 100 P is used. In various embodiments, the enteric agent can be a combination of the foregoing solutions or dispersions.

In certain embodiments, one or more coating system additives are used with the enteric agent. For example, one or more PlasACRYL™ additives can be used as an anti-tacking agent coating additive. Illustrative PlasACRYL™ additives include, but are not limited to, PlasACRYL™ HTP20 and PlasACRYL™T20.

In another embodiment, the delayed-release coating can degrade as a function of time when in aqueous solution without regard to the pH and/or presence of enzymes in the solution.

Such a coating can comprise a water insoluble polymer. Its solubility in aqueous solution is therefore independent of the pH. The term "pH independent" as used herein means that the water permeability of the polymer and its ability to release pharmaceutical ingredients is not a function of pH and/or is only very slightly dependent on pH. Such coatings can be used to prepare, for example, sustained release formulations. Suitable water insoluble polymers include pharmaceutically acceptable non-toxic polymers that are substantially insoluble in aqueous media, e.g., water, independent of the pH of the solution. Suitable polymers include, but are not limited to, cellulose ethers, cellulose esters, or cellulose ether-esters, i.e., a cellulose derivative in which some of the hydroxy groups on the cellulose skeleton are substituted with alkyl groups and some are modified with alkanoyl groups. Examples include ethyl cellulose, acetyl cellulose, nitrocellulose, and the like. Other examples of insoluble polymers include, but are not limited to, lacquer, and acrylic and/or methacrylic ester polymers, polymers or copolymers of acrylate or methacrylate having a low quaternary ammonium content, or mixture thereof and the like. Other examples of insoluble polymers include EUDRAGIT RS®, EUDRAGIT RL®, and EUDRAGIT NE®. Insoluble polymers can include polyvinyl esters, polyvinyl acetals, polyacrylic acid esters, butadiene styrene copolymers, and the like. In one embodiment, colonic delivery is achieved by use of a slowly eroding wax plug (e.g., various PEGS, including for example, PEG6000).

In a further embodiment, the delayed-release coating can be degraded by a microbial enzyme present in the gut flora. In one embodiment, the delayed-release coating can be degraded by bacteria present in the small intestine. In another embodiment, the delayed-release coating can be degraded by bacteria present in the large intestine.

In various embodiments, the modified release formulation can be designed for release in the colon. Various colon-specific delivery approaches can be utilized. For example, the modified release formulation can be formulated using a colon-specific drug delivery system (CODES) as described for example, in Li et al., AAPS PharmSciTech (2002), 3(4): 1-9, the entire contents of which are incorporated herein by reference. Drug release in such a system is triggered by colonic microflora coupled with pH-sensitive polymer coatings. For example, the formulation can be designed as a core tablet with three layers of polymer. The first coating is an acid-soluble polymer (e.g., EUDRAGIT E), the outer coating is enteric, along with a hydroxypropyl methylcellulose barrier layer interposed in between. In another embodiment, colon delivery can be achieved by formulating the pharmaceutical composition (e.g., comprising a microbial cocktail) with specific polymers that degrade in the colon such as, for example, pectin. The pectin can be further gelled or crosslinked with a cation such as a zinc cation. In an embodiment, the formulation is in the form of ionically crosslinked pectin beads which are further coated with a polymer (e.g., EUDRAGIT polymer). Additional colon specific formulations include, but are not limited to, pressure-controlled drug delivery systems (prepared with, for example, ethylcellulose) and osmotic controlled drug delivery systems (i.e., ORDS-CT).

Formulations for colon specific delivery of the bacterial isolates (and/or additional therapeutic agents), as described herein, can be evaluated using, for example, in vitro dissolution tests. For example, parallel dissolution studies in different buffers can be undertaken to characterize the behavior of the formulations at different pH levels. Alternatively, in vitro enzymatic tests can be carried out. For example, the formulations can be incubated in fermenters containing suitable medium for bacteria, and the amount of drug released at different time intervals is determined. Drug release studies can also be done in buffer medium containing enzymes or rat or guinea pig or rabbit cecal contents and the amount of drug released in a particular time is determined. In a further embodiment, in vivo evaluations can be carried out using animal models such as dogs, guinea pigs, rats, and pigs. Further, clinical evaluation of colon specific drug delivery formulations can be evaluated by calculating drug delivery index (DDI) which considers the relative ratio of RCE (relative colonic tissue exposure to the drug) to RSC (relative amount of drug in blood i.e. that is relative systemic exposure to the drug). Higher drug DDI indicates better colon drug delivery. Absorption of drugs from the colon can be monitored by colonoscopy and intubation.

In various embodiments, the present formulation provides for substantial uniform delivery of the bacterial isolates (and/or additional therapeutic agent) in the area of release in the GI tract. In an embodiment, the present formulation minimizes patchy or heterogeneous release of the bacterial isolates.

In various embodiments, the present formulations provide for release of multiple doses of the bacterial isolates along the GI tract. For example, the composition and/or formulation can release multiple doses of the bacterial isolates at different locations along the intestines, at different times, and/or at different pH. The overall release profile of such a formulation can be adjusted using, for example, multiple particle types or multiple layers. For example, in one embodiment, the first dose of the bacterial isolates can be formulated for release in, for example, the small intestine (e.g., one or more of duodenum, jejunum, ileum), whereas the second dose is formulated for delayed release in, for example, the large intestines (e.g., one or more of cecum, ascending, transverse, descending or sigmoid portions of the colon, and rectum). In another example, the first dose of the bacterial isolates can be formulated for release in, for example, the small intestine (e.g., one or more of duodenum, jejunum, ileum), whereas the second dose is formulated for delayed release in, for example, another part of the small intestine (e.g., one or more of duodenum, jejunum, ileum). In another embodiment, the first dose of the bacterial isolates can be formulated for release in, for example, the large intestine (e.g., one or more of cecum, ascending, transverse, descending or sigmoid portions of the colon, and rectum), whereas the second dose is formulated for delayed release in, for example, another part of the large intestine (e.g., one or more of cecum, ascending, transverse, descending or sigmoid portions of the colon, and rectum). In various embodiments, the composition and/or formulation can release at least one dose, at least two doses, at least three doses, at least four doses, or at least five doses of the bacterial isolates at different locations along the intestines, at different times, and/or at different pH.

In some embodiments, the bacterial isolates described herein are in the form of live, vegetative cells. In some embodiments, the bacterial isolates described herein are in the form of spores. In some embodiments, the bacterial isolates described herewith are lyophilized. By way of non-limiting example, lyophilization can be via methods known in the art, including those described in U.S. Pat. No. 7,799,328, the contents of which are hereby incorporated by reference in their entirety. In some embodiments, lyophilized bacterial isolates described herein are placed in an enterically coated soft gel or capsule.

In various embodiments, formulations can take the form of those described in one or more of U.S. Pat. Nos. 8,535,713 and 8,9117,77 and US Patent Publication Nos. 20120141585, 20120141531, 2006/001896, 2007/0292523, 2008/0020018, 2008/0113031, 2010/0203120, 2010/0255087, 2010/0297221, 2011/0052645, 2013/0243873, 2013/0330411, 2014/0017313, and 2014/0234418, the contents of which are hereby incorporated by reference in their entirety.

In various embodiments, formulations can take the form of those as described in International Patent Publication No. WO 2008/135090, the contents of which are hereby incorporated by reference in their entirety.

In various embodiments, formulations can take the form of those described in one or more of U.S. Pat. Nos. 4,196,564; 4,196,565; 4,247,006; 4,250,997; 4,268,265; 5,317,849; 6,572,892; 7,712,634; 8,074,835; 8,398,912; 8,440,224; 8,557,294; 8,646,591; 8,739,812; 8,810,259; 8,852,631; and 8,911,788 and US Patent Publication Nos. 2014/0302132; 2014/0227357; 20140088202; 20130287842; 2013/0295188; 2013/0307962; and 20130184290, the contents of which are hereby incorporated by reference in their entirety.

Administration and Dosage

It will be appreciated that the actual dose of a pharmaceutical composition described herein (e.g., a microbial cocktail comprising bacterial isolates and/or additional therapeutic agents) will vary according to, for example, the particular dosage form and the mode of administration to a subject. Many factors that may modify the action of the bacterial isolates (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

In various embodiments, the dose of the pharmaceutical composition (e.g., comprising a microbial cocktail) is effective to modulate a patient's microbiome to favor an ecological balance, i.e. treating or preventing a disorder related to intestinal dysbiosis described herein (including a gastrointestinal disorder).

In one aspect, a pharmaceutically active or therapeutically effective dose of a bacterial isolate administered to a subject (i.e., in single or multiple administrations) to treat at least one symptom of a disorder related to a gut dysbiosis comprises at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, or at least $10^{15}$ CFUs of the bacterial isolate. In another aspect, a pharmaceutically active or therapeutically effective dose of a bacterial isolate administered to a subject (i.e., in single or multiple administrations) to treat at least one symptom of a disorder related to a gut dysbiosis comprises at most $10^5$, at most $10^6$, at most $10^7$, at most $10^8$, at most $10^9$, at most $10^{10}$, at most $10^{11}$, at most $10^{12}$, at most $10^{13}$, at most $10^{14}$, or at most $10^{15}$ CFUs of the bacterial isolate. In a further aspect, a pharmacologically active or therapeutically effective dose of a bacterial isolate administered to a subject (i.e., in single or multiple administrations) to treat at least one symptom of a disorder related to a gut dysbiosis is selected from the group consisting of: from $10^8$ CFUs to $10^{14}$ CFUs, from $10^9$ CFUs to $10^{13}$ CFUs, from $10^{10}$ CFUs to $10^{12}$ CFUs, from $10^{10}$ CFUs to $10^{11}$ CFUs, from $10^9$ CFUs to $10^{14}$ CFUs, from $10^9$ CFUs to $10^{12}$ CFUs, from $10^9$ CFUs to $10^{11}$ CFUs, from $10^9$ CFUs to $10^{10}$ CFUs, from $10^{10}$ CFUs to $10^{14}$ CFUs, from $10^{10}$ CFUs to $10^{13}$ CFUs, from $10^{11}$ CFUs to $10^{14}$ CFUs, from $10^{11}$ CFUs to $10^{13}$ CFUs, from $10^{12}$ CFUs to $10^{14}$ CFUs, and from $10^{13}$ CFUs to $10^{14}$ CFUs of the bacterial isolate.

In an aspect, a pharmaceutical composition comprises one or more bacterial isolates, with each bacterial isolate present in each unit dose at one of the foregoing pharmaceutically active or therapeutically effective doses in a unit weight of about 0.2, 0.4, 0.6, 0.8 or 1.0 gram, or a unit volume of about 0.2, 0.4, 0.6, 0.8 or 1.0 milliliter.

In one aspect, a pharmaceutically active or therapeutically effective dose of a bacterial isolate administered to a subject (i.e., in single or multiple administrations) to treat at least one symptom of a disorder related to a gut dysbiosis comprises at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, or at least $10^{15}$ cells or spores of the bacterial isolate. In another aspect, a pharmaceutically active or therapeutically effective dose of a bacterial isolate administered to a subject i.e. in single or multiple administrations) to treat at least one symptom of a disorder related to a gut dysbiosis comprises at most $10^5$, at most $10^6$, at most $10^7$, at most $10^8$, at most $10^9$, at most $10^{10}$, at most $10^{11}$, at most $10^{12}$, at most $10^{13}$, at most $10^{14}$, or at most $10^5$ total cells or spores of the bacterial isolate. In a further aspect, a pharmacologically active or therapeutically effective dose of a bacterial isolate administered to a subject (i.e., in single or multiple administrations) to treat at least one symptom of a disorder related to a gut dysbiosis is selected from the group consisting of: from $10^8$ to $10^{14}$, from $10^9$ to $10^{13}$, from $10^{10}$ to $10^{12}$, from $10^{10}$ to $10^{11}$, from $10^9$ to $10^{14}$, from $10^9$ to $10^{12}$, from $10^9$ to $10^{11}$, from $10^9$ to $10^{10}$, from $10^{10}$ to $10^{14}$, from $10^{10}$ to $10^{13}$, from $10^{11}$ to $10^{14}$, from $10^{11}$ to $10^{13}$, from $10^{12}$ to $10^{14}$, and from $10^{13}$ to $10^{14}$ cells or spores of the bacterial isolate.

In an aspect, the pharmaceutically active or therapeutically effective dose cell count of a bacterial isolate is directed to live cells. In one aspect, a pharmaceutical composition comprises one or more bacterial isolates, with each bacterial isolates present in each dosage unit at one of the foregoing pharmaceutically active or therapeutically effective doses in a unit weight of about 0.2, 0.4, 0.6, 0.8 or 1.0 gram, or a unit volume of about 0.2, 0.4, 0.6, 0.8 or 1.0 milliliter.

In an aspect, a pharmaceutical composition described herein is in the form of a capsule, and each capsule comprises at least $10^5$, at least $10^6$, at least $10^7$, at least $10^8$, at least $10^9$, at least $10^{10}$, at least $10^{11}$, at least $10^{12}$, at least $10^{13}$, at least $10^{14}$, or at least $10^{15}$ cells or spores. In an aspect, a pharmaceutical composition described herein is in the form of a capsule, and each capsule comprises from $10^8$ to $10^{14}$, from $10^9$ to $10^{13}$, from $10^{10}$ to $10^{12}$, from $10^{10}$ to $10^{11}$, from $10^9$ to $10^{14}$, from $10^9$ to $10^{12}$, from $10^9$ to $10^{11}$, from $10^9$ to $10^{10}$, from $10^{10}$ to $10^{14}$, from $10^{10}$ to $10^{13}$, from $10^{11}$ to $10^{14}$, from $10^{11}$ to $10^{13}$, from $10^{12}$ to $10^{14}$, or from $10^{13}$ to $10^{14}$ cells or spores of a bacterial isolate.

In embodiments, a pharmaceutical composition comprises a microbial cocktail that comprises multiple bacterial isolates. In embodiments, at least two bacterial isolates are present in the microbial cocktail at about the same amounts (e.g., about the same number of total cells and/or about the same number of live cells). In embodiments, at least three bacterial isolates, at least four bacterial isolates, at least five bacterial isolates, at least six bacterial isolates, at least seven bacterial isolates, at least eight bacterial isolates, at least nine bacterial isolates, at least ten bacterial isolates, or more than ten bacterial isolates are present in the pharmaceutical composition at about the same amounts (e.g., about the same number of total cells and/or about the same number of live cells). In embodiments, all of the bacterial isolates of a microbial cocktail are present in about the same amounts.

In embodiments, at least two bacterial isolates of a microbial cocktail described herein are present in the microbial cocktail at different amounts (e.g., different numbers of total cells and/or different numbers of live cells). In embodiments, at least three, at least four, at least five, at least six, at least seven, at least eight, at least nine, at least ten, or more than ten bacterial isolates are present in the microbial cocktail at different amounts.

In embodiments, first and second bacterial isolates of a microbial cocktail are present in the microbial cocktail at different amounts, and a relative proportion of the first and second bacterial isolates to each other in the microbial cocktail is about the same as the relative proportion of first and second bacterial strains corresponding to the first and second bacterial isolates in a microbiota of a fecal sample of a human (e.g., a fecal microbiota of a donor of one or more of the first and second bacterial isolates or a fecal microbiota of a subject administered the first and second bacterial isolates).

In embodiments, first and second bacterial isolates of a microbial cocktail are present in the microbial cocktail at different amounts, and a relative proportion of the first and second bacterial isolates to each other in the microbial cocktail is different than or does not resemble a proportion of first and second bacterial strains corresponding to the first and second bacterial isolates in a microbiota of a fecal sample of a human (e.g., a fecal microbiota of a donor of one or more of the first and second bacterial isolates or a fecal microbiota of a subject administered the first and second bacterial isolates).

In embodiments, a pharmaceutical composition comprises one or more bacterial isolates at an amount or dosage which is at or above the minimum amount or dosage of the bacterial isolate required to be administered to a subject for engraftment of the bacterial isolate to occur in the intestine of the subject. For example, a minimum dosage of the bacterial isolate required for engraftment of the bacterial isolate into the intestine of the subject can be at least $10^6$ cells, at least $10^7$ cells, at least $10^8$ cells, at least $10^9$ cells, at least $10^{10}$ cells, at least $10^{11}$ cells, or at least $10^{12}$ cells. In embodiments a first and second bacterial isolate of a microbial cocktail engraft in the intestine of a subject at different minimal dosages or amounts, and a dosage or amount of each of the first and second bacterial isolate in the microbial cocktail varies corresponding to the respective minimal dosage or amount required for engraftment of the respective bacterial isolate.

In embodiments, a microbial cocktail comprises *Odoribacter splanchnicus* and *Faecalibacterium prausnitzii*, and the *O. splanchnicus* cells are more abundant in the microbial cocktail than the *F. prausnitzii* cells. In embodiments, a microbial cocktail comprises *O. splanchnicus* and *Faecalibacterium prausnitzii*, and the *O. splanchnicus* cells are less abundant in the microbial cocktail than the *F. prausnitzii* cells. In embodiments, a microbial cocktail comprises *O. splanchnicus* and *Faecalibacterium prausnitzii*, and the *O. splanchnicus* cells are more abundant in the microbial cocktail than the *F. prausnitzii* cells. In embodiments, a microbial cocktail comprises *O. splanchnicus* and *Eubacterium rectale*, and the *O. splanchnicus* cells are less abundant in the microbial cocktail than the *E. rectale* cells. In embodiments, a microbial cocktail comprises *O. splanchnicus* and *Akkermansia muciniphila*, and the *O. splanchnicus* cells are more abundant in the microbial cocktail than the *A. muciniphila* cells. In embodiments, a microbial cocktail comprises *O. splanchnicus* and *Bacteroides cellulosilyticus*, and the *O. splanchnicus* cells are more abundant in the microbial cocktail than the *B. cellulosilyticus* cells. In embodiments, a microbial cocktail comprises *O. splanchnicus* and *Roseburia faecis*, and the *O. splanchnicus* cells are less abundant in the microbial cocktail than the *R. faecis* cells. In embodiments, a microbial cocktail comprises *O. splanchnicus* and *Alistipes shahii*, and the *O. splanchnicus* cells are more abundant in the microbial cocktail than the *A. shahii* cells.

In embodiments, a microbial cocktail comprises *Eubacterium rectale*, the cells of which are more abundant in the microbial cocktail than the cells of any other single bacterial isolate of the microbial cocktail (i.e., *E. rectale* is the most abundant bacterial isolate in the microbial cocktail). In embodiments, a microbial cocktail comprises *E. rectale* and *F. prausnitzii*, and the *E. rectale* cells are more abundant in the microbial cocktail than the *F. prausnitzii* cells. In embodiments, a microbial cocktail comprises *E. rectale* and *A. shahii*, and the *E. rectale* cells are more abundant in the microbial cocktail than the *A. shahii* cells. In embodiments, a microbial cocktail comprises *E. rectale* and *R. faecis*, and the *E. rectale* cells are more abundant in the microbial cocktail than the *R. faecis* cells. In embodiments, a microbial cocktail comprises *E. rectale* and *A. muciniphila*, and the *E. rectale* cells are more abundant in the microbial cocktail than the *A. muciniphila* cells.

In embodiments, a microbial cocktail comprises *R. faecis* and *F. prausnitzii*, and the *R. faecis* cells are more abundant than the *F. prausnitzii* cells. In embodiments, a microbial cocktail comprises *R. faecis* and *F. prausnitzii*, and the *R. faecis* cells are more abundant than the *F. prausnitzii* cells. In embodiments, a microbial cocktail comprises *R. faecis* and *A. muciniphila*, and the *R. faecis* cells are more abundant than the *A. muciniphila* cells. In embodiments, a microbial cocktail comprises *R. faecis* and *A. shahii*, and the *R. faecis* cells are more abundant than the *A. shahii* cells. In embodiments, a microbial cocktail comprises *R. faecis* and *B. cellusloilyticus*, and the *R. faecis* cells are more abundant than the *B. cellulosilyticus* cells.

In embodiments, a microbial cocktail comprises *B. cellulosilyticus*, the cells of which are less abundant in the microbial cocktail than the cells of any other single bacterial isolate of the microbial cocktail (i.e., *B. cellulosilyticus* is the least abundant bacterial isolate in the microbial cocktail). In embodiments, a microbial cocktail comprises *B. cellulosilyticus* and *A. shahii*, and the *B. cellulosilyticus* cells are less abundant than the *A. shahii* cells. In embodiments, a microbial cocktail comprises *B. cellulosilyticus* and *A. muciniphila*, and the *B. cellulosilyticus* cells are less abundant than the *A. muciniphila* cells. In embodiments, a microbial cocktail comprises *B. cellulosilyticus* and *F. prausnitzii*, and the *B. cellulosilyticus* cells are less abundant than the *F. prausnitzii* cells.

In embodiments, a microbial cocktail comprises *A. shahii* and *A. muciniphila*, and the *A. shahii* cells are less abundant than the *A. muciniphila* cells. In embodiments, a microbial cocktail comprises *A. shahii* and *F. prausnitzii*, and the *A. shahii* cells are less abundant than the *F. prausnitzii* cells.

In embodiments, a microbial cocktail comprises multiple bacterial isolates belonging to the species *F. prausnitzii*, and the cells of one of the bacterial isolates are more abundant than the cells of at least one of the other bacterial isolates in the microbial cocktail. In embodiments, a microbial cocktail comprises two bacterial isolates belonging to the species *F. prausnitzii*, and the cells of one of the bacterial isolates are more abundant than the cells of the other bacterial isolate of the microbial cocktail.

In embodiments, a pharmaceutical composition comprises *O. splanchnicus* at a dosage of at least $10^8$ cells. In embodiments, a pharmaceutical composition comprises *O. splanchnicus* at a dosage of between $10^8$ to $10^9$ cells. In embodiments, a pharmaceutical composition comprises *O. splanchnicus* at a dosage of not more than $10^9$ cells. In embodiments, a pharmaceutical composition comprises *O. splanchnicus* at a dosage of at least $10^9$ cells.

In embodiments, a pharmaceutical composition comprises *B. cellulosilyticus* at a dosage of at least $10^7$ cells. In embodiments, a pharmaceutical composition comprises *B. cellulosilyticus* at a dosage of between $10^7$ to $10^8$ cells. In embodiments, a pharmaceutical composition comprises *B. cellulosilyticus* at a dosage of at least $10^8$ cells. In embodiments, a pharmaceutical composition comprises *B. cellulosilyticus* at a dosage of between $10^8$ to $10^9$ cells. In embodiments, a pharmaceutical composition comprises *B. cellulosilyticus* at a dosage of not more than $10^9$ cells. In embodiments, a pharmaceutical composition comprises *B. cellulosilyticus* at a dosage of at least $10^9$ cells.

In embodiments, a pharmaceutical composition comprises *A. shahii* at a dosage of at least $10^8$ cells. In embodiments, a pharmaceutical composition comprises *A. shahii* at a dosage of between $10^8$ to $10^9$ cells. In embodiments, a pharmaceutical composition comprises *A. shahii* at a dosage of not more than $10^9$ cells. In embodiments, a pharmaceutical composition comprises *A. shahii* at a dosage of at least $10^9$ cells.

In embodiments, a pharmaceutical composition comprises *A. muciniphila* at a dosage of at least $10^8$ cells. In embodiments, a pharmaceutical composition comprises *A. muciniphila* at a dosage of between $10^8$ to $10^9$ cells. In embodiments, a pharmaceutical composition comprises *A. muciniphila* at a dosage of not more than $10^9$ cells. In embodiments, a pharmaceutical composition comprises *A. muciniphila* at a dosage of at least $10^9$ cells.

In embodiments, a pharmaceutical composition comprises *R. faecis* at a dosage of at least $10^8$ cells. In embodiments, a pharmaceutical composition comprises *R. faecis* at a dosage of between $10^8$ to $10^9$ cells. In embodiments, a pharmaceutical composition comprises *A. muciniphila* at a dosage of not more than $10^9$ cells. In embodiments, a pharmaceutical composition comprises *A. muciniphila* at a dosage of at least $10^9$ cells. In embodiments, a pharmaceutical composition comprises *R. faecis* at a dosage of between 109 to $10^{10}$ cells. In embodiments, a pharmaceutical composition comprises *A. muciniphila* at a dosage of not more than $10^{10}$ cells.

In embodiments, a pharmaceutical composition comprises *F. prausnitzii* at a dosage of at least $10^8$ cells. In embodiments, a pharmaceutical composition comprises *F. prausnitzii* at a dosage of between $10^8$ to $10^9$ cells. In embodiments, a pharmaceutical composition comprises *F. prausnitzii* at a dosage of not more than $10^9$ cells. In embodiments, a pharmaceutical composition comprises *F. prausnitzii* at a dosage of at least $10^9$ cells. In embodiments, a pharmaceutical composition comprises *R. faecis* at a dosage of between $10^9$ to $10^{10}$ cells. In embodiments, a pharmaceutical composition comprises *F. prausnitzii* at a dosage of not more than $10^{10}$ cells. In embodiments, a pharmaceutical composition comprises *F. prausnitzii* at a dosage of at least $10^{10}$ cells. In embodiments, a pharmaceutical composition comprises *F. prausnitzii* at a dosage of not more than $10^{11}$ cells.

In embodiments, a pharmaceutical composition comprises *E. rectale* at a dosage of at least $10^8$ cells. In embodiments, a pharmaceutical composition comprises *E. rectale* at a dosage of between $10^8$ to $10^9$ cells. In embodiments, a pharmaceutical composition comprises *E. rectale* at a dosage of not more than $10^9$ cells. In embodiments, a pharmaceutical composition comprises *E. rectale* at a dosage of at least $10^9$ cells. In embodiments, a pharmaceutical composition comprises *E. rectale* at a dosage of between $10^9$ to $10^{10}$ cells. In embodiments, a pharmaceutical composition comprises *E. rectale* at a dosage of not more than $10^{10}$ cells. In embodiments, a pharmaceutical composition comprises *E. rectale* at a dosage of at least $10^{10}$ cells. In embodiments, a pharmaceutical composition comprises *E. rectale* at a dosage of between $10^{10}$ to $10^{11}$ cells. In embodiments, a pharmaceutical composition comprises *E. rectale* at a dosage of not more than $10^{11}$ cells. In embodiments, a pharmaceutical composition comprises *E. rectale* at a dosage of at least $10^{11}$ cells.

In embodiments, every about 200 mg of a pharmaceutical composition comprises a pharmacologically active dose. In embodiments, every about 75, 100, 125, 150, 175, 200, 250, 300, 350, 400, 450, 500, 750, 1000, 1500, or 2000 mg of a pharmaceutical composition comprises a pharmacologically active dose.

Individual doses of the pharmaceutical composition (e.g., comprising a microbial cocktail) can be administered in unit dosage forms (e.g., tablets or capsules) containing, for example, from about 0.01 mg to about 5,000 mg, from about 0.01 mg to about 4,000 mg, from about 0.01 mg to about 3,000 mg, from about 0.01 mg to about 2,000 mg, from about 0.01 mg to about 1,000 mg, from about 0.01 mg to about 950 mg, from about 0.01 mg to about 900 mg, from about 0.01 mg to about 850 mg, from about 0.01 mg to about 800 mg, from about 0.01 mg to about 750 mg, from about 0.01 mg to about 700 mg, from about 0.01 mg to about 650 mg, from about 0.01 mg to about 600 mg, from about 0.01 mg to about 550 mg, from about 0.01 mg to about 500 mg, from about 0.01 mg to about 450 mg, from about 0.01 mg to about 400 mg, from about 0.01 mg to about 350 mg, from about 0.01 mg to about 300 mg, from about 0.01 mg to about 250 mg, from about 0.01 mg to about 200 mg, from about 0.01 mg to about 150 mg, from about 0.01 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from about 0.1 mg to about 40 mg, from about 0.1 mg to about 30 mg, from about 0.1 mg to about 20 mg, from about 0.1 mg to about 10 mg, from about 0.1 mg to about 5 mg, from about 0.1 mg to about 3 mg, from about 0.1 mg to about 1 mg of the active ingredient per unit dosage form, or from about 5 mg to about 80 mg per unit dosage form. For example, a unit dosage form can include about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1,000 mg, about 2,000 mg, about 3,000 mg, about 4,000 mg, or about 5,000 mg of the active ingredient, inclusive of all values and ranges therebetween.

In one embodiment, the pharmaceutical composition (e.g., comprising a microbial cocktail) is administered at an amount of from about 0.01 mg to about 100 mg daily, an amount of from about 0.01 mg to about 5,000 mg daily, about 0.01 mg to about 4,000 mg daily, about 0.01 mg to about 3,000 mg daily, about 0.01 mg to about 2,000 mg daily, about 0.01 mg to about 1,000 mg daily, from about 0.01 mg to about 950 mg daily, from about 0.01 mg to about 900 mg daily, from about 0.01 mg to about 850 mg daily, from about 0.01 mg to about 800 mg daily, from about 0.01 mg to about 750 mg daily, from about 0.01 mg to about 700 mg daily, from about 0.01 mg to about 650 mg daily, from about 0.01 mg to about 600 mg daily, from about 0.01 mg to about 550 mg daily, from about 0.01 mg to about 500 mg daily, from about 0.01 mg to about 450 mg daily, from about 0.01 mg to about 400 mg daily, from about 0.01 mg to about 350 mg daily, from about 0.01 mg to about 300 mg daily, from about 0.01 mg to about 250 mg daily, from about 0.01 mg to about 200 mg daily, from about 0.01 mg to about 150 mg daily, from about 0.1 mg to about 100 mg daily, from about 0.1 mg to about 95 mg daily, from about 0.1 mg to about 90 mg daily, from about 0.1 mg to about 85 mg daily, from about 0.1 mg to about 80 mg daily, from about 0.1 mg to about 75 mg daily, from about 0.1 mg to about 70 mg daily, from about 0.1 mg to about 65 mg daily, from about 0.1 mg to about 60 mg daily, from about 0.1 mg to about 55 mg daily, from about 0.1 mg to about 50 mg daily, from about 0.1 mg to about 45 mg daily, from about 0.1 mg to about 40 mg daily, from about 0.1 mg to about 35 mg daily, from about 0.1 mg to about 30 mg daily, from about 0.1 mg to about 25 mg daily, from about 0.1 mg to about 20 mg daily, from about 0.1 mg to about 15 mg daily, from about 0.1 mg to about 10 mg daily, from about 0.1 mg to about 5 mg daily, from about 0.1 mg to about 3 mg daily, from about 0.1 mg to about 1 mg daily, or from about 5 mg to about 80 mg daily. In various embodiments, the bacterial isolates (and/or additional therapeutic agents) is administered at a daily dose of about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1,000 mg, about 2,000 mg, about 3,000 mg, about 4,000 mg, or about 5,000 mg inclusive of all values and ranges therebetween.

In some embodiments, a suitable dosage of the pharmaceutical composition (e.g., comprising a microbial cocktail) is in a range of about 0.01 mg/kg to about 100 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, about 20 mg/kg body weight, about 30 mg/kg body weight, about 40 mg/kg body weight, about 50 mg/kg body weight, about 60 mg/kg body weight, about 70 mg/kg body weight, about 80 mg/kg body weight, about 90 mg/kg body weight, or about 100 mg/kg body weight, inclusive of all values and ranges therebetween. In other embodiments, a suitable dosage of the composition in a range of about 0.01 mg/kg to about 100 mg/kg of body weight, in a range of about 0.01 mg/kg to about 90 mg/kg of body weight, in a range of about 0.01 mg/kg to about 80 mg/kg of body weight, in a range of about 0.01 mg/kg to about 70 mg/kg of body weight, in a range of about 0.01 mg/kg to about 60 mg/kg of body weight, in a range of about 0.01 mg/kg to about 50 mg/kg of body weight, in a range of about 0.01 mg/kg to about 40 mg/kg of body weight, in a range of about 0.01 mg/kg to about 30 mg/kg of body weight, in a range of about 0.01 mg/kg to about 20 mg/kg of body weight, in a range of about 0.01 mg/kg to about 10 mg/kg of body weight, in a range of about 0.01 mg/kg to about 9 mg/kg of body weight, in a range of about 0.01 mg/kg to about 8 mg/kg of body weight, in a range of about 0.01 mg/kg to about 7 mg/kg of body weight, in a range of 0.01 mg/kg to about 6 mg/kg of body weight, in a range of about 0.05 mg/kg to about 5 mg/kg of body weight, in a range of about 0.05 mg/kg to about 4 mg/kg of body weight, in a range of about 0.05 mg/kg to about 3 mg/kg of body weight, in a range of about 0.05 mg/kg to about 2 mg/kg of body weight, in a range of about 0.05 mg/kg to about 1.5 mg/kg of body weight, or in a range of about 0.05 mg/kg to about 1 mg/kg of body weight.

In accordance with certain embodiments, the pharmaceutical composition (e.g., comprising a microbial cocktail) can be administered, for example, more than once daily, about once per day, about every other day, about every third day, about once a week, about once every two weeks, about once every month, about once every two months, about once every three months, about once every six months, or about once every year.

In embodiments, a pharmaceutical composition can be administered to a patient in need thereof at least once daily for at least two consecutive days. In embodiments, a pharmaceutical composition is administered at least once daily for at least 3, 4, 5, 6, 7, 8, 9, 10, 11, 12, 13, 14, or 15 consecutive days. In embodiments, a pharmaceutical composition is administered at least once daily for at least 1, 2, 3, 4, 5, 6, 7, 8, 9, 10, 11, or 12 consecutive weeks. In embodiments, a pharmaceutical composition is administered at least twice, three times, four times, or five times per week for at least 1, 2, 3, 4, 5, 6, 7, 8, 9, 10, 11, or 12 consecutive weeks. In embodiments, a pharmaceutical composition is administered at least once daily for at most 4, 5, 6, 7, 8, 9, 10, 11, 12, 13, 14, 15, 16, 17, 18, 19, or 20 consecutive days or weeks. In embodiments, a pharmaceutical composition is administered at least once daily for at most 1, 2, 3, 4, 5, 6, 7, 8, 9, 10, 11, or 12 consecutive weeks or months. In embodiments, a pharmaceutical composition is administered at least once for at least 1, 2, 3, 4, 5, 6, 7, 8, 9, 10, 11, or 12 consecutive months or years, chronically for a subject's entire life span, or an indefinite period of time.

In embodiments, a pharmaceutical composition can be administered to a patient in need thereof at least twice daily for at least two consecutive days. In embodiments, a pharmaceutical composition is administered at least twice daily for at least 3, 4, 5, 6, 7, 8, 9, 10, 11, 12, 13, 14, or 15 consecutive days. In embodiments, a pharmaceutical composition is administered at least twice daily for at least 1, 2, 3, 4, 5, 6, 7, 8, 9, 10, 11, or 12 consecutive weeks. In embodiments, a pharmaceutical composition is administered at least twice daily for at most 4, 5, 6, 7, 8, 9, 10, 11, 12, 13, 14, 15, 16, 17, 18, 19, or 20 consecutive days or week.

In embodiments, a pharmaceutical composition is administered at least twice daily for at most 1, 2, 3, 4, 5, 6, 7, 8, 9, 10, 11, or 12 consecutive weeks or months. In embodiments, a pharmaceutical composition is administered at least twice for at least 1, 2, 3, 4, 5, 6, 7, 8, 9, 10, 11, or 12 consecutive months or years, chronically for a subject's entire life span, or an indefinite period of time.

In embodiments, a pharmaceutical composition can be administered to a patient in need thereof at least three times daily for at least two consecutive days. In embodiments, a pharmaceutical composition is administered at least three times daily for at least 3, 4, 5, 6, 7, 8, 9, 10, 11, 12, 13, 14, or 15 consecutive days. In embodiments, a pharmaceutical composition is administered at least three times daily for at least 1, 2, 3, 4, 5, 6, 7, 8, 9, 10, 11, or 12 consecutive weeks. In embodiments, a pharmaceutical composition is administered at least three times daily for at most 4, 5, 6, 7, 8, 9, 10, 11, 12, 13, 14, 15, 16, 17, 18, 19, or 20 consecutive days or weeks. In embodiments, a pharmaceutical composition is administered at least three times daily for at most 1, 2, 3, 4, 5, 6, 7, 8, 9, 10, 11, or 12 consecutive weeks or months. In embodiments, a pharmaceutical composition is administered at least three times for at least 1, 2, 3, 4, 5, 6, 7, 8, 9, 10, 11, or 12 consecutive months or years, chronically for a subject's entire life span, or an indefinite period of time.

In embodiments, a pharmaceutical composition can be administered to a patient in need thereof at a dosing schedule of at least once or twice daily for at least three consecutive days or weeks. In embodiments, a dose is administered at least once, twice, or three times daily for a period between 1 and 12 weeks, between 2 and 12 weeks, between 3 and 12 weeks, between 4 and 12 weeks, between 5 and 12 weeks, between 6 and 12 weeks, between 7 and 12 weeks, between 8 and 12 weeks, between 9 and 12 weeks, between 10 and 12 weeks, between 1 and 2 weeks, between 2 and 3 weeks, between 3 and 4 weeks, between 4 and 5 weeks, between 5 and 6 weeks, between 6 and 7 weeks, between 7 and 8 weeks, between 8 and 9 weeks, between 9 and 10 weeks, or between 10 and 11 weeks.

In embodiments, a pharmaceutical composition can be administered to a patient in need thereof at a dosing schedule of once-a-week, twice-a-week, or thrice-a-week. The term "once-a-week" means that a dose is administered typically only once in a week, for example, on the same day of each week. "Twice-a-week" means that a dose is administered typically only two times in a week, for example, on the same two days of each weekly period. "Thrice-a-week" means that a dose is administered typically only three times in a week, for example, on the same three days of each weekly period.

In embodiments, a pharmaceutical composition can be administered to a patient in need thereof, wherein the administration comprises a first dosing schedule followed by a second dosing schedule. In embodiments, a first dosing schedule comprises a treatment or induction dose. In embodiments, a second dosing schedule comprises a maintenance dose. For example, a pharmaceutically active maintenance dose of a second dosage schedule can be lower than or equal to a pharmaceutically active induction dose of a first dosing schedule. In other examples, a maintenance dose of a second dosing schedule can be higher than an induction dose of a first dosing schedule.

At least one of a first and second dosing schedule for administering a pharmaceutical composition can comprise administration of the composition at least once daily for at least one day. In embodiments, at least one of a first or second dosing schedule comprises administration of the composition at least once daily for at least 2, 3, 4, 5, 6, 7, 8, 9, 10, 11, 12, 13, 14, or 15 consecutive days. In embodiments, at least one of a first or second dosing schedule comprises administration of the composition at least once daily for at least 1, 2, 3, 4, 5, 6, 7, 8, 9, 10, 11, or 12 consecutive weeks. In embodiments, at least one of a first or second dosing schedule comprises administration of the composition for at most 4, 5, 6, 7, 8, 9, 10, 11, 12, 13, 14, 15, 16, 17, 18, 19, or 20 consecutive days or weeks. In embodiments, at least one of a first or second dosing schedule comprises administration of the composition for at most 1, 2, 3, 4, 5, 6, 7, 8, 9, 10, 11, or 12 consecutive weeks or months. In embodiments, at least one of a first or second dosing schedule comprises administration of the composition for at least 1, 2, 3, 4, 5, 6, 7, 8, 9, 10, 11, or 12 consecutive months or years, chronically for a subject's entire life span, or an indefinite period of time.

In embodiments, at least one of a first or second dosing schedule used in a method can be once-a-week, twice-a-week, or thrice-a-week.

In embodiments, at least one of a first and second dosing schedule can last for at least about 2, 4, 6, 8, 10, 12, 18, 24, 36, 48, 72, or 96 months. In embodiments, a second dosing schedule lasts permanently, for a treated subject's entire life span, or an indefinite period of time. In embodiments, at least one of a first and second dosing schedule is a continuous dosing schedule. In embodiments, at least one of a first and second dosing schedule is an intermittent dosing schedule. In embodiments, at least one of a first and second dosing schedule is an intermittent dosing schedule comprising a treatment period of at least 1, 2, 3, 4, 5, 6, 7, 8, 9, 10, 11, 12, 13, or 14 days followed by a resting period of at least 1, 2, 3, 4, 5, 6, 7, 8, 9, 10, 11, 12, 13, or 14 days. In embodiments, at least one of a first and second dosing schedule comprises administering a dose every other day, every two days, or every 3, 4, 5, 6, 7, 8 days. In embodiments, a dose is administered for an extended period of time with or without titration (or otherwise changing the dosage or dosing schedule).

In embodiments, the interval between a first and a second dosing schedule is at least about 1, 2, 3, 4, 5, 6, or 7 days, or at least about 1, 2, 3, 4, 5, 6, 7, 8, 9, 10, 11, or 12 weeks, or at least about 1, 2, 3, 4, 6, 7, 8, 9, 10, 11, or 12 months.

In embodiments, a second dosing schedule (e.g., a maintenance dose) comprises a dosage about 2, 3, 4, 5, 6, 7, 8, 9, 10, 20, 30, 40, 50, 75, 100, 200, 400, 800, 1000, 5000 or more fold lower than the dosage used in a first dosing schedule (e.g., an initial induction dose). In embodiments, a second dosing schedule (e.g., a maintenance dosing schedule) has an equal or lower dosing frequency than a first dosing schedule (e.g., an initial treatment dosing schedule). In embodiments, a second dosing schedule (e.g., a maintenance dosing schedule) has a higher dosing interval than a first dosing schedule (e.g., an initial treatment dosing schedule).

In various embodiments, methods described herein are useful in treatment of a human subject. In some embodiments, the human is a pediatric human. In other embodiments, the human is an adult human. In other embodiments, the human is a geriatric human. In other embodiments, the human may be referred to as a patient. In some embodiments, the human is a female. In some embodiments, the human is a male.

In certain embodiments, the human has an age in a range of from about 1 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In one aspect, a subject being treated is a human patient. In one aspect, a patient is a male patient. In one aspect, a patient is a female patient. In one aspect, a patient is a premature newborn. In one aspect, a patient is a term newborn. In one aspect, a patient is a neonate. In one aspect, a patient is an infant. In one aspect, a patient is a toddler. In one aspect, a patient is a young child. In one aspect, a patient is a child. In one aspect, a patient is an adolescent. In one aspect, a patient is a pediatric patient. In one aspect, a patient is a geriatric patient. In one aspect, a human patient is a child patient below about 18, 15, 12, 10, 8, 6, 4, 3, 2, or 1-year-old.

In another aspect, a human patient is an adult patient. In another aspect, a human patient is an elderly patient. In a further aspect, a human patient is a patient above about 30, 35, 40, 45, 50, 55, 60, 65, 70, 75, 80, 85, 90, or 95 years old. In another aspect, a patient is about between 1 and 5, between 2 and 10, between 3 and 18, between 21 and 50, between 21 and 40, between 21 and 30, between 50 and 90, between 60 and 90, between 70 and 90, between 60 and 80, or between 65 and 75 years old. In one aspect, a patient is a young old patient (65-74 years). In one aspect, a patient is a middle old patient (75-84 years). In one aspect, a patient is an old patient (>85 years).

Additional Therapeutic Agents and Combination Therapy or Co-Formulation

The pharmaceutical compositions described herein can include one or more additional therapeutic agents, which can be administered to a subject in need thereof in a method described herein. The additional therapeutic agent can be administered simultaneous or sequential with a microbial therapeutic (e.g., microbial cocktail) described herein. Further, the present compositions and formulations can comprise the additional therapeutic agent (e.g. via co-formulation). For example, the additional therapeutic agent and one or more bacterial isolates can be combined into a single formulation.

In one embodiment, the additional therapeutic agent and a microbial therapeutic (e.g., one or more bacterial isolates) are administered to a subject simultaneously. The term "simultaneously" as used herein, means that the additional therapeutic agent and the microbial therapeutic are administered with a time separation of no more than about 60 minutes, such as no more than about 30 minutes, no more than about 20 minutes, no more than about 10 minutes, no more than about 5 minutes, or no more than about 1 minute. Administration of the additional therapeutic agent and the microbial therapeutic can be by simultaneous administration of a single formulation (e.g., a formulation comprising the additional therapeutic agent and one or more bacterial isolates) or of separate formulations (e.g., a first formulation including the additional therapeutic agent and a second formulation including one or more bacterial isolates).

Co-administration does not require an additional therapeutic agent to be administered simultaneously, if the timing of its administration is such that the pharmacological activities of the additional therapeutic agent and the microbial therapeutic (e.g., one or more bacterial isolates) overlap in time. For example, the additional therapeutic agent and the microbial therapeutic can be administered sequentially. The term "sequentially" as used herein means that the additional therapeutic agent and the microbial therapeutic are administered with a time separation of more than about 60 minutes. For example, the time between the sequential administration of the additional therapeutic agent and the microbial therapeutic can be more than about 60 minutes, more than about 2 hours, more than about 5 hours, more than about 10 hours, more than about 1 day, more than about 2 days, more than about 3 days, or more than about 1 week apart. The optimal administration times will depend on the rates of metabolism, excretion, and/or the pharmacodynamic activity of the additional therapeutic agent and the microbial therapeutic being administered. Either of the additional therapeutic agent or the microbial therapeutic (e.g., one or more bacterial isolates) can be administered first.

In a further embodiment, the additional therapeutic agent and the microbial therapeutic (e.g., one or more bacterial isolates) are administered to a subject simultaneously but the release of additional therapeutic agent and the microbial therapeutic from their respective dosage forms (or single unit dosage form if co-formulated) in the GI tract occurs sequentially.

Co-administration also does not require multiple additional therapeutic agents to be administered to the subject by the same route of administration. Rather, each additional therapeutic agent can be administered by any appropriate route, for example, parenterally or non-parenterally.

In some embodiments, the additional therapeutic agent is an agent used in the current standard-of-care induction therapies for IBD such as UC. Such agents include but are not limited to 5-aminosalicylic acid (5-ASA), corticosteroids, or biologics (e.g., Infliximab, Adalimumab or Vedolizumab).

In some embodiments, the additional therapeutic agent is an anti-inflammatory agent such as steroidal anti-inflammatory agents or non-steroidal anti-inflammatory agents (NSAIDS). Steroids, particularly the adrenal corticosteroids and their synthetic analogues, are well known in the art. Examples of corticosteroids include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, diflupredenate, flucloronide, flunisolide, fluoromethalone, fluperolone, fluprednisolone, hydrocortisone, meprednisone, paramethasone, prednisolone, prednisone, beclomethasone dipropionate. (NSAIDS) that can be used, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. Additional anti-inflammatory agents are described, for example, in U.S. Pat. No. 4,537,776, the entire contents of which is incorporated by reference herein.

In some embodiments, the additional therapeutic agent is a probiotic. Probiotics suitable for use include, but are not limited to, *Saccharomyces boulardii; Lactobacillus rhamnosus* GG; *Lactobacillus plantarum* 299v; *Clostridium butyricum* M588; *Clostridium difficile* VP20621 (non-toxigenic *C. difficile* strain); combination of *Lactobacillus casei, Lactobacillus acidophilus* (Bio-K+CL1285); combination of *Lactobacillus casei, Lactobacillus bulgaricus, Streptococcus thermophilus* (Actimel); combination of *Lactobacillus acidophilus, Bifidobacterium bifidum* (Florajen3); combination of *Lactobacillus acidophilus, Lactobacillus bulgaricus delbrueckii* subsp. *bulgaricus, Lactobacillus bulgaricus casei, Lactobacillus bulgaricus plantarum, Bifidobacterium longum, Bifidobacterium infantis, Bifidobacterium breve,* and *Streptococcus salivarius* subsp. *thermophilus* (VSL #3)).

In an aspect, the present disclosure provides for administering a probiotic prior to administering a pharmaceutical composition comprising a non-selected fecal microbiota. In another aspect, the disclosure provides for co-administering a probiotic and a pharmaceutical composition comprising a non-selected fecal microbiota. In another aspect, the probiotic is selected from the group consisting of one or more *Akkermansia* or Parabacteroides species. In another aspect, the probiotic is selected from the group consisting of two or more *Akkermansia* or *Parabacteroides* species. In another aspect, the probiotic is selected from the group consisting of three or more *Akkermansia* or Parabacteroides species. In another aspect, the probiotic is selected from the group consisting of four or more *Akkermansia* or *Parabacteroides* species. In another aspect, the probiotic is selected from the group consisting of five or more *Akkermansia* or *Parabacteroides* species. In another aspect, the probiotic is selected from the group consisting of six or more *Akkermansia* or *Parabacteroides* species. In another aspect, the probiotic is selected from the group consisting of 1 to 3, 3 to 5, 5 to 8, or 8 to 10 *Akkermansia* or *Parabacteroides* species. A probiotic can be provided in a single dose or in multiple doses. When provided as a single composition, the single composition can comprise a single probiotic or a mixture of probiotics. When provided in multiple compositions, each composition can comprise a single probiotic or a mixture of probiotics.

In some embodiments, the additional therapeutic agent is a prebiotic. A prebiotic is a compound or compounds (e.g., comprising one or more nutrients) administered to a subject to promote the growth, proliferation, or activity of one or more microorganisms (e.g., bacteria) in the intestine of the subject (e.g., by providing a substrate to be metabolized by the one or more microorganisms). Without wishing to be bound by theory, prebiotics can be added to a pharmaceutical composition to nutritionally supplement bacteria in the endogenous microbiome of the subject and/or in the pharmaceutical composition itself, e.g., to stimulate the growth or activity of one or more strains of an uncultured population of fecal bacteria and/or one or more bacterial isolates. Additionally, one or more prebiotics can be added to a composition to buffer against "shock" to bacteria cells when transitioning those cells to a new environment, for example, subsequent to the isolation and/or purification of an uncultured population of fecal bacteria, or before or after freezing, freeze-drying, spray-drying, reconstitution in solution and the like.

Non-limiting examples of prebiotics that can be added to a pharmaceutical composition or administered to a subject include amino acids, lactic acid, ammonium nitrate, amylose, barley mulch, biotin, carbonate, cellulose, chitin, choline, fructooligosaccharides (FOSs), fructose, galactooligosaccharides (GOSs), glucose, glycerol, heteropolysaccharide, histidine, homopolysaccharide, hydroxyapatite, inulin, isomaltulose, lactose, lactulose, maltodextrins, maltose, mannooligosaccharides, nitrogen, oligodextrose, oligofructoses, oligofructose-enriched inulin, oligosaccharides, pectin, phosphate salts, phosphorus, polydextroses, polyols, potash, potassium, sodium nitrate, starch, sucrose, sulfur, sun fiber, tagatose, thiamine, trans-galactooligosaccharides, trehalose, vitamins, a water-soluble carbohydrate, and/or xylooligosaccharides (XOSs), and a combination thereof. Illustrative prebiotics include complex carbohydrates, amino acids, peptides, or other essential nutritional components for the survival of the bacterial composition.

In an aspect, a subject is not pretreated with a prebiotic nutrient prior to treatment with a pharmaceutical composition. In another aspect, the pharmaceutical composition is not supplemented with a prebiotic nutrient.

In embodiments, a prebiotic can be added (e.g., in dry or liquid forms) in a pharmaceutical composition described herein, for example, a composition comprising one or more bacterial isolates.

Alternately, or additionally, a prebiotic can be included (e.g., in dry or liquid forms) in a distinct pharmaceutical composition lacking a microbial therapeutic.

A prebiotic can be provided to a subject before, contemporaneously with, and/or after administration of a pharmaceutical composition comprising a microbial therapeutic (e.g., one or more bacterial isolates), either in the same pharmaceutical composition or in a separate pharmaceutical composition.

A prebiotic can be provided in a single dose or in multiple doses. When provided as a single composition, the single composition can comprise a single prebiotic or a mixture of prebiotics. When provided in multiple compositions, each composition can comprise a single prebiotic or a mixture of prebiotics.

As examples, when multiple doses are provided, a first composition comprising a prebiotic can include one specific prebiotic, e.g., inulin, and a second composition can include a second specific prebiotic, e.g., pectin. Alternately, a first composition can include a mixture of prebiotics, e.g., inulin and pectin and a second composition can include different mixture of prebiotics, e.g., inulin and a FOS. A first composition can include a mixture of prebiotics and a second composition can include one specific prebiotic.

The amount of prebiotic provided to a subject/patient and/or included in a composition depends on the specific prebiotic, the specific bacterial strain of beneficial bacteria, and/or the disease state of the subject/patient.

In some embodiments, the additional therapeutic agent is an antidiarrheal agent. Antidiarrheal agents suitable for use include, but are not limited to, DPP-IV inhibitors, natural opioids, such as tincture of opium, paregoric, and codeine, synthetic opioids, such as diphenoxylate, difenoxin and loperamide, bismuth subsalicylate, lanreotide, vapreotide and octreotide, motiln antagonists, COX2 inhibitors like celecoxib, glutamine, thalidomide and traditional antidiarrheal remedies, such as kaolin, pectin, berberine and muscarinic agents.

In some embodiments, the additional therapeutic agent can be an analgesic. Analgesics useful in the compositions and methods described herein include, without limitation, morphine, codeine, heroine, methadone and related compounds, thebaine, orpiavine, and their derivatives, buprenorphine, the piperidines, morphinans, benzomorphans, tetrahydroisoquinolines, thiambutanes, benzylamines, tilidine, viminol, nefopam, capsaicin(8-methyl-N-vanillyl-6E-nonenamide), "synthetic" capsaicin(N-vanillylnonamide), and related compounds.

In some embodiments, the additional therapeutic agent is an anti-bacterial agent, which includes, but is not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In some embodiments, the anti-bacterial agent can be any of the penicillin, cephalosporin, monobactam, and carbapenem antibiotics.

In one aspect, a method further comprises pretreating a subject with an antibiotic composition prior to administering a therapeutic bacterial or microbiota composition. In one aspect, an antibiotic composition administered herein comprises an antibiotic selected from the group consisting of rifabutin, clarithromycin, clofazimine, vancomycin, rifampicin, nitroimidazole, chloramphenicol, and a combination thereof. In another aspect, an antibiotic composition administered herein comprises an antibiotic selected from the group consisting of rifaximin, rifamycin derivative, rifampicin, rifabutin, rifapentine, rifalazil, bicozamycin, aminoglycoside, gentamycin, neomycin, streptomycin, paromomycin, verdamicin, mutamicin, sisomicin, netilmicin, retymicin, kanamycin, aztreonam, aztreonam macrolide, clarithromycin, dirithromycin, roxithromycin, telithromycin, azithromycin, bismuth subsalicylate, vancomycin, streptomycin, fidaxomicin, amikacin, arbekacin, neomycin, netilmicin, paromomycin, rhodostreptomycin, tobramycin, apramycin, and a combination thereof. In another aspect, a subject is not pretreated with an antibiotic composition prior to administering a therapeutic bacterial or microbiota composition. In another aspect, the pharmaceutical composition is not supplemented with an antibiotic composition. In a further aspect, a method further comprises pretreating a subject with an anti-inflammatory drug prior to administration of a therapeutic bacterial or microbiota composition. In yet another aspect, a subject is not pretreated with an anti-inflammatory drug prior to administering a therapeutic bacterial or microbiota composition. In another aspect, a therapeutic bacterial or microbiota composition is not supplemented with an anti-inflammatory.

For all additional therapeutic agent compositions and methods, targeting to various parts of the GI tract can be employed as described herein.

Methods of Treatment

An aspect of the present invention is a method of treating or preventing inflammatory bowel disease (IBD) in a subject in need thereof, the method comprising administering to the subject a plurality of bacterial isolates, wherein the plurality of bacterial isolates comprises *Bacteroides stercoris*, and at least two of *Bacteroides cellulosilyticus, Bacteroides uniformis, Subdoligranulum variabile, Anaerostipes hadrus, Odoribacter splanchnicus, Roseburia faecis, Faecalibacterium prausnitzii, Akkermansia muciniphila, Alistipes shahii*, and *Eubacterium rectale*, wherein at least two of the plurality of bacterial isolates are isolated from a stool of different human donors.

In embodiments, the *Bacteroides stercoris* comprises a 16S ribosomal ribonucleic acid (rRNA) sequence that has at least about 95%, or at least about 97%, or at least about 98%, or at least about 99% sequence identity with the nucleotide sequence of SEQ ID NO: 13. In embodiments, the plurality of bacterial isolates comprises at least one of *Bacteroides cellulosilyticus, Bacteroides uniformis, Odoribacter splanchnicus, Roseburia faecis, Anaerostipes hadrus, Faecalibacterium prausnitzii, Subdoligranulum variabile, Akkermansia muciniphila, Alistipes shahii*, and *Eubacterium rectale*. In embodiments, the plurality of bacterial isolates comprises at least two, or at least three, or at least four, or at least five, or at least six, or at least seven, or at least eight, or at least nine, or each of *Bacteroides cellulosilyticus, Bacteroides uniformis, Odoribacter splanchnicus, Roseburia faecis, Anaerostipes hadrus, Faecalibacterium prausnitzii, Subdoligranulum variabile, Akkermansia muciniphila, Alistipes shahii*, and *Eubacterium rectale*.

In embodiments, the plurality of bacterial isolates comprises at least four of *Bacteroides cellulosilyticus, Bacteroides uniformis, Odoribacter splanchnicus, Roseburia faecis, Anaerostipes hadrus, Faecalibacterium prausnitzii, Subdoligranulum variabile, Akkermansia muciniphila, Alistipes shahii*, and *Eubacterium rectale*. In embodiments, the plurality of bacterial isolates comprises at least five of *Bacteroides cellulosilyticus, Bacteroides uniformis, Odoribacter splanchnicus, Roseburia faecis, Anaerostipes hadrus, Faecalibacterium prausnitzii, Subdoligranulum variabile, Akkermansia muciniphila, Alistipes shahii*, and *Eubacterium rectale*. In embodiments, the plurality of bacterial isolates comprises at least six of *Bacteroides cellulosilyticus, Bacteroides uniformis, Odoribacter splanchnicus, Roseburia faecis, Anaerostipes hadrus, Faecalibacterium prausnitzii, Subdoligranulum variabile, Akkermansia muciniphila, Alistipes shahii*, and *Eubacterium rectale*. In embodiments, the plurality of bacterial isolates comprises at least seven of *Bacteroides cellulosilyticus, Bacteroides uniformis, Odoribacter splanchnicus, Roseburia faecis, Anaerostipes hadrus, Faecalibacterium prausnitzii, Subdoligranulum variabile, Akkermansia muciniphila, Alistipes shahii*, and *Eubacterium rectale*. In embodiments, the plurality of bacterial isolates comprises at least eight of *Bacteroides cellulosilyticus, Bacteroides uniformis, Odoribacter splanchnicus, Roseburia faecis, Anaerostipes hadrus, Faecalibacterium prausnitzii, Subdoligranulum variabile, Akkermansia muciniphila, Alistipes shahii*, and *Eubacterium rectale*.

In embodiments, the plurality of bacterial isolates comprises a 16S rRNA sequence that has at least about 95%, or at least about 97%, or at least about 98%, or at least about 99% sequence identity with nucleotide sequences selected from SEQ ID NOs: 1, 2, 3, 7, 8, 11, 14, 18, 19, 20, 22 and 23.

In embodiments, the plurality of bacterial isolates comprises: (a) a 16S rRNA sequence that is at least about 95%, or at least about 97%, or at least about 98%, or at least about 99% sequence identity with nucleotide sequence of SEQ ID NOs: 1 and/or 7, (b) a 16S rRNA sequence that is at least about 95%, or at least about 97%, or at least about 98%, or at least about 99% sequence identity with nucleotide sequence of SEQ ID NO: 2, (c) a 16S rRNA sequence that is at least about 95%, or at least about 97%, or at least about 98%, or at least about 99% sequence identity with nucleotide sequence of SEQ ID NO: 3. (d) a 16S rRNA sequence that is at least about 95%, or at least about 97%, or at least about 98%, or at least about 99% sequence identity with nucleotide sequence of SEQ ID NO: 8, (e) a 16S rRNA sequence that is at least about 95%, or at least about 97%, or at least about 98%, or at least about 99% sequence identity with nucleotide sequence of SEQ ID NO: 11 (f) a 16S rRNA sequence that is at least about 95%, or at least about 97%, or at least about 98%, or at least about 99% sequence identity with nucleotide sequence of SEQ ID NO: 13, (g) a 16S rRNA sequence that is at least about 95%, or at least about 97%, or at least about 98%, or at least about 99% sequence identity with nucleotide sequence of SEQ ID NO: 14, (h) a 16S rRNA sequence that is at least about 95%, or at least about 97%, or at least about 98%, or at least about 99% sequence identity with nucleotide sequence of SEQ ID NO: 18, (i) a 16S rRNA sequence that is at least about 95%, or at least about 97%, or at least about 98%, or at least about 99% sequence identity with nucleotide sequence of SEQ ID NO: 19, (j) a 16S rRNA sequence that is at least about 95%, or at least about 97%, or at least about 98%, or at least about 99% sequence identity with nucleotide sequence of SEQ ID NO: 20, and/or (k) a 16S rRNA sequence that is at least about 95%, or at least about 97%, or at least about 98%, or at least about 99% sequence identity with nucleotide sequence of SEQ ID NOs: 22 and/or 23.

In embodiments, the plurality of bacterial isolates comprises at least two bacterial isolates comprising *Faecalibacterium prausnitzii*, wherein the at least two bacterial isolates comprise different 16S rRNA sequences. In embodiments, the at least two bacterial isolates comprising *Faecalibacterium prausnitzii* comprise 16S rRNA sequences that are at least about 95%, or at least about 97%, or at least about 98%, or at least about 99% identity sequence identity with nucleotide sequences of SEQ ID NOs: 1 and/or 7. In embodiments, the at least two bacterial isolates comprising *Faecalibacterium prausnitzii* are isolated from a stool of different human donors.

Disclosed herein are methods of preventing or treating a disorder related to an intestinal dysbiosis in a subject in need thereof, comprising administering to the subject an effective amount of any herein-disclosed pharmaceutical composition. In embodiments, the disorder is selected from inflammatory bowel disease (IBD), irritable bowel syndrome (IBS), *C. difficile* infection (CDI), *C. difficile*-associated disease (CDAD), and antibiotic-induced adverse effect. In embodiments, the disorder is IBD selected from ulcerative colitis (UC), Crohn's disease (CD), and pouchitis. In embodiments, the method treats or prevents a nosocomial infection and/or a secondary emergent infection and/or treats and/or prevents the overgrowth of one or more pathogenic microorganisms in the GI tract of the subject. In embodiments, the method comprises maintenance of a normal intestinal microbiota. In embodiments, the method further comprises administering at least one prebiotic to the subject.

In various embodiments, provided herein is a method of modulating a microbiome of a subject in need thereof to provide or restore an ecological balance, comprising administering to the subject a composition described herein. For instance, in various embodiments, there is provided methods of diminishing or inhibiting one or more pathogenic bacteria by administering a composition described herein. In various embodiments, administration of one or more bacterial isolates described herein augments growth of at least one type of bacteria not detectably present in a patient's GI tract prior to administration and, in various embodiments, which is non-pathogenic.

In various embodiments, provided herein is a method of restoring or enhancing ecological control over gut pathogens or pathobionts in a subject in need thereof, comprising administering to the subject a composition described herein.

In various embodiments, a method comprises administering a composition described herein to treat a disease or condition associated with GI dysbiosis in a subject in need thereof.

In some embodiments, the subject has inflammatory bowel diseases (IBD), for example, Crohn's disease, colitis (e.g., UC or microscopic colitis), or pouchitis. IBD is a group of inflammatory conditions of the large intestine and, in some cases, the small intestine. Examples of IBD that can be treated by the compositions, formulations and methods described herein include, but are not limited to, Crohn's disease, UC, pouchitis, collagenous colitis, lymphocytic colitis, ischemic colitis, diversion colitis, Behçet's syndrome, infective colitis, and indeterminate colitis. In an embodiment, provided herein is a method of treating UC comprising administering a composition described herein to a subject in need thereof. In another embodiment, provided herein is a method of treating CD comprising administering a composition described herein to a subject in need thereof. In a further embodiment, provided herein is a method of treating pouchitis comprising administering a composition described herein to a subject in need thereof.

In various embodiments, a method comprises administering a composition described herein to treat UC in a subject in need thereof. UC is one form of IBD. It is a chronic disease of the colon, in which the lining of the colon becomes inflamed and develops tiny open sores, or ulcers, that produce pus and mucous. In some embodiments, methods described herein can ameliorate, reduce, or eliminate the inflammation and/or ulceration associated with UC. In some embodiments, methods described herein can ameliorate, reduce, or eliminate one or more symptoms associated with UC including but not limited to, abdominal discomfort or pain, frequent emptying of the colon, lose and urgent bowel movements, persistent diarrhea, bloody stool, loss of appetite, and weight loss. In some embodiments, methods described herein can reduce or prevent the delay in growth and development in children afflicted with UC.

In various embodiments, a method comprises administering a composition described herein to treat UC in a subject in need thereof. For example, a successful treatment of the subject can be measured using the indices below, e.g., the present methods cause a subject's activity score threshold to change from severe to moderate, mild, or remission; or cause a patient's score to change from moderate to mild or remission; or cause a patient's score to change from mild to remission:

| Index | Parameters assessed | Scoring system | Activity score thresholds | | | |
|---|---|---|---|---|---|---|
| | | | Remission | Mild | Moderate | Severe |
| Mayo score | Stool frequency Rectal bleeding Physician's global assessment Sigmoidoscopy | Cumulative score | 0-2 | 3-5 | 6-10 | 11-12 |
| UCDAI | Stool frequency Rectal bleeding Physician's global assessment Sigmoidoscopy | Cumulative score | 0-2 | | 3-8 | 9-12 |
| Rachmilewitz score (CAI) | Bowel movement frequency Blood in stools Physician's global assessment Abdominal pain/cramps Temperature EIMs Laboratory findings (ESR, hemoglobin) | Cumulative score | 0-4 | 5-10 | 11-17 | >17 |

-continued

| Index | Parameters assessed | Scoring system | Activity score thresholds | | | |
|---|---|---|---|---|---|---|
| | | | Remission | Mild | Moderate | Severe |
| Powell-Tuck index (St Mark's index) | Well-being Abdominal pain Bowel movement frequency Stool consistency Bleeding Anorexia Nausea/vomiting Abdominal tenderness Eye, joint, mouth, or skin complications Temperature Sigmoidoscopy | Cumulative score | ≤3 | 4-10 | 11-14 | >14 |
| SCCAI (Walmsley) | Bowel movement frequency (day) Bowel movement frequency (night) Urgency of defecation Blood in stool Well-being Extracolonic features | Cumulative score | ≤2 <2.5 | | 3-20 | |
| Lichtiger index | Diarrhea frequency Nocturnal diarrhea Visible blood (% of movements) Fecal incontinence Abdominal pain/cramping Well-being Abdominal tenderness Need for antidiarrheal medications | Cumulative score | ≤3 | 4-8 | 9-14 | >14 |
| Seo index | Bowel movement frequency Blood in stool ESR Hemoglobin Albumin | Cumulative score with components given different weightings (+constant to yield a mean value as close as possible to Truelove-Witts criteria) | <108 <120 | <150 | 150-220 | >220 |

In some embodiments, a method comprises administering a pharmaceutical composition described herein to treat IBS in a subject in need thereof. IBS is a common disorder that affects the colon and can cause cramping, abdominal pain, bloating, gas, diarrhea and constipation. IBS is classified based on the predominant symptom of diarrhea (IBS with predominant diarrhea, IBS-D), constipation (IBS with predominant constipation, IBS-C) or mixed symptoms (IBS with alternating constipation and diarrhea, IBS-A). Methods described herein can be effective in treating one or more of IBS-D, IBS-C, and/or IBS-A. In some embodiments, methods described herein (e.g., comprising administering a composition described herein) can reduce or eliminate one or more symptoms associated with one or more of IBS-D, IBS-C, and/or IBS-A.

In embodiments, a method comprises administering a pharmaceutical composition described herein to treat or prevent a disease/disorder associated with the presence of abnormal enteric microflora (e.g. intestinal dysbiosis) in a subject in need thereof. The disease/disorder can be selected from a gastro-intestinal disorder including irritable bowel syndrome or spastic colon, Functional Bowel Disease (FBD), including constipation predominant FBD, pain predominant FBD, upper abdominal FBD, Nonulcer Dyspepsia (NUD), gastro-esophageal reflux, inflammatory bowel disease including Crohn's disease, ulcerative colitis, indeterminate colitis, collagenous colitis, microscopic colitis, chronic *Clostridium difficile* infection, pseudomembranous colitis, mucous colitis, antibiotic associated colitis, idiopathic or simple constipation, diverticular disease, AIDS enteropathy, small bowel bacterial overgrowth, coeliac disease, polyposis coil, colonic polyps, chronic idiopathic pseudo obstructive syndrome, and toxic megacolon.

In embodiments, a method comprises administering a composition described herein to treat or prevent a disorder associated with a liver disorder in a subject in need thereof. Non-limiting examples of a liver disorder include primary biliary cirrhosis, Primary Sclerosing Cholangitis (PSC), fatty liver, and cryptogenic cirrhosis. In embodiments, such diseases/disorders are related to an intestinal dysbiosis of a subject.

In embodiments, a method comprises administering a composition described herein to treat or prevent a rheumatic disorder in a subject in need thereof. Non-limiting examples of a rheumatic disorder include rheumatoid arthritis, non-rheumatoid arthritis, non-rheumatoid factor positive arthritis, ankylosing spondylitis, Lyme disease, and Reiter's syndrome. In embodiments, such diseases/disorders are related to an intestinal dysbiosis of a subject.

In embodiments, a method comprises administering a composition described herein to treat or prevent an immune-mediated disorder in a subject in need thereof. Non-limiting examples of an immune-mediated disorder include glomerulonephritis, hemolytic uraemic syndrome, juvenile diabetes mellitus, mixed cryoglobulinaemia, polyarteritis, familial Mediterranean fever, amyloidosis, scleroderma, systemic lupus erythematosus, and Behçets syndrome. In embodiments, such diseases/disorders are related to an intestinal dysbiosis of a subject.

In embodiments, a method comprises administering a composition described herein to treat or prevent an autoimmune disorder in a subject in need thereof. Non-limiting examples of an autoimmune disorder include Acute Disseminated Encephalomyelitis (ADEM), acute necrotizing hemorrhagic leukoencephalitis, Addison's disease, agammaglobulinemia, alopecia areata, amyloidosis, ankylosing spondylitis, anti-GBM/anti-TBM nephritis, Antiphospholipid Syndrome (APS), autoimmune angioedema, autoimmune aplastic anemia, autoimmune dysautonomia, autoimmune hemolytic anemia, autoimmune hepatitis, autoimmune hyperlipidemia, autoimmune immunodeficiency, Autoimmune Inner Ear Disease (AIED), autoimmune myocarditis, autoimmune oophoritis, autoimmune pancreatitis, autoimmune retinopathy, Autoimmune Thrombocytopenic Purpura (ATP), autoimmune thyroid disease, autoimmune urticarial, axonal & neuronal neuropathies, Balo disease, Behcet's disease, bullous pemphigoid, cardiomyopathy, Castleman disease, celiac disease, Chagas disease, Chronic Inflammatory Demyelinating Polyneuropathy (CIDP), Chronic Recurrent Multifocal Ostomyelitis (CRMO), Churg-Strauss syndrome, cicatricial pemphigoid/benign mucosal pemphigoid, Crohn's disease, Cogan's syndrome, cold agglutinin disease, congenital heart block, Coxsackie myocarditis, CREST disease, essential mixed cryoglobulinemia, demyelinating neuropathies, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, experimental allergic encephalomyelitis, Evans syndrome, fibrosing alveolitis, giant cell arteritis (temporal arteritis), giant cell myocarditis, glomerulonephritis, Goodpasture's syndrome, Granulomatosis With Polyangiitis (GPA), Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, idiopathic thrombocytopenic purpura (ITP), IgA nephropathy, IgG4-related sclerosing disease, immunoregulatory lipoproteins, inclusion body myositis, interstitial cystitis, juvenile arthritis, juvenile idiopathic arthritis, juvenile myositis, Kawasaki syndrome, Lambert-Eaton syndrome, leukocytoclastic vasculitis, lichen planus, lichen sclerosus, ligneous conjunctivitis, linear IgA disease (LAD), lupus (systemic lupus erythematosus), chronic Lyme disease, Meniere's disease, microscopic polyangiitis, Mixed Connective Tissue Disease (MCTD), Mooren's ulcer, Mucha-Habermann disease, multiple sclerosis, myasthenia gravis, myositis, narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with *Streptococcus*), paraneoplastic cerebellar degeneration, Paroxysmal Nocturnal Hemoglobinuria (PNH), Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis nodosa, type I, II, & III autoimmune polyglandular syndromes, polymyalgia rheumatic, polymyositis, postmyocardial infarction syndrome, postpericardiotomy syndrome, progesterone dermatitis, primary biliary cirrhosis, Primary Sclerosing Cholangitis (PSC), psoriasis, psoriatic arthritis, idiopathic pulmonary fibrosis, pyoderma gangrenosum, pure red cell aplasia, Raynaud's phenomenon, reactive arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjögren's syndrome, sperm & testicular autoimmunity, stiff person syndrome, Subacute Bacterial Endocarditis (SBE), Susac's syndrome, sympathetic ophthalmia, Takayasu's arteritis, temporal arteritis/giant cell arteritis, Thrombocytopenic Purpura (TTP), Tolosa-Hunt syndrome, transverse myelitis, type 1 diabetes, asthma, ulcerative colitis, Undifferentiated Connective Tissue Disease (UCTD), uveitis, vasculitis, vesiculobullous dermatosis, vitiligo, and Wegener's granulomatosis. In embodiments, such disorders are related to an intestinal dysbiosis of a subject.

In embodiments, a method comprises administering a composition described herein to treat or prevent a neurological syndrome in a subject in need thereof. Non-limiting examples of a neurological syndrome include as chronic fatigue syndrome, migraine, multiple sclerosis, amyotrophic lateral sclerosis, myasthenia gravis, Gillain-Barré syndrome, Parkinson's disease, Alzheimer's disease, Chronic Inflammatory Demyelinating Polyneuropathy, and other degenerative disorders. In embodiments, such syndromes are related to an intestinal dysbiosis of a subject.

In embodiments, a method comprises administering a composition described herein to treat or prevent a psychiatric disorder in a subject in need thereof. Non-limiting examples of a psychiatric disorder include chronic depression, schizophrenia, psychotic disorders, manic depressive illness; regressive disorders including, Asperger's syndrome, Rett syndrome, Attention Deficit Hyperactivity Disorder (ADHD), and Attention Deficit Disorder (ADD); the regressive disorder; autism; Sudden Infant Death Syndrome (SIDS); anorexia nervosa. In embodiments, such diseases/disorders are related to an intestinal dysbiosis of a subject.

In embodiments, a method comprises administering a composition described herein to treat or prevent a dermatological condition in a subject in need thereof. Non-limiting examples of a dermatological condition include chronic urticaria, acne, dermatitis herpetiformis and vasculitis disorders. In embodiments, such diseases/disorders are related to an intestinal dysbiosis of a subject.

In embodiments, a method comprises administering a composition described herein to treat or prevent a cardiovascular and/or vascular disorder in a subject in need thereof. In embodiments, such diseases/disorders are related to an intestinal dysbiosis of a subject.

In embodiments, a method comprises administering a composition described herein to treat or prevent a bloodstream infection (BSI) in a subject in need thereof. Patients at risk for such BSIs include but are not limited to solid organ transplant patients; chronic kidney disease patients, e.g., on hemodialysis; and oncology patients. In embodiments, such BSIs are related to an intestinal dysbiosis of a subject.

In embodiments, a method comprises administering a composition described herein to treat or prevent a catheter or intravascular-line infection (e.g., central-line infection) in a subject in need thereof. In embodiments, such infections are related to an intestinal dysbiosis of a subject.

In embodiments, a method comprises administering a composition described herein to treat or prevent a skin or soft tissue infection in a subject in need thereof. In embodiments, such infections are related to an intestinal dysbiosis of a subject.

In embodiments, a method comprises administering a composition described herein to treat or prevent a surgical-site infection in a subject in need thereof. In embodiments, such infections are related to an intestinal dysbiosis of a subject.

In embodiments, a method comprises administering a composition described herein to treat or prevent a urinary tract infection (e.g., antibiotic-resistant urinary tract infections and catheter-associated urinary tract infections) in a subject in need thereof. In embodiments, such infections are related to an intestinal dysbiosis of a subject.

In embodiments, a method comprises administering a composition described herein to treat or prevent a wound infection in a subject in need thereof. In embodiments, such infections are related to an intestinal dysbiosis of a subject.

In embodiments, a method comprises administering a composition described herein to treat or prevent an infection in a subject in need thereof. Non-limiting examples of an infection include an antibiotic-resistant infection and an antibiotic-sensitive infection. In embodiments, such infections are related to an intestinal dysbiosis of a subject.

In embodiments, the pharmaceutical compositions and methods described herein can treat or prevent meningitis. In embodiments, the meningitis is related to an intestinal dysbiosis of a subject.

In embodiments, a method comprises administering a composition described herein to treat or prevent pneumonia, e.g., ventilator-associated pneumonia in a subject in need thereof. In embodiments, the pneumonia is related to an intestinal dysbiosis of a subject.

In embodiments, the compositions, formulations and methods described herein can be used in patient populations who are in an outpatient setting, hospitalized, and/or in long-term care facilities. Such patient populations are at risk for nosocomial infections. In embodiments, such infections are related to an intestinal dysbiosis of a subject.

In embodiments, a method comprises administering a composition described herein to treat or prevent Primary Sclerosing Cholangitis (PSC) in a subject in need thereof. For example, one or more bacterial isolates provided in a pharmaceutical composition administered to the subject can replace a dysbiotic gut microbiome with a healthy community, thereby, at least, reducing bile duct inflammation and/or improving liver function.

In embodiments, a method comprises administering a composition described herein to treat or prevent a diarrheal disease in a subject in need thereof. Non-limiting example s of a diarrheal disease include acute bloody diarrhea (e.g., dysentery), acute watery diarrhea (e.g., cholera), checkpoint inhibitor associated colitis, diarrhea due to food poisoning, persistent diarrhea, and traveler's diarrhea. In embodiments, the diarrhea is related to an intestinal dysbiosis of a subject.

In various embodiments, administration of a pharmaceutical composition described herein can reduce, ameliorate, or eliminate one or more symptom(s) associated with a herein-described condition, disease, or disorder. Exemplary symptoms include, but are not limited to, diarrhea, bloody stool, mouth sores, perianal disease, abdominal pain, abdominal cramping, fever, fatigue, weight loss, iron deficiency, anemia, appetite loss, weight loss, anorexia, delayed growth, delayed pubertal development, and inflammation of the skin, eyes, joints, liver, and bile ducts. In embodiments, the symptom is related to an intestinal dysbiosis of a subject.

In some embodiments, a method comprises administering a composition described herein to treat or prevent an infection by pathogenic bacteria and/or inhibiting the growth or decreasing the number of pathogenic bacteria in the GI tract of a subject in need thereof. In an embodiment, the pathogenic bacteria is enterobacteria such as *Salmonella*. In various embodiments, a method comprises administering a composition described herein to mitigate or prevent the overgrowth of various coliforms in a patient's gut (including coliforms that are virulent and/or antibiotic resistant). Illustrative coliforms include *Citrobacter, Enterobacter, Hafnia, Klebsiella*, and *Escherichia*. In some embodiments, the methods and compositions described herein prevent or diminish secondary infections with resistant organisms.

In still other embodiments, a method comprises administering a composition described herein to treat or prevent an infectious disease of the intestines in a subject in need thereof. Non-limiting examples of an infectious disease of the intestine include CDI and/or a CDAD, nosocomial infection, secondary emergent infection, amebiasis, intestinal tuberculosis, or parasitic disorder. In some embodiments, provided herein are methods for treating or preventing a CDI and/or a CDAD, comprising administering an effective amount of a pharmaceutical composition described herein to a subject or a patient need thereof. In various embodiments, the CDI or CDAD comprises one or more of: *C. difficile* diarrhea (CDD), *C. difficile* intestinal inflammatory disease, colitis, pseudomembranous colitis, fever, abdominal pain, dehydration and disturbances in electrolytes, megacolon, peritonitis, and perforation and/or rupture of the colon.

In various embodiments, a composition described herein is administered to a subject in need thereof to treat or prevent a disease or condition associated with GI dysbiosis in the context of initial onset or relapse/recurrence (e.g. due to continued or restarted antibiotic therapy). For example, in a subject that has previously suffered from a GI dysbiosis, the present pharmaceutical composition or formulation can be administered upon the first symptoms of recurrence in the subject. By way of non-limiting example, symptoms of recurrence include, in a mild case, about 5 to about 10 watery bowel movements per day, no significant fever, and only mild abdominal cramps while blood tests can show a mild rise in the white blood cell count up to about 15,000 (normal levels are up to about 10,000), and, in a severe case, more than about 12 watery stools per day, nausea, vomiting, high fever (e.g. about 102-104° F.), rectal bleeding, severe abdominal pain (e.g. with tenderness), abdominal distention, and a high white blood count (e.g. of about 15,000 to about 40,000).

In some embodiments, the methods described herein can be used to treat a subject or patient who is suffering from, or is susceptible to, a disease or condition associated with GI dysbiosis. For example, the subject can be undergoing or have undergone an initial and/or adjunctive therapy that renders the subject susceptible to a disease or condition associated with GI dysbiosis. In some embodiments, the subject is undergoing treatment, or has undergone treatment, with an antibiotic. For example, the subject can have taken an antibiotic during the past about 30 days and/or have an immune system that is weak (e.g. from a chronic illness). In another example, the patient can have recently been in the hospital, including in an intensive care unit. Accordingly, in some embodiments, a method comprises administering a composition described herein to treat or prevent a nosocomial infection and/or a secondary emergent infection and/or a hospital acquired infection (HAI) in a subject in need thereof.

In various embodiments, described herein are methods for treating antibiotic-induced adverse effects in the GI tract, comprising administering an effective amount of a microbial therapeutic (e.g., one or more bacterial isolates) to a subject in need thereof. In another embodiment, provided herein are methods for preventing an antibiotic-induced adverse effect in the GI tract, comprising administering an effective amount of a microbial therapeutic to a subject in need thereof.

In another aspect, a pharmaceutical composition or a plurality of pharmaceutical compositions, as disclosed herein, can be used in the manufacture of a medicament, e.g., for treating a herein-described condition, disease, or disorder in a subject in need thereof. In various embodiments, the bacterial isolates as described herein protect the intestinal microbiome from antibiotics-induced damage. In some embodiments, the methods described herein can treat or prevent an antibiotics-associated adverse effect including but not limited to diarrhea, nausea, vomiting, dysgeusia, colitis, and pseudomembranous colitis disease and/or symptoms. In an embodiment, methods described herein can be used to treat or prevent antibiotic-associated diarrhea (AAD).

Methods for measuring change and/or improvement in GI tract function can include, but are not limited to: endoscopy for direct examination of epithelium and mucosa; histological evaluation and/or tissue procurement for direct evaluation of structural changes and/or immune biomarkers; urine tests for assessment of permeability with non-absorbable sugars and LPS levels; stool tests for assessment of inflammation and/or microbiota changes (for example by PCR); and/or blood tests for assessment of specific markers, including CD4+ cell counts, Th17 cell counts, and/or LPS levels.

In embodiments, the present disclosure provides a method for treating a disorder (e.g., *C. difficile* infection, autism spectrum disorder (ASD), inflammatory bowel disease, ulcerative colitis, Crohn's disease, or another indication listed herein) in a subject in need thereof, where the method comprises administering to the subject a pharmaceutically active dose of a pharmaceutical composition described herein. In embodiments, the present disclosure provides a method for treating a disorder (e.g., *C. difficile* infection, ASD, inflammatory bowel disease, ulcerative colitis, or Crohn's disease) in a subject in need thereof, where the method comprises administering daily to the subject a pharmaceutically active dose of a pharmaceutical composition described herein. In embodiments, a pharmaceutical composition is administered to a patient in need thereof at least once daily for at least two consecutive days. In embodiments, a pharmaceutical composition is administered at least once daily for at least 3, 4, 5, 6, 7, 8, 9, 10, 11, 12, 13, 14, or 15 consecutive days. In embodiments, a pharmaceutical composition is administered at least once daily for at least 1, 2, 3, 4, 5, 6, 7, 8, 9, 10, 11, or 12 consecutive weeks. In embodiments, a pharmaceutical composition is administered at least twice, three times, four times, or five times per week for at least 1, 2, 3, 4, 5, 6, 7, 8, 9, 10, 11, or 12 consecutive weeks. In embodiments, a pharmaceutical composition is administered at least once daily for at most 4, 5, 6, 7, 8, 9, 10, 11, 12, 13, 14, 15, 16, 17, 18, 19, or 20 consecutive days or weeks. In embodiments, a pharmaceutical composition is administered at least once daily for at most 1, 2, 3, 4, 5, 6, 7, 8, 9, 10, 11, or 12 consecutive weeks or months. In embodiments, a pharmaceutical composition is administered at least once for at least 1, 2, 3, 4, 5, 6, 7, 8, 9, 10, 11, or 12 consecutive months or years, chronically for a subject's entire life span, or an indefinite period of time.

In embodiments, a pharmaceutical composition is administered to a patient in need thereof at least twice daily for at least two consecutive days. In embodiments, a pharmaceutical composition is administered at least twice daily for at least 3, 4, 5, 6, 7, 8, 9, 10, 11, 12, 13, 14, or 15 consecutive days. In embodiments, a pharmaceutical composition is administered at least twice daily for at least 1, 2, 3, 4, 5, 6, 7, 8, 9, 10, 11, or 12 consecutive weeks. In embodiments, a pharmaceutical composition is administered at least twice daily for at most 4, 5, 6, 7, 8, 9, 10, 11, 12, 13, 14, 15, 16, 17, 18, 19, or 20 consecutive days or week. In embodiments, a pharmaceutical composition is administered at least twice daily for at most 1, 2, 3, 4, 5, 6, 7, 8, 9, 10, 11, or 12 consecutive weeks or months. In embodiments, a pharmaceutical composition is administered at least twice for at least 1, 2, 3, 4, 5, 6, 7, 8, 9, 10, 11, or 12 consecutive months or years, chronically for a subject's entire life span, or an indefinite period of time.

In embodiments, a pharmaceutical composition is administered to a patient in need thereof at least three times daily for at least two consecutive days. In embodiments, a pharmaceutical composition is administered at least three times daily for at least 3, 4, 5, 6, 7, 8, 9, 10, 11, 12, 13, 14, or 15 consecutive days. In embodiments, a pharmaceutical composition is administered at least three times daily for at least 1, 2, 3, 4, 5, 6, 7, 8, 9, 10, 11, or 12 consecutive weeks. In embodiments, a pharmaceutical composition is administered at least three times daily for at most 4, 5, 6, 7, 8, 9, 10, 11, 12, 13, 14, 15, 16, 17, 18, 19, or 20 consecutive days or weeks. In embodiments, a pharmaceutical composition is administered at least three times daily for at most 1, 2, 3, 4, 5, 6, 7, 8, 9, 10, 11, or 12 consecutive weeks or months. In embodiments, a pharmaceutical composition is administered at least three times for at least 1, 2, 3, 4, 5, 6, 7, 8, 9, 10, 11, or 12 consecutive months or years, chronically for a subject's entire life span, or an indefinite period of time.

In embodiments, the present disclosure provides a method for treating a disorder (e.g., *C. difficile* infection, ASD, inflammatory bowel disease, ulcerative colitis, or Crohn's disease) in a subject in need thereof, where the method comprises administering orally to the subject a pharmaceutically active dose of a pharmaceutical composition comprising one or more live, non-pathogenic, bacterial isolates described herein, where the dose is administered at a dosing schedule of at least once or twice daily for at least three consecutive days or weeks. In embodiments, a dose is administered at least once, twice, or three times daily for a period between 1 and 12 weeks, between 2 and 12 weeks, between 3 and 12 weeks, between 4 and 12 weeks, between 5 and 12 weeks, between 6 and 12 weeks, between 7 and 12 weeks, between 8 and 12 weeks, between 9 and 12 weeks, between 10 and 12 weeks, between 1 and 2 weeks, between 2 and 3 weeks, between 3 and 4 weeks, between 4 and 5 weeks, between 5 and 6 weeks, between 6 and 7 weeks, between 7 and 8 weeks, between 8 and 9 weeks, between 9 and 10 weeks, or between 10 and 11 weeks.

In embodiments, the present disclosure provides a method for treating a disorder (e.g., *C. difficile* infection, ASD, inflammatory bowel disease, ulcerative colitis, or Crohn's disease) in a subject in need thereof, where the method comprises a combination treatment or therapy. For example, the method can comprise a double combination therapy, a triple combination therapy, or a quadruple combination therapy.

In yet another aspect, described herein is a plurality of pharmaceutical compositions, e.g., two or more pharmaceutical compositions, as disclosed herein, for use in the prevention or treatment a condition, disease, or disorder in a subject in need thereof. In embodiments, a first composition comprises one or more bacterial isolates having a first characteristic and a second composition comprises one or more bacterial isolates having a second characteristic. In embodiments, a first composition comprises one or more bacterial isolates having a first characteristic, a second composition comprises one or more bacterial isolates having a second characteristic, and a third composition comprises one or more bacterial isolates having a third characteristic. In embodiments, a first composition comprises one or more bacterial isolates having a first characteristic, a second composition comprises one or more bacterial isolates having a second characteristic, a third composition comprises one or more bacterial isolates having a third characteristic, and a fourth composition comprises one or more bacterial isolates having a fourth characteristic. As used herein, a characteristic of a bacterial isolate can include, for example: an ability of a bacterial isolate to produce or enhance production of at least one short-chain fatty acid (SCFA) in a gut of a subject administered the composition (e.g., represented by bacterial isolates provided in Table 2); an ability of a bacterial isolate to modulate cytokine production in a eukaryotic cell (e.g., a host cell of a subject administered the composition) (e.g., represented by bacterial isolates provided in Table 3); a correspondence to a bacterial strain more highly abundant in a healthy subject relative to a patient with UC (e.g., the bacterial isolate comprises a 16S rRNA sequence having at least 97% identity to a 16S rRNA sequence of the bacterial strain) (e.g., represented by bacterial isolates provided in Table 4); an ability to produce an aryl hydrocarbon capable of binding to and activating an AhR of a host cell of the subject (e.g., represented by bacterial isolates provided in Table 6); and a combination thereof.

Described herein is a method for preventing or treating a condition, disease or disorder in a subject in need thereof, comprising administering to the subject an effective amount of one or more pharmaceutical compositions comprising one or more bacterial isolates disclosed herein. In an embodiment, the method comprises administering to the subject one or more bacterial isolates comprising a 16S rRNA sequence at least 95% identical to a 16S rRNA sequence of one or more of the bacterial isolates provided in Table 1. In an embodiment, the method comprises administering to the subject one or more bacterial isolates comprising a 16S rRNA sequence at least 95% identical to the 16S rRNA sequence of one or more of the bacterial isolates provided in any one of Table 2, Table 3, or Table 4. In an embodiment, the method comprises administering to the subject one or more bacterial isolates comprising a 16S rRNA sequence at least 95% identical to a 16S rRNA sequence of one or more of the bacterial isolates provided in Table 6.

In an embodiment, the method comprises administering to the subject a plurality of bacterial isolates comprising 16S rRNA sequences at least 95% identical to 16S rRNA sequences of each of the bacterial isolates provided in any one of Tables 7-43. In an embodiment, the method comprises administering to the subject one or more bacterial isolates comprising a 16S rRNA sequence at least 95% identical to the 16S rRNA sequence of one or more of the bacterial isolates provided in Table 44.

In embodiments, a plurality of bacterial isolates administered to a subject in a method described herein are administered in the same pharmaceutical composition. In embodiments, a plurality of bacterial isolates administered to a subject in a method described herein are administered in separate pharmaceutical compositions. For example, a method can comprise administering to a subject in need thereof an effective amount of a plurality of pharmaceutical compositions, e.g., two or more pharmaceutical compositions, as disclosed herein. The plurality of pharmaceutical compositions can be provided simultaneously or sequentially. Thus, if a subject is to be treated with, for example, three bacterial isolates, a first composition can comprise two of the bacterial isolates and the second composition can comprise the third bacterial isolate. In a different example, if a subject is to be treated with three bacterial isolates, a first composition can comprise the first bacterial isolate, the second composition can comprise the second bacterial isolate, and the third composition can comprise the third bacterial isolate.

In embodiments, disclosed herein is a method of treating a disorder, disease, or condition involving a dysbiosis of an intestinal microbiota in a subject in need thereof, the method comprising administering to the subject a pharmaceutical composition described herein, wherein the pharmaceutical composition comprises one or more bacterial isolates, wherein the one or more bacterial isolates are each administered at a particular dose (e.g., a particular number of cells or a particular number of live cells). In an embodiment, the method comprises administering a pharmaceutical composition comprising one or more bacterial isolates, wherein the one or more bacterial isolates comprises one or more of *O. splanchnicus, B. cellulosilyticus, A. shahii, A. muciniphila, R. faecis, F. prausnitzii, E. rectale,* and *S. variabile*, wherein each of the one or more bacterial isolates is administered at a dosage of at least $10^7$ cells, between $10^7$ to $10^8$ cells, not more than $10^8$ cells, at least $10^8$ cells, between $10^8$ to $10^9$ cells, not more than $10^9$ cells, at least $10^9$ cells, between $10^9$ to $10^{10}$ cells, not more than $10^{10}$ cells, at least $10^{10}$ cells, between $10^{10}$ to $10^{11}$ cells, not more than $10^{11}$ cells, at least $10^{11}$ cells, between $10^{11}$ to $10^{12}$ cells, not more than $10^{12}$ cells, and at least $10^{12}$ cells.

In another aspect, disclosed herein are a plurality of pharmaceutical compositions, e.g., two or more pharmaceutical compositions, as disclosed herein, for use in the prevention or treatment of a condition, disease, or disorder in a subject in need thereof. In embodiments, a first composition comprises one or more bacterial isolates described herein. In embodiments, a second composition comprises an uncultured fecal microbiota (e.g., a substantially complete fecal microbiota purified from a stool sample) or a preparation of uncultured fecal bacteria. A subject can be treated with the first and second compositions in any order to treat or prevent a disorder. For example, in one embodiment a subject is treated with a composition comprising an uncultured fecal microbiota (or a preparation of uncultured fecal bacteria), followed by a composition comprising one or more bacterial isolates. In another embodiment, a subject is treated with a composition comprising one or more bacterial isolates followed by a composition comprising an uncultured fecal microbiota (or a preparation of uncultured fecal bacteria). In still other embodiments, a subject can be treated with a composition comprising one or more bacterial isolates and a composition comprising an uncultured fecal microbiota (or a preparation of uncultured fecal bacteria) simultaneously (for example, with a composition comprising both the bacterial isolate(s) and uncultured fecal microbiota (or preparation of uncultured fecal bacteria), or with multiple compositions each comprising one of the bacterial isolate(s) or an uncultured fecal microbiota or a preparation of uncultured fecal bacteria).

In an embodiment, a method for treating or preventing a condition, disease or disorder of a subject comprises administration to the subject of: (i) a pharmaceutical composition comprising one or more bacterial isolates; and (ii) an uncultured fecal microbiota or a preparation of uncultured fecal bacteria. For example, the one or more bacterial isolates can be administered before or after the uncultured fecal microbiota (or preparation of uncultured fecal bacteria), or at the same time (e.g., in different compositions or together in the same composition). In another embodiment, a method for treating a disorder of a subject comprises administration to the subject of: (i) a pharmaceutical composition comprising one or more bacterial isolates; and (ii) one or more antibiotics. For example, the one or more bacterial isolates can be administered before or after the uncultured fecal microbiota (or preparation of uncultured fecal bacteria), or at the same time (e.g., in different compositions or together in the same composition). Typically, the antibiotic is administered to the subject prior to administration of the one or more bacterial isolates, in order to purge the subject's intestine of harmful and/or pathogenic bacteria prior to replenishment of the gut with bacteria from the bacterial isolate(s). In an embodiment, a method for treating a disorder of a subject comprises administration to the subject of: (i) a pharmaceutical composition comprising one or more bacterial isolates; and (ii) a prebiotic. For example, the one or more bacterial isolates can be administered before or after the prebiotic, or at the same time (e.g., in different compositions or together in the same composition). For each of the above examples, it is further understood that any given component in a method of treatment can be administered multiple times. For example, an uncultured fecal microbiota (or a preparation of uncultured fecal bacteria) can be administered to the subject, followed by one or more bacterial isolates, followed by a second administration of the uncultured fecal microbiota (or preparation of uncultured fecal bacteria).

In an embodiment, a method for treating or preventing a condition, disease or disorder of a subject comprises administration to the subject of: (i) a pharmaceutical composition comprising one or more bacterial isolates; (ii) an uncultured fecal microbiota (or preparation of uncultured fecal bacteria); and (iii) one or more antibiotics. The different components of (i)-(iii) can be administered to the subject in any order. For example, a subject can be administered one or more antibiotics, followed by an uncultured fecal microbiota (or preparation of uncultured fecal bacteria), followed by one or more bacterial isolates. In another example, the subject can be administered one or more antibiotics, followed by one or more bacterial isolates, followed by an uncultured fecal microbiota (or preparation of uncultured fecal bacteria). For each of the above examples, it is further understood that any given component in a method of treatment can be administered multiple times. For example, an antibiotic can be administered to the subject, followed by an uncultured fecal microbiota, followed by one or more bacterial isolates, followed by a second administration of the uncultured fecal microbiota (or preparation of uncultured fecal bacteria).

In an embodiment, a method for treating or preventing a condition, disease or disorder of a subject comprises administration to the subject of: (i) a pharmaceutical composition comprising one or more bacterial isolates; (ii) an uncultured fecal microbiota (or preparation of uncultured fecal bacteria); and (iii) one or more prebiotics. The different components of (i)-(iii) can be administered to the subject in any order. For example, a subject can be administered one or more prebiotics, followed by an uncultured fecal microbiota (or preparation of uncultured fecal bacteria), followed by one or more bacterial isolates. In another example, the subject can be administered one or more prebiotics, followed by one or more bacterial isolates, followed by an uncultured fecal microbiota (or preparation of uncultured fecal bacteria). In another example, the subject can be administered one or more prebiotics following administration of one or both of the one or more bacterial isolates and/or the uncultured fecal microbiota (or preparation of uncultured fecal bacteria). For each of the above examples, it is further understood that any given component in a method of treatment can be administered multiple times. For example, an uncultured fecal microbiota (or preparation of uncultured fecal bacteria) can be administered to a subject, followed by a one or more bacterial isolates, followed by a prebiotic, followed by a second administration of the uncultured fecal microbiota (or preparation of uncultured fecal bacteria).

In an embodiment, a method for treating or preventing a condition, disease or disorder of a subject comprises administration to the subject of: (i) a pharmaceutical composition comprising one or more bacterial isolates; (ii) an uncultured fecal microbiota (or preparation of uncultured fecal bacteria); (iii) one or more prebiotics; and (iv) one or more antibiotics. The different components of (i)-(iv) can be administered to the subject in any order. For example, a subject can be administered one or more antibiotics, followed by one or more prebiotics, followed by an uncultured fecal microbiota (or preparation of uncultured fecal bacteria), followed by one or more bacterial isolates. In another example, the subject can be administered one or more antibiotics, followed by one or more prebiotics, followed by one or more bacterial isolates, followed by an uncultured fecal microbiota (or preparation of uncultured fecal bacteria). In another example, the prebiotic can be administered after one or both of the one or more bacterial isolates and/or the uncultured fecal microbiota (or preparation of uncultured fecal bacteria). For each of the above examples, it is further understood that any given component in a method of treatment can be administered multiple times. For example, an antibiotic can be administered to a subject, followed by an uncultured fecal microbiota (or preparation of uncultured fecal bacteria), followed by one or more bacterial isolates, followed by a prebiotic, followed by a second administration of the uncultured fecal microbiota (or preparation of uncultured fecal bacteria).

In each of the above combination treatments, the duration of time between different treatments (e.g., between administration of an uncultured fecal microbiota (or preparation of uncultured fecal bacteria) and one or more bacterial isolates) can be at least 1 hour, at least 2 hours, at least 6 hours, at least 12 hours, at least 1 day, at least 2 days, at least 3 days, at least 4 days, at least 5 days, at least 6 days, at least 1 week, at least 2 weeks, at least 3 weeks, at least 4 weeks, at least 5 weeks, at least 6 weeks, at least 7 weeks, at least 8 weeks, or greater than 8 weeks.

In embodiments, the pharmaceutical composition is used in a method for treating a disorder related to an intestinal dysbiosis in a subject, e.g., a GI disorder.

Kits

Described herein are kits comprising any herein-disclosed pharmaceutical composition and instructions for use.

The instructions can describe, for example, dosing information. As examples, the frequency of administration and dose of a composition, e.g., the number of capsules of a pharmaceutical composition to be administered at a given time, and the number of times of administration per day/week). In embodiments in which the kit comprises more than one composition (e.g., a microbial therapeutic and an additional pharmaceutical composition lacking a microbial therapeutic), the instructions can describe the dosing of each composition.

For example, one composition can be administered before another composition, e.g., sequential administration of the two pharmaceutical compositions separated by minutes, hours, days, weeks, months, or longer. Alternately, two compositions can be administered simultaneously.

Methods of Manufacture

Disclosed herein is a method of manufacturing a pharmaceutical composition comprising a microbial cocktail, the method comprising combining two or more bacterial isolates to form the microbial cocktail.

Disclosed herein is a method of manufacturing a pharmaceutical composition that comprises one or more bacterial isolates, the method comprising selecting the one or more bacterial isolates based on at least one of the following characteristics: (i) an ability to produce a particular amount, concentration or level of one or more short-chain fatty acids (SCFAs) such as butyrate as measured in a functional assay (e.g., represented by bacterial isolates provided in Table 2); (ii) an ability to induce a particular amount, concentration or level of cytokine production or release by a eukaryotic cell incubated with the bacterial isolate in a functional assay (e.g., represented by bacterial isolates provided in Table 3); (iii) a greater relative abundance of the bacterial isolate in a healthy human subject relative to a patient with an intestinal dysbiosis (e.g., ulcerative colitis (UC)), or a greater relative abundance of the bacterial isolate in a human subject in remission from an intestinal dysbiosis (e.g., UC) relative to a patient having the intestinal dysbiosis (e.g., represented by bacterial isolates provided in Table 4); and/or (iv) an ability to produce a particular amount, concentration or level of one or more aryl hydrocarbons as measured in a functional assay, such that the one or more aryl hydrocarbons are capable of inducing an aryl hydrocarbon receptor of a host cell of a subject administered the pharmaceutical composition (e.g., represented by bacterial isolates provided in Table 6). The method can further comprise incorporating the one or more bacterial isolates into the pharmaceutical composition.

In embodiments, only one bacterial isolate comprising characteristic (i) is selected and incorporated into the pharmaceutical composition. In embodiments, only one bacterial isolate comprising characteristic (ii) is selected and incorporated into the pharmaceutical composition. In embodiments, only one bacterial isolate comprising characteristic (iii) is selected and incorporated into the pharmaceutical composition. In embodiments, only one bacterial isolate comprising characteristic (iv) is selected and incorporated into the pharmaceutical composition. In embodiments, the pharmaceutical composition comprises only one bacterial isolate.

Disclosed herein is a method of manufacturing a pharmaceutical composition that comprises a plurality of bacterial isolates, the method comprising selecting the plurality of bacterial isolates based on at least one of the following characteristics: (i) an ability of the bacterial isolate to produce one or more short-chain fatty acids (SCFAs) in a gut of a subject administered the pharmaceutical composition; (ii) an ability of the bacterial isolate to modulate cytokine production in a host cell of a subject administered the pharmaceutical composition; (iii) a greater relative abundance of the bacterial isolate in a healthy human subject relative to a patient with an intestinal dysbiosis (e.g., ulcerative colitis (UC)), or a greater relative abundance of the bacterial isolate in a human subject in remission from an intestinal dysbiosis (e.g., UC) relative to a patient having the intestinal dysbiosis; and/or (iv) an ability to release an aryl hydrocarbon capable of inducing an aryl hydrocarbon receptor of a host cell of a subject administered the pharmaceutical composition. The method can further comprise incorporating the plurality of bacterial isolates into a microbial cocktail, and incorporating the microbial cocktail into the pharmaceutical composition.

In embodiments, two or more bacterial isolates comprising characteristic (i) can be selected and incorporated into the microbial cocktail; two or more bacterial isolates comprising characteristic (ii) can be selected and incorporated into the microbial cocktail; two or more bacterial isolates comprising characteristic (iii) can be selected and incorporated into the microbial cocktail; and/or two or more bacterial isolates comprising characteristic (iv) can be selected and incorporated into the microbial cocktail.

In embodiments, at least one bacterial isolate comprising characteristic (i) can be selected and incorporated into the microbial cocktail, and at least one bacterial isolate comprising characteristic (ii) can be selected and incorporated into the microbial cocktail. In embodiments, at least one bacterial isolate comprising characteristic (i) can be selected and incorporated into the microbial cocktail, and at least one bacterial isolate comprising characteristic (iii) can be selected and incorporated into the microbial cocktail. In embodiments, at least one bacterial isolate comprising characteristic (ii) can be selected and incorporated into the microbial cocktail, and at least one bacterial isolate comprising characteristic (iii) can be selected and incorporated into the microbial cocktail. In embodiments, at least one bacterial isolate comprising characteristic (i) can be selected and incorporated into the microbial cocktail, and at least one bacterial isolate comprising characteristic (iv) can be selected and incorporated into the microbial cocktail. In embodiments, at least one bacterial isolate comprising characteristic (ii) can be selected and incorporated into the microbial cocktail, and at least one bacterial isolate comprising characteristic (iv) can be selected and incorporated into the microbial cocktail. In embodiments, at least one bacterial isolate comprising characteristic (iii) can be selected and incorporated into the microbial cocktail, and at least one bacterial isolate comprising characteristic (iv) can be selected and incorporated into the microbial cocktail.

In embodiments, at least one bacterial isolate comprising characteristic (i) can be selected and incorporated into the microbial cocktail, at least one bacterial isolate comprising characteristic (ii) can be selected and incorporated into the microbial cocktail, and at least one bacterial isolate comprising characteristic (iii) can be selected and incorporated into the microbial cocktail. In embodiments, at least one bacterial isolate comprising characteristic (i) can be selected and incorporated into the pharmaceutical composition, at least one bacterial isolate comprising characteristic (ii) can be selected and incorporated into the microbial cocktail, and at least one bacterial isolate comprising characteristic (iv) can be selected and incorporated into the microbial cocktail. In embodiments, at least one bacterial isolate comprising characteristic (ii) can be selected and incorporated into the pharmaceutical composition, and at least one bacterial isolate comprising characteristic (iii) can be selected and incorporated into the microbial cocktail, and at least one bacterial isolate comprising characteristic (iv) can be selected and incorporated into the microbial cocktail.

In embodiments, at least one bacterial isolate comprising characteristic (i) can be selected and incorporated into the microbial cocktail, at least one bacterial isolate comprising characteristic (ii) can be selected and incorporated into the microbial cocktail, at least one bacterial isolate comprising characteristic (iii) can be selected and incorporated into the microbial cocktail, and at least one bacterial isolate comprising characteristic (iv) can be selected and incorporated into the microbial cocktail.

In embodiments, a bacterial isolate comprising characteristic (i) is not selected. In embodiments, a bacterial isolate comprising characteristic (ii) is not selected. In embodiments, a bacterial isolate comprising characteristic (iii) is not selected. In embodiments, a bacterial isolate comprising characteristic (iv) is not selected.

In embodiments, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or greater than 20 bacterial isolates are selected based on characteristics (i) to (iv) and incorporated into a microbial cocktail.

In embodiments, all bacterial isolates incorporated into a microbial cocktail are selected based on at least one of characteristics (i) to (iii). In embodiments, all bacterial isolates incorporated into a microbial cocktail are selected based on at least two of characteristics (i) to (iii). In embodiments, all bacterial isolates incorporated into a microbial cocktail are selected based on all three of characteristics (i) to (iii). In embodiments, all bacterial isolates incorporated into a composition are selected based on characteristic (i). In embodiments, all bacterial isolates incorporated into a composition are selected based on only characteristic (i).

In embodiments, all bacterial isolates incorporated into a composition are selected based on characteristic (ii). In embodiments, all bacterial isolates incorporated into a composition are selected based on only characteristic (ii). In embodiments, all bacterial isolates incorporated into a composition are selected based on characteristic (iii). In embodiments, all bacterial isolates incorporated into a composition are selected based on only characteristic (iii). In embodiments, all bacterial isolates incorporated into a microbial cocktail are selected based on at least one of characteristics (i) to (iv). In embodiments, all bacterial isolates incorporated into a microbial cocktail are selected based on at least two of characteristics (i) to (iv). In embodiments, all bacterial isolates incorporated into a microbial cocktail are selected based on at least three of characteristics (i) to (iv). In embodiments, all bacterial isolates incorporated into a microbial cocktail are selected based on all four of characteristics (i) to (iv). In embodiments, all bacterial isolates incorporated into a composition are selected based on characteristic (iv). In embodiments, all bacterial isolates incorporated into a composition are selected based on only characteristic (iv).

In embodiments, a bacterial isolate comprising *Odoribacter sphlanchnicus* is selected and incorporated into a pharmaceutical composition on the basis of the bacterial isolate exhibiting at least one of characteristic (i), characteristic (ii), characteristic (iii), and characteristic (iv). In embodiments, a bacterial isolate comprising *Odoribacter sphlanchnicus* is selected and incorporated into a pharmaceutical composition on the basis of the bacterial isolate exhibiting at least two of characteristic (i), characteristic (ii) characteristic (iii), and characteristic (iv). In embodiments, a bacterial isolate comprising *Odoribacter sphlanchnicus* is selected and incorporated into a pharmaceutical composition on the basis of the bacterial isolate exhibiting at least three of characteristic (i), characteristic (ii), characteristic (iii) and characteristic (iv). In embodiments, a bacterial isolate comprising *Odoribacter sphlanchnicus* is selected and incorporated into a pharmaceutical composition on the basis of the bacterial isolate exhibiting each of characteristic (i), characteristic (ii), characteristic (iii), and characteristic (iv).

In embodiments, a bacterial isolate comprising *Faecalibacterium prausnitzii* is selected and incorporated into a pharmaceutical composition on the basis of the bacterial isolate exhibiting at least one of characteristic (i), characteristic (ii) and characteristic (iii). In embodiments, a bacterial isolate comprising *Faecalibacterium prausnitzii* is selected and incorporated into a pharmaceutical composition on the basis of the bacterial isolate exhibiting at least two of characteristics (i), characteristic (ii) and characteristic (iii). In embodiments, a bacterial isolate comprising *Faecalibacterium prausnitzii* is selected and incorporated into a pharmaceutical composition on the basis of the bacterial isolate exhibiting each of characteristic (i), characteristic (ii) and characteristic (iii).

In embodiments, a bacterial isolate comprising *Eubacterium rectale* is selected and incorporated into a pharmaceutical composition on the basis of the bacterial isolate exhibiting at least one of characteristic (i) and characteristic (iii). In embodiments, a bacterial isolate comprising *Eubacterium rectale* is selected and incorporated into a pharmaceutical composition on the basis of the bacterial isolate exhibiting each of characteristic (i) and characteristic (ii).

In embodiments, a bacterial isolate comprising *Roseburia faecis* is selected and incorporated into a pharmaceutical composition on the basis of the bacterial isolate exhibiting characteristic (i).

In embodiments, a bacterial isolate comprising *Akkermansia muciniphila* is selected and incorporated into a pharmaceutical composition on the basis of the bacterial isolate exhibiting at least one of characteristic (ii) and characteristic (iii). In embodiments, a bacterial isolate comprising *Akkermansia muciniphila* is selected and incorporated into a pharmaceutical composition on the basis of the bacterial isolate exhibiting each of characteristic (ii) and characteristic (iii).

In embodiments, a bacterial isolate comprising *Alistipes shahii* is selected and incorporated into a pharmaceutical composition on the basis of the bacterial isolate exhibiting at least one of characteristic (ii) and characteristic (iii). In embodiments, a bacterial isolate comprising *Alistipes shahii* is selected and incorporated into a pharmaceutical composition on the basis of the bacterial isolate exhibiting each of characteristic (ii) and characteristic (iii).

In embodiments, a bacterial isolate comprising *Bacteroides cellulosilyticus* is selected and incorporated into a pharmaceutical composition on the basis of the bacterial isolate exhibiting characteristic (iii).

In embodiments, a bacterial isolate comprising *Subdoligranulum variabile* is selected and incorporated into a pharmaceutical composition on the basis of the bacterial isolate exhibiting at least one of characteristic (i), characteristic (ii) and characteristic (iii). In embodiments, a bacterial isolate comprising *Subdoligranulum variabile* is selected and incorporated into a pharmaceutical composition on the basis of the bacterial isolate exhibiting at least two of characteristics (i), characteristic (ii) and characteristic (iii). In embodiments, a bacterial isolate comprising *Subdoligranulum variabile* is selected and incorporated into a pharmaceutical composition on the basis of the bacterial isolate exhibiting each of characteristic (i), characteristic (ii) and characteristic (iii).

In embodiments, a bacterial isolate can be selected for inclusion in a pharmaceutical composition described herein based on its ability to produce a particular amount or concentration of an SCFA such as butyrate (i.e., based on characteristic (i)) as measured in a functional assay. For example, a series of bacterial isolates can be screened for an ability to produce a threshold concentration of an SCFA when incubated with an organic substrate capable of being converted to an SCFA during a period of time. In embodiments, the substrate can comprise at least one of an oligosaccharide (e.g., a fructooligosaccharide (FOS) or an xylooligosaccharide (XOS)), sunfiber/partially hydrolyzed guar gum (PHGG), or barley malt.

The bacterial isolate can be incubated with the substrate for any period of time sufficient to allow conversion of the substrate to the SCFA, for example at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, at least 24 hours, at least 25 hours, at least 26 hours, at least 27 hours, at least 28 hours, at least 29 hours, at least 30 hours, at least 35 hours, at least 40 hours, at least 44 hours, at least 48 hours, or greater than 48 hours.

In embodiments, a bacterial isolate can be selected for inclusion in a pharmaceutical composition described herein based on a production of SCFA (e.g., butyrate) over a duration of time (e.g., 24 hours) at a level of at least 5 mM, at least 10 mM, at least 15 mM, at least 20 mM, at least 25 mM, at least 30 mM, at least 35 mM, at least 40 mM, at least 45 mM at least 50 mM, at least 60 mM, at least 70 mM, at least 80 mM, at least 90 mM, at least 100 mM, or greater than 100 mM. In embodiments, a bacterial isolate selected for inclusion in a pharmaceutical composition is provided in Table 2, or comprises a 16S rRNA sequence at least 95% identical to a 16S rRNA sequence corresponding to a SEQ ID NO of a bacterial isolate provided in Table 2.

In embodiments, a bacterial isolate can be selected for inclusion in a pharmaceutical composition described herein based on its ability to modulate production and/or release of one or more cytokines by a eukaryotic cell incubated with the bacterial isolate (i.e., based on characteristic (ii)), as measured in a functional assay. For example, a series of bacterial isolates can be screened for an ability to modulate production and/or release of one or more cytokines from a eukaryotic cell incubated with each bacterial isolate. Examples of eukaryotic cells that can be used in the functional assay include an intestinal cell, an epithelial cell, an intestinal mucosal cell, an intestinal epithelial cell, an intestinal lamina propria cell, an endothelial cell, fibroblast, a stromal cell, a macrophage, a B lymphocyte, a T lymphocyte, a mast cell, and a peripheral blood mononuclear cell (PBMC). In embodiments, the eukaryotic cell can be a human cell.

The bacterial isolate can be incubated with the eukaryotic cell for any period of time sufficient to allow modulation of cytokine expression, for example at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, at least 24 hours, at least 25 hours, at least 26 hours, at least 27 hours, at least 28 hours, at least 29 hours, at least 30 hours, at least 35 hours, at least 40 hours, at least 44 hours, at least 48 hours, or greater than 48 hours.

In embodiments, a bacterial isolate can be selected for inclusion in a pharmaceutical composition described herein based on the induction of IL-10 by a population of eukaryotic cells (e.g., population of PBMCs) incubated with the bacterial isolate during a period of time (e.g., 24 hours), as measured in a functional assay. For example, the bacterial isolate can induce IL-10 at a concentration of at least 1000 pg/ml, at least 1500 pg/ml, at least 2000 pg/ml, at least 2500 pg/ml, at least 3000 pg/ml, at least 3500 pg/ml, at least 4000 pg/ml, at least 5000 pg/ml, at least 6000 pg/ml, at least 7000 pg/ml, at least 8000 pg/ml, at least 9000 pg/ml, at least 10,000 pg/ml, or greater than 10,000 pg/ml. In embodiments, a bacterial isolate selected for inclusion in a pharmaceutical composition is provided in Table 3, or comprises a 16S rRNA sequence at least 95% identical to a 16S rRNA sequence corresponding to a SEQ ID NO of a bacterial isolate provided in Table 3.

In embodiments, a bacterial isolate can be selected for inclusion in a pharmaceutical composition described herein based on a limited production of GM-CSF by a population of eukaryotic cells (e.g., population of PBMCs) incubated with the bacterial isolate during a period of time (e.g., 24 hours), as measured in a functional assay. For example, the bacterial isolate can limit production of GM-CSF to a concentration of no more than 5 pg/ml, 10 pg/ml, 15 pg/ml, 20 pg/ml, 25 pg/ml, 30 pg/ml, 35 pg/ml, 40 pg/ml, 45 pg/ml, 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, 100 pg/ml, 105 pg/ml, 110 pg/ml, 115 pg/ml, 120 pg/ml, 125 pg/ml, 130 pg/ml, 135 pg/ml, 140 pg/ml, 145 pg/ml, 150 pg/ml, 155 pg/ml, 160 pg/ml, 165 pg/ml, 170 pg/ml, 175 pg/ml, 180 pg/ml, 185 pg/ml, 190 pg/ml, 195 pg/ml, or 200 pg/ml. In embodiments, a bacterial isolate selected for inclusion in a pharmaceutical composition is provided in Table 3, or comprises a 16S rRNA sequence at least 95% identical to a 16S rRNA sequence corresponding to a SEQ ID NO of a bacterial isolate provided in Table 3.

In embodiments, a bacterial isolate can be selected for inclusion in a pharmaceutical composition described herein based on a limited production of IL-12 by a population of eukaryotic cells (e.g., population of PBMCs) incubated with the bacterial isolate during a period of time (e.g., 24 hours), as measured in a functional assay. For example, the bacterial isolate can limit production of IL-12 to a concentration of no more than 5 pg/ml, 10 pg/ml, 15 pg/ml, 20 pg/ml, 25 pg/ml, 30 pg/ml, 35 pg/ml, 40 pg/ml, 45 pg/ml, 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, 100 pg/ml, 105 pg/ml, 110 pg/ml, 115 pg/ml, 120 pg/ml, 125 pg/ml, 130 pg/ml, 135 pg/ml, 140 pg/ml, 145 pg/ml, 150 pg/ml, 155 pg/ml, 160 pg/ml, 165 pg/ml, 170 pg/ml, 175 pg/ml, 180 pg/ml, 185 pg/ml, 190 pg/ml, 195 pg/ml, or 200 pg/ml. In embodiments, a bacterial isolate selected for inclusion in a pharmaceutical composition is provided in Table 3, or comprises a 16S rRNA sequence at least 95% identical to a 16S rRNA sequence corresponding to a SEQ ID NO of a bacterial isolate provided in Table 3.

In embodiments, a bacterial isolate can be selected for inclusion in a pharmaceutical composition described herein based on a limited production of IFN-gamma by a population of eukaryotic cells (e.g., population of PBMCs) incubated with the bacterial isolate during a period of time (e.g., 24 hours), as measured in a functional assay. For example, the bacterial isolate can limit production of IFN-gamma to a concentration of no more than 5 pg/ml, 10 pg/ml, 15 pg/ml, 20 pg/ml, 25 pg/ml, 30 pg/ml, 35 pg/ml, 40 pg/ml, 45 pg/ml, 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, 100 pg/ml, 105 pg/ml, 110 pg/ml, 115 pg/ml, 120 pg/ml, 125 pg/ml, 130 pg/ml, 135 pg/ml, 140 pg/ml, 145 pg/ml, 150 pg/ml, 155 pg/ml, 160 pg/ml, 165 pg/ml, 170 pg/ml, 175 pg/ml, 180 pg/ml, 185 pg/ml, 190 pg/ml, 195 pg/ml, or 200 pg/ml. In embodiments, a bacterial isolate selected for inclusion in a pharmaceutical composition is provided in Table 3, or comprises a 16S rRNA sequence at least 95% identical to a 16S rRNA sequence corresponding to a SEQ ID NO of a bacterial isolate provided in Table 3.

In embodiments, a bacterial isolate can be selected for inclusion in a pharmaceutical composition described herein based on a limited production of TNF-alpha by a population of eukaryotic cells (e.g., population of PBMCs) incubated with the bacterial isolate during a period of time (e.g., 24 hours), as measured in a functional assay. For example, the bacterial isolate can limit production of TNF-alpha to a concentration of no more than 20 pg/ml, 30 pg/ml, 40 pg/ml, 50 pg/ml, 75 pg/ml, 100 pg/ml, 150 pg/ml, 200 pg/ml, 250 pg/ml, 300 pg/ml, 350 pg/ml, 400 pg/ml, 450 pg/ml, 500 pg/ml, 550 pg/ml, 600 pg/ml, 650 pg/ml, 700 pg/ml, 750 pg/ml, 800 pg/ml, 850 pg/ml, 900 pg/ml, 950 pg/ml, 1000 pg/ml, 1100 pg/ml, 1200 pg/ml, 1300 pg/ml, 1400 pg/ml, 1500 pg/ml, 1600 pg/ml, 1700 pg/ml, 1800 pg/ml, 1900 pg/ml, 2000 pg/ml, 2100 pg/ml, 2200 pg/ml, 2300 pg/ml, 2400 pg/ml, or 2500 pg/ml. In embodiments, a bacterial isolate selected for inclusion in a pharmaceutical composition is provided in Table 3, or comprises a 16S rRNA sequence at least 95% identical to a 16S rRNA sequence corresponding to a SEQ ID NO of a bacterial isolate provided in Table 3.

In embodiments, a bacterial isolate can be selected for inclusion in a pharmaceutical composition described herein based on a limited production of IL-23 by a population of eukaryotic cells (e.g., population of PBMCs) incubated with the bacterial isolate during a period of time (e.g., 24 hours), as measured in a functional assay. For example, the bacterial isolate can limit production of IL-23 to a concentration of no more than 5 pg/ml, 10 pg/ml, 15 pg/ml, 20 pg/ml, 25 pg/ml, 30 pg/ml, 35 pg/ml, 40 pg/ml, 45 pg/ml, 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, 100 pg/ml, 105 pg/ml, 110 pg/ml, 115 pg/ml, 120 pg/ml, 125 pg/ml, 130 pg/ml, 135 pg/ml, 140 pg/ml, 145 pg/ml, 150 pg/ml, 155 pg/ml, 160 pg/ml, 165 pg/ml, 170 pg/ml, 175 pg/ml, 180 pg/ml, 185 pg/ml, 190 pg/ml, 195 pg/ml, 200 pg/ml, 250 pg/ml, or 300 pg/ml. In embodiments, a bacterial isolate selected for inclusion in a pharmaceutical composition is provided in Table 3, or comprises a 16S rRNA sequence at least 95% identical to a 16S rRNA sequence corresponding to a SEQ ID NO of a bacterial isolate provided in Table 3.

In embodiments, a bacterial isolate can be selected for inclusion in a pharmaceutical composition described herein based on an IL-10:IL-12 ratio produced by a population of eukaryotic cells (e.g., population of PBMCs) incubated with the bacterial isolate during a period of time (e.g., 24 hours), as measured in a functional assay. For example, the bacterial isolate can generate an IL-10:IL-12 ratio of at least 20, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 325, at least 350, at least 375, at least 400, at least 425, at least 450, at least 475, at least 500, at least 550, at least 600, at least 650, at least 700, at least 750, at least 800, at least 850, at least 900, at least 950, at least 1000, at least 1100, at least 1200, at least 1300, at least 1400, at least 1500, at least 1600, at least 1700, at least 1800, at least 1900, at least 2000, at least 2200, at least 2400, at least 2600, at least 2800, at least 3000, at least 3200, at least 3400, at least 3600, at least 3800, at least 4000, or greater than 4000. In an embodiment, the bacterial isolate is provided in Table 3, or comprises a 16S rRNA sequence at least 95% identical to a 16S rRNA sequence corresponding to a SEQ ID NO of a bacterial isolate provided in Table 3.

In embodiments, a bacterial isolate can be selected for inclusion in a pharmaceutical composition described herein based on an IL-10:TNF-alpha ratio produced by a population of eukaryotic cells (e.g., population of PBMCs) incubated with the bacterial isolate during a period of time (e.g., 24 hours), as measured in a functional assay. For example, the bacterial isolate can generate an IL-10:TNF-alpha ratio of at least 0.5, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, at least 55, at least 60, at least 65, at least 70, at least 75, at least 80, at least 85, at least 90, at least 95, or at least 100. In embodiments, a bacterial isolate selected for inclusion in a pharmaceutical composition is provided in Table 3, or comprises a 16S rRNA sequence at least 95% identical to a 16S rRNA sequence corresponding to a SEQ ID NO of a bacterial isolate provided in Table 3.

In embodiments, a bacterial isolate can be selected for inclusion in a pharmaceutical composition described herein based on its ability to produce a threshold amount or concentration of one or more aryl hydrocarbons for activating an AhR of a host cell of a subject administered the pharmaceutical composition (i.e., based on characteristic (iv)), as measured in a functional assay. For example, a series of bacterial isolates can be screened for an ability to modulate production and/or release of one or more aryl hydrocarbons after incubation with tryptophan or a tryptophan intermediate in a functional assay. In embodiments, the aryl hydrocarbon is selected from the group consisting of indole, indole-3-acetic acid (IAA), indole-3-aldehyde (IAId), indole-3-lactic acid, indole-3-carbinol (I3C), indole-3-acetonitrile (I3ACN), 3,3'-diindolylmethane (DIM), 2-(indol-3-ylmethyl)-3,3'-diindolylmethane (Ltr-1), indolo[3,2-b]carbazole (ICZ), 2-(1'H-indole-3' carbonyl)-thiazole-4-carboxylic acid methyl ester (ITE), 3-methyl-indole (skatole), tryptamine, kynurenine, kynurenate, indigo, indirubin, indoxyl-3-sulfate (I3S), xanthurenic acid, cinnabarinic acid, and any combination thereof.

The bacterial isolate can be incubated in a functional assay (e.g., in the presence of tryptophan or a tryptophan intermediate) for any period of time sufficient to allow production of the aryl hydrocarbon by the bacterial isolate, for example at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, at least 24 hours, at least 25 hours, at least 26 hours, at least 27 hours, at least 28 hours, at least 29 hours, at least 30 hours, at least 31 hours, at least 32 hours, at least 33 hours, at least 34 hours, at least 35 hours, at least 36 hours, at least 37 hours, at least 38 hours, at least 39 hours, at least 40 hours, at least 41 hours, at least 42 hours, at least 43 hours, at least 44 hours, at least 45 hours, at least 46 hours, at least 47 hours, at least 48 hours, or greater than 48 hours.

In embodiments, the functional assay can measure an absolute amount or concentration of one or more aryl hydrocarbons capable of activating an AhR of a host cell. In other embodiments, the functional assay can measure a relative amount of one or more aryl hydrocarbons. In an example, an amount of production of an aryl hydrocarbon by a bacterial isolate can be relative to blank media not containing a bacterial isolate. Alternatively, the functional assay can measure the amount or concentration of an aryl hydrocarbon produced by a bacterial isolate relative to that produced by one or more control bacterial strains. In an embodiment, the control bacterial strain is known to produce an aryl hydrocarbon, for example the aryl hydrocarbon being measured in the assay. Exemplary control strains that can be used in a functional assay to measure one or more aryl hydrocarbons are bacterial strains that are a member of the genus *Peptostreptococcus* (e.g., *Peptostreptococcus anaerobius* or *Peptostreptococcus russellii*) In an embodiment, the functional assay comprises comparison of a level of an aryl hydrocarbon produced by a bacterial isolate of interest over a period of time (e.g., 48 hours) to a level of the same aryl hydrocarbon produced by one or more of the control strains *Peptostreptococcus anaerobius* or *Peptostreptococcus russellii* over the same period of time. In certain embodiments, a pharmaceutical composition comprises a bacterial isolate capable of producing an aryl hydrocarbon at a level of at least 1.1×, at least 1.2×, at least 1.3×, at least 1.4×, at least 1.5×, at least 1.6×, at least 1.7×, at least 1.8×, at least 1.9×, at least 2×, at least 2.1×, at least 2.2×, at least 2.3×, at least 2.4×, at least 2.5×, at least 2.6×, at least 2.7×, at least 2.8×, at least 2.9×, at least 3×, at least 4×, at least 5×, at least 6×, at least 7×, at least 8×, at least 9×, at least 10×, at least 11×, at least 12×, at least 13×, at least 14×, at least 15×, at least 16×, at least 17×, at least 18×, at least 19×, at least 20×, at least 21×, at least 22×, at least 23×, at least 24×, at least 25×, at least 26×, at least 27×, at least 28×, at least 29×, at least 30×, at least 35×, at least 40×, at least 45×, at least 50×, at least 60×, at least 70×, at least 80×, at least 90×, at least 100×, at least 110×, at least 120×, at least 130×, at least 140×, at least 150×, at least 160×, at least 170×, at least 180×, at least 190×, at least 200×, at least 210×, at least 220×, at least 230×, at least 240×, at least 250×, or greater than 250× relative to a control bacterial strain (e.g. a *Peptostreptococcus* strain such as *Peptostreptococcus anaerobius* or *Peptostreptococcus russellii*)), or compared to blank media alone.

In embodiments, a bacterial isolate can be selected for inclusion in a pharmaceutical composition described herein based on the production of kynurenate (i.e., kynurenic acid) during a period of time (e.g., 48 hours), as measured in a functional assay. For example, the bacterial isolate can be selected if it can produce kynurenate at a concentration of at least 0.1 µM kynurenate, at least 0.2 µM kynurenate, at least 0.3 µM kynurenate, at least 0.4 µM kynurenate, at least 0.5 µM kynurenate, at least 0.6 µM kynurenate, at least 0.7 µM kynurenate, at least 0.8 µM kynurenate, at least 0.9 µM kynurenate, at least 1 µM kynurenate, at least 1.5 µM kynurenate, at least 2 µM kynurenate, at least 2.5 µM kynurenate, at least 3 µM kynurenate, at least 3.5 µM kynurenate, at least 4 µM kynurenate, at least 4.5 µM kynurenate, at least 5 µM kynurenate, or greater than 5 µM kynurenate. In embodiments, the selected bacterial isolate is provided in Table 6, or comprises a 16S rRNA sequence at least 95% identical to a 16S rRNA sequence corresponding to a SEQ ID NO of a bacterial isolate provided in Table 6. In an embodiment, the selected bacterial isolate comprises *Odoribacter splanchnicus*. In an embodiment, the selected bacterial isolate comprises a 16S rRNA sequence at least 95% identical to the 16S rRNA sequence corresponding to SEQ ID NO: 6.

In other embodiments, a bacterial isolate can be selected for inclusion in a pharmaceutical composition described herein based on production of kynurenate at a higher level than blank media or a control bacterial strain (e.g., positive control bacterial strain capable of producing kynurenate, such as a strain that is a member of the *Peptostreptococcus* genus), as measured in a functional assay. For example, a bacterial isolate can be selected if it can produce kynurenate at a higher level than at least one of the control strains *Peptostreptococcus anaerobius* or *Peptostreptococcus russellii* over a duration of time. In embodiments, a bacterial isolate is selected if it can produce kynurenate at a level of at least 1.1×, at least 1.2×, at least 1.3×, at least 1.4×, at least 1.5×, at least 1.6×, at least 1.7×, at least 1.8×, at least 1.9×, at least 2×, at least 2.1×, at least 2.2×, at least 2.3×, at least 2.4×, at least 2.5×, at least 2.6×, at least 2.7×, at least 2.8×, at least 2.9×, at least 3×, at least 4×, at least 5×, at least 6×, at least 7×, at least 8×, at least 9×, at least 10×, at least 11×, at least 12×, at least 13×, at least 14×, at least 15×, at least 16×, at least 17×, at least 18×, at least 19×, at least 20×, at least 21×, at least 22×, at least 23×, at least 24×, at least 25×, at least 26×, at least 27×, at least 28×, at least 29×, at least 30×, at least 35×, at least 40×, at least 45×, at least 50×, at least 60×, at least 70×, at least 80×, at least 90×, at least 100×, at least 110×, at least 120×, at least 130×, at least 140×, at least 150×, at least 160×, at least 170×, at least 180×, at least 190×, at least 200×, at least 210×, at least 220×, at least 230×, at least 240×, at least 250×, or greater than 250× relative to at least one of the control strains *Peptostreptococcus anaerobius* or *Peptostreptococcus rus-*

*sellii*, or relative to blank media alone. In embodiments, the bacterial isolate is provided in Table 6, or comprises a 16S rRNA sequence at least 95% identical to a 16S rRNA sequence corresponding to a SEQ ID NO of a bacterial isolate provided in Table 6. In an embodiment, the bacterial isolate comprises *Odoribacter splanchnicus*. In an embodiment, the bacterial isolate comprises a 16S rRNA sequence at least 95% identical to the 16S rRNA sequence corresponding to SEQ ID NO: 2.

In embodiments, a bacterial isolate can be selected for inclusion in a pharmaceutical composition described herein based on the production of indole-3-acetic acid (IAA) during a period of time (e.g., 48 hours), as measured in a functional assay. For example, the bacterial isolate can be selected if it can produce IAA at a concentration of at least 0.1 μM IAA, at least 0.2 μM IAA, at least 0.3 μM IAA, at least 0.4 μM IAA, at least 0.5 μM IAA, at least 0.6 μM IAA, at least 0.7 μM IAA, at least 0.8 μM IAA, at least 0.9 μM IAA, at least 1 μM IAA, at least 1.5 μM IAA, at least 2 μM IAA, at least 2.5 μM IAA, at least 3 μM IAA, at least 4 μM IAA, at least 5 μM IAA, at least 6 μM IAA, at least 7 μM IAA, at least 8 μM IAA, at least 9 μM IAA, at least 10 μM IAA, at least 20 μM IAA, at least 30 μM IAA, at least 40 μM IAA, at least 50 μM IAA, at least 60 μM IAA, at least 70 μM IAA, at least 80 μM IAA, at least 90 μM IAA, at least 100 μM IAA, at least 110 μM IAA, at least 120 μM IAA, at least 130 μM IAA, at least 140 μM IAA, at least 150 μM IAA, at least 160 μM IAA, at least 170 μM IAA, at least 180 μM IAA, at least 190 μM IAA, at least 200 μM IAA or greater than 200 μM IAA. In embodiments, the selected bacterial isolate is provided in Table 6, or comprises a 16S rRNA sequence at least 95% identical to a 16S rRNA sequence corresponding to a SEQ ID NO of a bacterial isolate provided in Table 6. In an embodiment, the selected bacterial isolate comprises *Odoribacter splanchnicus*. In an embodiment, the selected bacterial isolate comprises a 16S rRNA sequence at least 95% identical to the 16S rRNA sequence corresponding to SEQ ID NO: 2. In an embodiment, the selected bacterial isolate comprises *Clostridium aldenense*. In an embodiment, the selected bacterial isolate comprises a 16S rRNA sequence at least 95% identical to the 16S rRNA sequence corresponding to SEQ ID NO: 10.

In other embodiments, a bacterial isolate can be selected for inclusion in a pharmaceutical composition described herein based on production of indole-3-acetoc acid (IAA) at a higher level than blank media or a control bacterial strain (e.g., positive control bacterial strain capable of producing IAA, such as a strain that is a member of the *Peptostreptococcus* genus), as measured in a functional assay. For example, a bacterial isolate can be selected if it can produce IAA at a higher level than at least one of the control strains *Peptostreptococcus anaerobius* or *Peptostreptococcus russellii* over a duration of time. In embodiments, a bacterial isolate is selected if it can produce IAA at a level of at least 1.1×, at least 1.2×, at least 1.3×, at least 1.4×, at least 1.5×, at least 1.6×, at least 1.7×, at least 1.8×, at least 1.9×, at least 2×, at least 2.1×, at least 2.2×, at least 2.3×, at least 2.4×, at least 2.5×, at least 2.6×, at least 2.7×, at least 2.8×, at least 2.9×, at least 3×, at least 4×, at least 5×, at least 6×, at least 7×, at least 8×, at least 9×, at least 10×, at least 11×, at least 12×, at least 13×, at least 14×, at least 15×, at least 16×, at least 17×, at least 18×, at least 19×, at least 20×, at least 21×, at least 22×, at least 23×, at least 24×, at least 25×, at least 26×, at least 27×, at least 28×, at least 29×, at least 30×, at least 35×, at least 40×, at least 45×, at least 50×, at least 60×, at least 70×, at least 80×, at least 90×, at least 100×, at least 110×, at least 120×, at least 130×, at least 140×, at least 150×, at least 160×, at least 170×, at least 180×, at least 190×, at least 200×, at least 210×, at least 220×, at least 230×, at least 240×, at least 250×, or greater than 250× relative to at least one of the control strains *Peptostreptococcus anaerobius* or *Peptostreptococcus russellii*, or relative to blank media alone. In embodiments, the selected bacterial isolate is provided in Table 6, or comprises a 16S rRNA sequence at least 95% identical to a 16S rRNA sequence corresponding to a SEQ ID NO of a bacterial isolate provided in Table 6. In an embodiment, the selected bacterial isolate comprises *Odoribacter splanchnicus*. In an embodiment, the selected bacterial isolate comprises a 16S rRNA sequence at least 95% identical to the 16S rRNA sequence corresponding to SEQ ID NO: 2. In an embodiment, the selected bacterial isolate comprises *Clostridium aldenense*. In an embodiment, the selected bacterial isolate comprises a 16S rRNA sequence at least 95% identical to the 16S rRNA sequence corresponding to SEQ ID NO: 10.

In embodiments, a bacterial isolate can be selected for inclusion in a pharmaceutical composition described herein based on the production of indole-3-lactic acid during a period of time (e.g., 48 hours), as measured in a functional assay. For example, the bacterial isolate can be selected if it can produce indole-3-lactic acid at a concentration of at least 0.1 μM indole-3-lactic acid, at least 0.2 μM indole-3-lactic acid, at least 0.3 μM indole-3-lactic acid, at least 0.4 μM indole-3-lactic acid, at least 0.5 μM indole-3-lactic acid, at least 0.6 μM indole-3-lactic acid, at least 0.7 μM indole-3-lactic acid, at least 0.8 μM indole-3-lactic acid, at least 0.9 μM indole-3-lactic acid, at least 1 μM indole-3-lactic acid, at least 1.5 μM indole-3-lactic acid, at least 2 μM indole-3-lactic acid, at least 2.5 μM indole-3-lactic acid, at least 3 μM indole-3-lactic acid, at least 3.5 μM indole-3-lactic acid, at least 4 μM indole-3-lactic acid, at least 4.5 μM indole-3-lactic acid, at least 5 μM indole-3-lactic acid, or greater than 5 μM indole-3-lactic acid. In embodiments, the selected bacterial isolate is provided in Table 6, or comprises a 16S rRNA sequence at least 95% identical to a 16S rRNA sequence corresponding to a SEQ ID NO of a bacterial isolate provided in Table 6.

In other embodiments, a bacterial isolate can be selected for inclusion in a pharmaceutical composition described herein based on production of indole-3-lactic acid at a higher level than blank media or a control bacterial strain (e.g., positive control bacterial strain capable of producing indole-3-lactic acid, such as a strain that is a member of the *Peptostreptococcus* genus), as measured in a functional assay. For example, a bacterial isolate can be selected if it can produce indole-3-lactic acid at a higher level than at least one of the control strains *Peptostreptococcus anaerobius* or *Peptostreptococcus russellii* over a duration of time. In embodiments, a bacterial isolate is selected if it can produce indole-3-lactic acid at a level that is at least 1.1×, at least 1.2×, at least 1.3×, at least 1.4×, at least 1.5×, at least 1.6×, at least 1.7×, at least 1.8×, at least 1.9×, at least 2×, at least 2.1×, at least 2.2×, at least 2.3×, at least 2.4×, at least 2.5×, at least 2.6×, at least 2.7×, at least 2.8×, at least 2.9×, at least 3×, at least 4×, at least 5×, at least 6×, at least 7×, at least 8×, at least 9×, at least 10×, at least 11×, at least 12×, at least 13×, at least 14×, at least 15×, at least 16×, at least 17×, at least 18×, at least 19×, at least 20×, at least 21×, at least 22×, at least 23×, at least 24×, at least 25×, at least 26×, at least 27×, at least 28×, at least 29×, at least 30×, at least 35×, at least 40×, at least 45×, at least 50×, at least 60×, at least 70×, at least 80×, at least 90×, at least 100×, at least 10×, at least 120×, at least 130×, at least 140×, at least 150×, at least 160×, at least 170×, at least 180×, at least 190×, at least 200×, at least 210×, at least 220×, at least 230×, at least 240×, at least 250×, or greater than 250× relative to at least one of the control strains *Peptostreptococcus anaerobius* or *Peptostreptococcus russellii*, or relative to blank media alone. In embodiments, the selected bacterial isolate is provided in Table 6, or comprises a 16S rRNA sequence at least 95% identical to a 16S rRNA sequence corresponding to a SEQ ID NO of a bacterial isolate provided in Table 6.

In embodiments, a bacterial isolate can be selected for inclusion in a pharmaceutical composition described herein based on the production of indole during a period of time (e.g., 48 hours), as measured in a functional assay. For example, the bacterial isolate can be selected if it can produce indole at a concentration of at least 0.1 µM indole, at least 0.2 µM indole, at least 0.3 µM indole, at least 0.4 µM indole, at least 0.5 µM indole, at least 0.6 µM indole, at least 0.7 µM indole, at least 0.8 µM indole, at least 0.9 µM indole, at least 1 µM indole, at least 1.5 µM indole, at least 2 µM indole, at least 2.5 µM indole, at least 3 µM indole, at least 3.5 µM indole, at least 4 µM indole, at least 4.5 µM indole, at least 5 µM indole, or greater than 5 µM indole. In embodiments, the selected bacterial isolate is provided in Table 6, or comprises a 16S rRNA sequence at least 95% identical to a 16S rRNA sequence corresponding to a SEQ ID NO of a bacterial isolate provided in Table 6. In an embodiment, the selected bacterial isolate comprises *Clostridium* sp. (e.g., *Clostridium aldenense*). In an embodiment, the selected bacterial isolate comprises a 16S rRNA sequence at least 95% identical to the 16S rRNA sequence corresponding to SEQ ID NO: 10.

In other embodiments, a bacterial isolate can be selected for inclusion in a pharmaceutical composition described herein based on production of indole at a higher level than blank media or a control bacterial strain (e.g., positive control bacterial strain capable of producing indole, such as a strain that is a member of the *Peptostreptococcus* genus), as measured in a functional assay. For example, a bacterial isolate can be selected if it can produce indole at a higher level than at least one of the control strains *Peptostreptococcus anaerobius* or *Peptostreptococcus russellii* over a duration of time. In embodiments, a bacterial isolate is selected if it can produce indole at a level that is at least 1.1×, at least 1.2×, at least 1.3×, at least 1.4×, at least 1.5×, at least 1.6×, at least 1.7×, at least 1.8×, at least 1.9×, at least 2×, at least 2.1×, at least 2.2×, at least 2.3×, at least 2.4×, at least 2.5×, at least 2.6×, at least 2.7×, at least 2.8×, at least 2.9×, at least 3×, at least 4×, at least 5×, at least 6×, at least 7×, at least 8×, at least 9×, at least 10×, at least 11×, at least 12×, at least 13×, at least 14×, at least 15×, at least 16×, at least 17×, at least 18×, at least 19×, at least 20×, at least 21×, at least 22×, at least 23×, at least 24×, at least 25×, at least 26×, at least 27×, at least 28×, at least 29×, at least 30×, at least 35×, at least 40×, at least 45×, at least 50×, at least 60×, at least 70×, at least 80×, at least 90×, at least 100×, at least 110×, at least 120×, at least 130×, at least 140×, at least 150×, at least 160×, at least 170×, at least 180×, at least 190×, at least 200×, at least 210×, at least 220×, at least 230×, at least 240×, at least 250×, or greater than 250× relative to at least one of the control strains *Peptostreptococcus anaerobius* or *Peptostreptococcus russellii*, or relative to blank media alone. In embodiments, the selected bacterial isolate is provided in Table 6, or comprises a 16S rRNA sequence at least 95% identical to a 16S rRNA sequence corresponding to a SEQ ID NO of a bacterial isolate provided in Table 6. In an embodiment, the selected bacterial isolate comprises *Clostridium* sp. (e.g., *Clostridium aldenense*). In an embodiment, the selected bacterial isolate comprises a 16S rRNA sequence at least 95% identical to the 16S rRNA sequence corresponding to SEQ ID NO: 10.

In embodiments, a bacterial isolate can be selected for inclusion in a pharmaceutical composition described herein based on the production of kynurenine during a period of time (e.g., 48 hours), as measured in a functional assay. For example, the bacterial isolate can be selected if it can produce kynurenine at a concentration of at least 0.1 µM kynurenine, at least 0.2 µM kynurenine, at least 0.3 µM kynurenine, at least 0.4 µM kynurenine, at least 0.5 µM kynurenine, at least 0.6 µM kynurenine, at least 0.7 µM kynurenine, at least 0.8 µM kynurenine, at least 0.9 µM kynurenine, at least 1 µM kynurenine, at least 1.5 µM kynurenine, at least 2 µM kynurenine, at least 2.5 µM kynurenine, at least 3 µM kynurenine, at least 3.5 µM kynurenine, at least 4 µM kynurenine, at least 4.5 µM kynurenine, at least 5 µM kynurenine, or greater than 5 µM kynurenine. In embodiments, the selected bacterial isolate is provided in Table 6, or comprises a 16S rRNA sequence at least 95% identical to a 16S rRNA sequence corresponding to a SEQ ID NO of a bacterial isolate provided in Table 6. In an embodiment, the selected bacterial isolate comprises *Odoribacter splanchnicus*. In an embodiment, the selected bacterial isolate comprises a 16S rRNA sequence at least 95% identical to the 16S rRNA sequence corresponding to SEQ ID NO: 2. In an embodiment, the selected bacterial isolate comprises *Bacteroides stercoris*. In an embodiment, the selected bacterial isolate comprises a 16S rRNA sequence at least 95% identical to the 16S rRNA sequence corresponding to SEQ ID NO: 13.

In other embodiments, a bacterial isolate can be selected for inclusion in a pharmaceutical composition described herein based on production of kynurenine at a higher level than blank media or a control bacterial strain (e.g., positive control bacterial strain capable of producing kynurenine, such as a strain that is a member of the *Peptostreptococcus* genus), as measured in a functional assay. For example, a bacterial isolate can be selected if it can produce kynurenine at a higher level than at least one of the control strains *Peptostreptococcus anaerobius* or *Peptostreptococcus russellii* over a duration of time. In embodiments, a bacterial isolate is selected if it can produce kynurenine at a level that is at least 1.1×, at least 1.2×, at least 1.3×, at least 1.4×, at least 1.5×, at least 1.6×, at least 1.7×, at least 1.8×, at least 1.9×, at least 2×, at least 2.1×, at least 2.2×, at least 2.3×, at least 2.4×, at least 2.5×, at least 2.6×, at least 2.7×, at least 2.8×, at least 2.9×, at least 3×, at least 4×, at least 5×, at least 6×, at least 7×, at least 8×, at least 9×, at least 10×, at least 11×, at least 12×, at least 13×, at least 14×, at least 15×, at least 16×, at least 17×, at least 18×, at least 19×, at least 20×, at least 21×, at least 22×, at least 23×, at least 24×, at least 25×, at least 26×, at least 27×, at least 28×, at least 29×, at least 30×, at least 35×, at least 40×, at least 45×, at least 50×, at least 60×, at least 70×, at least 80×, at least 90×, at least 100×, at least 110×, at least 120×, at least 130×, at least 140×, at least 150×, at least 160×, at least 170×, at least 180×, at least 190×, at least 200×, at least 210×, at least 220×, at least 230×, at least 240×, at least 250×, or greater than 250× relative to at least one of the control strains *Peptostreptococcus anaerobius* or *Peptostreptococcus russellii*, or relative to blank media alone. In an embodiment, the selected bacterial isolate comprises *Odoribacter* sp. In an embodiment, the selected bacterial isolate comprises a 16S rRNA sequence at least 95% identical to the 16S rRNA sequence corresponding to SEQ ID NO: 2. In an embodiment, the selected bacterial isolate comprises *Bacteroides stercoris*. In an embodiment, the selected bacterial isolate comprises a 16S rRNA sequence at least 95% identical to the 16S rRNA sequence corresponding to SEQ ID NO: 13.

In embodiments, a bacterial isolate can be selected for inclusion in a pharmaceutical composition described herein based on the production of tryptamine during a period of time (e.g., 48 hours), as measured in a functional assay. For example, the bacterial isolate can be selected if it can produce tryptamine at a concentration of at least 0.1 µM tryptamine, at least 0.2 µM tryptamine, at least 0.3 µM tryptamine, at least 0.4 µM tryptamine, at least 0.5 µM tryptamine, at least 0.6 µM tryptamine, at least 0.7 µM tryptamine, at least 0.8 µM tryptamine, at least 0.9 µM tryptamine, at least 1 µM tryptamine, at least 1.5 µM tryptamine, at least 2 µM tryptamine, at least 2.5 µM tryptamine, at least 3 µM tryptamine, at least 3.5 µM tryptamine, at least 4 µM tryptamine, at least 4.5 µM tryptamine, at least 5 µM tryptamine, or greater than 5 µM tryptamine. In embodiments, the selected bacterial isolate is provided in Table 6, or comprises a 16S rRNA sequence at least 95% identical to a sequence corresponding to a SEQ ID NO of a bacterial isolate provided in Table 6. In embodiments, the selected bacterial isolate is provided in Table 6, or comprises a 16S rRNA sequence at least 95% identical to a 16S rRNA sequence corresponding to a SEQ ID NO of a bacterial isolate provided in Table 6. In an embodiment, the selected bacterial isolate comprises *Odoribacter splanchnicus*. In an embodiment, the selected bacterial isolate comprises a 16S rRNA sequence at least 95% identical to the 16S rRNA sequence corresponding to SEQ ID NO: 2.

In other embodiments, a bacterial isolate can be selected for inclusion in a pharmaceutical composition described herein based on production of tryptamine at a higher level than blank media or a control bacterial strain (e.g., positive control bacterial strain capable of producing tryptamine, such as a strain that is a member of the *Peptostreptococcus* genus), as measured in a functional assay. For example, a bacterial isolate can be selected if it can produce tryptamine at a higher level than at least one of the control strains *Peptostreptococcus anaerobius* or *Peptostreptococcus russellii* over a duration of time. In embodiments, a bacterial isolate is selected if it can produce tryptamine at a level that is at least 1.1×, at least 1.2×, at least 1.3×, at least 1.4×, at least 1.5×, at least 1.6×, at least 1.7×, at least 1.8×, at least 1.9×, at least 2×, at least 2.1×, at least 2.2×, at least 2.3×, at least 2.4×, at least 2.5×, at least 2.6×, at least 2.7×, at least 2.8×, at least 2.9×, at least 3×, at least 4×, at least 5×, at least 6×, at least 7×, at least 8×, at least 9×, at least 10×, at least 11×, at least 12×, at least 13×, at least 14×, at least 15×, at least 16×, at least 17×, at least 18×, at least 19×, at least 20×, at least 21×, at least 22×, at least 23×, at least 24×, at least 25×, at least 26×, at least 27×, at least 28×, at least 29×, at least 30×, at least 35×, at least 40×, at least 45×, at least 50×, at least 60×, at least 70×, at least 80×, at least 90×, at least 100×, at least 110×, at least 120×, at least 130×, at least 140×, at least 150×, at least 160×, at least 170×, at least 180×, at least 190×, at least 200×, at least 210×, at least 220×, at least 230×, at least 240×, at least 250×, or greater than 250× relative to at least one of the control strains *Peptostreptococcus anaerobius* or *Peptostreptococcus russellii*, or relative to blank media alone. In an embodiment, the selected bacterial isolate comprises *Odoribacter splanchnicus*. In embodiments, the selected bacterial isolate is provided in Table 6, or comprises a 16S rRNA sequence at least 95% identical to a 16S rRNA sequence corresponding to a SEQ ID NO of a bacterial isolate provided in Table 6. In an embodiment, the selected bacterial isolate comprises *Odoribacter splanchnicus*. In the selected bacterial isolate comprises a 16S rRNA sequence at least 95% identical to the 16S rRNA sequence corresponding to SEQ ID NO: 2.

In an embodiment, a method of manufacture comprises selecting one or more bacterial isolates comprising a 16S rRNA sequence that is at least 95% identical to the 16S rRNA sequence of one or more of the bacterial isolates provided in Table 1, and incorporating the one or more bacterial isolates into a pharmaceutical composition. In an embodiment, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or greater than 20 bacterial isolates comprising a 16S rRNA sequence that is at least 95% identical to the 16S rRNA sequence of one or more of the bacterial isolates provided in Table 1 are selected and incorporated into a microbial cocktail.

In an embodiment, a method of manufacture comprises selecting one or more bacterial isolates comprising a 16S rRNA sequence that is at least 95% identical to the 16S rRNA sequence of one or more of the bacterial isolates provided in Tables 2-4, and incorporating the one or more bacterial isolates into a pharmaceutical composition. In an embodiment, a method of manufacture comprises selecting one or more bacterial isolates comprising a 16S rRNA sequence at least 95% identical to the 16S rRNA sequence of one or more of the bacterial isolates provided in Table 6, and incorporating the one or more bacterial isolates into a pharmaceutical composition.

In an embodiment, a method of manufacture comprises selecting bacterial isolates comprising 16S rRNA sequences at least 95% identical to the 16S rRNA sequences of each of the bacterial isolates provided in one of Tables 7-44, incorporating the bacterial isolates into a microbial cocktail, and incorporating the microbial cocktail into a pharmaceutical composition.

In embodiments, one or more bacterial isolates can be rationally selected for inclusion in a pharmaceutical composition described herein based on one or more desired traits or characteristics exhibited or possessed by the isolate. Non-limiting examples of a trait possessed or exhibited by a bacterial isolate that can form the basis of rational selection can include: a coding or non-coding DNA sequence; an RNA sequence; a polypeptide sequence; production or lack of production of a particular RNA or protein product; activity or inactivity of a metabolic pathway; production or lack of production of a particular metabolic product; production or lack of production of a particular ligand or set of ligands; ability to induce or inhibit production of a compound or pathway in a target cell (e.g., eukaryotic cell), association of the presence or abundance of the strain with the existence or severity of a condition or indication (e.g. in a human patient); and the particular taxonomic classification of the strain, including genus or species.

In embodiments, a method of manufacture comprises selecting a dosage of a bacterial isolate to be incorporated into a pharmaceutical composition, and incorporating the bacterial isolate into the pharmaceutical composition at the selected dosage. In an embodiment, selecting a dosage of a bacterial isolate comprises determining a threshold or minimum dosage required for engraftment of the bacterial isolate in the intestine of a subject administered the bacterial isolate, and selecting a dosage of the bacterial isolate that is above the threshold or minimum dosage.

Embodiments

Embodiment 1: A pharmaceutical composition comprising a cocktail of at least two bacterial isolates, wherein at least one of the bacterial isolates comprises a 16S rRNA sequence that is at least 95% identical to a 16S rRNA sequence of a bacterial isolate provided in Table 1, and wherein the at least two bacterial isolates are isolated from stool samples of different donors.

Embodiment 2: The pharmaceutical composition of embodiment 1, wherein at least two of the bacterial isolates comprise a 16S rRNA sequence that is at least 95% identical to a 16S rRNA sequence of a bacterial isolate provided in Table 1.

Embodiment 3: The pharmaceutical composition of embodiment 1 or embodiment 2, wherein at least three of the bacterial isolates comprise a 16S rRNA sequence that is at least 95% identical to a 16S rRNA sequence of a bacterial isolate provided in Table 1.

Embodiment 4: The pharmaceutical composition of any one of embodiments 1 to 3, wherein at least four of the bacterial isolates comprise a 16S rRNA sequence that is at least 95% identical to a 16S rRNA sequence of a bacterial isolate provided in Table 1.

Embodiment 5: The pharmaceutical composition of any one of embodiments 1 to 4, wherein at least five of the bacterial isolates comprise a 16S rRNA sequence that is at least 95% identical to a 16S rRNA sequence of a bacterial isolate provided in Table 1.

Embodiment 6: The pharmaceutical composition of any one of embodiments 1 to 5, wherein at least six of the bacterial isolates comprise a 16S rRNA sequence that is at least 95% identical to a 16S rRNA sequence of a bacterial isolate provided in Table 1.

Embodiment 7: The pharmaceutical composition of any one of embodiments 1 to 6, wherein at least seven of the bacterial isolates comprise a 16S rRNA sequence that is at least 95% identical to a 16S rRNA sequence of a bacterial isolate provided in Table 1.

Embodiment 8: The pharmaceutical composition of any one of embodiments 1 to 7, wherein at least eight of the bacterial isolates comprise a 16S rRNA sequence that is at least 95% identical to a 16S rRNA sequence of a bacterial isolate provided in Table 1.

Embodiment 9: The pharmaceutical composition of any one of embodiments 1 to 8, wherein at least nine of the bacterial isolates comprise a 16S rRNA sequence that is at least 95% identical to a 16S rRNA sequence of a bacterial isolate provided in Table 1.

Embodiment 10: The pharmaceutical composition of any one of embodiments 1 to 9, wherein at least ten of the bacterial isolates comprise a 16S rRNA sequence that is at least 95% identical to a 16S rRNA sequence of a bacterial isolate provided in Table 1.

Embodiment 11: A pharmaceutical composition comprising a plurality of bacterial isolates, wherein the plurality of bacterial isolates comprises at least two bacterial isolates selected from the group consisting of *Eubacterium rectale*, *Odoribacter splanchnicus* and *Subdoligranulum variabile*, wherein the at least two bacterial isolates are isolated from stool samples of different donors.

Embodiment 12: The pharmaceutical composition of embodiment 11, wherein the *Subdoligranulum variabile* comprises a 16S rRNA sequence that is at least 95% identical to at least one of SEQ ID NO: 22 or SEQ ID NO: 23.

Embodiment 13: The pharmaceutical composition of embodiment 11 or embodiment 12, wherein the *Odoribacter* comprises a 16S rRNA sequence that is at least 95% identical to SEQ ID NO: 2.

Embodiment 14: The pharmaceutical composition of any one of embodiments 11 to 13, wherein the *Eubacterium rectale* comprises a 16S rRNA sequence that is at least 95% identical to SEQ ID NO: 8.

Embodiment 15: The pharmaceutical composition of any one of embodiments 11 to 13, wherein the at least two bacterial isolates do not include *Eubacterium rectale*.

Embodiment 16: The pharmaceutical composition of any one of embodiment 11, embodiment 12, embodiment 13, or embodiment 14, wherein the at least two bacterial isolates do not include *Odoribacter splanchnicus*.

Embodiment 17: The pharmaceutical composition of any one of embodiment 11, embodiment 13, or embodiment 14, wherein the at least two bacterial isolates do not include *Subdoligranulum variabile*.

Embodiment 18: The pharmaceutical composition of any one of embodiments 11 to 14 or embodiment 17, wherein the at least two bacterial isolates comprise *Odoribacter splanchnicus* and *Eubacterium rectale*.

Embodiment 19: The pharmaceutical composition of embodiment 18, wherein the plurality of bacterial isolates further comprises at least one of *Bacteroides cellulosilyticus*, *Faecalibacterium prausnitzii*, *Alistipes shahii*, and *Blautia obeum*.

Embodiment 20: The pharmaceutical composition of embodiment 19, wherein the plurality of bacterial isolates further comprises each of *Bacteroides cellulosilyticus*, *Faecalibacterium prausnitzii*, *Alistipes shahii*, and *Blautia obeum*.

Embodiment 21: The pharmaceutical composition of embodiment 19 or embodiment 20, wherein the *Bacteroides cellulosilyticus* comprises a 16S rRNA sequence that is at least 95% identical to SEQ ID NO: 14.

Embodiment 22: The pharmaceutical composition of any one of embodiments 19 to 21, wherein the *Faecalibacterium prausnitzii* comprises a 16S rRNA sequence that is at least 95% identical to at least one of SEQ ID NO: 1 or SEQ ID NO: 7.

Embodiment 23: The pharmaceutical composition of any one of embodiments 19 to 22, wherein the *Alistipes shahii* comprises a 16S rRNA sequence that is at least 95% identical to SEQ ID NO: 18.

Embodiment 24: The pharmaceutical composition of any one of embodiments 19 to 23, wherein the *Blautia obeum* comprises a 16S rRNA sequence that is at least 95% identical to SEQ ID NO: 9.

Embodiment 25: The pharmaceutical composition of embodiment 18, wherein the plurality of bacterial isolates further comprises at least one of *Bacteroides cellulosilyticus*, *Bacteroides stercoris*, *Faecalibacterium prausnitzii*, *Alistipes shahii*, *Anaerostipes hadrus*, *Roseburia faecis*, and *Blautia obeum*.

Embodiment 26: The pharmaceutical composition of embodiment 25, wherein the plurality of bacterial isolates further comprises each of *Bacteroides cellulosilyticus*, *Bacteroides stercoris*, *Faecalibacterium prausnitzii*, *Alistipes shahii*, *Anaerostipes hadrus*, and *Roseburia faecis*

Embodiment 27: The pharmaceutical composition of embodiment 25 or embodiment 26, wherein the *Bacteroides cellulosilyticus* comprises a 16S rRNA sequence that is at least 95% identical to SEQ ID NO: 14.

Embodiment 28: The pharmaceutical composition of any one of embodiments 25 to 27, wherein the *Bacteroides stercoris* comprises a 16S rRNA sequence that is at least 95% identical to SEQ ID NO: 13.

Embodiment 29: The pharmaceutical composition of any one of embodiments 25 to 28, wherein the *Faecalibacterium*

*prausnitzii* comprises a 16S rRNA sequence that is at least 95% identical to at least one of SEQ ID NO: 1 or SEQ ID NO: 7.

Embodiment 30: The pharmaceutical composition of any one of embodiments 25 to 29, wherein the *Alistipes shahii* comprises a 16S rRNA sequence that is at least 95% identical to SEQ ID NO: 18.

Embodiment 31: The pharmaceutical composition of any one of embodiments 25 to 30, wherein the *Anaerostipes hadrus* comprises a 16S rRNA sequence that is at least 95% identical to SEQ ID NO: 3.

Embodiment 32: The pharmaceutical composition of any one of embodiments 25 to 31, wherein the *Roseburia faecis* comprises a 16S rRNA sequence that is at least 95% identical to SEQ ID NO: 19.

Embodiment 33: The pharmaceutical composition of embodiment 25, wherein the plurality of bacterial isolates does not comprise at least one of *Blautia obeum* and *Anaerostipes hadrus*.

Embodiment 34: The pharmaceutical composition of embodiment 18, wherein the plurality of bacterial isolates further comprises each of *Bacteroides cellulosilyticus, Bacteroides stercoris, Faecalibacterium prausnitzii, Alistipes shahii, Blautia obeum*, and *Roseburia faecis*.

Embodiment 35: The pharmaceutical composition of embodiment 34, wherein the *Bacteroides cellulosilyticus* comprises a 16S rRNA sequence that is at least 95% identical to SEQ ID NO: 14.

Embodiment 36: The pharmaceutical composition of embodiment 34 or embodiment 35, wherein the *Bacteroides stercoris* comprises a 16S rRNA sequence that is at least 95% identical to SEQ ID NO: 13.

Embodiment 37: The pharmaceutical composition of any one of embodiments 34 to 36, wherein the *Faecalibacterium prausnitzii* comprises a 16S rRNA sequence that is at least 95% identical to at least one of SEQ ID NO: 1 or SEQ ID NO: 7.

Embodiment 38: The pharmaceutical composition of any one of embodiments 34 to 37, wherein the *Alistipes shahii* comprises a 16S rRNA sequence that is at least 95% identical to SEQ ID NO: 18.

Embodiment 39: The pharmaceutical composition of any one of embodiments 34 to 38, wherein the *Blautia obeum* comprises a 16S rRNA sequence that is at least 95% identical to SEQ ID NO: 9.

Embodiment 40: The pharmaceutical composition of any one of embodiments 34 to 39, wherein the *Roseburia faecis* comprises a 16S rRNA sequence that is at least 95% identical to SEQ ID NO: 19.

Embodiment 41: The pharmaceutical composition of embodiment 18, wherein the plurality of bacterial isolates further comprises at least one of *Bacteroides cellulosilyticus, Bacteroides stercoris, Alistipes shahii*, and *Roseburia faecis*.

Embodiment 42: The pharmaceutical composition of embodiment 41, wherein the plurality of bacterial isolates further comprises each of *Bacteroides cellulosilyticus, Bacteroides stercoris, Alistipes shahii*, and *Roseburia faecis*.

Embodiment 43: The pharmaceutical composition of embodiment 41 or embodiment 42, wherein the *Bacteroides cellulosilyticus* comprises a 16S rRNA sequence that is at least 95% identical to SEQ ID NO: 14.

Embodiment 44: The pharmaceutical composition of any one of embodiments 41 to 43, wherein the *Bacteroides stercoris* comprises a 16S rRNA sequence that is at least 95% identical to SEQ ID NO: 13.

Embodiment 45: The pharmaceutical composition of any one of embodiments 41 to 44, wherein the *Roseburia faecis* comprises a 16S rRNA sequence that is at least 95% identical to SEQ ID NO: 19.

Embodiment 46: The pharmaceutical composition of any one of embodiments 41 to 45, wherein the *Alistipes shahii* comprises a 16S rRNA sequence that is at least 95% identical to SEQ ID NO: 18.

Embodiment 47: The pharmaceutical composition of embodiment 18, wherein the plurality of bacterial isolates further comprises at least one of *Faecalibacterium prausnitzii, Bacteroides stercoris, Roseburia faecis*, and *Anaerostipes hadrus*.

Embodiment 48: The pharmaceutical composition of embodiment 47, wherein the plurality of bacterial isolates further comprises each of *Faecalibacterium prausnitzii, Bacteroides stercoris, Roseburia faecis*, and *Anaerostipes hadrus*.

Embodiment 49: The pharmaceutical composition of embodiment 47 or embodiment 48, wherein the *Faecalibacterium prausnitzii* comprises a 16S rRNA sequence that is at least 95% identical to at least one of SEQ ID NO: 1 or SEQ ID NO: 7.

Embodiment 50: The pharmaceutical composition of any one of embodiment 47 to 49, wherein the *Bacteroides stercoris* comprises a 16S rRNA sequence that is at least 95% identical to SEQ ID NO: 13.

Embodiment 51: The pharmaceutical composition of any one of embodiment 47 to 50, wherein the *Roseburia faecis* comprises a 16S rRNA sequence that is at least 95% identical to SEQ ID NO: 19.

Embodiment 52: The pharmaceutical composition of any one of embodiment 47 to 51, wherein the *Anaerostipes hadrus* comprises a 16S rRNA sequence that is at least 95% identical to SEQ ID NO: 3.

Embodiment 53: The pharmaceutical composition of embodiment 18, wherein the plurality of bacterial isolates further comprises at least one of *Bacteroides cellulosilyticus, Bacteroides stercoris, Blautia obeum*, and *Alistipes shahii*.

Embodiment 54: The pharmaceutical composition of embodiment 53, wherein the plurality of bacterial isolates further comprises each of *Bacteroides cellulosilyticus, Bacteroides stercoris, Blautia obeum*, and *Alistipes shahii*.

Embodiment 55: The pharmaceutical composition of embodiment 53 or embodiment 54, wherein the *Bacteroides cellulosilyticus* comprises a 16S rRNA sequence that is at least 95% identical to SEQ ID NO: 14.

Embodiment 56: The pharmaceutical composition of any one of embodiments 53 to 55, wherein the *Bacteroides stercoris* comprises a 16S rRNA sequence that is at least 95% identical to SEQ ID NO: 13.

Embodiment 57: The pharmaceutical composition of any one of embodiments 53 to 56, wherein the *Blautia obeum* comprises a 16S rRNA sequence that is at least 95% identical to SEQ ID NO: 9.

Embodiment 58: The pharmaceutical composition of any one of embodiments 53 to 57, wherein the *Alistipes shahii* comprises a 16S rRNA sequence that is at least 95% identical to SEQ ID NO: 18.

Embodiment 59: The pharmaceutical composition of embodiment 18, wherein the plurality of bacterial isolates further comprises at least one of *Faecalibacterium prausnitzii, Bacteroides stercoris, Alistipes shahii*, and *Roseburia faecis*.

Embodiment 60: The pharmaceutical composition of embodiment 59, wherein the plurality of bacterial isolates further comprises each of *Faecalibacterium prausnitzii*, *Bacteroides stercoris*, *Alistipes shahii*, and *Roseburia faecis*.

Embodiment 61: The pharmaceutical composition of embodiment 59 or embodiment 60, wherein the *Faecalibacterium prausnitzii* comprises a 16S rRNA sequence that is at least 95% identical to at least one of SEQ ID NO: 1 or SEQ ID NO: 7.

Embodiment 62: The pharmaceutical composition of any one of embodiments 59 to 61, wherein the *Bacteroides stercoris* comprises a 16S rRNA sequence that is at least 95% identical to SEQ ID NO: 13.

Embodiment 63: The pharmaceutical composition of any one of embodiments 59 to 62, wherein the *Alistipes shahii* comprises a 16S rRNA sequence that is at least 95% identical to SEQ ID NO: 18.

Embodiment 64: The pharmaceutical composition of any one of embodiments 59 to 63, wherein the *Roseburia faecis* comprises a 16S rRNA sequence that is at least 95% identical to SEQ ID NO: 19.

Embodiment 65: The pharmaceutical composition of embodiment 18, wherein the plurality of bacterial isolates further comprises at least one of *Faecalibacterium prausnitzii*, *Bacteroides stercoris*, *Blautia obeum*, and *Roseburia faecis*.

Embodiment 66: The pharmaceutical composition of embodiment 65, wherein the plurality of bacterial isolates further comprises each of *Faecalibacterium prausnitzii*, *Bacteroides stercoris*, *Blautia obeum*, and *Roseburia faecis*.

Embodiment 67: The pharmaceutical composition of embodiment 65 or embodiment 66, wherein the *Faecalibacterium prausnitzii* comprises a 16S rRNA sequence that is at least 95% identical to at least one of SEQ ID NO: 1 or SEQ ID NO: 7.

Embodiment 68: The pharmaceutical composition of any one of embodiments 65 to 67, wherein the *Bacteroides stercoris* comprises a 16S rRNA sequence that is at least 95% identical to SEQ ID NO: 13.

Embodiment 69: The pharmaceutical composition of any one of embodiments 65 to 68, wherein the *Blautia obeum* comprises a 16S rRNA sequence that is at least 95% identical to SEQ ID NO: 9.

Embodiment 70: The pharmaceutical composition of any one of embodiments 65 to 69, wherein the *Roseburia faecis* comprises a 16S rRNA sequence that is at least 95% identical to SEQ ID NO: 19.

Embodiment 71: The pharmaceutical composition of any one of embodiments 1 to 18, wherein the plurality of bacterial isolates comprises at least one of *Bacteroides stercoris* and *Clostridium aldenense*.

Embodiment 72: The pharmaceutical composition of embodiment 71, wherein the plurality of bacterial isolates produces an aryl hydrocarbon for binding to an aryl hydrocarbon receptor.

Embodiment 73: The pharmaceutical composition of embodiment 71 or embodiment 72, wherein the aryl hydrocarbon receptor is expressed by a cell of a subject administered the composition.

Embodiment 74: The pharmaceutical composition of embodiment 73, wherein the cell is an intestinal cell or an immune cell.

Embodiment 75: The pharmaceutical composition of any one of embodiments 71 to 74, wherein the aryl hydrocarbon is selected from the group consisting of indole, indole-3-acetic acid (IAA), indole-3-aldehyde (IAld), indole-3-lactic acid, indole-3-carbinol (I3C), indole-3-acetonitrile (I3ACN), 3,3'-diindolylmethane (DIM), 2-(indol-3-ylmethyl)-3,3'-diindolylmethane (Ltr-1), indolo[3,2-b]carbazole (ICZ), 2-(1'H-indole-3' carbonyl)-thiazole-4-carboxylic acid methyl ester (ITE), 3-methyl-indole (skatole), tryptamine, kynurenine, kynurenate, indigo, indirubin, indoxyl-3-sulfate (I3S), xanthurenic acid, cinnabarinic acid, and any combination thereof.

Embodiment 76: The pharmaceutical composition of embodiment 75, wherein the aryl hydrocarbon is IAA.

Embodiment 77: The pharmaceutical composition of embodiment 76, wherein the IAA is secreted at a concentration of at least 1 µM.

Embodiment 78: The pharmaceutical composition of embodiment 76, wherein the IAA is secreted at a concentration of at least 10 µM.

Embodiment 79: The pharmaceutical composition of embodiment 76, wherein the IAA is secreted at a concentration of at least 20 µM.

Embodiment 80: The pharmaceutical composition of embodiment 76, wherein the IAA is secreted at a concentration of at least 40 µM.

Embodiment 81: The pharmaceutical composition of embodiment 76, wherein the IAA is secreted at a concentration of at least 50 µM.

Embodiment 82: The pharmaceutical composition of embodiment 76, wherein the IAA is secreted at a concentration of at least 75 µM.

Embodiment 83: The pharmaceutical composition of embodiment 76, wherein the IAA is secreted at a concentration of at least 100 µM.

Embodiment 84: The pharmaceutical composition of embodiment 11, wherein the at least two bacterial isolates comprise *Eubacterium rectale* and *Subdoligranulum variabile*.

Embodiment 85: The pharmaceutical composition of embodiment 84, wherein the plurality of bacterial isolates further comprises at least one of *Faecalibacterium prausnitzii*, *Coprococcus comes*, *Anaerostipes hadrus*, and *Roseburia faecis*.

Embodiment 86: The pharmaceutical composition of embodiment 84 or embodiment 85, wherein the plurality of bacterial isolates further comprises each of *Faecalibacterium prausnitzii*, *Coprococcus comes*, *Anaerostipes hadrus*, and *Roseburia faecis*.

Embodiment 87: The pharmaceutical composition of any one of embodiments 84 to 86, wherein the *Faecalibacterium prausnitzii* comprises a 16S rRNA sequence that is at least 95% identical to at least one of SEQ ID NO: 1 or SEQ ID NO: 7.

Embodiment 88: The pharmaceutical composition of any one of embodiments 84 to 87, wherein the *Anaerostipes hadrus* comprises a 16S rRNA sequence that is at least 95% identical to SEQ ID NO: 3.

Embodiment 89: The pharmaceutical composition of any one of embodiments 84 to 88, wherein the *Roseburia faecis* comprises a 16S rRNA sequence that is at least 95% identical to SEQ ID NO: 19.

Embodiment 90: The pharmaceutical composition of any one of embodiments 84 to 89, wherein the *Coprococcus comes* comprises a 16S rRNA sequence that is at least 95% identical to SEQ ID NO: 17.

Embodiment 91: The pharmaceutical composition of any one of embodiments 1 to 18, wherein the plurality of bacterial strains does not include at least one of *Faecalibacterium prausnitzii*, *Roseburia faecis*, *Bacteroides cellulosilyticus*, *Alistipes shahii*, or *Blautia obeum*.

Embodiment 92: A pharmaceutical composition comprising a plurality of bacterial isolates, wherein the plurality of bacterial isolates comprises *Roseburia faecis* and *Bacteroi-*

*des cellulosilyticus*, and at least one of *Faecalibacterium prausnitzii* and *Alistipes shahii*, and wherein at least two of the plurality of bacterial isolates are isolated from stool samples of different donors.

Embodiment 93: The pharmaceutical composition of embodiment 92, wherein the plurality of bacterial isolates further comprises at least one of *Eubacterium rectale*, *Anaerostipes hadrus*, and *Blautia obeum*.

Embodiment 94: The pharmaceutical composition of embodiment 92 or embodiment 93, wherein the plurality of bacterial isolates comprises each of *Roseburia faecis*, *Bacteroides cellulosilyticus*, *Faecalibacterium prausnitzii*, *Alistipes shahii*, *Eubacterium rectale*, and *Anaerostipes hadrus*.

Embodiment 95: The pharmaceutical composition of any one of embodiments 92 to 94, wherein the *Roseburia faecis* comprises a 16S rRNA sequence that is at least 95% identical to SEQ ID NO: 19.

Embodiment 96: The pharmaceutical composition of any one of embodiments 92 to 95, wherein the *Bacteroides cellulosilyticus* comprises a 16S rRNA sequence that is at least 95% identical to SEQ ID NO: 14.

Embodiment 97: The pharmaceutical composition of any one of embodiments 92 to 96, wherein the *Faecalibacterium prausnitzii* comprises a 16S rRNA sequence that is at least 95% identical to at least one of SEQ ID NO: 1 or SEQ ID NO: 7.

Embodiment 98: The pharmaceutical composition of any one of embodiments 92 to 97, wherein the *Alistipes shahii* comprises a 16S rRNA sequence that is at least 95% identical to SEQ ID NO: 18.

Embodiment 99: The pharmaceutical composition of any one of embodiments 93 to 98, wherein the *Eubacterium rectale* comprises a 16S rRNA sequence that is at least 95% identical to SEQ ID NO: 8.

Embodiment 100: The pharmaceutical composition of any one of embodiments 93 to 99, wherein the *Anaerostipes hadrus* comprises a 16S rRNA sequence that is at least 95% identical to SEQ ID NO: 3.

Embodiment 101: The pharmaceutical composition of any one of embodiments 92 to 100, wherein the plurality of bacterial isolates does not comprise at least one of *Anaerostipes hadrus* and *Blautia obeum*.

Embodiment 102: The pharmaceutical composition of embodiment 92, wherein the plurality of bacterial isolates comprises each of *Roseburia faecis*, *Bacteroides cellulosilyticus*, *Faecalibacterium prausnitzii*, *Alistipes shahii*, and further comprises *Eubacterium rectale* and *Blautia obeum*.

Embodiment 103: The pharmaceutical composition of embodiment 102, wherein the *Roseburia faecis* comprises a 16S rRNA sequence that is at least 95% identical to SEQ ID NO: 19.

Embodiment 104: The pharmaceutical composition of embodiment 102 or embodiment 103, wherein the *Bacteroides cellulosilyticus* comprises a 16S rRNA sequence that is at least 95% identical to SEQ ID NO: 14.

Embodiment 105: The pharmaceutical composition of any one of embodiments 102 to 104, wherein the *Faecalibacterium prausnitzii* comprises a 16S rRNA sequence that is at least 95% identical to at least one of SEQ ID NO: 1 or SEQ ID NO: 7.

Embodiment 106: The pharmaceutical composition of any one of embodiments 102 to 105, wherein the *Alistipes shahii* comprises a 16S rRNA sequence that is at least 95% identical to SEQ ID NO: 18.

Embodiment 107: The pharmaceutical composition of any one of embodiments 102 to 106, wherein the *Eubacterium rectale* comprises a 16S rRNA sequence that is at least 95% identical to SEQ ID NO: 8.

Embodiment 108: The pharmaceutical composition of any one of embodiments 102 to 107, wherein the *Blautia obeum* comprises a 16S rRNA sequence that is at least 95% identical to SEQ ID NO: 9.

Embodiment 109: The pharmaceutical composition of any one of embodiment 1 to 108, wherein one or more of the plurality of bacterial isolates secretes a short-chain fatty acid (SCFA) in an intestine of a subject administered the composition.

Embodiment 110: The pharmaceutical composition of embodiment 109, wherein the SCFA is selected from the group consisting of acetic acid, butyric acid, caproic acid, formic acid, heptanoic acid, isobutyric acid, isocaproic acid, isovaleric acid, propionic acid, valeric acid, and a combination thereof.

Embodiment 111: The pharmaceutical composition of embodiment 109 or embodiment 110, wherein the SCFA is butyric acid.

Embodiment 112: The pharmaceutical composition of embodiment 111, wherein a level of the butyric acid produced by the one or more bacterial isolates over a period of 24 hours is at least 5 mM.

Embodiment 113: The pharmaceutical composition of embodiment 111, wherein a level of the butyric acid produced by the one or more bacterial isolates over a period of 24 hours is at least 10 mM.

Embodiment 114: The pharmaceutical composition of embodiment 111, wherein a level of the butyric acid produced by the one or more bacterial isolates over a period of 24 hours is at least 15 mM.

Embodiment 115: The pharmaceutical composition of embodiment 111, wherein a level of the butyric acid produced by the one or more bacterial isolates over a period of 24 hours is at least 20 mM.

Embodiment 116: The pharmaceutical composition of embodiment 111, wherein a level of the butyric acid produced by the one or more bacterial isolates over a period of 24 hours is at least 25 mM.

Embodiment 117: The pharmaceutical composition of embodiment 111, wherein a level of the butyric acid produced by the one or more bacterial isolates over a period of 24 hours is at least 30 mM.

Embodiment 118: The pharmaceutical composition of embodiment 111, wherein a level of the butyric acid produced by the one or more bacterial isolates over a period of 24 hours is at least 35 mM.

Embodiment 119: The pharmaceutical composition of embodiment 111, wherein a level of the butyric acid produced by the one or more bacterial isolates over a period of 24 hours is at least 40 mM.

Embodiment 120: The pharmaceutical composition of embodiment 111, wherein the one or more bacterial isolates producing at least one SCFA comprises a 16S rRNA sequence that is at least 95% identical to a 16S rRNA sequence of a bacterial isolate provided in Table 2.

Embodiment 121: A pharmaceutical composition comprising a plurality of bacterial isolates, wherein the plurality of bacterial isolates comprises a bacterial isolate comprising *Parabacteroides merdae* and at least one of *Alistipes finegoldii* and *Alistipes onderdonkii*.

Embodiment 122: The pharmaceutical composition of embodiment 121, wherein the plurality of bacterial isolates comprises both *Alistipes finegoldii* and *Alistipes onderdonkii*.

Embodiment 123: The pharmaceutical composition of embodiment 122, wherein the plurality of bacterial isolates further comprises at least one of *Akkermansia muciniphila, Dorea longicatena, Blautia obeum, Blautia* sp., *Bacteroides uniformis* or *Bacteroides vulgatus*.

Embodiment 124: The pharmaceutical composition of embodiment 123, wherein the plurality of bacterial isolates comprises each of *Akkermansia muciniphila, Dorea longicatena, Blautia* sp., *Bacteroides uniformis* and *Bacteroides vulgatus*.

Embodiment 125: The pharmaceutical composition of embodiment 123 or embodiment 124, wherein the *Parabacteroides merdae* comprises a 16S rRNA sequence that is at least 95% identical to SEQ ID NO: 5.

Embodiment 126: The pharmaceutical composition of any one of embodiments 123 to 125, wherein the *Akkermansia muciniphila* comprises a 16S rRNA sequence that is at least 95% identical to SEQ ID NO: 20.

Embodiment 127: The pharmaceutical composition of any one of embodiments 123 to 126, wherein the *Alistipes finegoldii* comprises a 16S rRNA sequence that is at least 95% identical to SEQ ID NO: 15.

Embodiment 128: The pharmaceutical composition of any one of embodiments 123 to 127, wherein the *Dorea longicatena* comprises a 16S rRNA sequence that is at least 95% identical to SEQ ID NO: 6.

Embodiment 129: The pharmaceutical composition of any one of embodiments 123 to 128, wherein the *Alistipes onderdonkii* comprises a 16S rRNA sequence that is at least 95% identical to SEQ ID NO: 4.

Embodiment 130: The pharmaceutical composition of any one of embodiments 123 to 129, wherein the *Blautia* sp. comprises a 16S rRNA sequence that is at least 95% identical to SEQ ID NO: 34.

Embodiment 131: The pharmaceutical composition of any one of embodiments 123 to 130, wherein the *Bacteroides uniformis* comprises a 16S rRNA sequence that is at least 95% identical to at least one of SEQ ID NO: 11 and SEQ ID NO: 16.

Embodiment 132: The pharmaceutical composition of any one of embodiments 123 to 131, wherein the *Bacteroides vulgatus* comprises a 16S rRNA sequence that is at least 95% identical to SEQ ID NO: 12.

Embodiment 133: The pharmaceutical composition of any one of embodiments 121 to 132, wherein the plurality of bacterial isolates does not include one of *Alistipes finegoldii* and *Alistipes onderdonkii*.

Embodiment 134: The pharmaceutical composition of embodiment 133, wherein the plurality of bacterial isolates does not include *Alistipes finegoldii*.

Embodiment 135: The pharmaceutical composition of embodiment 121, wherein the plurality of bacterial isolates comprises *Alistipes finegoldii* and further comprises *Akkermansia muciniphila, Dorea longicatena, Blautia obeum, Blautia* sp., *Bacteroides uniformis* and *Bacteroides vulgatus*.

Embodiment 136: The pharmaceutical composition of embodiment 135, wherein the *Parabacteroides merdae* comprises a 16S rRNA sequence that is at least 95% identical to SEQ ID NO: 5.

Embodiment 137: The pharmaceutical composition of embodiment 135 or embodiment 136, wherein the *Akkermansia muciniphila* comprises a 16S rRNA sequence that is at least 95% identical to SEQ ID NO: 20.

Embodiment 138: The pharmaceutical composition of any one of embodiments 135 to 137, wherein the *Alistipes finegoldii* comprises a 16S rRNA sequence that is at least 95% identical to SEQ ID NO: 15.

Embodiment 139: The pharmaceutical composition of any one of embodiments 135 to 138, wherein the *Dorea longicatena* comprises a 16S rRNA sequence that is at least 95% identical to SEQ ID NO: 6.

Embodiment 140: The pharmaceutical composition of any one of embodiments 135 to 139, wherein the *Blautia obeum* comprises a 16S rRNA sequence that is at least 95% identical to SEQ ID NO: 9.

Embodiment 141: The pharmaceutical composition of any one of embodiments 135 to 140, wherein the *Blautia* sp. comprises a 16S rRNA sequence that is at least 95% identical to SEQ ID NO: 34.

Embodiment 142: The pharmaceutical composition of any one of embodiments 135 to 141, wherein the *Bacteroides uniformis* comprises a 16S rRNA sequence that is at least 95% identical to at least one of SEQ ID NO: 11 and SEQ ID NO: 16.

Embodiment 143: The pharmaceutical composition of any one of embodiments 135 to 142, wherein the *Bacteroides vulgatus* comprises a 16S rRNA sequence that is at least 95% identical to SEQ ID NO: 12.

Embodiment 144: A pharmaceutical composition comprising a plurality of bacterial isolates, wherein the plurality of bacterial isolates comprises *Alistipes finegoldii* and at least one of *Bacteroides uniformis* and *Dorea longicatena*.

Embodiment 145: The pharmaceutical composition of embodiment 144, wherein the plurality of bacterial isolates further comprises at least one of *Akkermansia muciniphila, Bacteroides vulgatus*, and *Blautia* sp.

Embodiment 146: The pharmaceutical composition of embodiment 145, wherein the plurality of bacterial isolates comprises each of *Bacteroides uniformis, Dorea longicatena, Akkermansia muciniphila, Bacteroides vulgatus*, and *Blautia* sp.

Embodiment 147: The pharmaceutical composition of embodiment 145 or embodiment 146, wherein the *Alistipes finegoldii* comprises a 16S rRNA sequence that is at least 95% identical to SEQ ID NO: 15.

Embodiment 148: The pharmaceutical composition of any one of embodiments 145 to 147, wherein the *Bacteroides uniformis* comprises a 16S rRNA sequence that is at least 95% identical to SEQ ID NO: 11.

Embodiment 149: The pharmaceutical composition of any one of embodiments 145 to 148, wherein the *Dorea longicatena* comprises a 16S rRNA sequence that is at least 95% identical to SEQ ID NO: 6.

Embodiment 150: The pharmaceutical composition of any one of embodiments 145 to 149, wherein the *Akkermansia muciniphila* comprises a 16S rRNA sequence that is at least 95% identical to SEQ ID NO: 20.

Embodiment 151: The pharmaceutical composition of any one of embodiments 145 to 150, wherein the *Bacteroides vulgatus* comprises a 16S rRNA sequence that is at least 95% identical to SEQ ID NO: 12.

Embodiment 152: The pharmaceutical composition of any one of embodiments 145 to 151, wherein the *Blautia* sp. comprises a 16S rRNA sequence that is at least 95% identical to SEQ ID NO: 34.

Embodiment 153: The pharmaceutical composition of any one of embodiments 144 to 152, wherein the plurality of bacterial isolates does not comprise one of *Bacteroides uniformis* or *Dorea longicatena*.

Embodiment 154: The pharmaceutical composition of any one of embodiments 1 to 153, wherein the plurality of bacterial isolates comprises at least one bacterial isolate provided in Table 3.

Embodiment 155: The pharmaceutical composition of embodiment 154, wherein the at least one bacterial isolate modulates cytokine production or release by a eukaryotic cell.

Embodiment 156: The pharmaceutical composition of embodiment 155, wherein the at least one bacterial isolate decreases production or release of a pro-inflammatory cytokine by the eukaryotic cell.

Embodiment 157: The pharmaceutical composition of embodiment 156, wherein the pro-inflammatory cytokine is selected from the group consisting of: IFNγ, IL-12p70, IL-1 (e.g., IL-1α, IL-1β), IL-6, IL-8, IL-12, IL-17, IL-18, IL-23, MCP1, MIP1α, MIP1β, TNFα, TNF-γ, and a combination thereof.

Embodiment 158: The pharmaceutical composition of any one of embodiments 155 to 157, wherein the at least one bacterial isolate increases production or release of an anti-inflammatory cytokine by the eukaryotic cell.

Embodiment 159: The pharmaceutical composition of embodiment 158, wherein the anti-inflammatory cytokine is selected from the group consisting of: IL-10, IL-13, IL-4, IL-5, TGF-β, and a combination thereof.

Embodiment 160: The pharmaceutical composition of embodiment 159, wherein the anti-inflammatory cytokine is IL-10.

Embodiment 161: The pharmaceutical composition of embodiment 160, wherein the at least one bacterial isolate induces the eukaryotic cell to produce or release at least 500 pg/ml of IL-10.

Embodiment 162: The pharmaceutical composition of embodiment 160, wherein the at least one bacterial isolate induces the eukaryotic cell to produce or release at least 1000 pg/ml of IL-10.

Embodiment 163: The pharmaceutical composition of embodiment 160, wherein the at least one bacterial isolate induces the eukaryotic cell to produce or release at least 1500 pg/ml of IL-10.

Embodiment 164: The pharmaceutical composition of embodiment 160, wherein the at least one bacterial isolate induces the eukaryotic cell to produce or release at least 2000 pg/ml of IL-10.

Embodiment 165: The pharmaceutical composition of embodiment 160, wherein the at least one bacterial isolate induces the eukaryotic cell to produce or release at least 2500 pg/ml of IL-10.

Embodiment 166: The pharmaceutical composition of embodiment 160, wherein the at least one bacterial isolate induces the eukaryotic cell to produce or release at least 3000 pg/ml of IL-10.

Embodiment 167: The pharmaceutical composition of any one of embodiments 154 to 160, wherein the eukaryotic cell is a cultured cell.

Embodiment 168: The pharmaceutical composition of embodiment 167, wherein the cultured cell is a peripheral blood mononuclear cell (PBMC).

Embodiment 169: The pharmaceutical composition of any one of embodiments 154 to 168, wherein the eukaryotic cell is a cell of a subject administered the composition.

Embodiment 170: The pharmaceutical composition of embodiment 169, wherein the cell of the subject is selected from the group consisting of: an epithelial cell, an intestinal lamina propria cell, an endothelial cell, a fibroblast, a stromal cell, a macrophage, a B lymphocyte, a T lymphocyte, a mast cell, and a peripheral blood mononuclear cell (PBMC).

Embodiment 171: The pharmaceutical composition of embodiment 170, wherein the cell of the subject is an epithelial cell and the epithelial cell is an intestinal epithelial cell.

Embodiment 172: The pharmaceutical composition of any one of embodiments 1 to 171, wherein the pharmaceutical composition is formulated as a capsule for oral administration.

Embodiment 173: The pharmaceutical composition of embodiment 172, wherein the capsule comprises a delayed-release coating.

Embodiment 174: The pharmaceutical composition of embodiment 172 or embodiment 173, wherein the capsule comprises a hydrophobic coating.

Embodiment 175: The pharmaceutical composition of any one of embodiments 1 to 173, wherein the pharmaceutical composition is formulated for delivery of the cocktail to the intestine.

Embodiment 176: The pharmaceutical composition of embodiment 175, wherein the pharmaceutical composition is formulated for delivery of the cocktail to the small intestine.

Embodiment 177: The pharmaceutical composition of embodiment 175 or embodiment 176, wherein the composition is formulated for delivery of the cocktail to the large intestine.

Embodiment 178: The pharmaceutical composition of any one of embodiments 1 to 177, wherein the cocktail is lyophilized.

Embodiment 179: The pharmaceutical composition of any one of embodiments 1 to 178, wherein the pharmaceutical composition further comprises at least one of a pharmaceutically acceptable antioxidant, cryoprotectant, lyoprotectant, binder, disintegrant, excipient, filler, preservative, acid suppressant, antacid, H2 antagonist, and/or proton pump inhibitor.

Embodiment 180: A method of treating or preventing a disorder related to an intestinal dysbiosis in a subject in need thereof, wherein the method comprises administering to the subject a pharmaceutical composition of any one of embodiments 1 to 179.

Embodiment 181: The pharmaceutical composition of embodiment 180, wherein the disorder is selected from the group consisting of inflammatory bowel disease (IBD), irritable bowel syndrome (IBS), *C. difficile* infection (CDI), *C. difficile*-associated disease (CDAD), an antibiotic-induced adverse effect, and a combination thereof.

Embodiment 182: A method of treating or preventing inflammatory bowel disease (IBD) in a subject in need thereof, comprising administering to the subject a plurality of bacterial isolates, wherein one of the bacterial isolates comprises *Bacteroides cellulosilyticus*, and wherein at least two of the plurality of bacterial isolates are isolated from stool samples of different donors.

Embodiment 183: The method of embodiment 182, wherein the *Bacteroides cellulosilyticus* comprises a 16S rRNA sequence that is at least 95% identical to SEQ ID NO: 26.

Embodiment 184: The method of embodiment 182 or embodiment 183, wherein the plurality of bacterial isolates further comprises *Odoribacter splanchnicus*.

Embodiment 185: A method of manufacturing a cocktail of bacterial isolates, the method comprising selecting a first bacterial isolate based on a level of a short-chain fatty acid (SCFA) produced by the first bacterial isolate; selecting a second bacterial isolate based on a relative abundance of a corresponding bacterial strain in a healthy human subject versus a subject having inflammatory bowel disease, wherein the second bacterial isolate comprises a 16S rRNA sequence at least 97% identical to a 16S rRNA sequence of the corresponding bacterial strain; and combining the first and second bacterial isolates to produce the cocktail of bacterial isolates.

Embodiment 186: The method of embodiment 185, wherein the first bacterial isolate comprises a 16S rRNA sequence at least 95% identical to a 16S rRNA sequence of a bacterial isolate provided in Table 2.

Embodiment 187: The method of embodiment 185 or embodiment 186, wherein the second bacterial isolate comprises a 16S rRNA sequence at least 95% identical to a 16S rRNA sequence of a bacterial isolate provided in Table 4.

Embodiment 188: The method of any one of embodiments 185 to 187, wherein the method further comprises selecting a third bacterial isolate based on a modulation by the bacterial isolate of a level of a cytokine produced by a eukaryotic cell.

Embodiment 189: The method of embodiment 188, wherein the third bacterial isolate comprises a 16S rRNA sequence at least 95% identical to a 16S rRNA sequence of a bacterial isolate provided in Table 3.

Embodiment 190: The method of any one of embodiments 185 to 189, wherein the method further comprises selecting a fourth bacterial isolate based on a level of an aryl hydrocarbon produced by the fourth bacterial isolate.

Embodiment 191: The method of embodiment 190, wherein the fourth bacterial isolate comprises a 16S rRNA sequence at least 95% identical to a 16S rRNA sequence of a bacterial isolate provided in Table 6.

Embodiment 192: A pharmaceutical composition comprising a microbial cocktail, wherein the microbial cocktail comprises: a first human-derived bacterial isolate which induces an IL-10:IL-12 ratio of at least 50 or an IL-10:TNF-alpha ratio of at least 1 when incubated with a population of eukaryotic cells in a first functional assay; and a second human-derived bacterial isolate which produces a short chain fatty acid (SCFA) at a concentration of at least 10 mM as measured by a second functional assay; wherein the first and second bacterial isolates are capable of engrafting into the intestine of a subject following administration of the pharmaceutical composition to the subject.

Embodiment 193: The pharmaceutical composition of embodiment 192, wherein the IL-10:IL-12 ratio is at least 100.

Embodiment 194: The pharmaceutical composition of embodiment 192, wherein the IL-10:IL-12 ratio is at least 500.

Embodiment 195: The pharmaceutical composition of embodiment 192, wherein the IL-10:IL-12 ratio is at least 1000.

Embodiment 196: The pharmaceutical composition of embodiment 192, wherein the IL-10:IL-12 ratio is at least 2000.

Embodiment 197: The pharmaceutical composition of embodiment 192, wherein the IL-10:TNF-alpha ratio is at least 2.

Embodiment 198: The pharmaceutical composition of embodiment 192, wherein the IL-10:TNF-alpha ratio is at least 5.

Embodiment 199: The pharmaceutical composition of embodiment 192, wherein the IL-10:TNF-alpha ratio is at least 10.

Embodiment 200: The pharmaceutical composition of embodiment 192, wherein the IL-10:TNF-alpha ratio is at least 20.

Embodiment 201: The pharmaceutical composition of any one of embodiments 192 to 200, wherein the population of eukaryotic cells comprises a population of PBMCs.

Embodiment 202: The pharmaceutical composition of any one of embodiments 192 to 201, wherein the first human-derived bacterial isolate is incubated with the population of eukaryotic cells for about 24 hours.

Embodiment 203: The pharmaceutical composition of any one of embodiments 178 to 188, wherein the SCFA is butyrate.

Embodiment 204: The pharmaceutical composition of any one of embodiments 192 to 203, wherein the SCFA is produced at a concentration of at least 20 mM.

Embodiment 205: The pharmaceutical composition of any one of embodiments 192 to 204, wherein the SCFA is produced at a concentration of at least 25 mM.

Embodiment 206: The pharmaceutical composition of any one of embodiments 192 to 205, wherein the SCFA is produced at a concentration of at least 30 mM.

Embodiment 207: The pharmaceutical composition of any one of embodiments 192 to 206, wherein the SCFA is produced at a concentration of at least 35 mM.

Embodiment 208: The pharmaceutical composition of any one of embodiments 192 to 207, wherein the second functional assay comprises incubating the second bacterial isolate with a substrate.

Embodiment 209: The pharmaceutical composition of embodiment 208, wherein the substrate comprises at least one of an oligosaccharide, sunfiber, or barley malt.

Embodiment 210: The pharmaceutical composition of embodiment 209, wherein the oligosaccharide comprises at least one of a fructooligosaccharide (FOS) and an xylooligosaccharide (XOS).

Embodiment 211: The pharmaceutical composition of embodiment 210, wherein the substrate comprises both of a fructooligosaccharide (FOS) and an xylooligosaccharide (XOS).

Embodiment 212: The pharmaceutical composition of any one of embodiments 192 to 211, wherein the second bacterial isolate comprises a 16S rRNA sequence at least 95% identical to a 16S rRNA sequence of a bacterial isolate provided in Table 2.

Embodiment 213: The pharmaceutical composition of any one of embodiments 192 to 212, wherein the second bacterial isolate comprises *Anaerostipes* sp.

Embodiment 214: The pharmaceutical composition of embodiment 213, wherein the *Anaerostipes* sp. is *Anaerostipes hadrus*.

Embodiment 215: The pharmaceutical composition of any one of embodiments 192 to 214, wherein the second bacterial isolate comprises a 16S rRNA sequence at least 95% identical to the sequence corresponding to SEQ ID NO: 3.

Embodiment 216: The pharmaceutical composition of any one of embodiments 192 to 215, wherein the second bacterial isolate comprises *Roseburia* sp.

Embodiment 217: The pharmaceutical composition of embodiment 216, wherein the *Roseburia* sp. is *Roseburia faecis*.

Embodiment 218: The pharmaceutical composition of any one of embodiments 192 to 217, wherein the second bacterial isolate comprises a 16S rRNA sequence at least 95% identical to the sequence corresponding to SEQ ID NO: 19.

Embodiment 219: The pharmaceutical composition of any one of embodiments 192 to 218, wherein the second bacterial isolate comprises *Eubacterium* sp.

Embodiment 220: The pharmaceutical composition of embodiment 219, wherein the *Eubacterium* sp. is *Eubacterium rectale*.

Embodiment 221: The pharmaceutical composition of any one of embodiments 192 to 220, wherein the second bacterial isolate comprises a 16S rRNA sequence at least 95% identical to the sequence corresponding to SEQ ID NO: 8.

Embodiment 222: The pharmaceutical composition of any one of embodiments 192 to 221, wherein the second bacterial isolate comprises *Coprococcus* sp.

Embodiment 223: The pharmaceutical composition of embodiment 222, wherein the *Coprococcus* sp. is *Coprococcus comes*.

Embodiment 224: The pharmaceutical composition of any one of embodiments 192 to 223, wherein the second bacterial isolate comprises a 16S rRNA sequence at least 95% identical to the sequence corresponding to SEQ ID NO: 17.

Embodiment 211: The pharmaceutical composition of any one of embodiments 192 to 224, wherein the first bacterial isolate comprises a 16S sequence at least 95% identical to a 16S rRNA sequence of a bacterial isolate provided in Table 3.

Embodiment 212: A pharmaceutical composition, comprising a microbial cocktail, wherein the microbial cocktail comprises: a first human-derived bacterial isolate capable of producing a short chain fatty acid (SCFA) at a concentration of at least 10 mM, as measured by a first functional assay; and a second human-derived bacterial isolate capable of producing, as measured by a second functional assay, at least one of (i) indole at a level at least 5× greater than a level of indole produced by a control bacterial strain; (ii) tryptamine at a level at least 1.4× greater than a level of tryptamine produced by a control bacterial strain; (iii) kynurenate at a level at least 1.4× greater than a level of kynurenate produced by a control bacterial strain; (iv) kynurenine at a level at least 2.5× greater than a level of kynurenine produced by a control bacterial strain; and (v) indole-3-acetic acid at a level at least 2× greater than a level of indole-3-acetic acid produced by a control bacterial strain; wherein the control bacterial strain is selected from at least one of *Peptostreptococcus russellii* and *Peptostreptococcus anaerobius*; wherein the first and second bacterial isolates engraft in the intestine of a subject following administration of the pharmaceutical composition to the subject.

Embodiment 213: The pharmaceutical composition of embodiment 212, wherein the second functional assay comprises separately incubating the second bacterial isolate and the control strain with tryptophan.

Embodiment 214: The pharmaceutical composition of embodiment 212 or embodiment 213, wherein the second bacterial isolate produces indole at a level at least 50× greater than the level of indole produced by the control bacterial strain.

Embodiment 215: The pharmaceutical composition of any one of embodiments 212 to 214, wherein the second bacterial isolate produces indole at a level at least 100× greater than the level of indole produced by the control bacterial strain.

Embodiment 216: The pharmaceutical composition of any one of embodiments 212 to 215, wherein the second bacterial isolate produces indole at a level at least 150× greater than the level of indole produced by the control bacterial strain.

Embodiment 217: The pharmaceutical composition of any one of embodiments 214 to 216, wherein the second bacterial isolate comprises *Clostridium aldenense*.

Embodiment 218: The pharmaceutical composition of any one of embodiments 214 to 217, wherein the second bacterial isolate comprises a 16S rRNA sequence at least 95% identical to SEQ ID NO: 10.

Embodiment 219: The pharmaceutical composition of any one of embodiments 212 to 218, wherein the second bacterial isolate produces tryptamine at a level at least 1.5× greater than the level of tryptamine produced by the control bacterial strain.

Embodiment 220: The pharmaceutical composition of embodiment 219, wherein the second bacterial isolate comprises *Odoribacter splanchnicus*.

Embodiment 221: The pharmaceutical composition of embodiment 219 or embodiment 220, wherein the second bacterial isolate comprises a 16S rRNA sequence at least 95% identical to SEQ ID NO: 2.

Embodiment 222: The pharmaceutical composition of any one of embodiments 212 to 218, wherein the second bacterial isolate produces kynurenate at a level at least 1.5× greater than the level of kynurenate produced by the control bacterial strain.

Embodiment 223: The pharmaceutical composition of embodiment 222, wherein the second bacterial isolate comprises *Odoribacter splanchnicus*.

Embodiment 224: The pharmaceutical composition of embodiment 222 or embodiment 223, wherein the second bacterial isolate comprises a 16S rRNA sequence at least 95% identical to SEQ ID NO: 2.

Embodiment 225: The pharmaceutical composition of any one of embodiments 212 to 224, wherein the second bacterial isolate produces kynurenine at a level at least 3× greater than the level of tryptamine produced by the control bacterial strain.

Embodiment 226: The pharmaceutical composition of embodiment 225, wherein the second bacterial isolate comprises *Odoribacter splanchnicus* or *Bacteroides stercoris*.

Embodiment 227: The pharmaceutical composition of embodiment 225 or embodiment 226, wherein the second bacterial isolate comprises a 16S rRNA sequence at least 95% identical to SEQ ID NO: 2 or SEQ ID NO: 13.

Embodiment 228: The pharmaceutical composition of at least one of embodiments 225 to 227, wherein the control bacterial strain comprises *Peptostreptococcus anaerobius*.

Embodiment 229: The pharmaceutical composition of any one of embodiments 212 to 228, wherein the second bacterial isolate produces indole-3-acetic acid at a level at least 3× greater than the level of indole-3-acetic acid produced by the control bacterial strain.

Embodiment 230: The pharmaceutical composition of embodiment 229, wherein the second bacterial isolate produces indole-3-acetic acid at a level at least 8× greater than the level of indole-3-acetic acid produced by the control bacterial strain.

Embodiment 231: The pharmaceutical composition of embodiment 230, wherein the second bacterial isolate comprises *Odoribacter splanchnicus* or *Clostridium aldenense*.

Embodiment 232: The pharmaceutical composition of embodiment 230 or embodiment 231, wherein the second bacterial isolate comprises a 16S rRNA sequence at least 95% identical to SEQ ID NO: 2 or SEQ ID NO: 10.

Embodiment 233: The pharmaceutical composition of any one of embodiments 212 to 232, wherein the SCFA is butyrate.

Embodiment 234: The pharmaceutical composition of any one of embodiments 212 to 233, wherein the SCFA is produced at a concentration of at least 20 mM.

Embodiment 235: The pharmaceutical composition of any one of embodiments 212 to 234, wherein the SCFA is produced at a concentration of at least 25 mM.

Embodiment 236: The pharmaceutical composition of any one of embodiments 212 to 235, wherein the SCFA is produced at a concentration of at least 30 mM.

Embodiment 237: The pharmaceutical composition of any one of embodiments 212 to 236, wherein the SCFA is produced at a concentration of at least 35 mM.

Embodiment 238: The pharmaceutical composition of any one of embodiments 212 to 237, wherein the second functional assay comprises incubating the second bacterial isolate with a substrate.

Embodiment 239: The pharmaceutical composition of embodiment 238, wherein the substrate comprises at least one of an oligosaccharide, sunfiber, or barley malt.

Embodiment 240: The pharmaceutical composition of embodiment 239, wherein the oligosaccharide comprises at least one of a fructooligosaccharide (FOS) and an xylooligosaccharide (XOS).

Embodiment 241: The pharmaceutical composition of embodiment 240, wherein the substrate comprises both of a fructooligosaccharide (FOS) and an xylooligosaccharide (XOS).

Embodiment 242: The pharmaceutical composition of any one of embodiments 212 to 241, wherein the second bacterial isolate comprises a 16S rRNA sequence at least 95% identical to a 16S rRNA sequence of a bacterial isolate provided in Table 2.

Embodiment 243: A method of treating inflammatory bowel disease comprising administering the pharmaceutical composition of any one of embodiments 192 to 242 to a subject in need thereof.

Embodiment 244: The method of embodiment 243, wherein a dosage of at least one of the first bacterial isolate and second bacterial isolate is less than $10^{10}$ cells/ml.

Embodiment 245: A pharmaceutical composition comprising a plurality of bacterial isolates, wherein the plurality of bacterial isolates comprises *Bacteroides cellulosilyticus* and at least one of *Odoribacter splanchnicus*, *Roseburia faecis*, *Faecalibacterium prausnitzii*, *Akkermansia muciniphila*, *Alistipes shahii*, *Subdoligranulum variabile*, and *Eubacterium rectale*, wherein at least two of the plurality of bacterial isolates are isolated from stool samples of different donors.

Embodiment 246: The pharmaceutical composition of embodiment 245, wherein the plurality of bacterial isolates comprises *Odoribacter splanchnicus*.

Embodiment 247: The pharmaceutical composition of embodiment 246, wherein the plurality of bacterial isolates comprises *Faecalibacterium prausnitzii*.

Embodiment 248: The pharmaceutical composition of embodiment 247, wherein the plurality of bacterial isolates comprises two different bacterial isolates that are each members of the species *Faecalibacterium prausnitzii*.

Embodiment 249: The pharmaceutical composition of embodiment 247, wherein the plurality of bacterial isolates comprises *Subdoligranulum variabile*.

Embodiment 250: The pharmaceutical composition of embodiment 248, wherein the plurality of bacterial isolates comprises *Roseburia faecis*, *Akkermansia muciniphila*, *Alistipes shahii*, and *Eubacterium rectale*.

Embodiment 251: The pharmaceutical composition of embodiment 249, wherein the plurality of bacterial isolates comprises *Roseburia faecis*, *Akkermansia muciniphila*, *Alistipes shahii*, and *Eubacterium rectale*.

Embodiment 252: A pharmaceutical composition comprising a plurality of bacterial isolates, wherein the plurality of bacterial isolates comprises two different bacterial isolates that are each members of the species *Faecalibacterium prausnitzii*.

Embodiment 253: The composition of embodiment 252, wherein the two different bacterial isolates are isolated from stool samples of different human donors.

Embodiment 254: The composition of embodiment 252, wherein the plurality of bacterial isolates further comprises at least one of *Bacteroides cellulosilyticus*, *Odoribacter splanchnicus*, *Roseburia faecis*, *Akkermansia muciniphila*, *Alistipes shahii*, and *Eubacterium rectale*.

Embodiment 255: The composition of embodiment 252, wherein the plurality of bacterial isolates further comprises each of *Bacteroides cellulosilyticus*, *Odoribacter splanchnicus*, *Roseburia faecis*, *Akkermansia muciniphila*, *Alistipes shahii*, and *Eubacterium rectale*.

Embodiment 256: A method of treating or preventing inflammatory bowel disease (IBD) in a subject in need thereof, comprising administering to the subject a first pharmaceutical composition comprising a bacterial isolate comprising *Bacteroides cellulosilyticus*, and administering to the subject a second pharmaceutical composition comprising a second bacterial isolate.

Embodiment 257: The method of embodiment 256, wherein the plurality of bacterial isolates further comprises at least one of *Faecalibacterium prausnitzii*, *Odoribacter splanchnicus*, *Roseburia faecis*, *Akkermansia muciniphila*, *Alistipes shahii*, *Subdoligranulum variabile* and *Eubacterium rectale*.

Embodiment 258: The method of embodiment 256, wherein the plurality of bacterial isolates further comprises each of *Faecalibacterium prausnitzii*, *Odoribacter splanchnicus*, *Roseburia faecis*, *Akkermansia muciniphila*, *Alistipes shahii*, *Subdoligranulum variabile* and *Eubacterium rectale*.

Embodiment 259: The method of embodiment 256, wherein the plurality of bacterial isolates further comprises each of *Odoribacter splanchnicus*, *Roseburia faecis*, *Akkermansia muciniphila*, *Alistipes shahii*, *Eubacterium rectale*, and two different bacterial isolates that are each members of the species *Faecalibacterium prausnitzii*.

Embodiment 260: A method of manufacture, the method comprising culturing *Bacteroides cellulosilyticus* as a pure culture; and lyophilizing bacteria from the pure culture of *B. cellulosilyticus* to produce a *B. cellulosilyticus* lyophilate.

Embodiment 261: The method of embodiment 260, further comprising combining the *B. cellulosilyticus* lyophilate with a second lyophilate, wherein the second lyophilate is produced by lyophilizing bacteria from a pure culture of at least one of *Faecalibacterium prausnitzii*, *Odoribacter splanchnicus*, *Roseburia faecis*, *Akkermansia muciniphila*, *Alistipes shahii*, *Subdoligranulum variabile* and *Eubacterium rectale*.

Embodiment 262: A pharmaceutical composition comprising a plurality of bacterial isolates, wherein an amount of cells of a first bacterial isolate of the plurality of bacterial isolates is at least 1% greater than an amount of cells of a second bacterial isolate of the plurality of bacterial isolates, wherein the plurality of bacterial isolates are selected from the group consisting of: *Bacteroides cellulosilyticus*, *Faecalibacterium prausnitzii*, *Subdogranulum variabile*, *Eubacterium rectale*, *Odoribacter splanchnicus*, *Alistipes shahii*, *Roseburia faecis* and *Akkermansia muciniphila*.

Embodiment 263: The pharmaceutical composition of embodiment 262, wherein the amount of cells of the first bacterial isolate is at least 10% greater than the amount of cells of the second bacterial isolate.

Embodiment 264: The pharmaceutical composition of embodiment 262 or 263, wherein the first bacterial isolate comprises one of *Eubacterium rectale* and *Faecalibacterium prausnitzii*.

Embodiment 265: The pharmaceutical composition of embodiment 262 or 263, wherein the second bacterial isolate comprises one of *Alistipes shahii*, and *Akkermansia muciniphila*.

Embodiment 266: The pharmaceutical composition of embodiment 262 or 263, wherein each of the first and second bacterial isolates comprises *Faecalibacterium prausnitzii*.

Embodiment 267: The pharmaceutical composition of embodiment 266, wherein the first bacterial isolate comprises a 16S rRNA sequence that is at least 95% identical to SEQ ID NO: 7.

Embodiment 268: The pharmaceutical composition of embodiment 266 or 267, wherein the second bacterial isolate comprises a 16S rRNA sequence that is at least 95% identical to SEQ ID NO: 1.

Embodiment 269: A pharmaceutical composition comprising a plurality of bacterial isolates, wherein an amount of cells of a first bacterial isolate of the plurality of bacterial isolates is at least 10% greater than an amount of cells of a second bacterial isolate of the plurality of bacterial isolates, wherein each of the first and second bacterial isolates comprises *Faecalibacterium prausnitzii*.

Embodiment 270: The pharmaceutical composition of embodiment 269, wherein the amount of cells of the first bacterial isolate is at least 10% greater than the amount of cells of the second bacterial isolate.

Embodiment 271: The pharmaceutical composition of embodiment 269 or 270, wherein the first bacterial isolate comprises a 16S rRNA sequence that is at least 95% identical to SEQ ID NO: 7.

Embodiment 272: The pharmaceutical composition of any one of embodiments 269 to 271, wherein the second bacterial isolate comprises a 16S rRNA sequence that is at least 95% identical to SEQ ID NO: 1.

Embodiment 273: A pharmaceutical composition comprising a bacterial isolate, wherein the bacterial isolate comprises a 16S rRNA sequence that is at least 97% identical to a 16S rRNA sequence of a bacterial strain that is either (i) enriched in a group of healthy subjects over a group of patients with ulcerative colitis (UC) and/or (ii) correlated with clinical remission of one or more UC symptoms in a group of patients following treatment of each patient of the group of patients with a fecal microbiota transplant, wherein a cross-sectional combined p-value of the bacterial strain is less than $1\times10^{-10}$.

Embodiment 274: The pharmaceutical composition of embodiment 273, wherein the bacterial isolate comprises a 16S rRNA sequence that is at least 99% identical to a 16S rRNA sequence of the bacterial strain.

Embodiment 275: The pharmaceutical composition of embodiment 273 or 274, wherein the bacterial isolate comprises at least one of *Odoribacter splanchnicus, Eubacterium rectale, Bacteroides cellulosilyticus* and *Alistipes shahii*.

Embodiment 276: The pharmaceutical composition of any one of embodiments 273 to 275, wherein the cross-sectional combined p-value of the bacterial strain is less than $1\times10^{-14}$.

Embodiment 277: The pharmaceutical composition of any one of embodiments 273 to 276, wherein the bacterial isolate comprises at least one of *Odoribacter splanchnicus* and *Alistipes shahii*.

Embodiment 278: The pharmaceutical composition of any one of embodiments 273 to 277, wherein the cross-sectional combined p-value of the bacterial strain is less than $1\times10^{-20}$.

Embodiment 279: The pharmaceutical composition of any one of embodiments 273 to 278, wherein the bacterial isolate comprises *Alistipes shahii*.

Embodiment 280: The pharmaceutical composition of embodiment 279, wherein the *Alistipes shahii* comprises a 16S rRNA sequence that is at least 97% identical to SEQ ID NO: 18.

Embodiment 281: A method of treating inflammatory bowel disease comprising administering the pharmaceutical composition of any one of embodiments 245 to 280 to a subject in need thereof.

Embodiment 282: A pharmaceutical composition comprising a bacterial mixture comprising a plurality of bacterial isolates, wherein the plurality of bacterial isolates comprises two or more bacterial isolates that are each a member of the genus *Bacteroides*, wherein at least one of the two or more bacterial isolates comprises *Bacteroides cellulosilyticus* or *Bacteroides stercoris*.

Embodiment 283: The pharmaceutical composition of embodiment 282, wherein the two or more bacterial isolates comprise a bacterial isolate comprising *Bacteroides cellulosilyticus* and a bacterial isolate comprising *Bacteroides stercoris*.

Embodiment 284: The pharmaceutical composition of embodiment 283, wherein the bacterial isolate comprising *Bacteroides cellulosilyticus* comprises a 16S rRNA sequence having the sequence shown in SEQ ID NO: 14.

Embodiment 285: The pharmaceutical composition of embodiment 284, wherein the bacterial isolate comprising *Bacteroides stercoris* comprises a 16S rRNA sequence having the sequence shown in SEQ ID NO: 13.

Embodiment 286: The pharmaceutical composition of embodiment 285, wherein the bacterial mixture further comprises two bacterial isolates comprising *Faecalibacterium prausnitzii*.

Embodiment 287: The pharmaceutical composition of embodiment 286, wherein one of the two bacterial isolates comprising *Faecalibacterium prausnitzii* comprises a 16S rRNA sequence having the sequence shown in SEQ ID NO: 7, and the other of the two bacterial isolates comprising *Faecalibacterium prausnitzii* comprises a 16S rRNA sequence having the sequence shown in SEQ ID NO: 1.

Embodiment 288: The pharmaceutical composition of embodiment 287, wherein the bacterial mixture further comprises a bacterial isolate comprising *Odoribacter splanchnicus*.

Embodiment 289: The pharmaceutical composition of embodiment 288, wherein the bacterial isolate comprising *Odoribacter splanchnicus* comprises a 16S rRNA sequence having the sequence shown in SEQ ID NO: 2.

Embodiment 290: The pharmaceutical composition of embodiment 289, wherein the bacterial mixture further comprises a bacterial isolate comprising *Akkermansia muciniphila*.

Embodiment 291: The pharmaceutical composition of embodiment 290, wherein the bacterial isolate comprising *Akkermansia muciniphila* comprises a 16S rRNA sequence having the sequence shown in SEQ ID NO: 20.

Embodiment 292: The pharmaceutical composition of embodiment 291, wherein the bacterial mixture further comprises a bacterial isolate comprising *Eubacterium rectale*.

Embodiment 293: The pharmaceutical composition of embodiment 292, wherein the bacterial isolate comprising *Eubacterium rectale* comprises a 16S rRNA sequence having the sequence shown in SEQ ID NO: 8.

Embodiment 294: The pharmaceutical composition of embodiment 293, wherein the bacterial mixture further comprises a bacterial isolate comprising *Roseburia faecis*.

Embodiment 295: The pharmaceutical composition of embodiment 294, wherein the bacterial isolate comprising *Roseburia faecis* comprises a 16S rRNA sequence having the sequence shown in SEQ ID NO: 19.

Embodiment 296: The pharmaceutical composition of embodiment 295, wherein the bacterial mixture further comprises a bacterial isolate comprising *Alistipes shahii*.

Embodiment 297: The pharmaceutical composition of embodiment 296, wherein the bacterial isolate comprising *Alistipes shahii* comprises a 16S rRNA sequence having the sequence shown in SEQ ID NO: 18.

Embodiment 298: A method of treating inflammatory bowel disease comprising administering the pharmaceutical composition of any one of embodiments 282 to 297 to a subject in need thereof.

Embodiment 299: A pharmaceutical composition comprising a cocktail of at least two bacterial isolates, wherein at least one of the bacterial isolates comprises a 16S rRNA sequence that is at least 95% identical to a 16S rRNA sequence of a bacterial isolate provided in any one of Tables 1-51, and wherein the at least two bacterial isolates are isolated from stool samples of different donors.

Embodiment 300: A method of treating inflammatory bowel disease comprising administering the pharmaceutical composition of embodiment 299 to a subject in need thereof.

EXAMPLES

The examples herein are provided to illustrate advantages and benefits of the present technology and to further assist a person of ordinary skill in the art with preparing or using compositions of the present technology. The examples herein are also presented in order to more fully illustrate the preferred aspects of the present technology. The examples should in no way be construed as limiting the scope of the present disclosure, as defined by the appended claims. The examples can include or incorporate any of the variations, aspects or embodiments of the present technology described above. The variations, aspects or embodiments described above may also further each include or incorporate the variations of any or all other variations, aspects or embodiments of the present technology.

Example 1: Isolating and Growing Bacterial Isolates

Stool samples from candidate human donors was collected and screened for the presence of pathogens. Six donors whose stool samples did not contain pathogens were selected. Donor stool was then collected in Whirl-Pak® filter bags, suspended in buffer (12.5% glycerol and 0.9% PBS, pH 7.4), and homogenized. Filtrate was diluted ~$10^3$× in PBS containing 0.05% cysteine and either plated on solid Isolation Media (IM; see below for each strain) or inoculated into IM broth, and grown under anaerobic conditions. Bacterial isolates were purified from plates by picking bacterial colonies and from IM broth by diluting to extinction. Once purified, each bacterial isolate was grown in IM broth under anaerobic conditions for further characterization, and aliquots frozen at −80° C. in 20% glycerol to make stocks.

Isolation Media (IM) for Strains

The following IM was used to culture strains used in this study. In each case, agar was omitted for cultures grown in broth.

1. Complex Gut Medium (CGM)

CGM was used to culture bacteria from the following genus and species:

*Alistipes onderdonkii* (e.g., a bacterial isolate having SEQ ID NO: 4, which was isolated from stool of a disease-screened and healthy human donor ("Donor E"));

*Bacteroides uniformis* (e.g., a bacterial isolate having SEQ ID NO: 11 or SEQ ID NO:16; which were each isolated from stool of a disease-screened and healthy human donor (respectively "Donor K" and "Donor E")).

Formulation (Per Liter):

| | |
|---|---|
| Tryptone | 2 g |
| Peptone from casein | 2 g |
| Yeast extract | 1 g |
| D-glucose | 0.4 g |
| L-cysteine | 0.5 g |
| D-(+)-Cellobiose | 1 g |
| D-(+)-Maltose | 1 g |
| D-(−) Fructose | 1 g |
| Meat extract | 5 g |
| MgSO$_4$•7H$_2$O | 0.0025 g |
| NaHCO$_3$ | 0.4 g |
| NaCl$_2$ | 0.08 g |
| Phosphate buffer | 100 mM |
| CaCl$_2$ | 0.8% |
| Vitamin K (menadione) | 5.8 mM |
| FeSO$_4$ | 1.44 mM |
| Histidine hematin | 0.1% |
| Tween80 | 0.05% |
| ATCC Vitamin mix | 1% |
| ATCC Trace Mineral mix | 1% |
| Acetic acid | 30 mM |
| Isovaleric acid | 1 mM |
| Propionic acid | 8 mM |
| Butyric acid | 4 mM |
| Resazurin | 4 mM |
| Agar | 1.5% |
| Final pH 7.0 ± 0.2 | |

2. Minimal mucin media (Min muc)

Minimal mucin media was used to culture bacteria from the following genus and species:

*Dorea longicatena* (e.g., a bacterial isolate having SEQ ID NO: 6, which was isolated from stool of a disease-screened and healthy human donor ("Donor F")).

Formulation (Per Liter):

| | |
|---|---|
| 5X Minimum salts (see below) | 11.28 g |
| Agar | 12 g |
| Mucin from porcine stomach Type II | 2.5 g |
| Final pH 6.8 ± 0.2 | |

5× Minimum Salts (HiMedia® M1253) (Used in Min Muc Media)

Formulation (Per Liter):

| | |
|---|---|
| Disodium phosphate | 33.9 g |
| Potassium phosphate | 15 g |

-continued

| | |
|---|---|
| Sodium chloride | 2.5 g |
| Ammonium chloride | 5 g |

3. Veggie Brain Heart Infusion Agar with Supplements (vBHI3)

vBHI3 media was used to culture bacteria from the following genus and species:

*Odoribacter splanchnicus* (e.g., a bacterial isolate having SEQ ID NO: 2, which was isolated from stool of a disease-screened and healthy human donor ("Donor G"));

*Bacteroides cellulosilyticus* (e.g., a bacterial isolate having SEQ ID NO: 14, which was isolated from stool of a disease-screened and healthy human donor ("Donor G"));

*Blautia obeum* (e.g., a bacterial isolate having SEQ ID NO: 9, which was isolated from stool of a disease-screened and healthy human donor ("Donor G"));

*Blautia sp.*, (e.g., a bacterial isolate having SEQ ID NO: 34, which was isolated from stool of a disease-screened and healthy human donor ("Donor H");

*Parabacteroides merdae* (e.g., a bacterial isolate having SEQ ID NO: 5, which was isolated from stool of a disease-screened and healthy human donor ("Donor" ("Donor H")).

Formulation (Per Liter):

| | |
|---|---|
| HiVeg ™ Peptone No. 3 (HiMedia ® RM005V) | 10 g |
| HiVeg ™ Special Infusion (HiMedia ® RM188V) | 7.5 g |
| HiVeg ™ Infusion (HiMedia ® RM191V) | 10 g |
| Dextrose | 2 g |
| Sodium Chloride | 5 g |
| Disodium phosphate | 2.5 g |
| Agar | 12 g |
| L-cysteine | 0.005 g |
| Hemin | 0.05 mg |
| Vitamin K | 0.0025 mg |
| Final pH 7.4 ± 0.2 | |

4. Veggie Brain Heart Infusion Agar with Supplements and Sodium Taurocholate (vBHI3+NaTau)

vBHI3+NaTau media was used to culture bacteria from the following genus and species:

*Anaerostipes hadrus* (e.g., a bacterial isolate having SEQ ID NO: 3, which was isolated from stool of a disease-screened and healthy human donor ("Donor G"));

*Clostridium aldenense* (e.g., a bacterial isolate having SEQ ID NO: 10, which was isolated from stool of a disease-screened and healthy human donor ("Donor G")).

Formulation (Per Liter):

Use recipe for Veggie Brain Heart Infusion agar with supplements (vBHI3)

Plus Sodium taurocholate 1 g

Final pH 7.4±0.2

5. 0.2× Veggie Brain Heart Infusion Agar with Supplements and Mucin (vBHI3+Mucin)

vBHI3+mucin media was used to culture bacteria from the following genus and species:

*Alistipes finegoldii* (e.g., a bacterial isolate having SEQ ID NO: 15, which was isolated from stool of a disease-screened and healthy human donor ("Donor E")).

Formulation (Per Liter):

| | |
|---|---|
| HiVeg ™ Peptone No. 3 (HiMedia ® RM005V) | 2 g |
| HiVeg ™ Special Infusion (HiMedia ® RM188V) | 1.5 g |
| HiVeg ™ Infusion (HiMedia ® RM191V) | 2 g |
| Dextrose | 0.4 g |
| Sodium Chloride | 1 g |
| Disodium phosphate | 0.5 g |
| Agar | 12 g |
| L-cysteine | 0.005 g |
| Hemin | 0.05 mg |
| Vitamin K | 0.0025 mg |
| Mucin from porcine stomach Type II | 2.5 g |
| Final pH 7.4 ± 0.2 | |

6. Veggie Reinforced Clostridial Medium with Rumen (vRCM+Rumen)

vRCM+rumen media was used to culture bacteria from the following genus and species:

*Coprococcus comes* (e.g., a bacterial isolate having SEQ ID NO: 17, which was isolated from stool of a disease-screened and healthy human donor ("Donor J")).

Formulation (Per Liter):

| | |
|---|---|
| Differential Reinforced Clostridial HiVeg broth (see below) | 29 g |
| Noble agar | 12 g |
| Rumen fluid | 30% |
| L-cysteine | 0.005 g |
| Final pH 7.2 ± 0.2 | |

Differential Reinforced Clostridial HiVeg™ Broth (HiMedia MV549) (Used in vRCM+Rumen Media)

Formulation (Per Liter):

| | |
|---|---|
| HiVeg ™ peptone | 10 g |
| HiVeg ™ extract | 10 g |
| Yeast extract | 1.5 g |
| Starch | 1 g |
| Sodium acetate | 5 g |
| Glucose | 1 g |
| L-cysteine hydrochloride | 0.5 g |

7. Wilkins-Chalgren Anaerobe Agar with Cooked Meat (WCA+CM)

WCA+CM media was used to culture bacteria from the following genus and species:

*Eubacterium rectale* (e.g., a bacterial isolate having SEQ ID NO: 8, which was isolated from stool of a disease-screened and healthy human donor ("Donor F")).

Formulation (Per Liter):

| | |
|---|---|
| Wilkins-Chalgren Anaerobe broth (see below) | 33 g |
| Noble agar | 12 g |
| Ground cooked meat granules | 10 g |
| L-cysteine | 0.005 g |
| Hemin | 0.05 mg |
| Vitamin K | 0.0025 mg |
| Final pH 7 ± 0.2 | |

Wilkins-Chalgren Anaerobe Broth (Oxoid CM0643) (Used in WCA+CM Media)

Formulation (Per Liter):

| | |
|---|---|
| Tryptone | 10 g |
| Gelatin peptone | 10 g |
| Yeast extract | 5 g |

| | |
|---|---|
| Glucose | 1 g |
| Sodium chloride | 5 g |
| L-Arginine | 1 g |
| Sodium pyruvate | 1 g |
| Menadione | 0.0005 g |
| Haemin | 0.005 g |
| Final pH 7.1 ± 0.2 | |

8. Yeast Casitone Fatty Acids Agar with Carbohydrates (YCFAC)

YCFAC media was used to culture bacteria from the following genus and species:

*Faecalibacterium prausnitzii* (e.g., a bacterial isolate having SEQ ID NO: 1 or SEQ ID NO: 7, which were each isolated from stool of a disease-screened and healthy human donor (respectively "Donor E" and "Donor F");

*Alistipes shahii* (e.g., a bacterial isolate having SEQ ID NO: 18, which was isolated from stool of a disease-screened and healthy human donor ("Donor E");

*Bacteroides uniformis* (e.g., a bacterial isolate having SEQ ID NO: 11 or SEQ ID NO:16; which were each isolated from stool of a disease-screened and healthy human donor (respectively "Donor K" and "Donor E"));

*Bacteroides vulgatus* (e.g., a bacterial isolate having SEQ ID NO: 12, which was isolated from stool of a disease-screened and healthy human donor ("Donor K");

*Roseburia faecis* (e.g., a bacterial isolate having SEQ ID NO: 19, which was isolated from stool of a disease-screened and healthy human donor ("Donor E");

*Bacteroides stercoris* (e.g., a bacterial isolate having SEQ ID NO: 13, which was isolated from stool of a disease-screened and healthy human donor ("Donor K").

Media was pre-purchased from Anaerobe Systems (Cat #AS-675)

Formulation (Per Liter):

| | |
|---|---|
| Casitone | 10.00 g |
| Yeast Extract | 2.50 g |
| Sodium Bicarbonate | 4.00 g |
| Glucose | 2.00 g |
| Cellobiose | 2.00 g |
| Maltose | 2.00 g |
| Potassium Phosphate Monobasic | 0.45 g |
| Potassium Phosphate Dibasic | 0.45 g |
| Sodium Chloride | 0.90 g |
| Ammonium Sulfate | 0.90 g |
| Magnesium Sulfate Heptahydrate | 0.09 g |
| Calcium Chloride | 0.09 g |
| Hemin (0.1% solution) | 10.00 mL |
| Vitamin Mix | 10.00 mL |
| L-Cysteine (25.0% solution) | 4.00 mL |
| Resazurin (0.025% solution) | 4.00 mL |
| Volatile Fatty Acid Solution | 2.90 mL |
| Agar | 15.00 g |
| Final pH 6.8 ± 0.3 | |

9. HiVeg™ *Brucella* Blood Agar (vBBA)

vBBA media was used to culture bacteria from the following genus and species:

*Phascolarctobacterium faecium* (e.g., a bacterial isolate having SEQ ID NO: 21, which was isolated from stool of a disease-screened and healthy human donor ("Donor K").

Media can be purchased as a dehydrated mix (*Brucella* HiVeg Agar Base; HiMedia MV074), followed by addition of L-cysteine and horse serum.

Formulation (Per Liter):

| | |
|---|---|
| HiVeg hydrolysate | 10 g |
| HiVeg peptone | 10 g |
| Yeast extract | 2 g |
| Dextrose | 1 g |
| Sodium chloride | 5 g |
| Sodium bisulphite | 0.1 g |
| Agar | 15 g |
| Horse serum | 50 mL |
| L-cysteine | 0.005 g |
| Final pH 7.0 ± 0.2 | |

10. Minimal Media+Purified Mucin

Minimal media+purified mucin was used to culture bacteria from the following genus and species:

*Akkermansia muciniphila* (e.g., a bacterial isolate having SEQ ID NO: 20, which was isolated from stool of a disease-screened and healthy human donor ("Donor F").

Formulation (Per Liter):

| | |
|---|---|
| Monopotassium phosphate | 0.4 g |
| Disodium phosphate | 0.53 g |
| Ammonium chloride | 0.3 g |
| Sodium chloride | 0.3 g |
| Magnesium chloride | 0.047 g |
| Calcium chloride | 0.11 g |
| Sodium bicarbonate | 4 g |
| Sodium sulfite | 0.005 g |
| L-cysteine | 0.005 g |
| ATCC Trace Mineral solution | 10 mL |
| ATCC Vitamin solution | 10 mL |
| Ethanol-purified Type III mucin | 2.5 g |

11. M10+Rumen Fluid+Mucin

M10+rumen fluid+mucin was used to culture bacteria from the following genus and species:

*Subdoligranulum variabile* (e.g., a bacterial isolate having SEQ ID NO: 22, which was isolated from stool of a disease-screened and healthy human donor ("Donor F").

*Alistipes putredinis* (e.g., a bacterial isolate having SEQ ID NO: 35, which was isolated from stool of a disease-screened and healthy human donor ("Donor #") Formulation (per liter):

| | |
|---|---|
| Potassium phosphate monobasic | 1.3 mM |
| Sodium chloride | 0.76 mM |
| Potassium phosphate dibasic | 1.7 mM |
| ATCC Trace Mineral Solution | 10 mL |
| Sodium bicarbonate | 1 g |
| Clarified rumen fluid | 300 mL |
| Type II mucin | 5 g |
| ATCC Vitamin solution | 10 mL |
| Acetic acid | 170 μL |
| Propionic acid | 60 μL |
| Butyric acid | 40 μL |
| Isobutyric acid | 10 μL |
| n-valeric acid | 10 μL |
| Isovaleric acid | 10 μL |
| DL-α-methylbutyric acid | 10 μL |
| L-cysteine | 0.005 g |
| Hemin | 0.05 mg |
| Vitamin K | 0.0025 mg |
| Final pH 6.8 ± 0.2 | |

Example 2: Bacterial Isolates that Produce a Short-Chain Fatty Acid (SCFA)

A functional assay was developed for screening bacterial isolates for production of butyrate. Bacterial isolates were isolated from stool samples of healthy human donors and grown in liquid culture as described above. Cells were pelleted by centrifugation and resuspended in deep well plates in 150 µL of fresh culture media and 150 µL of assay buffer (0.1M sodium phosphate buffer (pH 7) containing 2 grams/200 mL sodium phosphate buffer of each of fructooligosaccharides (FOS), xylooligosaccharides (XOS), sunfiber/partially hydrolyzed guar gum (PHGG) and barley malt). Plates were incubated at 37° C. in an anaerobic chamber for 6 hours or 24 hours on a plate shaker at 200 rpm in order to allow fermentation of carbohydrates to butyrate. Following incubation, cells were pelleted and 100 µl of supernatant was transferred to a fresh vial for SCFA extraction.

100 µl of supernatant was mixed with 10 µl of 50% sulfuric acid and 500 µl of diethyl ether containing 5 mM 2-methylpentanoic acid in a 2 mL glass vial. Samples were centrifuged at 3,220 g for 10 minutes to obtain a clear phase boundary. SCFA levels were measured using a Gas Chromatograph (GC) with a Flame Ionization Detector (FID) using the following parameters:

Injection: A 1 µL sample injected at a sample depth of 8 mm with a fast plunger speed and four sample washes.
Inlet: Split mode at 225° C. with a 20:1 split ratio.
Carrier Gas: Helium
Oven: Isothermal temperature program at 140° C. for 5 min.
Column: Nitroterephthalic-acid modified/polyethylene glycol (PEG) capillary column that is 0.25 mm in diameter, approximately 30 m long with a 0.25 µm film thickness. Column kept at a constant flow of 6.0 mL/min.
Flame Ionization Detector (FID): Temperature set at 225° C. Flow rate for hydrogen is 30.0 mL/min. Flow rate for air is 400.0 mL/min. Makeup flow of helium is 20.0 mL/min.

Levels of butyrate were determined as net concentrations (t24-t0, and t6-t0) and as a percent of total SCFAs produced, on a per carbon basis.

Figure 1B:
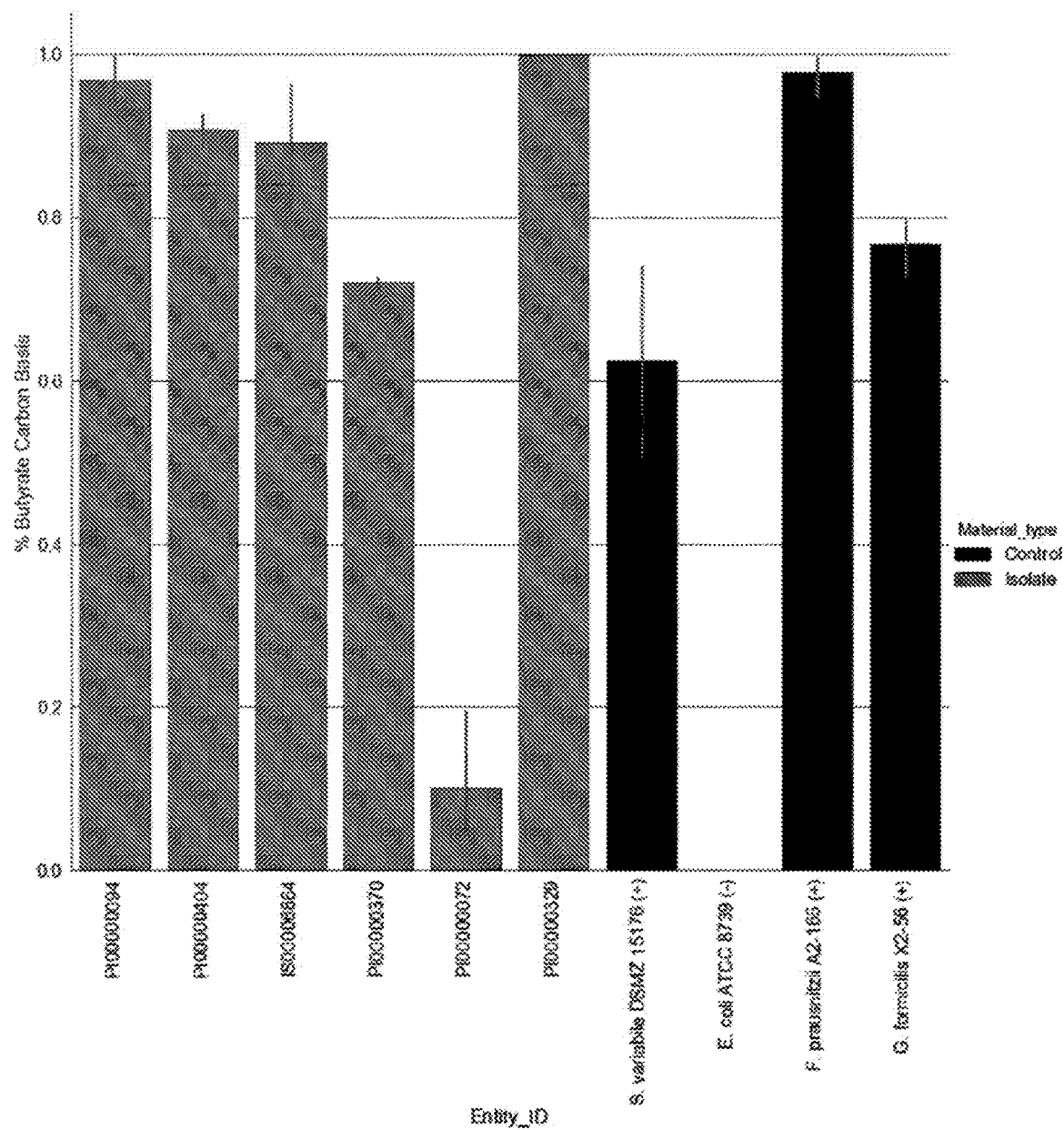
FIG. 1B shows the percentage of converted butyrate normalized to carbon count.

FIG. 1A shows butyrate concentration (mM) produced by bacterial isolates after 24 hours incubation in substrate buffer. For these same bacterial isolates, FIG. 1B shows the % butyrate produced of total SCFA production per carbon after 24 hours incubation in substrate buffer. Taxonomic information for each isolate, as well as SEQ ID NOs corresponding to each 16S rRNA sequence, can be found in Table 2. Also shown is data for positive control strains DSM 15176 (*Subdoligranulum variabile*), DSM 17677 (*Faecalibacterium prausnitzii* A2-165), and ATCC 27749 (*Gemmiger formicilis* X2-56). The *E. coli* ATCC 8739 strain, which does not secrete butyrate, was used as a negative control. The two *S. variabile* strains listed in Table 2 (IS00007359 and IS00007357) are also predicted to produce butyrate based on their taxonomic similarity to strain DSM 15176.

The ability of these bacterial isolates to produce butyrate (e.g., in the gut of a subject administered one or more of the bacterial isolates) makes them excellent candidates for inclusion in a pharmaceutical composition (e.g., microbial cocktail) described herein for the treatment of an intestinal dysbiosis (e.g. IBD or ulcerative colitis) in a subject in need thereof.

Example 3: Bacterial Isolates that Modulate Cytokine Production

Functional assays were developed for screening bacterial isolates for modulation of human immune cells, e.g., by influencing specific cytokine production in human peripheral blood mononuclear cells (PBMC).

A screen was performed to identify bacterial strains that induce production of anti-inflammatory cytokines while not inducing (or possibly inhibiting) production of pro-inflammatory cytokines from host cells. Bacterial isolates were co-cultured with human PBMCs and the levels of six cytokines measured. The six cytokines were: IL-10, a significant anti-inflammatory cytokine; GM-CSF, which evidence suggests has protective effects on gut immunology; and IL-12p70, IFN-gamma, TNF-alpha, and IL-23 and which are believed to have pro-inflammatory effects.

Bacterial isolates were cultured in liquid culture as described above and cells were washed and re-suspended at $1 \times 10^9$ CFU/mL (optionally, stored at −80° C. until the later co-culture step). Human PBMCs were seeded into 24-well plates and incubated in 5% $CO_2$ overnight. Bacterial isolates were added to the PBMCs at a multiplicity of infection (MOI) of 0.4×, 2×, or 10× and co-cultured for 24 hours. The co-culture supernatants were then collected and cytokine levels (of IL-10, IL-12, IFN-gamma, GM-CSF, TNF-alpha, and IL-23) were quantified by Luminex.

Tables 46 and 46a show the results of the assay for isolates assayed using PBMCs from three human donors (results in pg/ml). Also shown is data for positive control strain DSM 17677 (*Faecalibacterium prausnitzii* A2-165) and negative controls (*E. coli* ATCC 8739, PBMCs alone, and cell culture medium alone). Each of the tested isolates induced an anti-inflammatory profile, characterized by high levels of IL-10 production and/or low levels of IL-12, TNF-alpha, IFN-gamma, and/or IL-23, as shown by the ratios of IL-10/IL-12 and IL-10/TNF-alpha in Tables 46 and 46a. The bacterial isolates identified as beneficial in immunomodulation in the PBMC assay are each identified above in Table 3, along with the Sequence Identifier (SEQ ID NO) for their respective 16S rRNA sequences.

The ability of these bacterial isolates to induce an anti-inflammatory cytokine profile from host cells (e.g., in the gut of a subject administered one or more of the bacterial isolates) makes them excellent candidates for inclusion in a pharmaceutical composition (e.g., microbial cocktail) described herein for the treatment of an intestinal dysbiosis (e.g. IBD or ulcerative colitis) in a subject in need thereof.

TABLE 46

| ID Number | Taxonomy | IL-10 | GM-CSF | IL-12p70 | IFN-gamma | TNF-alpha | IL-23 | IL-10/IL12 | IL-10/TNF-alpha |
|---|---|---|---|---|---|---|---|---|---|
| PI00000072 | *O. splanchnicus* | 3149 | 29.32 | 14.50 | 13.28 | 364.1 | 34.15 | 217.3 | 8.65 |
| PI00000395 | *A. shahii* | 2885 | 49.93 | 41.39 | 13.65 | 693.3 | 110.6 | 69.70 | 4.16 |
| PI00000094 | *A. hadrus* | 3453 | 72.88 | 8.54 | 12.55 | 523.8 | 114.9 | 404.5 | 6.59 |
| PI00000146 | *B. stercoris* | 1751 | 76.53 | 57.68 | 4.37 | 1147 | 465.0 | 30.35 | 1.53 |

TABLE 46-continued

| ID Number | Taxonomy | IL-10 | GM-CSF | IL-12p70 | IFN-gamma | TNF-alpha | IL-23 | IL-10/IL12 | IL-10/TNF-alpha |
|---|---|---|---|---|---|---|---|---|---|
| PI00000137 | B. uniformis | 2811 | 91.25 | 21.38 | 6.62 | 1225 | 226.3 | 131.5 | 2.29 |
| PI00000352 | B. uniformis | 3032 | 64.37 | 92.60 | 29.75 | 2680 | 309.3 | 32.74 | 1.13 |
| PI00000138 | B. vulgatus | 2751 | 62.21 | 57.46 | 21.72 | 1680 | 135.0 | 47.88 | 1.64 |
| PI00000097 | C. aldenense | 2041 | 49.93 | 11.90 | 3.81 | 968.0 | 95.46 | 171.5 | 2.11 |
| PI00000370 | C. comes | 3639 | 117.3 | 69.71 | 24.28 | 2713 | 180.2 | 52.20 | 1.34 |
| PI00000329 | F. prausnitzii | 1672 | 10.73 | 0.63 | 1.72 | 45.23 | 7.74 | 2637 | 36.96 |
| IS00006632 | F. prausnitzii | 2760 | 45.88 | 7.85 | 3.99 | 565.8 | 71.72 | 351.8 | 4.88 |
| DSM 17677 | F. prausnitzii | 3949 | 46.47 | 23.08 | 6.24 | 2398 | 73.16 | 171.1 | 1.65 |
| ATCC 8739 | E. coli | 3585 | 479.0 | 351.57 | 361.42 | 27867 | 1999 | 10.20 | 0.13 |
| | PBMC only | | 0.85 | 13.38 | 1.66 | 0.50 | 2.49 | 3.72 | 0.51 | 0.34 |
| | Cell culture medium only | | 0.05 | 0.50 | 0.04 | 0.16 | 0.40 | 0.07 | 1.23 | 0.13 |

TABLE 46a

| ID Number | Taxonomy | IL-10 | GM-CSF | IL-12p70 | IFN-gamma | TNF-alpha | IL-23 | IL-10/IL12 | IL-10/TNF-alpha |
|---|---|---|---|---|---|---|---|---|---|
| IS00007180 | A. muciniphila | 2136 | 44.53 | 33.12 | 12.86 | 511.2 | 79.19 | 64.49 | 4.18 |
| IS00007359 | S. variabile | 2948 | 66.14 | 51.30 | 14.70 | 971.8 | 157.5 | 57.48 | 3.03 |
| IS00007357 | S. variabile | 1788 | 26.46 | 3.25 | 2.14 | 136.7 | 1.29 | 550.4 | 13.08 |
| DSM 17677 | F. prausnitzii | 1790 | 64.04 | 20.14 | 13.58 | 1249 | 117 | 88.89 | 1.43 |
| ATCC 8739 | E. coli | 2561 | 180.2 | 1371 | 487 | 10386 | 4113 | 1.87 | 0.25 |
| | PBMC only | 2.41 | 3.34 | 1.66 | 3.60 | 0.53 | 5.04 | 1.45 | 4.52 |
| | Cell culture medium only | 0.25 | 3.34 | 1.66 | 3.60 | 0.13 | 3.76 | 0.15 | 1.95 |

Example 4: Reduction of Inflammatory Markers

The anti-inflammatory activity of a microbial cocktail comprising bacterial isolates described herein was tested. The PBMC assay described in Example 3 was modified by co-incubating the PBMCs with viable E. coli to induce an inflammatory response, thus generating a sensitized platform incorporating the physiologically and disease (e.g., IBD) relevant PBMC cell type for determining the capacity of a bacterial consortium to reduce inflammation.

Bacterial isolates were cultured in liquid culture as described above and cells were washed and re-suspended at $1×10^9$ CFU/mL (optionally, stored at −80° C. until the later co-culture step). Human PBMCs were seeded into 24-well plates and incubated in 5% $CO_2$ overnight. For consortia assays each individual bacterial isolate was added to the PBMCs at a multiplicity of infection (MOI) of 0.4 and co-cultured for 24 hours. The MOI of E. coli was kept at 0.4 in all experiments. The co-culture supernatants were then collected and cytokine levels (of IL-10, IL-12, IFN-gamma, TNF-alpha, and IL-23) were quantified by Luminex.

Figure 4A:
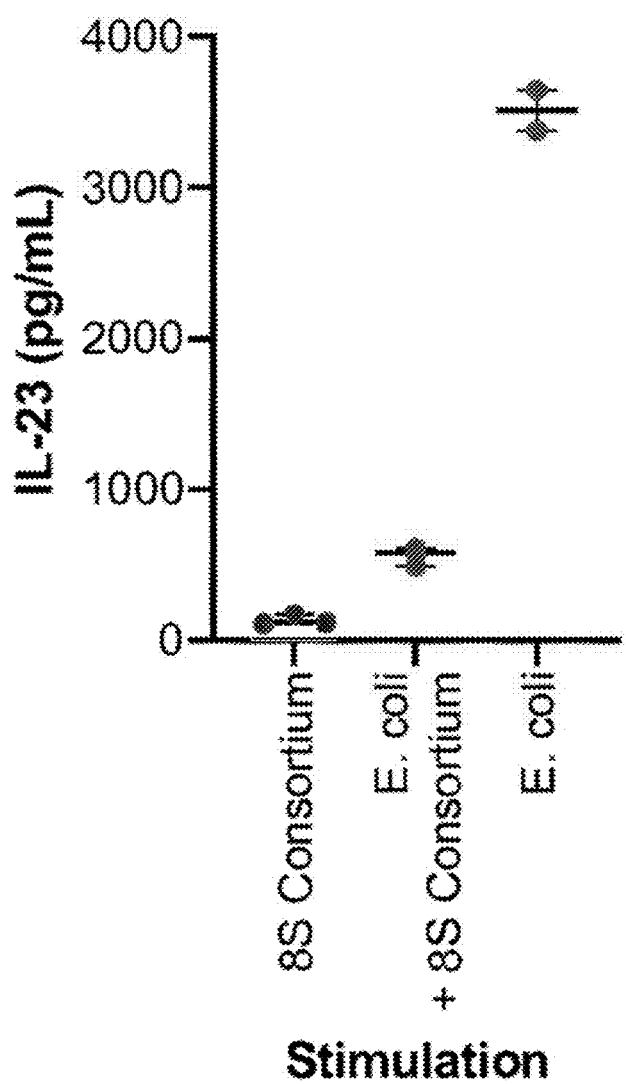
FIG. 4A-E shows the anti-inflammatory effects of an 8-strain bacterial cocktail when incubated with PBMCs treated with inflammation-inducing $E.\ coli$ on IL-23 (FIG. 4A), TNF-$\alpha$ (FIG. 4B), IL-10 (FIG. 4C), IFN-$\gamma$ (FIG. 4D) and IL-12p70 (FIG. 4E).
Figure 4B:
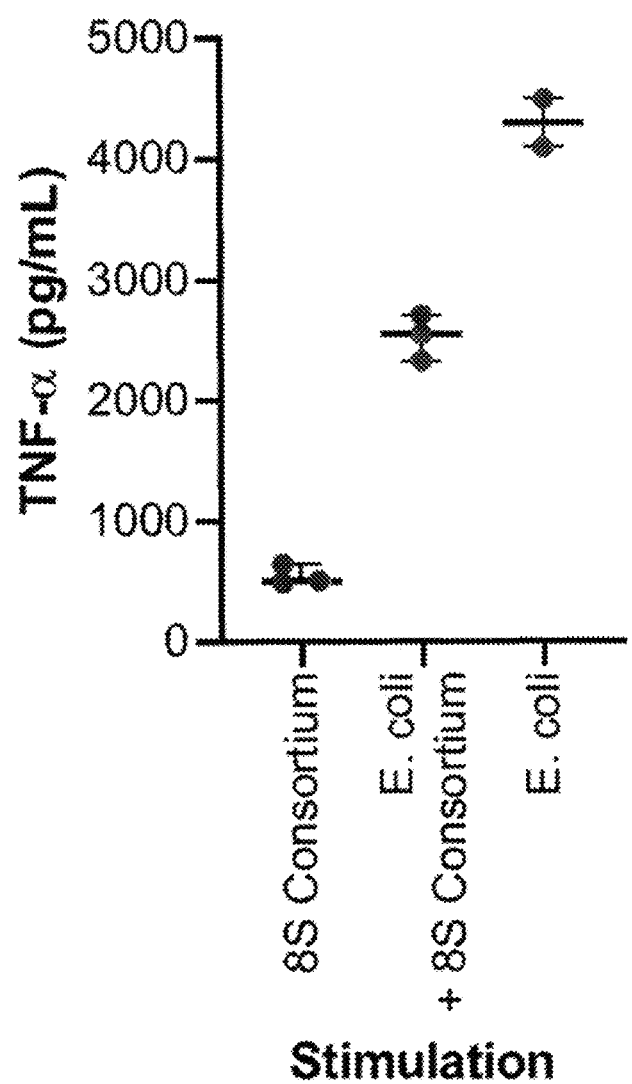
Figure 4C:
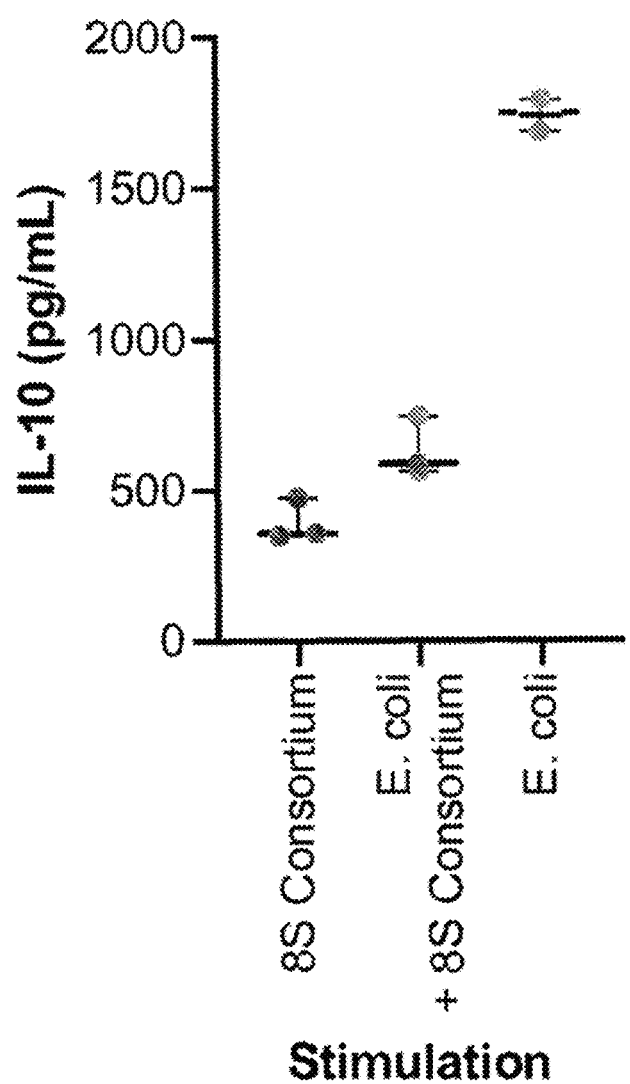
Figure 4D:
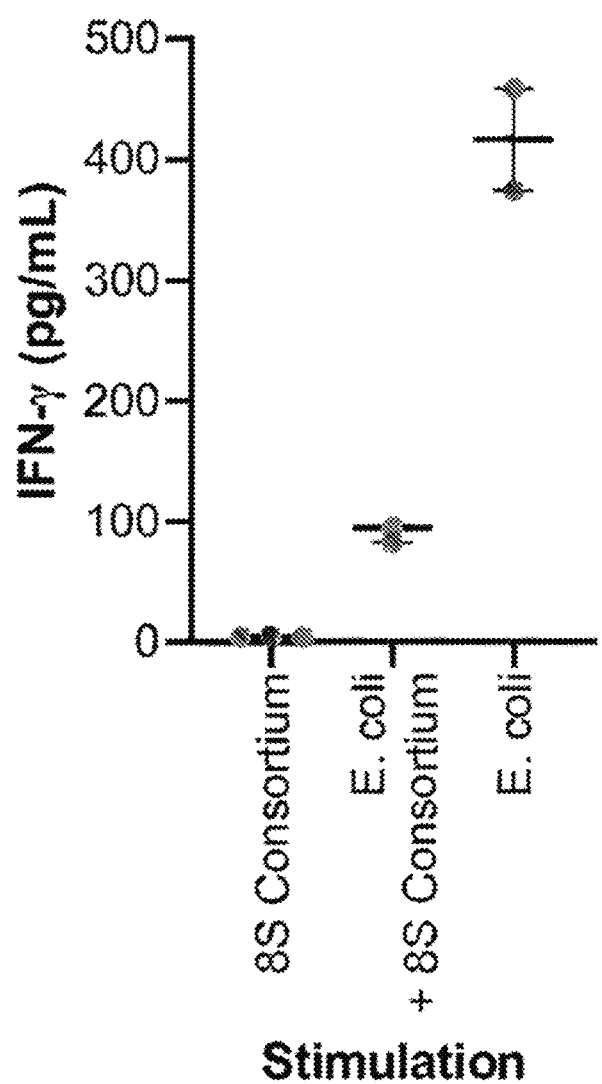
Figure 4E:
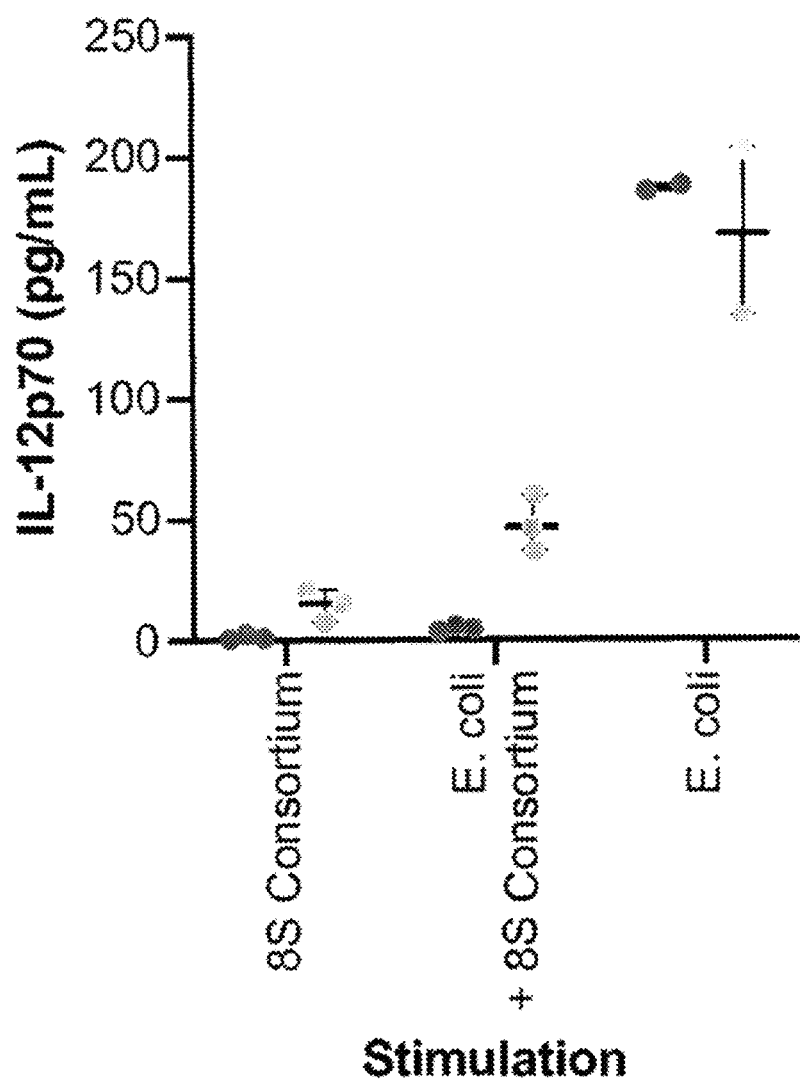
Figure 5A:
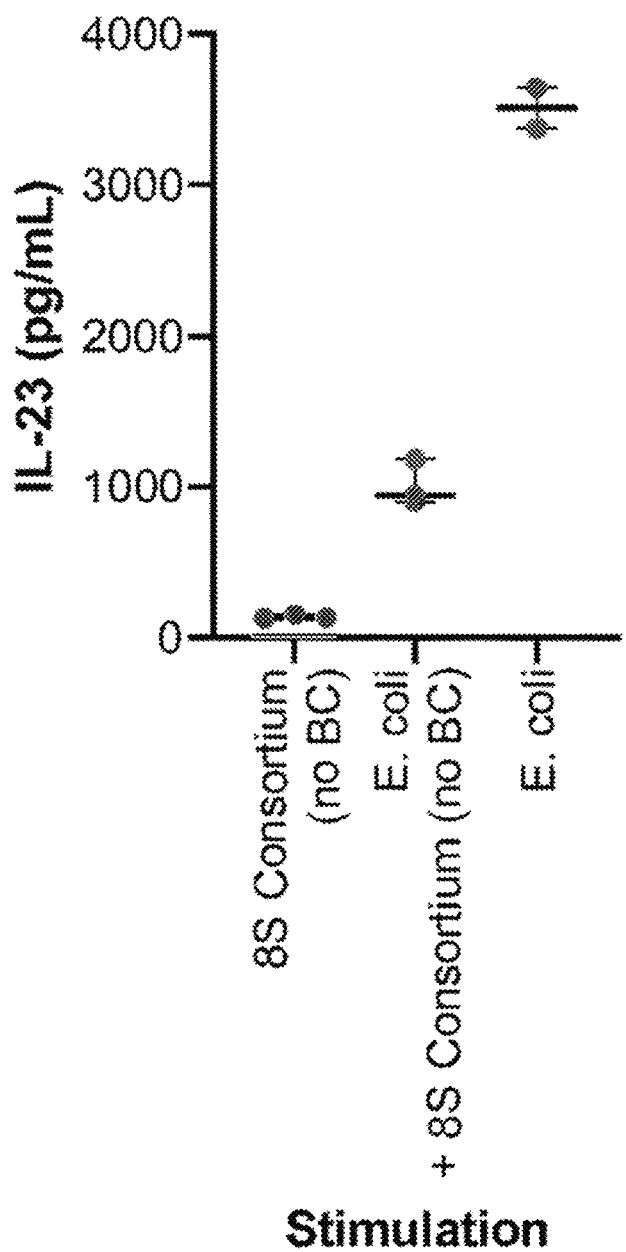
FIG. 5A-E shows the anti-inflammatory effects of a 7-strain bacterial cocktail when incubated with PBMCs treated with inflammation-inducing $E.\ coli$ on IL-23 (FIG. 5A), TNF-$\alpha$ (FIG. 5B), IL-10 (FIG. 5C), IFN-$\gamma$ (FIG. 5D) and IL-12p70 (FIG. 5E).
Figure 5B:
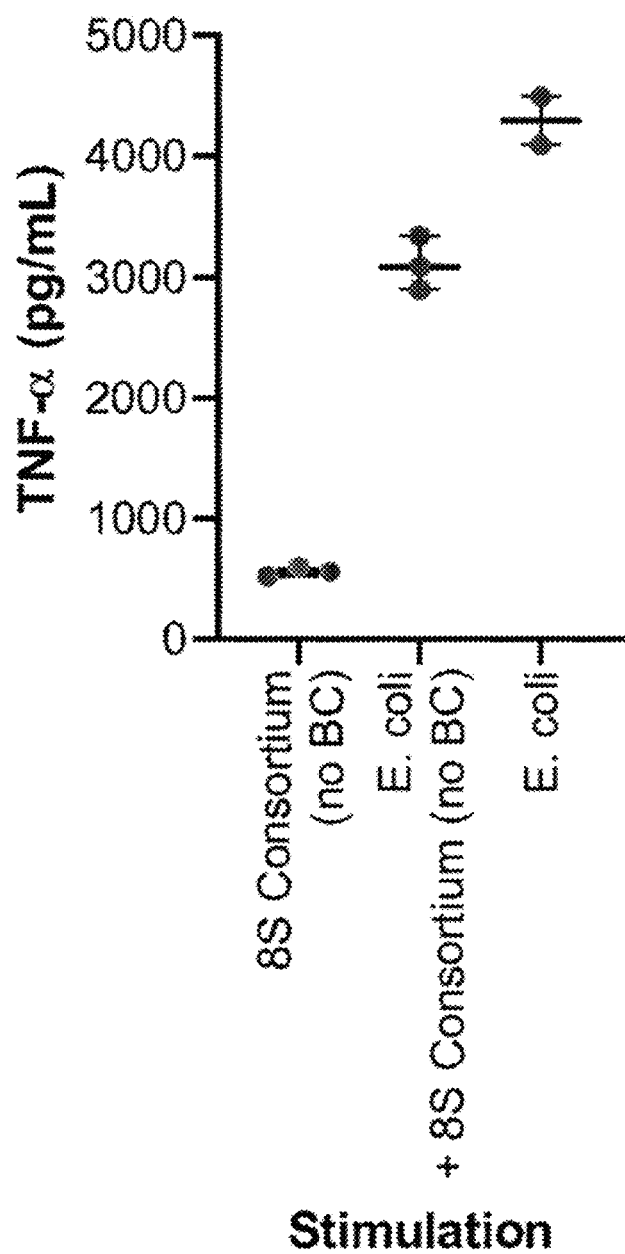
Figure 5C:
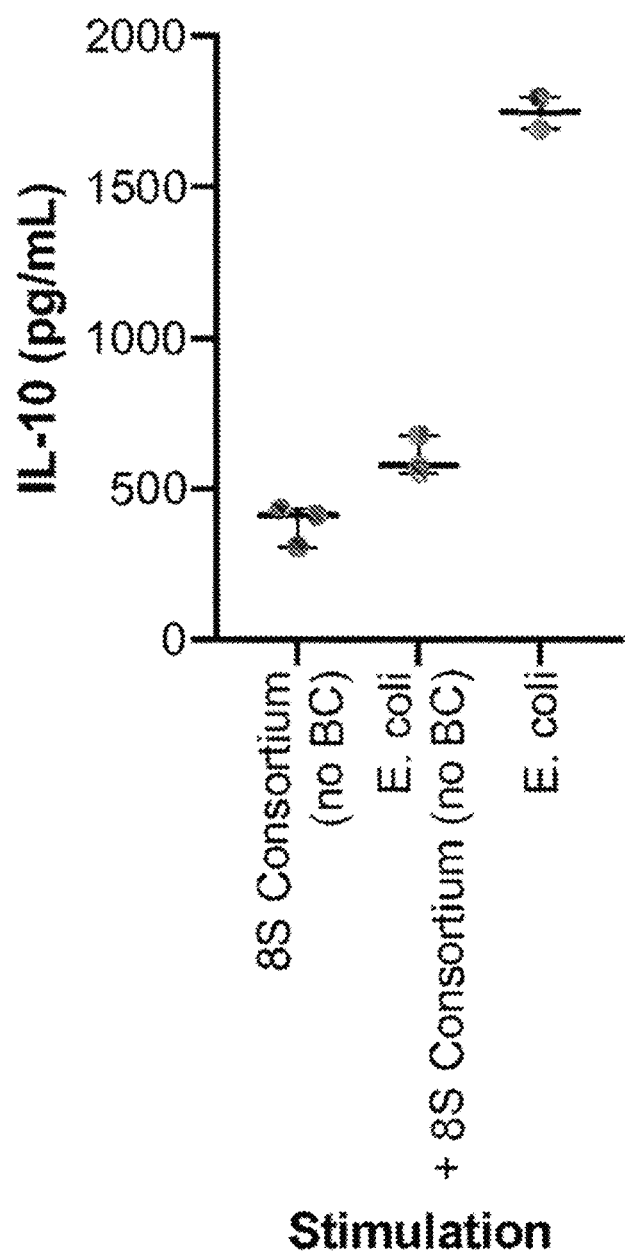
Figure 5D:
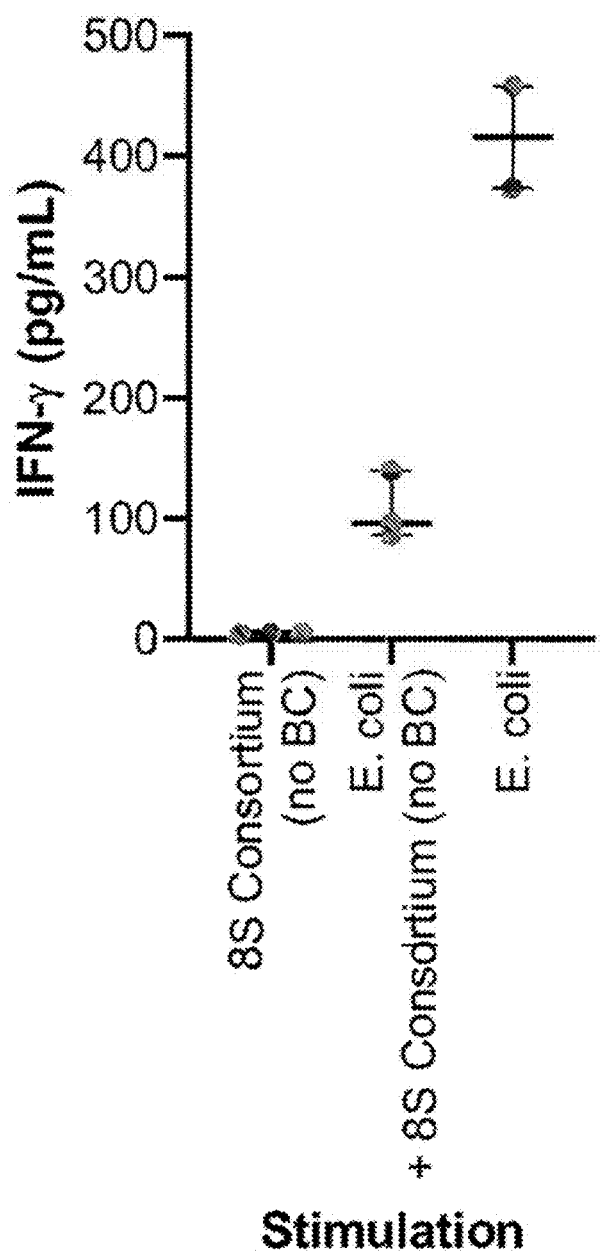
Figure 5E:
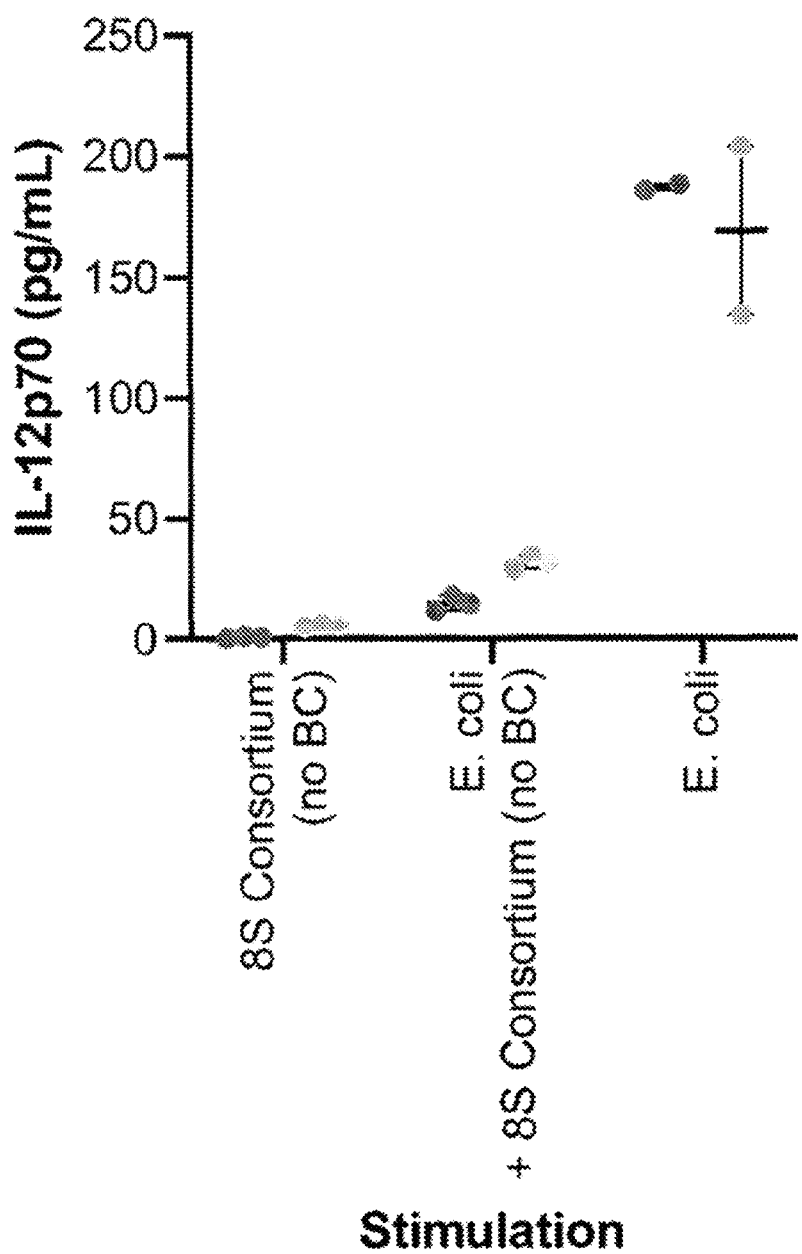

FIG. 4A-E and FIG. 5A-E shows the anti-inflammatory effects of incubation of the PBMC/E. coli mixture with 8-strain and 7-strain microbial cocktails, respectively. The 8-strain microbial cocktail consisted of Odoribacter splanchnicus (PI00000072), two isolates of Faecalibacterium prausnitzii (IS00006632 and PI00000329) Akkermansia muciniphila (IS00007180), Bacteroides cellulosilyticus (PI00000316), Eubacterium rectale, (IS00006864) Alistipes shahii (PI00000395) and Roseburia faecis (PI00000404). The 7-strain microbial cocktail included the same strains, except B. cellulosilyticus was removed. Incubation with each microbial cocktail reduced the anti-inflammatory effect of treatment with E. coli, as shown by reduced levels of IL-23 (FIGS. 4A and 5A), TNF-α (FIGS. 4B and 5B), IL-10 (FIGS. 4C and 5C), IFN-γ (FIGS. 4D and 5D) and IL12-p70 (FIGS. 4E and 5E).

Example 5: Bacterial Isolates Enriched in Healthy Subjects

A mechanism agnostic empirical approach was developed to identify species associated with reducing the dysbiosis associated with Ulcerative Colitis (UC). 16S ribosomal DNA (rDNA) and shotgun metagenomic sequences were incorporated from interventional (FMT), cross-sectional and time series datasets to develop predictive features associated with either a healthy status or clinical response to FMT. These features were used to rank and select bacterial phylogenetic clades for (i) enrichment in healthy subjects over patients diagnosed with UC; and/or (ii) association/correlation with clinical remission or response of UC symptoms in UC patients following FMT treatment. Clades were ranked based on a "cross-sectional combined p-value" which compares the presence and abundances of bacterial strains in fecal material between healthy subjects and patients with UC. The lower the value, the more likely the organisms in the clade are having an effect on the treatment, inhibition or prevention of UC based on: (i) depletion of the strain in UC patients and/or (ii) high abundance of the strain in healthy subjects. Isolated bacterial strains were then selected from donor stool samples by 16S rDNA similarity to the ranked phylogenetic clades or by ranking their 16S rDNA directly according to the aforementioned criteria.

Twenty-three bacterial strains were identified as enriched in healthy subjects relative to UC patients. To identify bacterial isolates corresponding to the twenty-three bacterial strains, microbiota extracted from stool samples of donors were screened for bacteria having at least 97% identity to the 16S rRNA sequence of each identified bacterial strain. Table 47 shows these isolates' taxonomic information, sequence identifier (SEQ ID NO) for its 16S rRNA sequence, and cross-sectional combined p-value.

TABLE 47

| Isolate Latin Name | ID Number | SEQ ID NO for 16S rRNA Sequence | Cross sectional combined p-value |
|---|---|---|---|
| Faecalibacterium prausnitzii | PI00000329 | 1 | 8.0E−3 |
| Odoribacter splanchnicus | PI00000072 | 2 | 1.31E−15 |
| Anaerosapes hadrus | PI00000094 | 3 | 1.37E−04 |
| Alisapes onderdonkii | IS00004389 | 4 | 1.35E−17 |
| Parabacteroides merdae | IS00006167 | 5 | 1.30E−07 |
| Dorea longicatena | IS00006618 | 6 | 2.00E−05 |
| Faecalibacterium prausnitzii | IS00006632 | 7 | 0.123420709 |
| Eubacterium rectale | IS00006864 | 8 | 2.69E−11 |
| Blautia obeum | PI00000053 | 9 | 3.91E−05 |
| Bacteroides uniformis | PI00000137 | 11 | 5.38E−06 |
| Bacteroides vulgatus | PI00000138 | 12 | 0.001351122 |
| Bacteroides cellulosilyticus | PI00000316 | 14 | 4.04E−12 |
| Alisapes finegoldii | PI00000340 | 15 | 1.13E−18 |
| Bacteroides uniformis | PI00000352 | 16 | 3.66E−06 |
| Alistipes shahii | PI00000395 | 18 | 6.30E−21 |
| Akkermansia muciniphila | IS00007180 | 20 | 7.0E−8 |
| Phascolarctobacterium faecium | PI00000289 | 21 | 7.0E−9 |
| Subdoligranulum variabile | IS00007359 | 22 | 1.0E−5 |
| Subdoligranulum variabile | IS00007357 | 23 | 1.0E−3 |
| Blautia sp. | IS00002788 | 34 | 2.0E−10 |
| Alistipes putredinis | IS00008139 | 35 | 1.0E−10 |
| Alistipes putredinis | IS00008142 | 36 | 1.0E−10 |
| Alistipes putredinis | IS00008177 | 37 | 1.0E−10 |

An additional ten bacterial isolates having a 16S rRNA sequence at least 95% identical to a bacterial isolate of Table 47 were also characterized. Table 48 lists each isolates' identification number, the ID number of the related bacterial isolate from Table 47, the percent identity of the isolate's 16S rRNA sequence to the related isolate in Table 47, the cross-sectional combined p value of the isolate, and the isolate's sequence identifier (SEQ ID NO). These data demonstrate that the functionality of the bacterial isolates identified in Table 47 in relieving one or more symptoms of UC is exemplary only and is also possessed by a larger group of related isolates (e.g., sharing at least 95% 16S rRNA sequence identity with the bacterial isolates of Table 47).

TABLE 48

| ID Number | Related to ID Number of Table 47 | % identity of 16S to ID Number of Table 47 | Cross sectional combined p-value | SEQ ID NO. for 16S rRNA Sequence |
|---|---|---|---|---|
| PI00000070 | PI00000072 | 98.6 | 1.31E−15 | 24 |
| PI00000092 | PI00000094 | 98.1 | 1.17E−05 | 25 |
| PI00000339 | IS00004389 | 96.6 | 1.13E−18 | 26 |
| PI00000327 | IS00006167 | 99.4 | 1.13E−07 | 27 |
| PI00000056 | PI00000053 | 96.2 | 3.91E−05 | 28 |
| PI00000152 | PI00000138 | 98.7 | 0.001351122 | 29 |
| PI00000043 | PI00000316 | 99.2 | 2.71E−11 | 30 |
| IS00003009 | PI00000340 | 97.6 | 2.15E−11 | 31 |
| PI00000052 | PI00000352 | 96.6 | 2.85E−11 | 32 |
| PI00000330 | PI00000395 | 95.3 | 1.13E−18 | 33 |

Example 6: Production of Aryl Hydrocarbons by Bacterial Isolates

A functional assay was developed for screening bacterial isolates for activation of the aryl hydrocarbon receptor (AhR), e.g., in gut epithelial cells of a subject administered the bacterial isolate.

AhR is a transcription factor that regulates gene expression. The signaling pathways of the transcription factor AhR are inducible by a number of small molecular weight chemicals, including polycyclic aromatic hydrocarbons, bacterial toxic pigments, and physiological compounds such as tryptophan derivatives or dietary indoles. The most notable of these xenobiotic chemicals are aromatic (aryl) hydrocarbons from which the receptor derives its name.

Bacteria capable of activating the AhR pathway were identified via two methods: metabolomics analysis and functional screening.

For metabolomics analysis, an assay was developed to assess the ability of bacterial isolates to produce known AhR ligands. Each isolate to be screened was grown in liquid culture as described above, with all media supplemented with 0.6 mM tryptophan. Cells were pelleted by centrifugation and resuspended in fresh culture media containing 0.6 mM tryptophan. Plates were incubated at 37° C. in an anaerobic chamber for 48 hours to allow for growth and production of tryptophan metabolites. Following incubation, cells were pelleted by centrifugation and supernatants were sterile filtered through 0.2 μm filters. 200 μL of sterile filtered supernatant was then shipped to Metabolon, Inc. (Morrisville, NC) for untargeted metabolomics analysis. Metabolomics data for each strain was analyzed to identify production of tryptophan metabolites and AhR ligands. Metabolomics data is reported in relative metabolite abundance.

For functional screening, the same supernatants generated for untargeted metabolomics were evaluated using a cell-based genetic reporter assay using a luciferase reporter gene to assess AhR response (Indigo Biosciences; State College, PA). Reporter cells were incubated with serially diluted bacterial supernatants with a maximum supernatant concentration of 1% by volume. Fluorescence was measured and compared to the results from a positive control chemical (MeBio), blank media negative control, and supernatants from positive control strains of Peptostreptococcus russellii and Peptostreptococcus anaerobius to evaluate ability to activate the AhR pathway. Functional screen data is reported in relative fluorescence units.

Figure 2A:
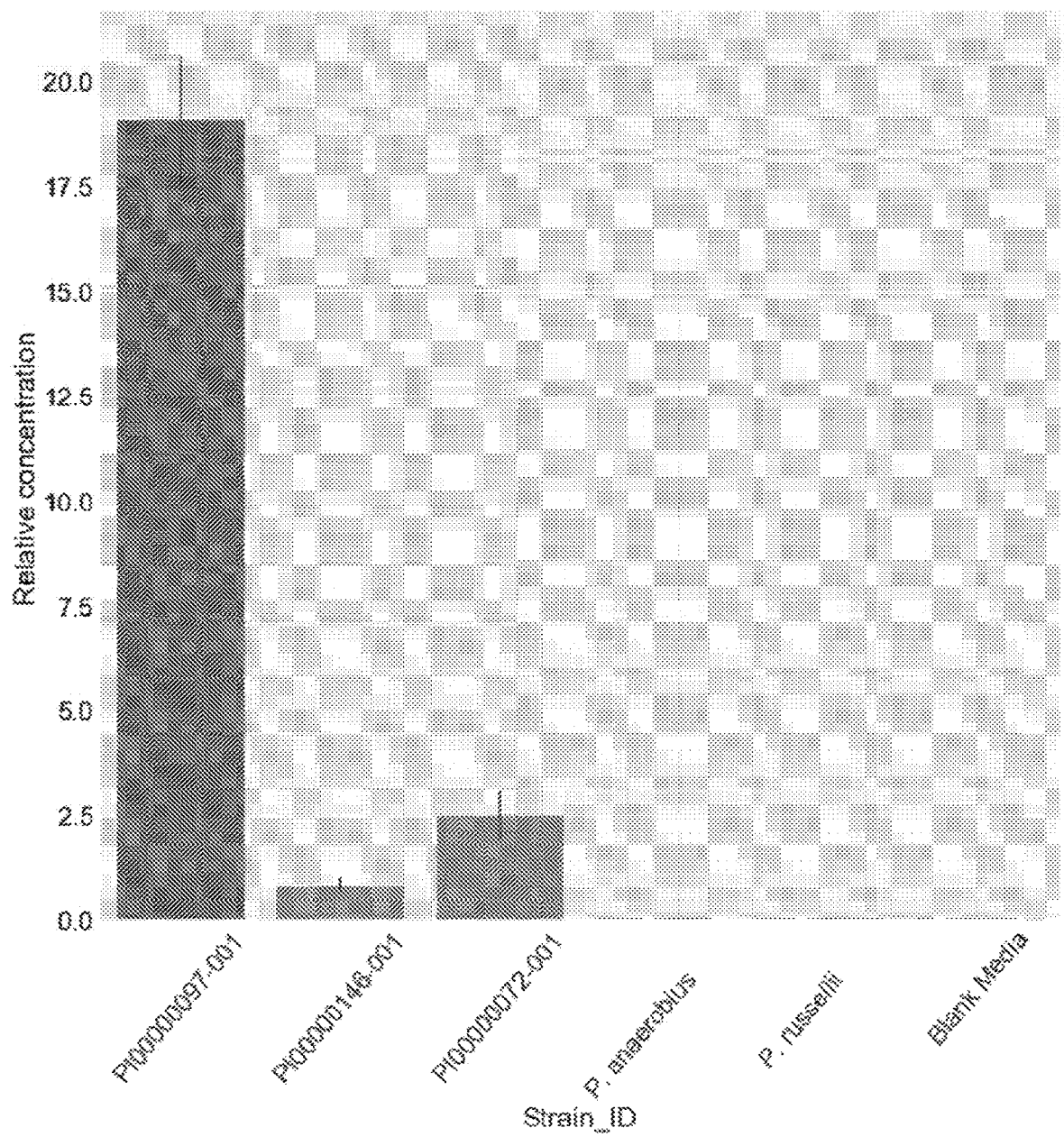
FIG. 2A to FIG. 2E show production by bacterial isolates of aryl hydrocarbons, namely indole (FIG. 2A), tryptamine (FIG. 2B), kynurenic acid (FIG. 2C), kynurenine (FIG. 2D), and indole-3-acetic acid (FIG. 2E).
Figure 2B:
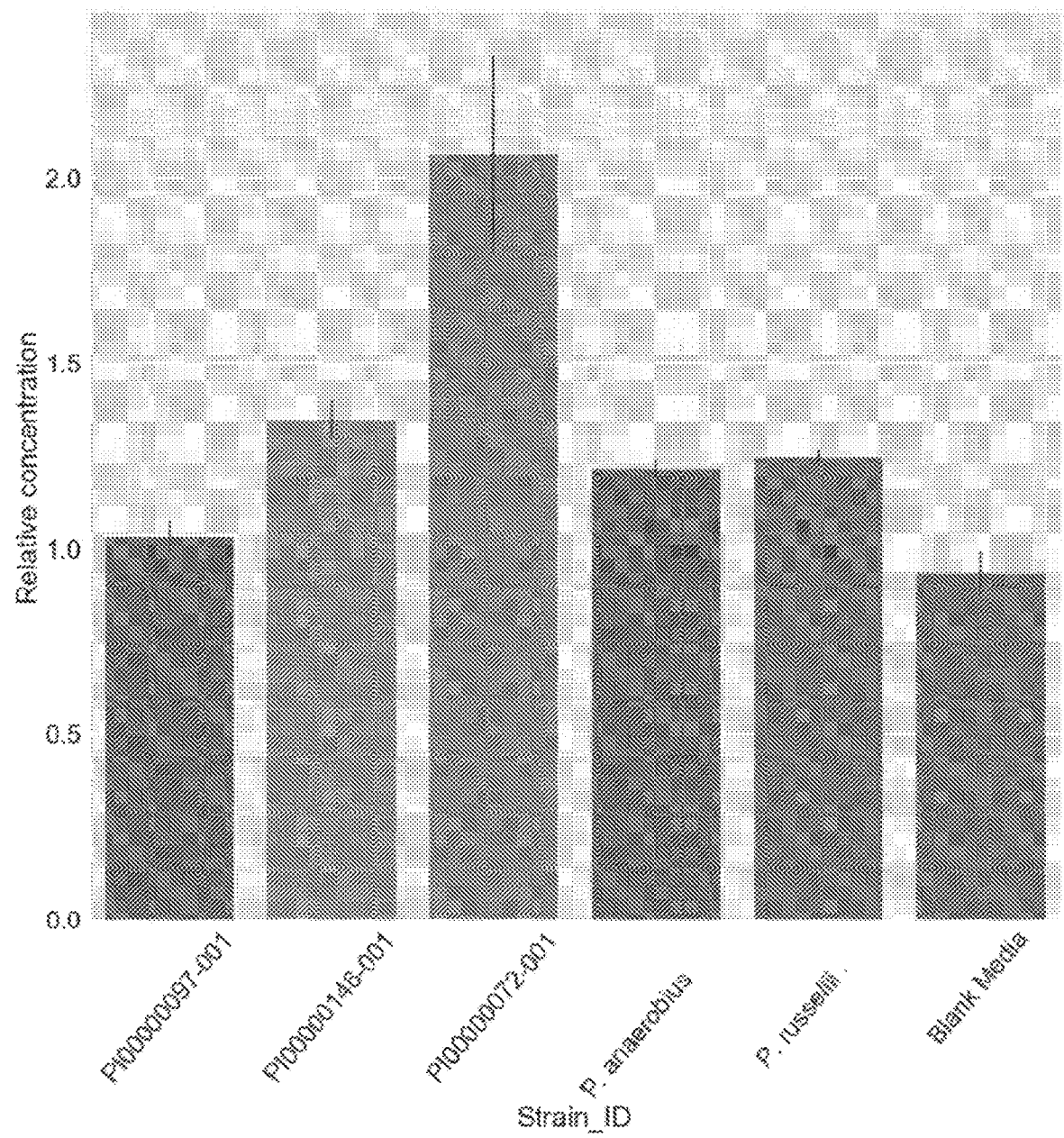
Figure 2C:
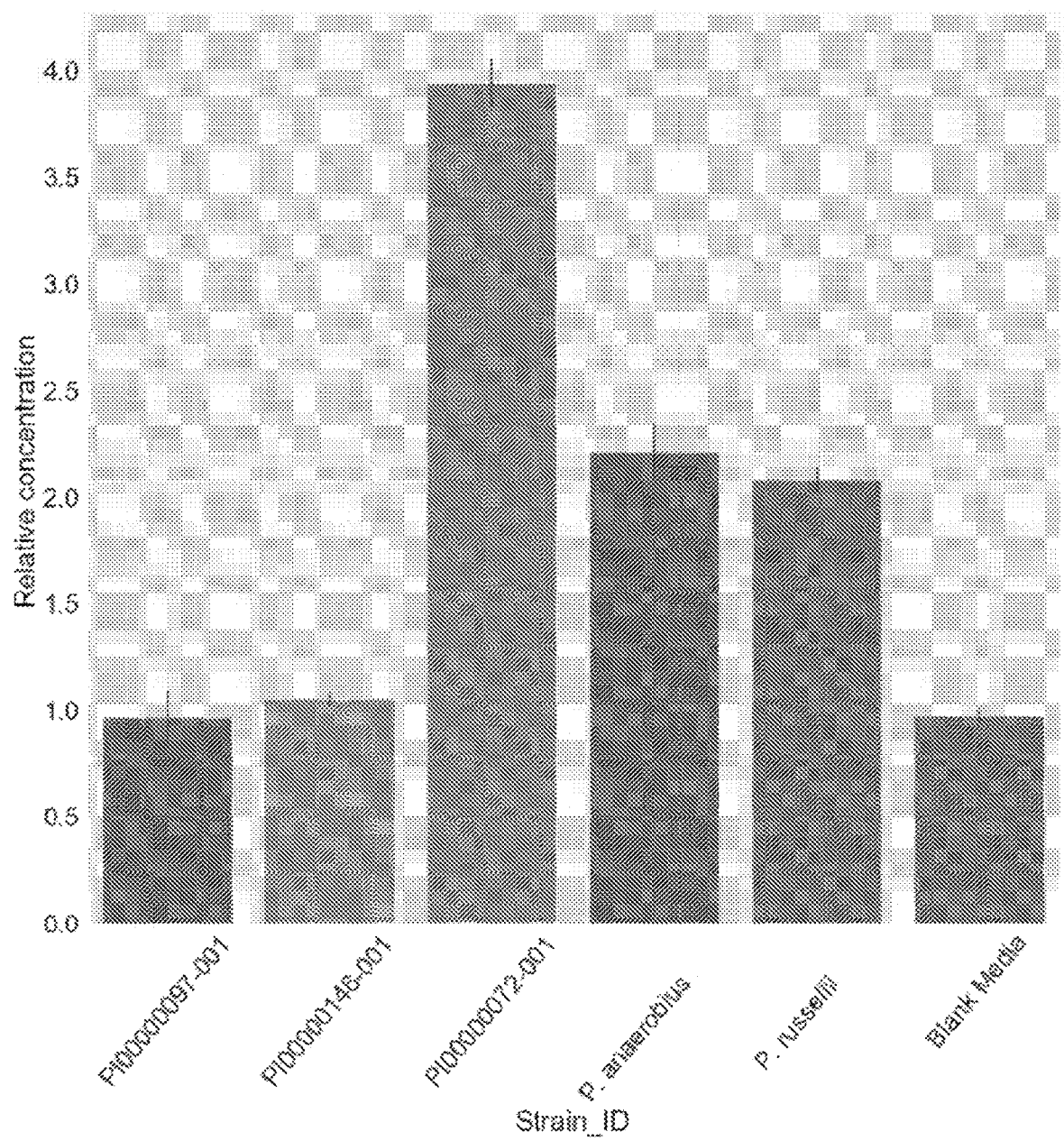
Figure 2D:
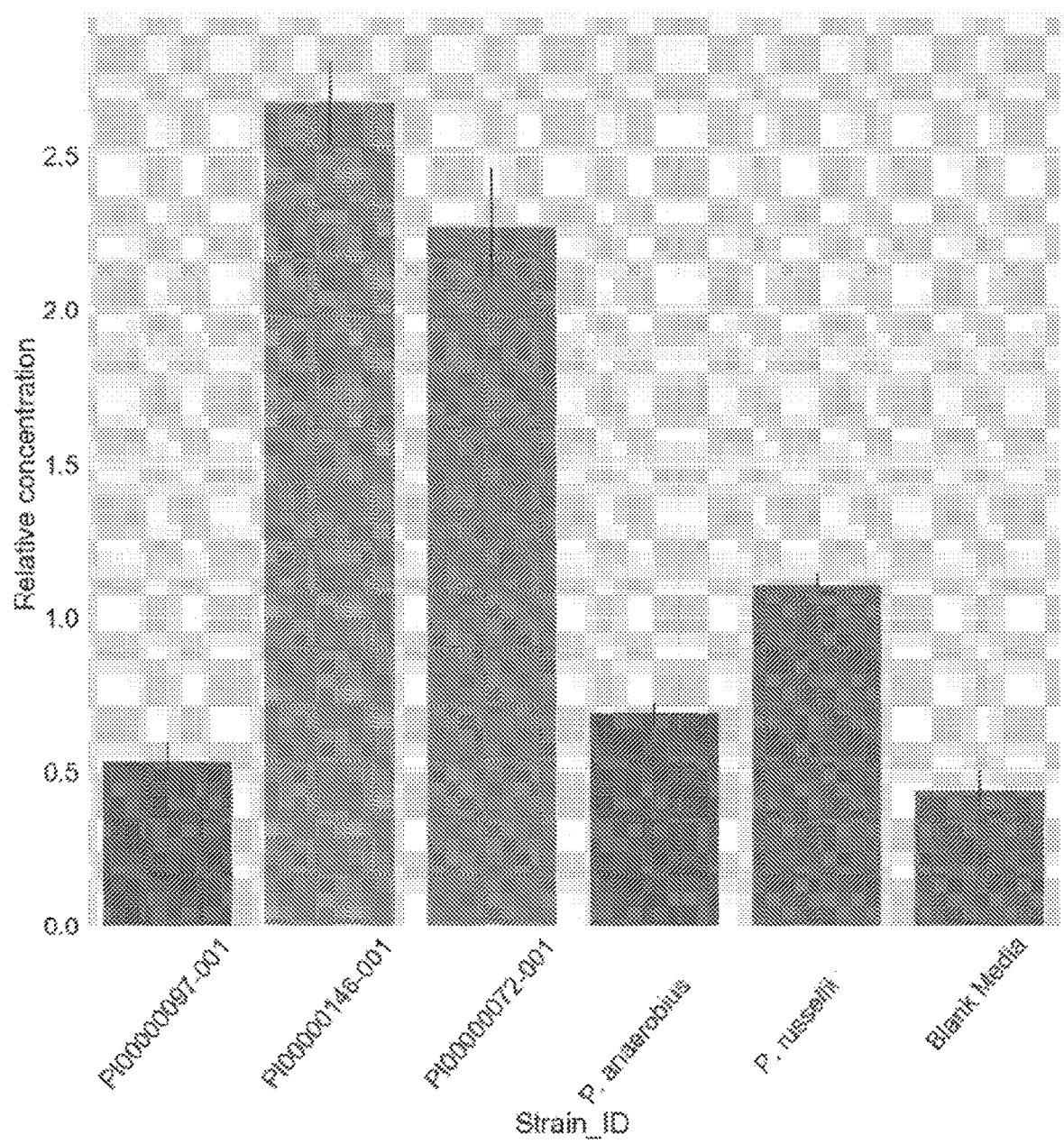
Figure 2E:
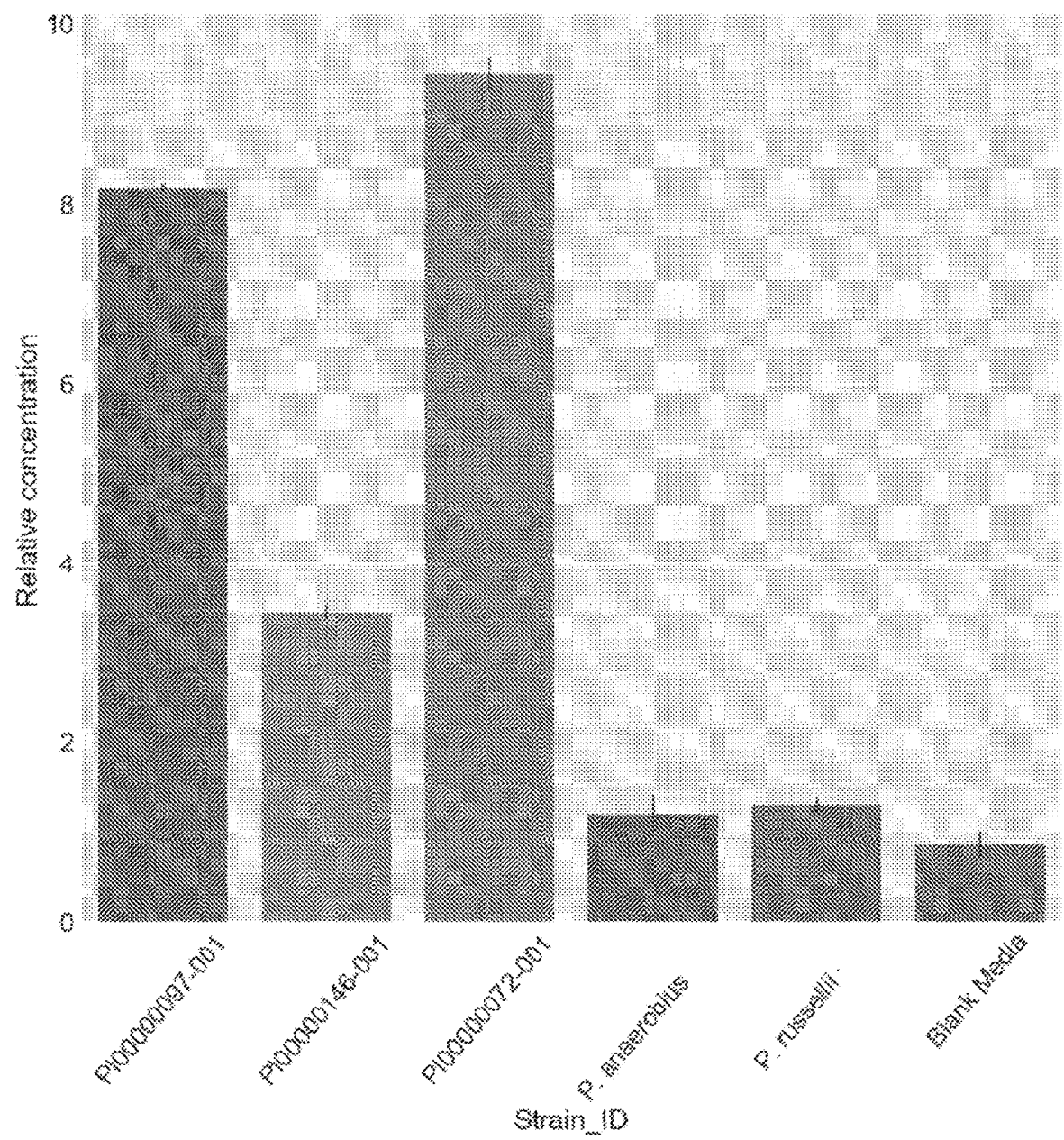

FIG. 2A to FIG. 2E show relative production of the aryl hydrocarbons: indole (FIG. 2A), tryptamine (FIG. 2B), kynurenic acid (FIG. 2C), kynurenine (FIG. 2D), and indole-3-acetic acid (FIG. 2E).

As shown in FIG. 2A-FIG. 2E, all three of the bacterial isolates PI00000072 (Odoribacter splanchnicus), PI00000097 (Clostridium aldenense), and PI00000146 (Bacteroides stercoris) produce aryl hydrocarbons at levels above the blank media control and Peptostreptococcus controls. Each of the three bacterial isolates identified as producers of aryl hydrocarbons in the AhR assay are identified above in Table 6, along with the Sequence Identifier (SEQ ID NO) for each 16S rRNA sequence.

Absolute levels of certain aryl hydrocarbons produced by bacterial isolates were also quantified. Table 49 shows levels of indole-3-acetic acid produced by bacterial isolates described herein, while Table 50 shows levels of kynurenic acid produced by bacterial isolates described herein.

TABLE 49

| Isolate Latin Name | ID Number | SEQ ID NO. for 16S rRNA Sequence | Indole-3-Acetic Acid (μM) |
|---|---|---|---|
| Clostridium aldenense | PI00000097 | 10 | 5.9 |
| Dorea longicatena | IS00006618 | 6 | 3.45 |

TABLE 49-continued

| Isolate Latin Name | ID Number | SEQ ID NO. for 16S rRNA Sequence | Indole-3-Acetic Acid (µM) |
|---|---|---|---|
| Parabacteroides merdae | IS00006167 | 5 | 2.05 |
| Odoribacter splanchnicus | PI00000072 | 2 | 1.45 |
| Blank media | — | — | 0.23 |

TABLE 50

| Isolate Latin Name | ID Number | SEQ ID NO. for 16S rRNA Sequence | Kynurenic Acid (nM) |
|---|---|---|---|
| Bacteroides uniformis | PI00000352 | 16 | 58 |
| Bacteroides uniformis | PI00000137 | 11 | 49 |
| Odoribacter splanchnicus | PI00000072 | 2 | 45 |
| Blank media | — | — | 0 |

Example 7: Induction of AhR by Bacterial Isolates

A bacterial isolate or a culture supernatant extracted from cells of the bacterial isolate following growth can be contacted with eukaryotic cultured cells which express AhR, e.g., a mammalian cell line, for characterization of the effects of the one or more aryl hydrocarbons on AhR activity. Pure cultures of bacterial isolates were grown for 48 hours in the respective media shown in Table 1, which was supplemented with 0.6 mM tryptophan. Cultures were centrifuged at 3200×g for 15 minutes and supernatants collected. Supernatants were sterile filtered first through a 0.4 µm filter, followed by a 0.2 µm filter. Supernatants were then tested for an ability to activate AhR using the Indigo Biosciences Human Aryl Receptor Reporter Assay System, using the manufacturer's directions and protocol. Briefly, supernatants were diluted to 4% and incubated for 22-24 hours with a human liver cell line (Huh7) transfected with a luciferase reporter gene functionally linked to an AhR-responsive promoter. Following addition of luciferase substrate, intensity of light emission (in units of Relative Light Units, or RLU) was quantified using a plate-reading luminometer.

Results of the assay are shown in Table 51 for three bacterial isolates described herein. This shows that the compositions described herein are capable of activating AhR in a cell of a subject administered the composition.

TABLE 51

| Isolate Latin Name | ID Number | SEQ ID NO. for 16S rRNA Sequence | Relative Light Units (RLU) |
|---|---|---|---|
| Odoribacter splanchnicus | PI00000072 | 2 | 35849 |
| Clostridium aldenense | PI00000097 | 10 | 56627 |
| Bacteroides stercoris | PI00000146 | 13 | 30900 |
| Blank media | — | — | 8706 |

Example 8: Engraftment of Bacterial Isolates

Figure 3:
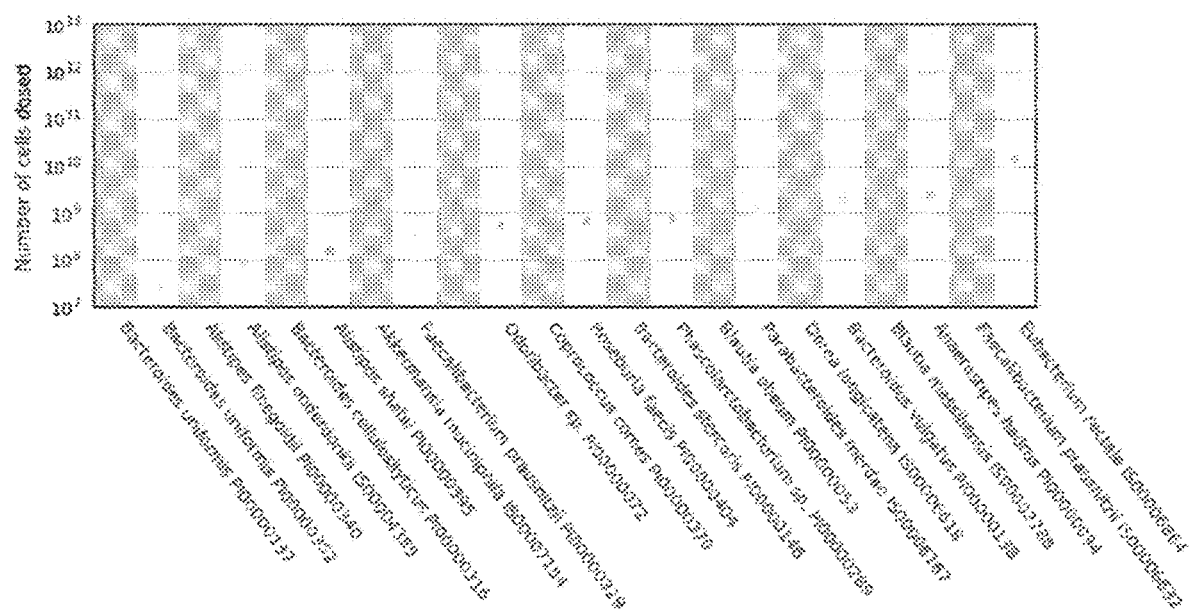
FIG. 3 shows the relationship between the dosage of various bacterial strains corresponding by 16S rRNA sequence to bacterial isolates and engraftment of the strains following the administration to a subject of uncultured fecal bacteria containing the strains.

FIG. 3 shows the relationship between the dosage of various bacterial strains corresponding by 16S rRNA sequence to bacterial isolates and engraftment of the strains in the gut of subject following administration to the subject of a substantially complete fecal microbiota (i.e., a preparation of uncultured fecal bacteria) containing the strains.

For each bacterial isolate corresponding to a given strain in the fecal microbiota, number of cells dosed to a patient was calculated by the following formula: frequency of bacteria in the administered composition having a 16S sequence matching the 16S sequence of the bacterial isolate×9×10$^{10}$ (approximate number of cells per gram of the administered composition)×cumulative dose of the composition administered to a patient (in grams). Engraftment of bacteria was measured for each unique 16S sequence by comparing relative abundances in the administered composition, the patient's baseline community, and the patient's post-treatment community. Positive engraftment was called for cases where the abundance in the patient's baseline was <20% of the administered material, and the post-treatment abundance increased at least 5-fold.

Results show that the minimum dose to achieve engraftment for most bacterial isolates screened (with the exception of the E. rectale isolate IS00006864) is below 10$^{10}$ cells.

Example 9: Engraftment of Bacterial Isolates

To assess the engraftment of bacterial isolates in the intestine of a subject following administration of a microbial cocktail, germ free C57BL/6 mice were inoculated via gavage with the 8-strain consortium described in Example 4 grown under anaerobic conditions. Fecal pellets were collected at 7, 14, 21 and 28 days and DNA was isolated for 16srRNA gene sequencing. Relative abundance of strains was determined based on 16S rRNA gene abundance.

Figure 6:
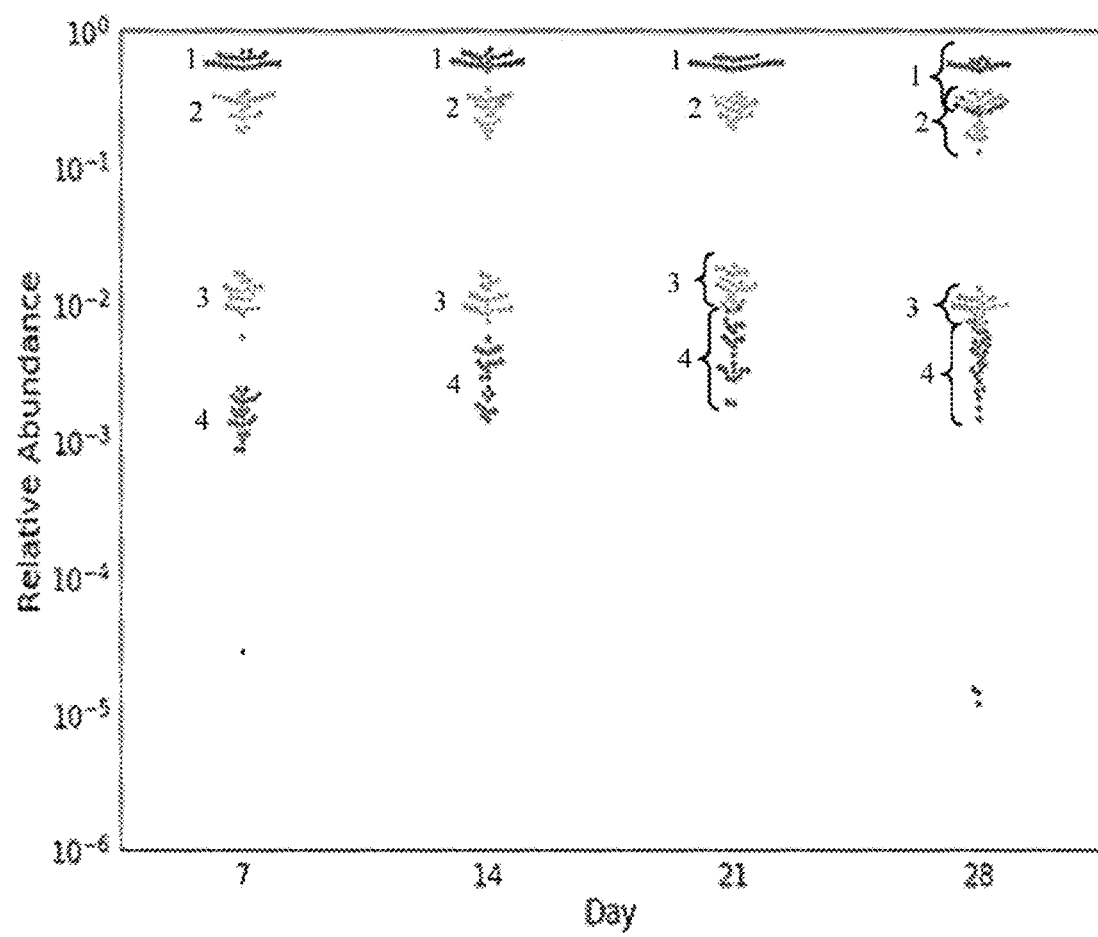
FIG. 6 shows the engraftment of four bacterial isolates following administration to germ free mice of a pharmaceutical composition comprising the isolates.

FIG. 6 shows the engraftment of four bacterial isolates (Bacteroides cellulosilyticus, Akkermansia muciniphila, Odoribacter sphlanchnicus, and Alistipes shahii) in the intestine of the germ free mice following administration of the microbial cocktail comprising the isolates.

Example 10: Production of a Therapeutic Agent

Bacterial isolates of any one of Tables 7-44 are independently cultured and mixed together before administration. Isolates are independently grown anaerobically in supportive media, e.g. at 37° C., pH 7, as shown in Example 1. After each isolate reaches a sufficient biomass, it is optionally preserved for banking by adding 15% glycerol and then frozen at −80° C. in 1 ml cryotubes.

Each bacterial isolate is then cultivated to a concentration of about 10$^{10}$ CFU/mL, then concentrated 20-fold by tangential flow microfiltration; the spent medium is exchanged by diafiltering with a preservative medium consisting of 2% gelatin, 100 mM trehalose, and 10 mM sodium phosphate buffer, or other suitable preservative medium. The suspension is freeze-dried to a powder and titrated.

After drying, the powder is blended with microcrystalline cellulose and magnesium stearate and formulated into a 250 mg gelatin capsule containing 10 mg of lyophilized powder (10$^8$ to 10$^{11}$ bacteria), 160 mg microcrystalline cellulose, 77.5 mg gelatin, and 2.5 mg magnesium stearate.

Example 11: Treatment of Ulcerative Colitis

A patient with a diagnosis of Ulcerative Colitis (UC) by endoscopy and histology consistent with diagnosis is treated with a pharmaceutical composition disclosed herein.

Efficacy is monitored as described in Travis, et al. Aliment Pharmacol Ther. 2011; 34(2):113-124 (which is incorporated by reference in its entirety), including one or more of the following indices (for each index, the associated publication is incorporated by reference in its entirety):

Clinical:
- Truelove and Witts (Truelove S C, Witts L J. Cortisone in ulcerative colitis. Final report on a therapeutic trial. BMJ 1955; 2: 1041-8),
- Powel-Tuck Index (St. Mark's Index; Powell-Tuck J, et al. Correlations between defined sigmoidoscopic appearances and other measures of disease activity in ulcerative colitis. Dig DisSci 1982; 27: 533-7),
- Clinical Activity Index (CAI; Rachmilewitz D. Coated mesalazine (5-aminosalicylic acid) versus sulphasalazine in the treatment of active ulcerative colitis: a randomised trial. BMJ 1989; 298: 82-6),
- Lichtiger Index (S. Lichtiger, D. H. Present Preliminary report: cyclosporin in treatment of severe active ulcerative colitis Lancet, 336 (1990), pp. 16-19),
- Seo Index (Seo M, et al. An index of disease activity in patients with ulcerative colitis. Am J Gastroenterol 1992; 87: 971-6),
- Physician's Global Assessment (Hanauer S et al., Mesalamine capsules for treatment of active ulcerative colitis: results of a controlled trial Am J Gastroenterol. 1993 August; 88(8):1188-97),
- Investigator's Global Evaluation (Hanauer S B et al., Budesonide enema for the treatment of active, distal ulcerative colitis and proctitis: a dose-ranging study. U.S. Budesonide enema study group Gastroenterology. 1998 September; 115(3):525-32).
- Simple Clinical Colitis Activity Index (Walmsley R S, et al., A simple clinical colitis activity index. Gut 1998; 43: 29-32),
- Improvement Based on Individual Symptom Scores (Levine et al., A randomized, double blind, dose-response comparison of balsalazide (6.75 g), balsalazide (2.25 g), and mesalamine (2.4 g) in the treatment of active, mild-to-moderate ulcerative colitis Am J Gastroenterol. 2002 June; 97(6):1398-407), and
- Patient-defined remission (Higgins P, et al. Is endoscopy necessary for the measurement of disease activity in ulcerative colitis. Am J Gastroenterol 2005; 100: 355-61).

Endoscopic:
- Truelove Witts Sigmoidoscopic Assessment (Seo M, et al. Evaluation of disease activity in patients with moderately active ulcerative colitis: comparisons between a new activity index and Truelove and Witts classification. Am J Gastroenterol 1995; 90: 1759-63),
- Baron Score (Baron J H, et al. Variation between observers in describing mucosal appearances in proctocolitis. BMJ 1964; 1: 89-92),
- Endoscopic Index (Rachmilewitz D. Coated mesalazine (5-aminosalicylic acid) versus sulphasalazine in the treatment of active ulcerative colitis: a randomised trial. BMJ 1989; 298: 82-6),
- Sigmoidoscopic Index (Hanauer S et al., Mesalamine capsules for treatment of active ulcerative colitis: results of a controlled trial Am J Gastroenterol. 1993 August; 88(8):1188-97),
- Sigmoidoscopic Inflammation Grade Score (Lémann M et al., Comparison of budesonide and 5-aminosalicylic acid enemas in active distal ulcerative colitis Aliment Pharmacol Ther. 1995 October; 9(5):557-62.),
- Mayo Score Flexible Proctosigmoidoscopy Assessment (Schroeder K W, et al. Coated oral 5-aminosalicylic acid therapy for mildly to moderately active ulcerative colitis. A randomized study. N Engl J Med 1987; 317: 1625-9), and
- Modified Baron Score (Rutgeerts P, et al. Infliximab for induction and maintenance therapy for ulcerative colitis. N Engl J Med 2005; 353: 2462-76).

Clinical and Endoscopic:
- Mayo Clinic Score (Schroeder K W, et al. Coated oral 5-aminosalicylic acid therapy for mildly to moderately active ulcerative colitis. A randomized study. N Engl J Med 1987; 317: 1625-9) and
- Sutherland Index (Sutherland L R, et al. 5-Aminosalicylic acid enema in the treatment of distal ulcerative colitis, proctosigmoiditis, and proctitis. Gastroenterology 1987; 92: 1894-8).

Quality of Life:
- Rating form of IBD Patient Concerns (Drossman D A et al. Health status and health care use in persons with inflammatory bowel disease. A national sample. Dig Dis Sci. 1991 December; 36(12):1746-55),
- Inflammatory Bowel Disease Questionnaire (Irvine E J, et al. Quality of life: a valid and reliable measure of outcome for clinical trials in inflammatory bowel disease. Gastroenterology. 1194; 106:287-96), and
- Short Form-36 (Ware J E et al. The MOS 36-item short-form health survey (SF-36). I. Conceptual framework and item selection Med Care. 1992 June; 30(6):473-83).

Histological:
- Riley Index (Riley S A, et al. Microscopic activity in ulcerative colitis: what does it mean?Gut 1991; 32: 174-8),
- Gebboes Index (Geboes K et al. A reproducible grading scale for histological assessment of inflammation in ulcerative colitis Gut. 2000 September; 47(3):404-9), and
- Chicago Index (Rubin D T, et al. Increased degree of histological inflammation predicts colectomy and hospitalization in patients with ulcerative colitis. Gastroenterology 2007; 132 (Suppl. 1): A-19 (Abstract 103)).

Example 12: In Vivo Testing of a Therapeutic Agent in Mice

A composition or various compositions comprising the nine isolates of any one of Tables 36-43 are provided. Alternatively, a therapeutic agent, e.g., without limitation, made via the methods of Example 10, comprising the nine isolates of any one of Tables 36-43 is provided.

A suitable murine model for UC is selected and provided. Illustrative models include chemical models (such as DSS, TNBS, oxazolone, acetic acid, and sulfhydryl inhibitors) and transgenic/knock out models (such as $TCR\alpha^{-/-}$, $WASP^{-/-}$, $Mdr1a^{-/-}$, $IL-2^{-/-}$, $Gui2^{-/-}$, IL-7 Tg, TRUC, TGFβRIIDN, and C3H/HeJBir). See World J Gastroenterol. 2007 Nov. 14; 13(42): 5581-5593 and Drug Des Devel Ther. 2013; 7: 1341-1357 (2013), the entire contents of which are incorporated by reference.

Taking DDS as anon-limiting example, oral administration of 3-5% DSS in drinking water to mice is undertaken. For instance, one cycle of 3%-5% DSS administration for 5-7 d, followed by regular water, results in extensive injury with complete crypt depletion (e.g. basal crypt) and relatively slow regeneration of colonic epithelium. Animals which develop UC-like symptoms are treated with the composition or various compositions comprising the nine isolates of any one of Tables 36-43 or a therapeutic agent (alternatively, the bacterial compositions can be administered concurrently with the DSS) and comparison is made to determine therapeutic effect (e.g. comparing one or more parameters, such as measuring clinical scores of colitis, including weight change, diarrhea, colorectal bleeding and survival; overall disease severity may be assessed by a clinical scoring system, and a disease activity index (DAI) score may be calculated for each animal). Alternative measures include endoscopy, histological analyses, microbiota analysis by 16S rRNA sequencing, and the like. A more detailed protocol is found in *Curr Protoc Immunol.* 2014 Feb. 4; 104: Unit-15.25, the entire contents of which are incorporated by reference. The present Example allows for variations in the detailed protocol is found in *Curr Protoc Immunol.* 2014 Feb. 4; 104: Unit-15.25 as necessary or desired to determine the presence or absence of a therapeutic effect.

Example 13: Treatment of UC

A composition or various compositions comprising the nine isolates of any one of Tables 36-43 are provided. Alternatively, a therapeutic agent, e.g., without limitation, made via the methods of Example 10, comprising the nine isolates of any one of Tables 36-43 is provided. A study of a UC as described in Example 11 is undertaken with such compositions as the therapeutic agent.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present disclosure is not entitled to antedate such publication by virtue of prior invention.

As used herein, all headings are simply for organization and are not intended to limit the disclosure in any manner. The content of any individual section may be equally applicable to all sections.

The invention claimed is:

1. A method of treating inflammatory bowel disease (IBD) in a subject with IBD in need thereof, the method comprising administering to the subject a plurality of bacterial isolates, wherein the plurality of bacterial isolates comprises *Bacteroides stercoris* and *Bacteroides cellulosilyticus*, and at least one of *Bacteroides uniformis, Subdoligranulum variabile, Anaerostipes hadrus, Odoribacter splanchnicus, Roseburia faecis, Faecalibacterium prausnitzii, Akkermansia muciniphila, Alistipes shahii,* and *Eubacterium rectale*, wherein the *Bacteroides stercoris* comprises a 16S ribosomal ribonucleic acid (rRNA) sequence that has at least 95% sequence identity with the nucleotide sequence of SEQ ID NO: 13.

2. The method of claim 1, wherein at least two of the plurality of bacterial isolates are isolated from a stool of different human donors.

3. The method of claim 1, wherein the plurality of bacterial isolates comprises at least two of *Bacteroides uniformis, Odoribacter splanchnicus, Roseburia faecis, Anaerostipes hadrus, Faecalibacterium prausnitzii, Subdoligranulum variabile, Akkermansia muciniphila, Alistipes shahii,* and *Eubacterium rectale*.

4. The method of claim 1, wherein the plurality of bacterial isolates comprises at least three of *Bacteroides uniformis, Odoribacter splanchnicus, Roseburia faecis, Anaerostipes hadrus, Faecalibacterium prausnitzii, Subdoligranulum variabile, Akkermansia muciniphila, Alistipes shahii,* and *Eubacterium rectale*.

5. The method of claim 1, wherein the plurality of bacterial isolates comprises at least four of *Bacteroides uniformis, Odoribacter splanchnicus, Roseburia faecis, Anaerostipes hadrus, Faecalibacterium prausnitzii, Subdoligranulum variabile, Akkermansia muciniphila, Alistipes shahii,* and *Eubacterium rectale*.

6. The method of claim 1, wherein the plurality of bacterial isolates comprises at least five of *Bacteroides uniformis, Odoribacter splanchnicus, Roseburia faecis, Anaerostipes hadrus, Faecalibacterium prausnitzii, Subdoligranulum variabile, Akkermansia muciniphila, Alistipes shahii,* and *Eubacterium rectale*.

7. The method of claim 1, wherein the plurality of bacterial isolates comprises at least six of *Bacteroides uniformis, Odoribacter splanchnicus, Roseburia faecis, Anaerostipes hadrus, Faecalibacterium prausnitzii, Subdoligranulum variabile, Akkermansia muciniphila, Alistipes shahii,* and *Eubacterium rectale*.

8. The method of claim 1, wherein the plurality of bacterial isolates comprises at least seven of *Bacteroides uniformis, Odoribacter splanchnicus, Roseburia faecis, Anaerostipes hadrus, Faecalibacterium prausnitzii, Subdoligranulum variabile, Akkermansia muciniphila, Alistipes shahii,* and *Eubacterium rectale*.

9. The method of claim 1, wherein the plurality of bacterial isolates comprises a 16S rRNA sequence that has at least 95% sequence identity with nucleotide sequences selected from SEQ ID NOs: 1, 2, 3, 7, 8, 11, 14, 18, 19, 20, 22 and 23.

10. The method of claim 1, wherein the plurality of bacterial isolates comprises:
 (a) a 16S rRNA sequence that has a least 95% sequence identity with nucleotide sequence of SEQ ID NOs: 1 and/or 7,
 (b) a 16S rRNA sequence that has at least 95% sequence identity with nucleotide sequence of SEQ ID NO: 2,
 (c) a 16S rRNA sequence that has at least 95% sequence identity with nucleotide sequence of SEQ ID NO: 3,
 (d) a 16S rRNA sequence that has at least 95% sequence identity with nucleotide sequence of SEQ ID NO: 8,
 (e) a 16S rRNA sequence that has at least 95% sequence identity with nucleotide sequence of SEQ ID NO: 11
 (f) a 16S rRNA sequence that has at least 95% sequence identity with nucleotide sequence of SEQ ID NO: 14, (g) a 16S rRNA sequence that has at least 95% sequence identity with nucleotide sequence of SEQ ID NO: 18,
(h) a 16S rRNA sequence that has at least 95% sequence identity with nucleotide sequence of SEQ ID NO: 19,
(i) a 16S rRNA sequence that has at least 95% sequence identity with nucleotide sequence of SEQ ID NO: 20, and/or
(j) a 16S rRNA sequence that has at least 95% sequence identity with nucleotide sequence of SEQ ID NOs: 22 and/or 23.

11. The method of claim 1, wherein the plurality of bacterial isolates comprises at least two bacterial isolates comprising *Faecalibacterium prausnitzii*, wherein at least two bacterial isolates comprise different 16S rRNA sequences.

12. The method of claim 11, wherein the at least two bacterial isolates comprising *Faecalibacterium prausnitzii* comprise 16S rRNA sequences that have at least 95% sequence identity with nucleotide sequences of SEQ ID NOs: 1 and/or 7.

13. The method of claim 11, wherein at least two bacterial isolates comprising *Faecalibacterium prausnitzii* are isolated from a stool of different human donors.

14. The method of claim 1, wherein the plurality of bacterial isolates comprises lyophilized bacteria.

15. The method of claim 1, wherein the plurality of bacterial isolates does not include *Escherichia coli*.

* * * * *